(12) United States Patent
Wang et al.

(10) Patent No.: US 10,662,174 B2
(45) Date of Patent: May 26, 2020

(54) BTK INHIBITOR

(71) Applicants: Hubei Bio-Pharmaceutical Industrial Technological Institute Inc., Wuhan (CN); Humanwell Healthcare (Group) Co., Ltd., Wuhan (CN)

(72) Inventors: Xuehai Wang, Wuhan (CN); Chengde Wu, Wuhan (CN); Yong Xu, Wuhan (CN); Chunli Shen, Wuhan (CN); Li'e Li, Wuhan (CN); Guoping Hu, Wuhan (CN); Yang Yue, Wuhan (CN); Jian Li, Wuhan (CN); Diliang Guo, Wuhan (CN); Nengyang Shi, Wuhan (CN); Lu Huang, Wuhan (CN); Shuhui Chen, Wuhan (CN); Ronghua Tu, Wuhan (CN); Zhongwen Yang, Wuhan (CN); Xuwen Zhang, Wuhan (CN); Qiang Xiao, Wuhan (CN); Hua Tian, Wuhan (CN); Yanping Yu, Wuhan (CN); Hailiang Chen, Wuhan (CN); Wenjie Sun, Wuhan (CN); Zhenyu He, Wuhan (CN); Jie Shen, Wuhan (CN); Jing Yang, Wuhan (CN); Jing Tang, Wuhan (CN); Wen Zhou, Wuhan (CN); Jing Yu, Wuhan (CN); Yi Zhang, Wuhan (CN); Quan Liu, Wuhan (CN)

(73) Assignee: HUBEI BIO-PHARMACEUTICAL INDUSTRIAL TECHNOLOGICAL INSTITUTE, INC., Wuhan (CN)

( * ) Notice: Subject to any disclaimer, the term of this patent is extended or adjusted under 35 U.S.C. 154(b) by 0 days.

(21) Appl. No.: 15/650,295

(22) Filed: Jul. 14, 2017

(65) Prior Publication Data

US 2017/0313683 A1    Nov. 2, 2017

Related U.S. Application Data

(63) Continuation of application No. PCT/CN2015/081686, filed on Jun. 17, 2015.

(30) Foreign Application Priority Data

Jan. 14, 2015    (CN) .......................... 2015 1 0018849

(51) Int. Cl.
*C07D 487/04* (2006.01)
*A61K 31/5025* (2006.01)
(Continued)

(52) U.S. Cl.
CPC .......... *C07D 401/14* (2013.01); *A61K 31/496* (2013.01); *A61K 31/505* (2013.01);
(Continued)

(58) Field of Classification Search
CPC .................................................. C07D 487/04
See application file for complete search history.

(56) References Cited

U.S. PATENT DOCUMENTS

2017/0152264 A1* 6/2017 Liu ...................... C07D 487/04

FOREIGN PATENT DOCUMENTS

CN    101674834 A    3/2010
CN    103814016 A    5/2014
(Continued)

OTHER PUBLICATIONS

Burger's Medicinal Chemistry,edited by Manfred E. Wolff, 5th Ed. Part 1, pp. 975-977 (1995). (Year: 1995).*
(Continued)

*Primary Examiner* — Emily A Bernhardt
(74) *Attorney, Agent, or Firm* — Westman, Champlin & Koehler, P.A.; Z. Peter Sawicki; Amanda M. Prose

(57) ABSTRACT

Provided are a series of BTK inhibitors, and specifically disclosed are a compound, pharmaceutically acceptable salt thereof, tautomer thereof or prodrug thereof represented by formula (I), (II), (III) or (IV).

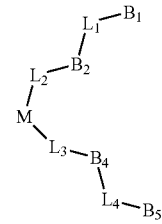

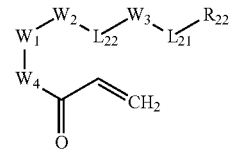

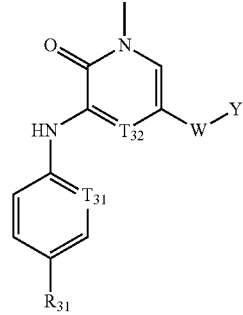

(Continued)

-continued

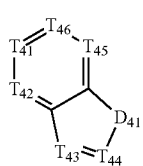
(IV)

8 Claims, No Drawings

(51) Int. Cl.
| | |
|---|---|
| C07D 401/14 | (2006.01) |
| C07D 471/04 | (2006.01) |
| A61K 31/505 | (2006.01) |
| C07D 401/04 | (2006.01) |
| A61K 31/506 | (2006.01) |
| C07D 239/48 | (2006.01) |
| C07D 239/04 | (2006.01) |
| C07D 213/74 | (2006.01) |
| C07D 213/73 | (2006.01) |
| C07D 401/12 | (2006.01) |
| C07D 235/04 | (2006.01) |
| A61K 31/5383 | (2006.01) |
| A61K 31/496 | (2006.01) |
| C07D 231/54 | (2006.01) |
| C07D 251/12 | (2006.01) |
| C07D 403/02 | (2006.01) |
| C07D 473/32 | (2006.01) |
| C07D 498/02 | (2006.01) |
| A61K 31/366 | (2006.01) |
| A61K 31/52 | (2006.01) |
| C07C 13/04 | (2006.01) |

(52) U.S. Cl.
CPC ........ *A61K 31/506* (2013.01); *A61K 31/5383* (2013.01); *C07D 213/73* (2013.01); *C07D 213/74* (2013.01); *C07D 231/54* (2013.01); *C07D 235/04* (2013.01); *C07D 239/04* (2013.01); *C07D 239/48* (2013.01); *C07D 251/12* (2013.01); *C07D 401/04* (2013.01); *C07D 401/12* (2013.01); *C07D 471/04* (2013.01); *A61K 31/366* (2013.01); *A61K 31/52* (2013.01); *C07C 13/04* (2013.01)

(56) References Cited

FOREIGN PATENT DOCUMENTS

| CN | 104024255 A | 9/2014 |
| CN | 104177338 A | 12/2014 |
| WO | 2008121742 A2 | 10/2008 |
| WO | 2012170976 A2 | 12/2012 |
| WO | 2014187262 A1 | 11/2014 |

OTHER PUBLICATIONS

Banker et al. "Modern Pharmaceutics", 3rd Ed. p. 596 (1996). (Year: 1996).*
Testa et al. Pure Appl. Chem. vol. 76, pp. 907-914 (2004). (Year: 2004).*
DeLucca et al. J.Med. Chem. 2016, 59, 7915-7935. (Year: 2016).*
Office action from EPO for EP application 15877553, dated Jun. 13, 2018.
International Search Report issued for PCT/CN2015/081686, dated Oct. 13, 2015.
Written Opinion of the International Searching Authority issued for PCT/CN2015/081686, dated Oct. 13, 2015.

* cited by examiner

BTK INHIBITOR

CROSS-REFERENCE TO RELATED APPLICATIONS

The application is a continuation application of PCT Application No. PCT/CN2015/081686 filed on Jun. 17, 2015, which claims a priority to and benefits of Chinese Patent Application No. 201510018849.6, filed with the State Intellectual Property Office of P. R. China on Jan. 14, 2015, the entire contents of which are incorporated herein by reference.

FIELD

The present disclosure relates to a series of BTK inhibitors, in particular to compounds of formulas (I), (II), (III) or (IV), or a pharmaceutically acceptable salt, a tautomer, a stereoisomer, an N-oxide, a hydrate, a solvate, a metabolite or a prodrug thereof.

BACKGROUND

Bruton's Tyrosine Kinase (BTK), a member of the non-receptor tyrosine kinase Tec family, is a key signaling enzyme expressed in all types of hematopoietic cells other than T lymphocytes and natural killer cell, and plays a crucial role in the B cell signaling pathway that binds a B-cell receptor (BCR) on surface of cells to stimulate the cellular response downstream.

BTK is a key regulator for B cell development, activation, signaling and survival (Kurosaki, *Curr Op Imm*, 2000, 276-281; Schaeffer and Schwartzberg, *Curr Op Imm* 2000, 282-288). In addition, BTK plays a role among many signaling pathways of hematopoietic cells in addition to the B cell signaling pathway, such as Toll-like receptor (TLR) and cytokine receptor-mediated TNF-α production in macrophages, immunoglobulin E receptor (FcεRI) signaling in mast cells, inhibition of Fas/APO-1 cell apoptosis in B-lineage lymphoid cells and collagen-stimulated platelet aggregation.

SUMMARY

Provided herein is a compound of formula (I), or a pharmaceutically acceptable salt, a tautomer, a stereoisomer, an N-oxide, a hydrate, a solvate, a metabolite, or a prodrug thereof;

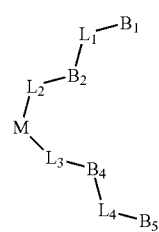

(I)

in which, M is selected from the following structural units:

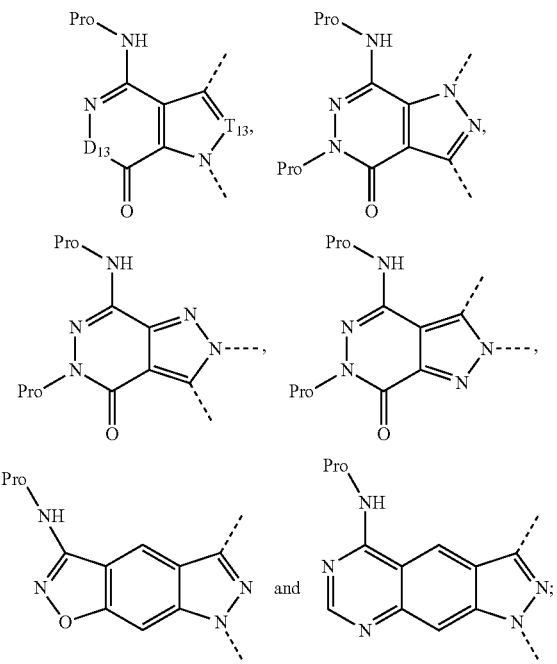

that is the compound of formula (I) is selected from:

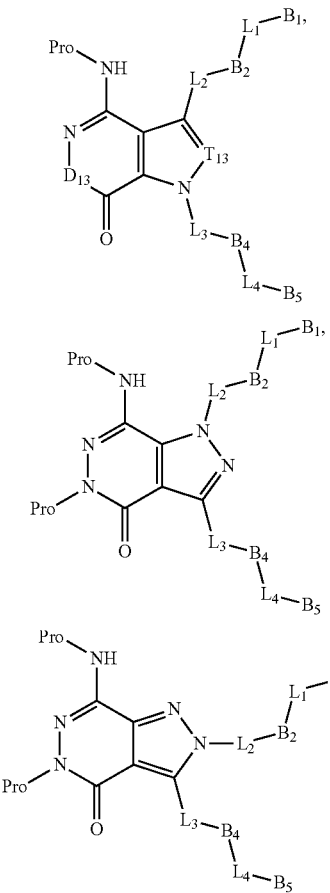

-continued

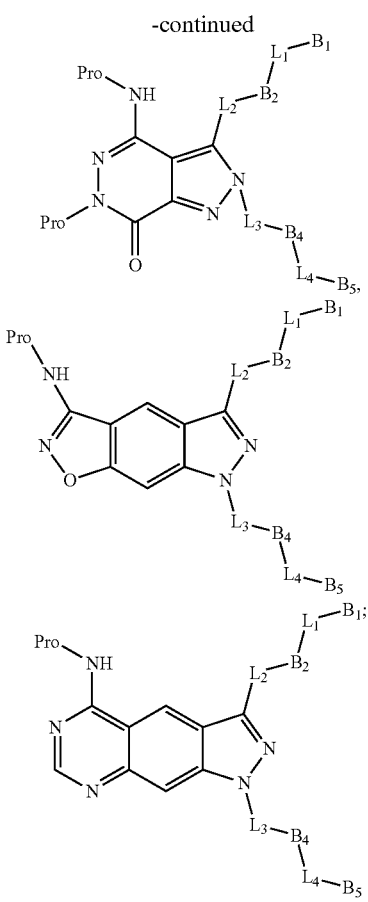

B₁ is selected from optionally substituted cycloalkyl, heterocycloalkyl, aryl, heteroaryl, aralkyl or heteroaralkyl;

each of L₁, L₂, L₃ and L₄ is independently selected from O, S, —[C(R₁)(R₁)]₀₋₃—, —[C(R₁)(R₁)]₀₋₃C(═O)[C(R₁)(R₁)]₀₋₃—, —[C(R₁)(R₁)]₀₋₃N(R₁)[C(R₁)(R₁)]₀₋₃—, —[C(R₁)(R₁)]₀₋₃N(R₁)C(═O)[C(R₁)(R₁)]₀₋₃—, —[C(R₁)(R₁)]₀₋₃N(R₁)S(═O)₂[C(R₁)(R₁)]₀₋₃—, —[C(R₁)(R₁)]₀₋₃S(═O)₂[C(R₁)(R₁)]₀₋₃—, —[C(R₁)(R₁)]₀₋₃S(═O)[C(R₁)(R₁)]₀₋₃—;

B₂ is selected from optionally substituted aryl or heteroaryl;

D₁₃ is selected from C(R₁)(R₁), N(R₁), N(Pro), O, S;

each Pro is independently selected from H, —C(═O)—O—CH₂—O—P(═O)(ONa)₂;

T₁₃ is selected from C(R₁), N;

each R₁ is independently selected from H, F, Cl, Br, I, OH, NH₂, CN, or optionally substituted $C_{1-12}$ alkyl or $C_{1-12}$ heteroalkyl;

B₄ is selected from optionally substituted $C_{1-12}$ alkyl, $C_{1-12}$ heteroalkyl, 5- to 12-membered aryl or 5- to 12-membered heteroaryl;

B₅ is selected from

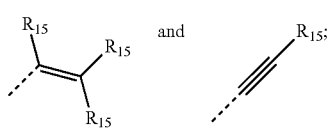

R₁₅ is selected from H, F, Cl, Br, I, OH, NH₂, CN, or optionally substituted $C_{1-12}$ alkyl or $C_{1-12}$ heteroalkyl;

each of heterocycloalkyl, heteroaryl, heteroaralkyl and heteroalkyl independently comprises 1, 2 or 3 of O, S, N, C(═O), S(═O) or S(═O)₂.

In some embodiments of the present disclosure, the substituents in B₁, B₂, B₄, R₁ and R₁₅ are each selected from F, Cl, Br, I, OH, NH₂, CN, or optionally substituted $C_{1-6}$ alkyl or $C_{1-6}$ heteroalkyl, the number of substituents for one same group is independently 0, 1, 2 or 3.

In some embodiments of the present disclosure, said $C_{1-6}$ alkyl or $C_{1-6}$ heteroalkyl is selected from

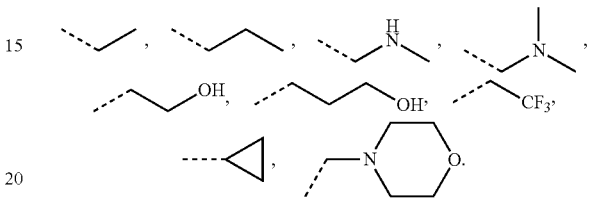

In some embodiments of the present disclosure, B₁ is selected from optionally substituted 3- to 12-membered cycloalkyl, 3- to 12-membered heterocycloalkyl, 5- to 12-membered aryl, 5- to 12-membered heteroaryl, 5- to 12-membered arylalkyl or 5- to 12-membered heteroarylalkyl.

In some embodiments of the present disclosure, B₁ is selected from the following optionally substituted

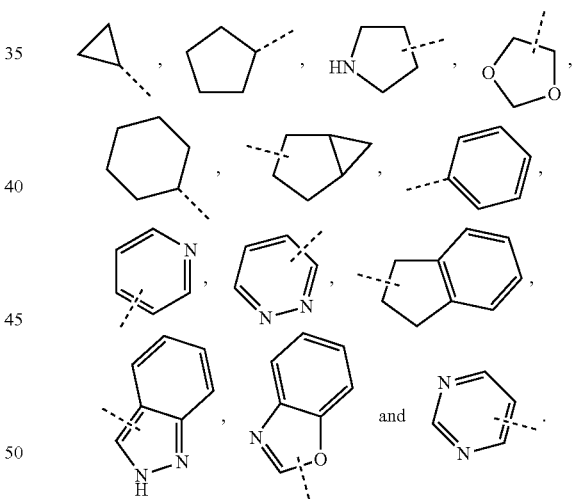

In some embodiments of the present disclosure, B₁ is selected from optionally substituted

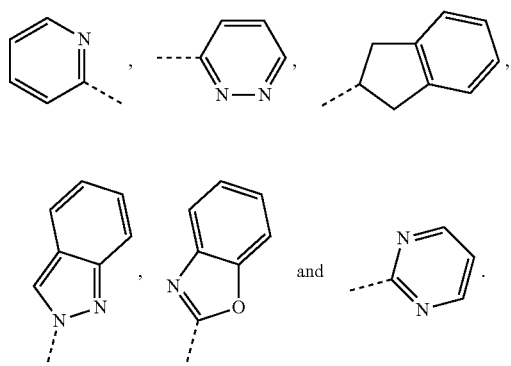

In some embodiments of the present disclosure, B₁ is selected from:

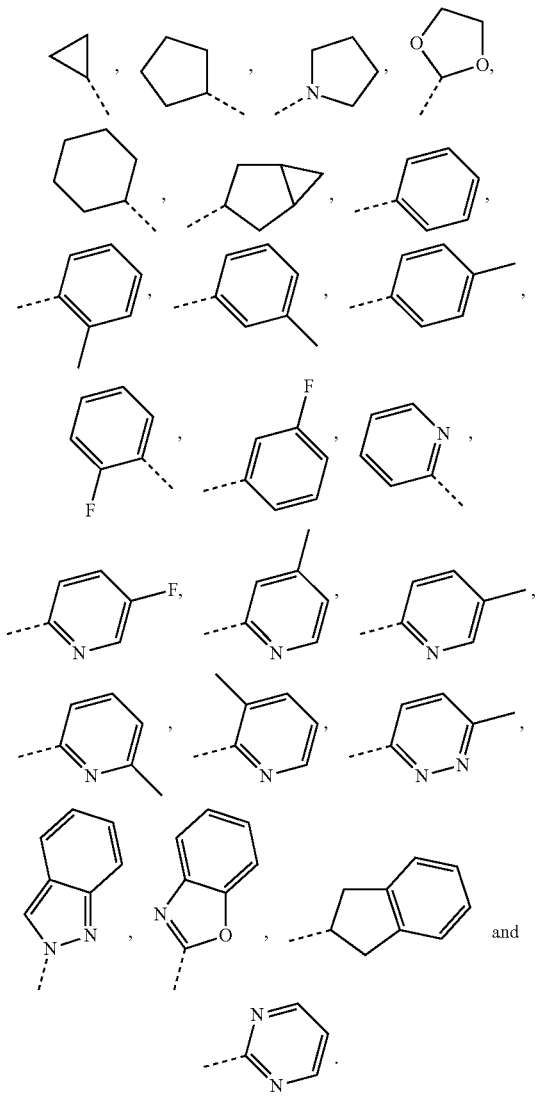

In some embodiments of the present disclosure, each of L₁, L₂, L₃ and L₄ is independently selected from a single bond, O, CH₂, NH,

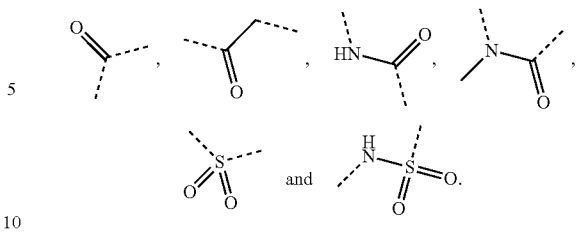

In some embodiments of the present disclosure, B₂ is selected from optionally substituted phenyl, pyridyl, pyrazolyl, indazolyl, thienyl, furyl or pyrrolyl.

In some embodiments of the present disclosure, B₂ is selected from

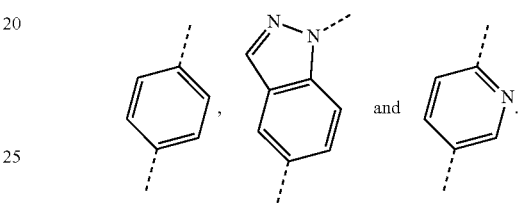

In some embodiments of the present disclosure, R₁ is selected from H, methyl, trifluoromethyl, hydroxymethyl, ethyl, hydroxyethyl, trifluoroethyl and cyclopropyl.

In some embodiments of the present disclosure, the structural unit

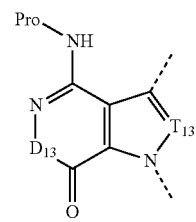

is selected from:

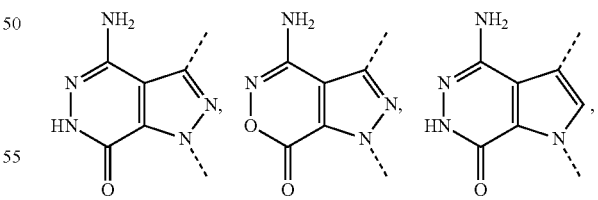

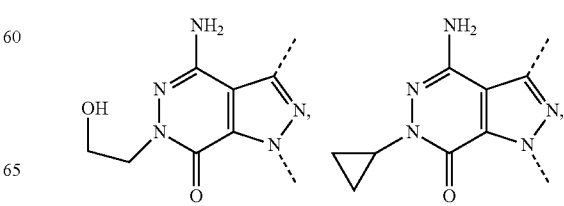

-continued
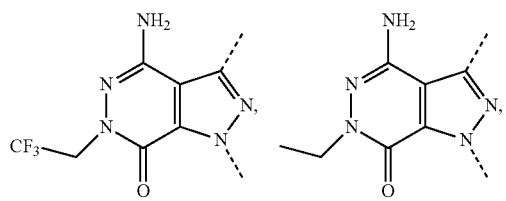
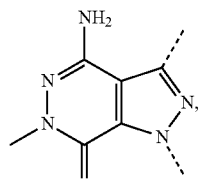
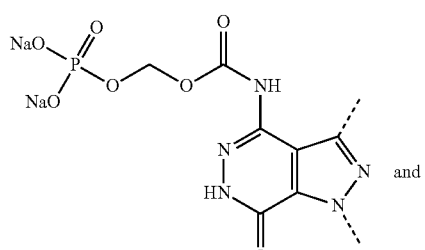
and
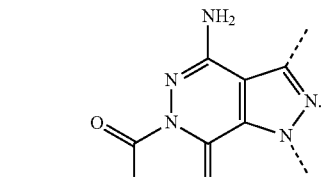
In some embodiments of the present disclosure, the structural unit
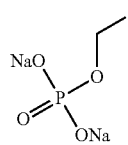
is selected from
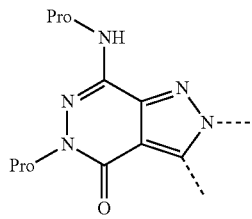
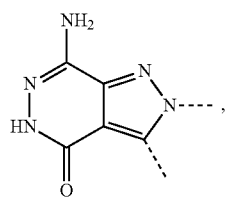
-continued
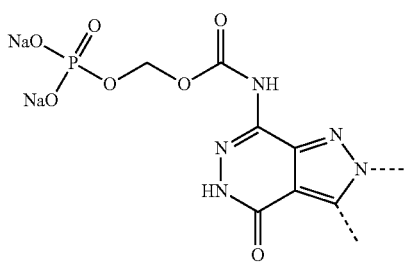
or
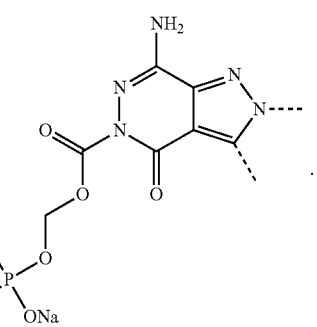
In some embodiments of the present disclosure, the structural unit
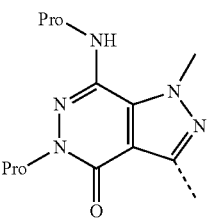
is selected from
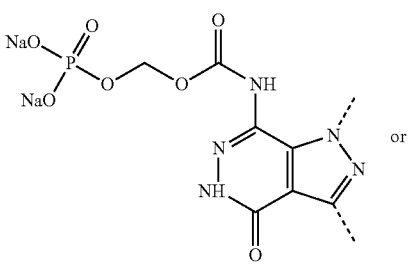
or

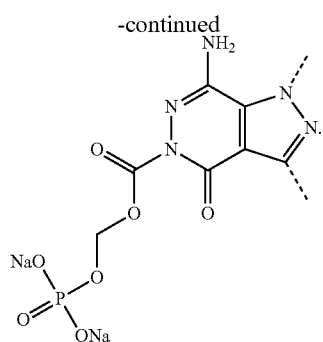

In some embodiments of the present disclosure, the structural unit

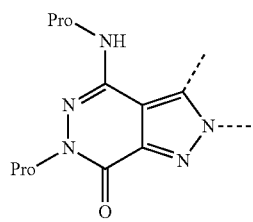

is selected from

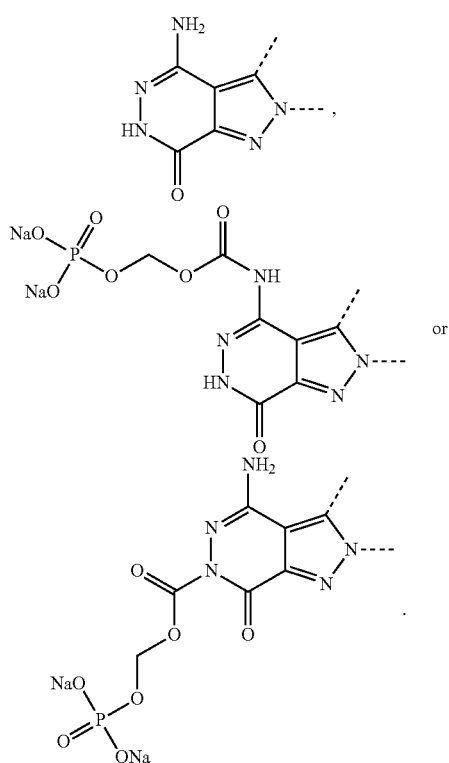

In some embodiments of the present disclosure, B₄ is selected from optionally substituted $C_{1-3}$ alkyl, $C_{1-3}$ heteroalkyl, 3- to 7-membered cycloalkyl, 3- to 7-membered heterocycloalkyl, phenyl, pyridyl, pyrazolyl, thienyl, furyl or pyrrolyl.

In some embodiments of the present disclosure, B₄ is selected from optionally substituted

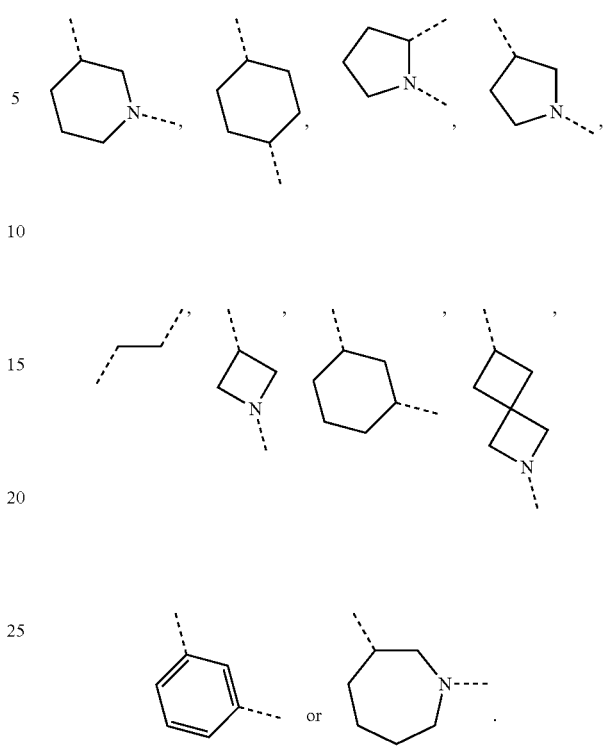

In some embodiments of the present disclosure, $R_{15}$ is selected from H, CN, or optionally substituted $C_{1-6}$ alkyl, $C_{1-6}$ heteroalkyl, 3-6 membered cycloalkyl or 3-6 membered heterocycloalkyl.

In some embodiments of the present disclosure, $R_{15}$ is selected from H, CN, Me,

In some embodiments of the present disclosure, B₅ is selected from

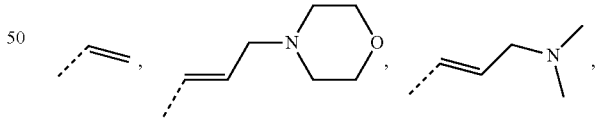

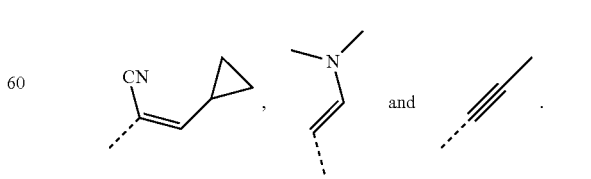

In some embodiments of the present disclosure, the compound is optionally selected from:

11 12

-continued
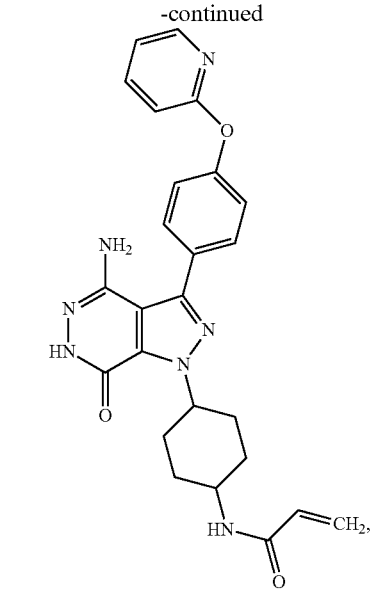
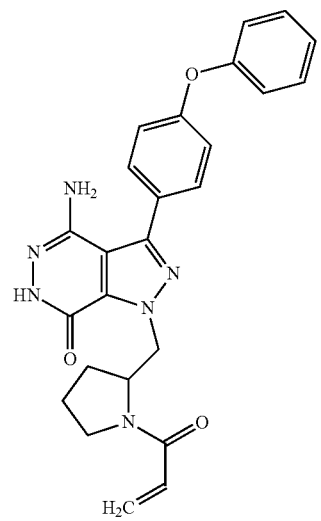
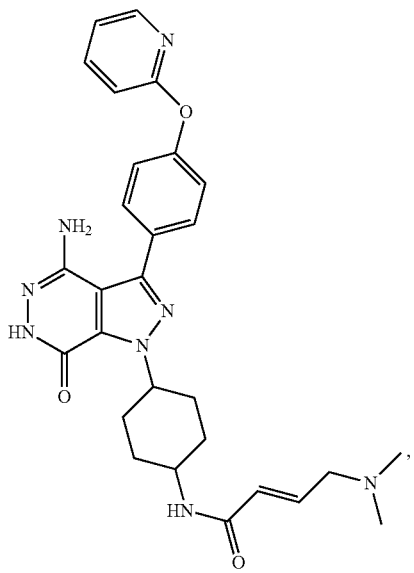
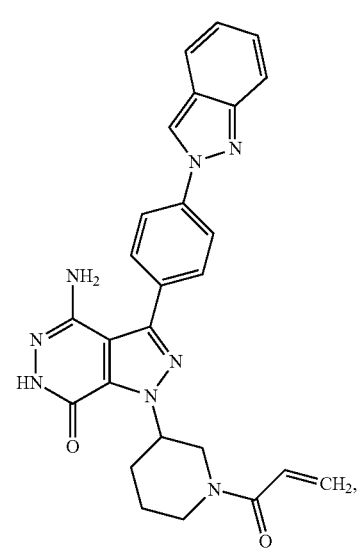
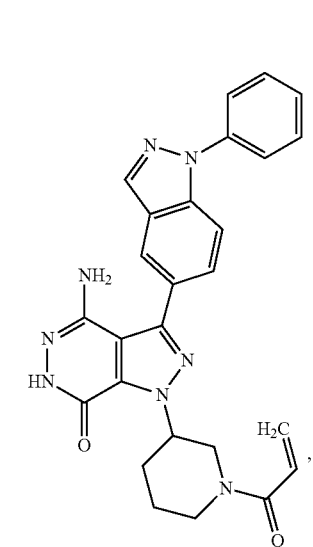

15
-continued
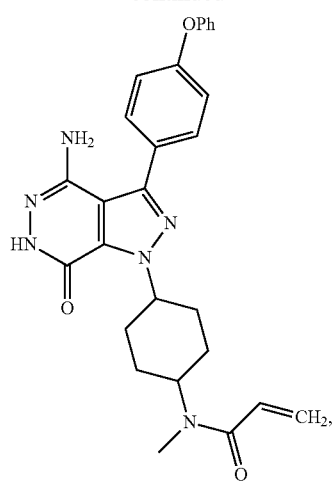
16
-continued
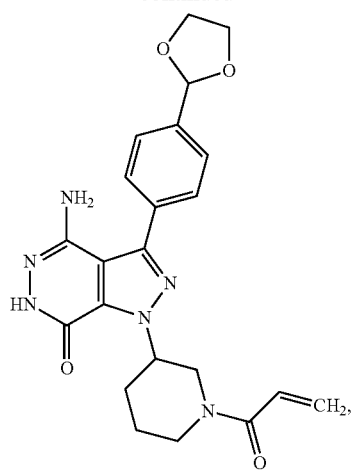
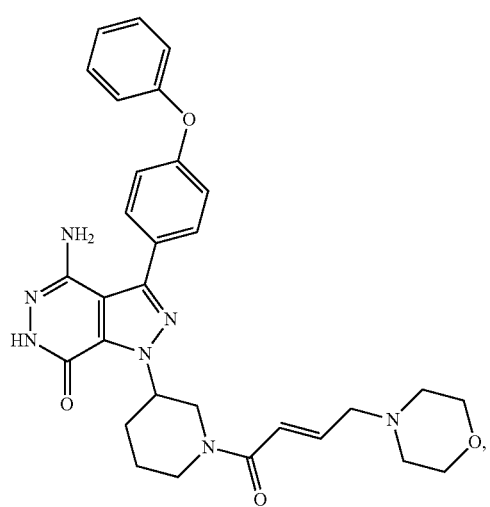
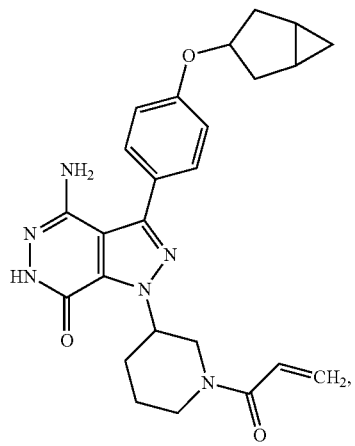
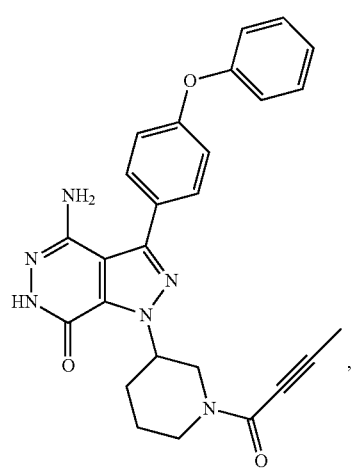
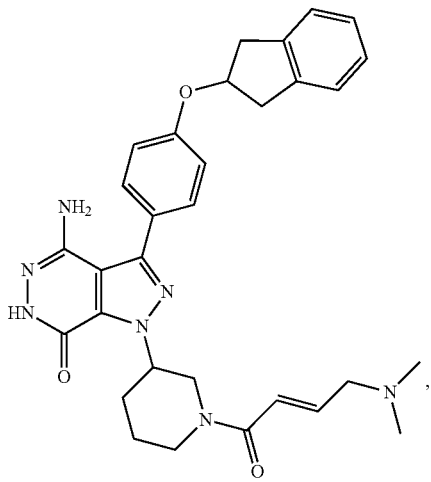

-continued
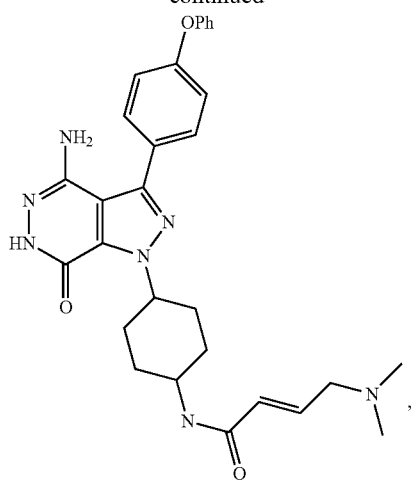
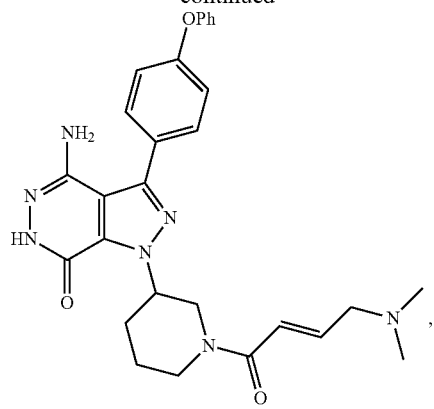
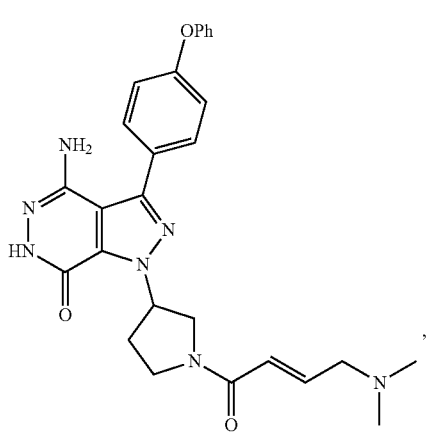
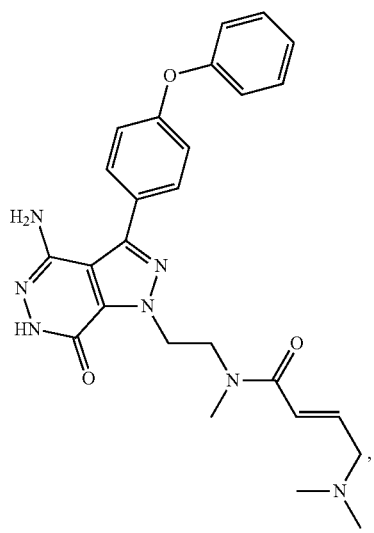
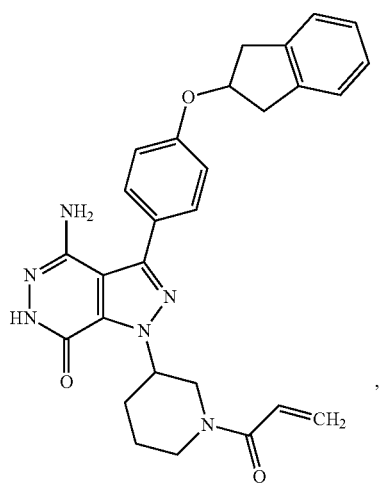
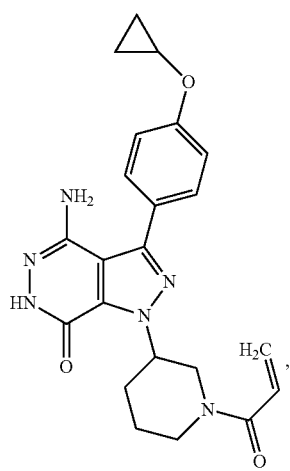

19
-continued
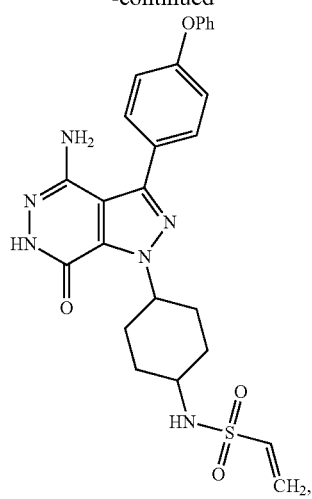
20
-continued
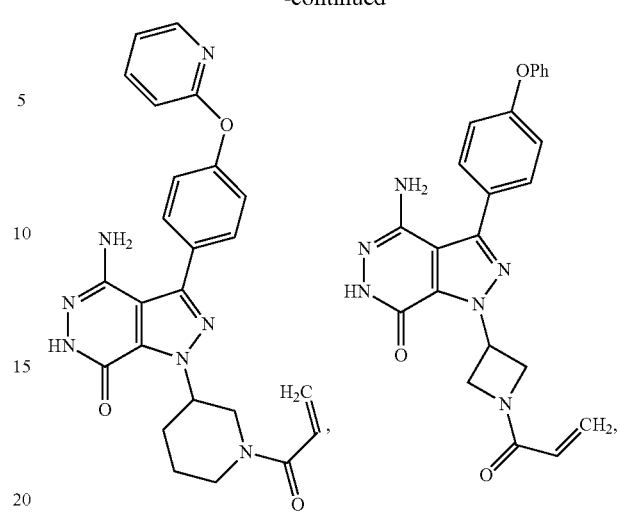
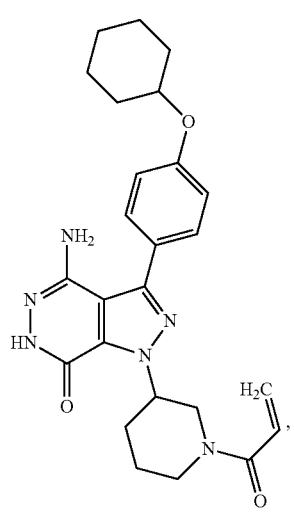
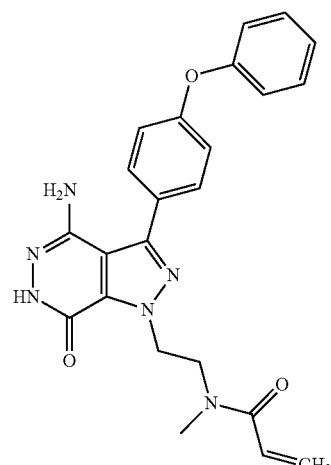
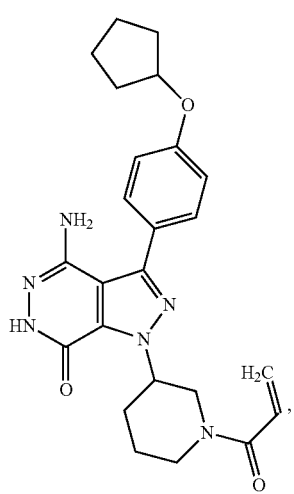
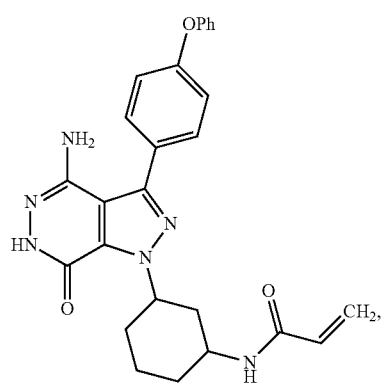

21
-continued
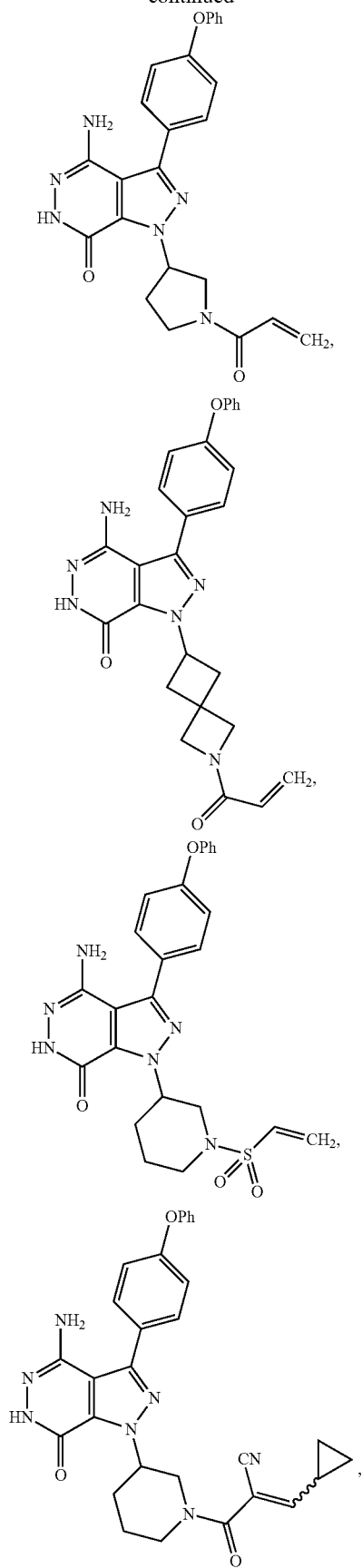
22
-continued
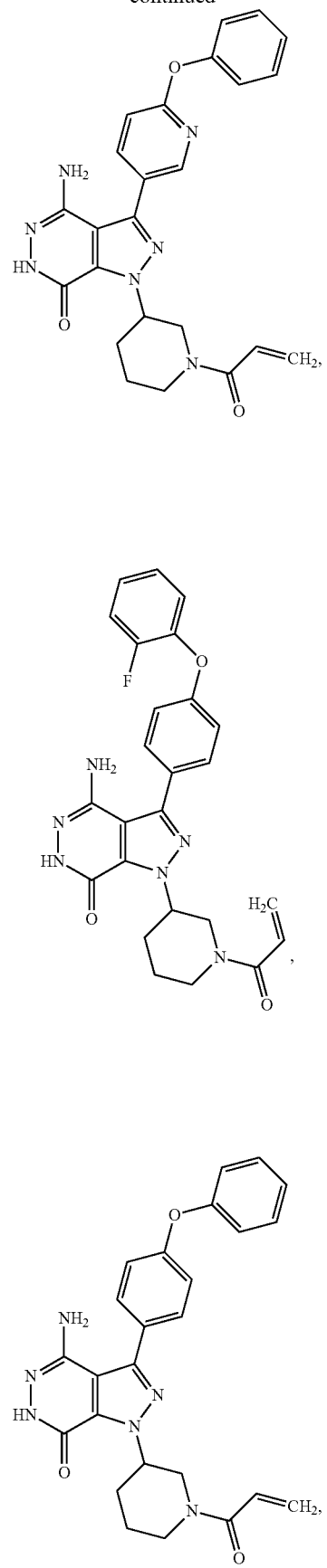

23
-continued
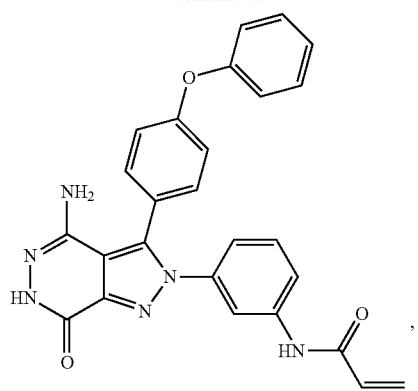
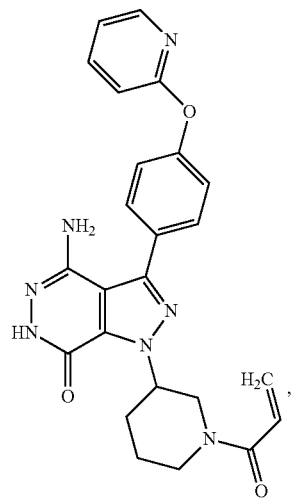
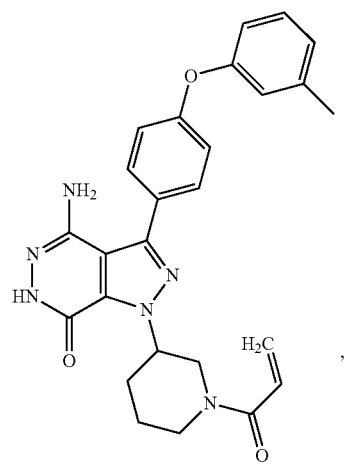
24
-continued
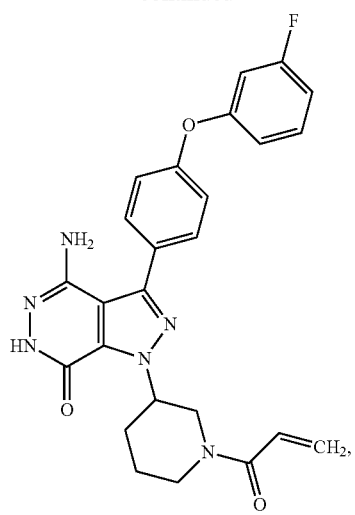
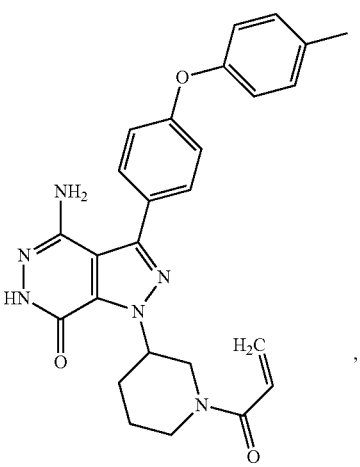
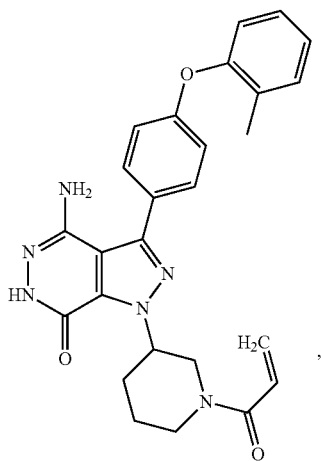

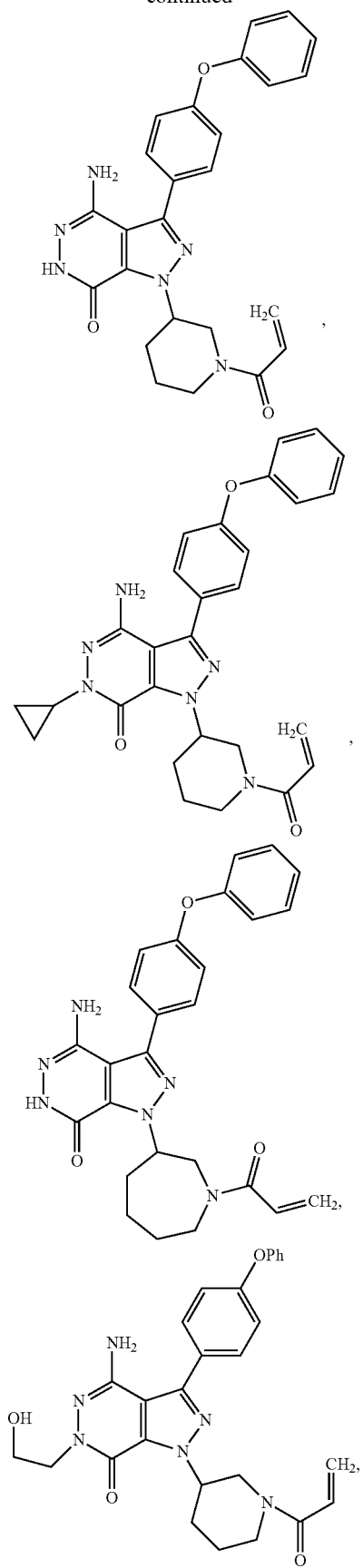
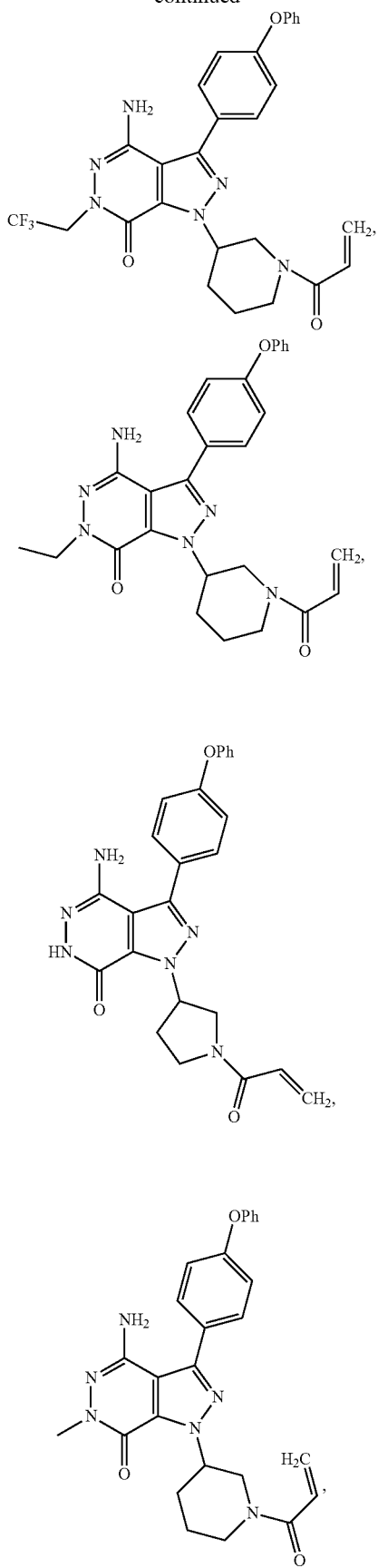

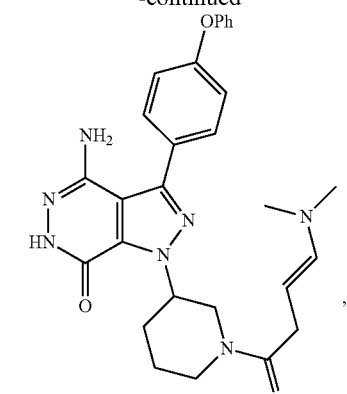
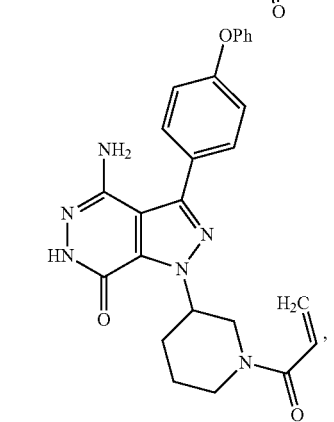
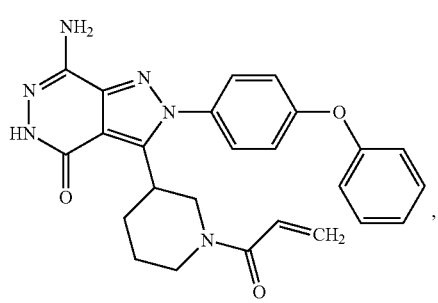
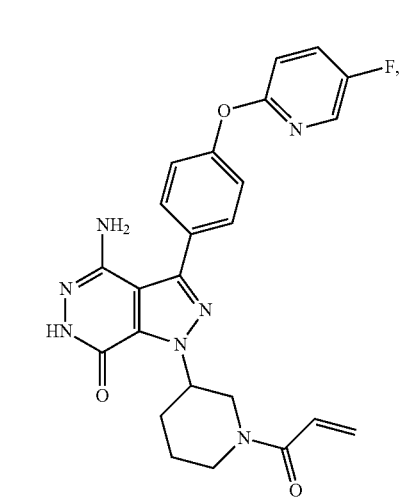
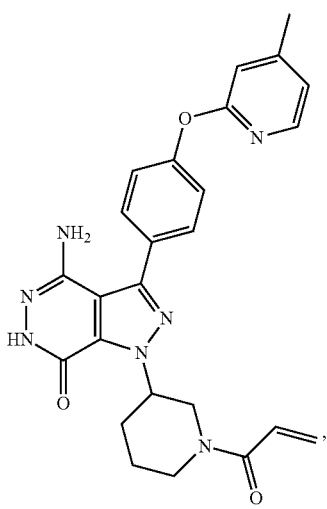
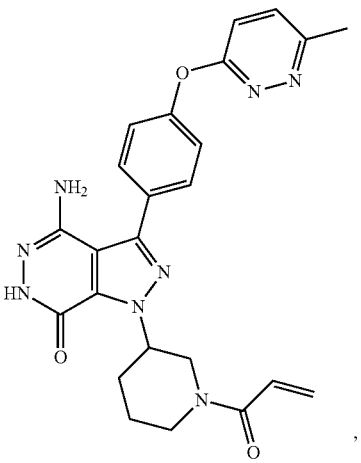
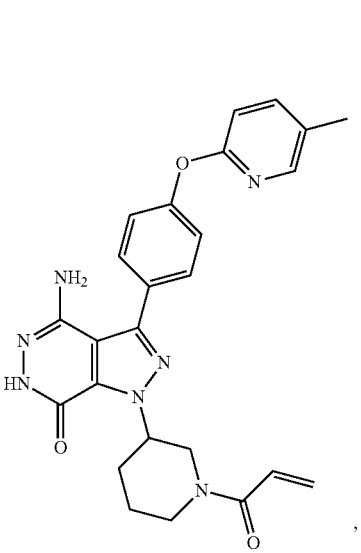

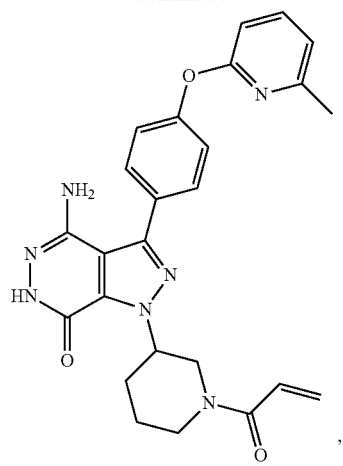
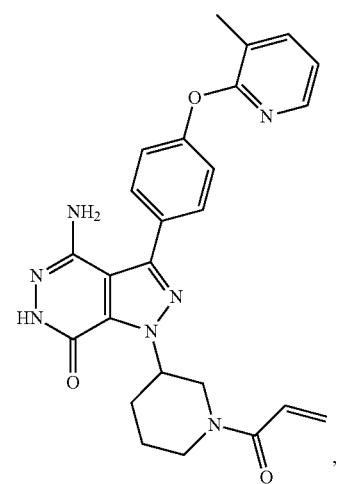
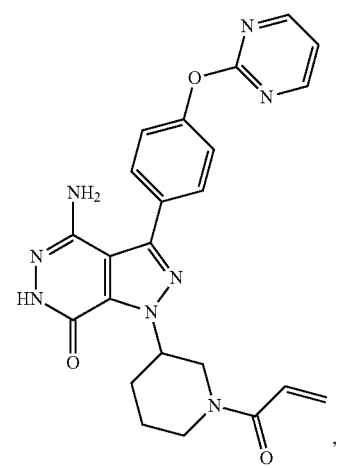
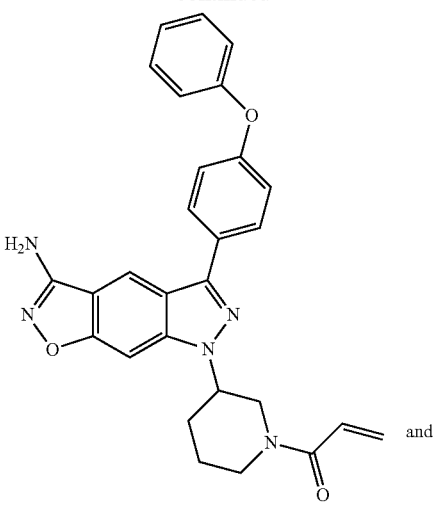
and
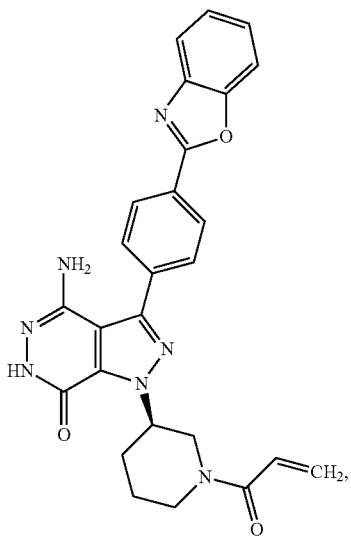
Optionally, the compound is selected from:

31
-continued
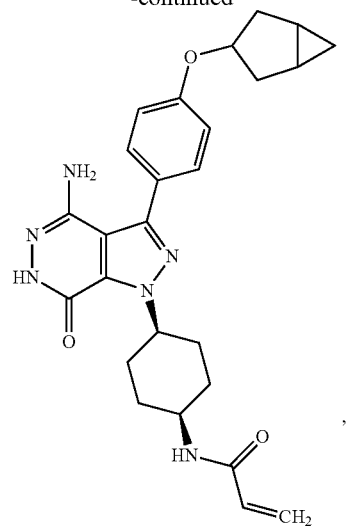
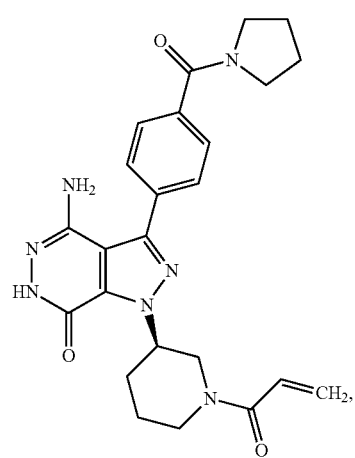
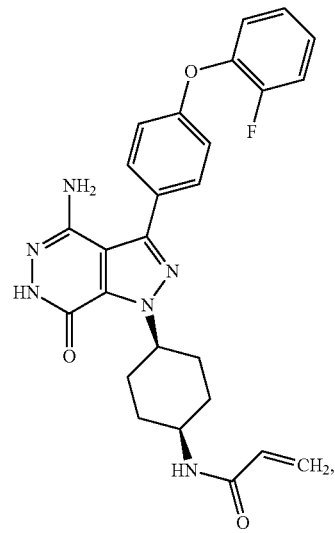
32
-continued
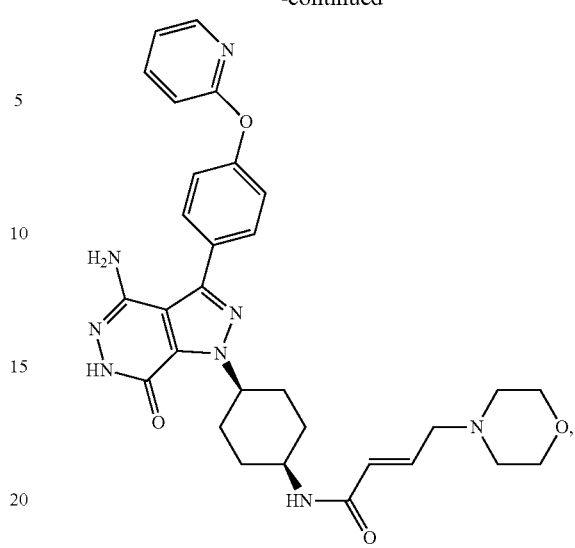
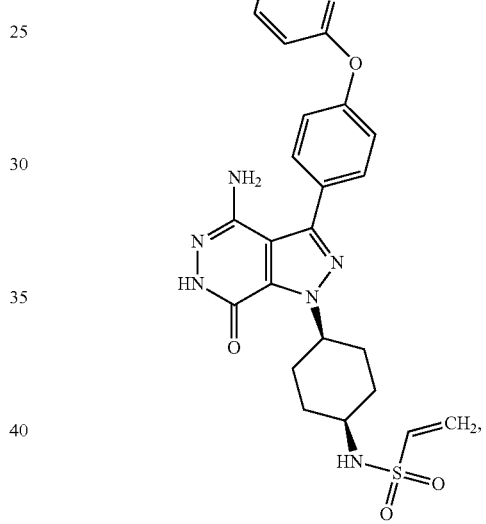
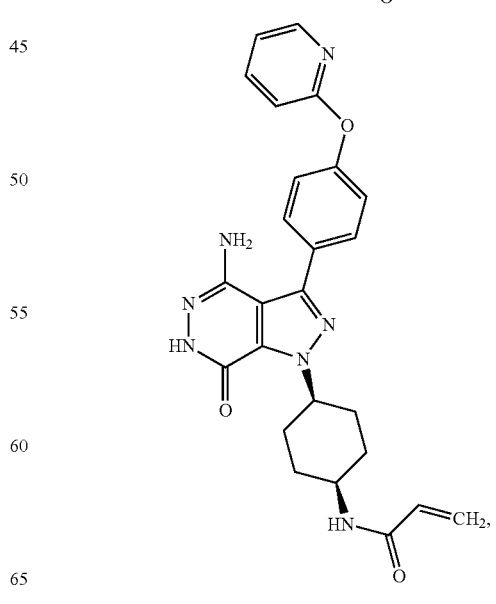

33
-continued
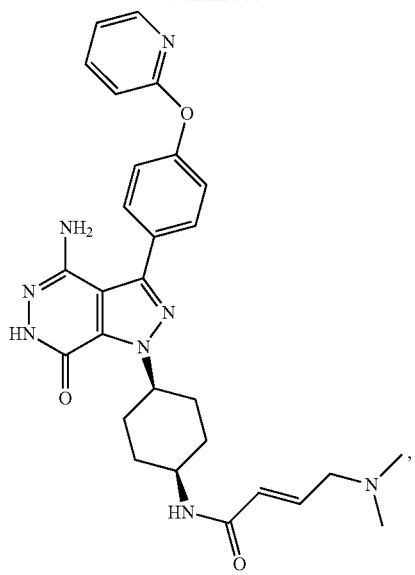
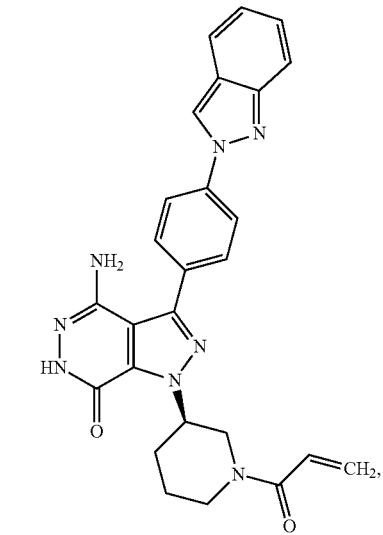
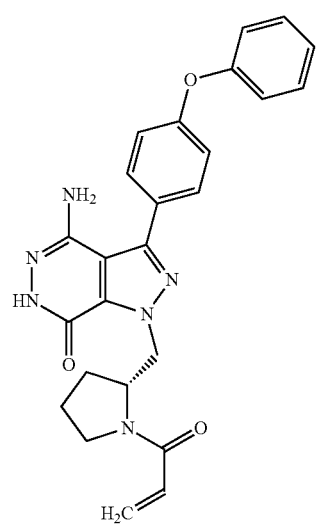
34
-continued
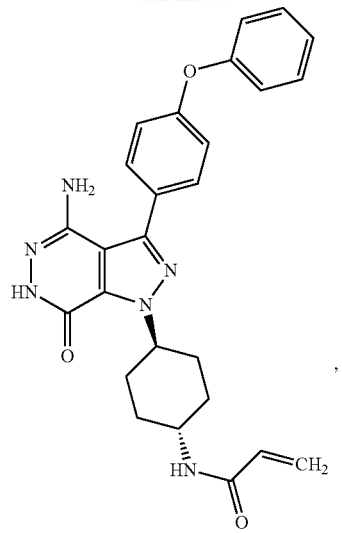
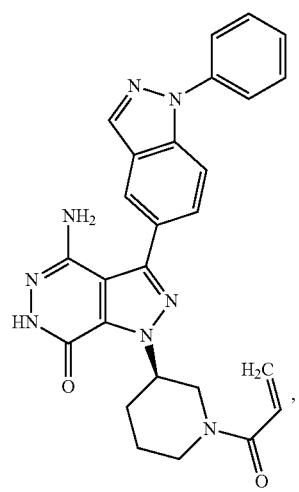
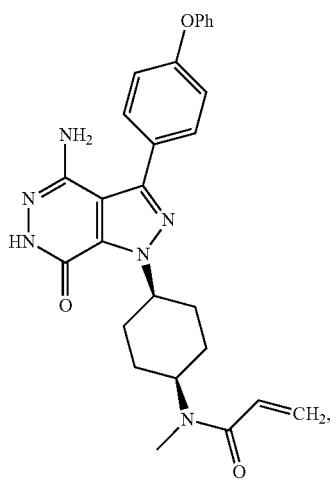

35
-continued
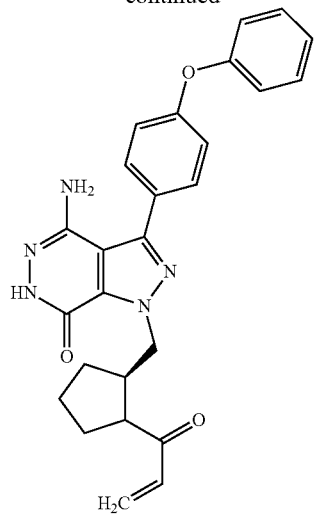
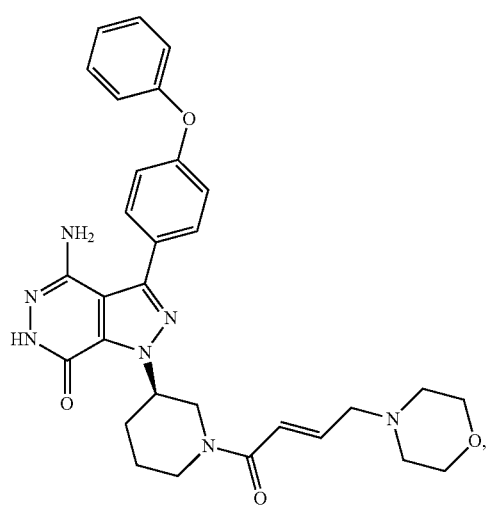
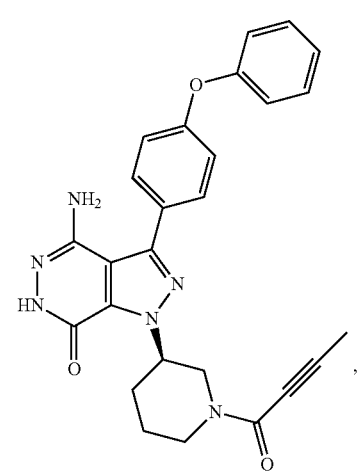
36
-continued
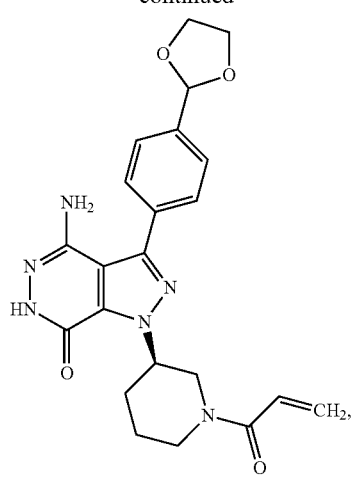
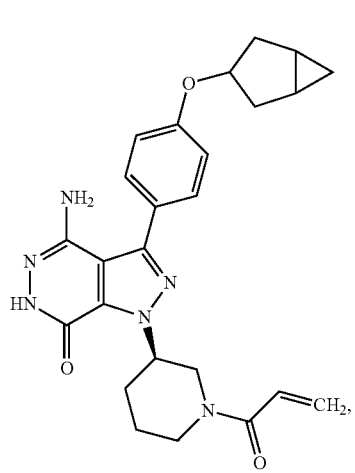
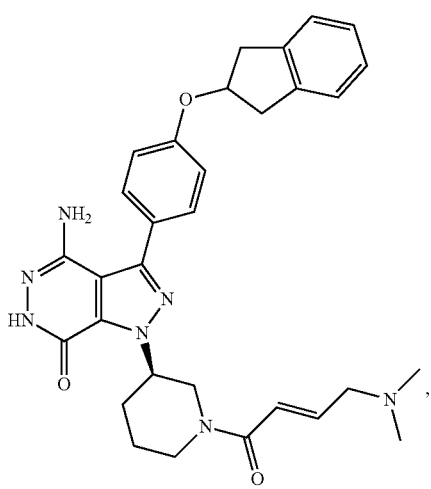

37
-continued
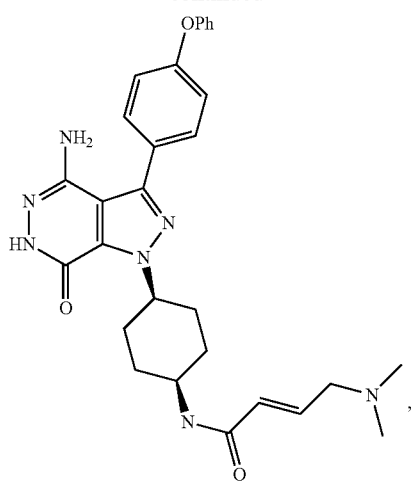
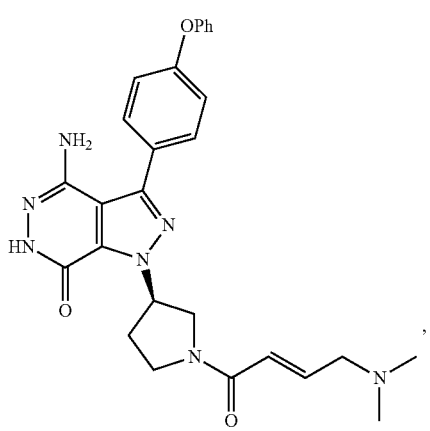
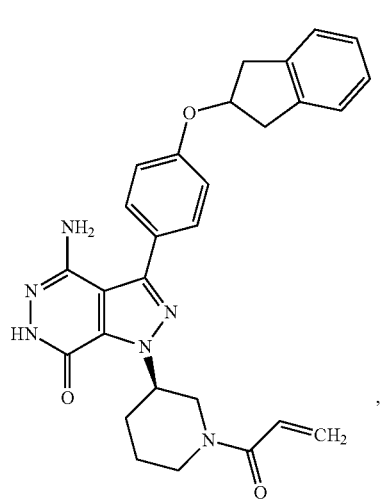
38
-continued
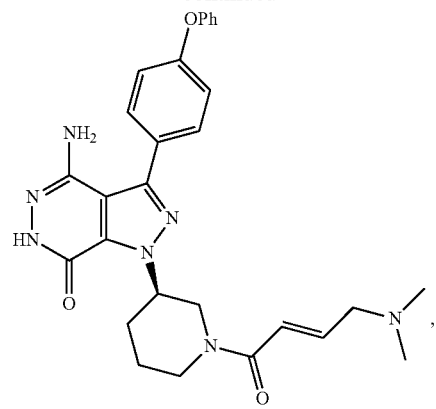
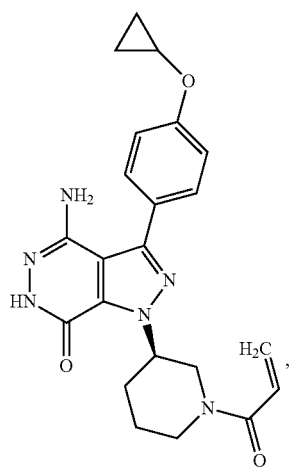
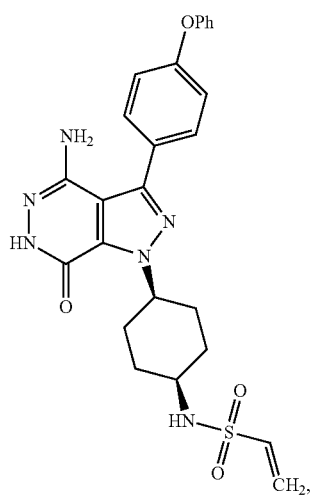

39
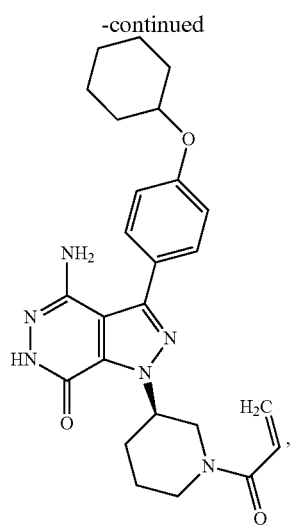
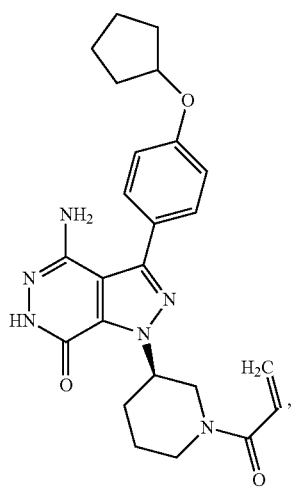
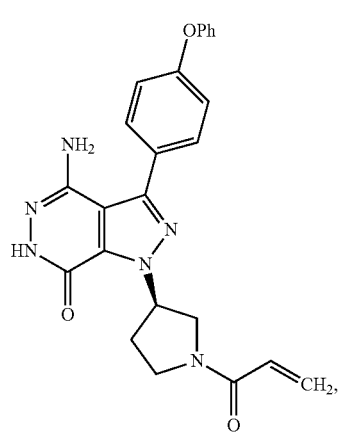
40
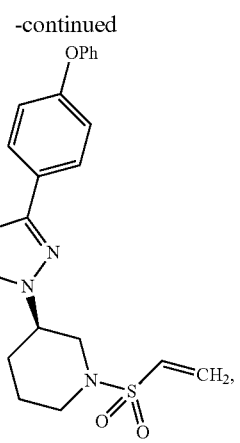
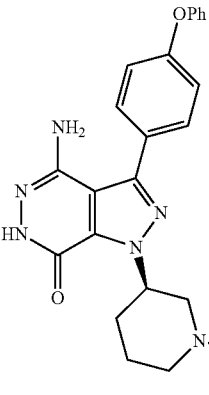
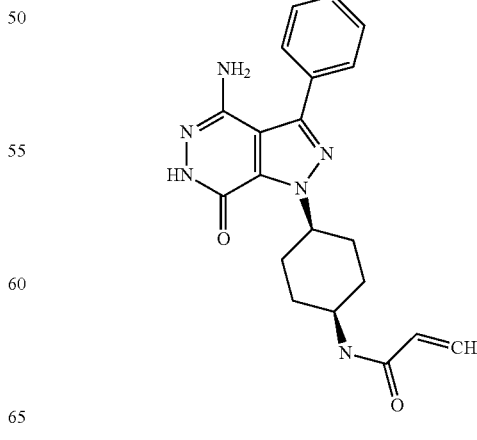

41
-continued
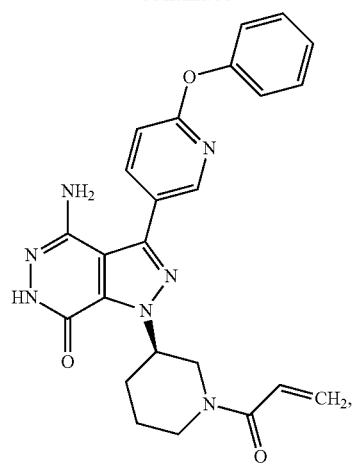
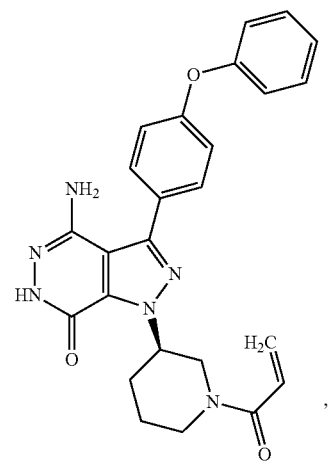
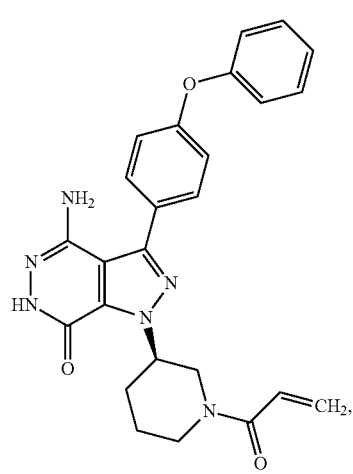
42
-continued
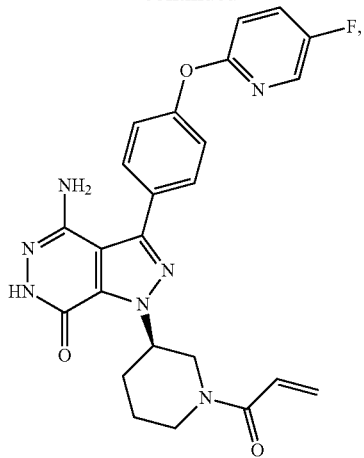
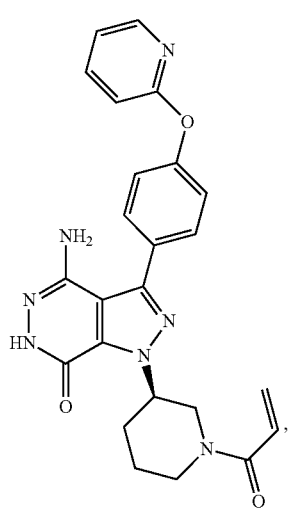
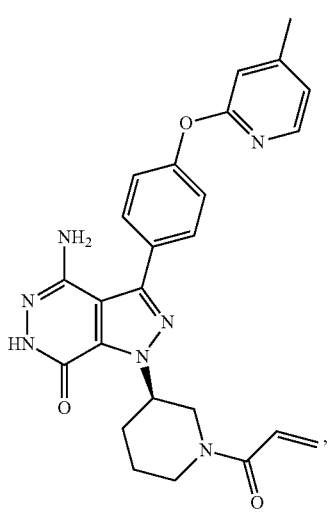

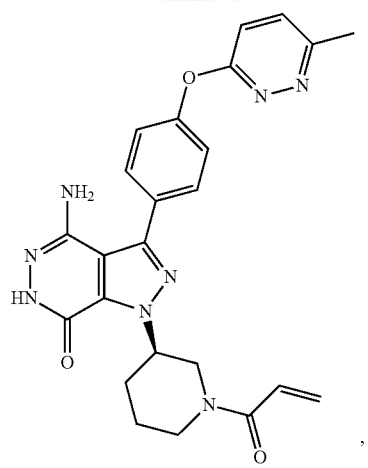
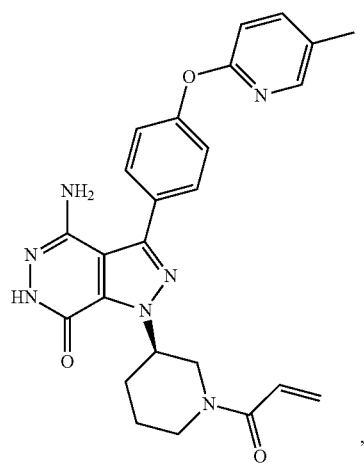
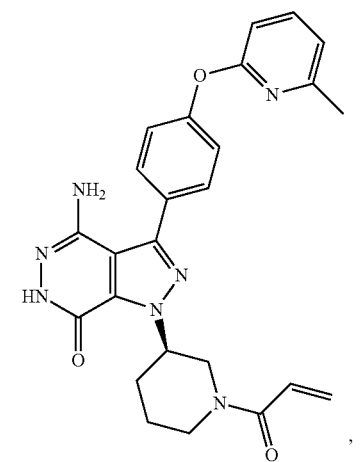
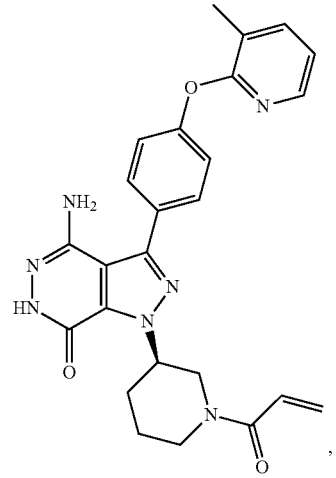
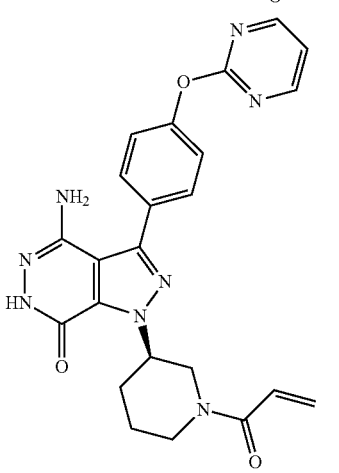
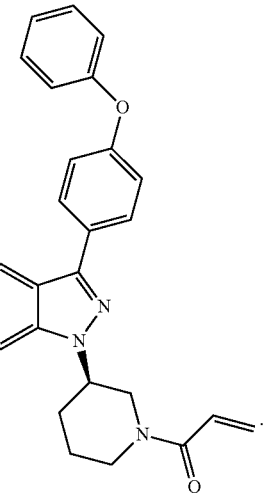
Also provided is a compound of formula (II), or a pharmaceutically acceptable salt, a tautomer, a stereoisomer, an N-oxide, a hydrate, a solvate, a metabolite, or a prodrug thereof;

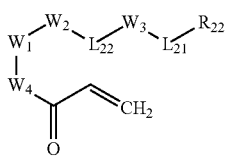
(II)

in which, $W_1$, $W_2$, $W_3$ and $W_4$ satisfy one of the following conditions:
$W_1$ is —NH—,
$W_2$ is selected from

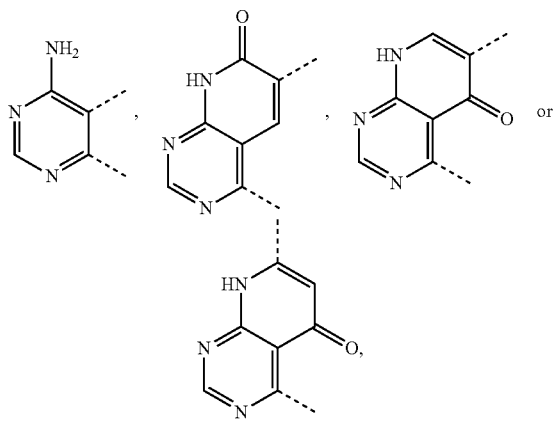

$W_3$ is

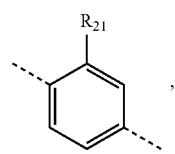

$W_4$ is

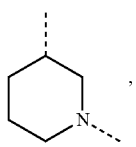

$W_2$ and $W_3$ together with $L_{21}$ and $L_{22}$ form

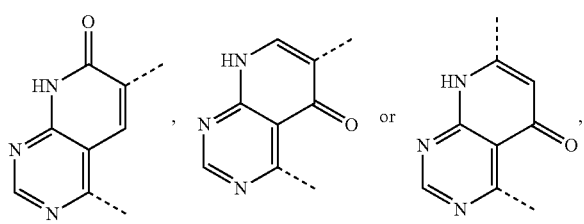

$W_2$ together with $L_{22}$ forms

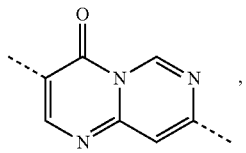

$W_1$ and $W_2$ together with $L_{22}$ form

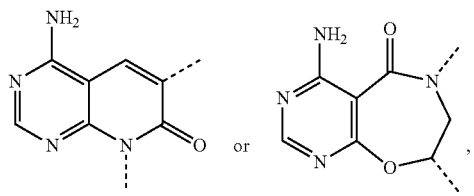

$W_2$ and $W_3$ together with $L_{22}$ form

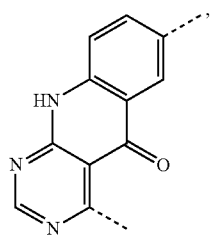

or
$W_2$ and $W_3$ together with $W_4$ form

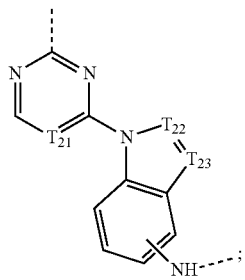

each of $R_{21}$ and $R_{22}$ is independently selected from H, halogen, or optionally substituted $C_{1-6}$ alkyl, $C_{1-6}$ heteroalkyl, aryl or heteroaryl,
each of $L_{21}$ and $L_{22}$ is independently selected from a single bond, O, S, N($R_2$), C($R_2$)($R_2$), $C_{1-3}$ oxoheteroalkyl, C(═O), S(═O) or S(═O)$_2$,
each of $T_{21}$, $T_{22}$ and $T_{23}$ is independently selected from N or C($R_2$),
$R_2$ is selected from H, halogen, OH, $NH_2$, CN, or optionally substituted $C_{1-6}$ alkyl or $C_{1-6}$ heteroalkyl,
each of heteroalkyl and heteroaryl independently comprises 1, 2 or 3 of O, S, N, C(═O), S(═O) or S(═O)$_2$.

In some embodiments of the present disclosure, the substituents in $R_{21}$ and $R_2$ are each selected from F, Cl, Br, I, OH, $NH_2$, CN, or optionally substituted $C_{1-6}$ alkyl or $C_{1-6}$ heteroalkyl, and the number of substituents for one same group is independently 0, 1, 2 or 3.

In some embodiments of the present disclosure, $C_{1-6}$ alkyl or $C_{1-6}$ heteroalkyl is selected from

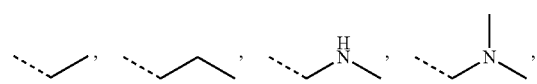

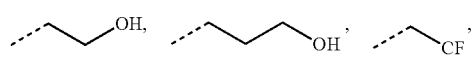

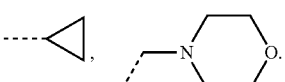

In some embodiments of the present disclosure, $R_{21}$ is selected from H, F, Cl, Br, I or methyl.

In some embodiments of the present disclosure, $R_{22}$ is selected from H, Me, phenyl.

In some embodiments of the present disclosure, each of $L_{21}$ and $L_{22}$ is independently selected from a single bond, O, NH, N(Me), —CH(OH)—, C(=O),

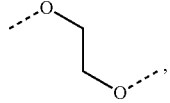

In some embodiments of the present disclosure, each of $T_{21}$, $T_{22}$ and $T_{23}$ is independently selected from N or C(F).

In some embodiments of the present disclosure, the compound is optionally selected from:

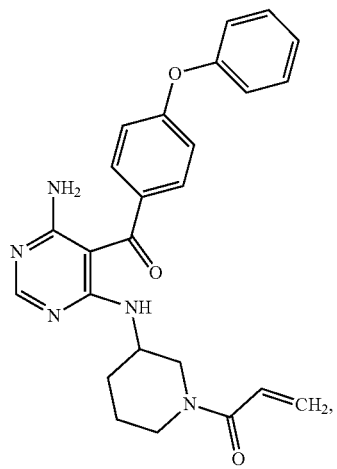

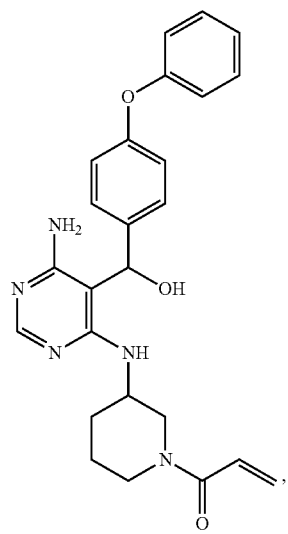

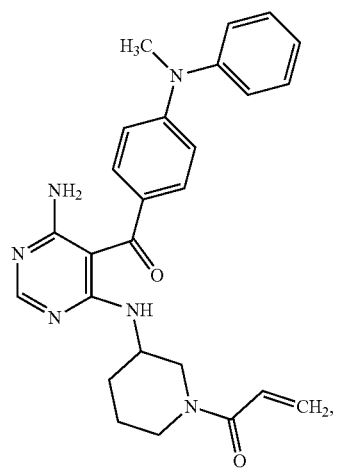

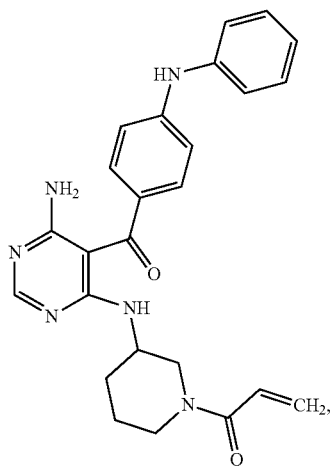

-continued
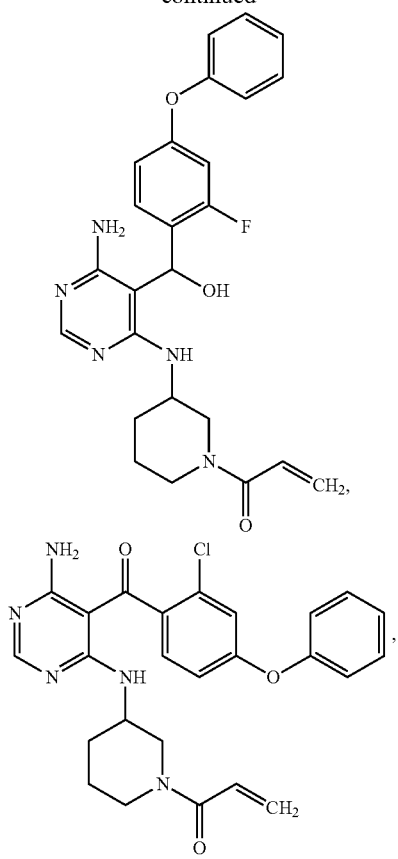
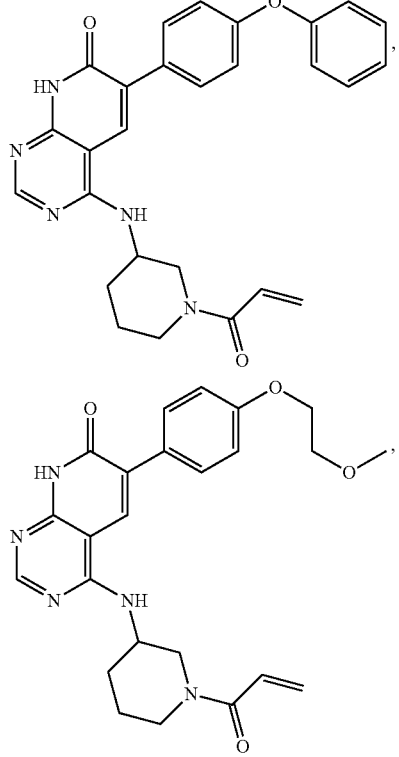
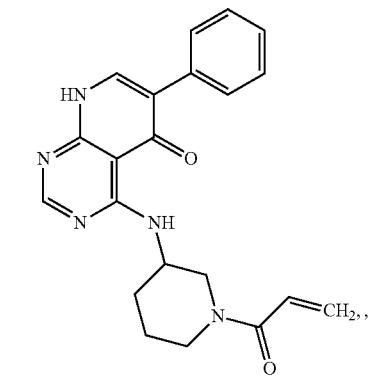
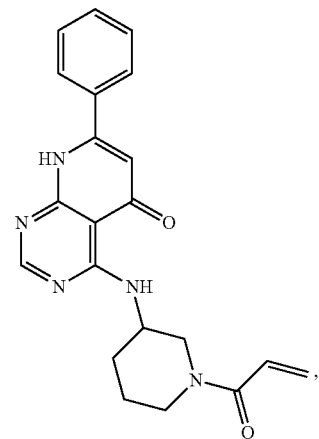

51
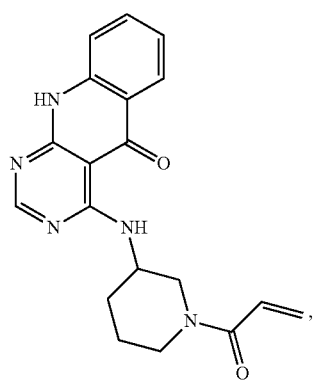
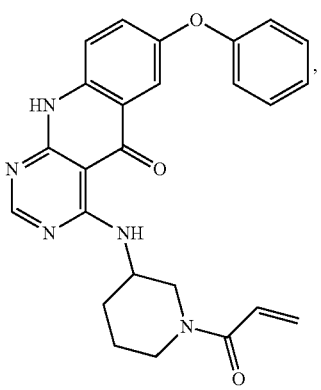
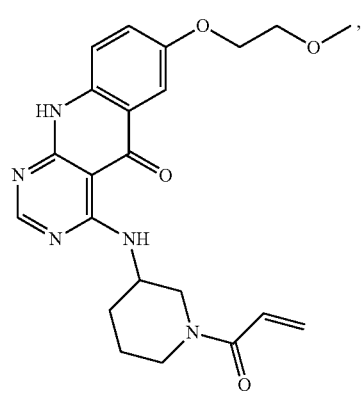
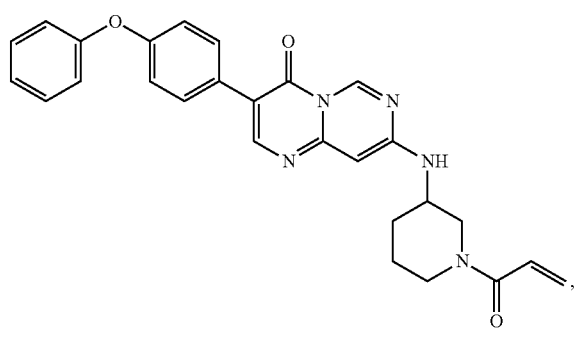
52
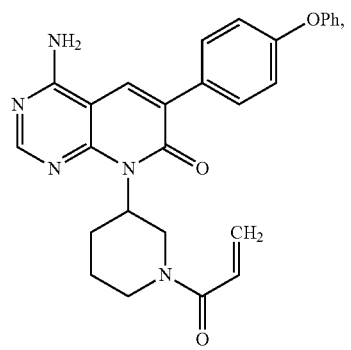
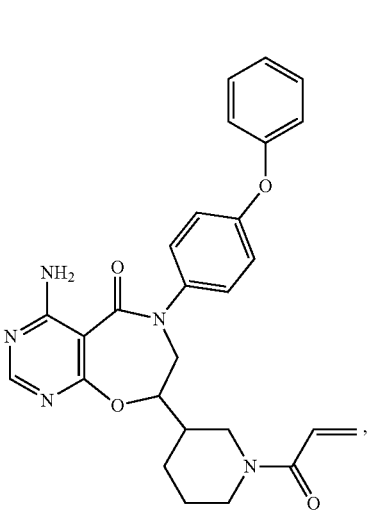
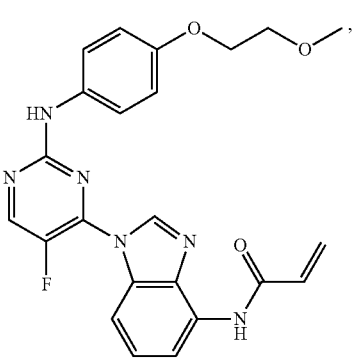
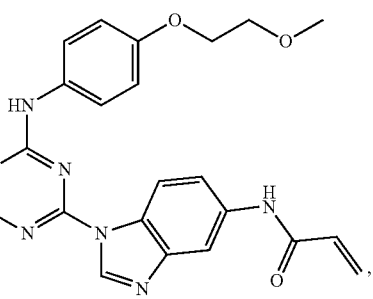

53
-continued
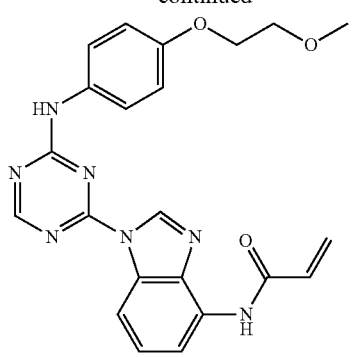
and
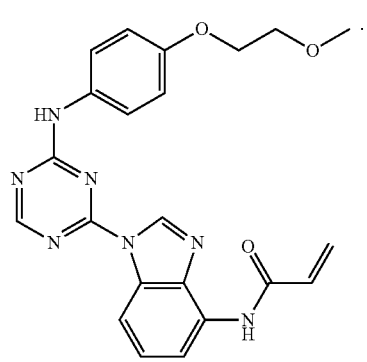
In some embodiments of the present disclosure, the compound is optionally selected from:
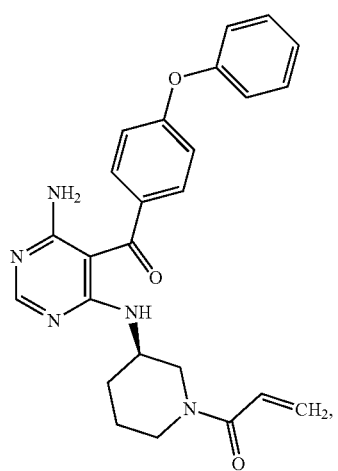
54
-continued
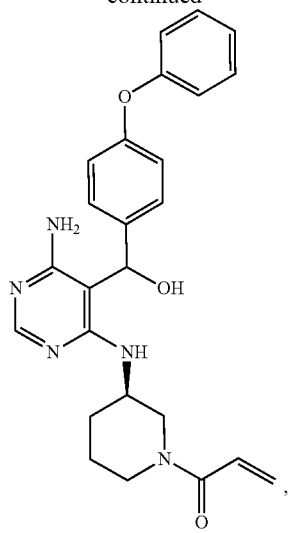
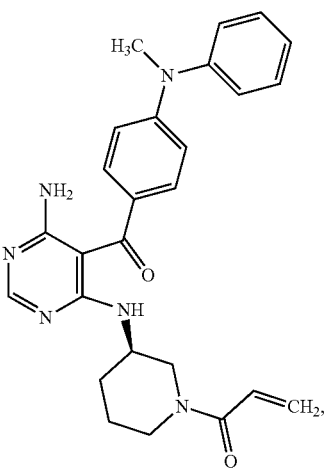
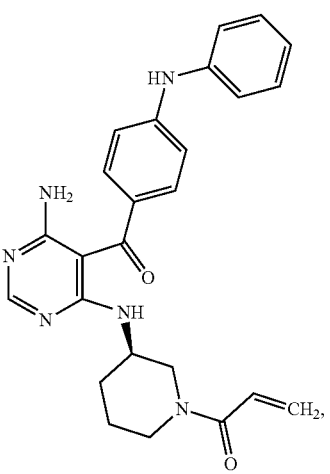

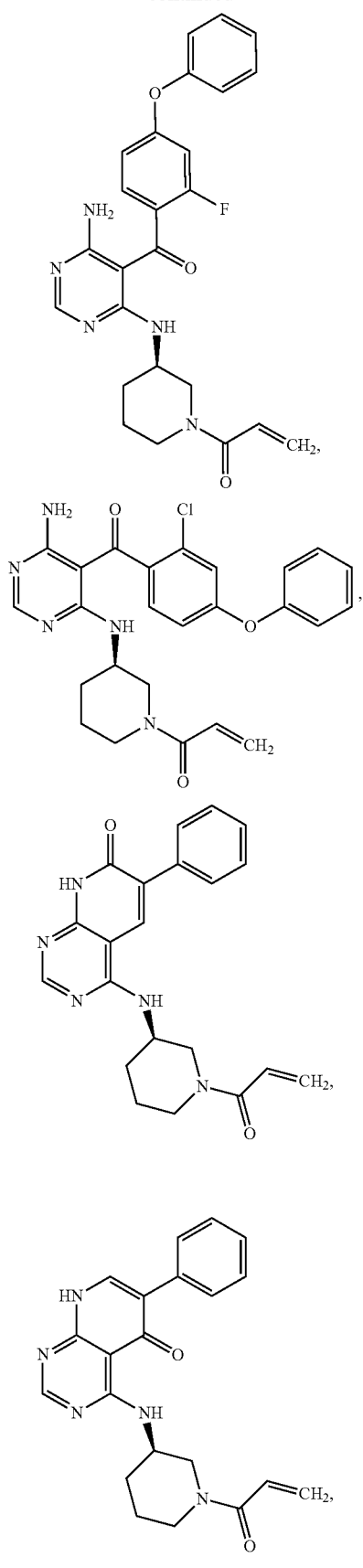
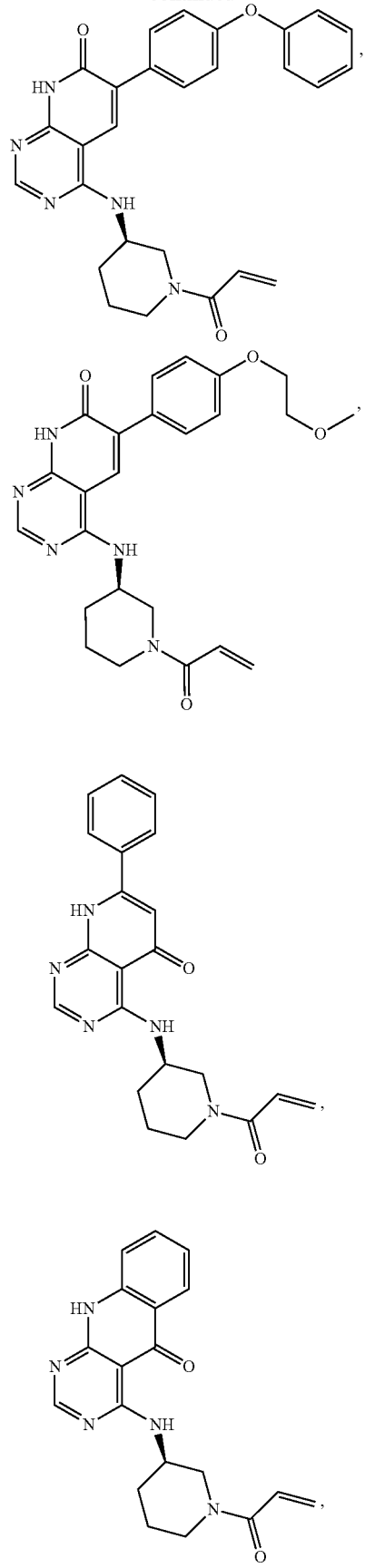

-continued
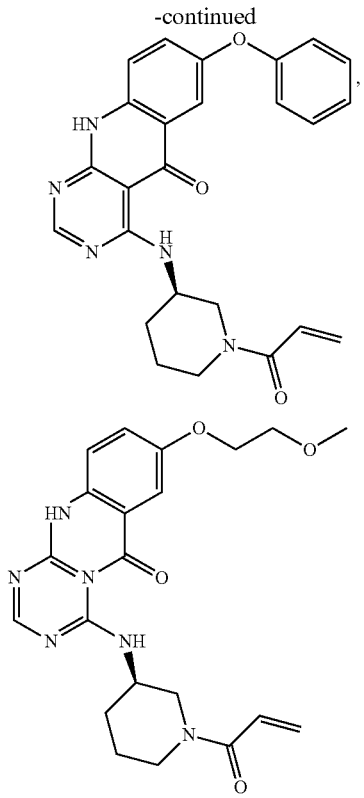
and
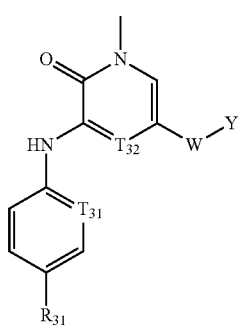
Further provided is a compound of formula (III), or a pharmaceutically acceptable salt, a tautomer, a stereoisomer, an N-oxide, a hydrate, a solvate, a metabolite, or a prodrug thereof;
(III)
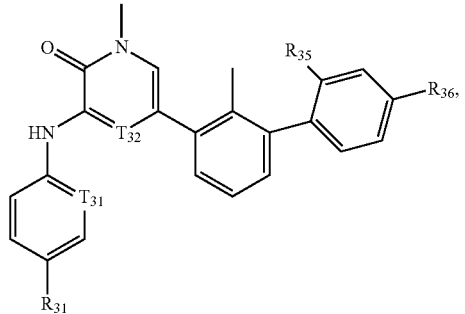
in which, Y is selected from
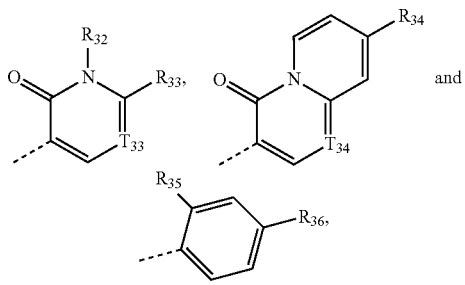
W is selected from
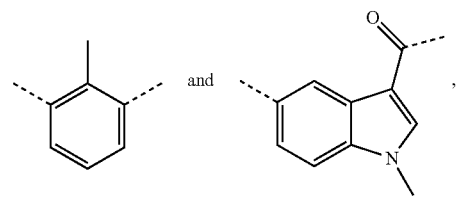
that is the compound of formula (III) is selected from:
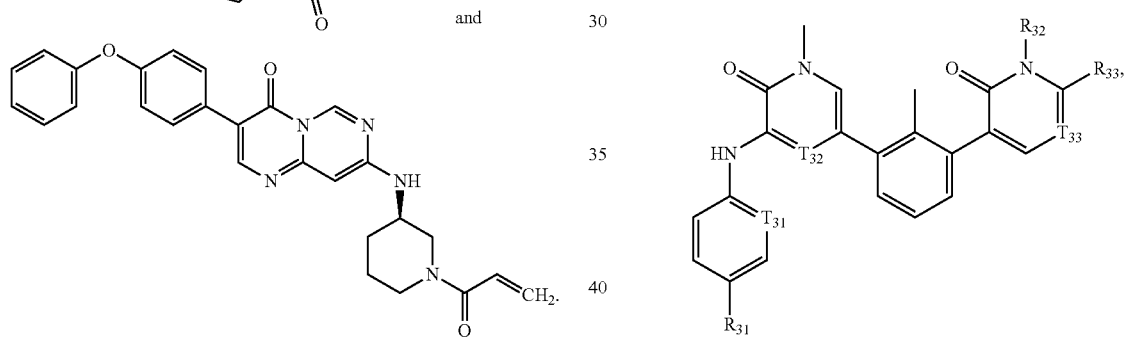
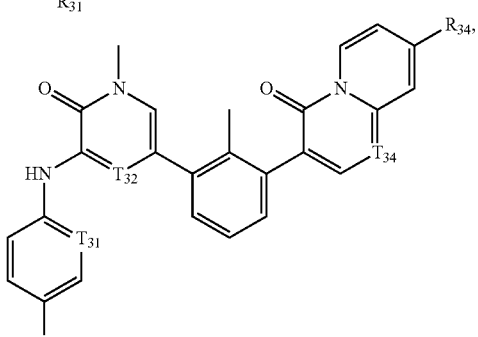

-continued

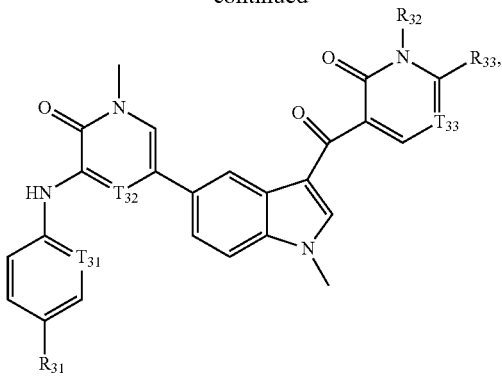

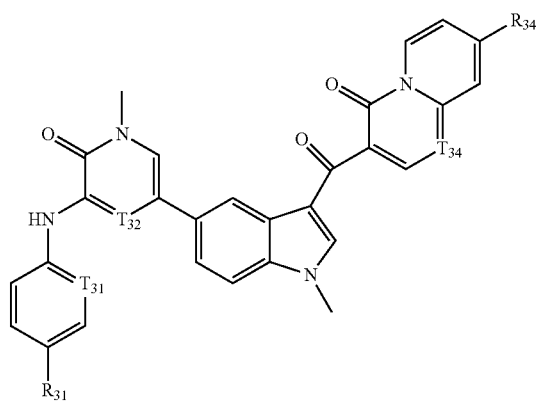

and

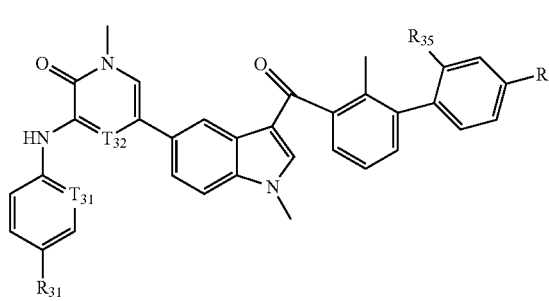

each of $T_{31}$, $T_{32}$, $T_{33}$ and $T_{34}$ is independently selected from $CR_3$, N, $R_3$ is selected from H, halogen, OH, $NH_2$, CN, or optionally substituted $C_{1-12}$ alkyl or $C_{1-12}$ heteroalkyl, $R_{31}$ is selected from optionally substituted

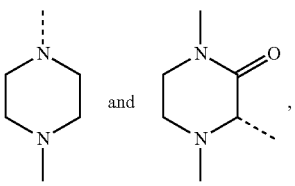

and $R_{32}$ is selected from H, or optionally substituted $C_{1-12}$ alkyl, $C_{1-12}$ heteroalkyl, aryl or heteroaryl, $R_{33}$ is selected from H, or optionally substituted aryl or heteroaryl, $R_{34}$ is selected from H, or optionally substituted $C_{1-12}$ alkyl or $C_{1-12}$ heteroalkyl, each of $R_{35}$ and $R_{36}$ is independently selected from H, halogen, OH, $NH_2$, CN, or optionally substituted $C_{1-12}$ alkyl or $C_{1-12}$ heteroalkyl, each of heteroalkyl and heteroaryl independently comprises 1, 2 or 3 of O, S, N, C(=O), S(=O) or S(=O)$_2$.

In some embodiments of the present disclosure, the substituents in $R_3$, $R_{31}$, $R_{32}$, $R_{33}$, $R_{34}$, $R_{35}$ and $R_{36}$ each are selected from F, Cl, Br, I, OH, $NH_2$, CN, or optionally substituted $C_{1-6}$ alkyl or $C_{1-6}$ heteroalkyl, the number of the substituents for one same group is independently 0, 1, 2 or 3.

In some embodiments of the present disclosure, $C_{1-6}$ alkyl or $C_{1-6}$ heteroalkyl is selected from

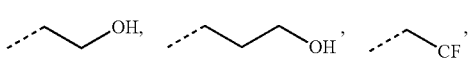

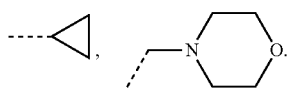

In some embodiments of the present disclosure, each of $T_{31}$, $T_{32}$, $T_{33}$ and $T_{34}$ is independently selected from CH, N.

In some embodiments of the present disclosure, $R_{32}$ is selected from H, Me, phenyl, benzyl.

In some embodiments of the present disclosure, $R_{33}$ is selected from H, or optionally substituted phenyl, benzyl, furyl, thienyl, thiazolyl, pyridyl, pyrrolyl or imidazolyl.

In some embodiments of the present disclosure, $R_{34}$ is selected from H, Me.

In some embodiments of the present disclosure, each of $R_{35}$ and $R_{36}$ is independently selected from halogen, cyclopropyl.

In some embodiments of the present disclosure, the compound is optionally selected from:

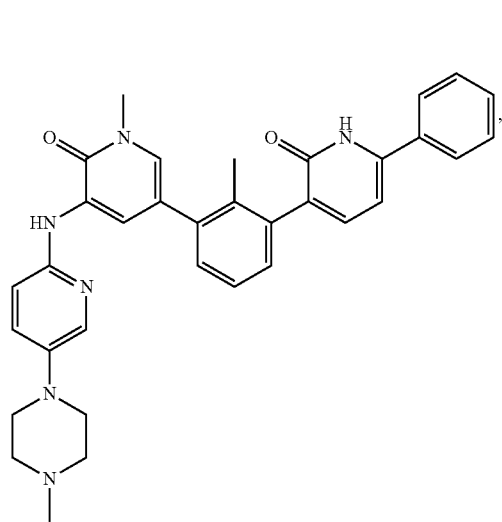
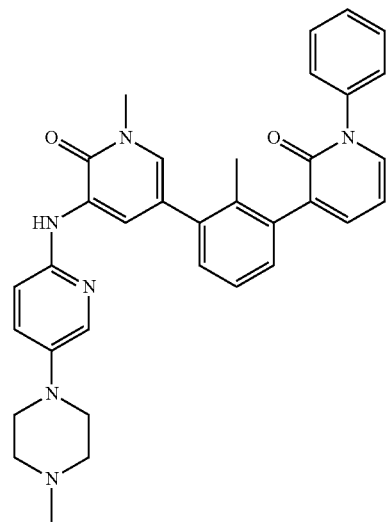
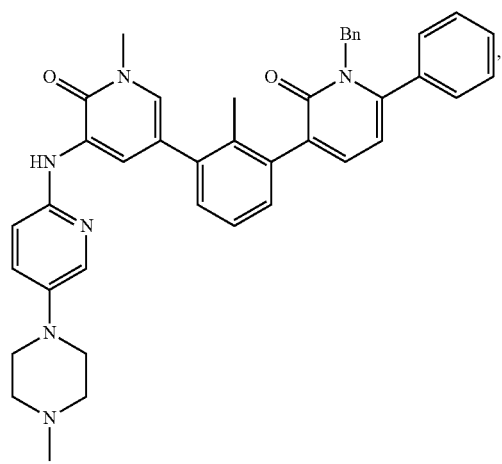
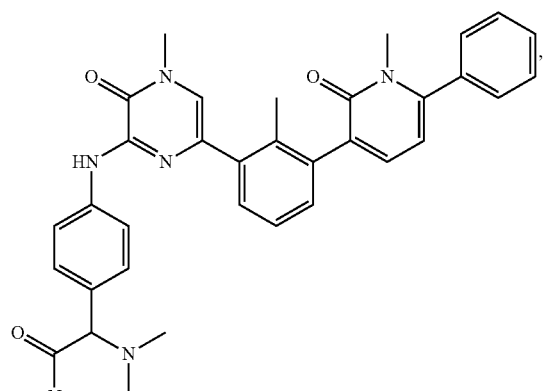
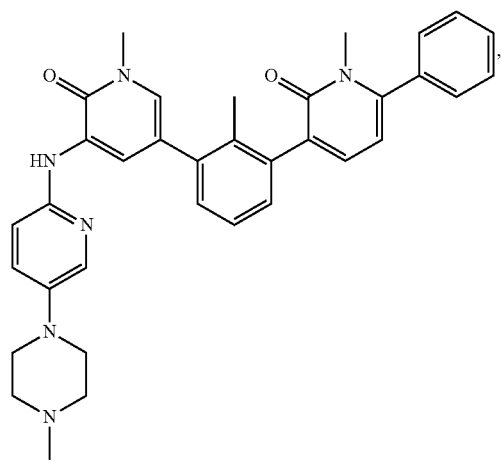
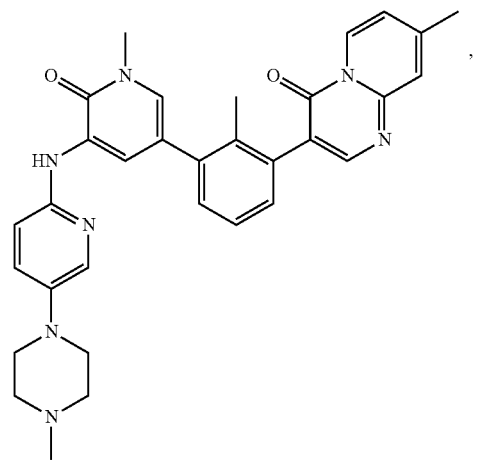

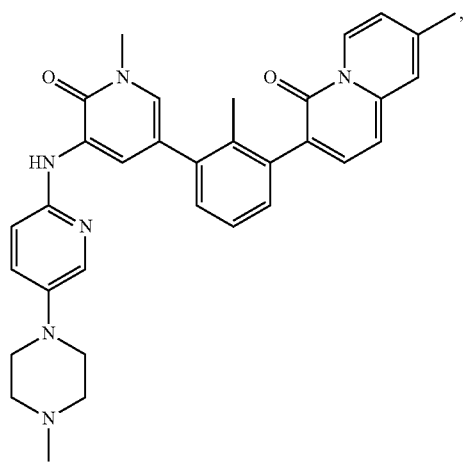
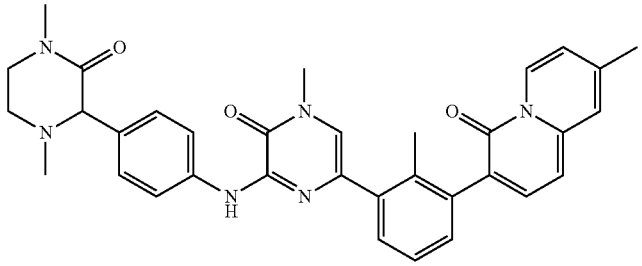
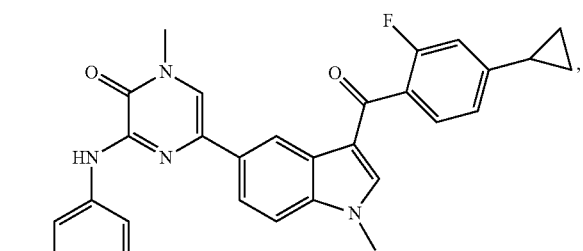
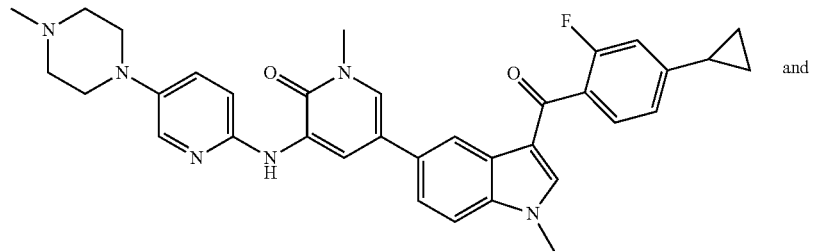
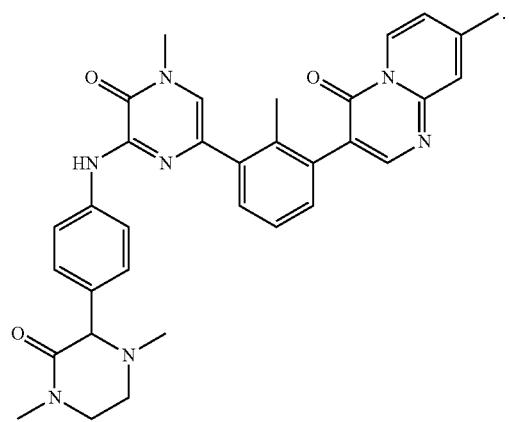

In some embodiments of the present disclosure, the compound is optionally selected from:

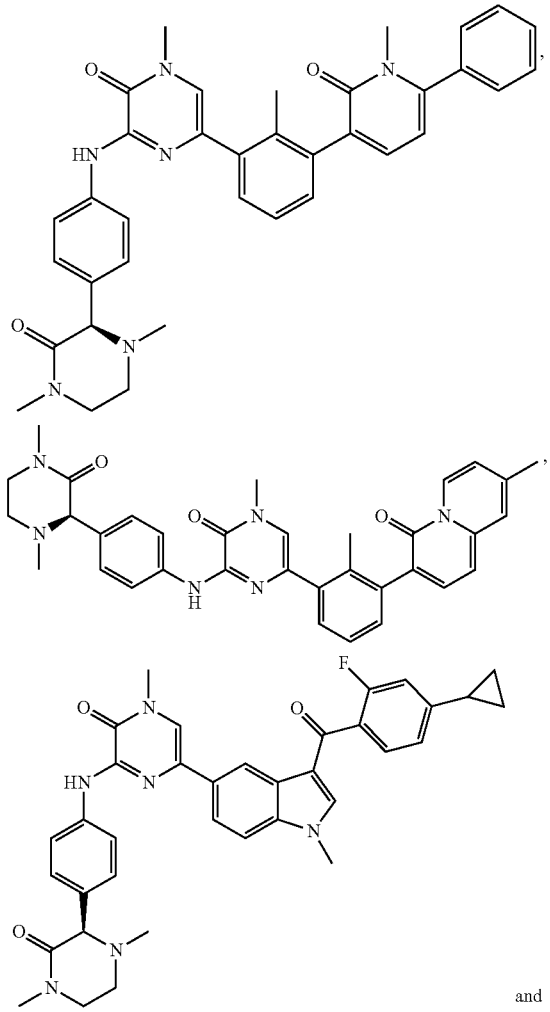

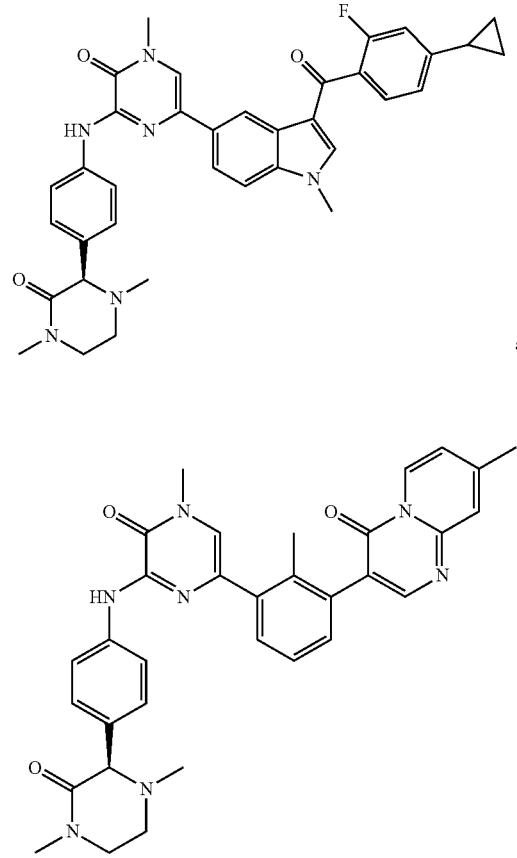

and

More further provided is a compound of formula (IV), or a pharmaceutically acceptable salt, a tautomer, a stereoisomer, an N-oxide, a hydrate, a solvate, a metabolite, or a prodrug thereof;

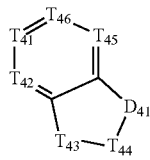

(IV)

in which, $T_{46}$ is selected from N or $C(R_{46})$, $R_{46}$ is selected from H, OH, $NH_2$, CN, -$L_{46}$-Ar—$R_4$,

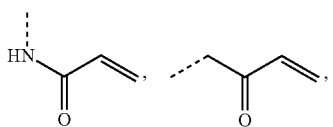

$L_{46}$ is selected from a single bond, O, S, $N(R_4)$, $C(R_4)(R_4)$, each of $T_{41}$, $T_{42}$, $T_{43}$, $T_{44}$ and $T_{45}$ is independently selected from N or $C(R_4)$, $R_4$ is selected from H, halogen, CN, OH, $NH_2$, or optionally substituted $C_{1-6}$ alkyl, $C_{1-6}$ heteroalkyl, 5- to 12-membered aryl, 5- to 12-membered heteroaryl, 5- to 12-membered aryl hetero radical or 5- to 12-membered heteroaryl hetero radical, in which the substituent is chosen from halogen, OH, $NH_2$, CN,

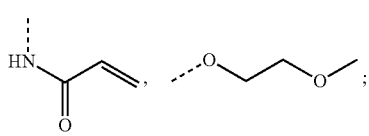

Ar represents 5-to 6-membered aryl or 5-to 6-membered heteroaryl, $D_{41}$ is selected from $N(R_4')$;

$R_4'$ is selected from H,

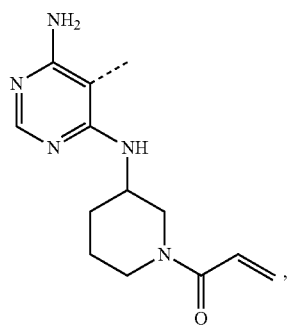

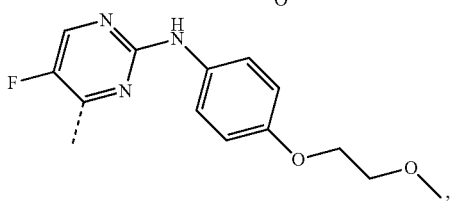

-continued

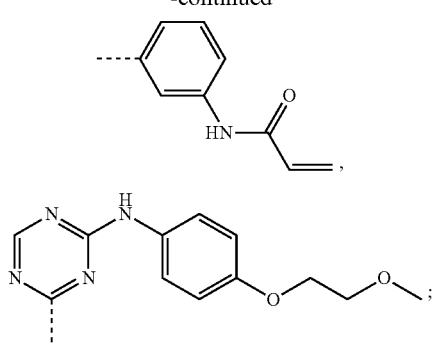

and each of heteroalkyl, heteroaryl, aryl hetero radical and heteroaryl hetero radical independently comprises 1, 2 or 3 of O, S, N, C(=O), S(=O) or S(=O)$_2$.

In some embodiments of the present disclosure, $L_{41}$ is selected from a single bond, O, NH.

In some embodiments of the present disclosure, Ar is phenyl, furyl, thienyl, thiazolyl, pyridyl, pyrrolyl, or imidazolyl.

In some embodiments of the present disclosure, $R_4$ is selected from H,

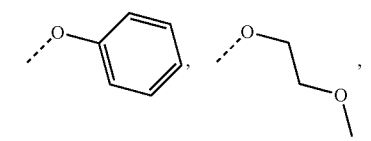

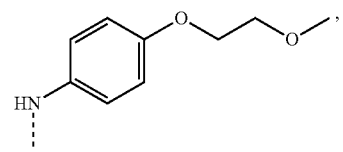

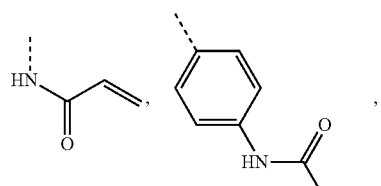

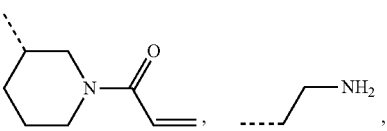

In some embodiments of the present disclosure, $R_{41}$ is selected from H,

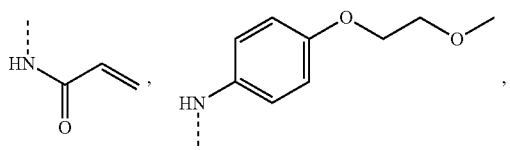

-continued

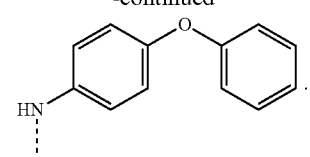

In some embodiments of the present disclosure, the compound is optionally selected from:

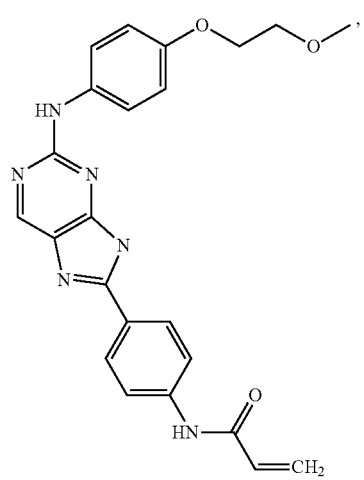

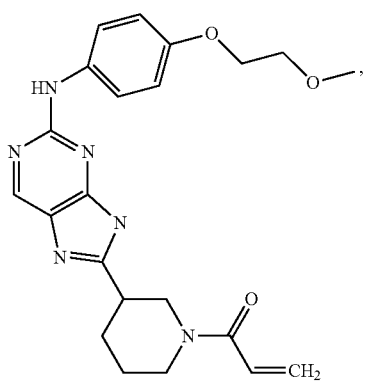

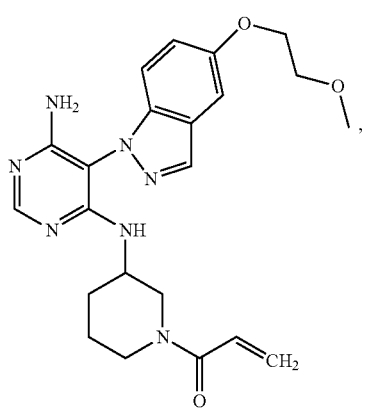

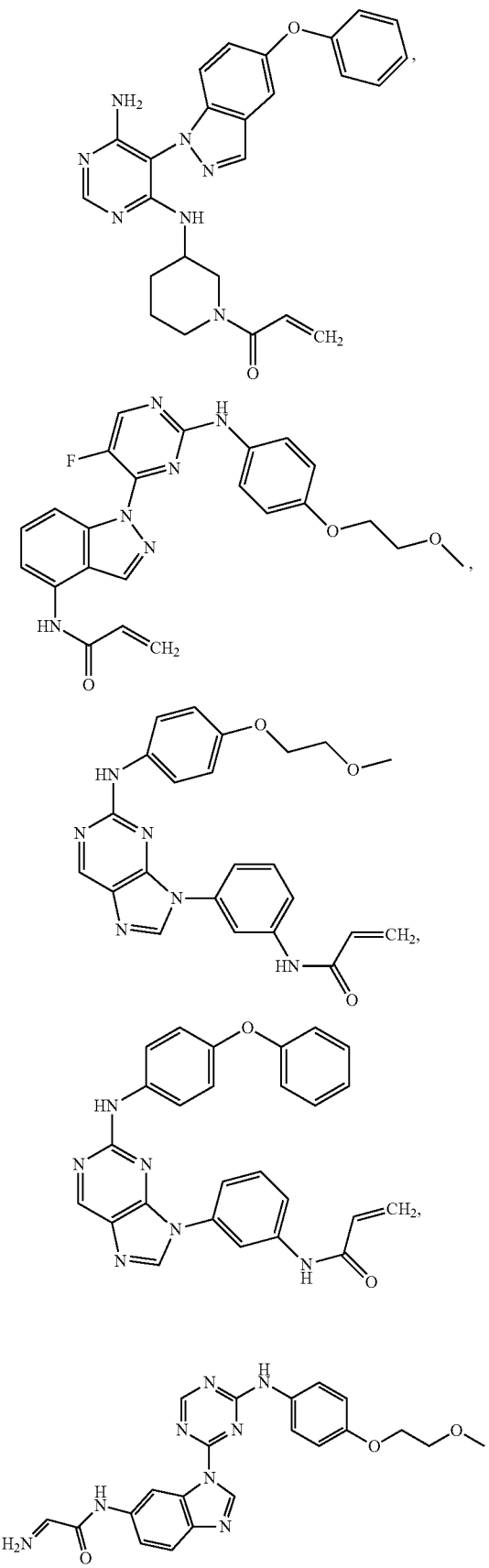

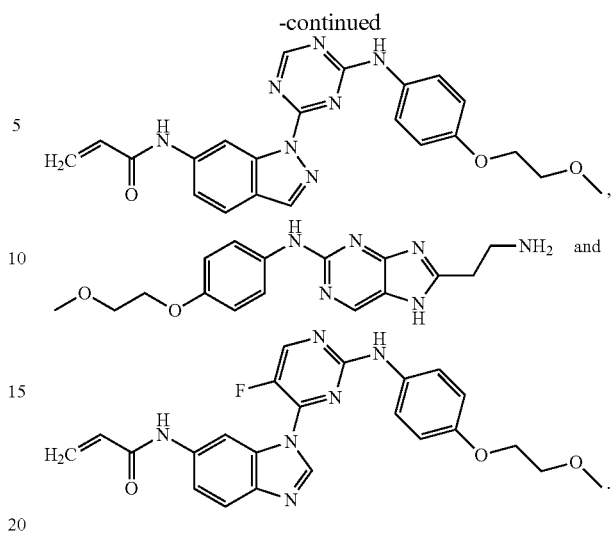

In some embodiments of the present disclosure, the compound is optionally selected from:

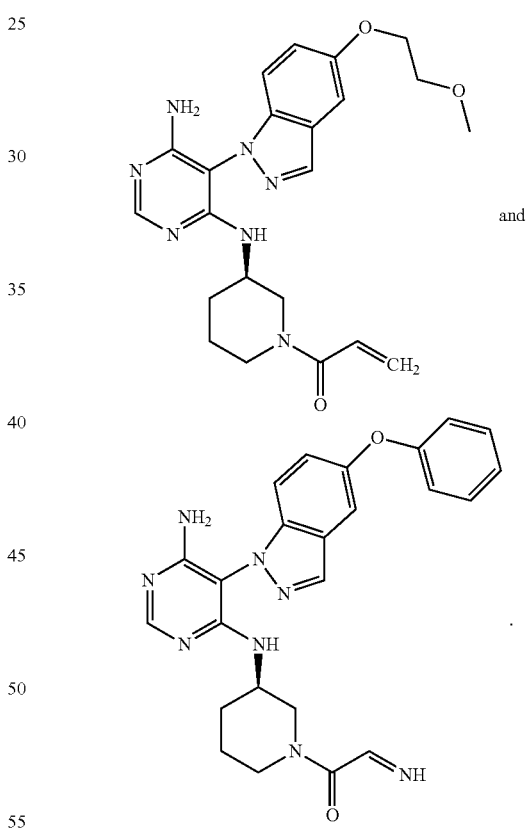

Also provided is use of the foregoing compound in the manufacture of medicament for inhibiting Bruton's tyrosine kinase.

Relative Definitions

The following terms and phrases used herein are intended to have the following meanings, unless otherwise specified. A particular term or phrase should not be construed to be uncertain or unclear without specified definition, but should be understood in the common sense. As a trade name appears in this disclosure, it is intended to refer to its corresponding commodity or its active ingredient.

$C_{1-12}$ is chosen from $C_1$, $C_2$, $C_3$, $C_4$, $C_5$, $C_6$, $C_7$, $C_8$, $C_9$, $C_{10}$, $C_{11}$ and $C_{12}$, and $C_{3-12}$ is chosen from $C_3$, $C_4$, $C_5$, $C_6$, $C_7$, $C_8$, $C_9$, $C_{10}$, $C_{11}$ and $C_{12}$. The term "pharmaceutically acceptable" as used herein, is intended to mean compounds, materials, compositions and/or preparations which are, within the scope of sound medical judgement, suitable for use in contact with tissues of human and animal without excessive toxicity, irritation, allergic response or other problems or complications commensurate with reasonable effect/ risk ratio.

The term "pharmaceutically acceptable salts" refer to a salt of the compound of the present disclosure prepared by contacting the compound containing one or more designated substituents with a relatively non-toxic acid or base. For example, when the compound contains a relatively acidic functional group, its base addition salt can be obtained by contacting a neutral form of such a compound with an adequate amount of bases in a pure solution or a suitable inert solvent. Examples of this pharmaceutically acceptable base addition salt include sodium, potassium, calcium, ammonium, organic amino or magnesium salts or other similar salts. Also, when the compound contains a relatively basic functional group, its acid addition salt can be obtained by contacting a neutral form of such a compound with an adequate amount of acids in a pure solution or a suitable inert solvent. Examples of this pharmaceutically acceptable acid addition salt include inorganic acid salts, including, such as hydrochloric acid, hydrobromic acid, nitric acid, carbonic acid, bicarbonate, phosphoric acid, monohydrogen phosphate, dihydrogen phosphate, sulfuric acid, hydrogen sulphate, hydroiodic acid, phosphorous acid and the like; organic acid salts, including, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; and salts of organic acid, such as salts of amino acid (such as, arginine), glucuronic acid and the like (see, Berge et al., "Pharmaceutical Salts", Journal of Pharmaceutical Science 66: 1-19 (1977)). In certain embodiments of the present disclosure, the compound contains both basic and acidic functional groups, so as to be converted to either base or acid addition salt.

Preferably, the neutral form of the compound can be regenerated by contacting the salt thereof with a base or acid and then isolating the resulting parent compound which differs from other forms of its salt in some physical properties, such as solubility in polar solvents, using conventional manners.

As used herein, "pharmaceutically acceptable salts" are derivatives of the compound in the present disclosure which was formed by contacting the parent compound with an acid or base. Examples of the pharmaceutically acceptable salt include, but are not limited to, inorganic acid or organic acid salts of basic groups (such as amine group), alkali metal or organic salts of acidic groups (such as carboxylic acid) and the like. The pharmaceutically acceptable salts typically are non-toxic, such as the quaternary ammonium salt of the parent compound or salts formed with non-toxic inorganic or organic acids. The non-toxic salts usually include, but are not limited to those derived from inorganic and organic acids which are selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalactaldehyde, propionic acid, salicylic acid, stearic acid, folinate, succinic acid, sulfamic acid, p-aminobenzenesulfonic acid, sulfuric acid, tannicacid, tartaric acid and p-toluenesulfonic acid.

The pharmaceutically acceptable salts of the present disclosure can be synthesized from the parent compound containing an acidic or basic group by means of a conventional chemical method, and typically be prepared by contacting the compound in a free acidic or basic form with a stoichiometric amount of suitable bases or acids in water or organic solvents or both, preferably, in a non-aqueous medium such as ether, ethyl acetate, ethanol, isopropanol or acetonitrile.

Except for the pharmaceutically acceptable salt thereof, the compound of the present disclosure also can be existed as a prodrug thereof which is easily to be converted into the present compound by chemical reaction under the physiological conditions in vitro or by chemical or biochemical reactions under environments in vivo.

The compound of the present disclosure can be existed as a non-solvent or solvate (including hydrate) thereof, generally speaking both of them being comparatively included in the present disclosure. The compound of the present disclosure also can be existed in polycrystalline or amorphous forms.

The compound of the present disclosure can contain asymmetric carbon atoms (that is optical center) or double bonds, and all of the racemate, the diastereomer, the geometrical isomer and the individual isomer thereof are included within the scope of the present disclosure.

The graphic representations of racemic, ambiscalemic and scalemic or enantiomerically pure compounds used herein are taken from Maehr, J. Chem. Ed. 1985, 62: 114-120. The absolute configuration of a stereogenic center is specified by a wedge bond or a dashed bond, unless otherwise specified. When containing olefinic double bonds or other geometric asymmetric centers, the compound described herein includes E, Z geometric isomers, unless otherwise specified; and all the tautomers thereof are also included within the scope of the present disclosure.

The compound of the present disclosure can contain one or more designated geometrical isomers or stereoisomers, and all of them are contemplated by applicator, including cis-isomers, trans-isomers, (−)-enantiomers, (+)-enantiomers, (R)-enantiomers, (S)-enantiomers, diastereoisomers, (D)-isomers and (L)-isomers, and racemic mixture thereof or other mixture (such as, enantiomer or diastereomer enriched mixture), all of the mixtures being within the scope of the present disclosure. Other asymmetric carbon atoms also can be existed in the substituents such as alkyl and the like, and all of the isomers and mixtures thereof are also included within the scope of the present disclosure.

Optically active (R)- and/or (S)-isomers as well as (D)-isomers and (L)-isomers may be prepared by using chiral synthons or chiral reagents, or using other conventional techniques, so that a desired enantiomer of the compound in the present disclosure can be prepared by asymmetric synthesis or derivatization with chiral auxiliaries, and specifically comprising the steps of isolating the resulting enantiomer from the diastereomeric mixture, and then cleaving the auxiliary groups in the enantiomer to provide the desired pure enantiomer. Alternatively, when the compound contains a basic functional group (e.g., an amino group) or an acidic functional group (e.g., a carboxyl group), an enantiomer of the compound can be prepared by contacting the compound with an appropriate amount of optically active acids or bases to form a diastereomeric salt, and resolving the diastereoisomer mixture by methods well known in the art such as fractional crystallization or chromatography to separate the enantiomer with the diastereoisomer followed by collection of the separated pure enantiomer. Generally, the separation of an enantiomer from a diastereoisomer is usually accomplished by chromatography on chiral stationary phase, and optionally in combination with chemical derivatization method (e.g., carbamate was generated by amine).

In the present disclosure, one or more atoms constituting the present compound may include non-natural proportions of atomic isotopes, and for example, the compound can be labeled with radioisotopes, such as tritium ($^3$H), iodine-125 ($^{125}$I) or C-14 ($^{14}$C). All the combinations of isotopes in the compound are included within the scope of the present disclosure, no matter the isotopes are radioactive or not.

The term "pharmaceutically acceptable carrier" refers to any preparation or carrier which is able to deliver an effective amount of the active substance of the present disclosure without interfering with the biological activity of the active substance and being non-toxic to a host or patient. The representative examples of such carrier include water, oil, vegetable and mineral matrix, cream matrix, lotion matrix, ointment matrix and so on, in which the matrix can contain suspending agents, tackifiers, transdermal enhancers and the like. The preparations of such a carrier are well known to those skilled in the art of cosmetics or local medicines, and the additional information thereof is described, for example, in Remington: The Science and Practice of Pharmacy, 21st Ed., Lippincott, Williams & Wilkins (2005), the entire content of which is incorporated herein by reference.

The term "excipient" generally refers to a carrier, diluent and/or medium required to formulate an effective pharmaceutical composition.

For any drugs or pharmacologically active agents, the term "effective amount" or "therapeutically effective amount" refers to a sufficient amount of a drug or agent that is non-toxic but is capable of achieving the desired effect. For the orally administered formulation described herein, the "effective amount" of an active substance in the formulation refers to its amount required to achieve the desired effect when used in association with one or more other active substances. The effective amount varies from person to person, depending on the age and general condition of the receptor and on the designated active substance. The appropriate effective amount in individual cases can be determined by a person skilled in the art in accordance with routine testing.

The term "active ingredient", "therapeutic agent", "active substance" or "active agent" refers to a chemical entity which is effective in treating a targeted disorder, disease or condition.

The term "substituted" means that at least one hydrogen on the designated atom is replaced with one or more substituents including variants of deuterium and hydrogen, provided that the designated atom's normal valence is not exceeded and the substituted structure is stable. When the substituent is a ketone group (i.e., =O), then two hydrogens on the atom are replaced, but hydrogens on aromatic group cannot be replaced by the ketone group. The term "optionally substituted" means that the hydrogens on the designated atom may be substituted or not substituted with one or more substituents unless otherwise specified. The type and number of the substituents are not specifically restricted at the substitution occurrence.

When any variable (e.g., R) occurs more than one time in any constituent or structure of the present compound, at each occurrence, its definition is independent. For example, if a group is substituted with 0 to 2 of R, the group may be optionally substituted with up to two of R, and R can be different groups at each occurrence. In addition, combinations of substituents and/or variables are permissible provided that the compound produced is stable.

When one of the variables is a single bond, it indicates that the two groups to which it is attached are directly connected. For example, when L represents a single bond in A-L-Z, it means that A-L-Z is actually A-Z.

As described herein, "- - - - - -" refers to a bond attached to an another group. For example, when M is

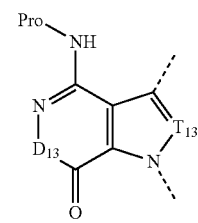

in the structure as described in formula (I), it means that the structure of formula (I) is

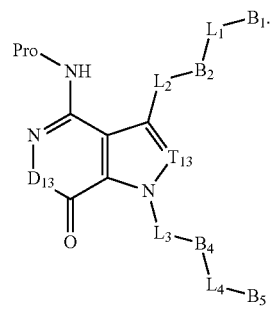

In addition, it should be noted that the descriptions "each . . . be independently", " . . . be each independently" and " . . . be independently" as used herein are interchangeable and all of them should be broadly interpreted. It means that the specific representations of a same variable are not affected with each other both in a same group and in a different group. For example, if R in a group of —C(R)(R)— is selected from F and Cl, the group —C(R)(R)— can be in one of the following forms:

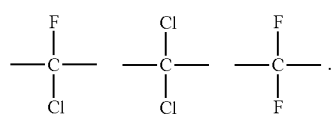

If a bond of a substituent can be cross-linked to two atoms on a ring, the substituent may be bound to any atom on the ring. When an atom of the listed substituent which is not specified is bound to a compound which is included in the general chemical structures but not specifically mentioned, such substituent may be bound to the compound through any of its atoms. Combinations of substituents and/or variants are permissible provided that the compound produced is stable. For example, in the structure units

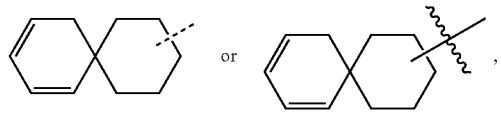

the substitution may be carried out at any position on the cyclohexane ring or the cyclohexadiene ring.

Substituent of alkyl or heteroalkyl is generally referred to "alkyl substituent" which may be one or more groups selected from the group consisting of, but not limited to, —R', —OR', =O, =NR', =N—OR', —NR'R'', —SR', halogen, —SiR'R''R''', OC(O)R', —C(O)R', —CO$_2$R', —CONR'R'', —OC(O)NR'R'', —NR''C(O)R', NR'C(O) NR''R''', —NR''C(O)$_2$R', —NR''''-C(NR'R''R''')=NR'''', NR''''C(NR'R'')=NR''', —S(O)R', —S(O)$_2$R', —S(O)$_2$NR''R''', NR''SO$_2$R', —CN, —NO$_2$, —N$_3$, —CH(Ph)$_2$ and fluoro (C$_1$-C$_4$)alkyl, and the number of such substituents is 0 to (2m'+1), in which m' is the total number of carbon atoms in the group. Preferably, each of R', R'', R''', R'''' and R''''' is independently selected from hydrogen, substituted or unsubstituted heteroalkyl, substituted or unsubstituted aryl (e.g., 1 to 3 of aryl substituted with halogen), substituted or unsubstituted alkyl, substituted or unsubstituted alkoxy, substituted or unsubstituted thioalkoxy or substituted or unsubstituted aralkyl. When one or more R groups are present in the compound of the present disclosure, each R group is independently selected, and when one or more R', R'', R''', R'''' and R''''' are present, they are also independently selected. R' and R'' together with nitrogen atom to which they are attached, form a 5-, 6- or 7-membered ring. For example, —NR'R'' is intended to include, but is not limited to, 1-pyrrolidinyl and 4-morpholinyl. According to the above discussion about substituents, it will be understood by those skilled in the art that the term "alkyl" is intended to include those groups containing one or more non-hydrogen groups that are bound to carbon atom, such as haloalkyl (e.g., —CF$_3$ or —CH$_2$CF$_3$), acyl (e.g., —C(O)CH$_3$, —C(O)CF$_3$ or —C(O)CH$_2$OCH$_3$) and the like.

Being similar to the substituent of alkyl, substituent of aryl or heteroaryl is generally referred to "aryl substituent" which may be selected from the following groups, for example, —R', —OR', —NR'R'', —SR', halogen, —SiR'R''R''', OC(O)R', —C(O)R', —CO2R', —CONR'R'', —OC(O)NR'R'', —NR''C(O)R', NR'C(O)NR''R''', —NR''C(O)2R', —NR''''-C(NR'R''R''')=NR'''', NR''''C(NR'R'')=NR''', —S(O)R', —S(O)$_2$R', —S(O)$_2$NR''R''', NR''SO$_2$R', —CN, —NO$_2$, —N$_3$, —CH(Ph)$_2$, fluoro(C$_1$-C$_4$)alkoxy, fluoro(C$_1$-C$_4$)alkyl and the like, and the number of such substituents is between 0 and the total open valences of the aromatic ring; in which preferably, each of R', R'', R''', R'''' and R''''' is independently selected from hydrogen, substituted or unsubstituted alkyl, substituted or unsubstituted heteroalkyl, substituted or unsubstituted alkyl or substituted or unsubstituted heteroaryl. When one or more R groups are present in the present compound, each R group is independently selected, and when one or more R', R'', R''', R'''' or R''''' are present, they are also independently selected.

Two substituents on adjacent atoms of an aryl or heteroaryl ring may be optionally substituted with substituents of the general formula -T-C(O)—(CRR')$_q$—U—, in which T and U are independently selected from —NR—, —O—, CRR'— or a single bond, and q is an integer from 0 to 3. Alternatively, two substituents on adjacent atoms of an aryl or heteroaryl ring may be optionally substituted with substituents of the general formula -A(CH$_2$)$_r$B—, in which A and B are independently selected from —CRR'—, —O—, —NR—, —S—, —S(O)—, S(O)$_2$—, —S(O)$_2$NR'— or a single bond, and r is an integer from 1 to 4. Optionally, a single bond on the ring which was newly-formed with the above substituents may be replaced with a double bond. Alternatively, two substituents on adjacent atoms of an aryl or heteroaryl ring may be optionally substituted with substituents of the general formula —(CRR')$_s$—X—(CR''R''')$_d$—, in which each of s and d is independently an integer from 0 to 3, and X is —O—, —NR'—, —S—, —S(O)—, —S(O)$_2$— or —S(O)$_2$NR'—. Preferably, each of substituents R, R', R'' and R''' is independently selected from hydrogen and substituted or unsubstituted (C$_1$-C$_6$) alkyl.

The term "halo" or "halogen" per se or as a part of another substituent, may refer to a fluorine, chlorine, bromine or iodine atom, unless otherwise specified. In addition, the term "haloalkyl" may refer to monohaloalkyl or polyhaloalkyl. For example, the term "halo (C$_1$-C$_4$) alkyl" may refer to, but not limited to, trifluoromethyl, 2,2,2-trifluoroethyl, 4-chlorobutyl, 3-bromopropyl and the like.

Examples of haloalkyl include, but not limited to, trifluoromethyl, trichloromethyl, pentafluoroethyl and pentachloroethyl. "Alkoxy" refers to an alkyl group as defined above with the indicated number of carbon atoms attached through an oxygen bridge. C$_{1-6}$ alkoxy refers to C$_1$ alkoxy, C$_2$ alkoxy, C$_3$ alkoxy, C$_4$ alkoxy, C$_5$ alkoxy or C$_6$ alkoxy. Examples of alkoxy include, but not limited to, methoxy, ethoxy, n-propoxy, isopropoxy, n-butoxy, sec-butoxy, t-butoxy, n-pentyloxy and S-pentyloxy. "Cycloalkyl" refers to a saturated cyclic group, such as cyclopropyl, cyclobutyl or cyclopentyl. 3-to 7-membered cycloalkyl refers to C$_3$ cycloalkyl, C$_4$ cycloalkyl, C$_5$ cycloalkyl, C$_6$ cycloalkyl or C$_7$ cycloalkyl. "Alkenyl" refers to a straight or branched chain hydrocarbon group having one or more carbon-carbon double bonds that may exist at any stable site on the chain, such as vinyl, and propenyl.

The term "halo" or "halogen" refers to fluorine, chlorine, bromine or iodine.

The term "hetero" refers to a heteroatom or a heteroatom radical (i.e., a radical containing a heteroatom), including atoms other than carbon (C) and hydrogen (H), and a radical that contains such a heteroatom, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, or optionally substituted —C(=O)N(H)—, —N(H)—, —C(=NH)—, —S(=O)$_2$ N(H)— or —S(=O) N(H)—, unless otherwise specified.

The term "ring" refers to a substituted or unsubstituted cycloalkyl, heterocycloalkyl, cycloalkenyl, heterocycloalkenyl, cycloalkynyl, heterocycloalkynyl, aryl or heteroaryl, unless otherwise specified. Such a ring includes a single, bicyclic, spirocyclic, fused or bridged ring. The number of atoms on a ring is usually defined as the member of the ring. For example, "5-to 7-membered ring" refers to a cycle which consists of 5 to 7 of atoms, and the ring optionally contains 1 to 3 of heteroatoms unless otherwise specified. The representative examples thereof are phenylpyridine and piperidinyl. It is noted that the term "5-to 7-membered heterocycloalkyl ring" includes pyridyl and piperidinyl, but excludes phenyl. The term "ring" also refers to a ring system containing at least one ring, each "ring" independently satisfying the above definition.

Unless otherwise specified, the term "heterocycle" or "heterocyclyl" refers to a stable monocyclic, bicyclic or tricyclic ring containing a heteroatom or hetero radical. Such a ring may be saturated, partially unsaturated or unsaturated (aromatic) which contains one or more carbon atoms and 1, 2, 3 or 4 of heteroatoms independently selected from N, O and S. Any heterocycle described above may be fused to a benzene ring to form a bicyclic ring. Heteroatom such as nitrogen and sulfur may be optionally oxidized, such as NO and $S(O)_p$, in which p is 0, 1 or 2. Nitrogen atom may be substituted or unsubstituted, such as N and NR, in which R is H or other substituents already defined herein. The heterocycle may be attached to a pendant group of any heteroatom or carbon atom to form a stable structure. The heterocycle may be substituted at a carbon or nitrogen position to obtain a stable structure, and nitrogen atom in such a heterocycle can be optionally quaternized. In a preferred embodiment, when the total number of sulfur and oxygen atoms in a heterocyclic ring is more than one, these heteroatoms are not adjacent to each other. In another preferred embodiment, the total number of sulfur and oxygen atoms in a heterocycle is not more than one. As used herein, the term "aromatic heterocyclic group" or "heteroaryl" refers to a stable 5-, 6- or 7-membered monocyclic or bicyclic, or 7-, 8-, 9- or 10-membered bicyclic heterocyclyl aromatic ring which contains one or more carbon atoms and 1, 2, 3 or 4 of heteroatoms independently selected from N, O and S. Nitrogen atom may be substituted or unsubstituted, such as N and NR, in which R is H or other substituents already defined herein. Heteroatom such as nitrogen and sulfur may be optionally oxidized, such as NO and $S(O)_p$, in which p is 0, 1 or 2. It should be noted that the total number of sulfur and oxygen atoms on an aromatic heterocycle is not more than one. The heterocycle defined herein also includes a bridged ring, formed by connecting one or more atoms (i.e., C, O, N, or S) to two non-adjacent carbon atoms or nitrogen atoms. A preferred bridged ring contains, but not limited to, one carbon atom, two carbon atoms, one nitrogen atom, two nitrogen atoms or one carbon-nitrogen group. It should be noted that a single ring is always converted into a tricyclic ring through a bridge, and the substituents on the ring can also be present in the bridge in a bridged ring.

Examples of heterocyclic compound include, but not limited to, acridinyl, azocin, benzimidazolyl, benzofuranyl, mercaptobenzofuranyl, mercaptobenzophenyl, benzoxazolyl, benzoxazolinyl, benzothiazolyl, benzotriazolyl, benzotetrazolyl, benzoisoxazolyl, benzoisothiazolyl, benzimidazolyl, carbazolyl, 4aH-carbazolyl, carbolinyl, chromanyl, chromene, cinnolinyl decahydroquinolyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, pyran, isoindolyl, isoindolinyl, indolyl, isoquinolyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, oxindolyl, pyrimidinyl, phenanthridine, phenanthroline, phenazine, phenothiazine, benzoxanthyl, phenoxazinyl, phthalazinyl, piperazinyl, piperidinyl, piperidonyl, 4-piperidonyl, piperonyl, pteridinyl, purinyl, pyranyl, pyrazinyl, pyrazolidyl, pyrazolinyl, pyrazolyl, pyridazinyl, pyridoxazole, pyridoimidazole, pyridothiazole, pyridyl, pyrimidinyl, pyrrolidinyl, pyrrolinyl, 2H-pyrrolyl, pyrrolyl, pyrazolyl, quinazolinyl, quinolinyl, 4H-quinolizinyl, quinoxaline, quinuclidinyl, tetrahydrofuranyl, tetrahydroisoquinolyl, tetrahydroquinolyl, tetrazolyl, 6H-1,2,5-thiadiazinyl, 1,2,3-thiadiazolyl 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthyl. Fused and spiro compounds are also included.

Unless otherwise specified, the term "hydrocarbyl" or its specific conception (like alkyl, alkenyl, alkynyl, phenyl and the like) per se or as part of another substituent, refers to a linear, branched or cyclic hydrocarbon radical or a combination thereof which may be fully saturated, mono- or poly-unsaturated, may be mono-substituted, di-substituted or poly-substituted, may be monovalent (e.g., methyl), divalent (e.g., methylene) or polyvalent (e.g., methyne), and may include a divalent or multivalent radical containing an indicated number of carbon atoms (e.g., $C_1$ to $C_{10}$ represents 1 to 10 of carbons). "Hydrocarbyl" includes but not limited to, an aliphatic or aromatic hydrocarbon group, in which the aliphatic hydrocarbon group can be chain aliphatic or cyclic aliphatic, especially including but not limited to alkyl, alkenyl or alkynyl, and the aromatic hydrocarbon group includes but not limited to a 6-to 12-membered aromatic hydrocarbon group, such as benzene, naphthalene and the like. In some embodiments, the term "hydrocarbyl" refers to a linear or branched radical or a combination thereof which may be fully saturated and mono- or poly-unsaturated, and may include a divalent or multivalent radical. Examples of the saturated hydrocarbon radical include, but not limited to, methyl, ethyl, n-propyl, isopropyl, n-butyl, t-butyl, isobutyl, sec-butyl, isobutyl, cyclohexyl, (cyclohexyl) methyl or cyclopropylmethyl, and a homologue or isomer of n-pentyl, n-hexyl, n-heptyl, n-octyl or other radicals. The unsaturated hydrocarbyl may has one or more double bonds or triple bonds, and examples thereof include, but not limited to, vinyl, 2-propenyl, butenyl, crotonyl, 2-isopentenyl, 2-(butadienyl), 2,4-pentadienyl, 3-(1,4-pentadienyl), ethynyl, 1-propynyl, 3-propynyl, or 3-butynyl, or a homologue or isomer of higher hydrocarbons.

Unless otherwise specified, the term "heterohydrocarbyl" or its specific conception (e.g., heteroalkyl, heteroalkenyl, heteroalkynyl, heteroaryl and the like) alone or in combination with another term, refers to a stable linear, branched or cyclic hydrocarbon radical or a combination thereof which is composed of an indicated number of carbon atoms and at least one heteroatom. In some embodiments, the term "heteroalkyl" alone or in combination with another term, refers to a stable linear or branched hydrocarbon radical or a combination thereof which is composed of an indicated number of carbon atoms and at least one heteroatom. In a typical embodiment, the heteroatom is selected from B, O, N and S, in which nitrogen or sulfur atom is optionally oxidized and nitrogen atom is also optionally quaternized. The heteroatom such as B, O, N and S, may be disposed at any internal position of the heterohydrocarbyl, including the position at which the heterohydrocarbyl is linked to the remainder of the molecule. Examples of the heteroalkyl include but not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —CH$_2$—CH=N—OCH$_3$ or —CH=CH—N(CH$_3$)—CH$_3$. At most 2 of heteroatoms can be continuous, such as —CH$_2$—NH—OCH$_3$.

The terms "alkoxy", "alkylamino" and "alkylthio (or thioalkoxy)" are conventional expressions, and refer to alkyls which are respectively linked to the remainder of the molecule through an oxygen atom, an amino group and a sulfur atom, respectively.

Unless otherwise specified, the term "cycloalkyl", "heterocycloalkyl" or its specific conception (such as aryl, heteroaryl, cycloalkyl, heterocycloalkyl, cycloalkenyl, heterocycloalkenyl, cycloalkynyl, heterocycloalkynyl and the like) alone or in combination with other terms, respectively represents cyclized "hydrocarbyl" or "heterohydrocarbyl". In addition, in terms of heterohydrocarbyl or heterocycloalkyl (such as heteroalkyl and heterocycloalkyl), heteroatom may occupy the position at which the heterocycle is linked to the remainder of the molecule. Examples of the cycloalkyl include but not limited to, cyclopentyl, cyclohexyl, 1-cyclohexenyl, 3-cyclohexenyl, cycloheptyl and the like. Non-limiting examples of the heterocycloalkyl include 1-(1, 2, 5, 6-tetrahydropyridyl), 1-piperidinyl, 2-piperidinyl, 3-piperidinyl, 4-morpholinyl, 3-morpholinyl, tetrahydrofuran-2-yl, tetrahydrofuran indol-3-yl, tetrahydrothiophen-2-yl, tetrahydrothiophen-3-yl, 1-piperazinyl or 2-piperazinyl.

Unless otherwise specified, the term "aryl" refers to a polyunsaturated aromatic hydrocarbon substituent which may be mono-substituted, di-substituted or poly-substituted, and monovalent, divalent or multivalent, and may be a monocyclic or polycyclic ring which is fused together or covalently bound to others, preferably 1 to 3 rings. The term "heteroaryl" refers to aryl (or a ring) which contains one to four of heteroatoms. In one exemplary embodiment, the heteroatom is selected from B, N, O and S, in which nitrogen or sulfur atom is optionally oxidized and nitrogen atom is also optionally quaternized. The heteroaryl may be linked to the remainder of the molecule through a heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. Any substituents of aryl or heteroaryl ring systems described above are selected from acceptable substituents described below.

For simplicity, when used in combination with other terms (e.g., aryloxy, arylthio and aralkyl), aryl includes both an aryl group and a heteroaryl ring as defined above. Thus, the term "aralkyl" is intended to refer to the group in which aryl is attached to alkyl, the examples thereof include benzyl, phenethyl, pyridylmethyl and the like, and also refer to an alkyl group in which one or more carbon atoms (such as those in methylene) is substituted with one or more substituents such as oxygen atom, the examples thereof include phenoxymethyl, 2-pyridyloxymethyl 3-(1-naphthyloxy) propyl and the like.

The term "leaving group" refers to a functional group or atom which can be substituted with another functional group or atom by substitution reaction (e.g., nucleophilic substitution reaction). For example, the representative leaving group includes trifluoromethanesulfonate; chlorine, bromine and iodine; sulfonate (such as methanesulfonate, tosylate, p-bromobenzenesulfonate, p-toluenesulfonate and the like); acyloxy (such as acetoxy, trifluoroacetoxy and the like).

The term "protecting group" includes but not limited to "amino protecting group", "hydroxy protecting group" and "mercapto protecting group". The term "amino protecting group" refers to a protecting group suitable for preventing the nitrogen atom on amino group from side reaction. The representative alkyl protecting groups include, but not limited to, formyl; acyl groups (such as alkanoyl (e.g., acetyl, trichloroacetyl or trifluoroacetyl)); alkoxycarbonyl groups (such as t-butoxycarbonyl (Boc)); arylmethoxycarbonyl groups (such as benzyloxycarbonyl (Cbz) and 9-fluorenylmethoxycarbonyl (Fmoc)); an arylmethyl group (such as benzyl (Bn), trityl (Tr) and 1,1-bis(4'-methoxyphenyl) methyl); a silyl group (such as trimethylsilyl (TMS) and t-butyldimethylsilyl (TBS) and the like). The term "hydroxy protecting group" refers to a protecting group suitable for preventing hydroxyl from side reaction. The representative hydroxy protecting group includes, but not limited to, an alkyl group (such as methyl, ethyl and t-butyl); an acyl group (such as alkanoyl (e.g., acetyl)); an arylmethyl group (such as benzyl (Bn), p-methoxybenzyl (PMB), 9-fluorenylmethyl (Fm) and diphenylmethyl (benzhydryl, DPM)); a silyl group (such as trimethylsilyl (TMS), t-butyl dimethylsilyl (TBS) and the like).

The compound of the present disclosure may be prepared by a variety of synthetic methods well known to those skilled in the art, including the specific examples listed below, examples thereof in combination with other chemical synthesis methods, and the equivalents thereof well known to the skilled person in the art. The preferred examples include, but not limited to those examples of the present disclosure.

The solvents used in the present disclosure are commercially available.

The following abbreviations are used throughout the specification:

aq: water
HATU: 2-(7-azobenzotriazole)-N,N,N',N'-tetramethyluronium hexafluorophosphate
EDC: N-(3-dimethylaminopropyl)-N'-ethylcarbodiimide hydrochloride
m-CPBA: 3-chloroperoxybenzoic acid
eq: equivalent, equivalence
CDI: carbonyl diimidazole
DCM: methylene chloride
PE: petroleum ether
DIAD: diisopropylazodicarboxylate
DMF: N,N-dimethylformamide
DMSO: dimethyl sulfoxide
EtOAc or EA: ethyl acetate
EtOH: ethanol
MeOH: methanol
CBz: benzyloxycarbonyl, an amine protecting group
BOC: tert-butylcarbonyl, an amine protecting group
HOAc: acetic acid
r.t.: room temperature
O/N: overnight
THF: tetrahydrofuran
Boc$_2$O: di-t-butyl dicarbonate
TFA: trifluoroacetic acid
DIPEA (equal to DIEA): diisopropylethylamine
TsOH: p-toluenesulfonic acid
NFSI: N-fluoro-N-(benzenesulfonyl)benzenesulfonamide
NCS: N-chlorosuccinimide
n-Bu$_4$NF: tetrabutylammonium fluoride
i-PrOH: 2-isopropanol mp: melting point
LDA: diisopropylamine lithium, 2M in THF/N-heptane
TLC: thin layer chromatography
HPLC: high pressure liquid chromatography
NIS: N-iodosuccinimide
DIPA: diisopropylamine
$Pd_2(dba)_3$: tris(dibenzylideneacetone)dipalladium
Xanphos: 2-dicyclohexylphosphonium-2',4',6'-triisopropylbiphenyl
DMAP: 4-dimethylaminopyridine
DME: ethylene glycol dimethyl ether
Pd/C: palladium-carbon catalyst
psi: pressure unit, 1 psi=6.89 kPa
$Pd(dppf)Cl_2$: [1,1'-bis(diphenylphosphino)ferrocene]palladium(II) dichloride
ISCO: a type of combiflash companion
t-BuNO2: tert-butyl nitrite
HCOOEt: ethyl formate
AIBN: azobisisobutyronitrile
NBS: N-bromosuccinimide
MeI: iodomethane
AcOK: potassium acetate
TEH or $Et_eN$: triethylamine
CAN: ammonium ceric nitrate
$N_2H_4$ or $NH_2$—$NH_2$: hydrazine hydrate
$C_4H_8O$. $BH3$: borane-tetrahydrofuran solution
$Pd(dba)_2$: di(dibenzylideneacetone)palladium
$Ph(PPh_3)_2Cl_2$: bis(triphenylphosphine)palladium(II) dichloride
LAH: lithium aluminum tetrahydride
DBU: 1,8-diazabicyclo undec-7-ene
$(BPin)_2$: bis(pinacolate)diboron
Bn: benzyl
V/V: volume ratio
W %: mass percentage The compounds are named by hand or ChemDraw® software, and the commercially available compounds are in the supplier catalog name.

DETAILED DESCRIPTION

The disclosure is described in detail by the following examples, but it is to be understood that the disclosure is not limited to those examples.

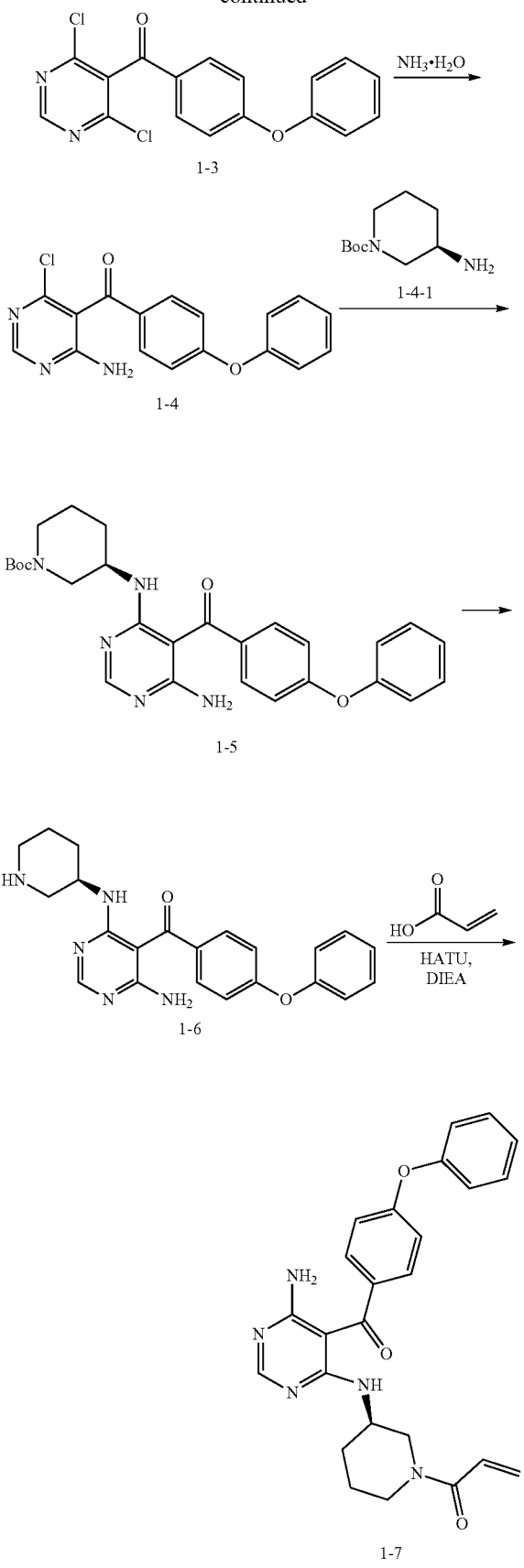

Example 1

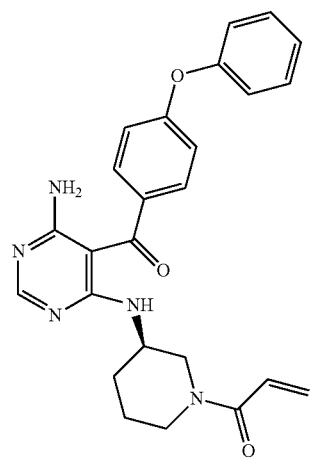 [SMILES: C=CC(=O)N1CCC[C@@H](Nc2ncnc(N)c2C(=O)c2ccc(Oc3ccccc3)cc2)C1]

Synthesis of Compound 1-2

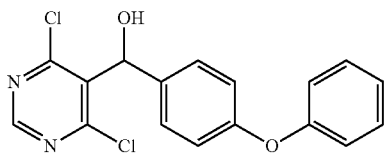 [SMILES: OC(c1ccc(Oc2ccccc2)cc1)c1c(Cl)ncnc1Cl]

To a solution of compound 1-1-1 (2.00 g, 13.42 mmol) in THF (30 mL) was added dropwise LDA (6.75 mL, 13.42 mmol) under nitrogen atmosphere at −78° C., and the reaction mixture was stirred at −78° C. for 1.5 h. To this solution, compound 1-1 (2.93 g, 14.77 mmol) in THF (10 mL) was added slowly, and then the reaction solution was reacted at −78° C. for 1.5 h. Then saturated $NH_4Cl$ (ammonium chloride) (aq., 50 mL) was added slowly to the solution to quench the reaction. The mixture was extracted with EtOAc (30 mL×2), and the organic phases were combined, dried over anhydrous $Na_2SO_4$ and concentrated to give a crude product which was purified by silica gel column chromatography (PE/EA=5:1) to give a purified compound 1-2 (700 mg, Yield 15%).

LCMS (ESI) m/z: 347 (M+1)

Synthesis of Compound 1-3

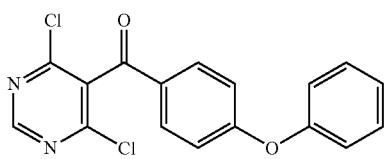

To a solution of compound 1-2 (700 mg, 2.02 mmol) in DCM (30 mL) was added active manganese dioxide ($MnO_2$) (3.51 g, 40.32 mmol), and then the reaction solution was reacted at 50° C. for 16 h, filtered rapidly and concentrated to give a crude residue which was purified by silica gel column chromatography (PE/EA=5:1) to give a purified compound 1-3 (200 mg, Yield 29%).

LCMS (ESI) m/z: 345 (M+1)

Synthesis of Compound 1-4

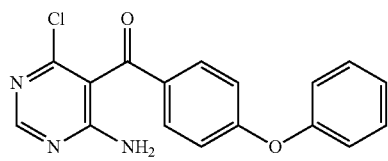 [SMILES: Nc1ncnc(Cl)c1C(=O)c1ccc(Oc2ccccc2)cc1]

To a solution of compound 1-3 (200 mg, 0.579 mmol) in THF (5 mL) was added ammonia solution ($NH_3 \cdot H_2O$) (aq., 406.12 mg, 11.59 mmol), and then the reaction solution was reacted under microwave at 80° C. for 0.5 h. The reaction was monitored by LCMS. The mixture was concentrated and the solvent was removed. Then the residue was diluted with water and extracted with EtOAc (10 mL×2). The organic phases were combined, dried over anhydrous $Na_2SO_4$ and concentrated to give compound 1-4 (0.15 g, Yield 79%) as brown oil.

LCMS (ESI) m/z: 326 (M+1)

Synthesis of Compound 1-5

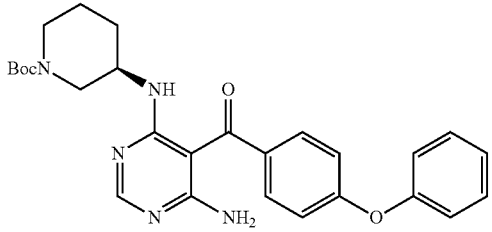 [SMILES: CC(C)(C)OC(=O)N1CCC[C@@H](Nc2ncnc(N)c2C(=O)c2ccc(Oc3ccccc3)cc2)C1]

To a solution of compound 1-4 (130 mg, 0.399 mmol) in i-PrOH (2 mL) was added compound 1-4-1 (159.85 mg, 0.798 mmol) and diisopropylamine (DIPA) (103.16 mg, 0.798 mmol), and then the reaction solution was stirred under microwave at 120° C. for 2 h. The reaction was monitored by LCMS. The mixture was concentrated and the solvent was removed. The residue was diluted with water and then extracted with EtOAc (20 mL×2). The organic phases were combined, dried over anhydrous $Na_2SO_4$ and concentrated to give compound 1-5 (160 mg, Yield 82%) as brown oil.

LCMS (ESI) m/z: 490 (M+1)

Synthesis of Compound 1-6

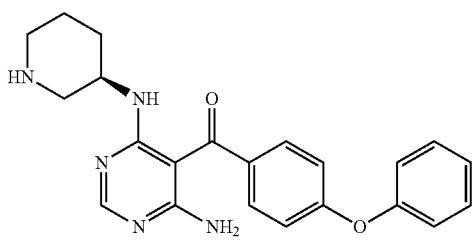 [SMILES: Nc1ncnc(N[C@@H]2CCCNC2)c1C(=O)c1ccc(Oc2ccccc2)cc1]

85

To a solution of compound 1-5 (150 mg, 0.306 mmol) in MeOH (1 mL) was added a solution of hydrogen chloride (HCl) in MeOH (3 mL, 4 M), and then the reaction solution was stirred at 10° C. for 0.5 h. The reaction was monitored by LCMS. The mixture was concentrated and the solvent was removed. The residue was dissolved in water, adjusted to be alkaline with saturate sodium carbonate solution ($Na_2CO_3$), extracted with EtOAc (20 mL) twice. The organic phases were combined, dried over anhydrous $Na_2SO_4$ and concentrated to give compound 1-6 (70 mg, Yield 59%) as brown oil.

Synthesis of Compound 1-7

To a solution of compound 1-6 (100 mg, 0.256 mmol) in DCM (1 mL) was separately added HATU (97.63 mg, 0.256 mmol), acrylic acid (AA) (18.5 mg, 0.256 mmol) and DIPEA (99.56 mg, 0.77 mmol), and then the reaction solution was reacted at 10° C. for 16 h. The solvent was removed by rotary evaporation, and the residue was dissolved in water and extracted with EtOAc (20 mL×2). The organic phases were combined, dried over anhydrous $Na_2SO_4$, concentrated and stripped to give a residue which was purified by preparative HPLC to give compound 1-7 (26.5 mg, Yield 24%) as white solid.

$^1$H NMR (400 MHz, MeOD): δ ppm 8.02-8.04 (m, 1H), 7.66-7.68 (m, 2H), 7.41-7.43 (m, 2H), 7.21-7.25 (m, 1H), 7.06-7.08 (m, 2H), 6.97-6.99 (m, 2H), 6.58-6.67 (m, 1H), 6.12-6.14 (m, 1H), 5.62-5.66 (m, 1H), 4.08-4.17 (m, 1H), 3.80-3.81 (m, 1H), 3.52-3.61 (m, 1H), 3.41-3.51 (m, 2H), 1.86-1.87 (m, 1H), 1.57-1.59 (m, 3H)

LCMS (ESI) m/z: 444 (M+1)

Scheme 2

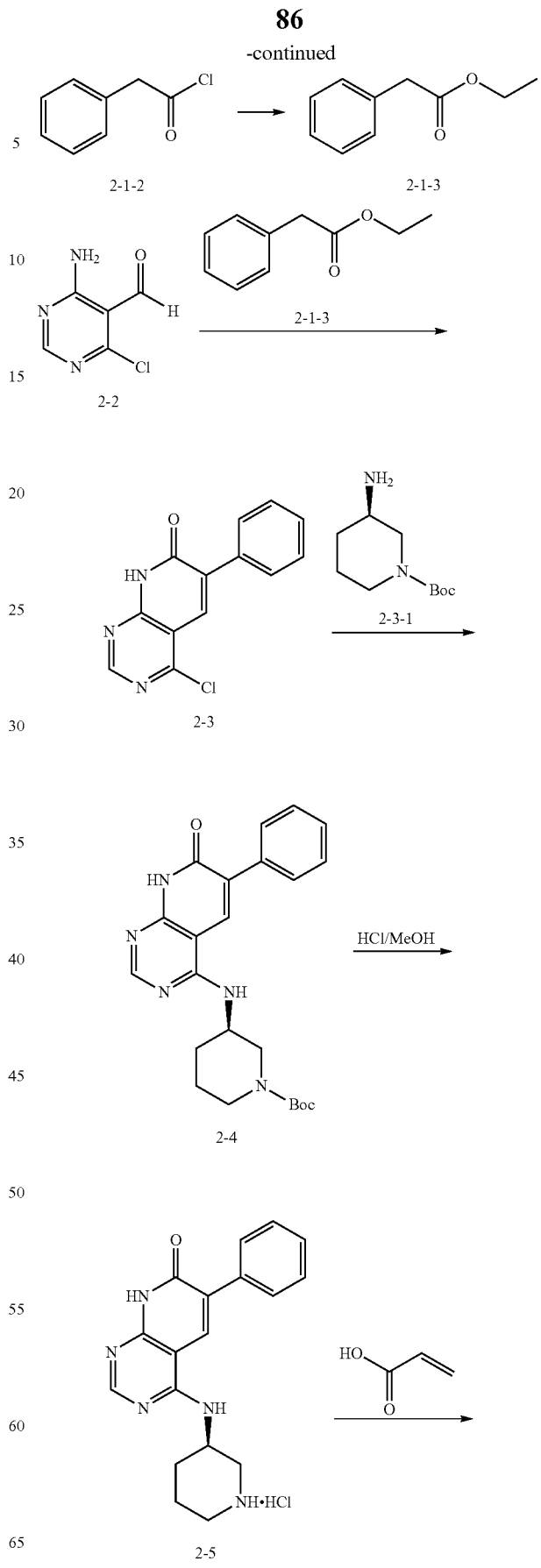

Synthesis of Compound 2-1-3

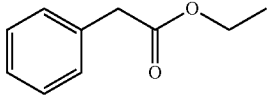

The solution of compound 2-1-2 (10 g, 30 mL) in EtOH (30 mL) was reacted at r.t. for 20 min, and the reaction solution was evaporated to give the title compound (10.62 g, crude) as colorless oil, without further purification.

Synthesis of Compound 2-3

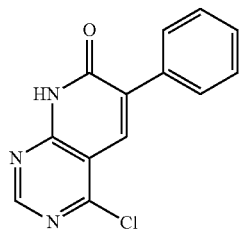 [SMILES: O=c1[nH]c2ncnc(Cl)c2cc1-c1ccccc1]

To a solution of compound 2-2 (400 mg, 1 eq) and compound 2-1-3 (625 mg, 1.5 eq) in DMSO (5 mL) was added dropwise DBU (463 mg, 1.2 eq) at 0° C., and then the reaction solution was reacted at r.t. for 16 h. To this solution was added water (60 mL), and the resulting solution was extracted with PE/EtOAc (2:1). The organic phase was dried over anhydrous $Na_2SO_4$ and concentrated to give a residue which was purified by silica gel column chromatography (10% to 40%, PE/EA) to afford the title compound (170 mg, 26%).

LCMS (ESI) m/z: 258 (M+H)

Synthesis of Compound 2-4

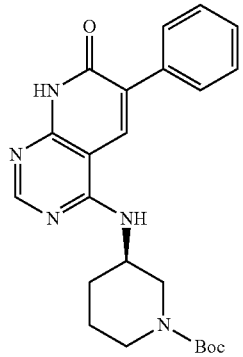 [SMILES: CC(C)(C)OC(=O)N1CCC[C@@H](Nc2ncnc3[nH]c(=O)c(-c4ccccc4)cc23)C1]

To a solution of compound 2-3 (170 mg, 1 eq) and compound 2-3-1 (139 mg, 1.05 eq) in i-PrOH (1.5 mL) was added DIPEA (128 mg, 1.5 eq), and then the reaction solution was reacted under microwave at 110° C. for 30 min. The reaction solution was concentrated to give the title compound (277 mg, crude).

LCMS (ESI) m/z: 422 (M+H)

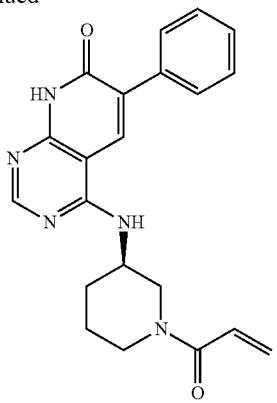

2-6

Example 2

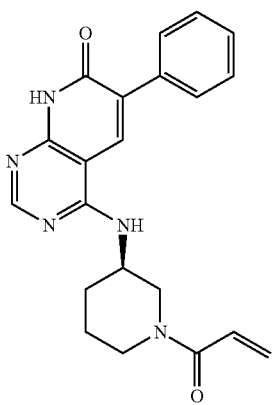

Synthesis of Compound 2-1-1

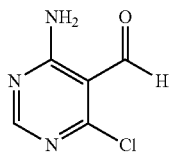

To a solution of compound 2-1 (1 g, 5.6 mmol) in dioxane (10 mL) was added dropwise $NH_3 \cdot H_2O$ (10 mL) under nitrogen atmosphere at 0° C., and then the reaction solution was warmed to r.t. and stirred for 1 h. To this solution was added water (50 mL), and the resulting solution was extracted with EtOAc (15 mL×3). The organic phase was dried over anhydrous $Na_2SO_4$, filtered and evaporated to give the title compound (0.64 g, 73%) as oil.

$^1$H NMR (CDCl$_3$ 400 MHz): δ ppm 10.39 (s, 1H), 8.78-8.75 (br, 1H), 8.40 (s, 1H), 6.14 (br, 1H)

Synthesis of Compound 2-5

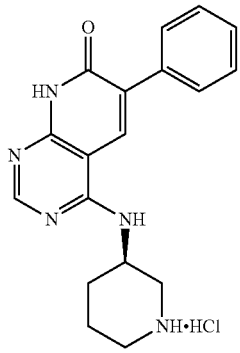

To a solution of HCl in MeOH (2 mL, 4 M) was added compound 2-4 (260 mg, 1 eq), and then the reaction solution was reacted at r.t. for 20 min. The reaction solution was concentrated to give the title compound (198 mg, crude).

LCMS (ESI) m/z: 322 (M+H)

Synthesis of Compound 2-6

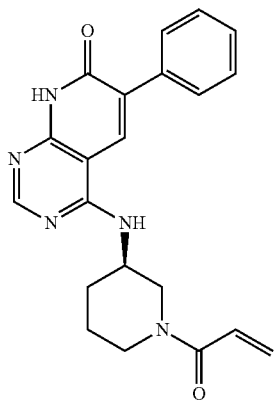 [SMILES: C=CC(=O)N1CCC[C@@H](Nc2ncnc3[nH]c(=O)c(-c4ccccc4)cc23)C1]

The mixture of compound 2-5 (199 mg, 0.62 mmol), acrylic acid (89 mg, 1.24 mmol), HATU (281 mg, 0.75 mmol) and DIEA (401 mg, 3.1 mmol) in DCM (4 mL) was reacted at r.t. for 16 h. The reaction solution was evaporated and the residue was purified by preparative HPLC to give the title compound (21 mg, 9%) as white solid.

LCMS (ESI) m/z: 376 (M+H)

$^1$H NMR (400 MHz, MeOD): δ ppm 8.36-8.28 (m, 2H), 7.70-7.68 (m, 2H), 7.42-7.34 (m, 3H), 6.79-6.72 (m, 1H), 6.21-6.15 (m, 1H), 5.75-5.68 (m, 1H), 4.59-4.00 (m, 3H), 3.19-3.14 (m, 1H), 2.96-2.88 (s, 1H), 2.15 (m, 1H), 1.92-1.60 (m, 3H)

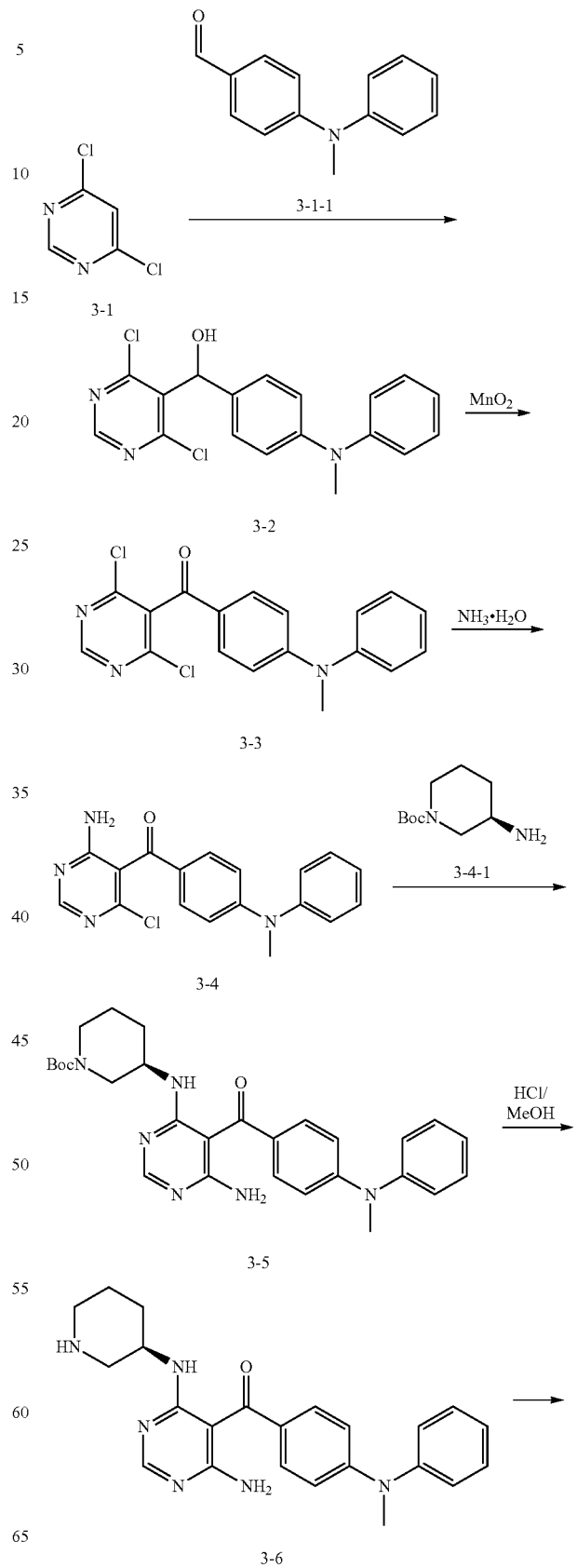

Scheme 3

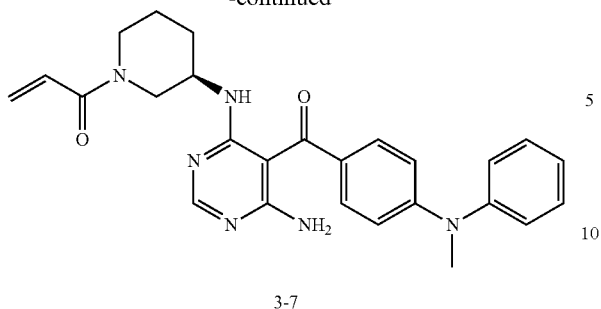

3-7

Example 3

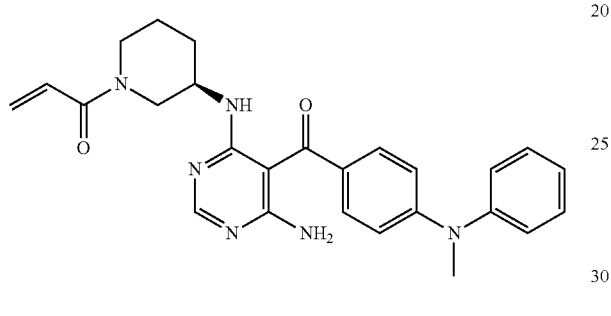

Synthesis of Compound 3-2

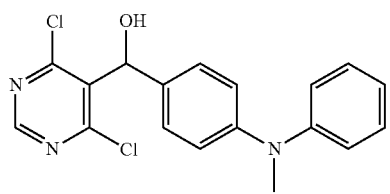 [SMILES: CN(c1ccccc1)c1ccc(C(O)c2c(Cl)ncnc2Cl)cc1]

To a solution of compound 3-1-1 (606 mg, 4.07 mmol) in THF (20 mL) was added dropwise LDA (3.6 mL, 4.27 mmol) under nitrogen atmosphere at −78° C., and then the reaction mixture was stirred at −78° C. for 0.5 h. To this solution, compound 3-1 (860 mg, 4.07 mmol) in THF (5 mL) was added slowly, and then the resulting solution was reacted at −78° C. for 2 h. The reaction was monitored by TLC (PE/EA=1:1) until the completion of reaction. Then saturated ammonium chloride (NH$_4$Cl) (aq., 50 mL) was added slowly to quench the reaction. The reaction mixture was extracted with EtOAc (10 mL×2), and the organic phases were combined, dried over anhydrous Na$_2$SO$_4$ and concentrated to give a crude product which was purified by silica gel column chromatography (PE/EA=5:1) to afford compound 3-2 (820 mg, Yield 56%).

LCMS (ESI) m/z: 360 (M+H)

Synthesis of Compound 3-3

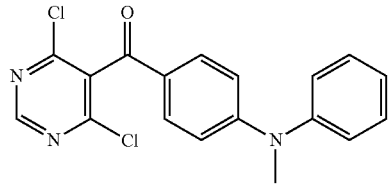 [SMILES: CN(c1ccccc1)c1ccc(C(=O)c2c(Cl)ncnc2Cl)cc1]

To a solution of compound 3-2 (820 mg, 2.28 mmol) in DCM (30 mL) was added active MnO$_2$ (1.983 g, 22.8 mmol), and then the reaction solution was reacted at 40° C. for 5 h, filtered and concentrated to give a residue which was purified by preparative thin layer chromatography (PE/EA=5:1) to afford compound 3-3 (814 mg, Yield 69%).

LCMS (ESI) m/z: 358 (M+H)

Synthesis of Compound 3-4

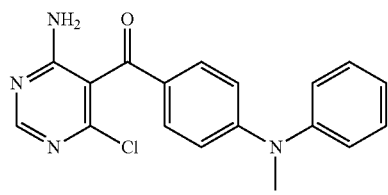 [SMILES: CN(c1ccccc1)c1ccc(C(=O)c2c(N)ncnc2Cl)cc1]

To a solution of compound 3-3 (560 mg, 2.2 mmol) in THF (10 mL) was added NH$_3$.H$_2$O (74.8 mg, 4.4 mmol), and then the reaction solution was stirred at 25° C. for 1 h. The reaction was monitored by TLC (PE/EA=1:1) until the completion of reaction. The reaction solution was diluted with water (10 mL) and extracted with EtOAc (10 mL×2). The organic phases were combined, dried over anhydrous Na$_2$SO$_4$ and concentrated to give compound 3-4 (736 mg, Yield 56%).

LCMS (ESI) m/z: 339 (M+H)

Synthesis of Compound 3-5

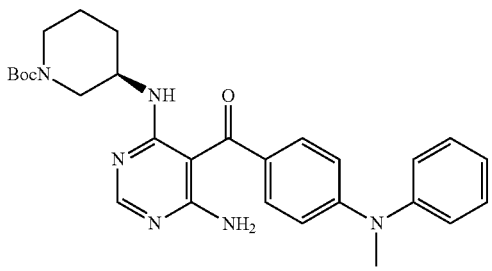 [SMILES: CN(c1ccccc1)c1ccc(C(=O)c2c(N)ncnc2N[C@@H]2CCCN(C(=O)OC(C)(C)C)C2)cc1]

To a solution of compound 3-4 (410 mg, 1.2 mmol) in i-PrOH (10 mL) was added compound 3-4-1 (360 mg, 1.8 mmol) and DIPA (310 mg, 2.4 mmol), and then the reaction solution was stirred under microwave at 110° C. for 2 h. The reaction was monitored by TLC (PE/EA=1:1) until the completion of reaction. The reaction solution was diluted with water (10 mL) and extracted with EtOAc (10 mL×2).

The organic phases were combined, dried over anhydrous Na₂SO₄ and concentrated to give compound 3-5 (602 mg, Yield 75%).

LCMS (ESI) m/z: 503 (M+H)

Synthesis of Compound 3-6

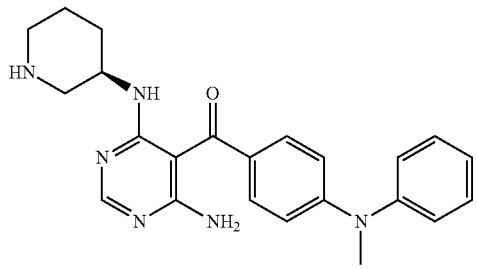 [SMILES: CN(c1ccccc1)c1ccc(C(=O)c2c(N)ncnc2N[C@@H]2CCCNC2)cc1]

To a solution of compound 3-5 (450 mg, 0.9 mmol) in DCM (10 mL) was added a solution of HCl in MeOH (3 mL, 4 M), and then the reaction solution was stirred at r.t. for 0.5 h. The reaction was monitored by TLC (DCM:MeOH=10:1) until the completion of reaction. The reaction solution was diluted with DCM (10 mL) and washed with water (20 mL). The aqueous phase was adjusted to pH 8 and extracted with DCM (10 mL×3). The organic phases were combined, dried over anhydrous Na₂SO₄ and concentrated to give compound 3-6 (362 mg, Yield 83%) which was used for the next step without further purification.

LCMS (ESI) m/z: 403 (M+H)

Synthesis of Compound 3-7

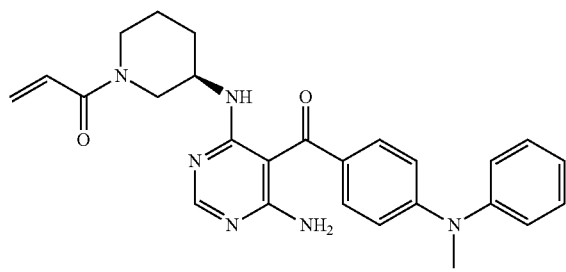 [SMILES: C=CC(=O)N1CCC[C@@H](Nc2ncnc(N)c2C(=O)c2ccc(N(C)c3ccccc3)cc2)C1]

To a solution of compound 3-6 (201 mg, 0.5 mmol) in DCM (1 mL) was separately added HATU (190 mg, 0.5 mmol), acrylic acid (36 mg, 0.5 mmol) and DIPEA (258 mg, 17 mmol), and then the reaction solution was stirred at 16° C. for 1 h. The reaction was monitored by LCMS until the completion of reaction. The reaction solution was washed with water (10 mL), and the organic phase was dried over anhydrous Na₂SO₄, concentrated and stripped to give a residue which was purified by preparative HPLC to afford compound 3-7 (30 mg, Yield 14%).

¹H NMR (400 MHz, CDCl₃): δ ppm 8.13 (s, 1H), 7.56-7.58 (m, 2H), 7.39-7.43 (m, 2H), 7.19-7.25 (m, 3H), 6.72-6.78 (m, 3H), 6.51-6.55 (m, 1H), 6.22-6.26 (m, 1H), 5.61-5.64 (m, 1H), 5.29-5.39 (m, 2H), 3.81-4.07 (m, 1H), 3.26-3.37 (m, 5H), 1.94-1.96 (m, 1H), 1.49-1.57 (m, 3H).

LCMS (ESI) m/z: 457 (M+1)

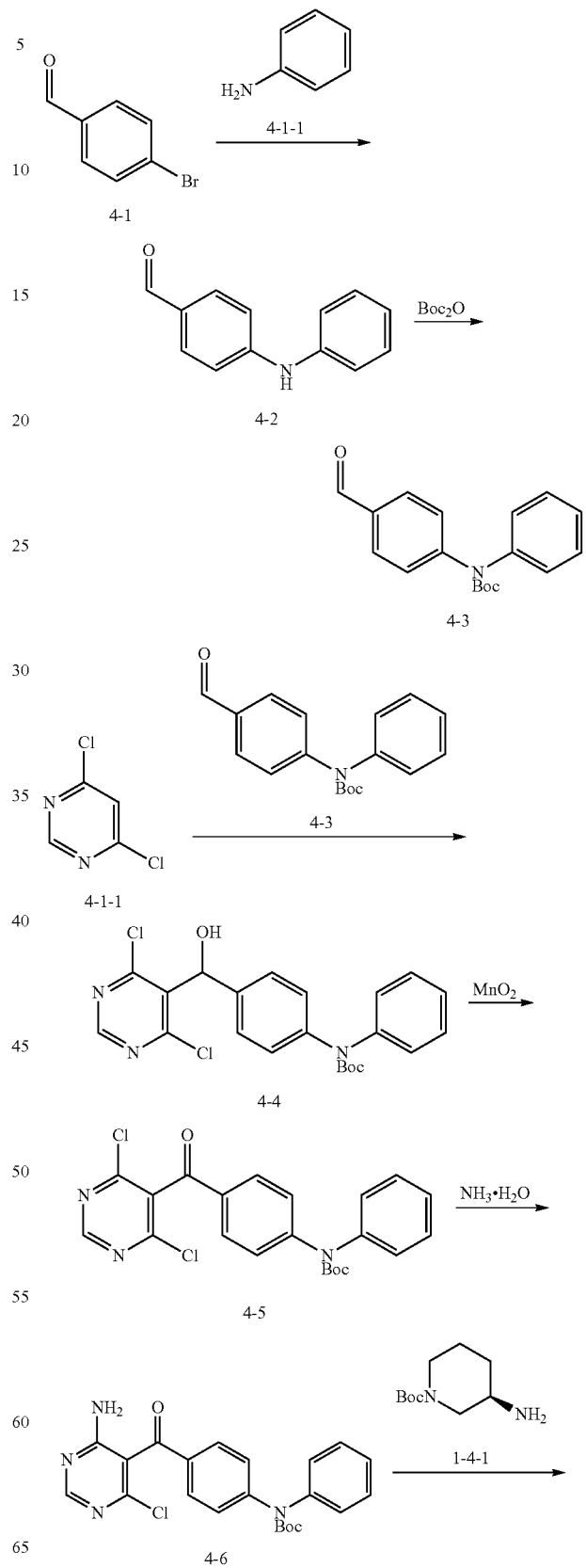

Scheme 4

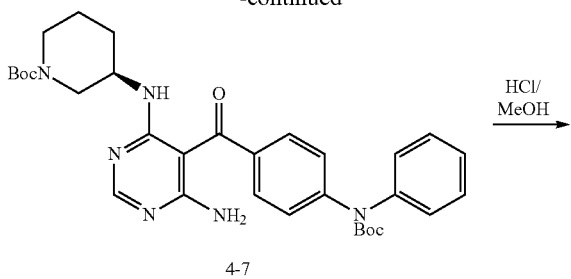

4-7

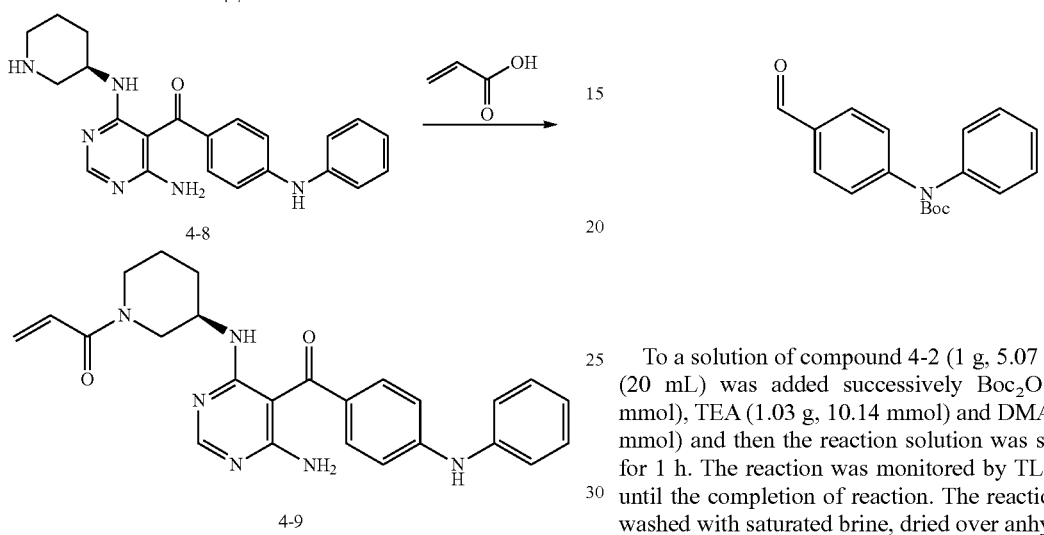

4-8

4-9

Example 4

Synthesis of Compound 4-2

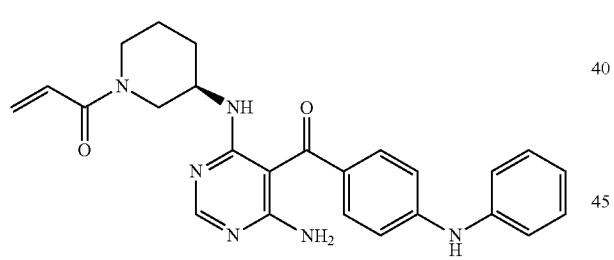

To a suspension of compound 4-1 (1 g, 5.4 mmol) and compound 4-1-1 (0.5 g, 5.4 mmol) in toluene (30 mL) was added successively Pd$_2$(dba)$_3$ (123 mg, 0.135 mmol), Xantphos (78 mg, 0.135 mmol) and Cs$_2$CO$_3$ (cesium carbonate) (3.52 g, 10.8 mmol) under nitrogen atmosphere, and then the reaction solution was heated to 110° C. and stirred for 16 h. The reaction was monitored by TLC (PE/EA=5:1) until the completion of reaction. The reaction solution was diluted with EtOAc (20 mL), filtered, concentrated and stripped to give a residue which was purified by silica gel column chromatography (PE/EA=4:1) to afford compound 4-2 (1.067 g, Yield 93%).

LCMS (ESI) m/z: 198 (M+1)

Synthesis of Compound 4-3

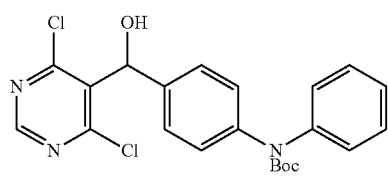

To a solution of compound 4-2 (1 g, 5.07 mmol) in DCM (20 mL) was added successively Boc$_2$O (1.33 g, 6.08 mmol), TEA (1.03 g, 10.14 mmol) and DMAP (0.12 g, 1.01 mmol) and then the reaction solution was stirred at 40° C. for 1 h. The reaction was monitored by TLC (PE/EA=5:1) until the completion of reaction. The reaction solution was washed with saturated brine, dried over anhydrous Na$_2$SO$_4$, filtered and concentrated to give a residue which was purified by silica gel column chromatography (PE/EA=5:1) to afford compound 4-3 (1.5 g, Yield 66%).

LCMS (ESI) m/z: 298 (M+1)

Synthesis of Compound 4-4

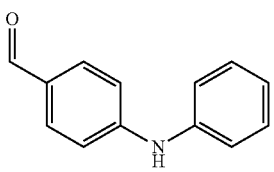 [SMILES: O=Cc1ccc(Nc2ccccc2)cc1]

To a solution of compound 4-1-1 (602 mg, 4.04 mmol) in THF (15 mL) was added dropwise LDA (4.2 mL, 4.2 mmol) under nitrogen atmosphere at −78° C., and then the reaction mixture was stirred at −78° C. for 0.5 h. To this solution, a solution of compound 4-3 (1 g, 3.37 mmol) in THF (5 mL) was added slowly, and then the reaction solution was reacted at −78° C. for 2 h. The reaction was monitored by TLC (PE/EA=5:1) until the completion of reaction. Then saturated NH$_4$Cl (aq., 50 mL) was added slowly to quench the reaction. The mixture was extracted with EtOAc (10 mL×2), and the organic phases were combined, dried over anhydrous Na$_2$SO$_4$ and concentrated to give a crude product which was purified by silica gel column chromatography (PE/EA=5:1) to afford compound 4-4 (1.5 g, Yield 66%).

LCMS (ESI) m/z: 446 (M+1)

Synthesis of Compound 4-5

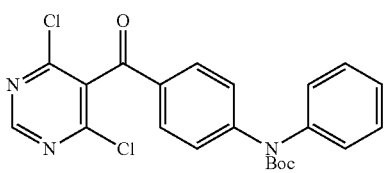 [SMILES: CC(C)(C)OC(=O)N(c1ccccc1)c1ccc(C(=O)c2c(Cl)ncnc2Cl)cc1]

To a solution of compound 4-4 (1 g, 2.24 mmol) in DCM (30 mL) was added active MnO₂ (1.95 g, 22.4 mmol), and then the reaction solution was stirred at 40° C. for 5 h. The reaction was monitored by TLC (PE/EA=5:1) until the completion of reaction. The reaction solution was filtered and concentrated to give a residue which was purified by preparative thin layer chromatography (PE/EA=5:1) to afford compound 4-5 (995 mg, Yield 63%).

Synthesis of Compound 4-6

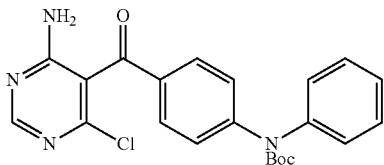 [SMILES: CC(C)(C)OC(=O)N(c1ccccc1)c1ccc(C(=O)c2c(N)ncnc2Cl)cc1]

To a solution of compound 4-5 (310 mg, 0.7 mmol) in THF (10 mL) was added NH₃·H₂O (74.8 mg, 2.8 mmol), and then the reaction solution was stirred under microwave at 80° C. for 1 h. The reaction was monitored by TLC (PE/EA=1:1) until the completion of reaction. The reaction solution was diluted with water (10 mL) and extracted with EtOAc (10 mL×2). The organic phases were combined, dried over anhydrous Na₂SO₄ and concentrated to give compound 4-6 (296 mg, Yield 95%).

Synthesis of Compound 4-7

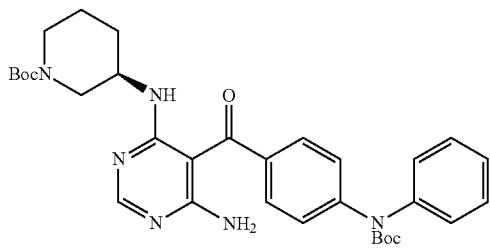 [SMILES: CC(C)(C)OC(=O)N1CCC[C@@H](Nc2ncnc(N)c2C(=O)c2ccc(N(C(=O)OC(C)(C)C)c3ccccc3)cc2)C1]

To a solution of compound 4-6 (280 mg, 0.6592 mmol) in i-PrOH (10 mL) was added compound 1-4-1 (198 mg, 0.988 mmol) and DIPA (170 mg, 1.32 mmol), and then the reaction solution was stirred under microwave at 110° C. for 2 h. The reaction was monitored by TLC (PE/EA=1:1) until the completion of reaction. The reaction solution was diluted with water (10 mL) and extracted with EtOAc (10 mL×2). The organic phases were combined, dried over anhydrous Na₂SO₄ and concentrated to give compound 4-7 (388 mg, Yield 57%).

LCMS (ESI) m/z: 589 (M+1)

Synthesis of Compound 4-8

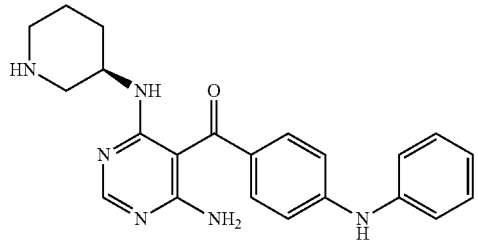 [SMILES: Nc1ncnc(N[C@@H]2CCCNC2)c1C(=O)c1ccc(Nc2ccccc2)cc1]

To a solution of compound 4-7 (320 mg, 0.54 mmol) in DCM (10 mL) was added dropwise a solution of HCl in MeOH (2 mL, 4 M), and then the reaction solution was stirred at r.t. for 0.5 h. The reaction was monitored by TLC (DCM:MeOH=10:1) until the completion of reaction. The reaction solution was diluted with DCM (10 mL) and washed with water (20 mL). The aqueous phase was adjusted to pH 8 and extracted with DCM (10 mL×3). The organic phases were combined, dried over anhydrous Na₂SO₄ and concentrated to give compound 4-8 (10 mg, Yield 50%) which was used for the next step without further purification.

Synthesis of Compound 4-9

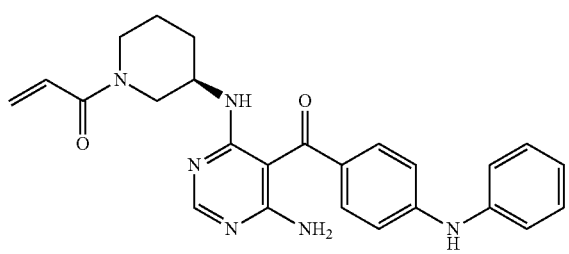 [SMILES: C=CC(=O)N1CCC[C@@H](Nc2ncnc(N)c2C(=O)c2ccc(Nc3ccccc3)cc2)C1]

To a solution of compound 4-8 (105 mg, 0.27 mmol) in DCM (5 mL) was separately added HATU (102.6 mg, 0.27 mmol), acrylic acid (19.5 mg, 0.27 mmol) and DIPEA (70 mg, 0.54 mmol), and then the reaction solution was stirred at 16° C. for 1 h. The reaction was monitored by LCMS until the completion of reaction. The reaction solution was concentrated and stripped to give a residue which was purified by preparative HPLC to afford compound 4-9 (20 mg, Yield 17%).

$^{1}$H NMR (400 MHz, CDCl₃): δ ppm 8.13 (s, 1H), 7.58-7.60 (m, 2H), 7.31-7.36 (m, 2H), 7.16-7.18 (m, 1H), 6.75-7.07 (m, 2H), 6.53-6.56 (m, 1H), 6.35-6.377 (m, 1H), 6.22-6.26 (m, 1H), 5.63-5.65 (m, 1H), 5.41-5.63 (m, 2H), 4.07-4.24 (m, 1H), 3.06-3.87 (m, 3H), 1.87-1.92 (m, 2H), 1.52-1.54 (m, 2H).

LCMS (ESI) m/z: 443 (M+1).

Scheme 5
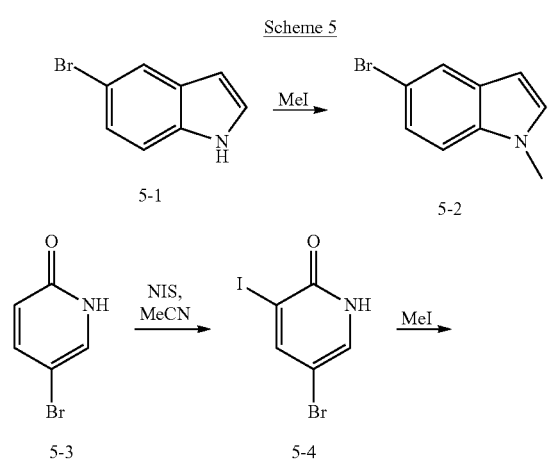
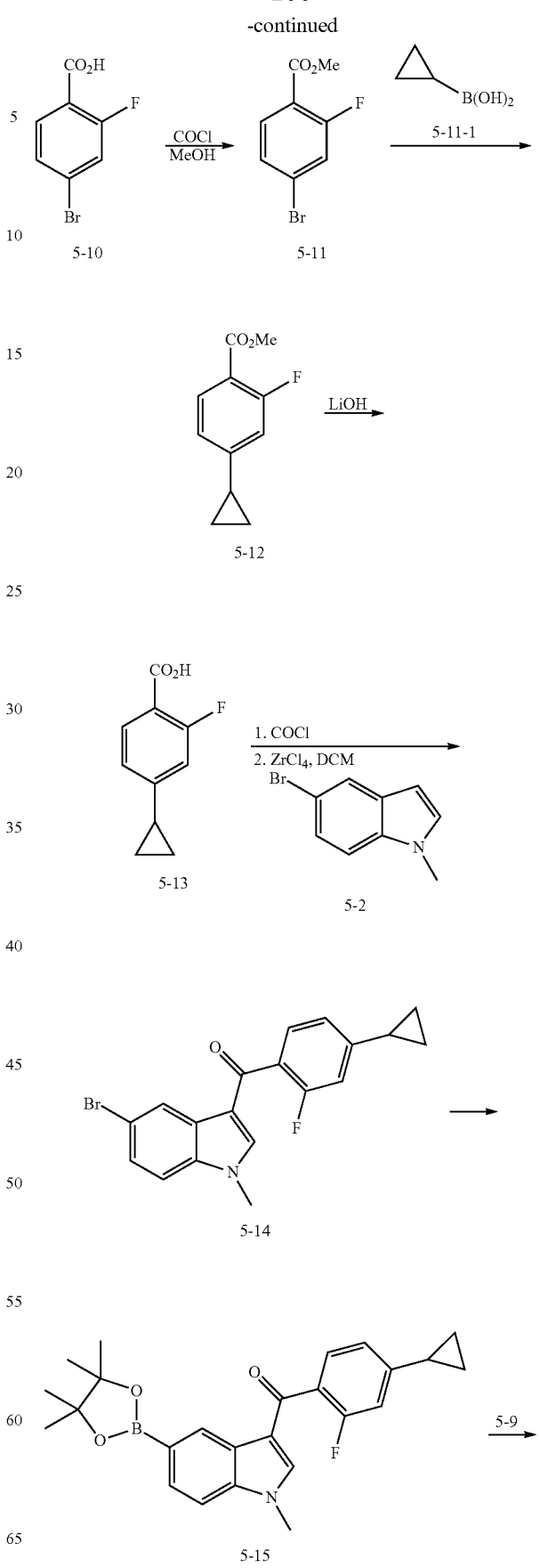

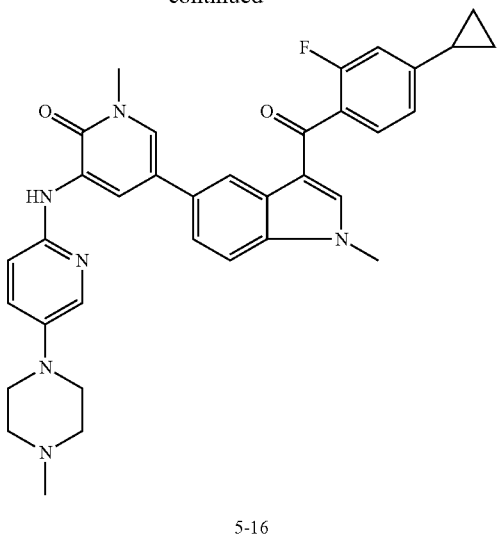

5-16

Example 5

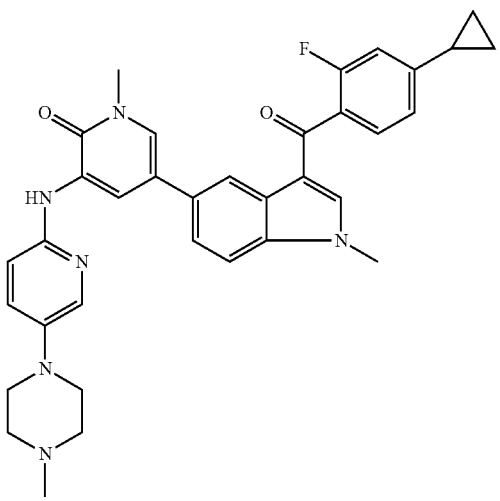 [SMILES: CN1CCN(c2ccc(Nc3cc(-c4ccc5c(c4)c(C(=O)c4ccc(C6CC6)cc4F)cn5C)cn(C)c3=O)nc2)CC1]

Synthesis of Compound 5-2

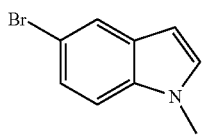

To a solution of compound 5-1 (5 g, 25.5 mmol) in dry DMF (100 mL) was added sodium hydride (NaH) (1.53 g, 38.26 mmol) under nitrogen atmosphere in an ice bath (0° C.), and then the reaction solution was warmed to r.t. and was reacted for 0.5 h. To this solution, all MeI (7.24 g, 38.26 mmol) was added at once and then the resulting solution was reacted at r.t. for 1 h. The reaction was monitored by TLC until the completion of reaction. Then saturated NH$_4$Cl (aq.) was added to the solution to quench the reaction. The reaction solution was extracted with EtOAc (100 mL) twice, and the organic phase was washed with saturated brine (50 mL×2), dried over anhydrous Na$_2$SO$_4$, filtered and concentrated to remove solvent, therefore obtaining compound 5-2 (4.9 g, Yield 91.5%).

$^1$HNMR (400 MHz, CDCl$_3$): δ ppm 7.74-7.75 (m, 1H), 7.28-7.31 (m, 1H), 7.18-7.21 (m, 1H), 7.04-7.06 (m, 1H), 6.41-6.43 (m, 1H), 3.78 (s, 3H)

Synthesis of Compound 5-4

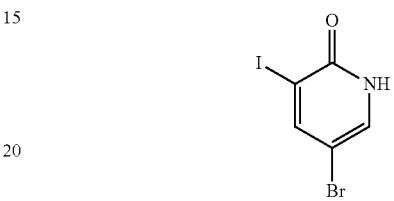

To compound 5-3 (10 g, 57.5 mmol) in acetonitrile (100 ml) was added NIS (13 g, 75.1 mmol) under nitrogen atmosphere, and then the reaction mixture was reacted at 90° C. for 2 h. The reaction was monitored by TLC until the completion of reaction. The reaction solution was filtered, and the filter cake was washed with MeOH and PE, and dried over anhydrous Na$_2$SO$_4$ to give compound 5-4 (10 g, Yield 58%) as yellow solid.

Synthesis of Compound 5-5

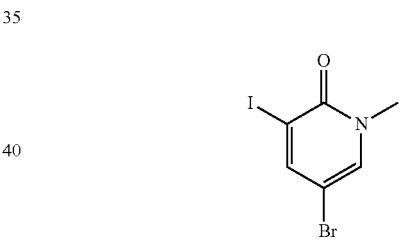

To a solution of compound 5-4 (10 g, 33.35 mmol) in DME (100 ml) was added MeI (9.47 g, 66.69 mmol) and K$_2$CO$_3$ (potassium carbonate) (9.22 g, 66.69 mmol), and then the reaction mixture was reacted at 100° C. for 2 h, filtered and concentrated to give compound 5-5 (10 g, Yield 95.5%).

LCMS (ESI) m/z: 314 (M+1).

Synthesis of Compound 5-7

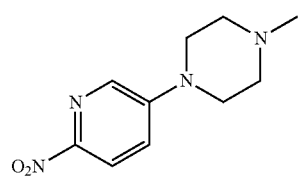 [SMILES: CN1CCN(c2ccc([N+](=O)[O-])nc2)CC1]

To a solution of compound 5-6 (100 mg, 0.985 mmol) in DMSO (3 ml) was added compound 5-6-1 (148 mg, 1.48 mmol), K$_2$CO$_3$ (204.25 mg, 1.48 mmol) and tetrabutylammonium fluoride (TBAF) (17.5 mg, 0.049 mmol), and then the reaction mixture was reacted at 80° C. for 16 h. The reaction was monitored by TLC until the completion of reaction. The reaction solution was poured into ice water (100 mL) and filtered, and the resulting filter cake was washed with water (50 mL) to give compound 5-7 (100 mg, Yield 91%).

$^1$HNMR (400 MHz, d$_6$-DMSO): δ ppm 8.22-8.23 (m, 1H), 8.10-8.12 (m, 1H), 7.43-7.47 (m, 1H), 3.44-3.47 (m, 4H), 2.39-2.42 (m, 4H), 2.19 (s, 3H).

Synthesis of Compound 5-8

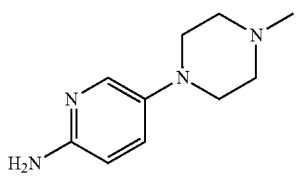

To a solution of compound 5-7 (3 g, 13.5 mmol) in MeOH (300 ml) was added Pd/C (3 g). The atmosphere in the vessel was replaced by hydrogen for several times, and then the reaction solution was reacted under a hydrogen pressure of 30 Psi at r.t. for 16 h. The reaction was monitored by TLC until the completion of reaction. The reaction solution was filtered and concentrated to remove solvent, therefore obtaining compound 5-8 (2.8 g, Yield 98.5%).

$^1$H NMR (400 MHz, d$_6$-DMSO): δ ppm 7.74-7.76 (m, 1H), 7.14-7.12 (m, 1H), 6.43-6.47 (m, 1H), 4.14 (br.s, 2H), 3.03-3.04 (m, 4H), 2.54-2.56 (m, 4H), 2.18 (s, 3H)

Synthesis of Compound 5-9

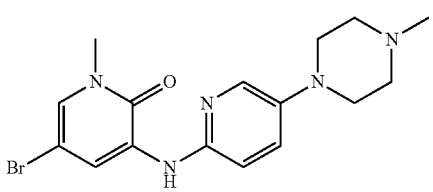 [SMILES: CN1CCN(c2ccc(Nc3cc(Br)cn(C)c3=O)nc2)CC1]

To a suspension of compound 5-8 (1 g, 3.13 mmol), compound 5-5 (600 mg, 3.13 mmol) and Cs$_2$CO$_3$ (3.12 g, 9.40 mmol) in 1,4-dioxane (10 mL) was added L-proline (147 mg, 0.652 mmol) and CuI (122 mg, 0.326 mmol) under nitrogen atmosphere, and then the reaction solution was heated to 120° C. and was stirred for 18 h. The resulting reaction solution was filtered and concentrated to remove the solvent. The residue was purified by silica gel column chromatography (DCM:MeOH=50:1 to 25:1) to give compound 5-9 (50 mg, Yield 4%).

LCMS (ESI) m/z: 378 (M+1)

Synthesis of Compound 5-11

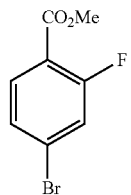

To a suspension of compound 5-10 (12 g, 54.79 mmol) in DCM (120 mL) was added oxalyl chloride (COCl) (10.43 g, 82.19 mmol) and two drops of DMF in a catalytic quantity at 0° C. under nitrogen atmosphere, and then the reaction solution was reacted under nitrogen atmosphere at r.t. for 3 h. Then the solvent was removed, MeOH (100 mL) was added, and the resulting reaction solution was reacted at r.t. for 18 h. After TLC indicated the reaction was complete, the reaction solution was concentrated, and the residue was dissolved in EtOAc (100 mL) and washed with saturated Na$_2$CO$_3$ (aq., 50 mL). The organic phase was dried over anhydrous Na$_2$SO$_4$, filtered, and concentrated to give purified compound 5-11 (12 g, Yield 93.97%).

Synthesis of Compound 5-12

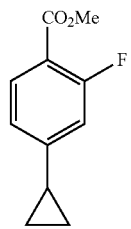

To a suspension of compound 5-11 (3 g, 12.87 mmol), compound 5-11-1 (1.44 g, 16.74 mmol) and K$_3$PO$_4$ (potassium phosphate) (5.47 g, 25.75 mmol) in toluene/THF/water (3:2:1) (50 mL) was added Pd(dppf)Cl$_2$ (941 mg, 1.287 mmol), and then the reaction solution was heated to 90° C. and stirred for 16 h under nitrogen atmosphere. After TLC indicated the reaction was complete, the resulting solution was extracted with EtOAc (30 mL×3), and the organic phase was dried over anhydrous Na$_2$SO$_4$, filtered, concentrated and stripped to give a residue which was purified with ISCO (PE:EtOAc=20:1) to afford compound 5-12 (2.5 g, Yield 100%).

Synthesis of Compound 5-13

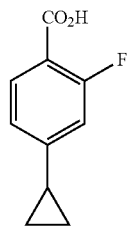

To a mixture of compound 5-12 (1.4 g, 7.21 mmol) in THF (10 mL), MeOH (3 mL) and water (3 mL) was added LiOH.H₂O (1.29 g, 1.41 mmol), and the reaction mixture was stirred at r.t. for 6 h. The reaction solution was cooled down with an ice bath, adjusted to pH 3 with 1N HCl and extracted with DCM (20 mL×3). The organic phases were combined, dried over anhydrous Na₂SO₄, filtered and stripped to give targeted compound 5-13 (1.3 g, Yield 90.55%) as white solid.

Synthesis of Compound 5-14

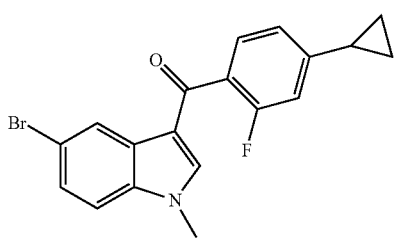 [SMILES: Cn1cc(C(=O)c2ccc(C3CC3)cc2F)c2cc(Br)ccc21]

To a suspension of compound 5-13 (1 g, 5.55 mmol) in DCM (10 mL) was added slowly COCl (0.92 g, 7.21 mmol) and one drop of DMF in a catalytic quantity under nitrogen atmosphere at 0° C. The reaction solution was reacted at r.t. for 3 h, followed by concentration to remove solvent. To this solution of compound 5-2 (1.51 g, 7.21 mmol) and ZrCl₄ (1.94 g, 8.32 mmol) in DCM (3 mL) was added the COCl under nitrogen atmosphere at 0° C., and the reaction mixture was warmed to r.t. and reacted for 16 h. The resulting reaction mixture was diluted with water (10 mL) and extracted with DCM (10 mL×3). The organic phases were combined, washed with saturated Na₂CO₃ (aq., 10 mL), dried over anhydrous Na₂SO₄, filtered, concentrated and stripped to give a residue which was purified with ISCO (PE:EtOAc=5:1) to afford compound 5-14 (540 mg, Yield 27%) as white solid.

LCMS (ESI) m/z: 374 (M+1)

Synthesis of Compound 5-15

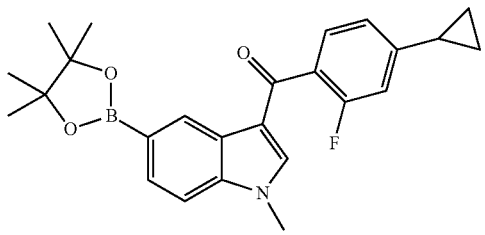 [SMILES: Cn1cc(C(=O)c2ccc(C3CC3)cc2F)c2cc(B3OC(C)(C)C(C)(C)O3)ccc21]

To a suspension of compound 5-14 (100 mg, 0.268 mmol), (BPin)₂ (89 mg, 0.349 mmol) and potassium acetate (79 mg, 0.806 mmol) in 1,4-dioxane (1 mL) was added Pd(dppf)Cl₂ (20 mg, 0.0268 mmol) under nitrogen atmosphere, and the reaction solution was heated to 100° C. and reacted for 18 h under nitrogen atmosphere. After TLC indicated the reaction was complete, the resulting solution was concentrated to remove solvent, and the residue was diluted with EtOAc (10 mL) and water (10 mL), and extracted with EtOAc (5 mL×3). The organic phases were combined, dried over anhydrous Na₂SO₄, filtered and stripped to give compound 5-15 (120 mg, Yield 100%) as black oil.

LCMS (ESI) m/z: 420 (M+1)

Synthesis of Compound 5-16

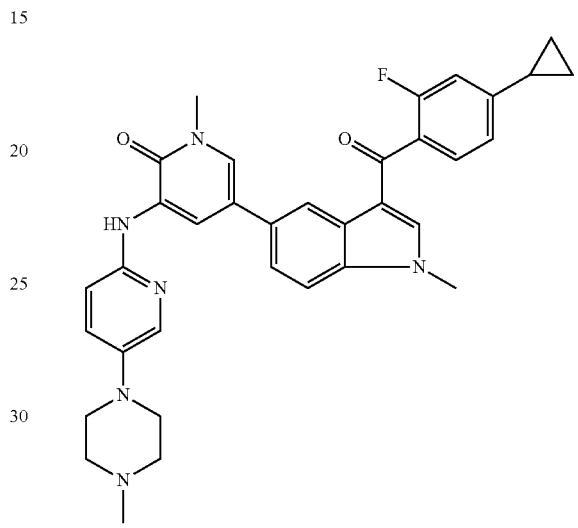

To a suspension of compound 5-15 (20 mg, 0.0528 mmol), compound 5-9 (29 mg, 0.0688 mmol) and Cs₂CO₃ (52 mg, 0.1 mmol) in 1,4-dioxane (0.5 mL) was added Pd(dppf)Cl₂ (4 mg, 0.00528 mmol) under nitrogen atmosphere, and then the reaction mixture was heated to 100° C. and stirred for 18 h under nitrogen atmosphere. The reaction was monitored by LCMS until the completion of reaction. The resulting solution was filtered, diluted with water (10 mL) and extracted with EtOAc (10 mL×3). The organic phases were combined, dried over anhydrous Na₂SO₄, filtered, concentrated and stripped to give a residue which was purified by preparative HPLC to afford compound 5-16 (16.58 mg, Yield 59%) as yellow solid.

¹H NMR (400 MHz, MeOD): δ ppm 8.47 (s, 1H), 8.01-8.08 (m, 3H), 7.76 (s, 1H), 7.76-7.78 (m, 2H), 7.51-7.59 (m, 1H), 7.42-7.44 (m, 1H), 7.29-7.32 (m, 1H), 7.01-7.03 (m, 1H), 6.93-6.95 (m, 1H), 3.87 (s, 3H), 3.76-3.80 (m, 5H), 3.62-3.65 (m, 2H), 3.30-3.33 (m, 2H), 3.11-3.17 (m, 2H), 2.97 (s, 3H), 1.99-2.02 (m, 1H), 1.05-1.11 (m, 2H), 0.77-0.80 (m, 2H).

LCMS (ESI) m/z: 591 (M+1)

Scheme 6
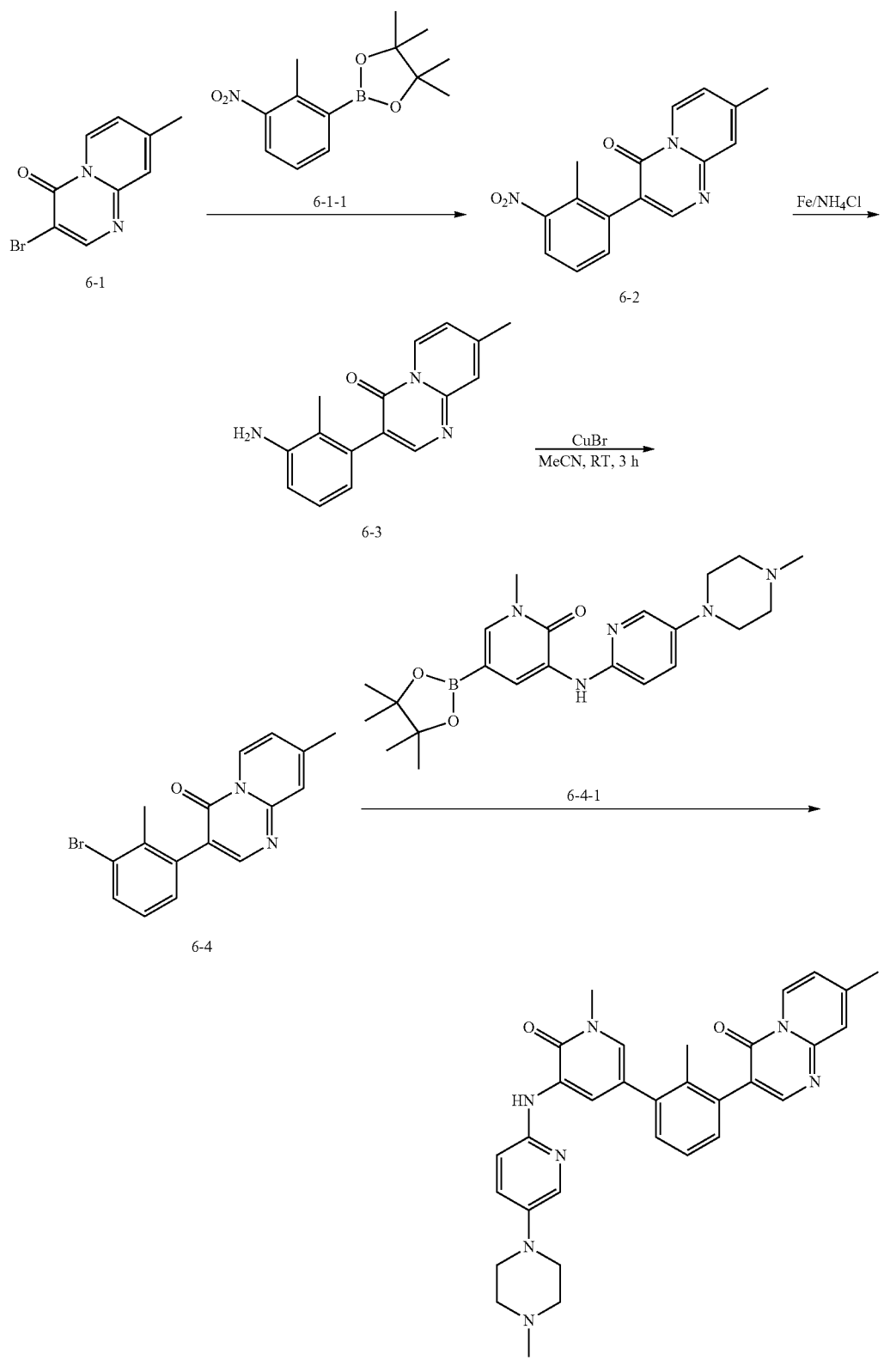

Example 6

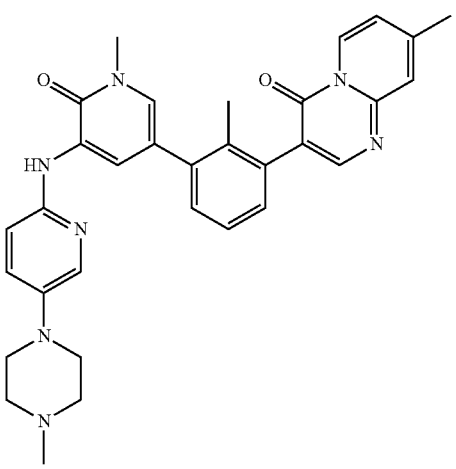 [SMILES: Cc1ccn2c(=O)c(-c3cccc(-c4cc(Nc5ccc(N6CCN(C)CC6)cn5)c(=O)n(C)c4)c3C)cnc2c1]

Synthesis of Compound 6-2

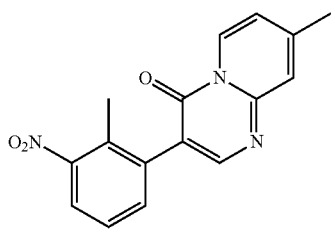 [SMILES: Cc1ccn2c(=O)c(-c3cccc([N+](=O)[O-])c3C)cnc2c1]

To a suspension of compound 6-1 (30 mg, 0.0795 mmol) and compound 6-1-1 (25 mg, 0.095 mol) in 1,4-dioxane (3 mL) was separately added $K_2CO_3$ (13 mg, 0.095 mol) and Pd(dppf)Cl$_2$ (0.01 g) under nitrogen atmosphere. The atmosphere in the vessel was replaced by nitrogen for several times, and then the reaction solution was heated to 100° C. and reacted 0/N. The solvent was removed by rotary evaporation, and the residue was purified by column chromatography to give compound 6-2 (25 mg, Yield 71%).

Synthesis of Compound 6-3

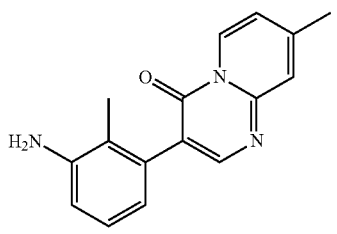

To a solution of compound 6-2 (0.44 g, 1.5 mmol) and NH$_4$Cl (0.48 g, 9 mmol) in EtOH (20 mL) and water (2 mL) added iron powder (0.5 g, 9 mmol), and the reaction solution was heated and refluxed for 1 h. The reaction was monitored by TLC until the completion of reaction. The solvent was removed by rotary evaporation, and the residue was purified by silica gel column chromatography to give compound 6-3 (0.3 g, Yield 77%).

LCMS (ESI) m/z: 266 (M+1)

Synthesis of Compound 6-4

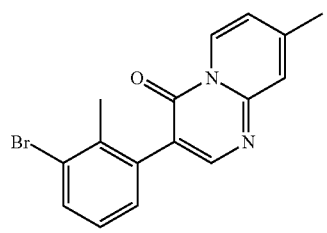 [SMILES: Cc1ccn2c(=O)c(-c3cccc(Br)c3C)cnc2c1]

The t-BuNO$_2$ (6 mg, 0.06 mmmol) and CuBr (11 mg, 0.075 mmol) was dissolved in CH$_3$CN (2 mL) and stirred at r.t. for 0.5 h, and compound 6-3 (20 mg, 0.05 mmmol) was added to this solution under nitrogen atmosphere and the reaction mixture was reacted at r.t. for 3 h. After TLC indicated the reaction was complete, then the reaction solution was filtered and concentrated to dryness by rotary evaporation to give a crude product which was purified by silica gel column chromatography (PE:EtOAc=5:1) to afford compound 6-4 (10 mg, Yield 62.5%).

Synthesis of Compound 6-5

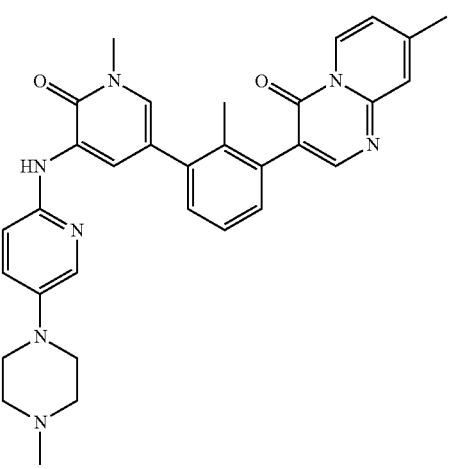 [SMILES: Cc1ccn2c(=O)c(-c3cccc(-c4cc(Nc5ccc(N6CCN(C)CC6)cn5)c(=O)n(C)c4)c3C)cnc2c1]

To a solution of compound 6-4 (20 mg, 0.06 mmol) and compound 6-4-1 (40 mg, 0.09 mmol) in 1,4-dioxane and water (3:1, 2 mL) was successively added Cs$_2$CO$_3$ (39 mg, 0.12 mmol) and Pd(dppf)Cl$_2$ (4 mg, 0.006 mmol) under nitrogen atmosphere. The atmosphere in the vessel was replaced by nitrogen for several times. Then the reaction solution was reacted under microwave at 100° C. for 0.5 h. The reaction was monitored by TLC until the completion of reaction. The reaction solution was filtered and concentrated to dryness by rotary evaporation to give a crude product which was purified by HPLC (HCl) to afford the title compound (13 mg, Yield 39.6%) as white solid.

$^1$H NMR (CDCl$_3$, 400 MHz): δ ppm 9.13-9.12 (m, 1H), 8.49-8.30 (m, 1H), 8.38 (s, 1H), 8.19 (s, 1H), 7.93 (s, 1H), 7.68 (s, 1H), 7.32-7.28 (m, 3H), 7.17-7.15 (m, 1H), 6.91 (s, 1H), 6.83-6.81 (m, 1H), 3.72-3.70 (m, 3H), 3.51-3.41 (m, 6H), 2.88 (s, 3H), 2.60 (s, 3H), 2.24 (s, 3H), 2.04-2.03 (m, 2H)
Example 7
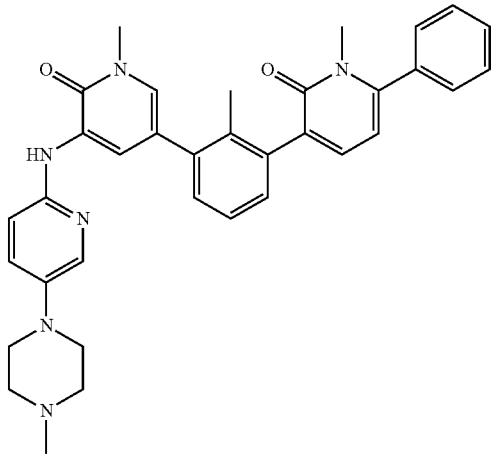 [SMILES: Cc1c(-c2cc(Nc3ccc(N4CCN(C)CC4)cn3)c(=O)n(C)c2)cccc1-c1ccc(-c2ccccc2)n(C)c1=O]
In Example 7, the systhesis process was similar to that in example 6.
LCMS (ESI) m/z: 573 (M+1)
Scheme 7
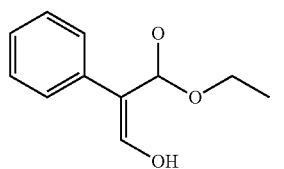
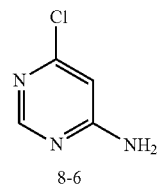
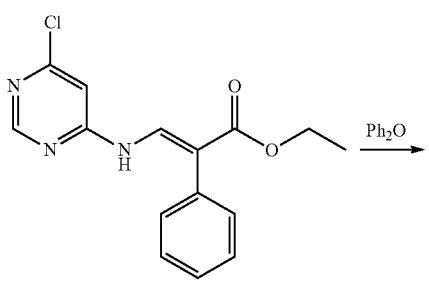
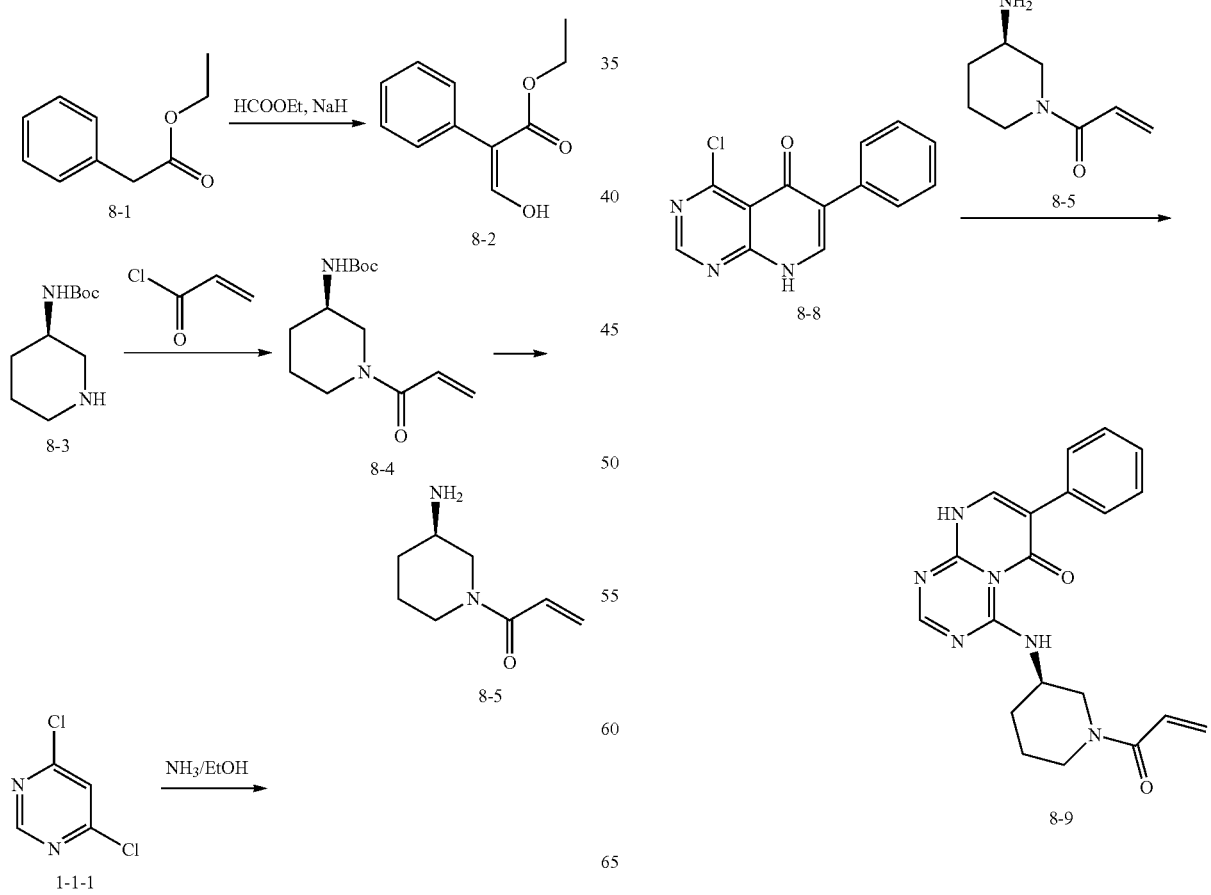

Example 8

Synthesis of Compound 8-2

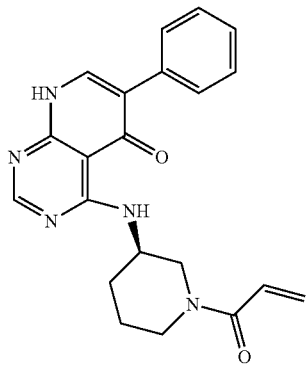

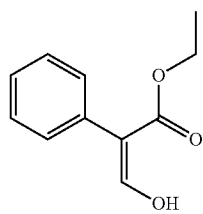

To a suspension of compound 8-1 (10 g, 0.061 mmol) and NaH (3.2 g, 0.079 mmol) in THF (50 mL) was added slowly HCOOEt (4.5 g, 0.061 mmol) at 0° C., and then the reaction solution was warmed slowly to r.t. and stirred O/N. The reaction was quenched by HCl, and the reaction solution was filtered. The organic phases were combined, washed with saturated brine, dried over anhydrous $Na_2SO_4$ and concentrated to give targeted product 8-2 (8 g, Yield 68%).

LCMS (ESI) m/z: 193 (M+1)

Synthesis of Compound 8-4

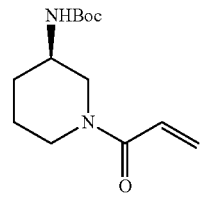 [SMILES: C=CC(=O)N1CCC[C@@H](NC(=O)OC(C)(C)C)C1]

To a solution of compound 8-3 (1 g, 5 mmol) in DCM (10 mL) was added DIPEA (1.29 g, 10 mmol) and acryloyl chloride (450 mg, 5 mmol) at 0° C., and the reaction solution was warmed slowly to r.t. and reacted for 1 h. After TLC indicated the reaction was complete, the reaction solution was concentrated to dryness, and the residue was purified by silica gel column chromatography to give compound 8-4 (1 g, Yield 78%).

LCMS (ESI) m/z: 255 (M+1)

Synthesis of Compound 8-5

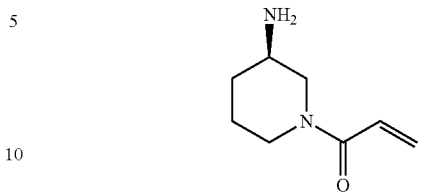

Compound 8-4 (1 g, 3.9 mmol) was dissolved in a solution of HCl in EtOAc (20 mL, 4 M), and then the mixture was stirred at r.t. for 6 h. The reaction was monitored by TLC until the completion of reaction. The reaction solution was concentrated to dryness, and the residue was purified by silica gel column chromatography to give compound 8-5 (0.2 g, Yield 33%).

LCMS (ESI) m/z: 155 (M+1)

Synthesis of Compound 8-6

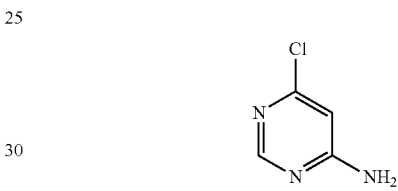

Compound 1-1-1 (10 g, 67.1 mmol) was disposed into a stainless steel vessel, and EtOH saturated with $NH_3$ (g) in advance (40 mL) was added. The reaction mixture was heated to 80° C., reacted for 1.5 h, and then cooled down to r.t., concentrated in vacuo and stripped to give a crude product which was triturated with water and filtered to afford compound 8-6 (6.7 g, Yield 77%).

$^1$H NMR (400 MHz, DMSO-$d_6$): δ ppm 8.20 (s, 1H), 7.22 (s, 2H), 6.45 (s, 1H)

Synthesis of Compound 8-7

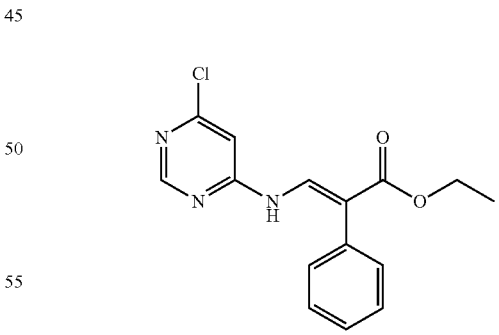

Compound 8-6 (2 g, 15.5 mmol) and compound 8-2 (3.57 g, 18.6 mmol) were dissolved in EtOH (140 mL), and then the reaction solution was heated and refluxed for 15 h. After TLC indicated the reaction was complete, then the reaction solution was cooled down to r.t., concentrated and stripped to give compound 8-7 (1.5 g, Yield 33%).

$^1$H NMR (CDCl$_3$ 400 MHz): δ ppm 10.81-10.78 (m, 1H), 8.57 (s, 1H), 8.06-8.03 (m, 1H), 7.38-7.28 (m, 5H), 6.76 (s, 1H), 4.33-4.28 (m, 2H), 1.34-1.31 (m, 3H)

Synthesis of Compound 8-8

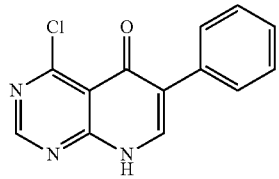 [SMILES: O=c1c(-c2ccccc2)c[nH]c2ncnc(Cl)c12]

Compound 8-7 (0.5 g, 1.65 mmol) was all added into boiling diphenyl ether (Ph₂O) (1 mL) at once, and the reaction mixture was reacted at reflux for 0.5 h. The reaction was monitored by TLC until the completion of reaction. The reaction solution was cooled down to r.t., diluted with hexane and filtered to give compound 8-8 (0.2 g, Yield 48%) as yellow solid.

Synthesis of Compound 8-9

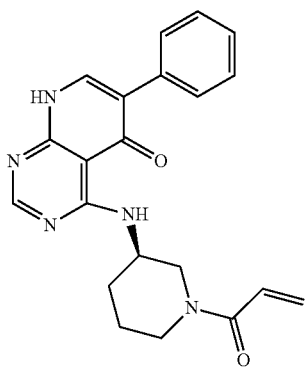 [SMILES: C=CC(=O)N1CCC[C@@H](Nc2ncnc3[nH]cc(-c4ccccc4)c(=O)c23)C1]

To compound 8-8 (0.1 g, 0.389 mmol) and DIPA (100 mg, 0.778 mmol) in EtOH (3 mL) was added compound 8-5 (60 mg, 0.389 mmol). The reaction was monitored by TLC until the completion of reaction. The solvent was removed by rotary evaporation, and the residue was purified by HPLC (acid) to give compound 8-9 (20 mg, Yield 14%).

$^1$H NMR (400 MHz, MeOD): δ ppm 8.24 (s, 1H), 7.69-7.67 (m, 2H), 7.45-7.39 (m, 3H), 7.33-7.29 (m, 1H), 6.81-6.78 (m, 1H), 6.31-6.18 (m, 1H), 5.79-5.71 (m, 1H), 4.08 (m, 1H), 3.38-3.32 (m, 4H), 2.14-2.05 (m, 1H), 1.95-1.91 (m, 1H), 1.75-1.66 (m, 2H).

LCMS (ESI) m/z: 330 (M+1)

Scheme 8

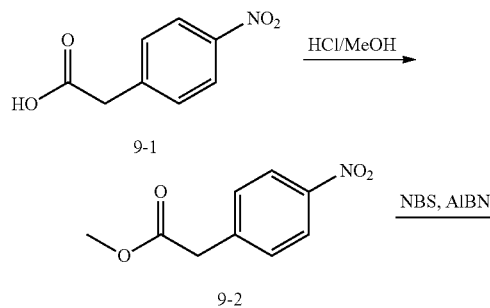

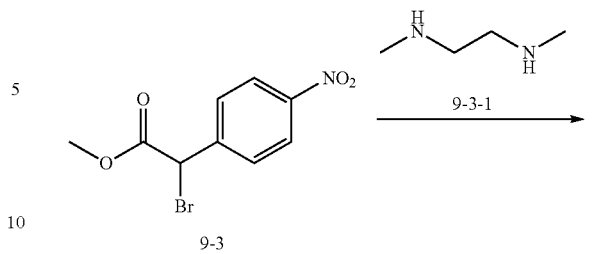

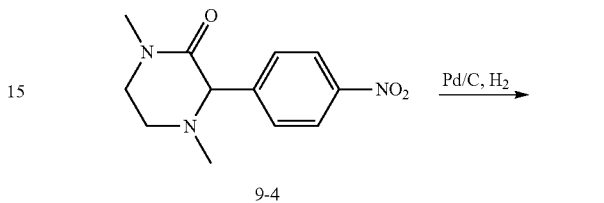

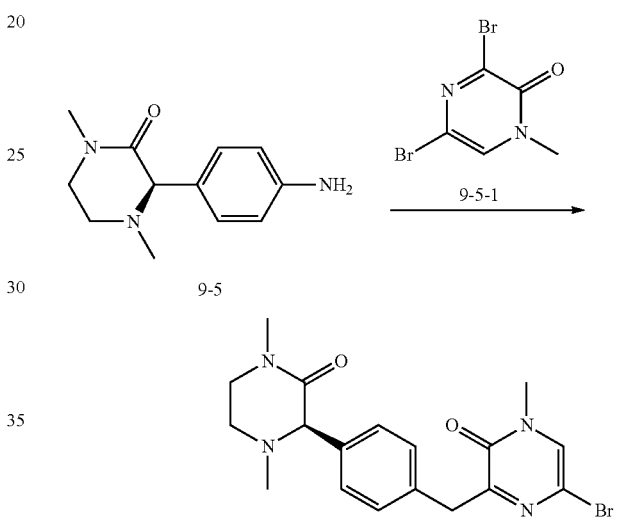

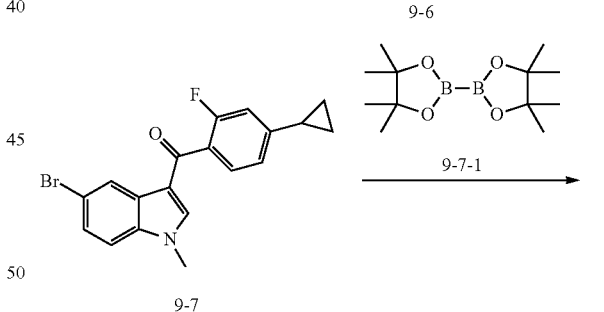

117

-continued

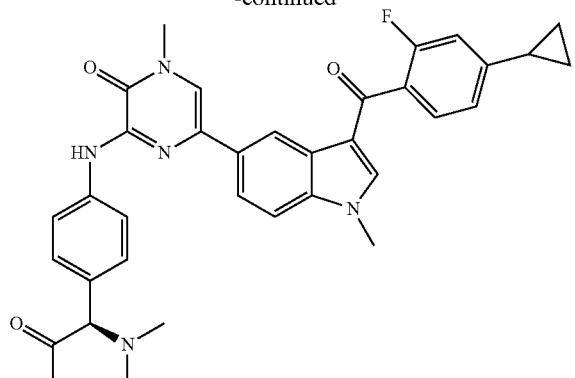

9-9

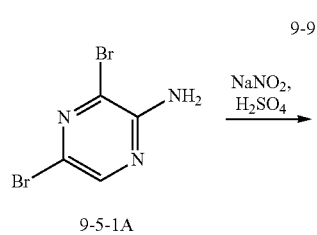

9-5-1A

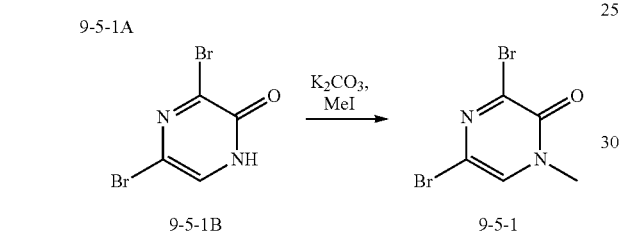

9-5-1B    9-5-1

Example 9

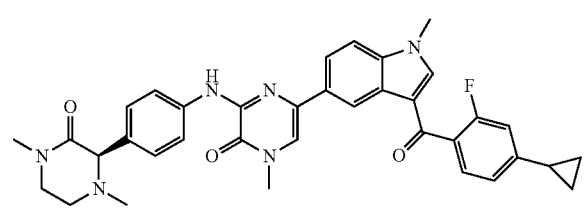 [SMILES: CN1CCN(C)[C@H](c2ccc(Nc3nc(-c4ccc5c(c4)c(C(=O)c4ccc(C6CC6)cc4F)cn5C)cn(C)c3=O)cc2)C1=O]

Synthesis of Compound 9-2

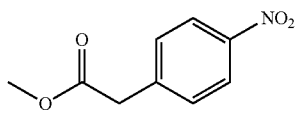

Compound 9-1 was refluxed in a solution of HCl in MeOH (500 ml) for 12 h, and then the resulting solution was concentrated to give compound 9-2 (brown solid, 53 g, Yield 100%).

$^1$H NMR (400 MHz, CDCl$_3$): δ ppm 8.21 (d, J=8 Hz, 2H), 7.48 (d, J=8 Hz, 2H), 3.77 (s, 2H), 3.75 (s, 3H).

Synthesis of Compound 9-3

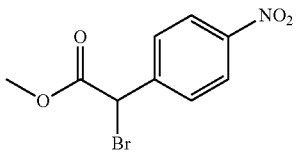

To a solution of compound 9-2 (20 g, 103 mmol) in carbon tetrachloride (CCl$_4$) (200 mL) was added AIBN (0.84 g, 5.15 mmol) and NBS (20 g, 113 mmol) under nitrogen atmosphere, and then the reaction solution was heated and refluxed for 12 h, then cooled down to 20° C., filtered and concentrated. The residue was purified by column chromatography to give the title compound 9-3 (brown oil, 8 g, Yield 29%).

$^1$H NMR (400 MHz, CDCl$_3$): δ ppm 8.19 (d, J=8.8 Hz, 2H), 7.71 (d, J=8.8 Hz, 2H), 5.38 (s, 1H), 3.79 (s, 3H).

Synthesis of Compound 9-4

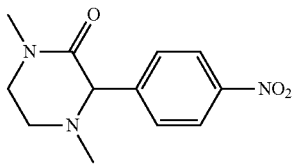 [SMILES: CN1CCN(C)C(c2ccc([N+](=O)[O-])cc2)C1=O]

To a solution of compound 9-3 (10 g, 36.5 mmol) in EtOH was added dropwise compound 9-3-1 (39 mL, 365 mmol) under nitrogen atmosphere at 0° C., and then the reaction solution was stirred at 20° C. for 2 h, followed by concentration. The residue was purified by column chromatography to give the title compound 9-4 (yellow solid, 5.5 g, Yield 56%).

$^1$H NMR (400 MHz, CDCl$_3$): δ ppm 8.16 (d, J=8.8 Hz, 2H), 7.59 (d, J=8.8 Hz, 2H), 3.80 (s, 1H), 3.60-3.80 (m, 1H), 3.15-3.30 (m, 1H), 3.00-3.10 (m, 1H), 2.93 (s, 3H), 2.60-2.75 (m, 1H), 2.15 (s, 3H).

Synthesis of Compound 9-5

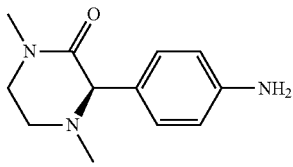 [SMILES: CN1CCN(C)[C@H](c2ccc(N)cc2)C1=O]

The mixture of compound 9-4 (5 g, 20 mmol) and Pd/C (0.5 g) in EtOH (100 mL) was reacted under hydrogen atmosphere at 20° C. for 2 h, and then filtered and stripped in vacuo to give a residue (4 g) which was purified by supercritical fluid chromatography (SFC) to afford the title compound 9-5 (1.8 g).

$^1$H NMR (400 MHz, CDCl$_3$): δ ppm 7.14 (d, J=8.8 Hz, 2H), 6.66 (d, J=8.8 Hz, 2H), 3.65-3.80 (m, 1H), 3.55-3.65 (m, 3H), 3.15-3.30 (m, 1H), 3.00-3.10 (m, 1H), 2.99 (s, 3H), 2.55-2.75 (m, 1H), 2.20 (s, 3H).

Synthesis of Compound 9-6

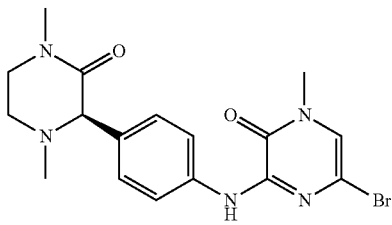 [SMILES: CN1CCN(C)[C@H](c2ccc(Nc3nc(Br)cn(C)c3=O)cc2)C1=O]

The solution of compound 9-5 (1.8 g, 8.2 mmol), compound 9-5-1 (2.2 g, 8.2 mmol) and TEA (1.25 mL, 9 mmol) in i-PrOH (100 ml) was heated and refluxed for 24 h under nitrogen atmosphere, followed by cooled down to 20° C. and concentrated. The residue was purified by column chromatography (DCM/MeOH=1/0 to 25/1) to afford the title compound 9-6 (white solid, 1.5 g, Yield 45%).

$^1$H NMR (400 MHz, CDCl$_3$): δ ppm 8.30 (s, 1H), 7.73 (d, J=8.4 Hz, 2H), 7.38 (d, J=8.8 Hz, 2H), 6.75 (s, 1H), 3.60-3.80 (m, 2H), 3.52 (s, 3H), 3.15-3.30 (m, 1H), 2.90-3.10 (m, 4H), 2.60-2.80 (m, 1H), 2.20 (s, 3H).

Synthesis of Compound 9-5-1B

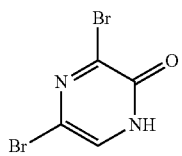

To a solution of compound 9-5-1A (15 g, 59 mmol) in HOAc (150 ml) was added dropwise H$_2$SO$_4$ (25 mL) under nitrogen atmosphere at 15 to 25° C., followed by dropwise a solution of NaNO$_2$ (8 g, 118 mmol) in water. The reaction solution was reacted at 15 to 25° C. for 2 h, and then poured into ice water (1000 mL), extracted with EtOAc (1000 mL×3). The organic phases were combined, dried over anhydrous Na$_2$SO$_4$, filtered and evaporated to give compound 9-5-1B (yellow solid, 12 g, Yield 80%).

$^1$H NMR (400 MHz, CDCl$_3$-d): δ ppm 7.55 (s, 1H).

Synthesis of Compound 9-5-1

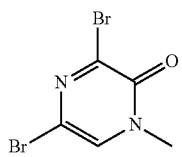

To a mixture of compound 9-5-1B (18 g, 20.9 mmol) and K$_2$CO$_3$ (19.6 g, 141.8 mmol) in acetone (300 mL) was added dropwise MeI (22 mL g, 354 mmol) under nitrogen atmosphere at 0° C., and then the reaction mixture was reacted at 20° C. for 3 h. The reaction was quenched with water (300 mL), and the reaction solution was extracted with EtOAc (500 mL×3). The organic phases were combined, washed with brine (50 mL), dried over anhydrous Na$_2$SO$_4$, filtered and evaporated to give compound 9-5-1 (yellow solid, 13 g, Yield 68%).

$^1$H NMR (400 MHz, CDCl$_3$): δ ppm 7.29 (s, 1H), 3.52 (s, 3H).

Synthesis of Compound 9-8

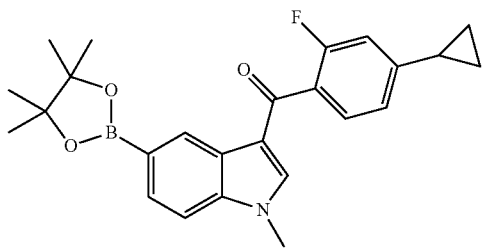 [SMILES: Cn1cc(C(=O)c2ccc(C3CC3)cc2F)c2cc(B3OC(C)(C)C(C)(C)O3)ccc21]

To a mixture of compound 9-7 (100 mg, 0.269 mmol), compound 9-7-1 ((BPin)$_2$) (87 mg, 0.32 mmol) and KOAc (52.8 mg, 0.538 mmol) in dioxane (7 ml) was added Pd(dppf)Cl$_2$ (10 mg, 10% wt eq.), and then the reaction mixture was reacted at 110° C. for 3 h and extracted with EtOAc. The organic phase was washed with water and brine, dried over anhydrous Na$_2$SO$_4$, filtered and evaporated to give compound 9-8 (120 mg) which was directly used for the next step without further purification.

Synthesis of Compound 9-9

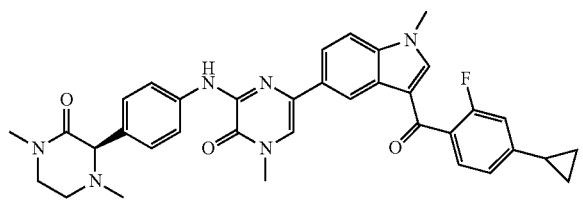 [SMILES: CN1CCN(C)[C@H](c2ccc(Nc3nc(-c4ccc5c(c4)c(C(=O)c4ccc(C6CC6)cc4F)cn5C)cn(C)c3=O)cc2)C1=O]

To a mixture of compound 9-8 (100 mg, 0.269 mmol), compound 9-6 (113 mg, 0.269 mmol) and Cs$_2$CO$_3$ (181.9 mg, 0.558 mmol) in dioxane (5 ml) and water (1.5 ml) was added Pd(dppf)Cl$_2$ (19.39 mg, 0.0279 mmol), and then the reaction mixture was reacted under microwave at 110° C. for 1 h, followed by extraction with EtOAc. The organic phase was washed with water and brine, dried over anhydrous Na$_2$SO$_4$, filtered and evaporated to give a residue which was purified by column chromatography to afford compound 9-9 (40 mg, Yield 23.2%).

LCMS (ESI) m/z 619 (M+1)

Scheme 9
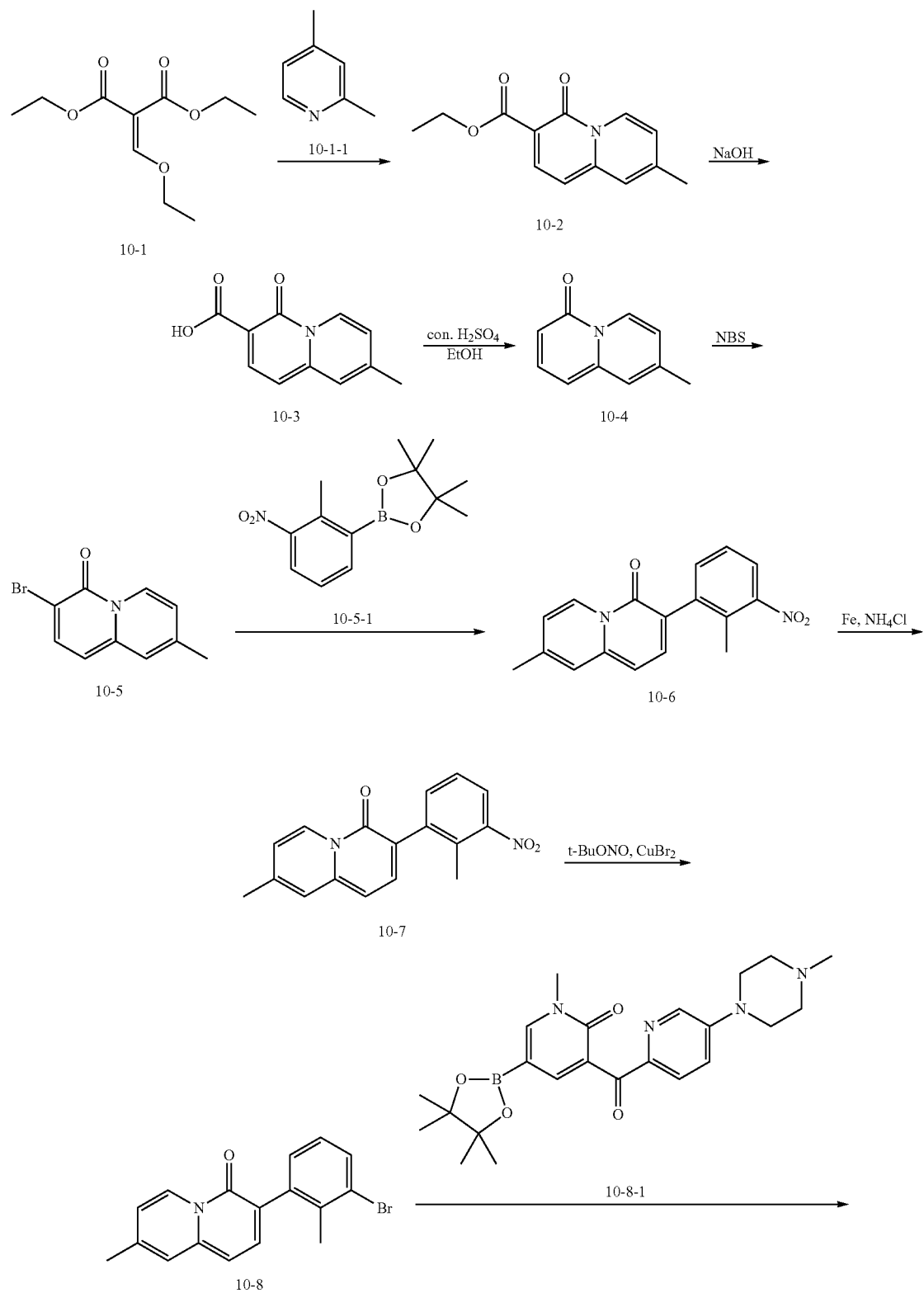

-continued

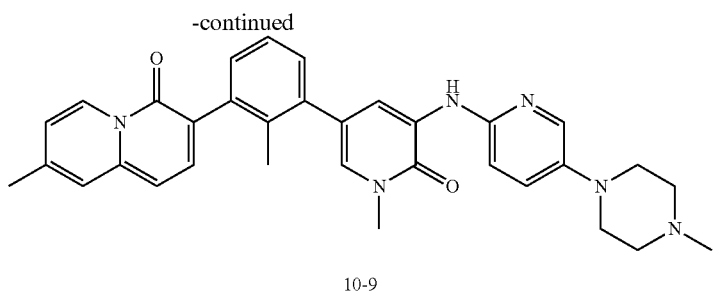

10-9

Example 10

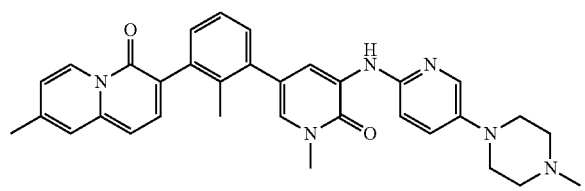

Synthesis of Compound 10-2

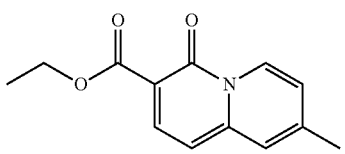 [SMILES: CCOC(=O)c1ccc2cc(C)ccn2c1=O]

To a mixture of DIPEA (15.7 mL) and THF (300 mL) was added dropwise n-BuLi (2.5 M, 44.94 mL, 0.11 mol) at −70° C., and then the reaction mixture was stirred at 10° C. for 0.5 h, followed by cooled down to −70° C. To this mixture, a solution of compound 10-1-1 (10 g, 0.107 mol) in THF (30 mL) was added dropwise and the resulting reaction mixture was stirred for 0.5 h, after which a solution of compound 10-1 (24.5 mL, 0.121 mol) in THF (30 mL) was added dropwise and the reaction was reacted at −20° C. for 2 h. The reaction was quenched with saturated NH$_4$Cl (aq.), and the reaction solution was evaporated and extracted with DCM. The organic phases were combined and concentrated to give brown oil. The oil was dissolved in p-xylene (50 mL), heated to 130° C. and reacted for 16 h, followed by concentration to afford a crude product 10-2 (28 g) which was directly used for the next step.

Synthesis of Compound 10-3

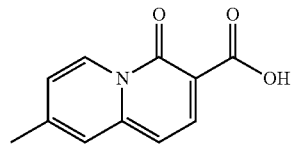

The mixture of compound 10-2 (28 g, 0.12 mol) and NaOH (19.4 g, 0.48 mol) in MeOH (100 mL) and water (50 mL) was reacted at 80° C. for 6 h, and then the reaction solution was cooled down and extracted with DCM and water. The aqueous phase was adjusted to pH 1 with HCl (concentrated) and extracted with DCM. The organic phases were combined, dried over anhydrous Na$_2$SO$_4$, filtered and evaporated to give compound 10-3 (10.5 g, Yield 43%).

Synthesis of Compound 10-4

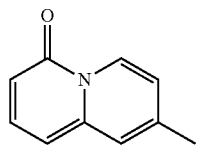

The mixture of compound 10-3 (10.5 g, 0.052 mol) in H$_2$SO$_4$ (concentrated) (22 mL), water (78 mL) and EtOH (100 mL) was refluxed at 90° C. and reacted for 2 h, and then the reaction solution was concentrated. The residue was extracted with DCM and water. The organic phases were combined, dried over anhydrous Na$_2$SO$_4$, filtered and evaporated to give compound 10-4 (4.5 g, Yield 55%).

LCMS (ESI) m/z: 160 (M+1)

Synthesis of Compound 10-5

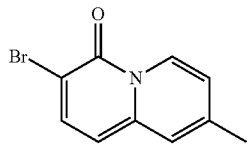

To a solution of compound 10-4 (3.5 g, 22 mmol) in acetonitrile (400 mL) was added NBS (3.9 g, 22 mmol) at −40° C., and then the resulting solution was reacted at r.t. for 20 min, followed by concentration. The residue was purified by preparative HPLC to give compound 10-5 (1.65 g, 31%).

$^1$H NMR (400 MHz, CDCl$_3$): δ ppm 9.10 (d, J=6.8 Hz, 1H), 7.95 (d, J=8.4 Hz, 1H), 6.92 (d, J=6.0 Hz, 1H), 6.47 (d, J=8.0 Hz, 1H), 5.25-5.27 (m, 1H), 2.42 (s, 3H).

Synthesis of Compound 10-6

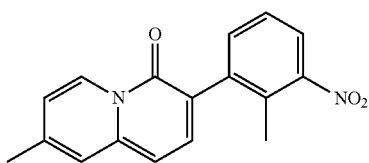

The mixture of compound 10-5 (1.1 g, 4.62 mmol), compound 10-5-1 (1.82 g, 6.94 mmol), $Cs_2CO_3$ (3.02 g, 9.24 mmol) and $Pd(dppf)Cl_2$ (1.0 g) in dioxane (100 mL) and water (30 mL) was reacted at 100° C. for 3 h, and then the reaction solution was concentrated and extracted with DCM and water. The organic phases were combined, dried over anhydrous $Na_2SO_4$, filtered and evaporated, and the residue was purified by column chromatography to give compound 10-6 (0.8 g, Yield 58%).

Synthesis of Compound 10-7

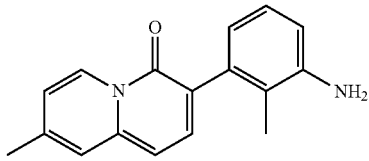 [SMILES: Cc1ccn2c(=O)c(-c3cccc([N+](=O)[O-])c3C)ccc2c1]

The mixture of compound 10-6 (0.36 g, 1.22 mmol), iron powder (0.41 g, 7.35 mmol), $NH_4Cl$ (0.39 g, 7.35 mmol) in EtOH (20 mL) and water (2 mL) (30 mL) was reacted at 80° C. for 2 h, and then the reaction solution was concentrated and extracted with DCM and water. The organic phases were combined, dried over anhydrous $Na_2SO_4$, filtered and evaporated, and the residue was purified by thin layer chromatography to give compound 10-7 (0.2 g, Yield 62%).

Synthesis of Compound 10-8

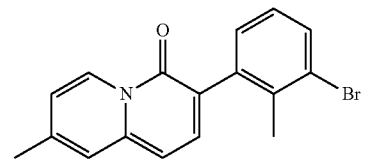 [SMILES: Cc1ccn2c(=O)c(-c3cccc(Br)c3C)ccc2c1]

To a solution of compound 10-7 (30 mg, 0.11 mmol) in acetonitrile (4 mL) was added t-$BuNO_2$ (0.02 mL, 0.17 mmol) at 0° C., and then the reaction mixture was reacted at 0° C. for 30 min. To this solution, a solution of $CuBr_2$ (29 mg, 0.13 mmol) in acetonitrile (1 mL) was added dropwise, and the resulting solution was reacted at 0° C. for 2 h, and then poured into brine and extracted with EtOAc. The organic phases were combined, dried over anhydrous $Na_2SO_4$, filtered and evaporated, and the residue was purified by thin layer chromatography to give compound 10-8 (20 mg, 55%).

LCMS (ESI) m/z: 328 (M+1)

Synthesis of Compound 10-9

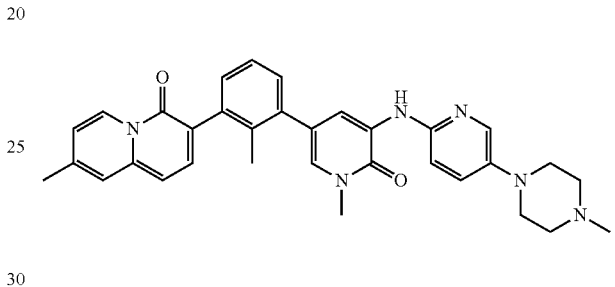

The mixture of compound 10-8 (30 mg, 0.092 mmol), compound 10-8-1 (84.7 mg, 0.12 mmol), $Cs_2CO_3$ (60 mg, 0.184 mmol) and $Pd(dppf)Cl_2$ (30 mg) in dioxane (1.5 mL) and water (0.5 mL) was reacted under microwave at 100° C. for 0.5 h, and then the resulting reaction solution was extracted with EtOAc and water. The organic phases were combined, dried over anhydrous $Na_2SO_4$, filtered and evaporated, and the residue was purified by thin layer chromatography and preparative HPLC to give compound 10-9 (3 mg, Yield 6%).

LCMS (ESI) m/z: 547 (M+1)

Scheme 10

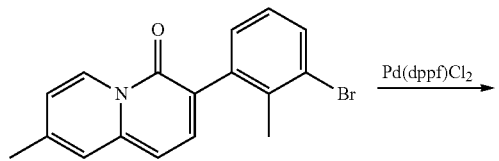

10-8

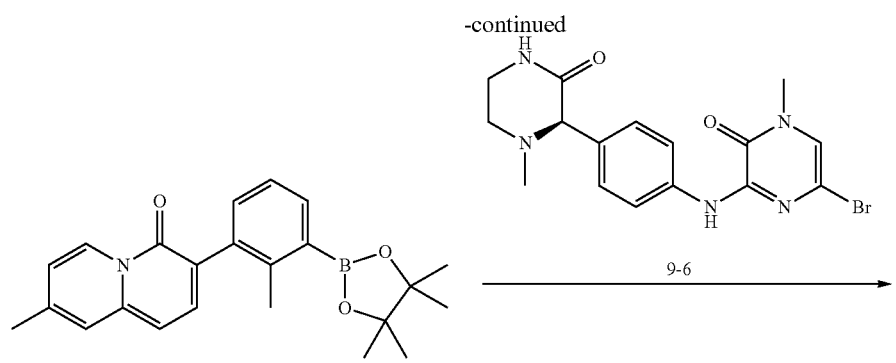

11-1

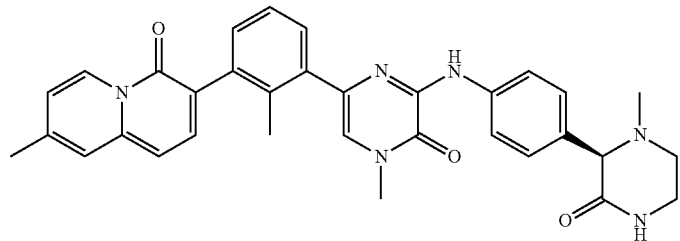

11-2

Example 11

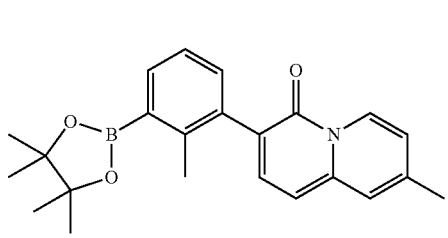

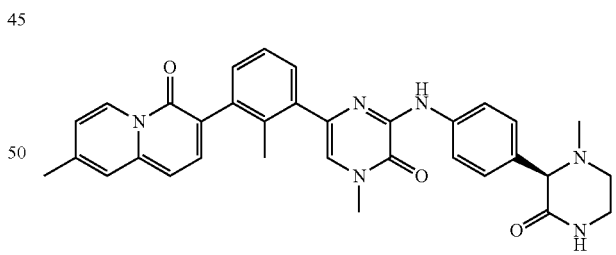

Synthesis of Compound 11-1

The mixture of compound 10-8 (15 mg, 0.046 mmol), (BPin)₂ (15 mg, 0.055 mmol), Pd(dppf)Cl₂ (15 mg) and AcOK (10 mg, 0.092 mmol) in dioxane (7 ml) was reacted at 110° C. for 5 h, and then the resulting solution was extracted with EtOAc and water. The organic phases were combined, dried over anhydrous Na₂SO₄, filtered and evaporated to give a crude compound 11-1 (130 mg) which was directly used for the next step.

Synthesis of Compound 11-2

The mixture of compound 11-1 (40 mg, 0.11 mmol), compound 9-6 (52 mg, 0.13 mmol), Cs₂CO₃ (72 mg, 0.22 mmol) and Pd(dppf)Cl₂(16 mg) in dioxane (1.5 mL) and water (0.5 mL) was reacted under microwave at 100° C. for 40 min, and then the resulting reaction solution was extracted with EtOAc and water. The organic phases were combined, dried over anhydrous Na₂SO₄, filtered and evaporated to give a residue which was purified by thin layer chromatography and preparative HPLC to give compound 11-2 (3 mg, Yield 5%).

LCMS (ESI) m/z: 561 (M+1)

Scheme 11
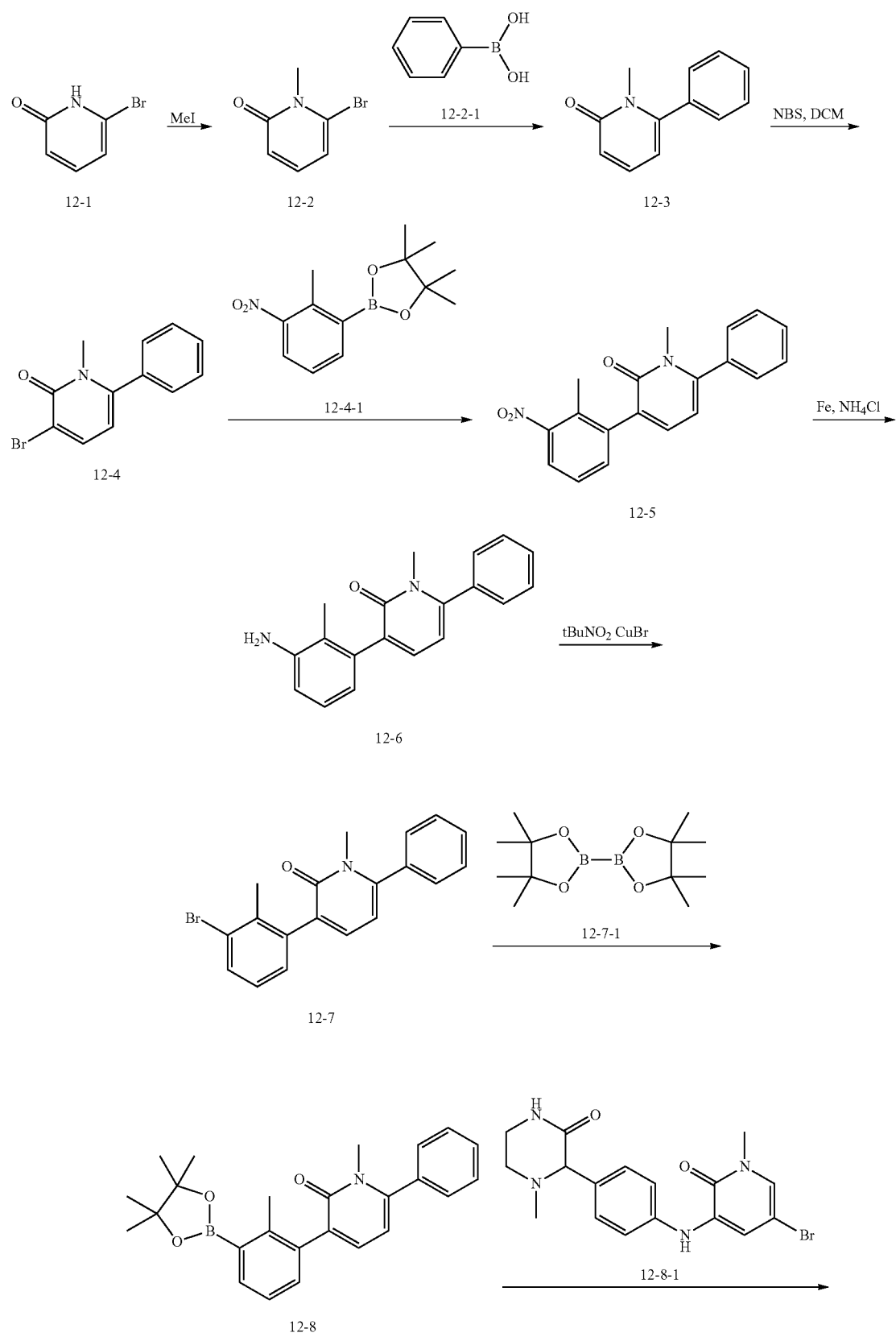

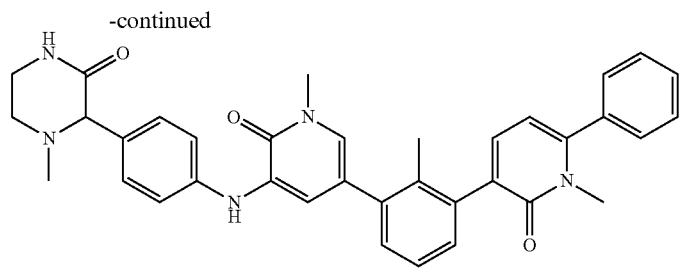

12-9

Example 12

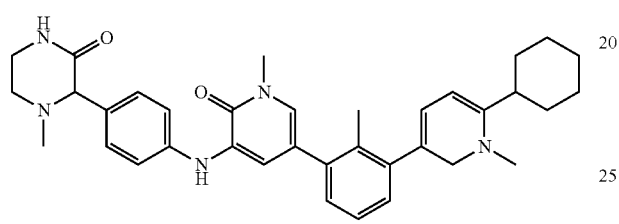

Synthesis of Compound 12-2

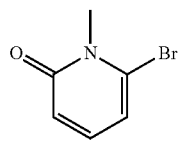

To a solution of compound 12-1 (1 g, 5.78 mmol) in DME (20 ml) was added K$_2$CO$_3$ (1.6 g, 11.7 mmol) and MeI (1 g, 3.65 mmol), and the reaction mixture was reacted at 80° C. for 4 h. The reaction was quenched with water (20 mL), and the reaction solution was extracted with DCM (30 mL×2). The organic phases were combined, dried over anhydrous Na$_2$SO$_4$, filtered and evaporated to give a residue which was purified by column chromatography to afford compound 12-2 (655 mg, Yield 60%).

Synthesis of Compound 12-3

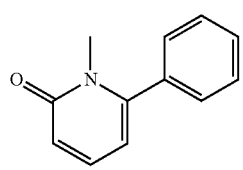

To a solution of compound 12-2 (1.2 g, 6.38 mmol) in dioxane (10 ml) and water (1 ml) was added compound 12-2-1 (0.856 g, 70 mmol), Pd(dppf)Cl$_2$ (396 mg, 0.64 mmol) and Na$_2$CO$_3$ (1.35 g, 12.76 mmol), and the reaction mixture was reacted under microwave at 110° C. for 1 h, followed by filtration. The filter cake was washed with MeOH (10 mL×3) and evaporated to remove the solvent. The residue was purified by column chromatography to give compound 12-3 (800 mg, Yield 68%).

LCMS (ESI) m/z: 186 (M+1)

Synthesis of Compound 12-4

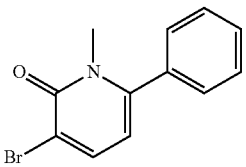

To a solution of compound 12-3 (800 mg, 4.32 mmol) in DCM (15 mL) was added NBS (807 mg, 4.32 mmol) at 0° C., and the reaction mixture was reacted at r.t. for 2 h, followed by washed with water and brine. The organic phase was dried over anhydrous Na$_2$SO$_4$, filtered and evaporated to give a residue which was purified by thin layer chromatography to afford compound 12-4 (500 mg, 44%).

Synthesis of Compound 12-5

To a mixture of compound 12-4 (200 mg, 0.757 mmol), compound 12-4-1 (278 g, 1.06 mmol) and Cs$_2$CO$_3$ (493 mg, 1.514 mmol) in dioxane (5 ml) and water (1.5 ml) was added Pd(dppf)Cl$_2$ (16 mg), and the reaction mixture was reacted under microwave at 110° C. for 40 min, followed by extraction with EtOAc. The organic phase was washed with water and brine, dried over anhydrous Na$_2$SO$_4$, filtered and evaporated to give a residue which was purified by column chromatography to afford compound 12-5 (130 mg, 54%).

Synthesis of Compound 12-6

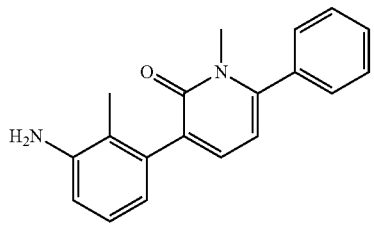 [SMILES: Cc1c(-c2ccc(-c3ccccc3)n(C)c2=O)cccc1[N+](=O)[O-]]

The mixture of compound 12-5 (130 mg, 0.405 mmol), iron powder (31 mg, 0.56 mmol) and NH$_4$Cl (30 mg, 0.56 mmol) in EtOH (15 ml) and water (1 ml) was reacted at reflux for 1.5 h, followed by cooled down and filtered. The solvent was removed, and the residue was washed with EtOAc. The organic phases were combined and concentrated to give compound 12-6 (115 mg, 98%).

Synthesis of Compound 12-7

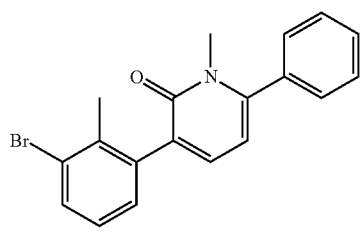 [SMILES: Cc1c(Br)cccc1-c1ccc(-c2ccccc2)n(C)c1=O]

The solution of CuBr (88 mg, 0.62 mmol) and t-BuNO$_2$ (250 mg, 2.478 mmol) in CH$_3$CN (6 ml) was reacted at r.t. for 1 h, after which compound 12-6 (120 mg, 0.413 mmol) was added and the resulting solution was reacted for 3 h, followed by filtration, concentration and extraction with EtOAc and water. The organic phase was washed with brine, dried over anhydrous Na$_2$SO$_4$, filtered and evaporated to give a residue which was purified by column chromatography to afford compound 12-7 (40 mg, 27.4%).

Synthesis of Compound 12-8

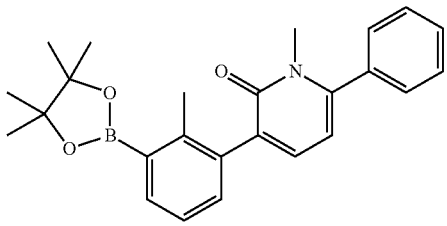 [SMILES: Cc1c(B2OC(C)(C)C(C)(C)O2)cccc1-c1ccc(-c2ccccc2)n(C)c1=O]

To a mixture of compound 12-7 (22 mg, 0.0602 mmol), KOAc (12.1 mg, 0.124 mmol) and compound 12-7-1 ((BPin)$_2$) (20 mg, 0.0704 mmol) in dioxane (7 ml) was added Pd(dppf)Cl$_2$ (4.3 mg, 0.0062 mmol), and the reaction mixture was reacted at 110° C. for 3 h, and then cooled down, filtrated, concentrated and extracted with EtOAc and water. The organic phase was washed with water and brine, dried over anhydrous Na$_2$SO$_4$, filtered and evaporated to give a residue which was purified by column chromatography to give compound 12-8 (12 mg, 43%).

LCMS (ESI) m/z: 402 (M+1)

Synthesis of Compound 12-9

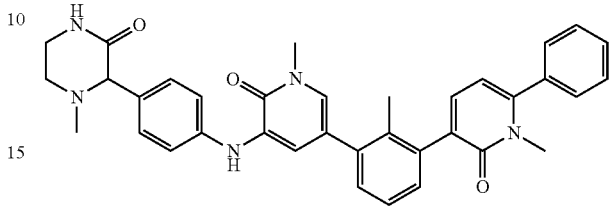

To a mixture of compound 12-8 (30 mg, 0.074 mmol), compound 12-8-1 (29.97 mg, 0.074 mmol) and Cs$_2$CO$_3$ in dioxane (5 ml) and water (1 ml) was added Pd(dppf)Cl$_2$ (5.1 mg, 0.0074 mmol), and the reaction mixture was reacted at 110° C. for 40 min, and then cooled down, filtrated, concentrated and extracted with EtOAc and water. The organic phase was washed with water and brine, dried over anhydrous Na$_2$SO$_4$, filtered and evaporated to give a residue which was purified by column chromatography to afford compound 12-9 (10 mg, 22%).

LCMS (ESI) m/z: 586 (M+1)

Scheme 12

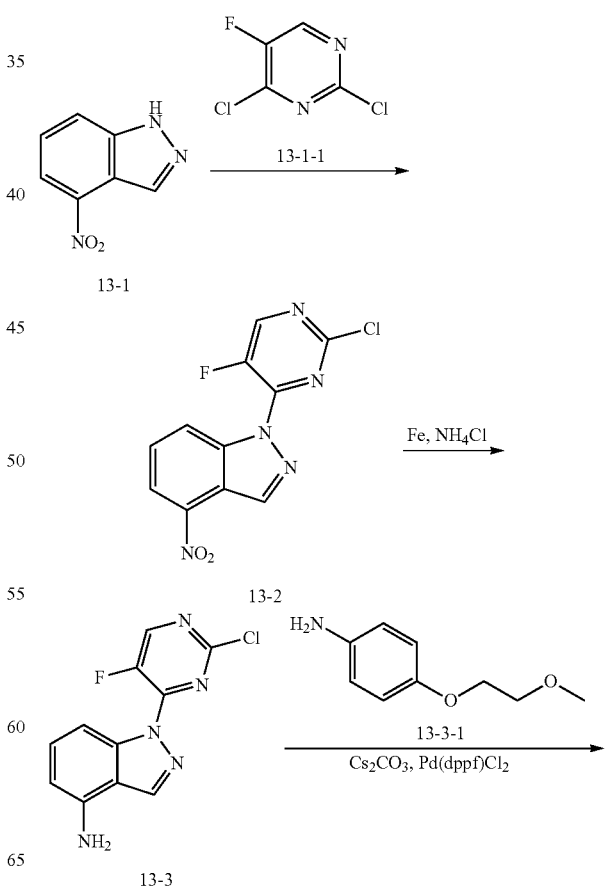

-continued

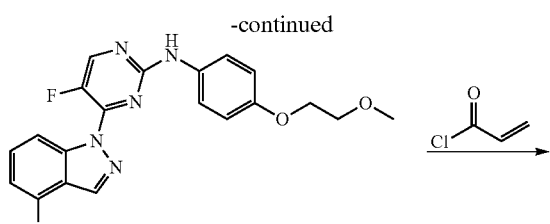

13-4

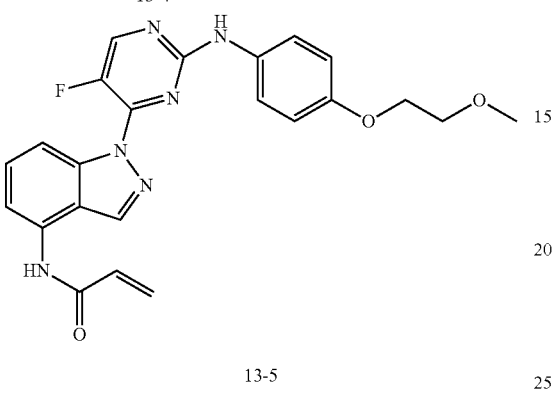

13-5

Example 13

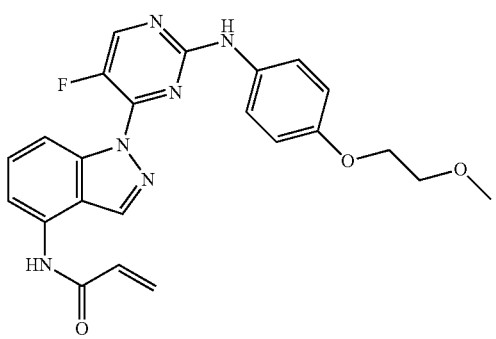 [SMILES: C=CC(=O)Nc1cccc2c1cnn2-c1nc(Nc2ccc(OCCOC)cc2)ncc1F]

Synthesis of Compound 13-2

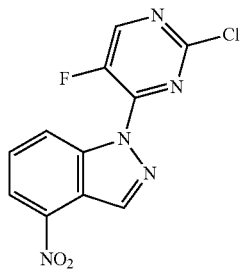 [SMILES: O=[N+]([O-])c1cccc2c1cnn2-c1nc(Cl)ncc1F]

To a solution of compound 13-1 (1.5 g, 9.2 mmol) in DMF (43.32 g, 19.25 mmol) was added NaH (43.32 g, 19.25 mmol) under nitrogen atmosphere at 0° C. and the reaction mixture was reacted at r.t. for 30 min, followed by cooled down to 0° C., after which a solution of compound 13-1-1 (1.53 g, 9.2 mmol) in DMF (10 mL) was added dropwise, and the resulting solution was reacted at r.t. for 12 h, quenched with water (20 mL) and extracted with DCM/MeOH (30 mL×2, v/v=10/1). The organic phases were combined, dried over anhydrous $Na_2SO_4$, filtered and evaporated to give a residue which was purified by column chromatography to give compound 13-2 (white solid, 630 mg, Yield 23%).

$^1$H NMR (400 MHz, $CDCl_3$): δ ppm 9.09-9.07 (t, 2H, J=3.6 Hz), 8.90-8.88 (d, 1H, J=8.4 Hz), 8.41-8.39 (d, 1H, J=8.0 Hz), 7.98-7.94 (t, 1H, J=8.2 Hz).

Synthesis of Compound 13-3

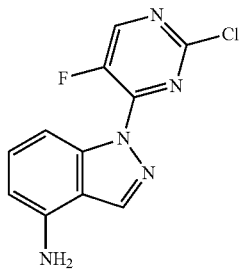 [SMILES: Nc1cccc2c1cnn2-c1nc(Cl)ncc1F]

To a solution of compound 13-2 (630 mg, 2.15 mmol) in EtOH/water (10 mL, v/v=5/1) was added iron powder (1.2 g, 21.5 mmol) and $NH_4Cl$ (1.15 g, 21.5 mmol), and the reaction solution was heated to 70° C. and reacted for 4 h, followed by cooled down and filtered. The filter cake was washed with MeOH (10 mL×3) and concentrated to remove the solvent. The residue was washed with water (10 mL) and extracted with EtOAc (10 mL×2). The organic phase was dried over anhydrous $Na_2SO_4$, filtered and evaporated to give compound 13-3 (yellow solid, 400 mg, Yield 71%).

$^1$H NMR (400 MHz, $d_6$-DMSO): δ ppm 8.87-8.86 (d, 1H, J=4.4 Hz), 8.67 (s, 1H), 7.61-7.59 (d, 1H, J=8.0 Hz), 7.32-7.28 (t, 1H, J=8.0 Hz), 6.49-6.47 (d, 1H, J=7.6 Hz), 6.20 (s, 2H).

Synthesis of Compound 13-4

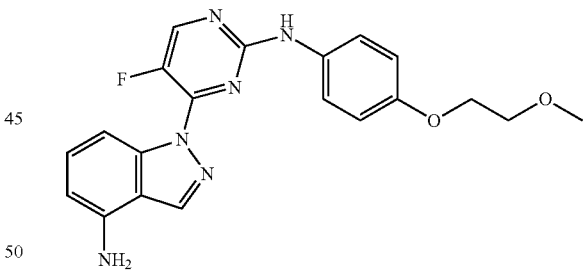

To a solution of compound 13-3 (370 mg, 1.41 mmol), compound 13-3-1 (247 mg, 1.48 mmol) and $Cs_2CO_3$ (690 mg, 2.12 mmol) in dioxane (5 mL) was added Pd(dppf)$Cl_2$ (102 mg, 0.14 mmol), and the reaction solution was heated to 80° C. and reacted for 5 h, followed by washed with water (5 mL) and extracted with DCM/MeOH (5 mL×3, v/v=10/1). The organic phases were combined, dried over anhydrous $Na_2SO_4$, filtered and evaporated to give a residue which was purified by column chromatography to afford compound 13-4 (yellow oil, 120 mg, Yield 22%).

$^1$H NMR (400 MHz, $CDCl_3$): δ ppm 8.39-8.38 (d, 1H, J=4.8 Hz), 8.26 (s, 1H), 7.74-7.72 (d, 1H, J=8.4 Hz), 7.48-7.46 (d, 2H, J=8.8 Hz), 7.25-7.21 (t, 1H, J=8 Hz), 6.97-6.95 (d, 3H, J=8.8 Hz), 6.54-6.52 (d, 1H, J=7.6 Hz), 4.21 (s, 2H), 4.16-4.14 (t, 2H, J=4.6 Hz), 3.79-3.77 (t, 2H, J=4.6 Hz), 3.48 (s, 3H).

Synthesis of Compound 13-5

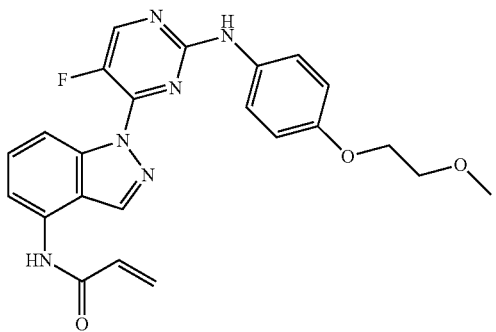 [SMILES: C=CC(=O)Nc1cccc2c1cnn2-c1nc(Nc2ccc(OCCOC)cc2)ncc1F]

To a solution of compound 13-4 (120 mg, 0.3 mmol) and TEA (92.3 mg, 0.9 mmol) in THF (2 mL) was added dropwise acryloyl chloride (54.8 mg, 0.6 mmol) at nitrogen atmosphere at 0° C., and the reaction mixture was reacted at r.t. for 1.5 h, followed by washed with water (2 mL) and extracted with EtOAc (3 mL×3). The organic phase was dried over anhydrous $Na_2SO_4$, filtered and evaporated to give a residue which was purified by preparative HPLC to afford compound 13-5 (white solid, 27.8 mg, Yield 21%).

$^1$H NMR (400 MHz, d$_6$-DMSO): δ ppm 10.39 (s, 1H), 9.64 (s, 1H), 8.72 (s, 1H), 8.63-8.62 (d, 1H, J=4 Hz), 8.28 (s, 1H), 7.97-7.95 (d, 1H, J=7.6 Hz), 7.58-7.56 (d, 2H, J=8.8 Hz), 7.52-7.48 (t, 1H, J=8.0 Hz), 6.93-6.91 (d, 2H, J=8.8 Hz), 6.70-6.63 (m, 1H), 6.38-6.33 (d, 1H, J=18.8 Hz), 5.87-5.85 (t, 1H, J=5.8 Hz), 4.08-4.06 (t, 2H, J=4.4 Hz), 3.67-3.64 (t, 2H, J=4.4 Hz), 3.31 (s, 3H).

Scheme 13

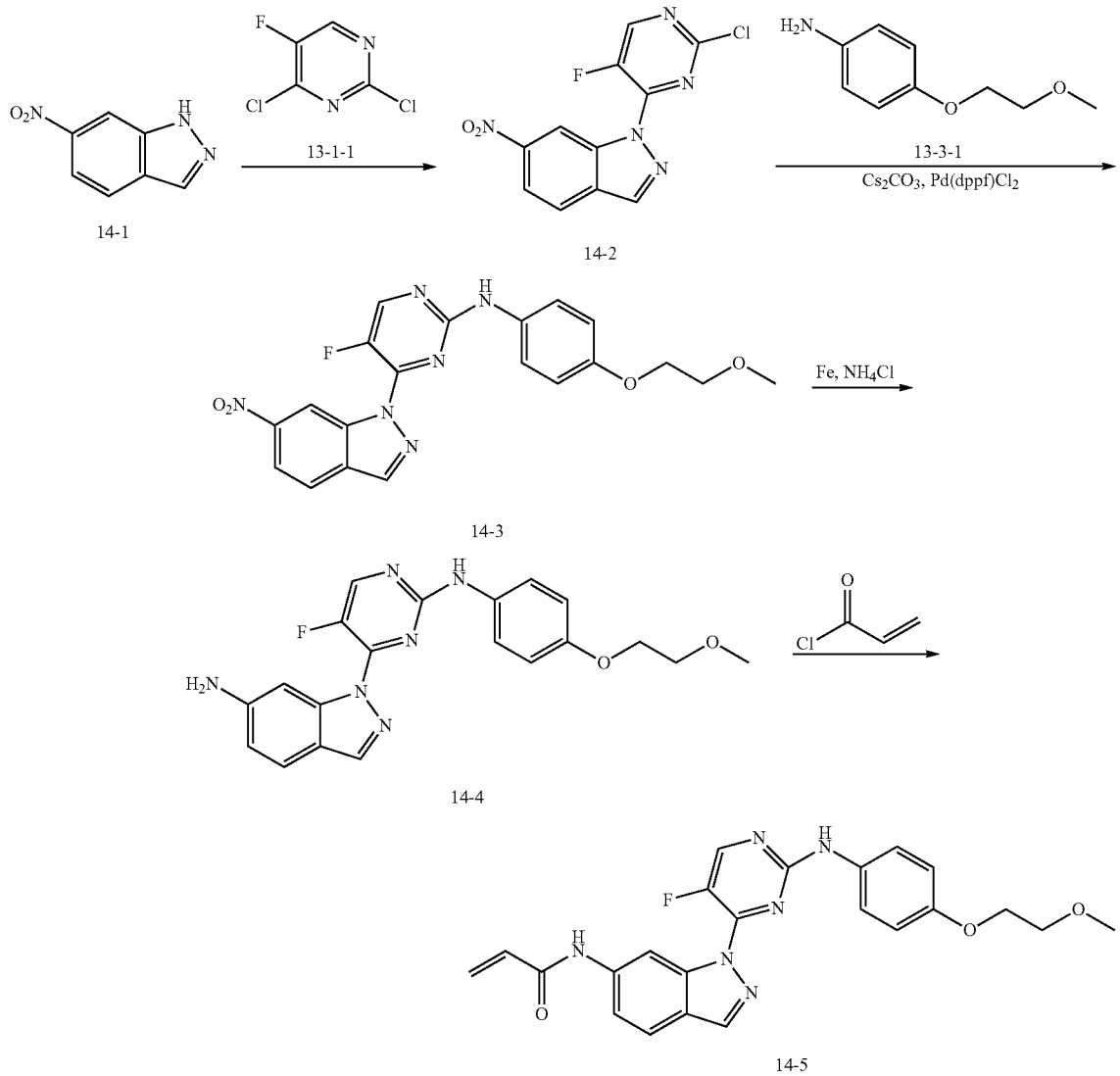

Example 14

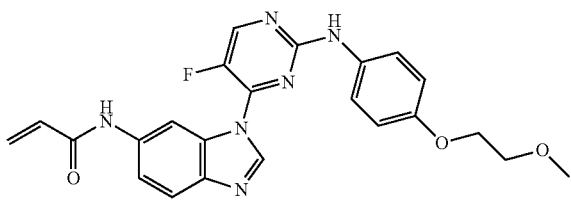 [SMILES: C=CC(=O)Nc1ccc2ncn(-c3nc(Nc4ccc(OCCOC)cc4)ncc3F)c2c1]

Synthesis of Compound 14-2

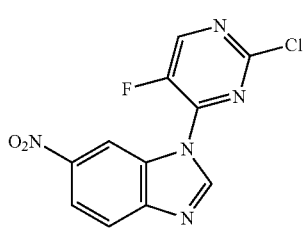 [SMILES: O=[N+]([O-])c1ccc2ncn(-c3nc(Cl)ncc3F)c2c1]

The solution of compound 14-1 (4 g, 24.5 mmol), compound 13-1-1 (4.28 g, 25.7 mmol) and DIPEA (4.7 g, 36.8 mmol) in DMF (50 mL) was reacted at 110° C. for 2 h, and then the reaction solution was quenched with water (100 mL) and extracted with EtOAc (50 mL×3). The organic phase was washed with brine (100 mL), dried over anhydrous $Na_2SO_4$, filtered and evaporated to give compound 14-2 (yellow solid, 3.5 g, Yield 49%).

Synthesis of Compound 14-3

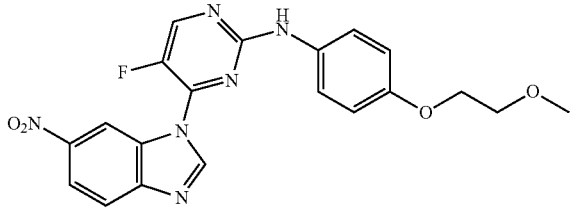 [SMILES: COCCOc1ccc(Nc2ncc(F)c(-n3cnc4ccc([N+](=O)[O-])cc43)n2)cc1]

To a solution of compound 14-2 (2 g, 6.8 mmol), compound 13-3-1 (1.28 g, 6.8 mmol) and $Cs_2CO_3$ (3.38 g, 10.2 mmol) in dioxane (20 mL) was added $Pd(dppf)Cl_2$ (500 mg, 0.68 mmol) and the reaction solution was heated to 80° C. and reacted for 2 h, after which water (20 mL) was added and the resulting solution was extracted with DCM (20 mL×3). The organic phases were combined, dried over anhydrous $Na_2SO_4$, filtered and evaporated to give a residue which was purified by column chromatography to afford compound 14-3 (yellow solid, 700 mg, Yield 24%).

$^1$H NMR (400 MHz, $d_6$-DMSO): δ ppm 9.88-9.84 (d, 1H, J=13.6 Hz), 9.01-9.00 (m, 1H), 8.82-8.80 (m, 1H), 8.28-8.26 (m, 1H), 8.04-8.01 (d, 1H, J=8.8 Hz), 7.57-7.55 (d, 2H, J=8.8 Hz), 6.95-6.89 (m, 2H), 4.08-4.03 (m, 3H), 3.66-3.64 (m, 2H), 3.17-3.16 (m, 2H).

Synthesis of Compound 14-4

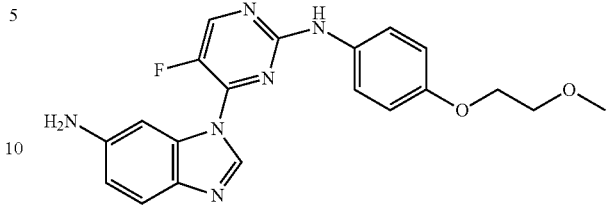

To a solution of compound 14-3 (300 mg, 0.71 mmol) in EtOH/water (6 mL, v/v=5/1) was added iron powder (198 mg, 3.54 mmol) and $NH_4Cl$ (187 mg, 3.54 mmol), and the reaction solution was heated to 50° C. and reacted for 4 h, followed by filtration and concentration. The residue was dissolved in EtOAc (10 mL) and washed with brine (10 mL). The organic phase was dried over anhydrous $Na_2SO_4$, filtered and evaporated to give compound 14-4 (yellow solid, 280 mg, Yield 100%).

$^1$H NMR (400 MHz, $d_6$-DMSO): δ ppm 9.67-9.64 (d, 1H, J=9.2 Hz), 8.70-8.54 (m, 2H), 8.34 (s, 1H), 8.00 (s, 1H), 7.59-7.55 (m, 2H), 7.21-77.23 (m, 2H), 6.93-6.87 (m, 2H), 6.68-6.66 (d, 1H, J=8.4 Hz), 5.06 (s, 2H), 4.08-4.06 (m, 2H), 3.65-3.64 (m, 2H), 3.17-3.16 (d, 1H, J=4.2 Hz).

Synthesis of Compound 14-5

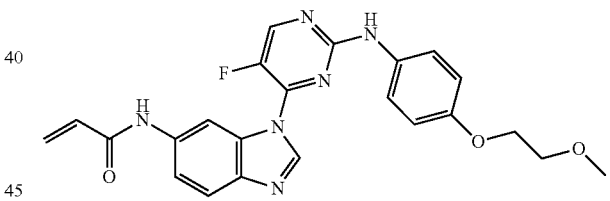

To a solution of compound 14-4 (230 mg, 0.58 mmol) and TEA (295 mg, 2.92 mmol) in THF (5 mL) was added dropwise acryloyl chloride (105 mg, 1.17 mmol) and the reaction solution was reacted at 0° C. for 1 h, after which water (5 mL) was added and the resulting solution was extracted with EtOAc (5 mL×2). The organic phase was washed with brine (5 mL), dried over anhydrous $Na_2SO_4$, filtered and evaporated to give a residue which was purified by preparative HPLC to afford compound 14-5 (white solid, 23.6 mg, Yield 9%).

$^1$H NMR (400 MHz, $CDCl_3$): δ ppm 8.417-8.408 (d, 1H, J=3.6 Hz), 7.770-7.749 (d, 1H, J=8.4 Hz), 7.662 (s, 1H), 7.454-7.432 (d, 2H, J=8.8 Hz), 7.354 (s, 1H), 7.278 (s, 1H), 6.979-6.957 (d, 2H, J=8.8 Hz), 6.496-6.457 (d, 1H, J=15.6 Hz), 6.362-6.294 (m, 1H), 5.817-5.791 (d, 1H, J=10.4 Hz), 4.139-4.116 (t, 2H), 3.768-3.745 (t, 2H), 3.456 (s, 3H).

Scheme 14
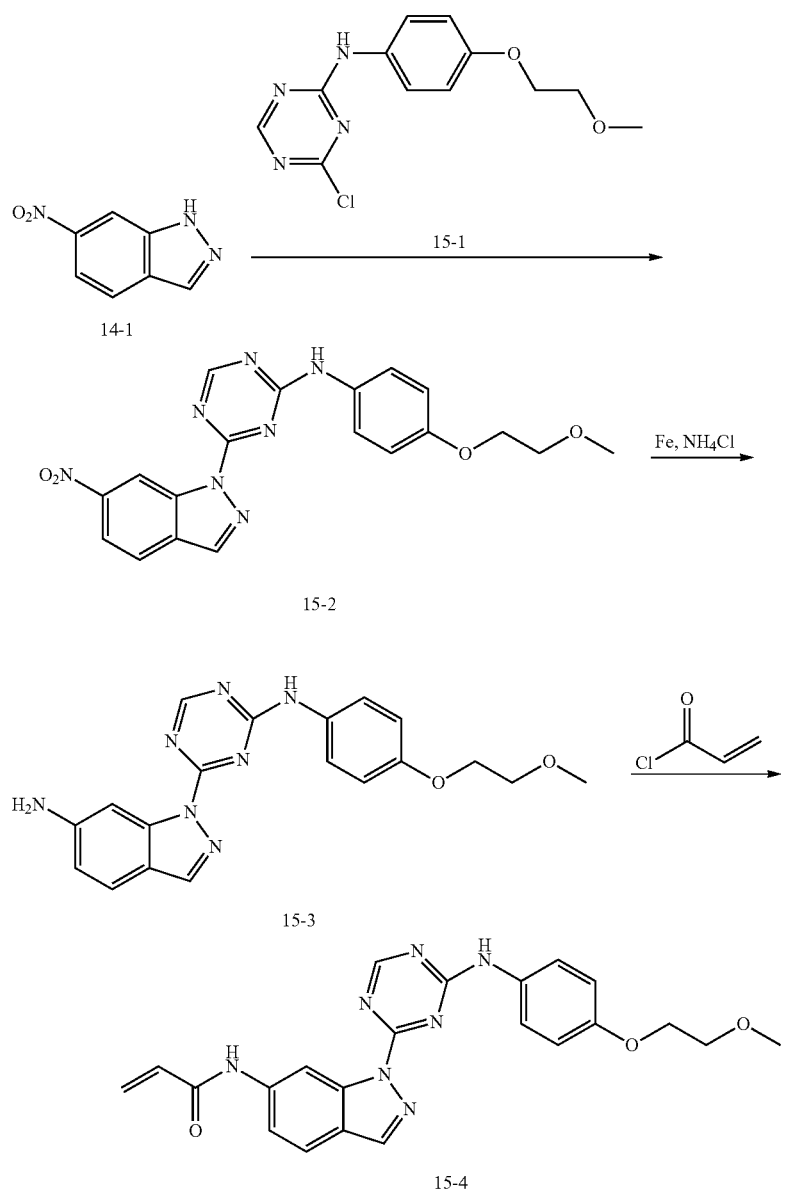
Example 15
Synthesis of Compound 15-2
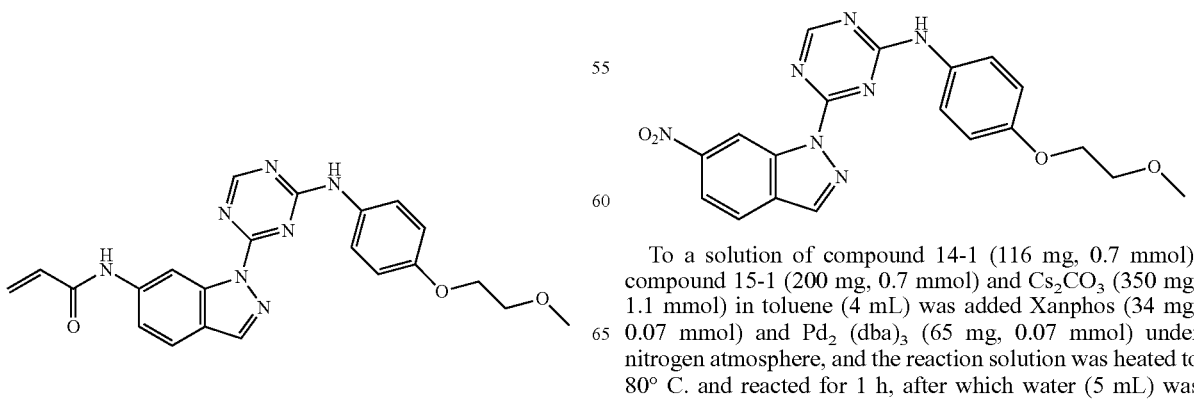
To a solution of compound 14-1 (116 mg, 0.7 mmol), compound 15-1 (200 mg, 0.7 mmol) and $Cs_2CO_3$ (350 mg, 1.1 mmol) in toluene (4 mL) was added Xanphos (34 mg, 0.07 mmol) and $Pd_2(dba)_3$ (65 mg, 0.07 mmol) under nitrogen atmosphere, and the reaction solution was heated to 80° C. and reacted for 1 h, after which water (5 mL) was added and the resulting solution was extracted with EtOAc (5 mL×3). The organic phases were combined, washed with brine (10 mL), dried over anhydrous Na$_2$SO$_4$, filtered and evaporated. The residue was recrystallized to give compound 15-2 (yellow solid, 190 mg, Yield 66%).

$^1$H NMR (400 MHz, CDCl$_3$): δ ppm 9.732-9.328 (m, 1H), 8.818-8.733 (d, 1H, J=3.4 Hz), 8.436-8.422 (m, 1H), 8.247-8.165 (m, 1H), 7.940-7.877 (m, 1H), 7.635 (s, 1H), 7.506-7.491 (m, 2H), 7.111-7.092 (d, 1H, J=7.6 Hz), 7.000-6.980 (d, 1H, J=8.0 Hz), 4.242-4.148 (d, 2H, J=37.6 Hz), 3.819-3.773 (d, 2H, J=18.4 Hz), 3.484-3.470 (m, 3H).

Synthesis of Compound 15-3

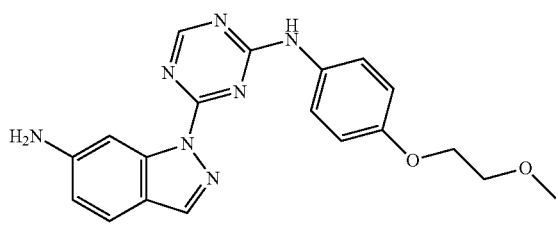 [SMILES: COCCOc1ccc(Nc2ncnc(-n3ncc4ccc(N)cc43)n2)cc1]

To a solution of compound 15-2 (190 mg, 0.46 mmol) in EtOH/water (12 mL, v/v=5/1) was added iron powder (261 mg, 4.6 mmol) and NH$_4$Cl (247 mg, 4.6 mmol), and the reaction solution was heated to 80° C. and reacted for 6 h, followed by filtration and concentration. The residue was dissolved in DCM (10 mL) and washed with brine (10 mL). The organic phase was dried over anhydrous Na$_2$SO$_4$, filtered and evaporated to give compound 15-3 (yellow solid, 110 mg).

LCMS (ESI) m/z: 378 (M+1)

Synthesis of Compound 15-4

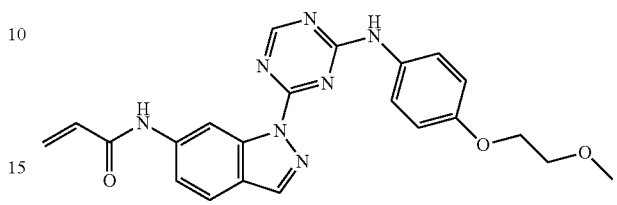

To a solution of compound 15-3 (100 mg, 0.26 mmol) and TEA (107 mg, 1.06 mmol) in THF (4 mL) was added dropwise acryloyl chloride (48 mg, 0.53 mmol) and the reaction solution was reacted at r.t. for 6 h, after which water (10 mL) was added and the resulting solution was extracted with EtOAc (5 mL×3). The organic phase was washed with brine (10 mL), dried over anhydrous Na$_2$SO$_4$, filtered and evaporated to give a residue which was purified by preparative HPLC to afford compound 15-4 (white solid, 17.5 mg, Yield 15%).

$^1$H NMR (400 MHz, MeOD): δ ppm 8.631 (s, 1H), 8.341 (s, 1H), 7.827-7.805 (d, 1H, J=8.8 Hz), 7.603-7.583 (d, 2H, J=8.0 Hz), 7.441 (m, 1H), 6.989-6.968 (d, 2H, J=8.4 Hz), 6.487 (m, 2H), 5.870-5.849 (d, 1H, J=8.4 Hz), 4.568 (s, 1H), 4.137 (brs, 2H), 3.755 (s, 2H), 3.439 (s, 3H).

Scheme 15

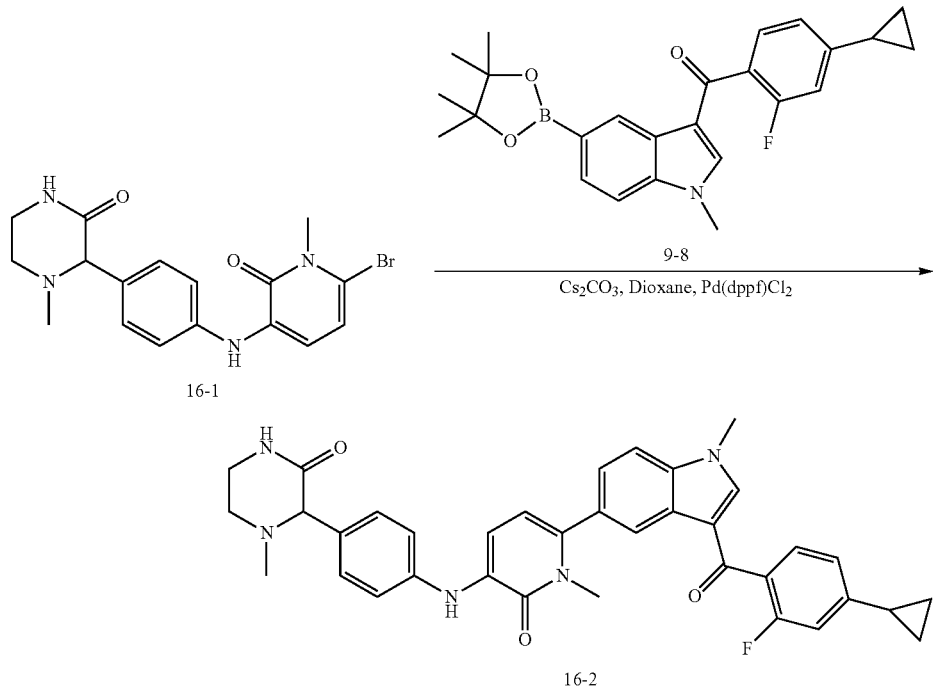

Example 16

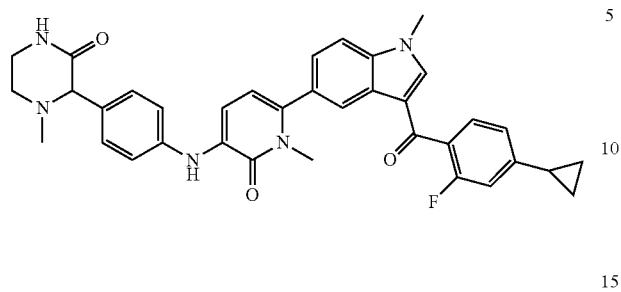

Synthesis of Compound 16-2

To a mixture of compound 16-1 (120 mg, 0.279 mmol), compound 9-8 (113 mg, 0.279 mmol) and Cs₂CO₃ (181.9 mg, 0.558 mmol) in dioxane (5 ml) and water (1 ml) was added Pd(dppf)Cl₂ (19.39 mg, 0.0279 mmol), and the reaction mixture was reacted under microwave at 110° C. for 40 min, followed by filtration and extraction with EtOAc. The organic phase was washed with water and brine, dried over anhydrous Na₂SO₄, filtered and evaporated to give a residue which was purified by column chromatography to afford compound 16-2 (40 mg, Yield 23.2%).

LCMS (ESI) m/z: 604 (M+1)

Scheme 16

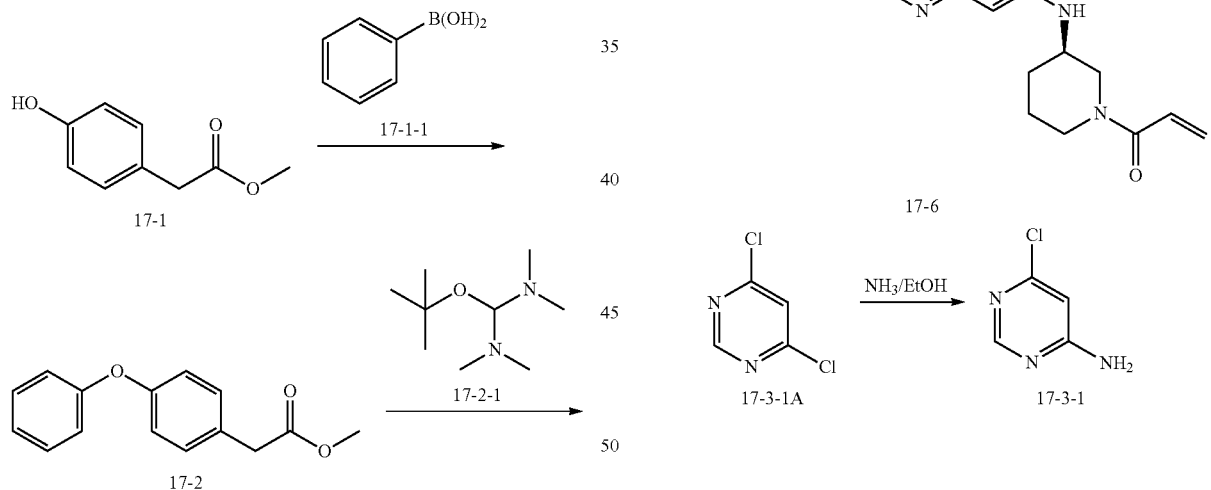

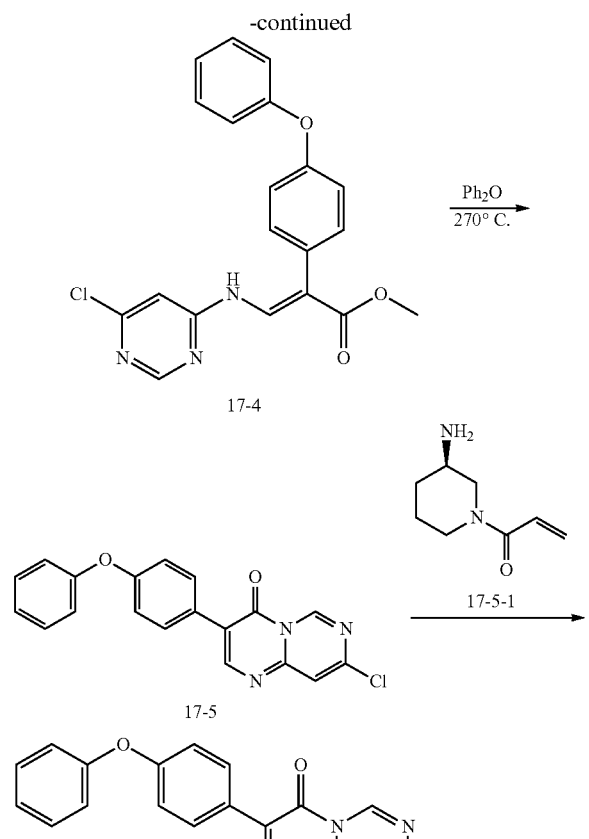

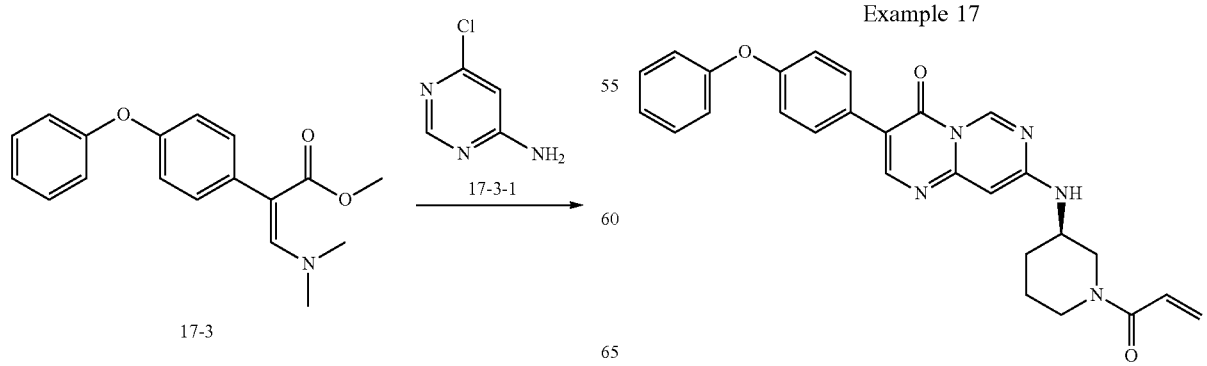

Example 17

Synthesis of Compound 17-2

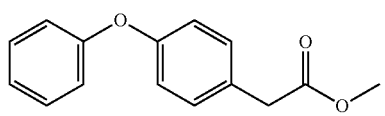 [SMILES: COC(=O)Cc1ccc(Oc2ccccc2)cc1]

The solution of compound 17-1 (3.32 g, 20.0 mmol), compound 17-1-1 (4.88 g, 40.0 mmol), copper acetate (Cu(OAc)$_2$) (3.58 g, 20.0 mmol), molecular sieves 4A and pyridine (8 mL) in DCM (80 mL) was stirred at r.t. O/N. The reaction solution was filtered and the filter cake was washed with EtOAc. The organic phases were combined, washed with saturated brine, dried over anhydrous Na$_2$SO$_4$, filtered and evaporated to give compound 17-2 (8 g, Yield 68%).

$^1$H NMR (400 MHz, CDCl$_3$): δ ppm 7.38-7.34 (m, 2H), 7.29-7.27 (m, 1H), 7.15-7.13 (t, 1H), 7.05-6.99 (m, 5H), 3.73 (s, 3H), 3.64 (s, 2H).

Synthesis of Compound 17-3

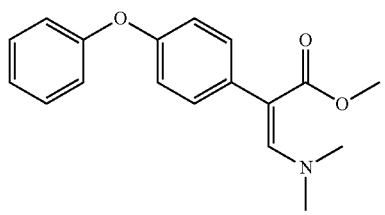 [SMILES: COC(=O)/C(=C\N(C)C)c1ccc(Oc2ccccc2)cc1]

To a solution of compound 17-2 (1 g, 5 mmol) in DCM (10 mL) was added DIPA (1.29 g, 10 mmol) and compound 17-2-1 (1 g, 7.5 mmol) at 0° C., and the reaction solution was stirred at r.t. for 1 h, followed by concentrated and stripped. The residue was purified by column chromatography to give compound 17-3 (1 g, Yield 78%).

LCMS (ESI) m/z: 298 (M+1)

Synthesis of Compound 17-4

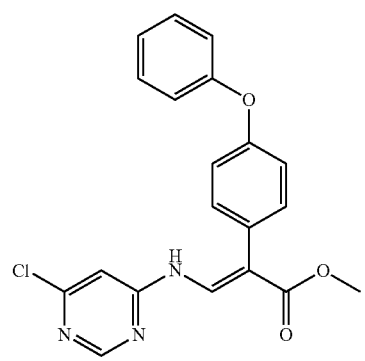 [SMILES: COC(=O)/C(=C/Nc1cc(Cl)ncn1)c1ccc(Oc2ccccc2)cc1]

The mixture of compound 17-3 (81 mg, 0.67 mmol) and compound 17-3-1 (0.2 g, 0.67 mmol) in t-butyl alcohol (3 mL) was heated and refluxed and stirred for 20 h, and then evaporated and stripped to give compound 17-4 (50 mg, Yield 20%).

$^1$H NMR (400 MHz, CDCl$_3$): δ ppm 8.48 (s, 1H), 8.32 (d, 1H), 7.31-7.19 (t, 2H), 7.17-7.14 (m, 3H), 7.09 (s, 1H), 7.03-6.98 (m, 4H), 6.65 (s, 1H), 3.72 (s, 3H)

Synthesis of Compound 17-5

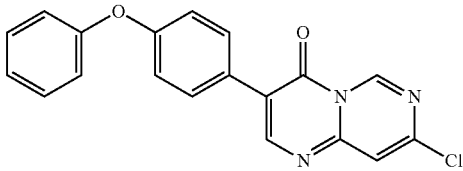 [SMILES: O=c1c(-c2ccc(Oc3ccccc3)cc2)cnc2cc(Cl)ncn12]

To boiling diphenyl ether (Ph$_2$O) (2 mL), compound 17-4 (0.15 g, 0.39 mmol) was added in portions, and the reaction solution was stirred for 4 h, followed by cooled down to r.t., diluted with n-hexane and filtered. The filter cake was dried to afford compound 17-5 (80 mg, Yield 62%).

$^1$H NMR (400 MHz, CDCl$_3$): δ ppm 9.70 (s, 1H), 8.51 (s, 1H), 7.81-7.79 (d, 2H), 7.61 (s, 1H), 7.42-7.38 (m, 1H), 7.19-7.17 (m, 1H), 7.09-7.06 (m, 5H).

Synthesis of Compound 17-6

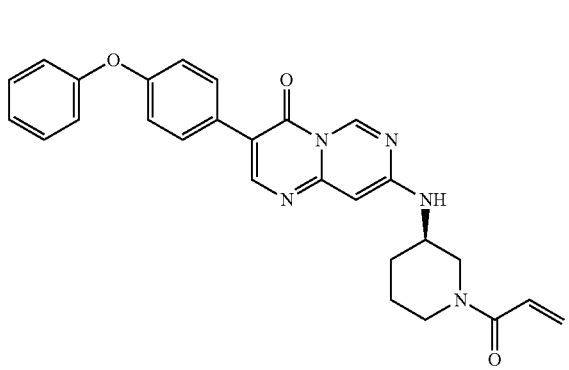 [SMILES: C=CC(=O)N1CCC[C@@H](Nc2cc3ncc(-c4ccc(Oc5ccccc5)cc4)c(=O)n3cn2)C1]

To a mixture of compound 17-5 (0.16 g, 0.46 mmol) and DIPA (178 mg, 1.38 mmol) in t-butyl alcohol (3 mL) was added compound 17-5-1 (0.1 g, 0.55 mmol), and then the reaction mixture was stirred at 50° C. for 0.5 h. The solvent was removed in vacuo and the residue was purified by preparative chromatograph to give compound 17-6 (20 mg, Yield 10%).

$^1$H NMR (400 MHz, MeOD): δ ppm 9.47 (s, 1H), 8.19 (s, 1H), 7.66-7.64 (d, 2H), 7.42-7.38 (m, 2H), 7.19-7.17 (m, 1H), 7.02-7.00 (m, 5H), 6.98-6.75 (m, 1H), 6.26-6.17 (m, 1H), 5.77-5.69 (m, 1H), 4.51-4.55 (m, 1H), 4.01-4.04 (m, 1H), 3.10-3.17 (m, 1H), 2.12-2.03 (m, 1H), 1.91-1.89 (m, 1H), 1.72-1.62 (m, 2H), 1.30-1.23 (m, 2H).

Synthesis of Compound 17-3-1

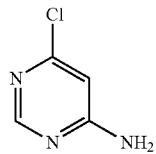

The solution of compound 17-3-1A (10 g, 67.1 mmol) in NH3/EtOH (40 mL) was added into a vessel and reacted at 100° C. for 1.5 h, followed by evaporation to dryness. The residue was triturated with water and filtered to give compound 17-3-1 (6.7 g, Yield 77%).
¹H NMR (400 MHz, CDCl$_3$): δ ppm 8.20 (s, 1H), 7.22 (s, 1H), 6.45 (s, 1H)
Scheme 17
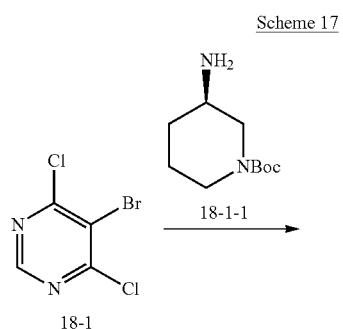
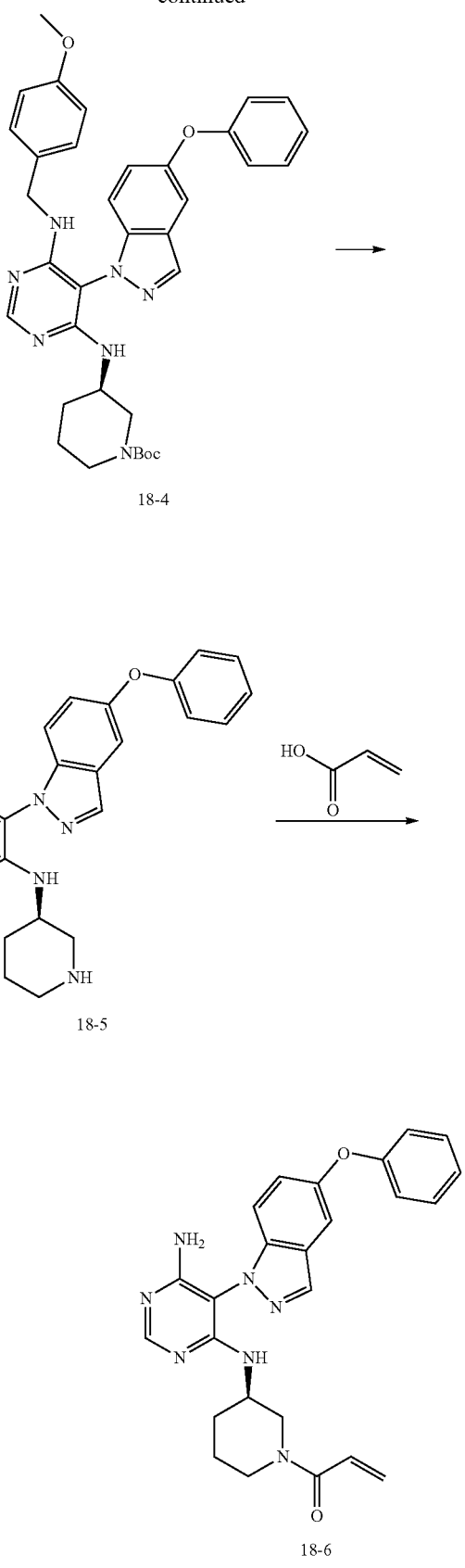

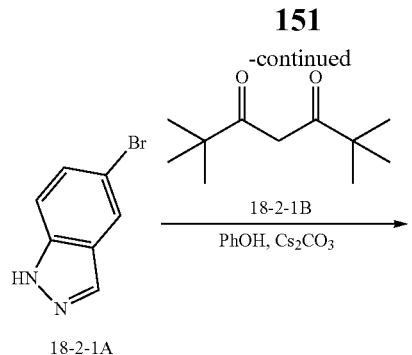

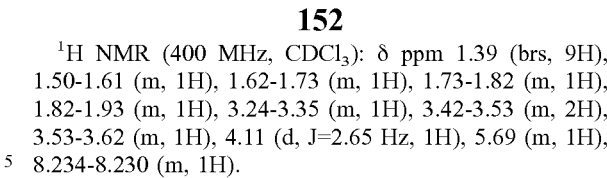

Example 18

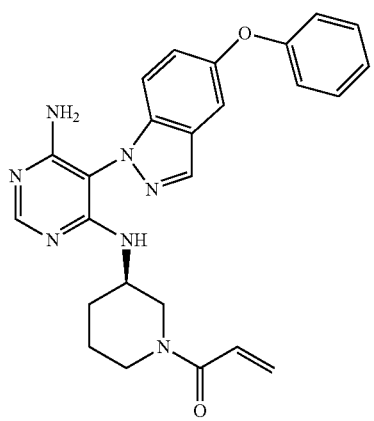 [SMILES: C=CC(=O)N1CCC[C@@H](Nc2ncnc(N)c2-n2ncc3cc(Oc4ccccc4)ccc32)C1]

Synthesis of Compound 18-2

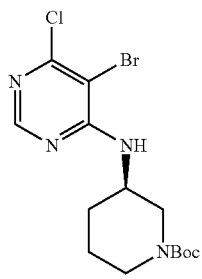 [SMILES: CC(C)(C)OC(=O)N1CCC[C@@H](Nc2ncnc(Cl)c2Br)C1]

To a mixture of compound 18-1-1 (1 g, 5 mmol) in DCM (10 mL) was added DIPA (1.29 g, 10 mmol) and compound 18-1 (1.13 g, 5 mmol) at 0° C., and the reaction solution was stirred at r.t. for 1 h, followed by evaporation. The solvent was removed and the residue was purified by column chromatography to give compound 18-2 (1 g, Yield 78%).

$^1$H NMR (400 MHz, CDCl$_3$): δ ppm 1.39 (brs, 9H), 1.50-1.61 (m, 1H), 1.62-1.73 (m, 1H), 1.73-1.82 (m, 1H), 1.82-1.93 (m, 1H), 3.24-3.35 (m, 1H), 3.42-3.53 (m, 2H), 3.53-3.62 (m, 1H), 4.11 (d, J=2.65 Hz, 1H), 5.69 (m, 1H), 8.234-8.230 (m, 1H).

Synthesis of Compound 18-3

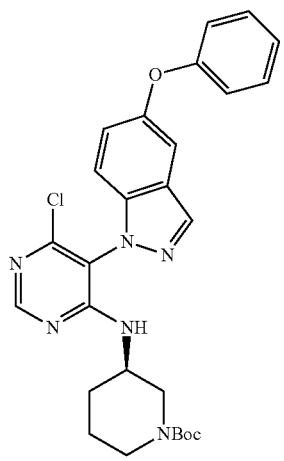 [SMILES: CC(C)(C)OC(=O)N1CCC[C@@H](Nc2ncnc(Cl)c2-n2ncc3cc(Oc4ccccc4)ccc32)C1]

To a mixture of compound 18-2 (2 g, 5.256 mmol) in dioxane (15 mL) was added compound 18-2-1 (1 g, 4.86 mmol), Cs$_2$CO$_3$ (3.2 g, 9.72 mmol) and Pd(dppf)Cl$_2$ (0.34 g, 0.486 mmol) at r.t., and the reaction mixture was stirred at 100° C. for 8 h, followed by evaporation to dryness at a decreased pressure. The residue was purified by column chromatography to give compound 18-3 (1 g, Yield 31%).

LCMS (ESI) m/z: 298 (M+1)

Synthesis of Compound 18-4

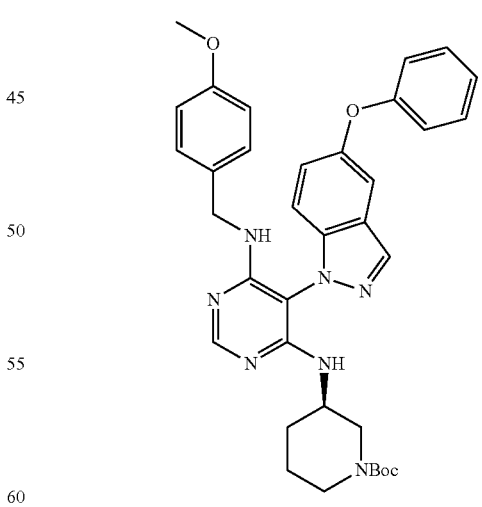

To a mixture of compound 18-3 (1.3 g, 2.5 mmol) in DMF (10 mL) was added methoxybenzylamine (0.69 g, 5 mmol) and potassium t-butoxide (0.56 g, 5 mmol) and the reaction mixture was stirred at 120° C. for 10 h, followed by cooled down to r.t., after which 40 mL water was added and the resulting solution was extracted with EtOAc (10 mL×3). The organic phases were combined, dried over anhydrous Na₂SO₄, filtered and concentrated to give a crude product which was purified by column chromatography to give compound 18-4 (0.8 g, Yield 53%).

¹H NMR (400 MHz, CDCl₃): δ ppm 1.40 (br. s., 9H), 1.45-1.55 (m, 2H), 1.84 (br. s., 3H), 2.97-3.18 (m, 1H), 3.33-3.49 (m, 1H), 3.73 (s, 3H), 3.76-3.80 (m, 2H), 3.91 (br. s., 2H), 4.39 (d, J=5.77 Hz, 1H), 6.76-6.86 (m, 3H), 7.01 (d, J=8.03 Hz, 2H), 7.12 (d, J=7.53 Hz, 1H), 7.19 (d, J=8.28 Hz, 3H), 7.34 (t, J=8.03 Hz, 4H), 7.62 (s, 1H), 8.20 (s, 1H).

Synthesis of Compound 18-5

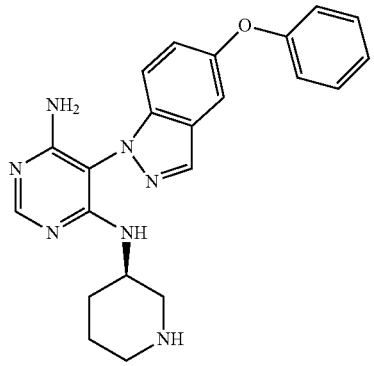 [SMILES: Nc1ncnc(N[C@@H]2CCCNC2)c1-n1ncc2cc(Oc3ccccc3)ccc21]

The mixture of compound 18-4 (0.4 g, 0.64 mmol) in TFA (5 mL) was stirred at 60° C. for 4 h, and then cooled down and concentrated to give a crude product 18-5 (0.2 g, Yield 78%).

LCMS (ESI) m/z: 402 (M+1)

Synthesis of Compound 18-6

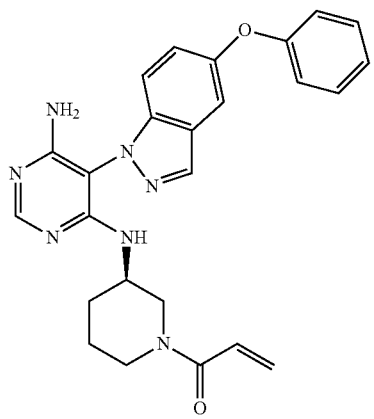 [SMILES: C=CC(=O)N1CCC[C@@H](Nc2ncnc(N)c2-n2ncc3cc(Oc4ccccc4)ccc32)C1]

To a solution of compound 18-5 (300 mg, 0.7 mmol) in DCM (10 mL) was added acrylic acid (60 mg, 0.7 mmol), DIPA (540 mg, 4.2 mmol) and HATU (0.27 g, 7 mmol), and the reaction solution was stirred at r.t. for 1 h, followed by concentrated to give a crude product which was purified by preparative chromatography to afford compound 18-6 (12.9 mg, Yield 4%).

¹H NMR (400 MHz, MeOD): δ ppm 7.68 (s, 2H), 7.34-7.53 (m, 3H), 7.16 (d, J=7.03 Hz, 1H), 7.06 (d, J=8.03 Hz, 2H), 6.61-6.88 (m, 2H), 6.05-6.25 (m, 1H), 5.51-5.57 (m, 2H), 4.15-4.27 (m, 1H), 3.99-4.10 (m, 1H), 3.88-3.98 (m, 1H), 3.69-3.79 (m, 1H), 1.82-2.19 (m, 3H), 1.58-1.75 (m, 1H), 1.31 (s, 1H).

Synthesis of Compound 18-2-1

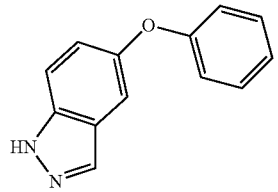 [SMILES: c1ccc(Oc2ccc3[nH]ncc3c2)cc1]

To a solution of compound 18-2-1A (10 g, 53 mmol) in DMF (50 mL) was added phenol (5 g, 53 mmol), CuCl (2.5 g, 26.5 mmol), compound 18-2-1B (5 g, 26.5 mmol) and Cs₂CO₃ (30 g, 106 mmol) and the reaction solution was stirred at 120° C. for 8 h, after which 40 mL water was added and the resulting solution was extracted with EtOAc (10 mL×3). The organic phases were combined, dried over anhydrous Na₂SO₄, filtered and concentrated to give a crude product which was purified by column chromatography eluting with 10/1 to 5/1 of PE/EtOAc to afford compound 18-2-1 (0.5 g, Yield 5%).

¹H NMR (400 MHz, CDCl₃): δ ppm 6.89 (d, J=8.03 Hz, 1H), 6.97 (d, J=8.03 Hz, 2H), 7.03-7.09 (m, 2H), 7.13-7.19 (m, 1H), 7.31 (d, J=7.53 Hz, 3H), 7.48-7.54 (m, 1H), 8.01 (s, 1H).

Example 19

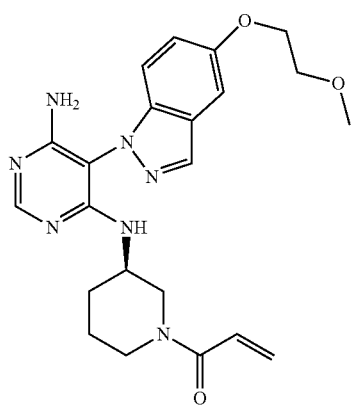 [SMILES: C=CC(=O)N1CCC[C@@H](Nc2ncnc(N)c2-n2ncc3cc(OCCOC)ccc32)C1]

In Example 19, the systhesis process was similar to that in Example 18.

¹H NMR (400 MHz, MeOD): δ ppm 1.31 (s, 1H), 1.58-1.75 (m, 1H), 1.82-2.19 (m, 4H), 3.27-3.29 (m, 1H), 3.69-3.79 (m, 1H), 3.88-3.98 (m, 1H), 3.99-4.10 (m, 1H), 4.15-4.27 (m, 1H), 5.61 (d, J=10.29 Hz, 1H), 6.05-6.25 (m, 1H), 6.61-6.88 (m, 2H), 7.06 (d, J=8.03 Hz, 2H), 7.16 (d, J=7.03 Hz, 1H), 7.34-7.53 (m, 4H), 7.68 (s, 2H).

Scheme 18
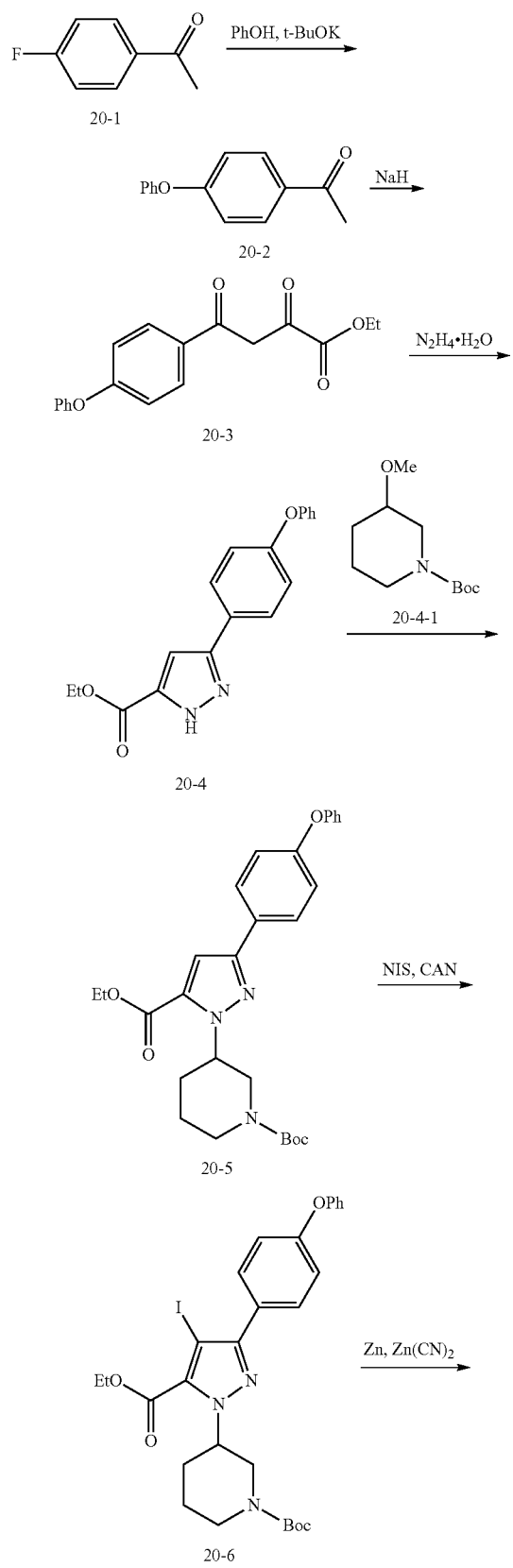
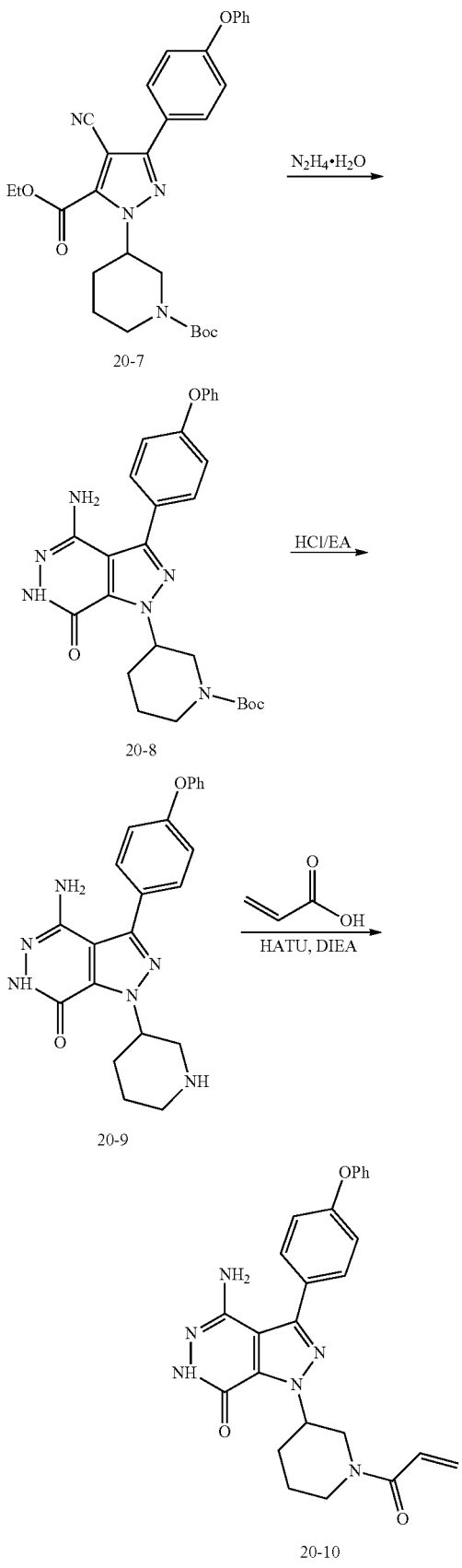

-continued

Example 20

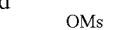

Synthesis of Compound 20-2

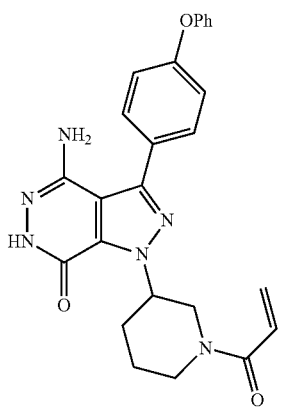 [SMILES: C=CC(=O)N1CCCC(n2nc(-c3ccc(Oc4ccccc4)cc3)c3c(N)n[nH]c(=O)c32)C1]

To a mixture of compound 20-1 (150 g, 1.087 mmol) and phenol (153.2 g, 1.63 mmol) in DMF (1500 mL), potassium t-butoxide (243 g, 2.17 mol) was added in portions and the reaction mixture was stirred at 100° C. for 14 h, after which 100 mL water was added and the resulting reaction mixture was extracted with EtOAc (500 mL×4). The organic phase was dried over anhydrous $Na_2SO_4$, filtered and concentrated to give a crude product which was purified by column chromatography to afford compound 20-2 (171 g, Yield 74.4%) as yellow solid.

$^1$H NMR (400 MHz, MeOD): δ ppm 7.96-7.94 (d, 2H), 7.43-7.39 (t, 2H), 7.23-7.19 (t, 1H), 7.09-7.07 (d, 2H), 7.02-7.00 (d, 2H), 2.58 (s, 3H).

Synthesis of Compound 20-3

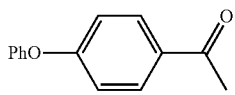

To a mixture of compound 20-2 (150 g, 0.707 mmol) and diethyl oxalate (258 g, 1.767 mmol) in toluene (2000 mL), NaH (50 g, 1.25 mol) was added in portions at 85° C., and the resulting mixture was stirred for 10 min, followed by adjusted to pH 5 with saturated citric acid and extracted with EtOAc (1000 mL×4). The organic phases were combined, dried over anhydrous $Na_2SO_4$, filtered and concentrated to give a crude product which was purified by column chromatography to afford compound 20-3 (135 g, Yield 60%) as yellow solid.

$^1$H NMR (400 MHz, MeOD): δ ppm 8.00-7.98 (d, 2H), 7.44-7.40 (d, 2H), 7.25-7.21 (t, 1H), 7.10-7.03 (m, 4H), 4.43-4.38 (m, 2H), 1.43-1.40 (t, 3H).

Synthesis of Compound 20-4

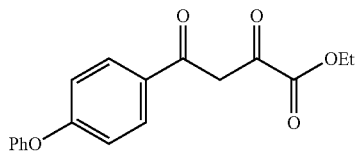 [SMILES: CCOC(=O)C(=O)CC(=O)c1ccc(Oc2ccccc2)cc1]

Compound 20-3 (100 g, 320.5 mmol) was dissolved in 200 mL HOAc and EtOH (200 mL) and the mixture was stirred for 0.5 h, after which $N_2H_4.H_2O$ (48 g, 961.5 mmol) was added and the resulting mixture was reacted for 0.5 h, followed by washed with 1000 mL water and extracted with DCM (1000 mL×3). The organic phases were combined, dried over anhydrous $Na_2SO_4$, filtered and concentrated to give compound 20-4 (75 g, Yield 76.5%) as yellow solid.

$^1$H NMR (400 MHz, MeOD): δ ppm 7.74-7.71 (d, 2H), 7.39-7.35 (t, 2H), 7.16-7.12 (t, 1H), 7.07-7.05 (t, 5H), 4.44-4.39 (m, 2H), 1.43-1.39 (t, 3H).

Synthesis of Compound 20-5

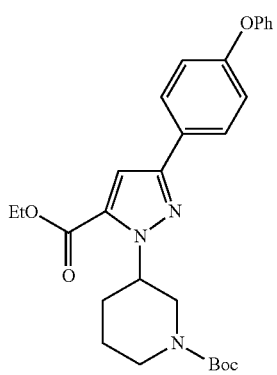 [SMILES: CCOC(=O)c1cc(-c2ccc(Oc3ccccc3)cc2)nn1C1CCCN(C(=O)OC(C)(C)C)C1]

To a mixture of compound 20-4 (70 g, 0.227 mol) and compound 20-4-1 (123.9 g, 0.454 mol) in DMF (700 mL) was added DBU (69 g, 0.454 mol), and the reaction mixture was stirred at 100° C. for 14 h, followed by adjusted to pH 5 with saturated citric acid and extracted with EtOAc (1000 mL×4). The organic phases were combined, dried over anhydrous $Na_2SO_4$, filtered and concentrated to give a crude product which was purified by column chromatography to afford compound 20-5 (15 g, Yield 13.5%) as white solid.

¹H NMR (400 MHz, MeOD): δ ppm 7.78 (d, 2H), 7.35 (t, 2H), 7.01-7.16 (m, 5H), 5.12-5.23 (m, 1H), 4.38 (m, 2H), 3.37 (t, 1H), 2.85 (t, 1H), 2.18 (s, 2H), 1.88 (s, 2H), 1.60-1.74 (m, 2H), 1.38-1.54 (m, 13H).

Synthesis of Compound 20-6

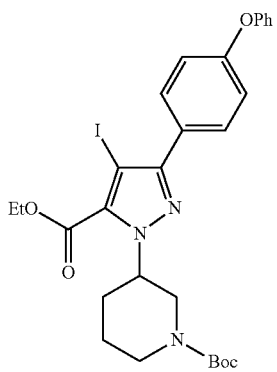 [SMILES: CCOC(=O)c1c(I)c(-c2ccc(Oc3ccccc3)cc2)nn1C1CCCN(C(=O)OC(C)(C)C)C1]

Compound 20-5 (3.6 g, 7.32 mmol), NIS (3.3 g, 14.64 mmol) and CAN (161 mg, 0.732 mmol) was dissolved in acetonitrile (72 mL) and the mixture was stirred at 90° C. for 5 h, followed by washed with 100 mL water and extracted with EtOAc (60 mL×4). The organic phases were combined, dried over anhydrous Na₂SO₄, filtered and concentrated to give a crude product which was purified by column chromatography to afford compound 20-6 (2.2 g, Yield 49%) as brown oil.

¹H NMR (400 MHz, CDCl₃): δ ppm 7.74 (d, 2H), 7.32-7.40 (m, 2H), 7.14 (t, 1H), 7.04-7.10 (m, 4H), 5.01-5.10 (m, 1H), 4.47 (q, 2H), 4.10 (s, 1H), 3.33 (s, 1H), 2.76-2.86 (m, 1H), 2.19 (s, 2H), 1.88 (s, 1H), 1.62 (s, 2H), 1.38-1.53 (m, 12H).

Synthesis of Compound 20-7

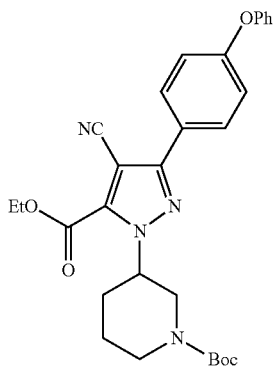 [SMILES: CCOC(=O)c1c(C#N)c(-c2ccc(Oc3ccccc3)cc2)nn1C1CCCN(C(=O)OC(C)(C)C)C1]

To a solution of compound 20-6 (2.5 g, 4.05 mmol), zinc power (526.5 mg, 8.1 mmol) and Zn(CN)₂ (947.7 mg, 8.1 mmol) in DMF (25 mL) was added Pd(dppf)Cl₂ (296.5 mg, 0.405 mol) and Pd₂(dba)₃ (370.5 mg, 0.405 mmol) under nitrogen atmosphere, and the reaction solution was stirred at 100° C. for 14 h, followed by washed with 50 mL water and extracted with EtOAc (50 mL×4). The organic phases were combined, dried over anhydrous Na₂SO₄, filtered and concentrated to give a crude product which was purified by column chromatography to afford compound 20-7 (0.74 g, Yield 37%) as white solid.

¹H NMR (400 MHz, CDCl₃): δ ppm 7.97 (d, 2H), 7.34-7.43 (m, 2H), 7.17 (t, 1H), 7.04-7.12 (m, 4H), 5.20 (s, 1H), 4.50 (q, 2H), 4.24 (s, 1H), 4.08 (s, 1H), 3.38 (t, 1H), 2.87 (t, 1H), 2.10-2.25 (m, 2H), 1.91 (s, 1H), 1.68 (s, 1H), 1.39-1.53 (m, 12H).

Synthesis of Compound 20-8

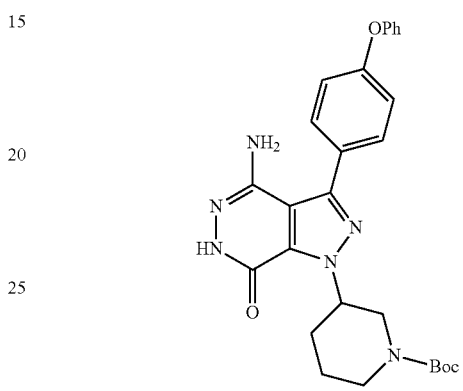

The mixture of compound 20-7 (1.5 g, 2.9 mmol) in N₂H₄.H₂O (25 mL) was stirred at 120° C. for 1 h, and the reaction mixture was washed with 20 mL water and extracted with DCM (30 mL×3). The organic phases were combined, dried over anhydrous Na₂SO₄, filtered and concentrated to give compound 20-8 (1.4 g, Yield 96.5%) as white solid.

Synthesis of Compound 20-9

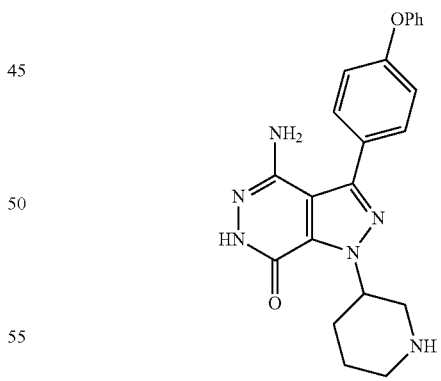

To a solution of compound 20-8 (1.3 g, 2.59 mL) in DCM (1 mL) was added a solution of HCl in EtOAc (10 mL, 4 M), and the reaction solution was stirred at 18° C. for 2 h, followed by filtration. The filter cake was washed with EtOAc and dried in an oven under vacuum to give compound 20-9 (1 g, Yield 88.5%) as white solid.

¹H NMR (400 MHz, d₆-DMSO): δ ppm 11.88 (s, 1H), 9.46-9.54 (m, 1H), 9.26-9.27 (m, 1H), 7.91 (d, 1H), 7.70 (d, 1H), 7.44 (t, 2H), 7.06-7.24 (m, 5H), 5.69-5.79 (m, 1H), 5.059 (d, 1H), 3.60 (d, 1H), 3.43 (d, 1H), 3.24 (d, 1H), 2.98 (d, 1H), 2.02-2.22 (m, 2H), 1.77-1.97 (m, 2H).

Synthesis of Compound 20-10

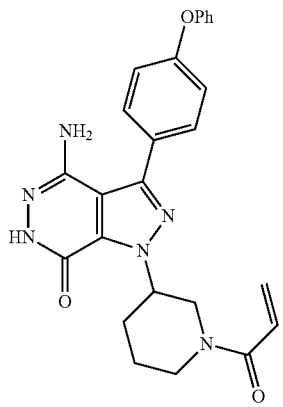 [SMILES: C=CC(=O)N1CCCC(n2nc(-c3ccc(Oc4ccccc4)cc3)c3c(N)n[nH]c(=O)c32)C1]

To a solution of compound 20-9 (1.2 g, 2.74 mmol) and HATU (1.15 g, 3 mmol) in DCM (15 mL) was added DIEA (2.1 g, 16.4 mmol), and then purged with nitrogen. Then acrylic acid (216 mg, 3 mmol) was added, and the resulting solution was stirred at 18° C. for 1.5 h, followed by washed with 30 mL water and extracted with DCM (30 mL×4). The organic phases were combined, dried over anhydrous Na$_2$SO$_4$, filtered and concentrated to give a crude product which was purified by column chromatography to afford compound 20-10 (392 mg, Yield 35%) as white solid.

$^1$H NMR (400 MHz, d$_6$DMSO): δ ppm 11.79 (s, 1H), 7.66-7.68 (d, 2H), 7.43-7.41 (t, 2H), 7.21-7.19 (t, 1H), 7.14-7.10 (t, 3H), 6.85-6.82 (m, 1H), 6.09-6.05 (t, 1H), 5.71 (d, 1H), 5.61 (d, 1H), 5.39 (s, 1H), 4.55 (d, 1H), 4.20-4.36 (m, 2H), 4.04 (s, 1H), 3.55 (d, 1H), 3.17 (d, 2H), 2.18 (s, 1H), 1.94 (d, 1H), 1.54 (s, 1H).

Synthesis of Compound 20-4-1

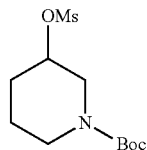 [SMILES: CC(C)(C)OC(=O)N1CCCC(OS(C)(=O)=O)C1]

To a mixture of compound 20-4-1A (200 g, 0.995 mol) and TEA (120.23 g, 1.19 mol) in DCM (700 mL), methylsufonyl chloride (125.24 g, 1.09 mol) was added in portions, and the reaction mixture was stirred at 18° C. for 1 h, followed by washed with water (1500 mL). The aqueous phase was extracted with DCM (500 mL×3), and then the organic phases were combined, dried over anhydrous Na$_2$SO$_4$, filtered and concentrated to give compound 20-4-1 (211 g, Yield 85%) as white solid.

$^1$H NMR (400 MHz, CDCl$_3$): δ ppm 4.72 (s, 1H), 3.55-3.70 (m, 2H), 3.40-3.50 (m, 1H), 3.27-3.38 (m, 1H), 3.09-3.16 (m, 1H), 3.05 (s, 3H), 1.76-2.02 (m, 3H), 1.47 (s, 9H).

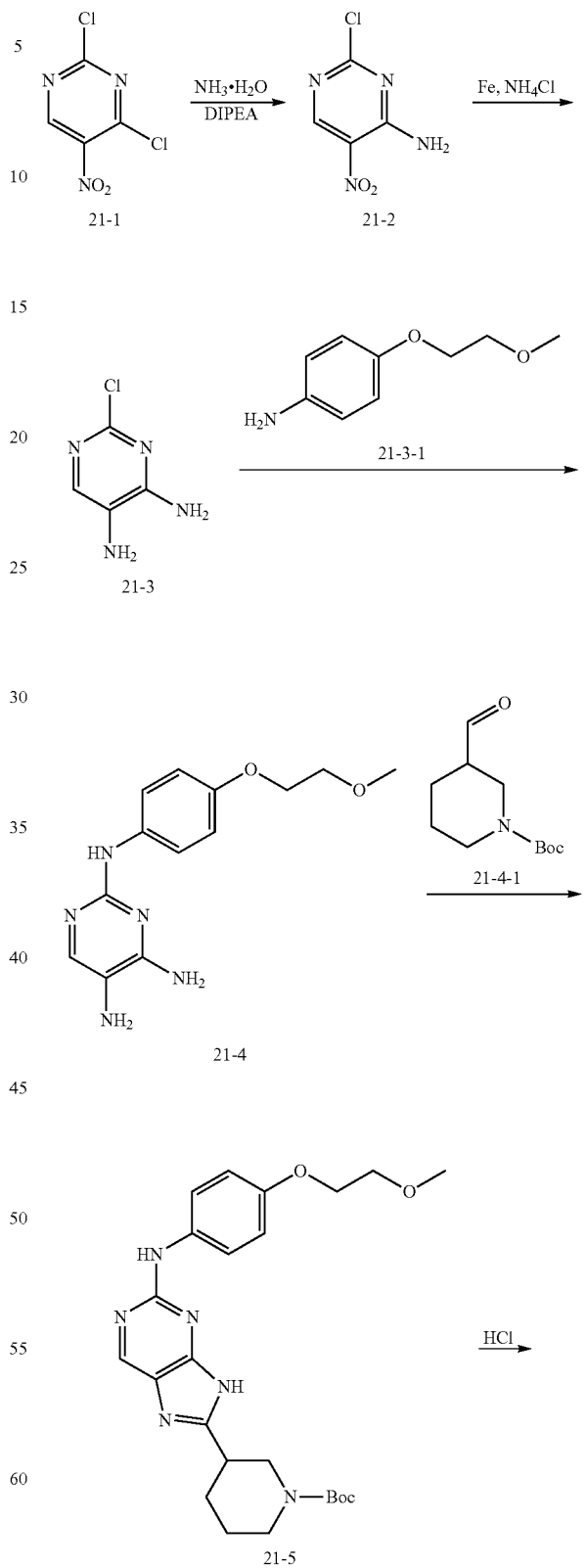

Scheme 19

163
-continued

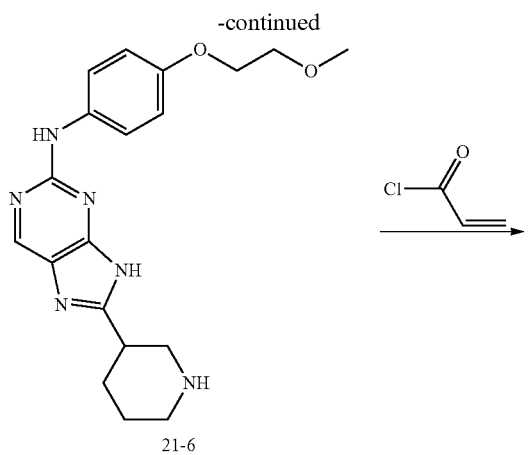
21-6

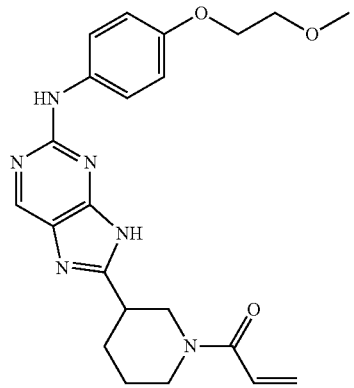 [SMILES: C=CC(=O)N1CCCC(c2nc3cnc(Nc4ccc(OCCOC)cc4)nc3[nH]2)C1]

164

Example 21

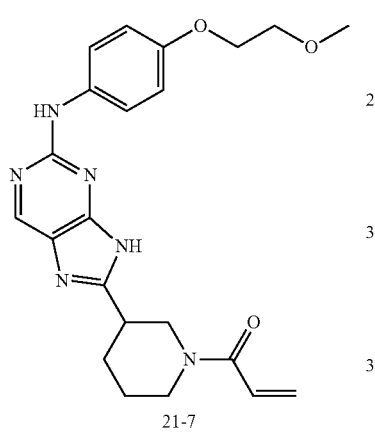
21-7

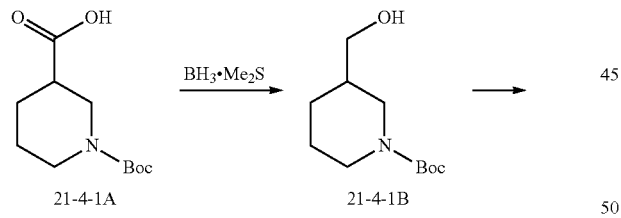

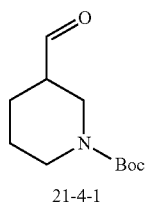
21-4-1

Synthesis of Compound 21-2

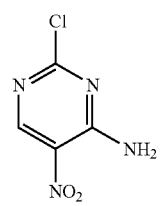 [SMILES: Nc1nc(Cl)ncc1[N+](=O)[O-]]

To a solution of NH$_3$.H$_2$O (aq., 24 mL) and DIPEA (37.2 mL) in DCM (400 mL) was added dropwise a solution of compound 21-1 (30 g, 15436 mmol) in DCM at 0° C., and the reaction solution was stirred at 0° C. for 1 h, followed by filtration. The filter cake was dried to give compound 21-2 (25 g, Yield 92.6%) as yellow solid.

LCMS (ESI) m/z: 175.0 (M+1)

Synthesis of Compound 21-3

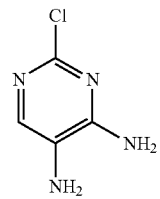

To a solution of compound 21-2 (20 g, 114.6 mmol) in EtOH/H$_2$O (4/1, 400 mL) was added iron powder (64 g, 1146 mmol) and NH$_4$Cl (aq., 62 g, 1146 mmol), the reaction solution was stirred at 100° C. for 4 h, followed by filtration. The filter cake was washed with MeOH (10 mL×3) and the filtrate was concentrated to give compound 21-3 (9 g, Yield 54.5%) as yellow solid.

Synthesis of Compound 21-4

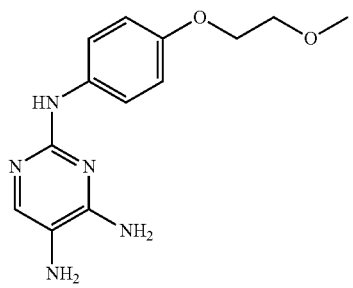 [SMILES: COCCOc1ccc(Nc2ncc(N)c(N)n2)cc1]

Compound 21-3 (4 g, 27.6 mmol) and compound 21-3-1 (5.2 g, 31.2 mmol) were dissolved in HCl/i-PrOH (2 mL/40 mL), and the mixture was heated to 100° C. and stirred for 14 h, followed by adjusted to pH 9 with $Na_2CO_3$ (aq.) and extracted with DCM (50 mL×4). The organic phase was dried over anhydrous $Na_2SO_4$, filtered and concentrated to give a crude product which was purified by column chromatography to afford compound 21-4 (1.1 g, Yield 14.7%) as black solid.

Synthesis of Compound 21-5

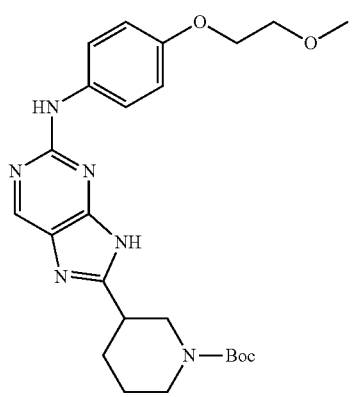 [SMILES: COCCOc1ccc(Nc2ncc3nc(C4CCCN(C(=O)OC(C)(C)C)C4)[nH]c3n2)cc1]

The solution of compound 21-4 (394 mg, 1.9 mmol) in $Na_2S_2O_5$ (6 mL, W %=16%) was stirred at 25° C. for 0.5 h, and evaporated to remove the solvent. The resulting residue and compound 21-4-1 (350 mg, 1.27 mmol) were dissolved in 5 mL DMF and stirred at 110° C. for 7 h. The reaction solution was washed with 20 mL water and extracted with EtOAc (20 mL×3). The organic phase was dried over anhydrous $Na_2SO_4$, filtered and concentrated to give compound 21-5 (400 mg, Yield 67%) as black oil.

$^1$H NMR (400 MHz, $CDCl_3$): δ ppm 8.697 (s, 1H), 7.52-7.50 (d, 2H), 7.24 (s, 1H), 6.92-6.90 (d, 2H), 4.13-4.11 (t, 2H), 3.78-3.75 (t, 4H), 3.47 (s, 3H), 3.11 (s, 1H), 2.11 (s, 1H), 1.92 (s, 2H), 1.58-1.49 (d, 11H), 1.27 (s, 1H).

Synthesis of Compound 21-6

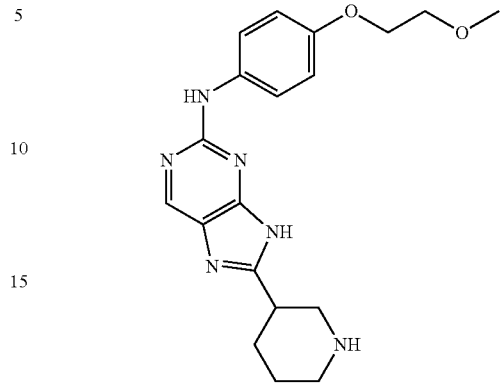

To a solution of compound 21-5 (400 mg, 0.853 mmol) in DCM (5 mL) was added a solution of HCl in EtOAc (10 mL, 4 M), and the reaction solution was stirred at 25° C. for 14 h, followed by adjusted to pH 9 with $NaHCO_3$ (aq.) and extracted with EtOAc (5 mL×4). The organic phase was dried over anhydrous $Na_2SO_4$, filtered and concentrated to give compound 21-6 (170 mg, Yield 54%) as brown solid.

$^1$H NMR (400 MHz, $CDCl_3$): δ ppm 8.66 (s, 1H), 7.55-7.52 (d, 2H), 7.00 (s, 1H), 6.95-6.93 (d, 2H), 4.14-4.11 (t, 2H), 3.77-3.75 (t, 2H), 3.46 (s, 3H), 3.28-3.25 (d, 2H), 3.13-3.11 (d, 2H), 2.82-2.81 (d, 1H), 2.04-1.69 (m, 3H), 1.66-1.57 (m, 3H).

Synthesis of Compound 21-7

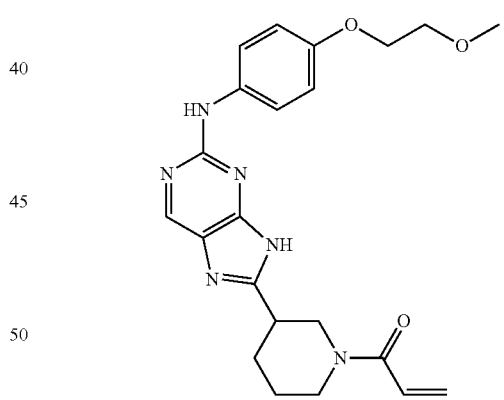

To a solution of compound 21-6 (60 mg, 0.162 mmol) and TEA (49.2 mg, 0.486 mmol) in THF (3 mL) was added dropwise acryloyl chloride (21.87 mg, 0.243 mmol) under nitrogen atmosphere at 0° C., and the reaction solution was stirred at 25° C. for 2 h, followed by washed with 10 mL water and extracted with DCM (5 mL×4). The organic phase was dried over anhydrous $Na_2SO_4$, filtered and concentrated to give a crude product which was purified by preparative chromatography to afford compound 21-7 (7.2 mg, Yield 10.6%) as white solid.

$^1$H NMR (400 MHz, MeOD): δ ppm 8.566 (s, 1H), 7.60-7.58 (d, 2H), 6.91-6.89 (d, 2H), 6.84-6.77 (d, 1H), 6.23-6.19 (d, 1H), 5.77-5.75 (d, 1H), 4.50-4.47 (d, 1H), 4.40-4.36 (d, 1H), 4.14-4.09 (d, 3H), 3.75-3.73 (d, 3H), 3.43 (s, 3H), 3.11-3.08 (d, 2H), 2.25 (s, 1H), 2.01-1.93 (d, 2H), 1.65-1.62 (d, 1H).

Synthesis of Compound 21-4-1B

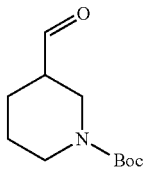 [SMILES: CC(C)(C)OC(=O)N1CCCC(C=O)C1]

To a solution of compound 21-4-1A (1.5 g, 6.73 mmol) in THF (30 mL) was added dropwise BH$_3$.Me$_2$S (3.4 mL, 33.6 mmol) under nitrogen atmosphere at 0° C., and the reaction mixture was stirred at 26° C. for 3 h, and then quenched with MeOH (50 mL), concentrated to give compound 21-4-1B (1.3 g, Yield 93%) as white solid.

$^1$H NMR (400 MHz, CDCl$_3$): δ ppm 3.73 (s, 2H), 3.49-3.51 (s, 2H), 3.02 (s, 2H), 1.79-1.76 (d, 2H), 1.62 (s, 1H), 1.46 (s, 10H), 1.30 (s, 1H).

Synthesis of Compound 21-4-1

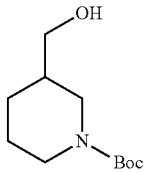

To a solution of compound 21-4-1B (1 g, 4.8 mmol) in DCM (20 mL), Dess-Martin oxidizer (6.1 g, 14.4 mmol) was added in portions, and the resulting solution was stirred at 25° C. for 14 h, followed by quenched with saturated sodium sulfite (Na$_2$SO$_3$) (aq., 20 mL), adjusted to pH 8 with NaHCO$_3$ (aq.) and extracted with DCM (20 mL×3). The organic phase was dried over anhydrous Na$_2$SO$_4$, filtered and concentrated to give compound 21-4-1 (850 mg, Yield 85.5%) as white solid.

$^1$H NMR (400 MHz, CDCl$_3$): δ ppm 9.702 (s, 1H), 3.94-3.91 (d, 1H), 3.66-3.63 (d, 1H), 3.35-3.30 (m, 1H), 3.12-3.06 (m, 1H), 2.42 (s, 1H), 1.96-1.95 (d, 1H), 1.71-1.65 (m, 2H), 1.46-1.36 (m, 10H).

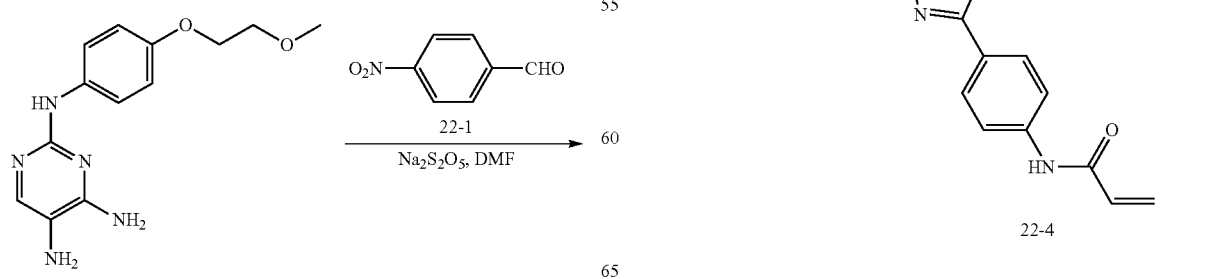

Example 22

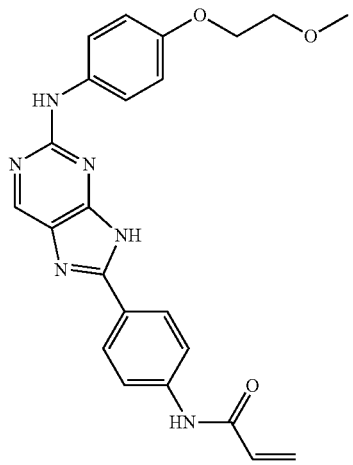 [SMILES: C=CC(=O)Nc1ccc(-c2nc3cnc(Nc4ccc(OCCOC)cc4)nc3[nH]2)cc1]

Synthesis of Compound 22-2

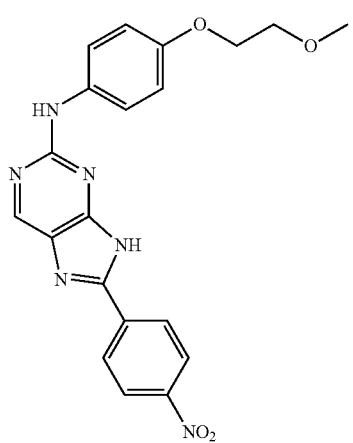 [SMILES: COCCOc1ccc(Nc2ncc3nc(-c4ccc([N+](=O)[O-])cc4)[nH]c3n2)cc1]

To a solution of compound 21-4 (500 mg, 3.3 mmol) in EtOH (10 mL) was added $Na_2S_2O_5$ (2 mL, W %=16%) at r.t., the reaction solution was stirred for 1 h, and EtOH was added during the stirring. The resulting reaction solution was filtered and the filtrate was concentrated to give a white intermediate (640 mg, 75.8 mmol). The intermediate was added into a solution of compound 22-1 (400 mg, 1.45 mmol) in DMF (4 mL) and the mixture was stirred at 110° C. for 10 h, followed by dilution with EtOAc (10 mL). The organic phase was washed with saturated brine (10 mL×5), dried over anhydrous $Na_2SO_4$, filtered and concentrated to give compound 22-2 (480 mg, Yield 81.3%) as yellow oil.

$^1$H NMR (400 MHz, $CDCl_3$): δ ppm 8.630 (s, 1H), 8.31-8.29 (m, 1H), 8.07 (s, 1H), 8.01-7.99 (d, 2H, J=8.8 Hz), 7.48-7.45 (d, 2H, J=8.8 Hz), 6.92-6.90 (d, 2H, J=8.4 Hz), 4.12-4.10 (t, 2H), 3.76-3.74 (t, 2H), 3.45 (s, 3H).

Synthesis of Compound 22-3

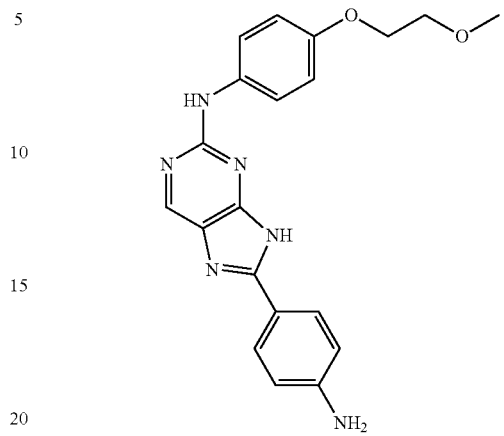

To a solution of compound 22-2 (480 mg, 1.18 mmol) in $EtOH/H_2O$ (24 mL, v/v=5/1) was added iron powder (662 mg, 11.8 mmol) and $NH_4Cl$ (aq., 626 mg, 11.8 mmol), and the reaction solution was stirred at 70° C. for 4 h, followed by filtration. The filtrate was concentrated and the concentrate was dissolved in 10 mL DCM. The organic phase was washed with saturated brine (10 mL), dried over anhydrous $Na_2SO_4$, filtered and concentrated to give compound 22-3 (300 mg, Yield 67.4%) as yellow oil.

$^1$H NMR (400 MHz, $d_6$-DMSO): δ ppm 12.88 (s, 1H), 9.18 (s, 1H), 8.59 (s, 1H), 7.84-7.82 (m, 2H), 7.69-7.67 (m, 2H), 6.89-6.87 (m, 2H), 6.65-6.63 (m, 2H), 5.75 (s, 1H), 5.66 (s, 2H), 4.08-4.04 (m, 2H), 3.65-3.63 (m, 2H), 3.17-3.16 (m, 3H).

Synthesis of Compound 22-4

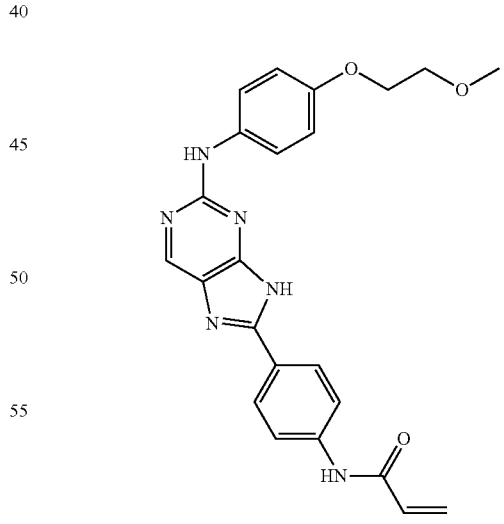

To a solution of compound 22-3 (100 mg, 0.26 mmol) and TEA (107 mg, 1.06 mmol) in THF (5 mL) was added dropwise acryloyl chloride (48 mg, 0.53 mmol) under nitrogen atmosphere at 0° C., and the reaction solution was stirred at r.t. for 6 h. Then, 10 mL water was added to the reaction solution, followed by extracted with EtOAc (5 mL×3) and washed with saturated brine (10 mL). The organic phase was dried over anhydrous Na₂SO₄, filtered and concentrated to give a crude product which was purified by preparative chromatography to afford compound 22-4 (24.3 mg, Yield 21.2%) as yellow solid.

¹H NMR (400 MHz, d₆-DMSO): δ ppm 10.39 (s, 1H), 9.30 (s, 1H), 8.72 (s, 1H), 8.14-8.12 (d, 2H, J=8.8 Hz), 7.84-7.82 (d, 2H, J=8.4 Hz), 7.71-7.69 (d, 2H, J=9.2 Hz), 6.91-6.88 (d, 2H, J=9.2 Hz), 6.466-6.441 (m, 1H), 6.32-6.28 (d, 1H, J=16.8 Hz), 5.82-5.79 (d, 1H, J=10 Hz), 4.07-4.04 (t, 2H), 3.66-3.64 (t, 2H), 3.35-3.33 (s, 3H).

Scheme 21

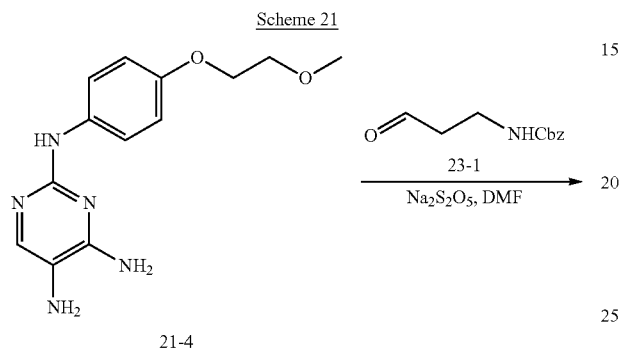

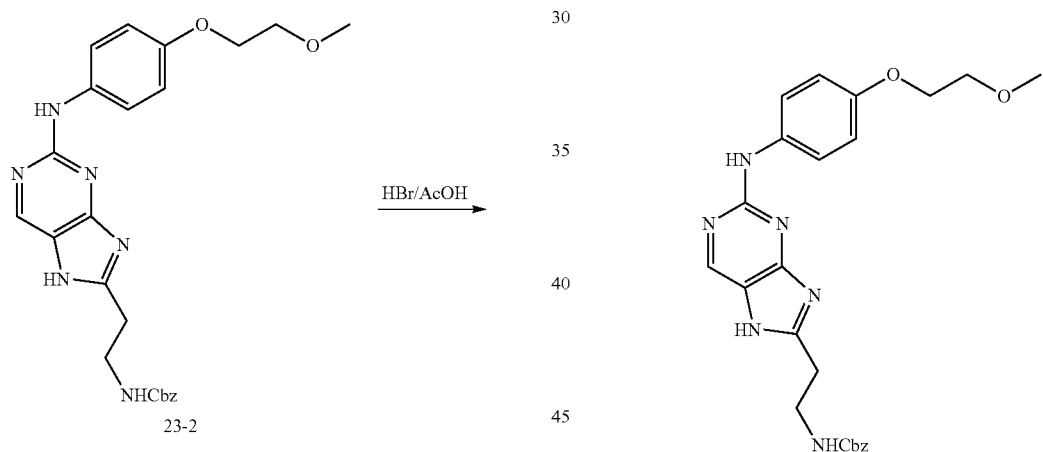

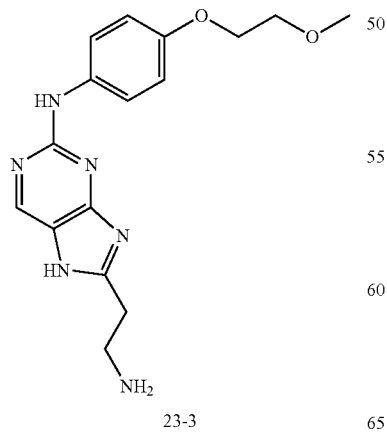

23-3

Example 23

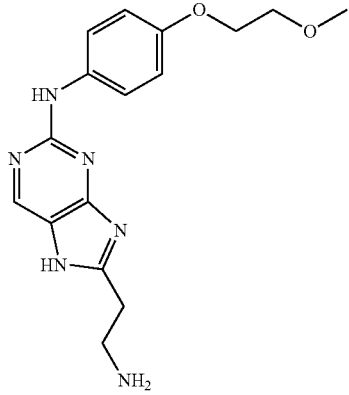 [SMILES: COCCOc1ccc(Nc2ncc3[nH]c(CCN)nc3n2)cc1]

Synthesis of compound 23-2

To a solution of compound 23-1 (2 g, 9.7 mmol) in EtOH (50 mL) was added Na₂S₂O₅ (10 mL, W %=16%) at r.t., the reaction solution was stirred for 1 h, and EtOH (50 mL) was added during the stirring. The resulting reaction solution was filtered and the filtrate was concentrated to give a white intermediate. The intermediate was added into a mixture of compound 21-4 (500 mg, 1.82 mmol) in DMF (10 mL) and the resulting mixture was stirred at 110° C. for 2.5 h, followed by dilution with DCM (10 mL). The organic phase was washed with saturated brine (10 mL×5), dried over anhydrous Na₂SO₄, filtered and concentrated to give compound 23-2 (300 mg, Yield 35.7%) as white solid.

LCMS (ESI) m/z: 463.3 (M+1)

Synthesis of Compound 23-3
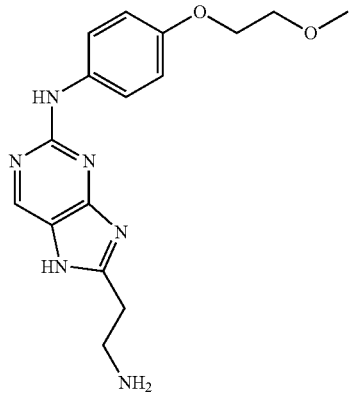 [SMILES: COCCOc1ccc(Nc2ncc3[nH]c(CCN)nc3n2)cc1]
The mixture of compound 23-2 (300 mL, 0.65 mmol) in HBr/AcOH (3 mL/2 mL) was stirred at r.t. for 1 h, followed by concentration to give a crude product which was purified by preparative chromatography to afford compound 23-3 (8.8 mg, Yield 4.1%) as white solid.
$^1$H NMR (400 MHz, MeOD): δ ppm 8.62 (s, 1H), 7.45-7.43 (d, 2H), 7.05-7.03 (d, 2H), 4.16-4.14 (t, 2H), 3.77-3.75 (t, 2H), 3.54-3.51 (t, 2H), 3.43 (s, 3H), 3.35-3.34 (d, 2H).
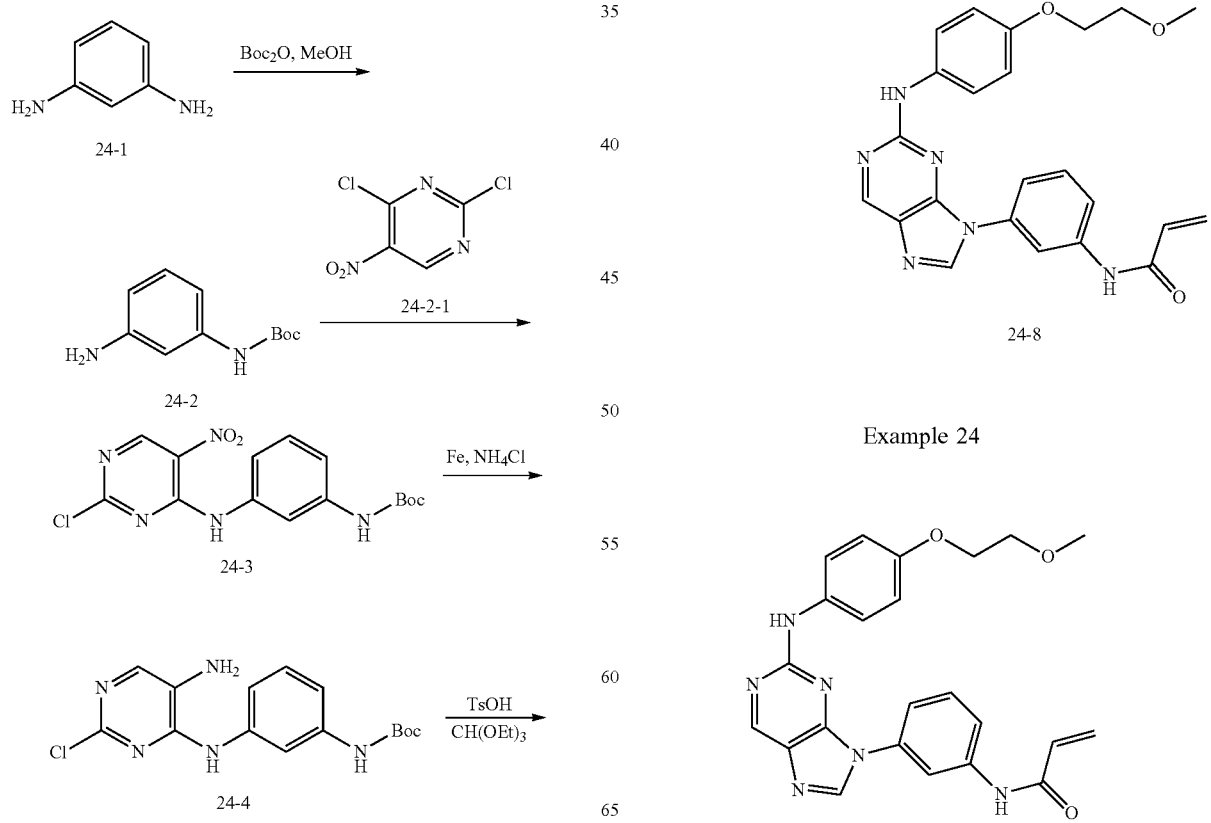
Example 24
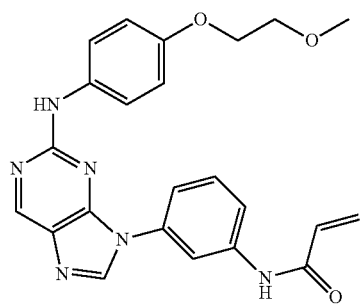 [SMILES: C=CC(=O)Nc1cccc(-n2cnc3cnc(Nc4ccc(OCCOC)cc4)nc32)c1]

Synthesis of Compound 24-2

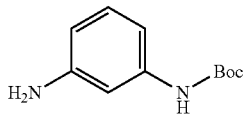

To a mixture of compound 24-1 (10 g, 92.59 mmol) in MeOH which was cooled down to −10° C., was added slowly Boc$_2$O (11.1 g, 50.93 mmol), and the reaction mixture was stirred for 2.5 h while remained at −10° C. during the stirring, followed by concentration to give a residue which was purified by chromatography to afford compound 24-2 (7.4 g, Yield 38.44%) as white solid.

$^1$H NMR (400 MHz, d$_6$-DMSO): δ ppm 8.95 (s, 1H), 6.83-6.77 (t, 2H), 6.51-6.49 (d, 1H, J=8 Hz), 6.15-6.12 (d, 1H, J=8.8 Hz), 4.93 (s, 2H), 1.43 (s, 9H).

Synthesis of Compound 24-3

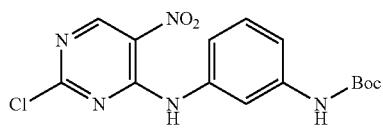 [SMILES: CC(C)(C)OC(=O)Nc1cccc(Nc2nc(Cl)ncc2[N+](=O)[O-])c1]

To a mixture of compound 24-2 (3.9 g, 20.24 mmol) in DCM (50 mL) which was cooled down to 0° C., was added DMAP (2.47 g, 20.24 mmol) and compound 24-2-1 (4 g, 19.23 mmol), and the reaction mixture was stirred at r.t. for 2 h. The residue was washed with water (50 mL), dried over anhydrous Na$_2$SO$_4$, filtered and concentrated to give compound 24-3 (2.5 g, Yield 33.8%) as yellow solid.

$^1$H NMR (400 MHz, d$_6$-DMSO$_6$): δ ppm 10.38 (s, 1H), 9.50 (s, 1H), 9.12 (s, 1H), 7.66 (s, 1H), 7.31 (s, 2H), 7.17 (s, 1H), 1.48 (s, 9H).

Synthesis of Compound 24-4

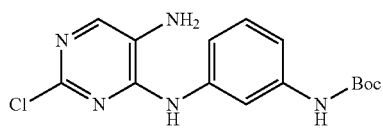 [SMILES: CC(C)(C)OC(=O)Nc1cccc(Nc2nc(Cl)ncc2N)c1]

To a solution of compound 24-3 (2.5 g, 6.85 mmol) in EtOH/H$_2$O (50 mL, v/v=5/1) was added iron powder (3.83 g, 68.49 mmol) and NH$_4$Cl (3.63 g, 68.49 mmol), and the reaction solution was stirred at 70° C. for 3 h, followed by filtration. The filter cake was washed with DCM (20 mL×3), and the organic phases were combined and concentrated to give a residue. The residue was dissolved in EtOAc (30 mL), washed with saturated brine (20 mL), dried over anhydrous Na$_2$SO$_4$, filtered and concentrated to give compound 24-4 (2.17 g, Yield 95%) as black solid.

$^1$H NMR (400 MHz, d$_6$-DMSO): δ ppm 9.38 (s, 1H), 8.73 (s, 1H), 7.76-7.50 (q, 2H), 7.19-7.07 (d, 1H), 5.40 (s, 1H), 1.47 (s, 9H).

Synthesis of Compound 24-5

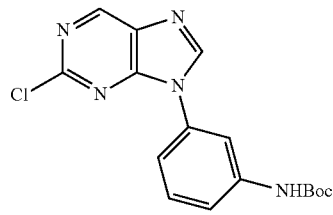 [SMILES: CC(C)(C)OC(=O)Nc1cccc(-n2cnc3cnc(Cl)nc32)c1]

The mixture of compound 24-4 (2.17 g, 6.48 mmol), TsOH (3.69 g, 19.43 mmol) and triethyl orthoformate (30 mL) was reacted at 100° C. for 3 h, and the reaction mixture was concentrated. The residue was dissolved in 50 mL water and extracted with DCM (50 mL×3). The organic phases were combined, dried over anhydrous Na$_2$SO$_4$, filtered and concentrated to give compound 24-5 (2.17 g, Yield 97%) as yellow solid.

$^1$H NMR (400 MHz, CDCl$_3$): δ ppm 9.08 (s, 1H), 8.39 (s, 1H), 8.05 (s, 1H), 7.95 (s, 1H), 7.50-7.40 (q, 1H), 7.38-7.27 (t, 1H), 1.54 (s, 9H).

Synthesis of Compound 24-6

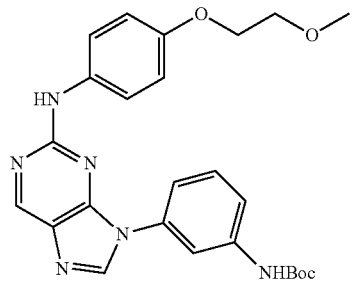 [SMILES: COCCOc1ccc(Nc2ncc3ncn(-c4cccc(NC(=O)OC(C)(C)C)c4)c3n2)cc1]

To a mixture of compound 24-5 (800 mg, 2.32 mmol), compound 24-5-1 (387 mg, 2.23 mmol) and Cs$_2$CO$_3$ (1.51 g, 4.64 mmol) in toluene (20 mL) was added Pd$_2$(dba)$_3$ (212 mg, 0.23 mmol) and Xanphos (110 mg, 0.23 mmol) under nitrogen atmosphere and the reaction mixture was stirred at 80° C. for 4 h, after which, 30 mL water was added, and the resulting reaction mixture was extracted with DCM (30 mL×6). The organic phases were combined, dried over anhydrous Na$_2$SO$_4$, filtered and concentrated to give a crude product which was purified by chromatography to afford compound 24-6 (340 mg, Yield 30.7%) as brown solid.

$^1$H NMR (400 MHz, d$_6$-DMSO): δ ppm 8.85 (s, 1H), 8.12 (s, 1H), 8.02 (s, 1H), 7.58-7.56 (d, 1H, J=8.8 Hz), 7.46-7.44 (q, 2H), 7.34-7.32 (d, 1H, J=7.6 Hz), 7.16 (s, 1H), 6.93-6.91 (d, 2H, J=8.8 Hz), 6.68 (s, 1H), 4.13-4.11 (q, 2H), 3.76-3.74 (q, 2H), 3.46 (s, 3H), 1.55 (s, 9H).

Synthesis of Compound 24-7

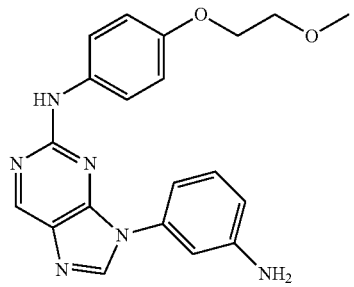 [SMILES: COCCOc1ccc(Nc2ncc3ncn(-c4cccc(N)c4)c3n2)cc1]

The mixture of compound 24-6 (340 mg, 0.71 mmol) in a solution of HCl in EtOAc (20 mL, 4 M) was stirred at r.t. for 1 h, and then concentrated to give compound 24-7 (260 mg, Yield 96.65%) as yellow solid.

LCMS (ESI) m/z: 298 (M+1)

Synthesis of Compound 24-8

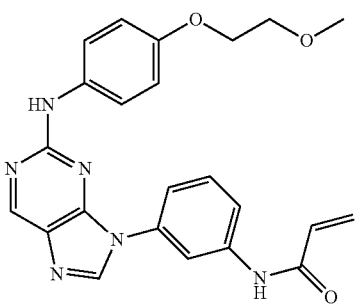 [SMILES: C=CC(=O)Nc1cccc(-n2cnc3cnc(Nc4ccc(OCCOC)cc4)nc32)c1]

To a mixture of compound 24-7 (100 mg, 0.26 mmol) and TEA (134 mg, 1.33 mmol) in THF (3 mL) was added dropwise acryloyl chloride (72 mg, 0.79 mmol) under nitrogen atmosphere at 0° C., and the reaction mixture was heated to r.t. and stirred for 3 h. Water (5 mL) was added to the reaction mixture, and the resulting reaction mixture was extracted with DCM (5 mL×3). The organic phases were combined, dried over anhydrous $Na_2SO_4$, filtered and concentrated to give a crude product which was purified by preparative chromatograph to afford compound 24-8 (50 mg, Yield 43.85%) as white solid.

$^1$H NMR (400 MHz, $CDCl_3$): δ ppm 8.83 (s, 1H), 8.31 (s, 1H), 8.15 (s, 1H), 7.57-7.50 (m, 6H), 6.91-6.89 (d, 2H, J=9.2 Hz), 6.53-6.48 (d, 1H, J=16.8 Hz), 6.35-6.28 (m, 1H), 5.87-5.84 (d, 1H, J=10.4 Hz), 4.11-4.09 (q, 2H), 3.76-3.74 (q, 2H), 3.49-3.46 (d, 3H, J=13.6 Hz).

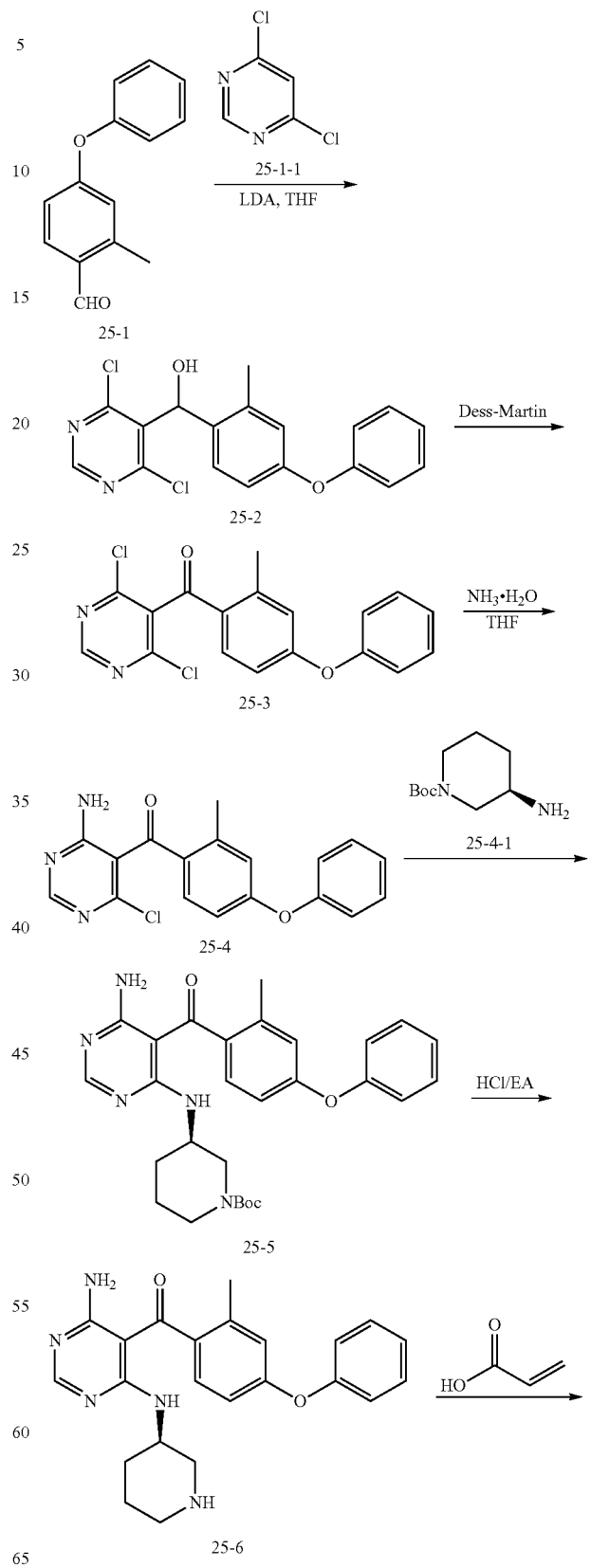

Scheme 23

-continued

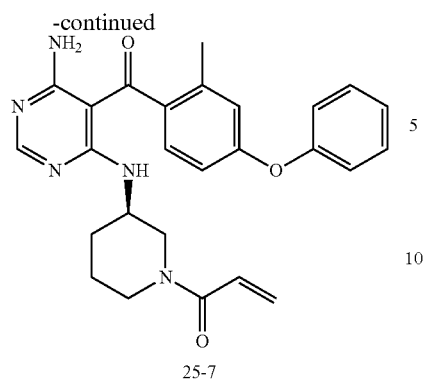

25-7

Example 25

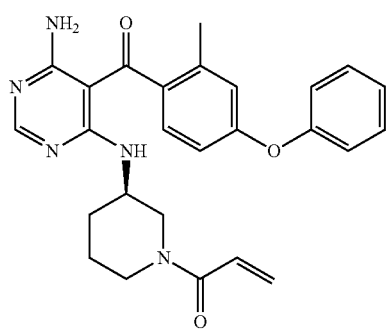 [SMILES: C=CC(=O)N1CCC[C@@H](Nc2ncnc(N)c2C(=O)c2ccc(Oc3ccccc3)cc2C)C1]

Synthesis of Compound 25-2

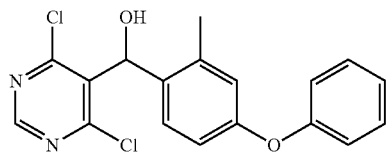

To a solution of compound 25-1-1 (1.47 g, 9.86 mmol) in THF (23 mL) was added dropwise LDA (4.9 mL, 9.86 mmol, 2M) under nitrogen atmosphere at −100° C. to −90° C. (bath of liquid ammonia and EtOH), and the reaction solution was stirred for 1.5 h while remained at such temperature. To this solution, a solution of compound 25-1 (2.3 g, 10.85 mmol) in THF (7.5 mL) was added and the resulting solution was stirred for 1.5 h at −100° C. to −90° C. The analysis by TLC (PE:EtOAc=3:1) indicated the reaction was complete. The reaction solution was warmed to −20° C. to −10° C., quenched with saturated NH$_4$Cl (aq.) and the aqueous phase was extracted with EtOAc (200 mL×2). The organic phase was dried over anhydrous Na$_2$SO$_4$, filtered and evaporated to give a residue as purified by column chromatography (PE:EtOAc=10:1) to afford the title compound (0.8 g, 14%) as oil.

$^1$H NMR (CDCl$_3$ 400 MHz): δ ppm 8.69-8.68 (m, 1H), 7.30-7.26 (m, 2H), 7.10-7.05 (m, 1H), 7.01-6.99 (m, 1H), 6.96-6.94 (m, 2H), 6.82-6.81 (m, 1H), 6.70 (m, 1H), 6.40 (m, 1H), 2.32 (s, 3H).

Synthesis of Compound 25-3

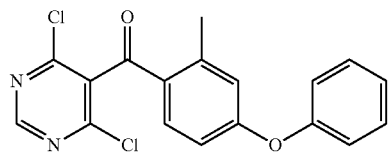 [SMILES: Cc1cc(Oc2ccccc2)ccc1C(=O)c1c(Cl)ncnc1Cl]

The mixture of compound 25-2 (90 mg, 0.249 mmol) and Dess-Martin Periodinane (127.06 mg, 0.299 mmol) in DCM (2 mL) was reacted at 24° C. for 2.5 h, and the reaction mixture was quenched with Na$_2$SO$_3$ (aq., 2 mL×3) and Na$_2$CO$_3$ (aq., 2 mL). The organic phase was dried over anhydrous Na$_2$SO$_4$, filtered and evaporated to give the title compound (80 mg) as yellow oil.

$^1$H NMR (CDCl$_3$ 400 MHz): δ ppm 8.871 (s, 1H), 7.449-7.410 (t, 2H, J=15.6 Hz), 7.307-7.285 (d, 1H, J=8.8 Hz), 7.270-7.248 (d, 1H, J=8.8 Hz), 7.117-7.098 (d, 2H, J=7.6 Hz), 6.940 (s, 1H), 6.784-6.778 (d, 1H, J=2.4 Hz), 2.71 (s, 3H).

Synthesis of Compound 25-4

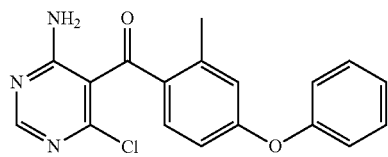 [SMILES: Cc1cc(Oc2ccccc2)ccc1C(=O)c1c(N)ncnc1Cl]

The mixture of compound 25-3 (80 mg, 0.223 mmol) and NH$_3$.H$_2$O (625.6 mg, 4.47 mmol) in THF (2 mL) was reacted 0.5 h under microwave at 80° C., and then concentrated to give the title compound (70 mg, 92%) as yellow solid.

$^1$H NMR (CDCl$_3$ 400 MHz): δ ppm 8.292 (s, 1H), 7.525-7.444 (m, 4H), 7.132-7.113 (d, 2H, J=7.6 Hz), 6.968-6.963 (d, 1H, J=2.0 Hz), 6.836-6.814 (t, 1H, J=8.8 Hz), 5.750 (s, 1H), 2.552 (s, 3H).

Synthesis of Compound 25-5

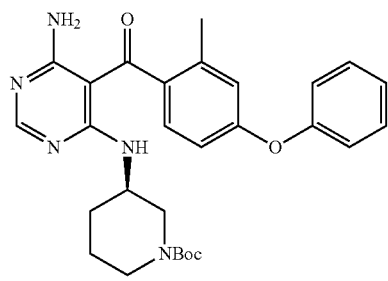 [SMILES: Cc1cc(Oc2ccccc2)ccc1C(=O)c1c(N)ncnc1N[C@@H]1CCCN(C(=O)OC(C)(C)C)C1]

The mixture of compound 25-4 (70 mg, 0.21 mmol), compound 25-4-1 (49.5 mg, 0.24 mmol) and DIPA (53.2 mg, 0.41 mmol) in isopropanol (2 mL) was refluxed for 20 h, and then concentrated. The residue was purified by column chromatography (10%-50% EtOAc/PE) to give the title compound (70 mg, 67.5%) as yellow solid.

LCMS (ESI) m/z: 503 (M+H)

Synthesis of Compound 25-6

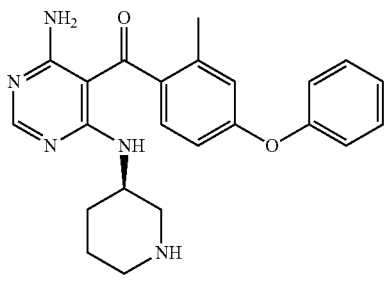 [SMILES: Cc1cc(Oc2ccccc2)ccc1C(=O)c1c(N)ncnc1N[C@@H]1CCCNC1]

The solution of compound 25-5 (60 mg, 0.12 mmol) in a solution of HCl in EtOAc (2 mL, 4 M) was reacted at r.t. for 2 h, and then concentrated to give the title compound (48 mg, 100%) as yellow solid.

$^1$H NMR (CDCl$_3$ 400 MHz): δ ppm 8.090 (s, 1H), 7.416-7.376 (t, 2H, J=19.6 Hz), 7.298 (s, 1H), 7.208-7.171 (t, 1H, J=14.8 Hz), 7.066-7.046 (d, 2H, J=8 Hz), 6.909-6.887 (d, 2H, J=8.8 Hz), 5.878 (br, 2H), 4.181-4.163 (m, 1H), 3.566-3.554 (m, 2H), 3.094-3.065 (d, 1H, J=11.6 Hz), 2.805 (m, 1H), 2.691 (m, 1H), 2.536-2.468 (m, 2H), 2.318 (s, 3H).

Synthesis of Compound 25-7

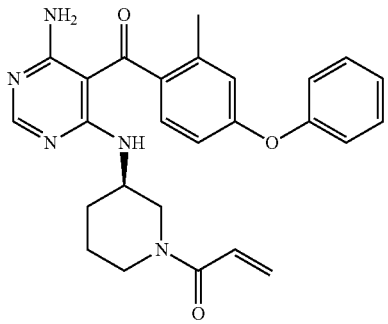 [SMILES: C=CC(=O)N1CCC[C@@H](Nc2ncnc(N)c2C(=O)c2ccc(Oc3ccccc3)cc2C)C1]

The mixture of compound 25-6 (48 mg, 0.12 mmol), acrylic acid (9.4 mg, 0.13 mmol), HATU (91.7 mg, 0.24 mmol) and DIEA (46.1 mg, 0.36 mmol) in DCM (2 mL) was reacted at r.t. for 8 h, and then the reaction was quenched with water (2 mL). The organic phase was dried over anhydrous Na$_2$SO$_4$, filtered and evaporated to give a residue which was purified by preparative HPLC to affoad the title compound (3.1 mg, 5.5%) as yellow solid.

$^1$H NMR (CDCl$_3$ 400 MHz): δ ppm 8.123 (s, 1H), 7.425-7.385 (t, 2H, J=16 Hz), 7.237-7.184 (m, 1H), 7.075-7.056 (d, 2H, J=7.6 Hz), 6.909-6.888 (d, 2H, J=8.4 Hz), 6.292-6.250 (t, 1H, J=16.8 Hz), 6.246 (d, 1H), 5.834 (m, 2H), 5.658 (m, 1H), 4.166 (m, 1H), 3.938-3.913 (m, 1H), 3.811 (m, 1H), 3.411-3.329 (m, 3H), 2.292 (s, 3H), 1.992 (br, 2H).

Example 26

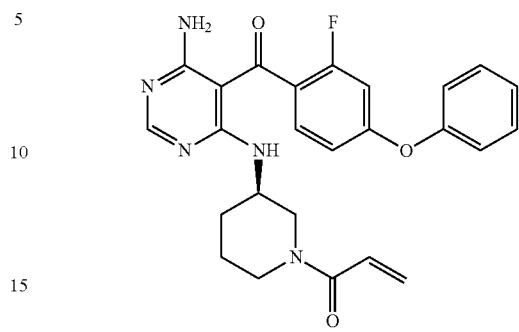

In example 26, the systhesis process was similar to that in example 25.

$^1$H NMR (CDCl$_3$ 400 MHz): δ ppm 8.114 (s, 1H), 8.09-8.07 (t, 1H), 7.49-7.45 (m, 1H), 7.37-7.33 (m, 2H), 7.19-7.15 (t, 1H, J=16 Hz), 6.95-6.92 (m, 3H), 6.62-6.59 (dd, 1H), 6.56-6.52 (m, 1H), 6.27-6.23 (d, 1H, J=16 Hz), 4.14-4.13 (m, 1H), 3.92 (m, 2H), 3.34-3.32 (m, 2H), 3.07-3.04 (m, 1H), 2.54-2.52 (m, 1H), 2.93-1.97 (m, 1H).

LCMS: m/z 462 (M+H$^+$)

Scheme 24

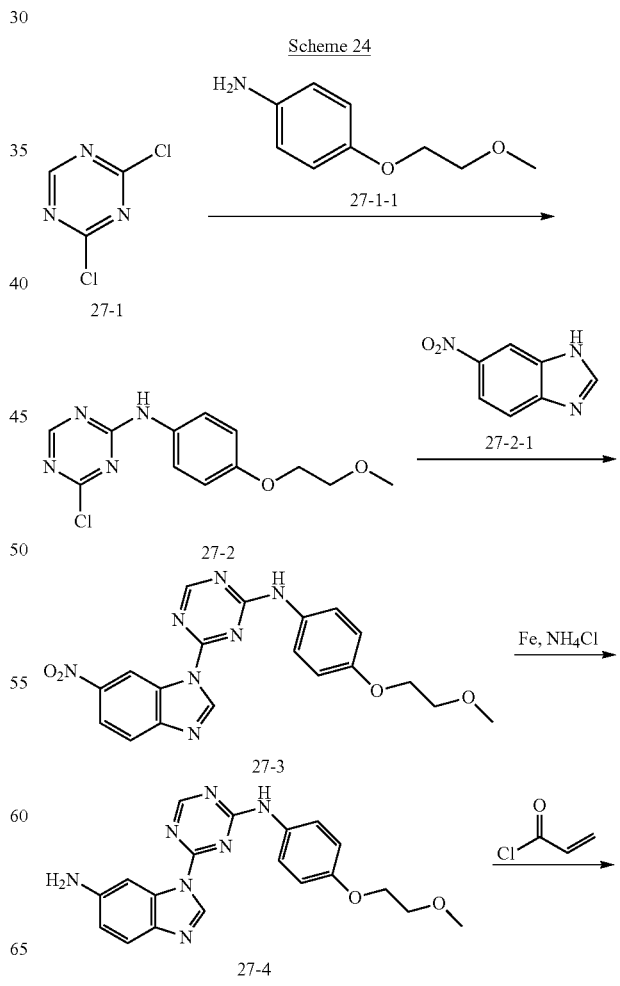

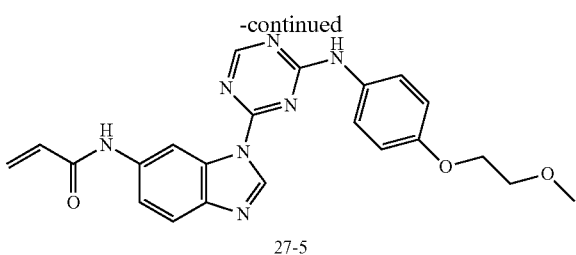

27-5

Example 27

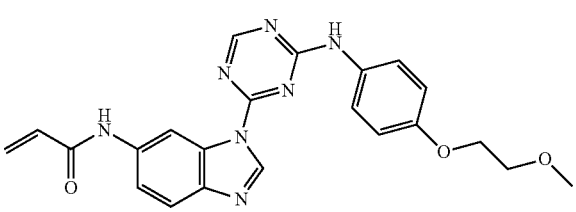 [SMILES: C=CC(=O)Nc1ccc2ncn(-c3ncnc(Nc4ccc(OCCOC)cc4)n3)c2c1]

Synthesis of Compound 27-2

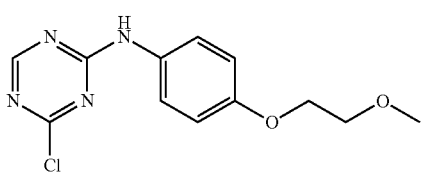 [SMILES: COCCOc1ccc(Nc2ncnc(Cl)n2)cc1]

To a solution of compound 27-1 in DMF (50 mL) was added dropwise DIPEA (4.55 g, 35.23 mmol) and compound 27-1-1 (5 g, 30.2 mmol) under nitrogen atmosphere at 0° C., and the reaction solution was reacted at 0° C. for 0.5 h, followed by warmed to r.t. and reacted for another 1 h. The resulting reaction solution was diluted with EtOAc (50 mL) and washed with brine (30 mL×3). The organic phase was dried over anhydrous Na$_2$SO$_4$, filtered and evaporated to give a residue was purified by column chromatography (3% to 8% of PE/EtOAc) to afford the title compound (360 mg, 26.3%) as white solid.

Synthesis of Compound 27-3

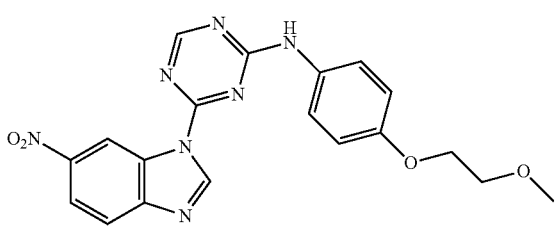 [SMILES: COCCOc1ccc(Nc2ncnc(-n3cnc4ccc([N+](=O)[O-])cc43)n2)cc1]

To a solution of compound 27-2 (200 mg, 0.714 mmol), compound 27-2-1 (116.4 mg, 0.714 mmol) and Cs$_2$CO$_3$ (349.3 mg, 1.07 mmol) in toluene (3 mL) was added Pd$_2$(dba)$_3$ (65.3 mg, 0.071 mmol) and Xanphos (34 mg, 0.071 mmol) under nitrogen atmosphere, and the reaction solution was reacted under microwave at 90° C. for 1 h, followed by extraction with water (3 mL) and DCM (5 mL×3). The organic phase was concentrated and the residue was recrystallized with PE (5 mL) to give the title compound (180 mg, 62%) as light green solid.

$^1$H NMR (400 MHz, d$_6$-DMSO): δ ppm 10.587 (s, 1H), 9.333 (s, 1H), 8.806 (s, 1H), 8.264-8.242 (d, 1H), 8.009-7.987 (d, 1H), 7.594-7.574 (d, 2H), 7.057-6.981 (m, 2H), 4.133 (s, 2H), 3.694 (s, 2H), 3.35-3.25 (s, 3H).

Synthesis of Compound 27-4

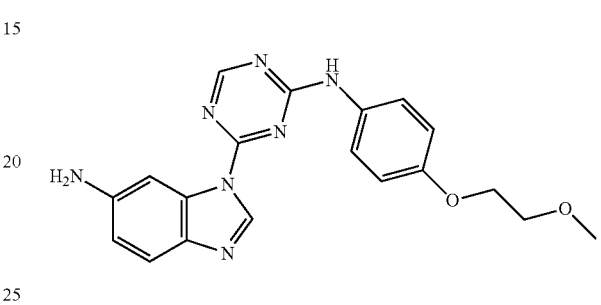

To a solution of compound 27-3 (160 mg, 0.393 mmol) in EtOH/water (5 mL) was added iron powder (220 mg, 3.93 mmol) and NH$_4$Cl (210.3 mg, 3.93 mmol), and the reaction solution was heated at 80° C. for 2 h, followed by filtration. The filtrate was concentrated, and the residue was washed with water (3 mL), extracted with DCM/MeOH (3 mL×2, v/v=10/1). The organic phase was dried over anhydrous Na$_2$SO$_4$, filtered and evaporated to give the title compound (150 mg, 100%) as green solid.

$^1$H NMR (CDCl$_3$ 400 MHz): δ ppm 8.896-8.783 (d, 1H), 8.612 (s, 1H), 7.558-7.387 (t, 4H), 7.011 (s, 2H), 6.721 (s, 1H), 4.184 (s, 2H), 3.793 (s, 2H), 3.483 (s, 3H).

Synthesis of Compound 27-5

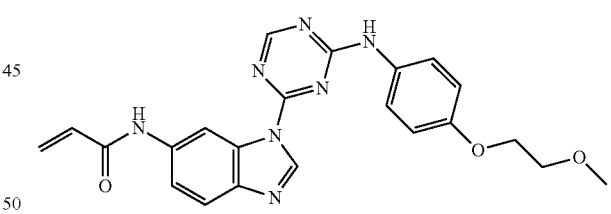

To a solution of compound 27-4 (150 mg, 0.4 mmol) in THF (3 mL) was added TEA (121.2 mg, 1.2 mmol) and acryloyl chloride (54.8 mg, 0.6 mmol) under nitrogen atmosphere at 0° C., and the reaction solution was reacted at r.t. for 1.5 h, followed by washed with water (3 mL) and extracted with DCM/MeOH (5 mL×2, v/v=10/1). The organic phase was dried over anhydrous Na$_2$SO$_4$, and the residue was purified by preparative HPLC to give the title compound (4.62 mg, 0.87%) as white solid.

$^1$H NMR (400 MHz, d$_6$-DMSO): δ ppm 10.453 (s, 1H), 10.358-10.319 (d, 1H), 8.925 (s, 1H), 8.848-8.783 (d, 1H), 7.733-7.711 (d, 1H), 7.610 (s, 2H), 7.014-6.994 (d, 2H), 6.538-6.471 (m, 1H), 6.323-6.281 (d, 1H), 5.793-5.751 (t, 1H), 4.084 (s, 2H), 3.674-3.652 (t, 2H), 3.35-3.25 (s, 3H).

LCMS: m/z 432 (M+H$^+$)

Scheme 25
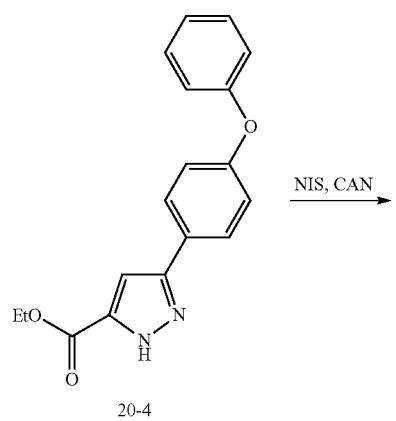
20-4
NIS, CAN →
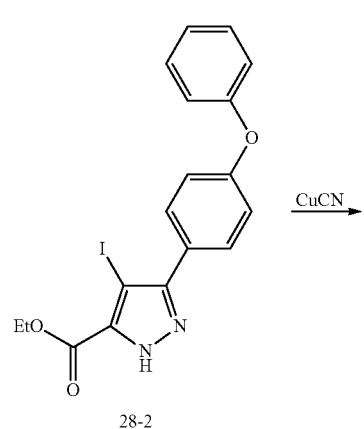
28-2
CuCN →
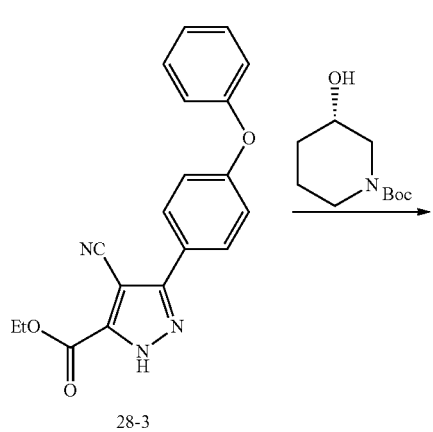
28-3
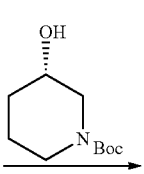
→
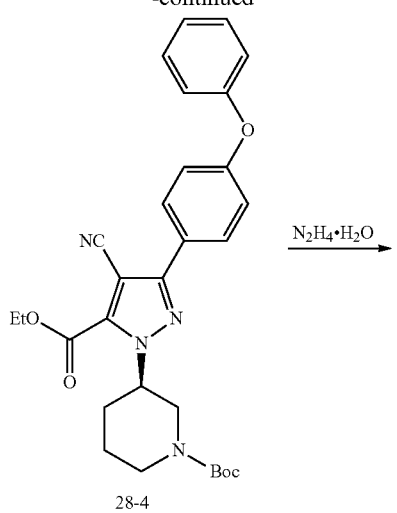
28-4
N₂H₄·H₂O →
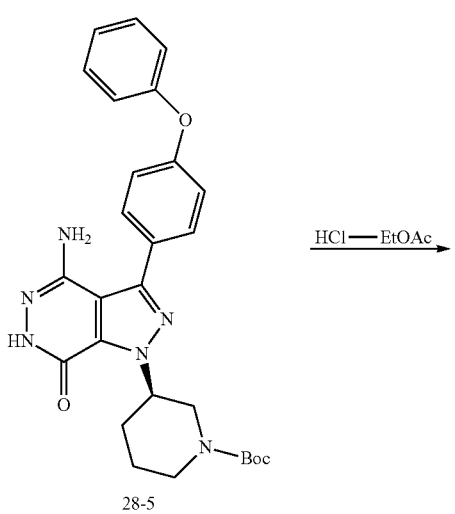
28-5
HCl—EtOAc →
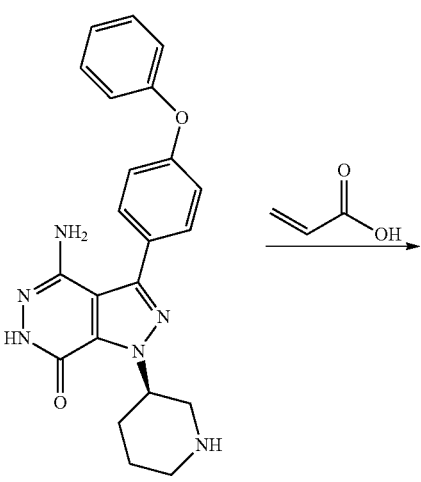
28-6

-continued

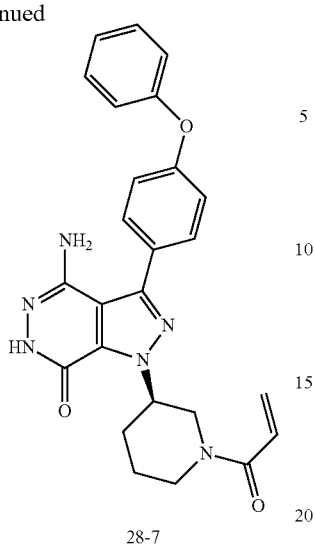

28-7

Example 28

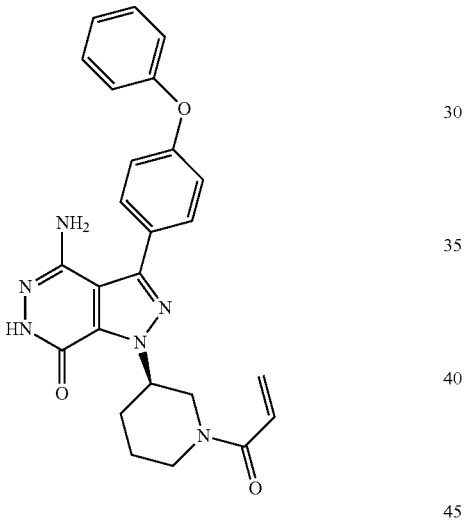

Synthesis of Compound 28-2

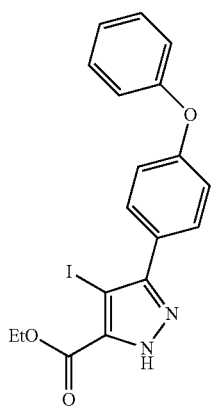 [SMILES: CCOC(=O)c1[nH]nc(-c2ccc(Oc3ccccc3)cc2)c1I]

The mixture of compound 20-4 (25.0 g, 81.2 mmol), NIS (18.3 g, 81.2 mmol) and CAN (6.7 g, 12.2 mmol) in acetonitrile (500 mL) was reacted under nitrogen atmosphere at 80° C. for 1 h. After LCMS indicated the reaction was complete, water (30 mL) was added to the reaction solution and the resulting reaction solution was extracted with EtOAc (1000 mL) twice. The organic phase was dried over anhydrous $Na_2SO_4$, filtered and evaporated to give a residue which was washed with DCM to afford the title compound (25.0 g, 71%) as white solid.

$^1$H NMR ($CDCl_3$ 400 MHz): δ ppm 11.57 (br, 1H), 7.73-7.71 (m, 2H), 7.40-7.38 (m, 2H), 7.18 (m, 1H), 7.11-7.08 (m, 4H), 4.45-4.40 (q, 2H), 1.43-1.40 (t, 3H).

Synthesis of Compound 28-3

To a solution of compound 28-2 (2.17 g, 5.0 mmol) and cuprous cyanide (CuCN) (0.9 g, 10 mmol) in DMF (22 mL) was added Pd(dppf)Cl$_2$ (366 mg, 0.5 mmol) and Pd$_2$(dba)$_3$ (458 mg, 0.5 mmol) under nitrogen atmosphere, and the reaction solution was stirred at 100° C. O/N. After LCMS indicated the reaction was complete, the reaction solution was cooled down to r.t. To the solution was added water and the resulting solution was extracted twice with EtOAc (150 mL). The organic phase was dried over anhydrous $Na_2SO_4$, filtered and evaporated. The residue was purified by column chromatography (PE:EtOAc=1:1) to give the title compound (1.48 g, 89%) as oil.

$^1$H NMR ($CDCl_3$ 400 MHz): δ ppm 7.93-7.91 (m, 2H), 7.43-7.39 (m, 2H), 7.22-7.18 (m, 1H), 7.12-7.08 (m, 4H), 4.51-4.45 (q, 2H), 1.47-1.43 (t, 3H).

Synthesis of Compound 28-4

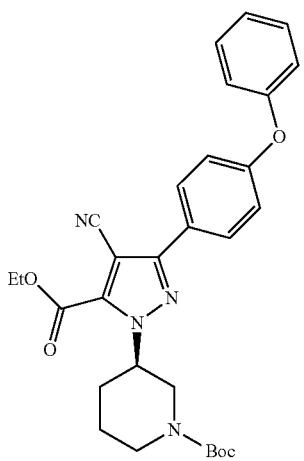 [SMILES: CCOC(=O)c1c(C#N)c(-c2ccc(Oc3ccccc3)cc2)nn1[C@@H]1CCCN(C(=O)OC(C)(C)C)C1]

To a solution of compound 28-3 (0.72 g, 2.16 mmol) and triphenylphosphine (PPh₃) (0.57 g, 2.16 mmol) in anhydrous THF (6 mL) was added dropwise DIAD (0.44 g, 0.64 mmol) and (S)-1-BOC-3-hydroxypiper (0.36 g, 1.80 mmol) under nitrogen atmosphere at 0° C., and the reaction solution was warmed to r.t. and stirred O/N. The analysis by TLC (PE:EtOAc=5:1) indicated the reaction was complete. To this solution was added dropwise saturated NH₄Cl, and the mixture was extracted with EtOAc (200 mL×3). The organic phase was dried over anhydrous Na₂SO₄, filtered and evaporated to give a residue which was purified by column chromatography (20:1 to 10:1 of PE:EtOAc) to afford the title compound (0.65 g, 59%) as white solid.

¹H NMR (CDCl₃ 400 MHz): δ ppm 7.99-7.97 (m, 2H), 7.42-7.38 (m, 2H), 7.20-7.16 (m, 1H), 7.12-7.08 (m, 4H), 5.22-5.21 (m, 1H), 4.54-4.49 (q, 2H), 4.35-4.09 (m, 2H), 3.43-3.37 (m, 1H), 2.92-2.86 (m, 1H), 2.20 (m, 2H), 1.92 (m, 1H), 1.70 (m, 1H), 1.53-1.48 (m, 12H).

Synthesis of Compound 28-5

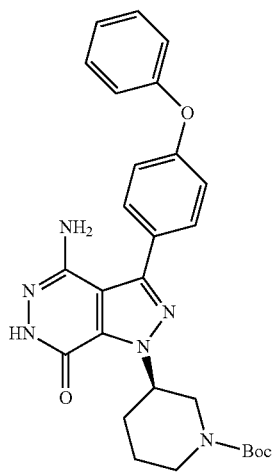 [SMILES: CC(C)(C)OC(=O)N1CCC[C@@H](n2nc(-c3ccc(Oc4ccccc4)cc3)c3c(N)n[nH]c(=O)c32)C1]

The solution of compound 28-4 (340.4 mg, 0.66 mmol) in N₂H₄·H₂O (85%, 6.0 mL) was heated and refluxed for 1.5 h, after which water (20 mL) was added to this solution and the resulting solution was extracted with DCM/MeOH (10/1, 20 mL) twice. The organic phase was dried over anhydrous Na₂SO₄, filtered and evaporated to give the title compound (300 mg, 93%) as white solid.

¹H NMR (CDCl₃ 400 MHz): δ ppm 10.61 (br, 1H), 7.57-7.55 (m, 2H), 7.35-7.33 (m, 2H), 7.10-7.07 (m, 1H), 7.05-7.01 (m, 4H), 5.44-5.37 (m, 1H), 5.05 (br, 2H), 4.19 (m, 1H), 4.00 (m, 1H), 3.40 (m, 1H), 2.83-2.78 (m, 1H), 2.16-2.12 (m, 2H), 1.89-1.84 (m, 1H), 1.71-1.67 (m, 1H), 1.35 (s, 9H).

Synthesis of Compound 28-6

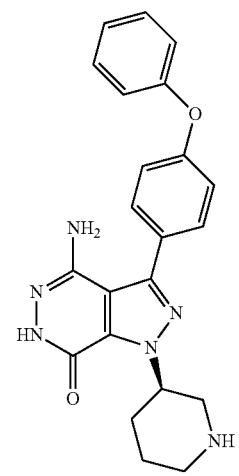 [SMILES: Nc1n[nH]c(=O)c2c1c(-c1ccc(Oc3ccccc3)cc1)nn2[C@@H]1CCCNC1]

To a solution of compound 28-5 (300 mg, 0.60 mmol) in EtOAc (2 mL) was added dropwise a solution of HCl in EtOAc (6 mL, 4 M) in an ice bath, and then the reaction solution was stirred at r.t. The analysis by TLC indicated the reaction was complete. The reaction solution was concentrated to give the title compound (263.1 mg, crude) as yellow solid which was directly used for the next step without further purification.

Synthesis of Compound 28-7

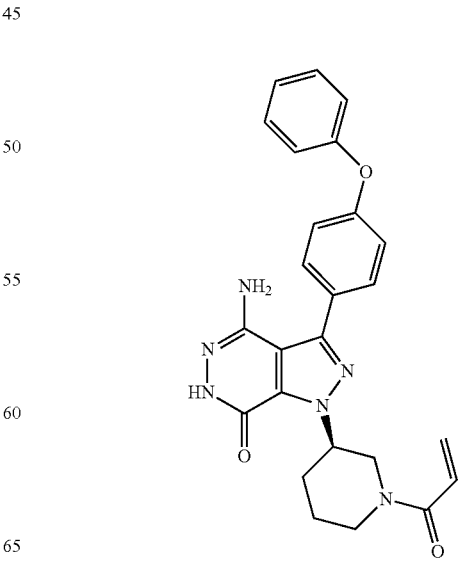

The solution of compound 28-6 (142.4 mg, 0.32 mmol), acrylic acid (25.8 mg, 0.352 mmol), DIPEA (168 mg, 1.30 mmol) and HATU (138 mg, 0.352 mmol) in DCM (7.2 mL) was reacted under nitrogen atmosphere at r.t. for 2 h. The reaction was monitored by LCMS. The reaction was quenched with water (20 mL), and the reaction solution was extracted with DCM (20 mL×2). The organic phase was dried over anhydrous Na$_2$SO$_4$, filtered and evaporated to give a residue which was purified by preparative HPLC to afford the title compound (14.8 mg, 10%) as white solid.

$^1$H NMR (CDCl$_3$ 400 MHz): δ ppm 113-10.06 (m, 1H), 7.57-7.55 (m, 2H), 7.33-7.32 (m, 2H), 7.12 (m, 1H), 7.08-7.02 (m, 4H), 6.58-6.55 (m, 1H), 6.25-6.17 (m, 1H), 5.64-5.56 (m, 1H), 5.42 (m, 1H), 4.80 (br, 2H), 4.57-4.51 (m, 1H), 4.25-4.23 (m, 1H), 3.91 (m, 1H), 3.56-3.53 (m, 1H), 3.51-3.42 (m, 1H), 3.13 (m, 1H), 2.81-2.78 (m, 1H), 2.36-2.17 (m, 3H), 1.94-1.91 (m, 1H), 1.70 (m, 1H).

LCMS: m/z 457 (M+H$^+$)

Scheme 26

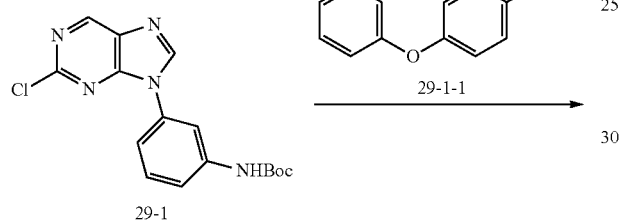

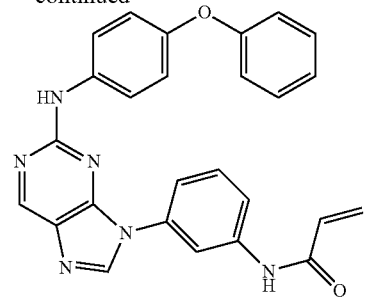

29-4

Example 29

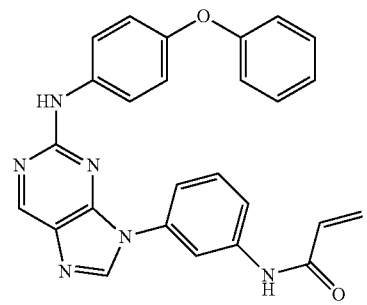 [SMILES: C=CC(=O)Nc1cccc(-n2cnc3cnc(Nc4ccc(Oc5ccccc5)cc4)nc32)c1]

Synthesis of Compound 29-2

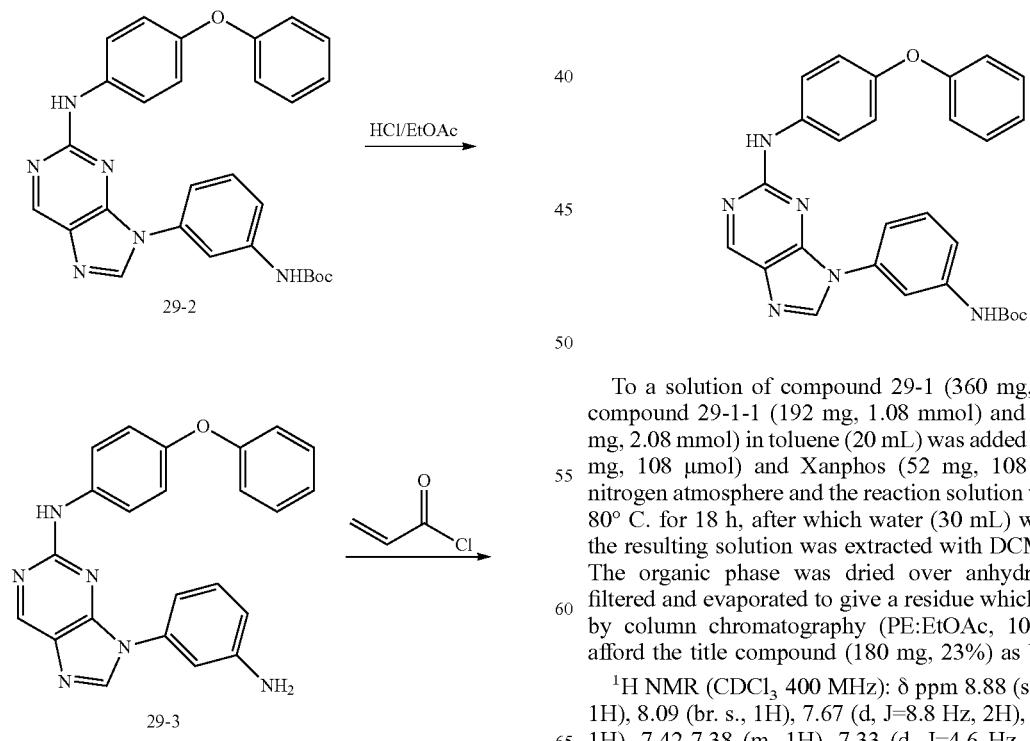

To a solution of compound 29-1 (360 mg, 1.08 mmol), compound 29-1-1 (192 mg, 1.08 mmol) and Cs$_2$CO$_3$ (678 mg, 2.08 mmol) in toluene (20 mL) was added Pd$_2$(dba)$_3$ (99 mg, 108 μmol) and Xanphos (52 mg, 108 μmol) under nitrogen atmosphere and the reaction solution was reacted at 80° C. for 18 h, after which water (30 mL) was added and the resulting solution was extracted with DCM (30 mL×6). The organic phase was dried over anhydrous Na$_2$SO$_4$, filtered and evaporated to give a residue which was purified by column chromatography (PE:EtOAc, 10:1 to 1:1) to afford the title compound (180 mg, 23%) as brown solid.

$^1$H NMR (CDCl$_3$ 400 MHz): δ ppm 8.88 (s, 1H), 8.13 (s, 1H), 8.09 (br. s., 1H), 7.67 (d, J=8.8 Hz, 2H), 7.49-7.42 (m, 1H), 7.42-7.38 (m, 1H), 7.33 (d, J=4.6 Hz, 1H), 7.30 (d, J=8.2 Hz, 2H), 7.10-7.03 (m, 1H), 7.03-6.97 (m, 4H), 6.70 (s, 1H), 1.50 (s, 9H).

Synthesis of Compound 29-3

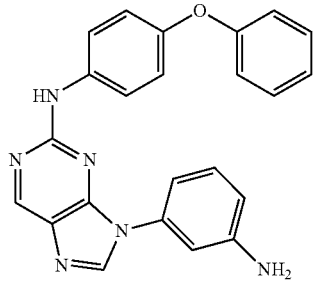 [SMILES: Nc1cccc(-n2cnc3cnc(Nc4ccc(Oc5ccccc5)cc4)nc32)c1]

The solution of compound 29-2 (120 mg, 242 mmol) in a solution of HCl in EtOAc (2 mL, 4 M) was reacted at r.t. for 1 h, and the reaction solution was concentrated to give the title compound (96 mg, 100%) as yellow solid.

Synthesis of Compound 29-4

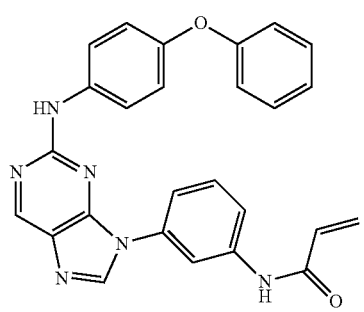 [SMILES: C=CC(=O)Nc1cccc(-n2cnc3cnc(Nc4ccc(Oc5ccccc5)cc4)nc32)c1]

To a solution of compound 29-3 (96 mg, 0.243 mmol) and TEA (73 mg, 0.73 mmol) in THF (10 mL) was added dropwise acryloyl chloride (22 mg, 0.243 mmol) under nitrogen atmosphere at 0° C. and the reaction solution was stirred and reacted at r.t. for 3 h, after which water (5 mL) was added and the resulting solution was extracted with DCM (5 mL×3). The organic phase was dried over anhydrous $Na_2SO_4$, filtered and evaporated to give a residue which was purified by preparative HPLC to afford the title compound (24 mg, 22%) as white solid.

$^1$H NMR (400 MHz, $d_6$-DMSO): δ ppm 10.42 (s, 1H), 9.76 (s, 1H), 8.92 (s, 1H), 8.58 (s, 1H), 8.39 (br. s., 1H), 7.82 (d, J=8.8 Hz, 2H), 7.62-7.46 (m, 3H), 7.32 (t, J=8.0 Hz, 2H), 7.05 (t, J=7.4 Hz, 1H), 6.90 (dd, J=4.8, 8.4 Hz, 3H), 6.38 (dd, J=10.2, 17.0 Hz, 1H), 6.19 (dd, J=1.6, 17.0 Hz, 1H), 5.71-5.64 (m, 1H)

Scheme 27

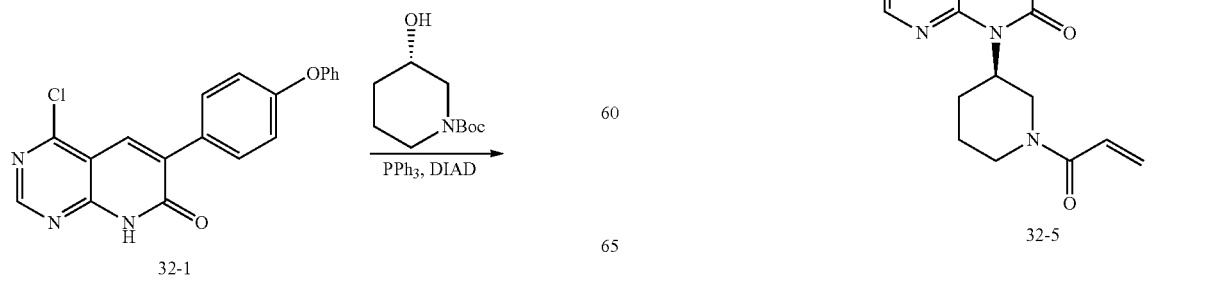

-continued

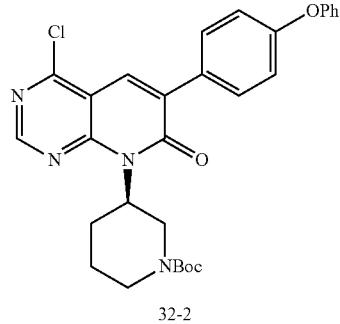

32-2

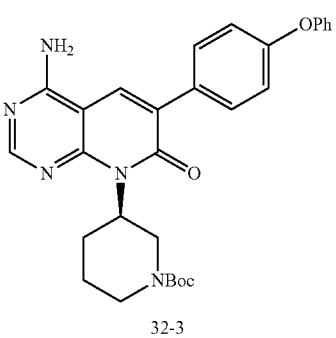

32-3

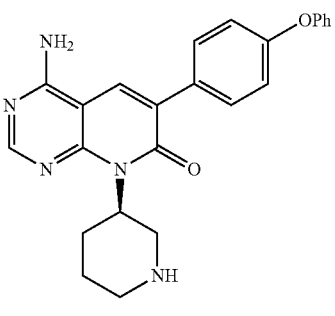

32-4

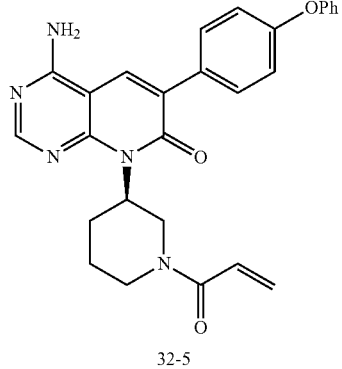

32-5

Example 30

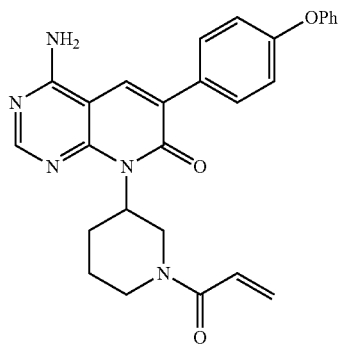 [SMILES: C=CC(=O)N1CCCC(n2c(=O)c(-c3ccc(Oc4ccccc4)cc3)cc3c(N)ncnc32)C1]

Synthesis of Compound 32-2

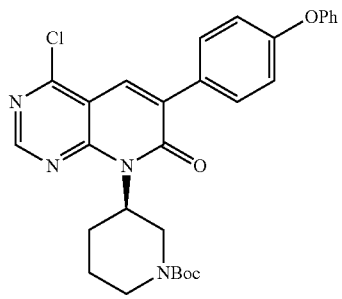 [SMILES: CC(C)(C)OC(=O)N1CCC[C@@H](n2c(=O)c(-c3ccc(Oc4ccccc4)cc3)cc3c(Cl)ncnc32)C1]

To PPh₃ (23 mg, 0.086 mmol) in anhydrous DCM (0.5 mL) was added DIAD (20 mg, 0.086 mmol) at 0° C., and the reaction mixture was stirred for 15 min, after which compound 32-1 (25 mg, 0.072 mmol) and (S)-1-BOC-3-hydroxypiper (29 mg, 0.140 mmol) were added and the resulting mixture was stirred at r.t. for 12 h. The analysis by TLC indicated the reaction was complete. To the mixture, H₂O (10 mL) was added, and the solution was extracted with EtOAc (30 mL×3). The organic phases were combined, dried over anhydrous Na₂SO₄, and concentrated to give a crude product which was purified by preparative TLC (PE/EtOAc=1:1) to afford compound 32-2 (30 mg, 86%) as white solid.

LCMS (ESI) m/z: 533 (M+1)

Synthesis of Compound 32-3

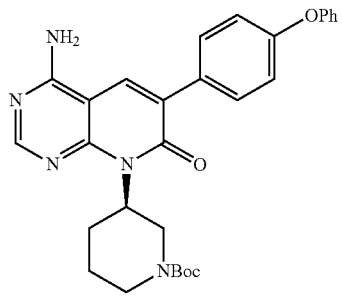 [SMILES: CC(C)(C)OC(=O)N1CCC[C@@H](n2c(=O)c(-c3ccc(Oc4ccccc4)cc3)cc3c(N)ncnc32)C1]

The compound 32-2 (25 mg, 0.028 mmol) was dissolved in a solution of saturated ammonia in MeOH and the reaction solution was stirred at 65° C. O/N, after which the reaction solution was concentrated to give a crude product which was purified by preparative TLC to afford compound 32-3 (20 mg, 83%) as colourless oily liquid.

LCMS (ESI) m/z: 514 (M+1)

Synthesis of Compound 32-5

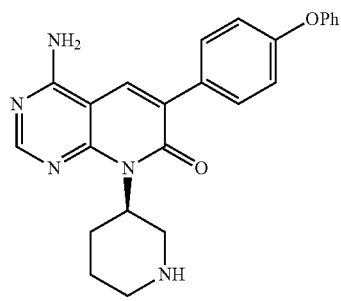 [SMILES: Nc1ncnc2c1cc(-c1ccc(Oc3ccccc3)cc1)c(=O)n2[C@@H]1CCCNC1]

The compound 32-3 (20 mg, 0.039 mmol) was dissolved in a solution of saturated HCl-MeOH and the reaction solution was stirred at r.t., after which the reaction solution was concentrated to give compound 32-4 (15 mg, 86%, crude) as yellow oily liquid.

LCMS (ESI) m/z: 414 (M+1)

Synthesis of Compound 32-5

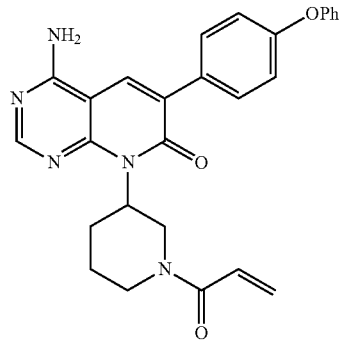 [SMILES: C=CC(=O)N1CCCC(n2c(=O)c(-c3ccc(Oc4ccccc4)cc3)cc3c(N)ncnc32)C1]

The mixture of acrylic acid (9 mg, 0.067 mmol), HATU (25 mg, 0.067 mmol) and N,N-DIPEA (9 mg, 0.067 mmol) was dissolved in DCM (1 mL) and the reaction mixture was stirred at r.t. for 10 min. To this mixture, compound 32-4 (15 mg, 0.033 mmol) was added, and the resulting reaction mixture was stirred for 30 min. After TLC and LCMS indicated the reaction was complete, the solvent was evaporated under the decreased pressure, and DCM (15 mL) and water (15 mL) were added into the residue, and then the resulting residue was extracted with DCM (15 mL×3). The organic phases were combined, dried over anhydrous Na₂SO₄, and concentrated to give a crude product which was purified by preparative HPLC to afford compound 32-5 (5 mg, 29%) as white solid.

$^1$H NMR (400 MHz, CDCl₃): δ ppm 8.33 (s, 1H), 8.22 (s, 1H), 7.70 (d, J=8.5 Hz, 2H), 7.45-7.33 (m, 2H), 7.17 (t, J=7.3 Hz, 1H), 7.06 (dd, J=4.5, 8.0 Hz, 4H), 6.24 (d, J=17.1

Hz, 1H), 5.84-5.67 (m, 2H), 4.70-4.62 (m, 1H), 4.59-4.49 (m, 1H), 4.26-4.05 (m, 2H), 2.03-1.85 (m, 2H), 1.77-1.64 (m, 1H), 1.47-1.35 (m, 2H).
LCMS (ESI) m/z: 468 (M+1)
Scheme 28
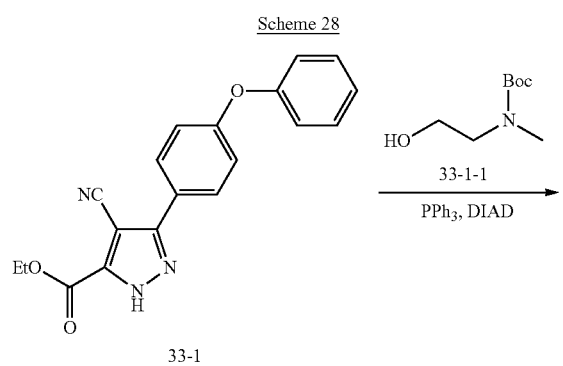
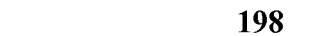
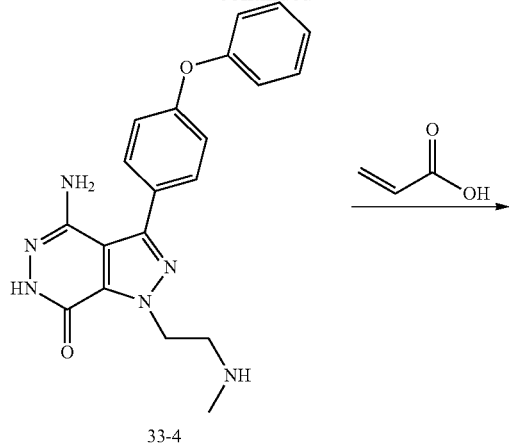
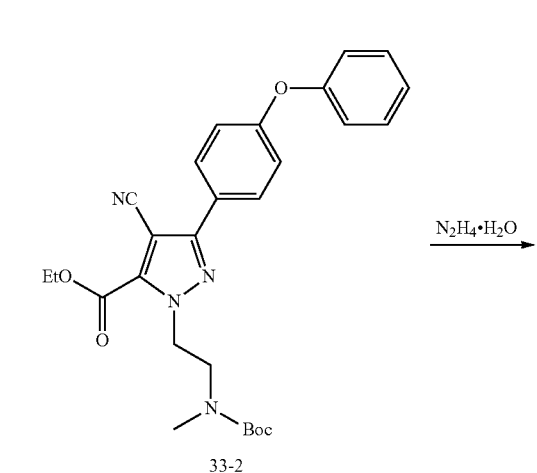
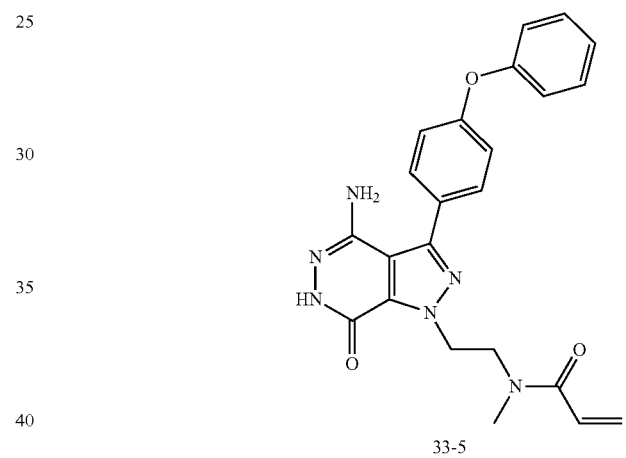
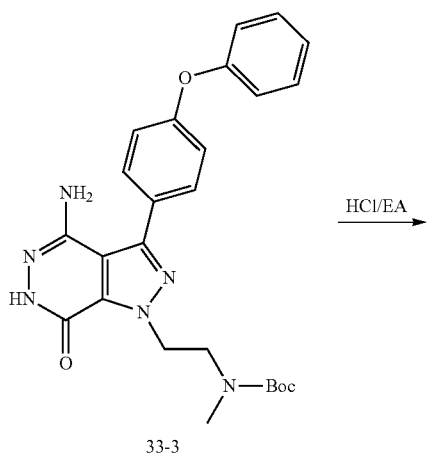
Example 31
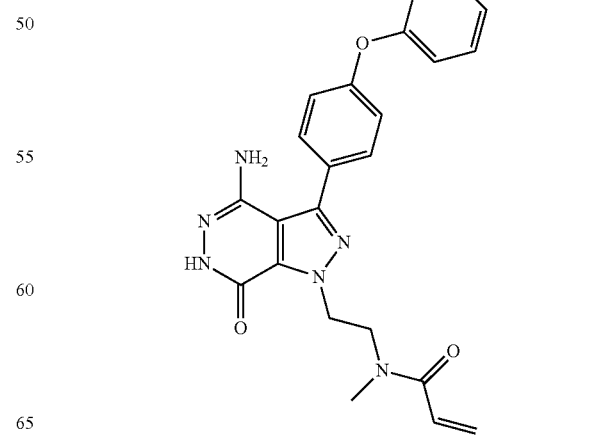

Synthesis of Compound 33-2

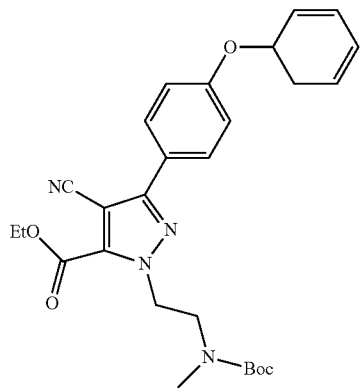 [SMILES: CCOC(=O)c1c(C#N)c(-c2ccc(OC3C=CC=CC3)cc2)nn1CCN(C)C(=O)OC(C)(C)C]

To a solution of PPh₃ (472 mg, 1.8 mmol) in anhydrous THF (10 mL) was added DIAD (364 mg, 1.8 mmol) at 0° C. and the reaction solution was stirred 15 min, after which compound 33-1 (500 mg, 1.5 mmol) and compound 33-1-1 (315 mg, 1.8 mmol) were added and the resulting reaction solution was stirred at r.t. for 4 h, after which the starting material disappeared. Water (40 mL) was added into the solution, and the resulting solution was extracted with EtOAc (50 mL×3). The organic phases were combined, dried over anhydrous Na₂SO₄ and concentrated to give a crude product which was purified by preparative TLC (PE/EtOAc=5:1) to afford compound 33-2 (600 mg, 81%) as white solid.

LCMS (ESI) m/z: 494 (M+1)

$^1$H NMR (400 MHz, CDCl₃): δ ppm 7.94 (br. s., 2H), 7.36 (t, J=7.6 Hz, 2H), 7.19-7.00 (m, 4H), 6.20 (br. s., 2H), 4.77 (br. s., 2H), 3.69 (br. s., 2H), 2.96-2.69 (m, 3H), 1.54 (br. s., 3H), 1.46 (s, 9H)

Synthesis of Compound 33-3

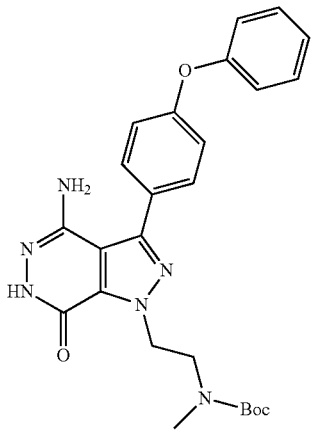 [SMILES: CN(CCn1nc(-c2ccc(Oc3ccccc3)cc2)c2c(N)n[nH]c(=O)c21)C(=O)OC(C)(C)C]

To N₂H₄·H₂O (85%, 10 mL) was added compound 33-2 (600 mg, 1.22 mmol), and the reaction solution was stirred at 120° C. for 1 h. To the solution was added water (50 mL) and the resulting solution was extracted three times with EtOAc (100 mL). The organic phases were combined, dried over anhydrous Na₂SO₄, filtered and concentrated to give compound 33-3 (400 mg, 75%, crude) as white solid.

LCMS: m/z, 477 (M+H)

Synthesis of Compound 33-4

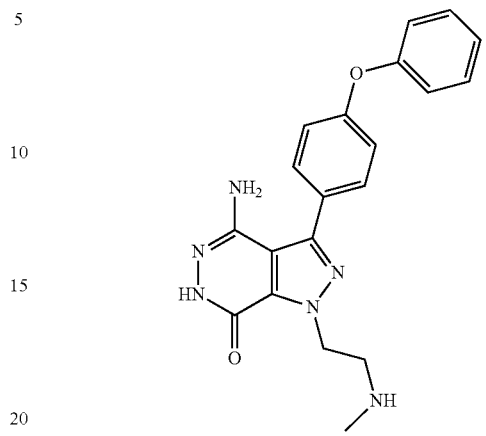

Compound 33-3 (400 mg, 0.839 mmol) was dissolved in a solution of saturated HCl-EtOAc (5 mL), and the reaction mixture was stirred at r.t. After TLC indicated the reaction was complete, the reaction solution was concentrated to give compound 33-4 (360 mg, 100%) as white solid.

LCMS (ESI) m/z: 377 (M+1)

Synthesis of Compound 33-5

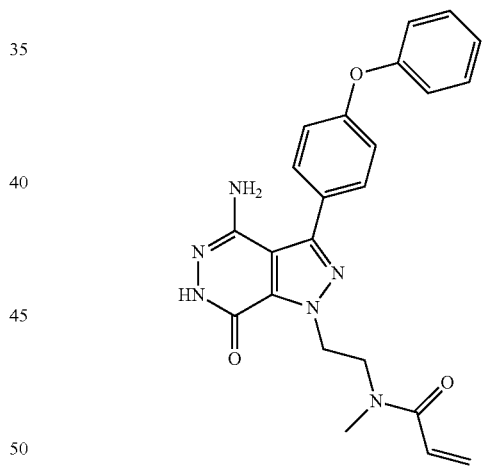

The mixture of acrylic acid (63 mg, 0.872 mmol), HATU (331 mg, 0.872 mmol) and N,N-DIPEA (112 mg, 0.872 mmol) was dissolved in DCM (5 mL) and the reaction mixture was stirred at r.t. for 10 min, after which compound 33-4 (300 mg, 0.727 mmol) was added and the resulting reaction mixture was stirred for 1 h. After TLC and LCMS indicated the reaction was complete, the solvent was removed under the decreased pressure, and DCM (50 mL) and water (60 mL) were added to the residue. The residue was extracted with DCM (50 mL×3), and then the organic phases were combined, dried over anhydrous Na₂SO₄ and concentrated to give a crude product which was purified by preparative chromatography to afford white solid 33-5 (50 mg, 16%).

LCMS (ESI) m/z: 431 (M+1)

201
<sup>1</sup>H NMR (400 MHz, CDCl<sub>3</sub>): δ ppm 11.60-10.62 (m, 1H), 7.61 (dd, J=3.5, 8.5 Hz, 2H), 7.45-7.33 (m, 2H), 7.22-6.96 (m, 5H), 6.56-6.37 (m, 1H), 6.27-6.00 (m, 1H), 5.69-5.43 (m, 1H), 5.41-5.27 (m, 2H), 5.07-4.76 (m, 2H), 3.97 (td, J=5.8, 16.6 Hz, 2H), 3.12-2.92 (m, 3H)
Scheme 29
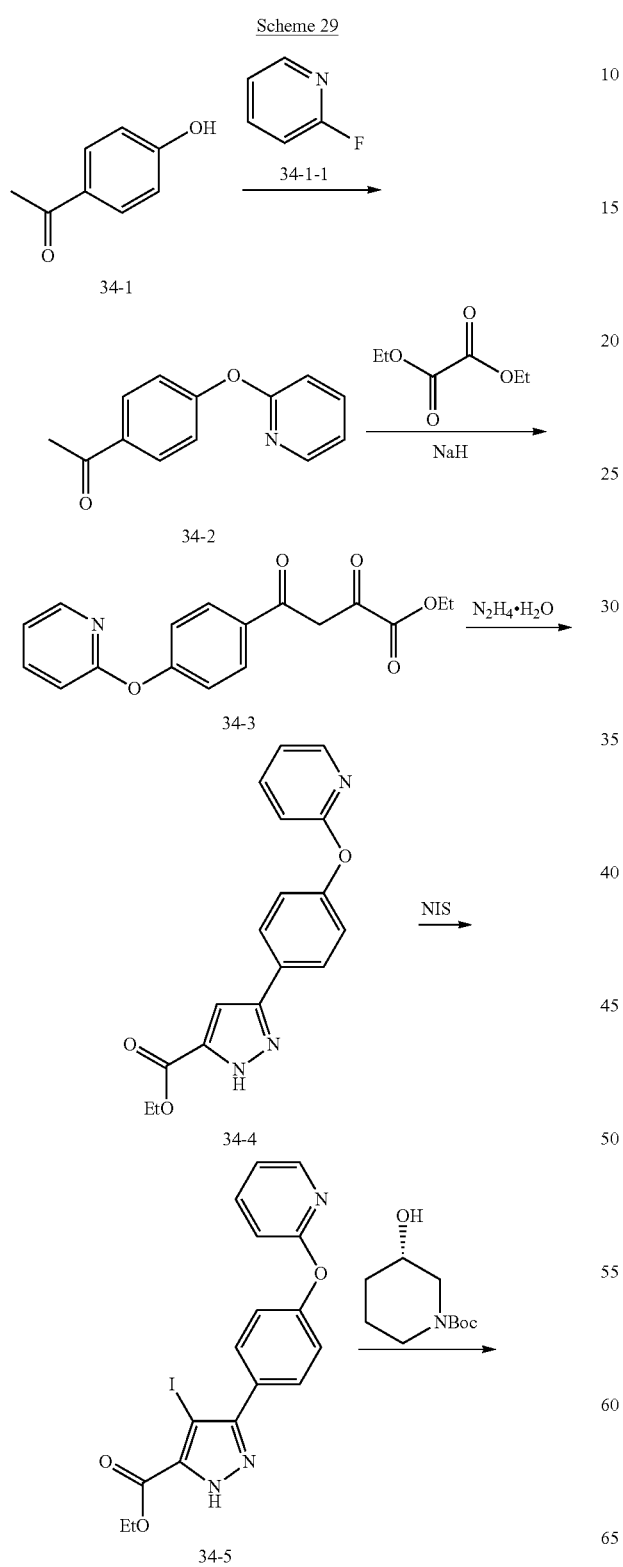
202
-continued
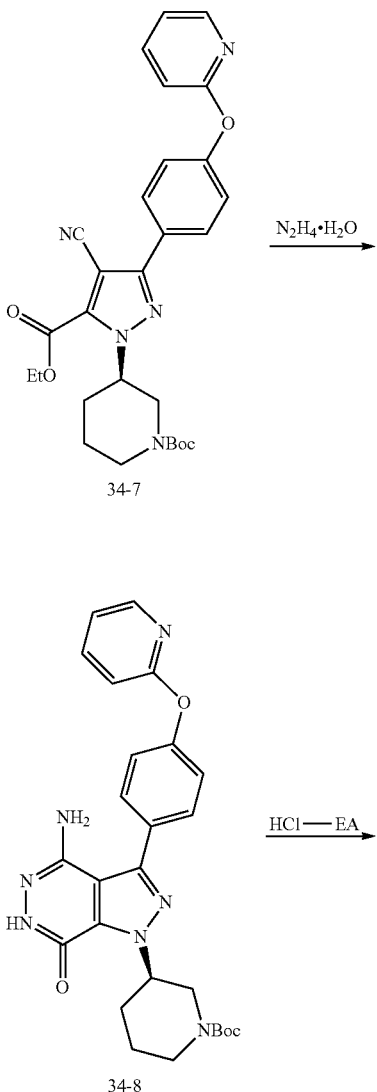

-continued

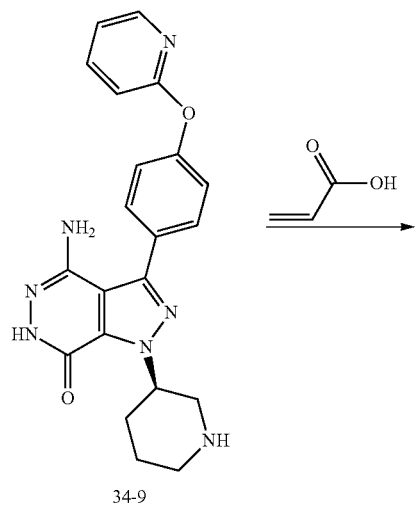

34-9

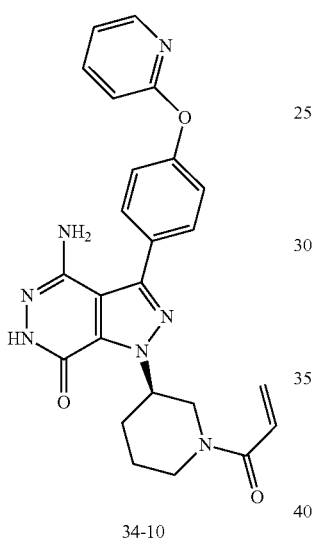

34-10

Example 32

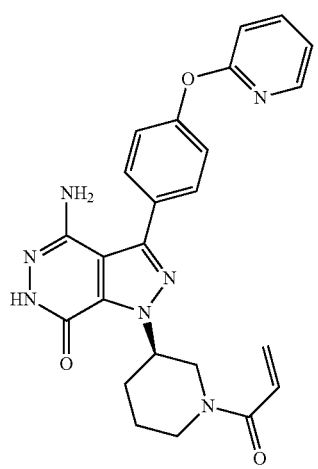

Synthesis of Compound 34-2

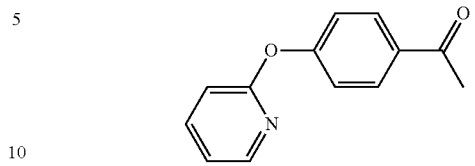

The mixture of compound 34-1 (4 g, 29.38 mmol), Cs$_2$CO$_3$ (5.56 g, 68.14 mmol) and compound 34-1-1 (19.15 g, 58.78 mmol) was dissolved in anhydrous DMF (50 mL), and the reaction mixture was stirred at 100° C. O/N. After TLC indicated the reaction was complete, the reaction solution was cooled down to r.t., the solvent was removed under the decreased pressure, and water (100 mL) was added to the residue. The residue was extracted with EtOAc (100 mL) three times, and then the organic phases were combined, dried over anhydrous Na$_2$SO$_4$ and concentrated to give a crude product which was purified by column chromatography (PE/EtOAc=5:1) to afford compound 34-2 (4.9 g, 79%) as white solid.

LCMS (ESI) m/z: 214 (M+1)

$^1$H NMR (400 MHz, CDCl$_3$): δ ppm (d, J=4.2 Hz, 1H), 8.01 (d, J=8.2 Hz, 2H), 7.74 (t, J=7.7 Hz, 1H), 7.20 (d, J=8.4 Hz, 2H), 7.09-7.02 (m, 1H), 6.99 (d, J=8.4 Hz, 1H), 2.59 (s, 1H)

Synthesis of Compound 34-3

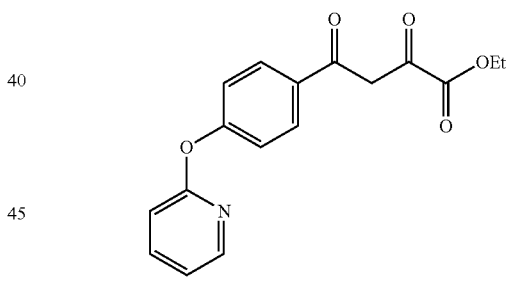

Compound 34-2 (4.9 g, 22.98 mmol) was dissolved in anhydrous THF (50 mL) and then NaH (1.65 g, 68.94 mmol) was added at 0° C. The reaction solution was stirred under nitrogen atmosphere for 1 h. To this solution, diethyl oxalate (6.72 g, 45.96 mmol) was added and the resulting solution was stirred at 80° C. for 1 h. Then the reaction was quenched with water (50 mL), and the reaction solution was extracted with DCM (100 mL×3). The organic phases were combined, dried over anhydrous Na$_2$SO$_4$ and concentrated to give a crude product which was purified by column chromatography (PE/EtOAc=1:1) to afford compound 34-3 (5 g, 69%) as yellow solid.

LCMS (ESI) m/z: 314 (M+1).

$^1$H NMR (400 MHz, CDCl$_3$): δ ppm 15.78-14.52 (m, 2H), 8.22 (dd, J=1.5, 4.9 Hz, 1H), 8.09-7.96 (m, 2H), 7.80-7.64 (m, 1H), 7.24-7.14 (m, 1H), 7.12-6.95 (m, 3H), 4.39 (q, J=7.2 Hz, 2H), 1.46-1.35 (m, 3H)

Synthesis of Compound 34-4

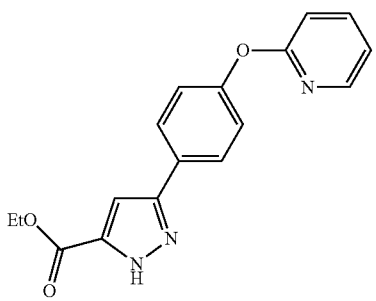 [SMILES: CCOC(=O)c1cc(-c2ccc(Oc3ccccn3)cc2)n[nH]1]

Compound 34-3 (5 g, 15.96 mmol) and HOAc (10 mL) were added to EtOH (20 mL) and the mixture was stirred for 0.5 h, after which $N_2H_4 \cdot H_2O$ (85%, 4 mL) was added dropwise and the resulting mixture was reacted for 0.5 h, followed by addition of $H_2O$ (100 mL) and extraction with EtOAc (100 mL×3). The organic phases were combined, dried over anhydrous $Na_2SO_4$ and concentrated to give compound 34-4 (3.8 g, crude) as slight yellow solid.

LCMS (ESI) m/z: 310 (M+1)

$^1$H NMR (400 MHz, $CDCl_3$): δ ppm 8.27-8.17 (m, 1H), 7.78-7.63 (m, 3H), 7.20 (d, J=8.5 Hz, 2H), 7.07-7.00 (m, 2H), 6.97 (d, J=8.0 Hz, 1H), 4.42 (q, J=7.0 Hz, 2H), 1.41 (t, J=7.3 Hz, 3H)

Synthesis of Compound 34-5

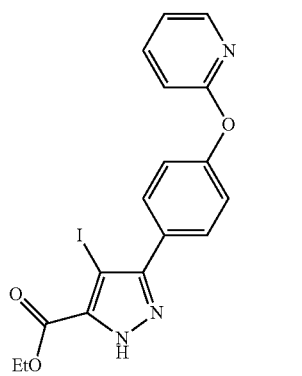 [SMILES: CCOC(=O)c1[nH]nc(-c2ccc(Oc3ccccn3)cc2)c1I]

Compound 34-4 (3.8 g, 12.29 mmol), N-Iodosuccinimide (3.26 g, 14.5 mmol) and CAN (658 mg, 1.2 mmol) were dissolved in acetonitrile (10 mL) and the mixture was reacted at 90° C. for 5 h, after which water (50 mL) was added and the reaction mixture was extracted with EtOAc (100 mL×3). The organic phases were combined, dried over anhydrous $Na_2SO_4$ and concentrated to give a crude product which was purified by column chromatography to afford compound 34-5 (4 g, 75%) as yellow solid.

LCMS (ESI) m/z: 436 (M+1)

$^1$H NMR (400 MHz, $CDCl_3$): δ ppm 8.26 (d, J=3.5 Hz, 1H), 7.82-7.69 (m, 3H), 7.24 (d, J=9.0 Hz, 2H), 7.10-7.03 (m, 1H), 6.98 (d, J=8.0 Hz, 1H), 4.47 (q, J=7.2 Hz, 2H), 1.46 (t, J=7.0 Hz, 3H)

Synthesis of Compound 34-6

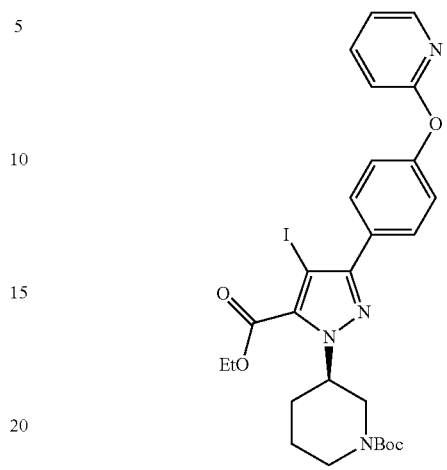

To a solution of $PPh_3$ (3.612 g, 13.79 mmol) in anhydrous DCM (50 mL) was added diisopropylazodicarboxylate (2.785 g, 13.79 mmol) at 0° C. and the reaction solution was stirred for 15 min, after which compound 34-5 (4 g, 9.19 mmol) and compound (S)-1-BOC-3-hydroxypiper (2.22 g, 11.03 mmol) were added and the resulting reaction solution was stirred at 40° C. for 12 h. After the starting materials disappeared, water (50 mL) was added into the solution, and the resulting solution was extracted with EtOAc (100 mL×3). The organic phases were combined, dried over anhydrous $Na_2SO_4$ and concentrated to give a crude product which was purified by column chromatography (PE/EtOAc=1:1) to afford compound 34-6 (2 g, 35%) as white solid.

LCMS (ESI) m/z: 619 (M+1)

$^1$H NMR (400 MHz, $CDCl_3$): δ ppm 8.236-8.226 (d, 1H), 7.830-7.809 (d, 2H), 7.707-7.689 (d, 1H), 7.221-7.200 (d, 2H), 7.040-7.024 (d, 1H), 7.010-6.936 (t, 1H), 6.202 (s, 2H), 5.048 (s, 1H), 4.489-4.436 (m, 2H), 4.238 (s, 1H), 3.323-3.284 (d, 1H), 2.833-2.775 (t, 1H), 2.183 (s, 1H), 1.884 (s, 1H), 1.646-1.616 (d, 1H), 1.498-1.458 (t, 12H).

Synthesis of Compound 34-7

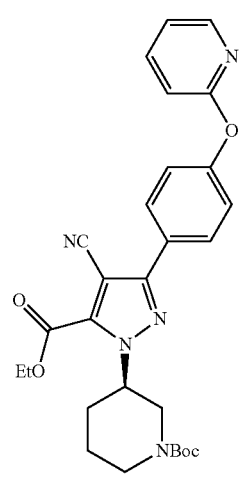 [SMILES: CCOC(=O)c1c(C#N)c(-c2ccc(Oc3ccccn3)cc2)nn1[C@@H]1CCCN(C(=O)OC(C)(C)C)C1]

The mixture of compound 34-6 (2 g, 3.23 mmol), zinc powder (420 mg, 6.46 mmol) and zinc cyanide (Zn(CN)$_2$) (756 mg, 6.46 mmol) was suspended in anhydrous DMF (10 mL), and to the solution was added Pd(dppf)Cl$_2$ (211 mg, 0.323 mmol) and Pd(dba)$_2$ (186 mg, 0.323 mmol), after which the reaction solution was reacted under nitrogen atmosphere at 100° C. for 14 h. To the reaction solution was added water (100 mL) and the reaction solution was extracted with DCM (100 mL×3). The organic phases were combined, dried over anhydrous Na$_2$SO$_4$ and concentrated to give a crude product which was purified by preparative TLC to afford compound 34-7 (200 mg, 13.3%) as yellow oil.

LCMS (ESI) m/z: 335 (M+1)

$^1$H NMR (400 MHz, CDCl$_3$): δ ppm 8.28-8.16 (m, 1H), 8.05 (d, J=8.5 Hz, 2H), 7.78-7.64 (m, 1H), 7.26-7.20 (m, 2H), 7.08-6.91 (m, 2H), 5.29-5.09 (m, 1H), 4.57-4.38 (m, 2H), 3.46-3.29 (m, 1H), 2.87 (t, J=12.0 Hz, 1H), 2.30-2.10 (m, 2H), 1.90 (br. s., 1H), 1.60 (br. s., 3H), 1.47 (d, J=6.5 Hz, 12H)

Synthesis of Compound 34-8

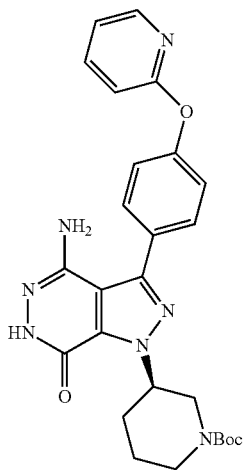 [SMILES: CC(C)(C)OC(=O)N1CCC[C@@H](n2nc(-c3ccc(Oc4ccccn4)cc3)c3c(N)n[nH]c(=O)c32)C1]

Compound 34-7 (200 mg, 0.135 mmol) was added into N$_2$H$_4$.H$_2$O (85%, 1 mL), and the reaction mixture was stirred at 120° C. for 1 h. To this mixture, water (20 mL) was added, and the resulting solution was extracted with DCM (30 mL×3). The organic phases were combined, dried over anhydrous Na$_2$SO$_4$, filtered and concentrated to give compound 34-8 (220 mg, crude) as white solid.

LCMS: m/z, 504 (M+H)

Synthesis of Compound 34-9

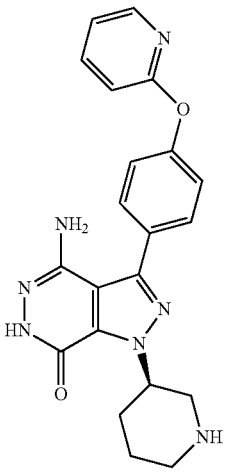 [SMILES: Nc1n[nH]c(=O)c2c1c(-c1ccc(Oc3ccccn3)cc1)nn2[C@@H]1CCCNC1]

Compound 34-8 (220 mg, 0.436 mmol) was dissolved in a solution of saturated HCl-EtOAc (2 mL), and the reaction solution was stirred at r.t. After LCMS indicated the reaction was complete, the reaction solution was concentrated to give compound 34-9 (200 mg, crude) as white solid.

LCMS (ESI) m/z: 404 (M+1)

Compound 34-10

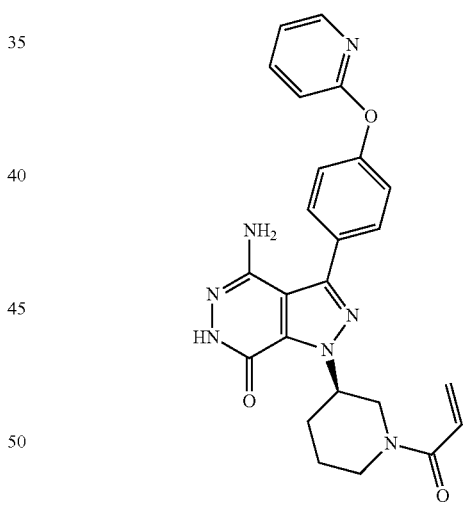

The mixture of acrylic acid (66 mg, 0.909 mmol), HATU (345 mg, 0.909 mmol) and N,N-DIPEA (544 mg, 1.818 mmol) was dissolved in DCM (5 mL) and the reaction mixture was stirred at r.t. for 10 min. To this mixture, compound 34-9 (200 mg, 0.455 mmol) was added, and the resulting reaction mixture was stirred for 30 min. After TLC indicated the reaction was complete, the solvent was evaporated under the decreased pressure, and DCM (50 mL) and water (50 mL) were added into the residue, and then the resulting residue was extracted with DCM (50 mL×3). The organic phases were combined, dried over anhydrous Na$_2$SO$_4$, and concentrated to give a crude product which was purified by preparative chromatography to afford compound 34-10 (35 mg, 17%) as white solid.

LCMS (ESI) m/z: 458 (M+1)

¹H NMR (400 MHz, CDCl₃): δ ppm 10.38 (br. s., 1H), 8.33-8.06 (m, 1H), 7.99-7.54 (m, 3H), 7.31 (d, J=8.0 Hz, 2H), 7.19-6.81 (m, 2H), 6.73-6.54 (m, 1H), 6.36-6.20 (m, 1H), 5.78-5.59 (m, 1H), 5.50 (br. s., 1H), 5.07-4.79 (m, 2H), 4.65-4.32 (m, 1H), 3.98 (br. s., 1H), 3.71-3.43 (m, 1H), 2.84 (d, J=11.5 Hz, 1H), 2.34 (br. s., 1H), 2.07-1.92 (m, 1H), 1.77 (br. s., 1H), 1.63 (br. s., 1H)
Scheme 30
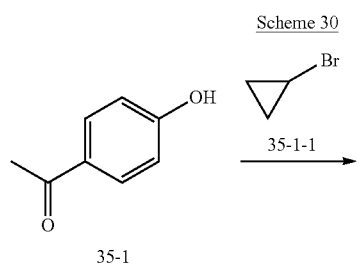
35-1
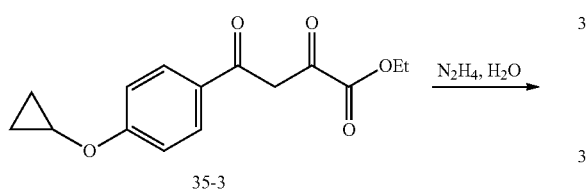
35-2
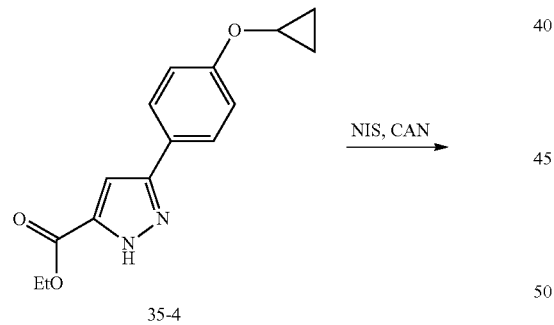
35-3
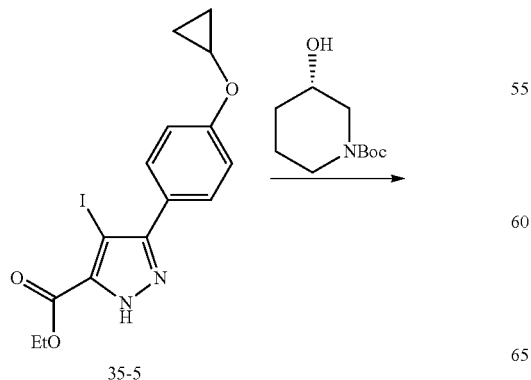
35-4
35-5
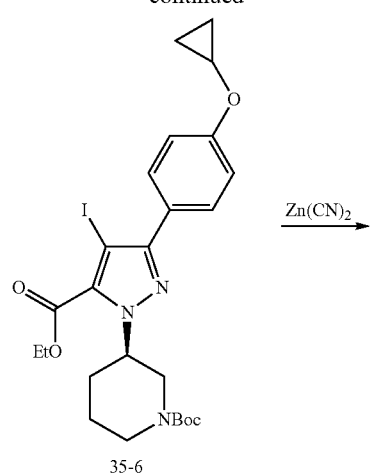
35-6
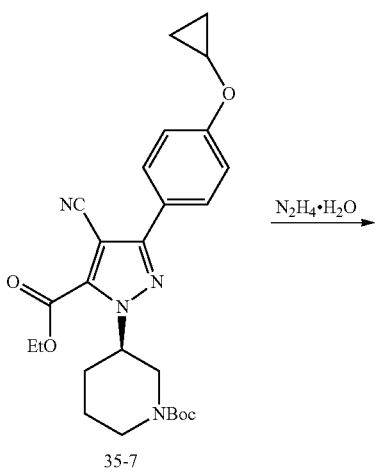
35-7
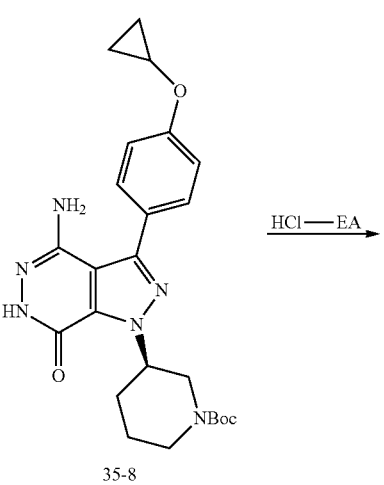
35-8

211
-continued

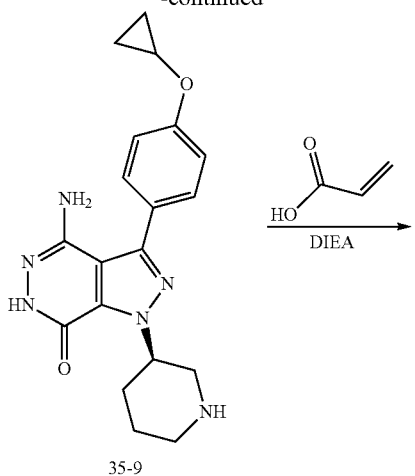

35-9

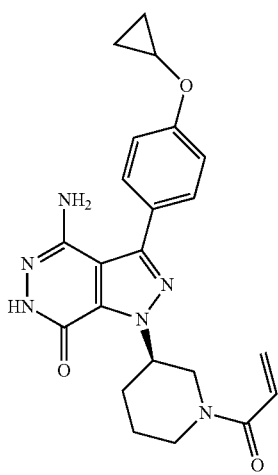 [SMILES: C=CC(=O)N1CCC[C@@H](n2nc(-c3ccc(OC4CC4)cc3)c3c(N)n[nH]c(=O)c32)C1]

35-10

Example 33

212

Compound 35-2

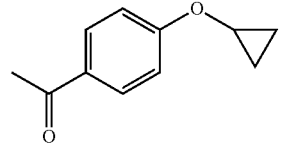

The mixture of compound 35-1 (5 g, 41.62 mmol), $Cs_2CO_3$ (27 g, 83.23 mmol) and compound 35-1-1 (10 g, 83.23 mmol) in anhydrous DMF (100 mL) was stirred at 100° C. O/N. After TLC indicated the reaction was complete, the reaction solution was cooled down to r.t., the solvent was evaporated under the decreased pressure, and water (200 mL) was added into the residue. Then the resulting residue was extracted with EtOAc (150 mL×3). The organic phases were combined, dried over anhydrous $Na_2SO_4$, and concentrated to give a crude product which was purified by column chromatography (PE/EtOAc=5:1) to afford compound 35-2 (2 g, 27%) as yellow solid.

LCMS (ESI) m/z: 177 (M+1)

$^1$H NMR (400 MHz, $CDCl_3$): δ ppm 7.92 (d, J=8.8 Hz, 2H), 7.07 (d, J=8.8 Hz, 2H), 3.87-3.66 (m, 1H), 2.55 (s, 3H), 0.89-0.66 (m, 4H)

Synthesis of Compound 35-3

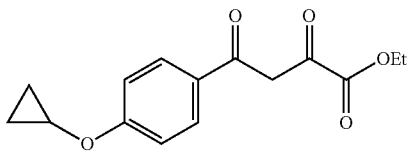 [SMILES: CCOC(=O)C(=O)CC(=O)c1ccc(OC2CC2)cc1]

Compound 35-2 (2 g, 11.35 mmol) was dissolved in anhydrous THF (20 mL) and then NaH (410 mg, 17.02 mmol) was added at 0° C. The reaction solution was stirred under nitrogen atmosphere for 1 h. To this solution, diethyl oxalate (3.32 g, 22.70 mmol) was added and the resulting solution was reacted at r.t. for 1 h. Then the reaction was quenched with water (50 mL), and the reaction solution was extracted with EtOAc (100 mL×3). The organic phases were combined, dried over anhydrous $Na_2SO_4$ and concentrated to give a crude product which was purified by column chromatography (PE/EtOAc=5:1) to afford compound 35-3 (2.2 g, 70%) as yellow oil.

LCMS (ESI) m/z: 277 (M+1)

$^1$H NMR (400 MHz, $CDCl_3$): δ ppm 15.40 (br. s., 2H), 7.92 (d, J=9.0 Hz, 2H), 7.06 (d, J=8.8 Hz, 2H), 4.39-4.23 (m, 2H), 3.84-3.60 (m, 1H), 1.41-1.29 (m, 3H), 0.86-0.63 (m, 4H)

Synthesis of Compound 35-4

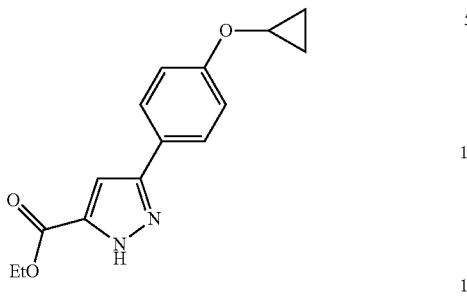

The mixture of compound 35-3 (2.2 g, 7.96 mmol) and HOAc (5 mL) was added into EtOH (20 mL), and the reaction solution was stirred for 0.5 h. To this solution was added dropwise N$_2$H$_4$—H$_2$O (85%, 4 mL) and the resulting solution was reacted for 30 min, after which water (100 mL) was added to the solution, and the resulting solution was extracted with DCM (100 mL×3). The organic phase was dried over anhydrous Na$_2$SO$_4$ and concentrated to give compound 35-4 (1.3 g, 60%) as white solid.

LCMS (ESI) m/z: 273 (M+1)

$^1$H NMR (400 MHz, CDCl$_3$): δ ppm 7.67 (d, J=8.6 Hz, 2H), 7.12 (d, J=8.6 Hz, 2H), 7.05 (s, 1H), 4.48-4.35 (m, 2H), 3.85-3.71 (m, 1H), 1.48-1.35 (m, 3H), 0.89-0.61 (m, 4H).

Synthesis of Compound 35-5

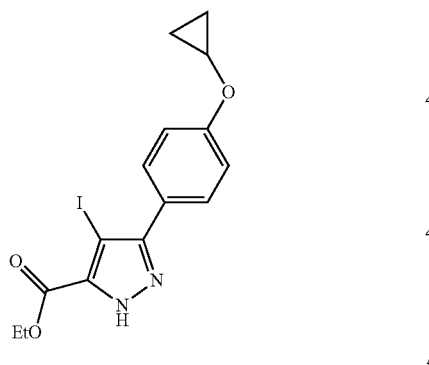

The mixture of compound 35-4 (1200 mg, 4.41 mmol), N-Iodosuccinimide (992 mg, 4.41 mmol) and CAN (242 mg, 0.0441 mmol) in acetonitrile (10 mL) was reacted at 90° C. for 1 h. To the reaction mixture was added water (50 mL), and the resulting solution was extracted with EtOAc (100 mL×3). The organic phase were combined, dried over anhydrous Na$_2$SO$_4$ and concentrated to give a crude product which was purified with column chromatography to afford compound 35-5 (1.2 g, 69%) as yellow solid.

LCMS (ESI) m/z: 399 (M+1)

$^1$H NMR (400 MHz, CDCl$_3$): δ ppm 7.66 (d, J=8.5 Hz, 2H), 7.15 (d, J=8.5 Hz, 2H), 4.43 (q, J=7.0 Hz, 2H), 3.85-3.69 (m, 1H), 1.42 (t, J=7.0 Hz, 3H), 0.85-0.74 (m, 4H)

Synthesis of Compound 35-6

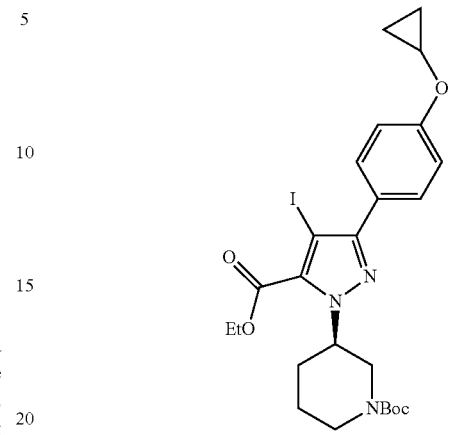

To a solution of PPh$_3$ (975 mg, 3.72 mmol) in anhydrous toluene (10 mL) was added diisopropylazodicarboxylate (750 mg, 3.72 mmol)) at 0° C. and the reaction solution was stirred 15 min, after which compound 35-5 (1200 mg, 3.1 mmol) and (S)-1-BOC-3-hydroxypiper (748 mg, 3.72 mmol) were added and the resulting reaction solution was stirred at 60° C. for 12 h, the starting materials disappeared. Water (100 mL) was added into the solution, and the resulting solution was extracted with EtOAc (100 mL×3). The organic phases were combined, dried over anhydrous Na$_2$SO$_4$ and concentrated to give a crude product which was purified by column chromatography (PE/EtOAc=9:1) to afford compound 35-6 (1100 mg, 64%) as yellow oil.

LCMS (ESI) m/z: 582 (M+1)

$^1$H NMR (400 MHz, CDCl$_3$): δ ppm 7.61 (d, J=8.6 Hz, 2H), 7.04 (d, J=8.6 Hz, 2H), 5.03-4.85 (m, 1H), 4.38 (q, J=7.2 Hz, 2H), 4.00 (d, J=9.9 Hz, 1H), 3.76-3.58 (m, 1H), 3.25 (br. s., 1H), 2.72 (dt, J=2.6, 12.7 Hz, 1H), 2.10 (br. s., 2H), 1.88-1.70 (m, 1H), 1.67-1.47 (m, 2H), 1.46-1.27 (m, 12H), 0.80-0.63 (m, 4H)

Synthesis of Compound 35-7

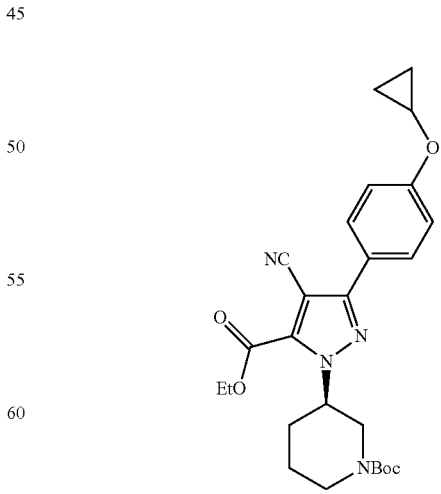

The mixture of compound 35-6 (1100 mg, 1.89 mmol), zinc powder (247 mg, 3.78 mmol), Zn(CN)$_2$ (444 mg, 3.78), Pd(dppf)Cl$_2$ (123 mg, 0.189 mol) and Pd(dba)$_2$ (109 mg, 0.189 mol) in anhydrous DMF (10 mL) was stirred under nitrogen atmosphere at 100° C. for 14 h. To the solution was added water (100 mL), and the resulting solution was extracted with DCM (100 mL×3). The organic phases were combined, dried over anhydrous $Na_2SO_4$ and concentrated to give a crude product which was purified by preparative TLC to afford compound 35-7 (400 mg, 44%) as yellow oil.

LCMS (ESI) m/z: 481 (M+1)

Synthesis of Compound 35-8

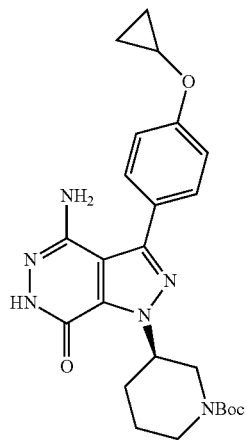 [SMILES: CC(C)(C)OC(=O)N1CCC[C@@H](n2nc(-c3ccc(OC4CC4)cc3)c3c(N)n[nH]c(=O)c32)C1]

Compound 35-7 (400 mg, 0.832 mmol) was added into $N_2H_4·H_2O$ (85%, 5 mL) and the reaction mixture was stirred at 120° C. for 1 h, after which $H_2O$ (20 mL) was added to the mixture, and the resulting solution was extracted with DCM (30 mL×3). The organic phases were combined, dried over anhydrous $Na_2SO_4$, filtered and concentrated to give compound 35-8 (400 mg, crude) as white solid.

LCMS (ESI) m/z: 467 (M+1)

Synthesis of Compound 35-9

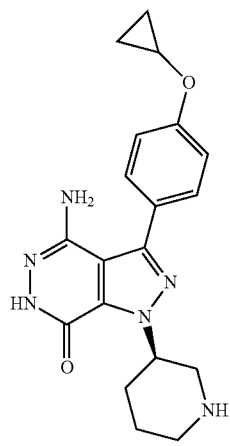 [SMILES: Nc1n[nH]c(=O)c2c1c(-c1ccc(OC3CC3)cc1)nn2[C@@H]1CCCNC1]

Compound 35-8 (400 mg, 0.857 mmol) was dissolved in a solution of saturated HCl-EtOAc (8 mL), and the reaction solution was stirred at r.t. After LCMS indicated the reaction was complete, the reaction solution was concentrated to give compound 35-9 (400 mg, crude) as white solid.

LCMS (ESI) m/z: 367 (M+1)

Synthesis of Compound 35-10

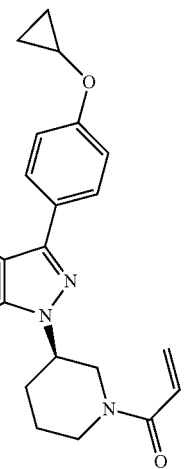

The mixture of acrylic acid (143 mg, 1.99 mmol), HATU (756 mg, 1.99 mmol) and N,N-DIPEA (516 mg, 1.99 mmol) in DCM (10 mL) was stirred at r.t. for 10 min, and then compound 35-9 (400 mg, 0.993 mmol) was added and the reaction solution was stirred for 0.5 h. After TLC indicated the reaction was complete, the solvent was evaporated under the decreased pressure, and DCM (50 mL) and water (50 mL) were added into the residue, and then the resulting residue was extracted with DCM (50 mL×3). The organic phases were combined, dried over anhydrous $Na_2SO_4$ and concentrated to give a crude product which was purified by preparative chromatography to afford compound 35-10 (60 mg, 14%) as white solid.

LCMS (ESI) m/z: 421 (M+1)

$^1$H NMR (400 MHz, CDCl$_3$): δ ppm 10.93-10.44 (m, 1H), 7.59 (d, J=8.5 Hz, 2H), 7.20 (d, J=8.0 Hz, 2H), 6.77-6.51 (m, 1H), 6.37-6.14 (m, 1H), 5.63 (br. s., 1H), 5.47 (br. s., 1H), 5.25-5.04 (m, 2H), 5.09-4.94 (m, 1H), 4.92-4.55 (m, 1H), 4.38-3.96 (m, 1H), 3.81 (br. s., 1H), 3.68-3.42 (m, 1H), 2.96-2.68 (m, 1H), 3.30-2.66 (m, 1H), 2.39-2.28 (m, 1H), 2.06-1.90 (m, 1H), 1.63 (br. s., 1H), 1.03-0.53 (m, 4H)

Example 34

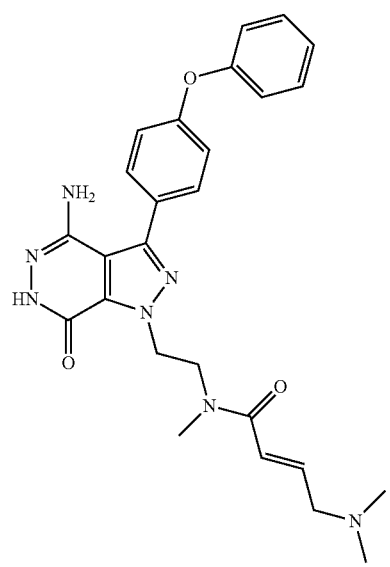 [SMILES: CN(C)C/C=C/C(=O)N(C)CCn1nc(-c2ccc(Oc3ccccc3)cc2)c2c(N)n[nH]c(=O)c21]

In Example 34, the synthesis process was similar to that in Example 31.
LCMS (ESI) m/z: 488 (M+1).
$^1$H NMR (400 MHz, CDCl$_3$): δ ppm 11.41-10.46 (m, 2H), 7.72-7.53 (m, 2H), 7.49-7.31 (m, 2H), 7.23-7.04 (m, 4H), 6.83-6.65 (m, 1H), 6.39-6.18 (m, 1H), 5.22 (d, J=15.0 Hz, 2H), 4.97 (d, J=3.7 Hz, 2H), 4.12-3.82 (m, 2H), 3.12-2.99 (m, 3H), 2.89 (d, J=6.0 Hz, 1H), 2.28-2.10 (m, 5H)
Scheme 31
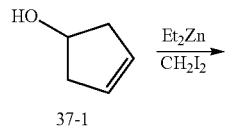
37-1
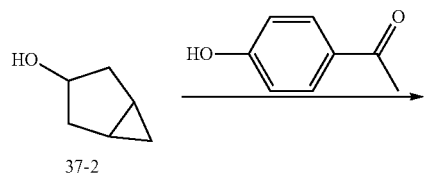
37-2
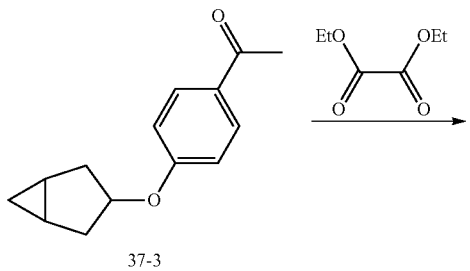
37-3
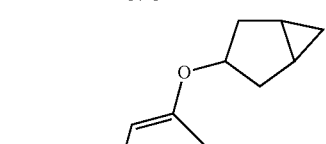
37-4
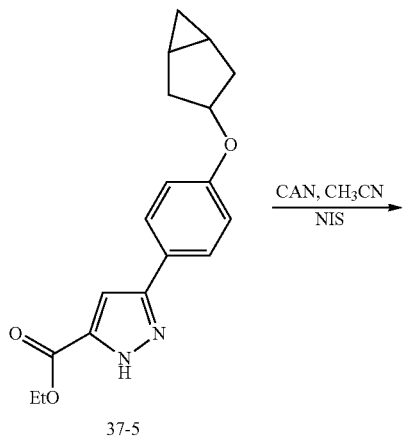
37-5
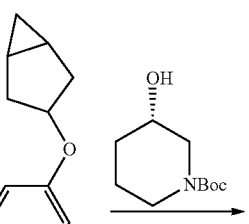
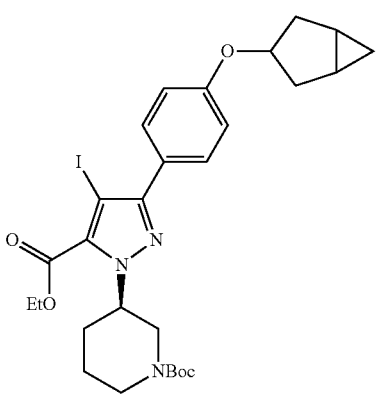
37-6
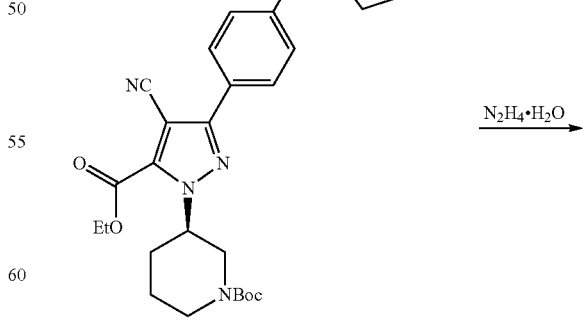
37-7
37-8

219
-continued

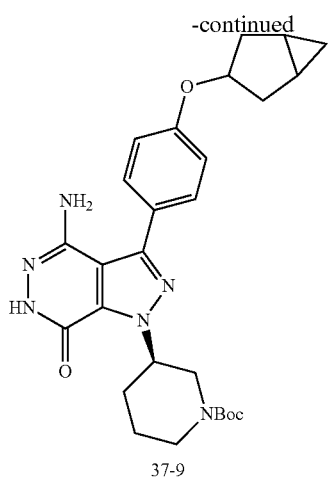

37-9

HCl—EA→

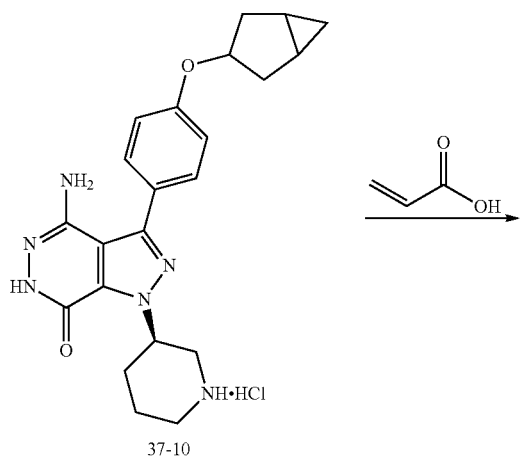

37-10

220

Example 35

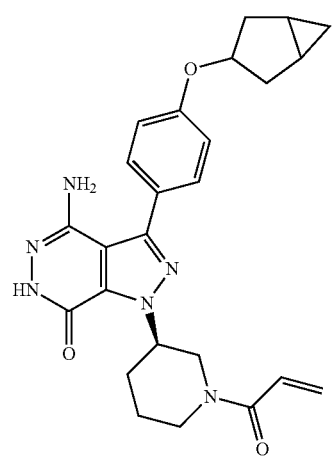 [SMILES: C=CC(=O)N1CCC[C@@H](n2nc(-c3ccc(OC4CC5CC5C4)cc3)c3c(N)n[nH]c(=O)c32)C1]

Synthesis of Compound 37-2

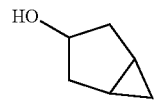

To anhydrous DCM (100 mL) was added diethylzinc (100 mL, 99.86 mmol, 1 M in n-hexane) at 0° C., followed by a mixture of diiodomethane (4.2 g, 49.93 mmol) and DCM (100 mL), and the reaction solution was stirred for 30 min. To this solution, compound 37-1 (4.2 g, 49.93 mmol) was added, and the resulting solution was stirred for 3 h followed by quenched with saturated $NH_4Cl$ and extracted with DCM (100 mL×3). The organic phases were combined, dried over anhydrous $Na_2SO_4$, and concentrated to give a crude product which was purified by column chromatography to afford compound 37-2 (2.5 g, 51%) as yellow oil.

$^1$H NMR (400 MHz, $CDCl_3$): δ ppm 4.35 (t, J=6.6 Hz, 1H), 2.21-1.97 (m, 2H), 1.71 (d, J=14.1 Hz, 3H), 1.38-1.20 (m, 2H), 0.64-0.29 (m, 2H)

Synthesis of Compound 37-3

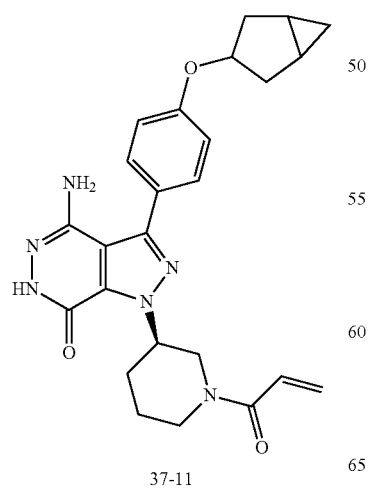

37-11

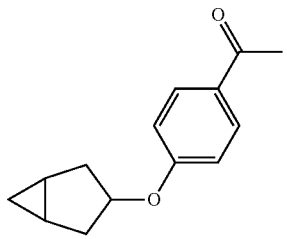 [SMILES: CC(=O)c1ccc(OC2CC3CC3C2)cc1]

To a solution of $PPh_3$ (8020 mg, 30.57 mmol) in anhydrous toluene (30 mL) was added diisopropylazodicarboxylate (6175 mg, 30.57 mmol) at 0° C. and the reaction solution was stirred 15 min, after which compound 37-2 (2500 mg, 25.47 mmol) and paracetamol (4160 mg, 30.57 mmol) were added and the resulting reaction solution was stirred at 60° C. for 12 h, the starting materials disappeared. Water (100 mL) was added into the solution, and the resulting solution was extracted with EtOAc (100 mL×3). The organic phases were combined, dried over anhydrous $Na_2SO_4$ and concentrated to give a crude product which was purified by column chromatography (PE/EtOAc=9:1) to afford compound 37-3 (1700 mg, 31%) as yellow oil.

LCMS (ESI) m/z: 217 (M+1).

$^1$H NMR (400 MHz, $CDCl_3$): δ ppm 7.90 (d, J=9.0 Hz, 2H), 6.87 (d, J=8.5 Hz, 2H), 4.54-4.36 (m, 1H), 2.54 (s, 3H), 2.42-2.29 (m, 2H), 1.62 (s, 2H), 1.33-1.14 (m, 2H), 0.66-0.34 (m, 2H)

Synthesis of Compound 17-4

To EtOH (20 mL) was added compound 37-4 (2 g, 6.32 mmol) and HOAc (2 mL) and the reaction mixture was stirred for 0.5 h, after which $N_2H_4.H_2O$ (1.2 g, 12.64 mmol) was added dropwise and resulting mixture was reacted for 30 min. To this mixture was added $H_2O$ (100 mL) and the solution was extracted with DCM (100 mL×3). The organic phases were combined, dried over anhydrous $Na_2SO_4$ and concentrated to give compound 37-5 (1.3 g, 70%) as slight yellow solid.

LCMS (ESI) m/z: 313 (M+1).

$^1$H NMR (400 MHz, $CDCl_3$): δ ppm 7.68-7.42 (m, 2H), 6.97 (s, 1H), 6.86 (d, J=8.4 Hz, 2H), 4.47-4.26 (m, 3H), 2.32 (dd, J=6.9, 12.9 Hz, 2H), 1.90 (dt, J=3.5, 8.3 Hz, 2H), 1.42-1.23 (m, 5H), 0.54-0.25 (m, 1H), 0.02 (q, J=4.0 Hz, 1H)

Synthesis of Compound 37-6

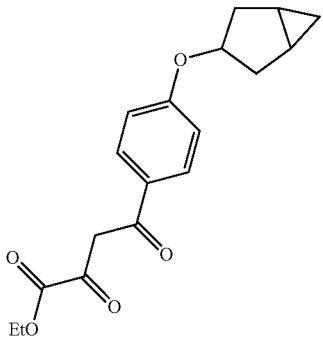 [SMILES: CCOC(=O)C(=O)CC(=O)c1ccc(OC2CC3CC3C2)cc1]

Compound 37-3 (1.7 g, 7.86 mmol) was dissolved in anhydrous THF (20 mL) and then NaH (628 mg, 15.72 mmol) was added at 0° C. The reaction solution was stirred under nitrogen atmosphere for 1 h. To this solution, diethyl oxalate (2.3 g, 15.72 mmol) was added and the resulting solution was reacted at r.t. for 1 h. Then the reaction was quenched with water (50 mL), and the reaction solution was extracted with EtOAc (100 mL×3). The organic phases were combined, dried over anhydrous $Na_2SO_4$ and concentrated to give a crude product which was purified by column chromatography (PE/EtOAc=5:1) to afford compound 37-4 (2 g, 80%) as yellow oil.

LCMS (ESI) m/z: 317 (M+1).

Synthesis of Compound 37-5

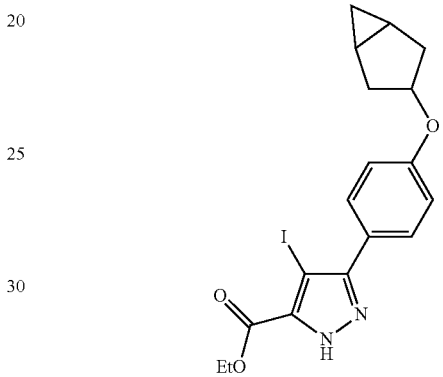

The mixture of compound 37-5 (1200 mg, 4.41 mmol), N-Iodosuccinimide (992 mg, 4.41 mmol) and CAN (242 mg, 0.0441 mmol) in acetonitrile (10 mL) was reacted at 90° C. for 1 h, after which water (50 mL) was added and the resulting mixture was extracted with EtOAc (100 mL×3). The organic phases were combined, dried over anhydrous $Na_2SO_4$ and concentrated to give a crude product which was purified by column chromatography to afford compound 37-6 (1.2 g, 69%) as white solid.

LCMS: m/z, 439 (M+H).

Synthesis of Compound 37-7

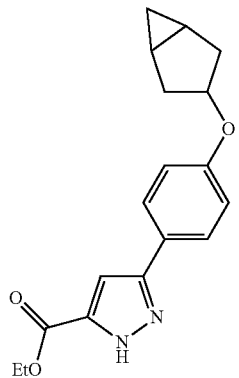 [SMILES: CCOC(=O)c1cc(-c2ccc(OC3CC4CC4C3)cc2)n[nH]1]

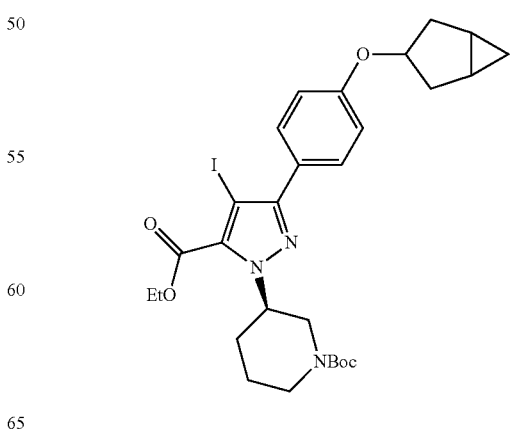

To a solution of $PPh_3$ (823 mg, 4.11 mmol) in anhydrous toluene (30 mL) was added diisopropylazodicarboxylate (830 mg, 4.11 mmol) at 0° C. and the reaction solution was stirred 15 min, after which compound 37-6 (1200 mg, 2.74 mmol) and compound (S)-1-BOC-3-Hydroxypiperidine (823 mg, 4.11 mmol) were added and the resulting reaction solution was stirred at 60° C. for 12 h, the starting materials disappeared. Water (100 mL) was added into the solution, and the resulting solution was extracted with EtOAc (100 mL×3). The organic phases were combined, dried over anhydrous Na$_2$SO$_4$ and concentrated to give a crude product which was purified by column chromatography (PE/EtOAc=6/1) to afford compound 37-7 (1.2 g, 71%) as white solid.

LCMS (ESI) m/z: 622 (M+1).

$^1$H NMR (400 MHz, CDCl$_3$): δ ppm 7.65 (d, J=8.5 Hz, 2H), 6.91 (d, J=8.5 Hz, 2H), 5.10-4.93 (m, 1H), 4.45 (q, J=7.5 Hz, 3H), 3.43-3.15 (m, 1H), 2.86-2.70 (m, 1H), 2.37 (dd, J=7.0, 13.1 Hz, 2H), 2.17 (br. s., 2H), 2.01-1.77 (m, 3H), 1.62 (d, J=8.0 Hz, 1H), 1.50-1.33 (m, 14H), 0.54-0.38 (m, 1H), 0.07 (d, J=5.0 Hz, 1H)

Synthesis of Compound 37-8

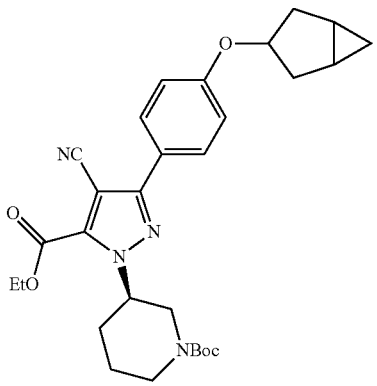 [SMILES: CCOC(=O)c1c(C#N)c(-c2ccc(OC3CC4CC4C3)cc2)nn1[C@@H]1CCCN(C(=O)OC(C)(C)C)C1]

The mixture of compound 37-7 (1100 mg, 1.77 mmol), zinc powder (231 mg, 3.54 mmol), Zn(CN)$_2$ (416 mg, 3.54 mmol), Pd(dppf)Cl$_2$ (115 mg, 0.177 mol) and Pd(dba)$_2$ (102 mg, 0.177 mol) in anhydrous DMF (20 mL) was stirred under nitrogen atmosphere at 100° C. for 14 h. To the reaction solution was added water (100 mL) and the resulting solution was extracted with DCM (100 mL×3). The organic phases were combined, dried over anhydrous Na$_2$SO$_4$ and concentrated to give a crude product which was purified by column chromatography to afford compound 37-8 (600 mg, 65%) as yellow oil.

LCMS (ESI) m/z: 521 (M+1).

Synthesis of Compound 37-9

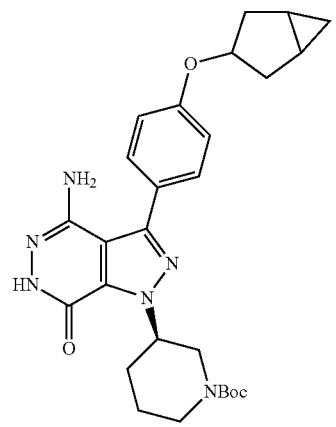 [SMILES: CC(C)(C)OC(=O)N1CCC[C@@H](n2nc(-c3ccc(OC4CC5CC5C4)cc3)c3c(N)n[nH]c(=O)c32)C1]

Compound 37-8 (600 mg, 1.15 mmol) was added into N$_2$H$_4$.H$_2$O (85%, 51 mL), and the reaction mixture was stirred at 120° C. for 1 h. To this mixture, water (20 mL) was added, and the resulting solution was extracted with DCM (30 mL×3). The organic phases were combined, dried over anhydrous Na$_2$SO$_4$, filtered and concentrated to give compound 37-9 (700 mg, crude) as white solid.

LCMS: m/z, 507 (M+H).

Synthesis of Compound 37-10

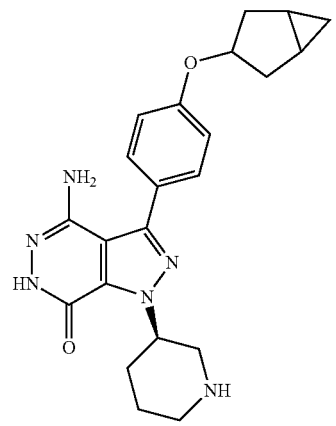 [SMILES: Nc1n[nH]c(=O)c2c1c(-c1ccc(OC3CC4CC4C3)cc1)nn2[C@@H]1CCCNC1]

Compound 37-9 (700 mg, 1.38 mmol) was dissolved in a solution of saturated HCl-EtOAc (10 mL), and the reaction solution was stirred at r.t. After TLC indicated the reaction was complete, the reaction solution was concentrated to give compound 37-10 (400 mg, crude) as white solid.

LCMS (ESI) m/z: 407 (M+1).

225

Compound 37-11

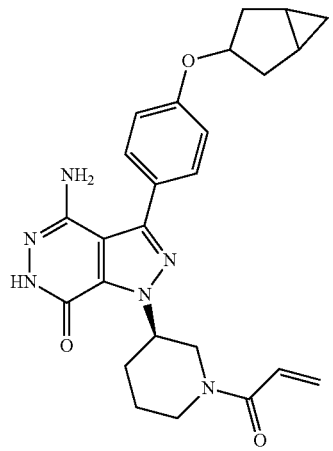 [SMILES: C=CC(=O)N1CCC[C@@H](n2nc(-c3ccc(OC4CC5CC5C4)cc3)c3c(N)n[nH]c(=O)c32)C1]

The mixture of acrylic acid (106 mg, 1.48 mmol), HATU (562 mg, 1.48 mmol) and N,N-DIPEA (381 mg, 2.95 mmol) in DCM (10 mL) was stirred at r.t. for 10 min, after which compound 37-10 (400 mg, 0.984 mmol) was added to this mixture, and the resulting reaction mixture was stirred for 30 min. After TLC indicated the reaction was complete, the solvent was evaporated under the decreased pressure, DCM (50 mL) and water (50 mL) were added into the residue, and the resulting residue was extracted with DCM (50 mL×3). The organic phases were combined, dried over anhydrous $Na_2SO_4$, and concentrated to give a crude product which was purified by preparative chromatography to afford compound 37-11 (60 mg, 13%) as white solid.

LCMS (ESI) m/z: 461 (M+1).

$^1$H NMR (400 MHz, CDCl$_3$): δ ppm 10.34-9.98 (m, 1H), 7.55 (d, J=8.5 Hz, 2H), 7.00 (d, J=8.5 Hz, 2H), 6.75-6.54 (m, 1H), 6.37-6.20 (m, 1H), 5.81-5.60 (m, 1H), 5.47 (br. s., 1H), 4.97-4.75 (m, 2H), 4.70-4.55 (m, 1H), 4.49 (quin, J=7.2 Hz, 1H), 4.36-3.98 (m, 1H), 3.68-3.43 (m, 1H), 3.26-2.84 (m, 1H), 2.52-2.17 (m, 4H), 1.99 (d, J=8.5 Hz, 3H), 1.76 (br. s., 1H), 1.47-1.35 (m, 2H), 0.50 (d, J=5.5 Hz, 1H), 0.09 (q, J=4.0 Hz, 1H)

Scheme 32

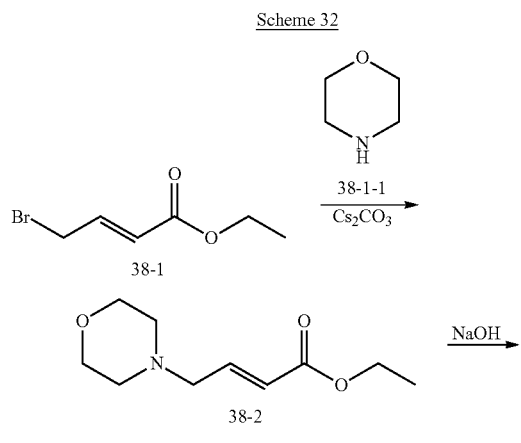

226

-continued

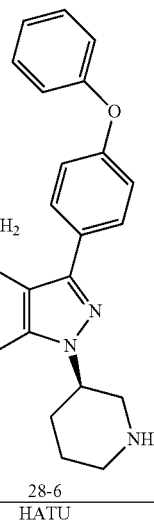

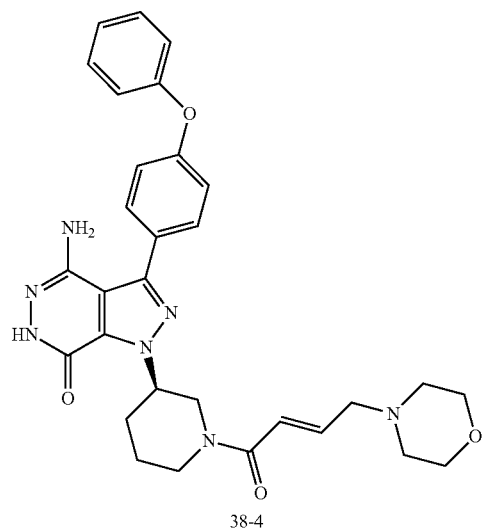

Example 36

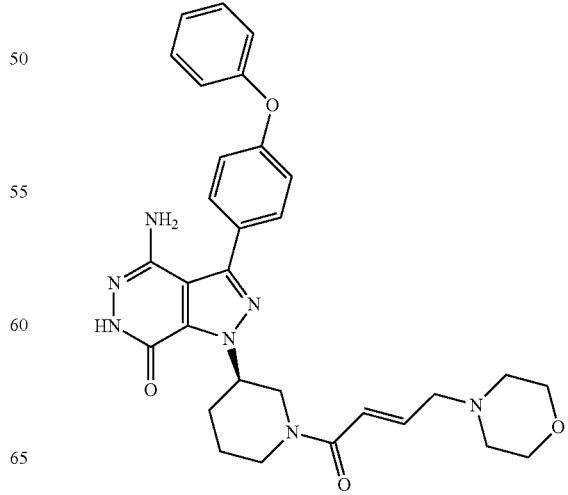

Synthesis of Compound 38-2

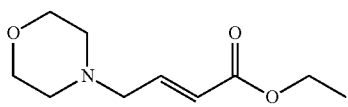

Compound 38-1 (300.00 mg, 1.55 mmol), Cs$_2$CO$_3$ (1.01 g, 3.10 mmol) and compound 38-1-1 (162.04 mg, 1.86 mmol) were dissolved in 1,4-dioxane (5 mL), and the reaction mixture was stirred at r.t. for 1 h. After TLC indicated the reaction was complete, the solvent was evaporated under the decreased pressure, water (50 mL) was added into the residue, and the resulting residue was extracted with EtOAc (100 mL×3). The organic phases were combined, dried over anhydrous Na$_2$SO$_4$, and concentrated to give a crude product which was purified by column chromatography (PE/EtOAc=2/1) to afford compound 38-2 (250 mg, 80.95%) as yellow oil.

$^1$H NMR (400 MHz, CDCl$_3$): δ ppm 7.08-6.65 (m, 1H), 6.15-5.69 (m, 1H), 4.39-3.93 (m, 2H), 3.89-3.30 (m, 4H), 3.24-2.83 (m, 2H), 2.77-2.10 (m, 4H), 1.29 (d, J=7.1 Hz, 2H)

Synthesis of Compound 38-3

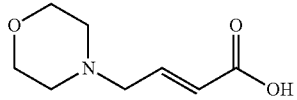 [SMILES: O=C(O)/C=C/CN1CCOCC1]

To a solution of compound 38-2 (250.00 mg, 1.25 mmol) in MeOH (4 mL) was added sodium hydroxide (NaOH) (100 mg, 2.5 mmol), and the reaction solution was stirred at r.t. for 4 h, and then adjusted to pH 6 with dilute HCl (2 M, 20 mL) and extracted with DCM (50 mL×4). The organic phases were combined, dried over anhydrous Na$_2$SO$_4$ and concentrated to give compound 38-3 (50 mg, crude) as yellow solid.

Synthesis of Compound 38-4

The mixture of compound 38-3 (15.00 mg, 87.62 μmop, HATU (28.34 mg, 74.54 μmop and N,N-DIPEA (9.63 mg, 74.54 μmol) in DCM (2 mL) was stirred at r.t. for 30 min, and then compound 28-6 (30.00 mg, 74.54 μmop was added and the reaction solution was stirred for 2 h. After TLC indicated the reaction was complete, the solvent was evaporated under the decreased pressure, and DCM (50 mL) and water (50 mL) were added into the residue. The resulting residue was extracted with DCM (50 mL×3). The organic phases were combined, dried over anhydrous Na$_2$SO$_4$, and concentrated to give a crude product which was purified by preparative chromatography to afford compound 38-4 (10.00 mg, 24.15%) as white solid.

LCMS (ESI) m/z: 556 (M+1).

$^1$H NMR (400 MHz, CDCl$_3$): δ ppm 10.29 (br. s., 1H), 7.63 (d, J=8.6 Hz, 2H), 7.48-7.33 (m, 2H), 7.24-7.02 (m, 5H), 6.84 (br. s., 1H), 6.50 (d, J=14.6 Hz, 1H), 5.57-5.44 (m, 1H), 4.95-4.77 (m, 2H), 4.63-4.47 (m, 1H), 4.28 (d, J=13.7 Hz, 1H), 3.99 (br. s., 1H), 3.71 (d, J=18.5 Hz, 4H), 3.52-3.40 (m, 1H), 3.22-3.06 (m, 2H), 2.87 (br. s., 1H), 2.46 (d, J=19.2 Hz, 4H), 2.33 (br. s., 1H), 2.00 (d, J=13.9 Hz, 1H)

Scheme 33

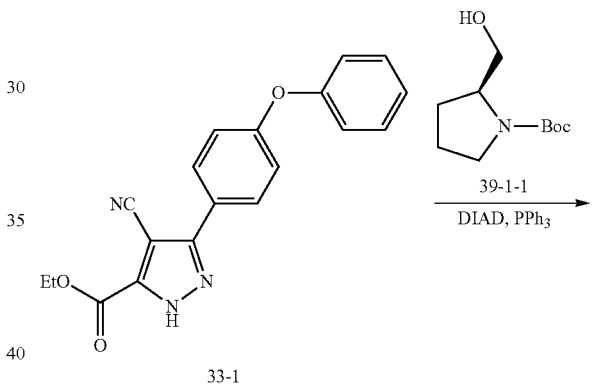

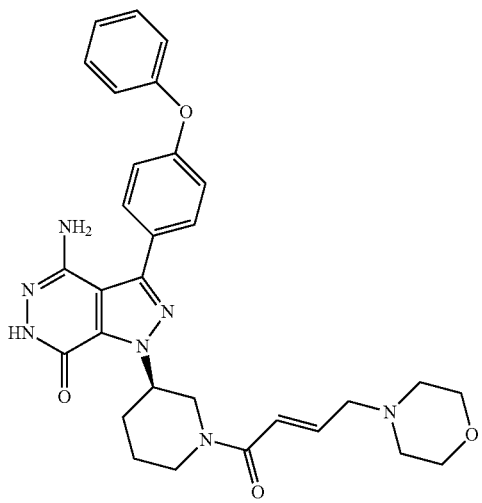 [SMILES: Nc1n[nH]c(=O)c2c1c(-c1ccc(Oc3ccccc3)cc1)nn2[C@@H]1CCCN(C(=O)/C=C/CN2CCOCC2)C1]

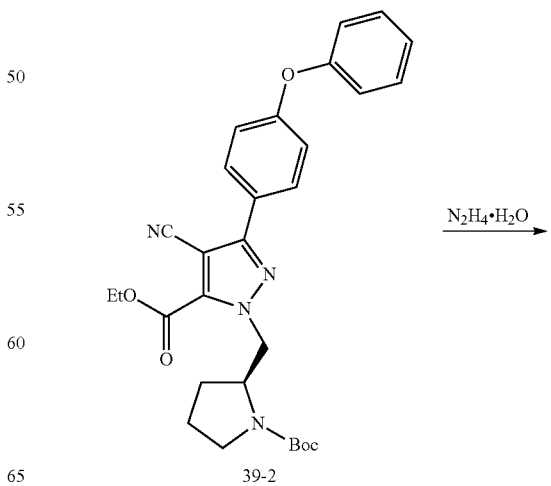

-continued

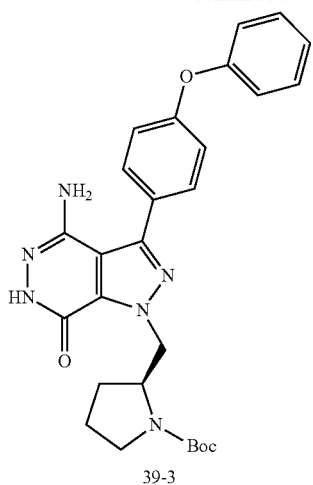

39-3

HCl—EA →

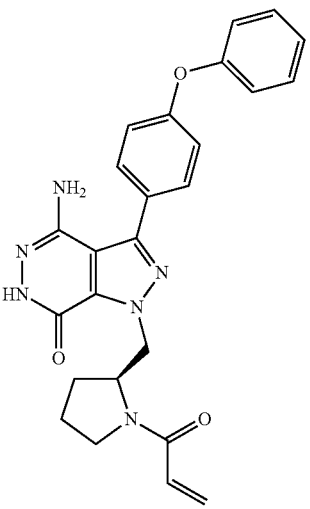 [SMILES: C=CC(=O)N1CCC[C@H]1Cn1nc(-c2ccc(Oc3ccccc3)cc2)c2c(N)n[nH]c(=O)c21]

Example 37

Compound 39-2

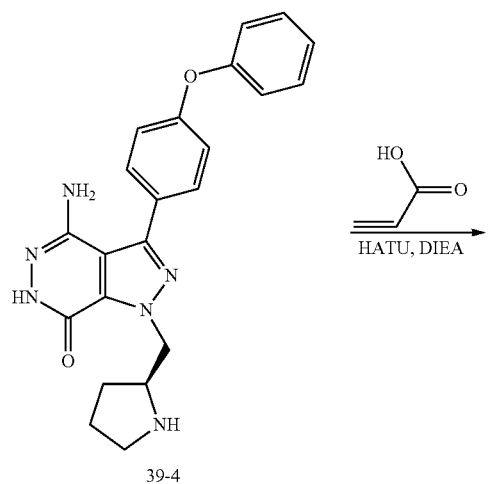

39-4

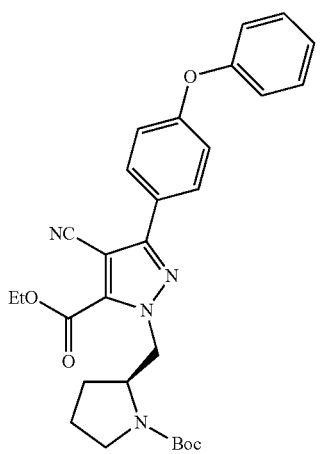 [SMILES: CCOC(=O)c1c(C#N)c(-c2ccc(Oc3ccccc3)cc2)nn1C[C@@H]1CCCN1C(=O)OC(C)(C)C]

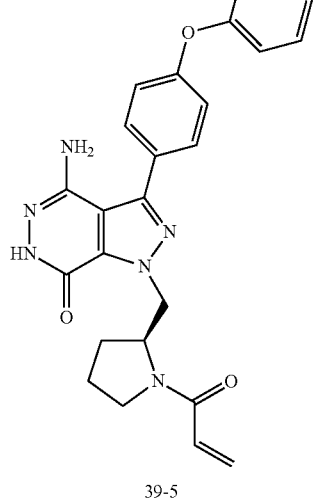

39-5

To a solution of PPh₃ (220.32 mg, 839.99 μmol) in anhydrous toluene (5 mL) was added diisopropylazodicarboxylate (169.85 mg, 839.99 μmol) at 0° C. and the reaction solution was stirred for 15 min, after which compound 33-1 (200.00 mg, 599.99 μmol) and compound 39-1-1 (144.91 mg, 719.99 μmol) were added and the resulting reaction solution was stirred at 60° C. for 12 h. Water (100 mL) was added into the solution, and the resulting solution was extracted with EtOAc (100 mL×3). The organic phases were combined, dried over anhydrous Na₂SO₄ and concentrated to give a crude product which was purified by column chromatography (PE/EtOAc=9:1) to afford compound 39-2 (200.00 mg, 64.53%) as white oil.

LCMS (ESI) m/z: 517 (M+1).

Compound 39-3

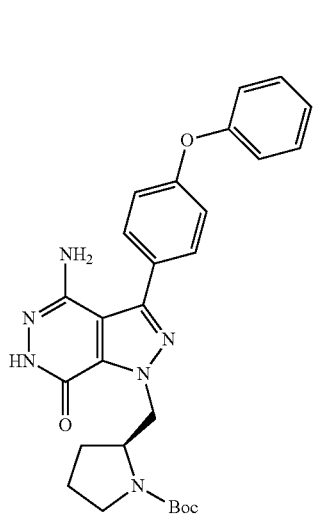 [SMILES: CC(C)(C)OC(=O)N1CCC[C@H]1Cn1nc(-c2ccc(Oc3ccccc3)cc2)c2c(N)n[nH]c(=O)c21]

Compound 39-5

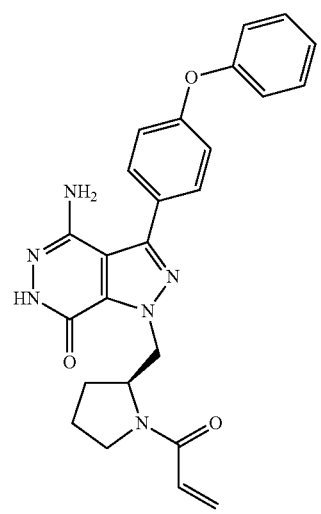

To N₂H₄·H₂O (85%, 5 mL) was added compound 39-2 (200.00 mg, 387.15 μmol) and the reaction mixture was stirred at 120° C. for 1 h, after which H₂O (20 mL) was added and the resulting solution was extracted with DCM (30 mL×3). The organic phases were combined, dried over anhydrous Na₂SO₄, filtered and concentrated to give compound 39-3 (200.00 mg, crude) as white solid.

LCMS (ESI) m/z: 503 (M+1).

Compound 39-4

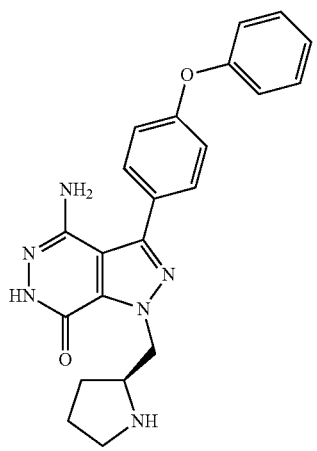 [SMILES: Nc1n[nH]c(=O)c2c1c(-c1ccc(Oc3ccccc3)cc1)nn2C[C@@H]1CCCN1]

Compound 39-3 (200.00 mg, 397.96 μmol) was dissolved in a solution of saturated HCl-EtOAc (5 mL), and the reaction mixture was stirred at r.t. for 1 h. After TLC indicated the reaction was complete, the reaction solution was concentrated to give compound 39-4 (180.00 mg, crude) as white solid.

LCMS (ESI) m/z: 403 (M+1).

The mixture of acrylic acid (48.34 mg, 670.89 μmol), HATU (255.09 mg, 670.89 μmol) and N,N-DIPEA (231.22 mg, 1.79 mmol) in DCM (5 mL) was stirred at r.t. for 10 min, after which compound 39-4 (180.00 mg, 447.26 μmol) was added and the resulting reaction mixture was stirred for 2 h. After TLC indicated the reaction was complete, the solvent was evaporated under the decreased pressure, and DCM (50 mL) and water (50 mL) were added to the residue. The resulting residue was extracted with DCM (50 mL×3), and then the organic phases were combined, dried over anhydrous Na₂SO₄ and concentrated to give a crude product which was purified by preparative chromatography to afford compound 39-5 (60.00 mg, 29.39%) white solid.

LCMS (ESI) m/z: 457 (M+1).

$^1$H NMR (400 MHz, CDCl$_3$): δ ppm 10.11-9.89 (m, 1H), 7.64 (dd, J=2.9, 8.6 Hz, 2H), 7.46-7.32 (m, 2H), 7.24-7.05 (m, 5H), 6.64 (dd, J=10.4, 16.5 Hz, 1H), 6.51-6.36 (m, 1H), 6.36-6.25 (m, 1H), 5.70-5.53 (m, 1H), 5.09-4.91 (m, 1H), 4.84 (dd, J=6.3, 13.3 Hz, 1H), 4.78-4.56 (m, 3H), 3.80-3.60 (m, 2H), 2.04-1.87 (m, 3H)

Example 38

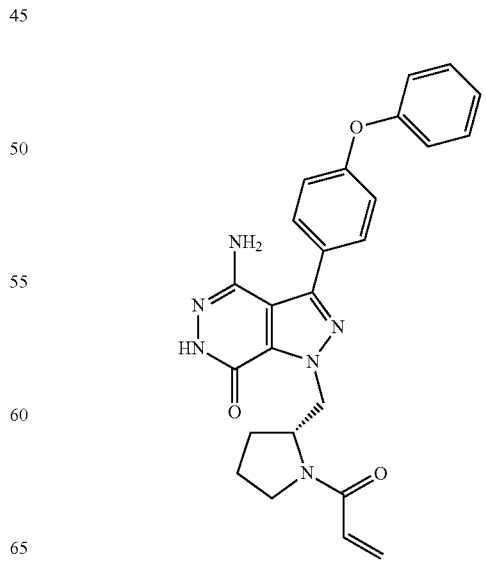

In Example 38, the systhesis process was similarly to that in Example 37.
LCMS (ESI) m/z: 457 (M+1).
$^1$H NMR (400 MHz, CDCl$_3$): δ ppm 9.55-9.24 (m, 1H), 7.66-7.58 (m, 2H), 7.48-7.35 (m, 2H), 7.22-7.06 (m, 5H), 6.62 (dd, J=10.4, 16.5 Hz, 1H), 6.47-6.37 (m, 1H), 6.36-6.26 (m, 1H), 5.68-5.55 (m, 1H), 4.98 (br. s., 1H), 4.89-4.78 (m, 1H), 4.77-4.68 (m, 1H), 4.44 (br. s., 2H), 3.78-3.60 (m, 2H), 2.04-1.88 (m, 3H)
Scheme 34
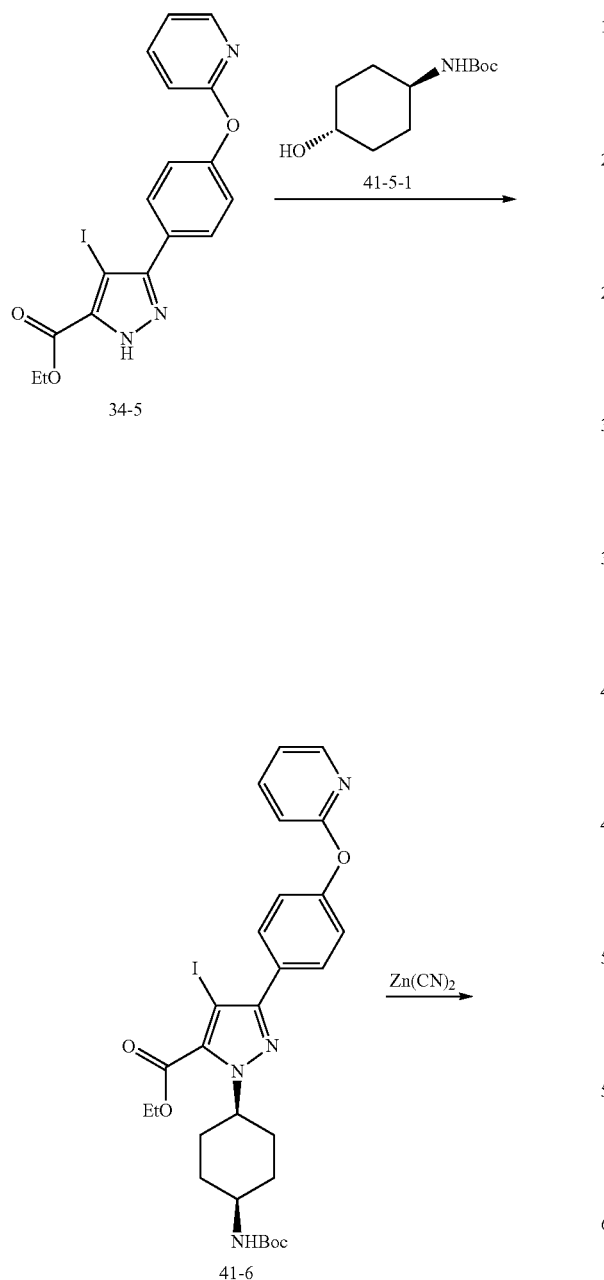
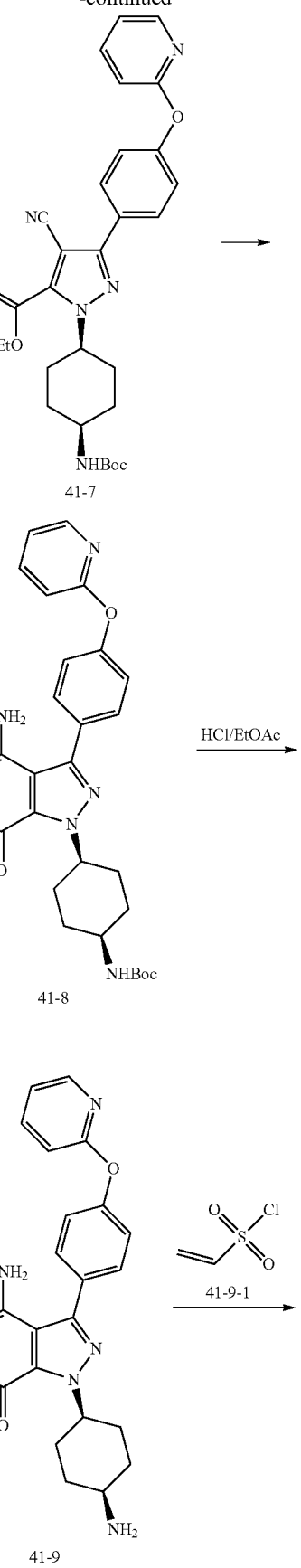

235
-continued

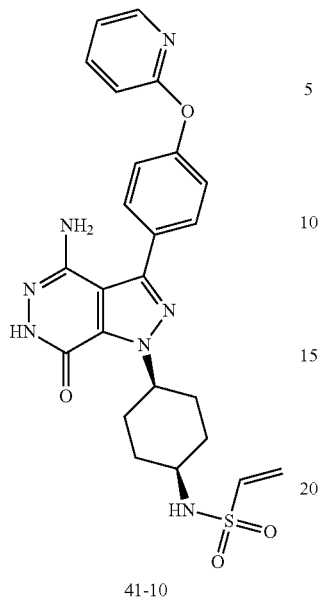

41-10

Example 39

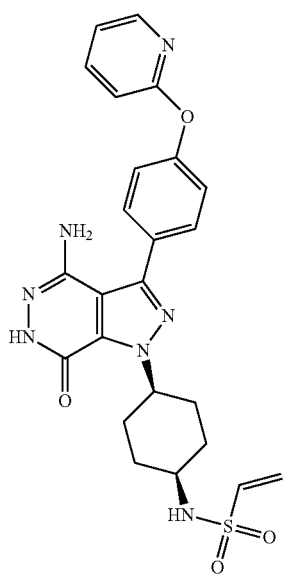 [SMILES: C=CS(=O)(=O)N[C@H]1CC[C@@H](n2nc(-c3ccc(Oc4ccccn4)cc3)c3c(N)n[nH]c(=O)c32)CC1]

236
Synthesis of Compound 41-6

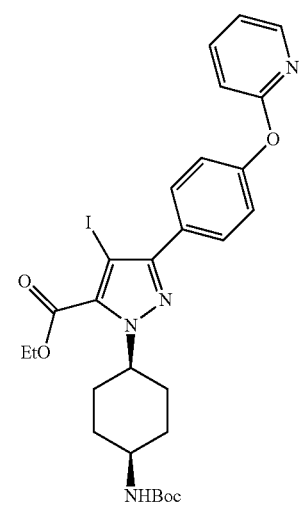 [SMILES: CCOC(=O)c1c(I)c(-c2ccc(Oc3ccccn3)cc2)nn1[C@H]1CC[C@@H](NC(=O)OC(C)(C)C)CC1]

To a solution of $PPh_3$ (4.22 g, 16.09 mmol) in anhydrous DCM (50 mL) was added diisopropylazodicarboxylate (3.25 g, 16.09 mmol) at 0° C. and the reaction solution was stirred 15 min, after which compound 34-5 (5.00 g, 11.49 mmol) and compound 41-5-1 (2.97 g, 13.79 mmol) were added and the resulting reaction solution was stirred at 40° C. for 12 h, the starting materials disappeared. Water (100 mL) was added into the solution, and the resulting solution was extracted with EtOAc (100 mL×3). The organic phases were combined, dried over anhydrous $Na_2SO_4$ and concentrated to give a crude product which was purified by column chromatography (PE/EtOAc=9:1) to afford compound 41-6 (7.00 g, 96.32%) as white solid.

LCMS (ESI) m/z: 633 (M+1).

Synthesis of Compound 41-7

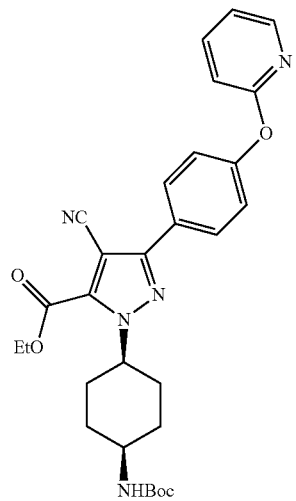 [SMILES: CCOC(=O)c1c(C#N)c(-c2ccc(Oc3ccccn3)cc2)nn1[C@H]1CC[C@@H](NC(=O)OC(C)(C)C)CC1]

Compound 41-6 (2.40 g, 3.79 mmol), zinc powder (496.25 mg, 7.59 mmol) and $Zn(CN)_2$ (890.04 mg, 7.58 mmol) were suspended in anhydrous DMF (10 mL), and $Pd(dppf)Cl_2$ (221.85 mg, 303.20 μmol) and $Pd(dba)_2$ (174.34 mg, 303.20 μmol) were added to the solution, after which the reaction solution was reacted under nitrogen atmosphere at 100° C. for 14 h. To the reaction solution was added water (100 mL) and the reaction solution was extracted with DCM (100 mL×3). The organic phases were combined, dried over anhydrous Na₂SO₄ and concentrated to give a crude product which was purified by column chromatography (PE/EtOAc=5/1) to afford compound 41-7 (1.70 g, 84.38%) as yellow oil.

LCMS (ESI) m/z: 532 (M+1).

Synthesis of Compound 41-8

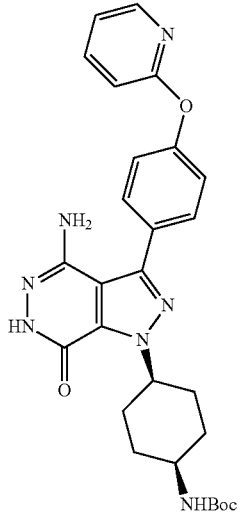

Compound 41-7 (1.70 g, 3.20 mmol) was added into N₂H₄.H₂O (85%, 10 mL), and the reaction mixture was stirred at 120° C. for 1 h. To this mixture, H₂O (50 mL) was added, and the resulting solution was extracted with DCM (30 mL×3). The organic phases were combined, dried over anhydrous Na₂SO₄, filtered and concentrated to give compound 41-8 (1.50 g, crude) as white solid.

LCMS (ESI) m/z: 518 (M+1).

Synthesis of Compound 41-9

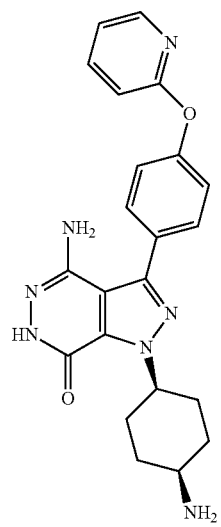 [SMILES: Nc1n[nH]c(=O)c2c1c(-c1ccc(Oc3ccccn3)cc1)nn2[C@H]1CC[C@@H](N)CC1]

Compound 41-8 (1.70 g, 3.28 mmol) was dissolved in a solution of saturated HCl-EtOAc (30 mL), and the reaction solution was stirred at r.t. After LCMS indicated the reaction was complete, the reaction solution was concentrated to give compound 41-9 (1.70 g, crude) as white solid.

LCMS (ESI) m/z: 418 (M+1).

Synthesis of Compound 41-10

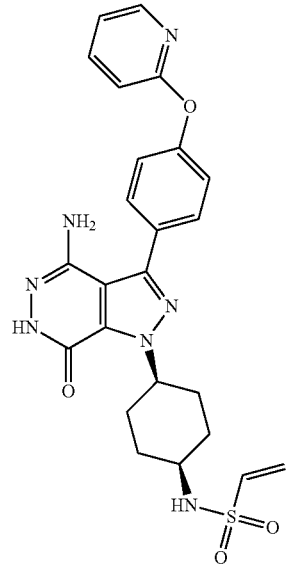 [SMILES: C=CS(=O)(=O)N[C@H]1CC[C@@H](n2nc(-c3ccc(Oc4ccccn4)cc3)c3c(N)n[nH]c(=O)c32)CC1]

Acrylic acid (60.63 mg, 479.09 μmol), HATU (275 mg, 0.718 mmol) and N,N-DIPEA (123.83 mg, 958.18 μmol) were dissolved in DCM (5 mL) and the reaction solution was stirred at r.t. for 10 min, and then compound 41-9 (200.00 mg, 479.09 μmol) was added and the reaction solution was stirred for 0.5 h. After TLC indicated the reaction was complete, the solvent was evaporated under the decreased pressure, DCM (50 mL) and water (50 mL) were added into the residue, and then the resulting residue was extracted with DCM (50 mL×3). The organic phases were combined, dried over anhydrous Na₂SO₄ and concentrated to give a crude product which was purified by preparative chromatography to afford compound 41-10 (15.00 mg, 6.17%) as white solid.

¹H NMR (400 MHz, CDCl₃): δ ppm 10.01 (br. s., 1H), 8.36-8.12 (m, 1H), 7.85-7.57 (m, 3H), 7.31 (d, J=8.4 Hz, 2H), 7.12-7.04 (m, 1H), 7.04-6.97 (m, 1H), 6.63-6.51 (m, 1H), 6.26 (d, J=16.3 Hz, 1H), 5.89 (d, J=9.7 Hz, 1H), 5.57 (br. s., 1H), 5.23 (br. s., 1H), 4.85 (br. s., 1H), 3.72 (br. s., 1H), 2.49-2.34 (m, 2H), 2.04 (d, J=13.0 Hz, 4H), 1.78 (t, J=13.2 Hz, 2H).

LCMS (ESI) m/z: 473 (M+1).

Example 40
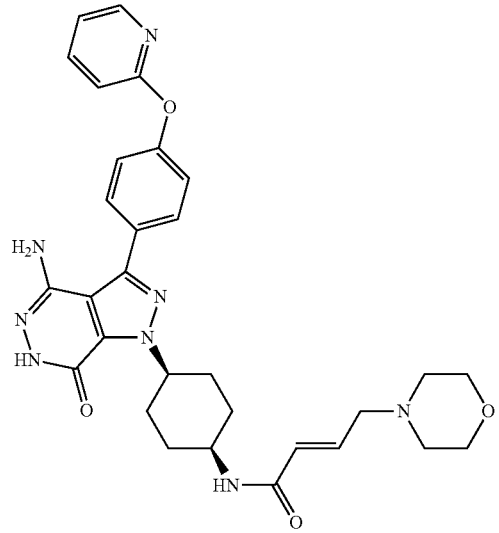 [SMILES: Nc1n[nH]c(=O)c2c1c(-c1ccc(Oc3ccccn3)cc1)nn2[C@H]1CC[C@@H](NC(=O)/C=C/CN2CCOCC2)CC1]
In Example 40, the systhesis process was similar to that in Example 39.
LCMS (ESI) m/z: 556 (M+1).
$^1$H NMR (400 MHz, CDCl$_3$): δ ppm 9.95-9.63 (m, 1H), 8.33-8.03 (m, 1H), 7.72 (d, J=8.6 Hz, 3H), 7.31 (d, J=8.4 Hz, 1H), 7.16-6.97 (m, 2H), 6.96-6.75 (m, 2H), 6.12 (d, J=15.7 Hz, 1H), 5.18 (br. s., 1H), 4.44 (br. s., 3H), 3.77 (d, J=4.2 Hz, 3H), 3.22 (d, J=6.0 Hz, 2H), 2.59 (br. s., 3H), 2.50-2.35 (m, 2H), 2.11-1.91 (m, 3H), 1.79 (t, J=13.5 Hz, 3H)
Scheme 35
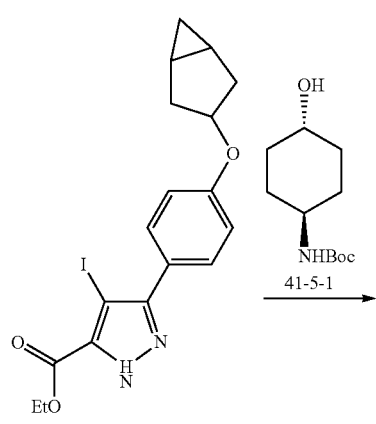
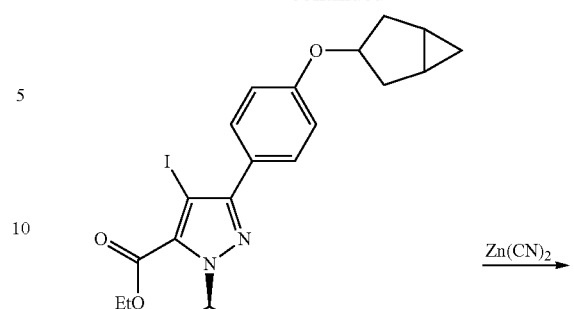
43-7
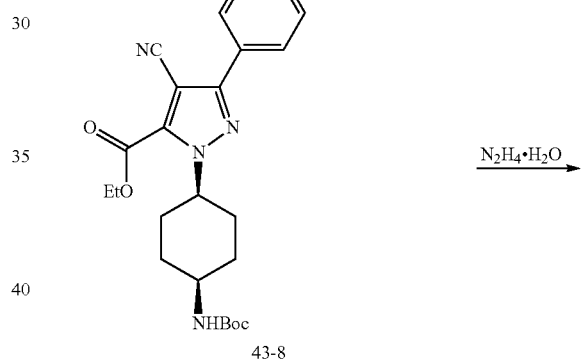
43-8
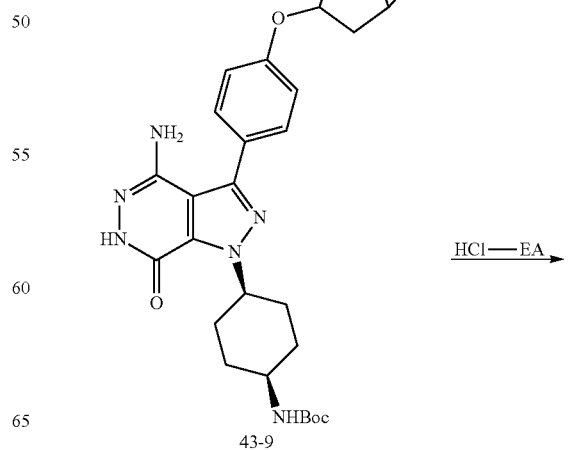
43-9

241

-continued

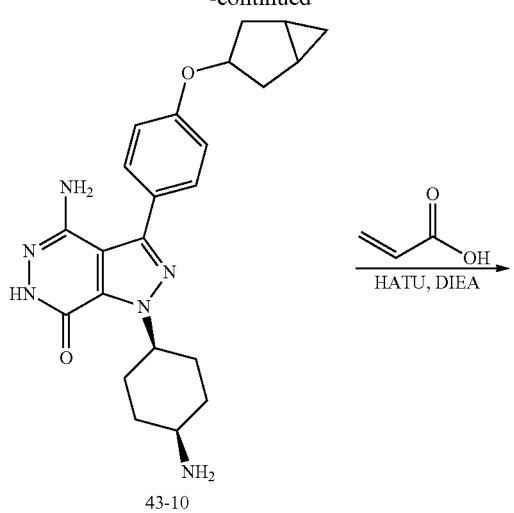

43-10

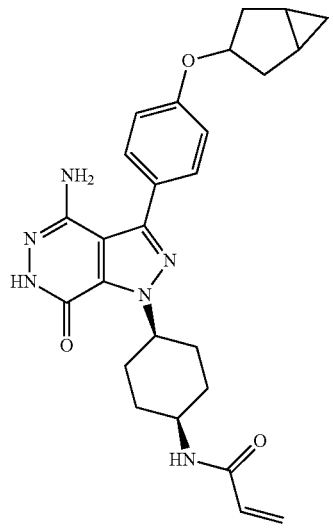 [SMILES: C=CC(=O)N[C@H]1CC[C@@H](n2nc(-c3ccc(OC4CC5CC5C4)cc3)c3c(N)n[nH]c(=O)c32)CC1]

43-11

Example 41

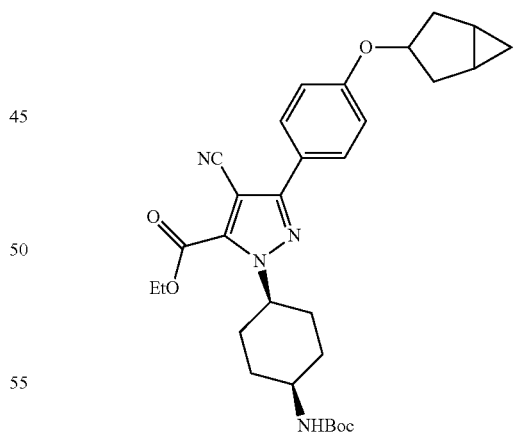

242

Synthesis of Compound 43-7

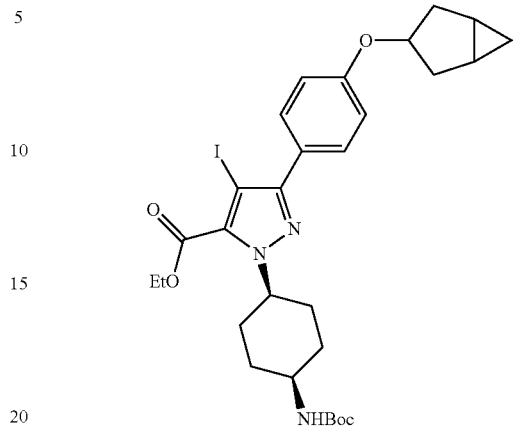

To a solution of PPh$_3$ (1.17 g, 4.47 mmol) in anhydrous toluene (30 mL) was added di-tertbutylazodicarboxylate (DBAD) (1.03 g, 4.47 mmol) at 0° C., and the reaction mixture was stirred for 15 min, after which compound 37-6 (1.40 g, 3.19 mmol) and compound 41-5-1 (894.05 mg, 4.15 mmol) were added and the resulting mixture was stirred at 60° C. for 12 h, the starting materials disappeared. To the mixture, water (100 mL) was added, and the solution was extracted with EtOAc (100 mL×3). The organic phases were combined, dried over anhydrous Na$_2$SO$_4$, and concentrated to give a crude product which was purified by column chromatography (PE/EtOAc=10/1) to afford compound 43-7 (2.00 g, 89.77%) as white solid.

LCMS (ESI) m/z: 636 (M+1).

Synthesis of Compound 43-8

The mixture of compound 43-7 (2.00 g, 3.15 mmol), zinc powder (411.56 mg, 6.29 mmol), Zn(CN)$_2$ (1.30 g, 11.07 mmol), Pd(dppf)Cl$_2$ (184.21 mg, 251.76 µmop and Pd(dba)$_2$ (230.76 mg, 252.00 µmop in anhydrous DMF (20 mL) was stirred under nitrogen atmosphere at 100° C. for 14 h. To the reaction solution was added water (100 mL) and the resulting reaction solution was extracted with DCM (100 mL×3). The organic phases were combined, dried over anhydrous Na$_2$SO$_4$ and concentrated to give a crude product which was purified by column chromatography to afford compound 43-8 (1.30 g, 77.19%) as yellow oil.

LCMS (ESI) m/z: 535 (M+1).

Synthesis of Compound 43-9

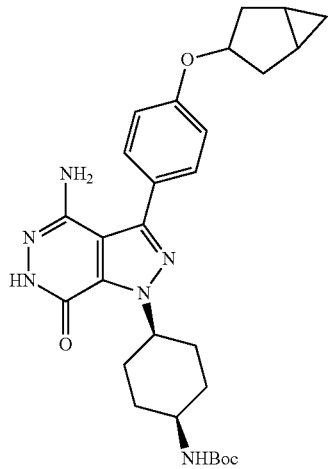 [SMILES: CC(C)(C)OC(=O)N[C@H]1CC[C@@H](n2nc(-c3ccc(OC4CC5CC5C4)cc3)c3c(N)n[nH]c(=O)c32)CC1]

Compound 43-8 (1.20 g, 2.24 mmol) was added into N₂H₄.H₂O (85%, 10 mL), and the reaction mixture was stirred at 120° C. for 1 h. To this mixture, H₂O (20 mL) was added, and the resulting solution was extracted with DCM (30 mL×3). The organic phases were combined, dried over anhydrous Na₂SO₄, filtered and concentrated to give compound 43-9 (1.10 g, crude) as white solid.

LCMS (ESI) m/z: 521 (M+1).

Synthesis of Compound 43-10

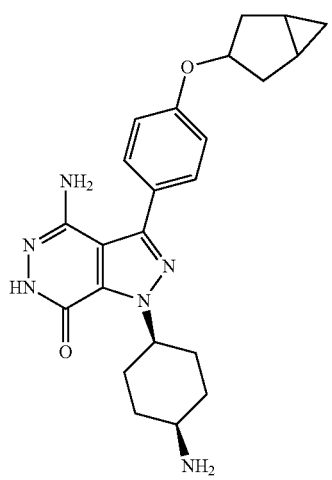 [SMILES: Nc1n[nH]c(=O)c2c1c(-c1ccc(OC3CC4CC4C3)cc1)nn2[C@H]1CC[C@@H](N)CC1]

Compound 43-9 (1.10 g, 2.11 mmol) was dissolved in a solution of saturated HCl-EtOAc (10 mL), and the reaction solution was stirred at r.t. After TLC indicated the reaction was complete, the reaction solution was concentrated to give compound 43-10 (800.00 mg, 90.16%) as white solid.

LCMS (ESI) m/z: 421 (M+1).

Synthesis of Compound 43-11

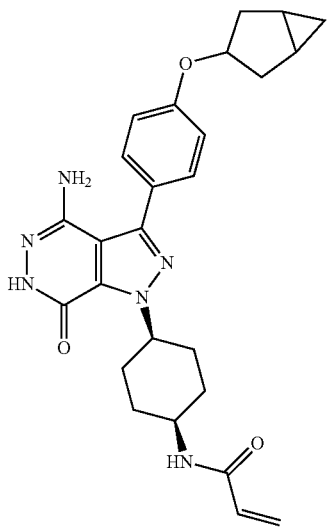 [SMILES: C=CC(=O)N[C@H]1CC[C@@H](n2nc(-c3ccc(OC4CC5CC5C4)cc3)c3c(N)n[nH]c(=O)c32)CC1]

The mixture of acrylic acid (82.25 mg, 1.14 mmol), HATU (542.53 mg, 1.43 mmol) and N,N-DIPEA (368.81 mg, 2.85 mmol) in DCM (8 mL) was stirred at r.t. for 10 min, after which compound 43-10 (400.00 mg, 951.23 μmol) was added to this mixture, and the resulting reaction mixture was stirred for 30 min. After TLC indicated the reaction was complete, the solvent was evaporated under the decreased pressure, and DCM (50 mL) and water (50 mL) were added into the residue. Then the resulting residue was extracted with DCM (50 mL×3). The organic phases were combined, dried over anhydrous Na₂SO₄ and concentrated to give a crude product which was purified by preparative chromatography to afford compound 43-11 (60 mg, 13%) as white solid.

LCMS (ESI) m/z: 475 (M+1).

¹H NMR (400 MHz, CDCl₃): δ ppm 7.60-7.48 (m, 2H), 7.04-6.95 (m, 1H), 6.33 (d, J=1.5 Hz, 1H), 6.30-6.18 (m, 1H), 5.63 (dd, J=1.5, 10.1 Hz, 1H), 5.23 (t, J=11.0 Hz, 1H), 4.49 (s, 1H), 4.43-4.35 (m, 1H), 3.39-3.24 (m, 1H), 2.53-2.32 (m, 4H), 1.99 (d, J=12.3 Hz, 3H), 1.87-1.75 (m, 1H), 1.67 (br. s., 1H), 1.51-1.35 (m, 3H), 1.01 (t, J=7.3 Hz, 2H), 0.56-0.44 (m, 1H), 0.14-0.02 (m, 1H)

Example 42

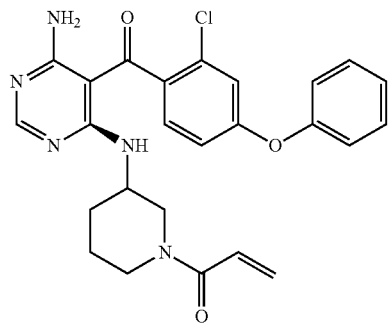

In Example 42, the systhesis process was similar to that in Example 25.

LCMS (ESI) m/z: 478 (M+1).
¹H NMR (400 MHz, CDCl₃): δ ppm 8.12 (s, 1H), 7.44-7.40 (m, 1H), 7.32-7.30 (m, 1H), 7.08-7.04 (m, 2H), 6.98-6.85 (m, 1H), 6.55-6.51 (m, 1H), 6.28-6.24 (d, 1H, J=16.8 Hz), 5.74-5.65 (m, 2H), 4.17 (m, 1H), 3.92-3.83 (m, 1H), 3.66-3.60 (m, 1H), 3.36-3.26 (m, 2H), 2.00 (m, 1H), 1.63 (m, 3H).
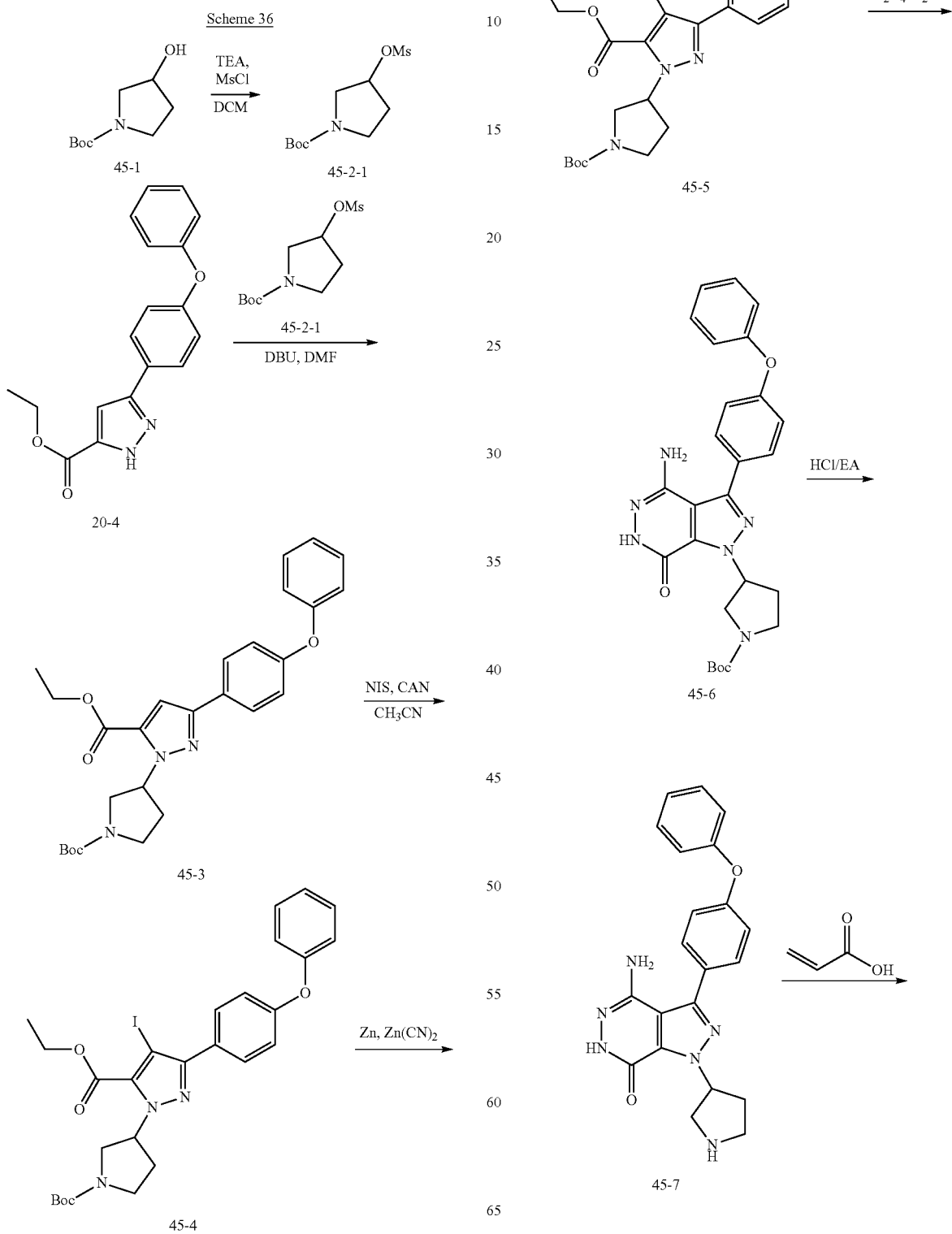

-continued

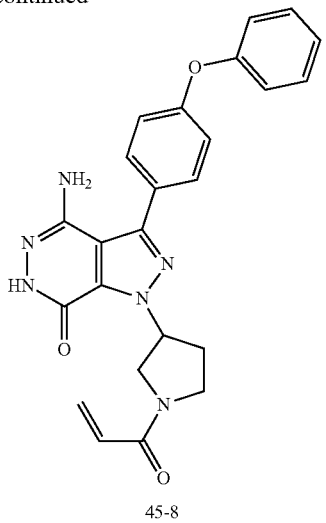

45-8

Example 43

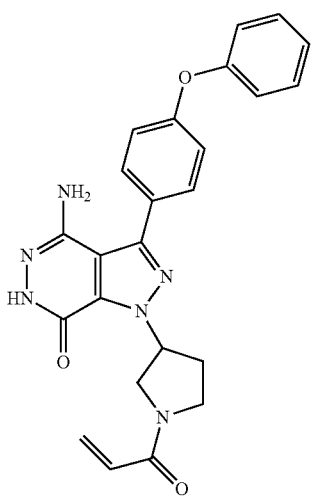 [SMILES: C=CC(=O)N1CCC(n2nc(-c3ccc(Oc4ccccc4)cc3)c3c(N)n[nH]c(=O)c32)C1]

Compound 45-2-1

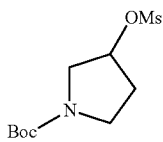

To a solution of compound 45-1 (10 g, 53.5 mmol) and TEA (6.5 g, 64.2 mmol) in DCM (100 mL) was added dropwise mesyl chloride (7.35 g, 64.2 mmol), and the reaction solution was reacted at r.t. for 1 h. To this solution, water (80 mL) was added and the resulting solution was extracted with DCM (100 mL×2). The organic phases were combined, dried over anhydrous $Na_2SO_4$, filtered and concentrated to give compound 45-2-1 (13.86 g, 98%) as colourless oil.

$^1$H NMR (400 MHz, CDCl$_3$): δ ppm 5.27 (s, 1H), 3.72-3.57 (m, 3H), 3.49 (s, 1H), 3.05 (s, 3H), 2.29 (s, 1H), 2.15 (s, 1H), 1.47 (s, 9H).

Compound 45-3

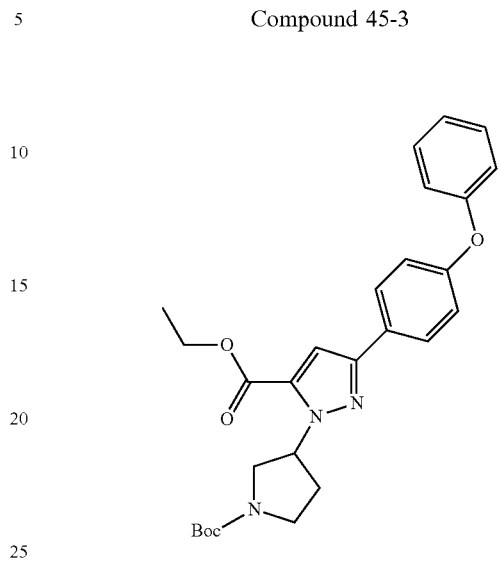

To a solution of compound 20-4 (7 g, 22.6 mmol) and compound 45-2-1 (12 g, 45.3 mmol) in DMF (70 mL) was added DBU (6.9 g, 45.3 mmol), and the reaction solution was stirred at 120° C. for 12 h, followed by concentration to give a crude product which was purified by column chromatography to afford compound 45-3 (10.41 g, 96%) as coloueless oil.

LCMS (ESI) m/z: 478 (M+1).

$^1$H NMR (400 MHz, CDCl$_3$): δ ppm 7.79-7.768 (d, 2H), 7.38-7.34 (t, 2H), 7.1427.11 (t, 2H), 7.05-7.03 (d, 4H), 4.39-4.37 (d, 2H), 3.86-3.7 (m, 3H), 3.582-3.54 (m, 1H), 3.41 (s, 1H), 2.59-2.53 (m, 1H), 2.37-2.32 (m, 1H), 1.48 (s, 9H), 1.44-1.40 (t, 3H).

Compound 45-4

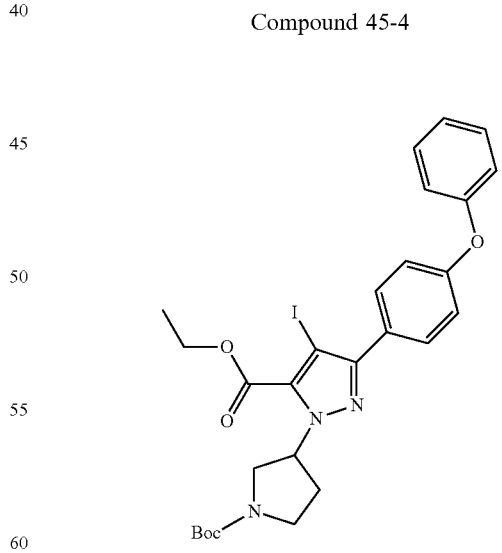

The mixture of compound 45-3 (9.4 g, 19.71 mmol), N-Iodosuccinimide (8.9 g, 39.42 mmol) and CAN (1.6 g, 2.9 mmol) in acetonitrile (200 mL) was reacted at 90° C. for 2.5 h, after which water (100 mL) was added to the mixture and the reaction mixture was extracted with DCM (200 mL×3). The organic phases were combined, dried over anhydrous Na$_2$SO$_4$ and concentrated to give a crude product which was purified by column chromatography to give compound 45-4 (7.6 g, 64%) as white solid.

LCMS (ESI) m/z: 604 (M+1).

$^1$H NMR (400 MHz, CDCl$_3$-d): δ ppm 7.77-7.75 (d, 2H), 7.39-7.35 (t, 2H), 7.14-7.09 (t, 1H), 7.07-7.05 (t, 4H), 4.48-4.46 (d, 2H), 3.83-3.41 (m, 5H), 2.57-2.56 (d, 1H), 2.36-2.30 (m, 1H), 1.48-1.46 (d, 12H).

Compound 45-5

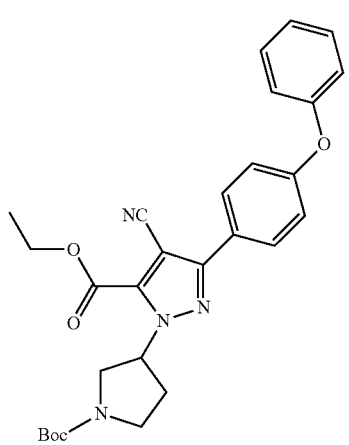 [SMILES: CCOC(=O)c1c(C#N)c(-c2ccc(Oc3ccccc3)cc2)nn1C1CCN(C(=O)OC(C)(C)C)C1]

The mixture of compound 45-4 (1.1 g, 1.82 mmol), zinc powder (237 mg, 3.65 mmol), Zn(CN)$_2$ (427 mg, 3.65 mmol), Pd(dppf)Cl$_2$ (132 mg, 0.18 mmol) and Pd$_2$(dba)$_3$ (164 mg, 0.18 mmol) in DMF (10 mL) was stirred under nitrogen atmosphere at 105° C. for 12 h, after which water was added to the mixture and the reaction mixture was extracted with EtOAc (50 mL×2). The organic phases were combined, dried, filtered and concentrated to give a crude product which was purified by column chromatography to give compound 45-5 (0.4 g, 44%) as yellow oil.

LCMS (ESI) m/z: 503 (M+1).

Compound 45-6

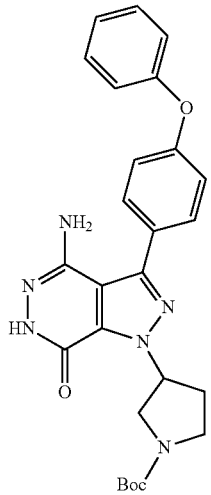 [SMILES: CC(C)(C)OC(=O)N1CCC(n2nc(-c3ccc(Oc4ccccc4)cc3)c3c(N)n[nH]c(=O)c32)C1]

The solution of compound 45-5 (170.7 mg, 0.34 mmol) in N$_2$H$_4$—H$_2$O (85%, 2.60 mL) was refluxed for 1.5 h, after which water (20 mL) was added and the reaction solution was extracted with DCM (20 mL×2). The organic phases were combined, dried over anhydrous Na$_2$SO$_4$, filtered and concentrated to give compound 45-6 (166 mg, crude) as yellow oil.

Compound 45-7

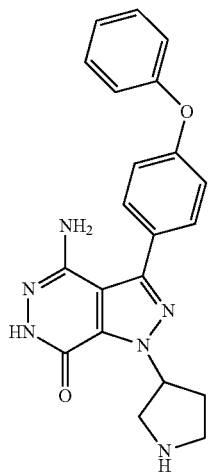 [SMILES: Nc1n[nH]c(=O)c2c1c(-c1ccc(Oc3ccccc3)cc1)nn2C1CCNC1]

The mixture of compound 45-6 (280 mg, 0.57 mmol) in saturated HCl-EtOAc (3 mL) was stirred at r.t. After LCMS indicated the reaction was complete, the reaction solution was concentrated to give compound 45-7 (189.7 mg, 78%) as yellow solid.

LCMS (ESI) m/z: 389 (M+1).

Compound 45-8

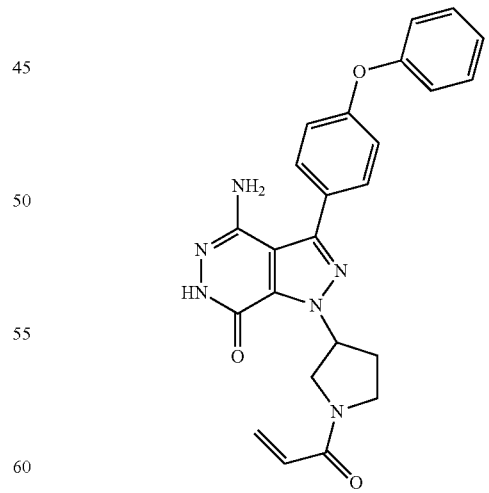

The solution of compound 45-7 (189.7 mg, 0.45 mmol), acrylic acid (35.6 mg, 0.495 mmol), N,N-DIPEA (232.2 mg, 1.18 mmol) and HATU (191 mg, 0.495 mmol) in DCM (10 mL) was stirred at r.t. for 12 h, after which water (20 mL) was added. Then the reaction solution was extracted with DCM (20 mL×2). The organic phases were combined, dried, filtered and concentrated to give a crude product which was purified by preparative chromatography to afford compound 45-8 (18 mg, 10%) as white solid.

LCMS (ESI) m/z: 443 (M+1).

$^1$H NMR (400 MHz, CDCl$_3$): δ ppm 10.47-10.27 (m, 1H), 7.71-7.54 (m, 2H), 7.50-7.35 (m, 2H), 7.25-7.18 (m, 1H), 7.18-7.06 (m, 3H), 6.63-6.39 (m, 2H), 6.35-6.23 (m, 1H), 5.78-5.65 (m, 1H), 5.08-4.76 (m, 2H), 4.28-3.96 (m, 3H), 3.87-3.72 (m, 1H), 2.77-2.42 (m, 2H).

Example 44

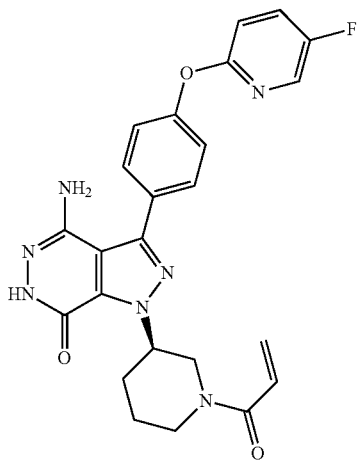 [SMILES: C=CC(=O)N1CCC[C@@H](n2nc(-c3ccc(Oc4ccc(F)cn4)cc3)c3c(N)n[nH]c(=O)c32)C1]

In Example 44, the systhesis process was similar to that in Example 32.

LCMS (ESI) m/z: 476 (M+1).

$^1$H NMR (400 MHz, CDCl$_3$): δ ppm 10.67-10.28 (m, 1H), 8.07 (d, J=3.1 Hz, 1H), 7.72 (d, J=8.4 Hz, 2H), 7.57-7.40 (m, 1H), 7.29 (s, 2H), 7.02 (dd, J=3.4, 8.9 Hz, 1H), 6.72-6.53 (m, 1H), 6.37-6.17 (m, 1H), 5.76-5.60 (m, 1H), 5.58-5.40 (m, 1H), 5.05 (br. s., 2H), 4.86-4.59 (m, 1H), 4.32-3.92 (m, 1H), 3.67-3.40 (m, 1H), 3.33-2.87 (m, 1H), 2.49-2.18 (m, 2H), 2.01 (d, J=13.7 Hz, 1H), 1.77 (br. s., 1H)

Example 45

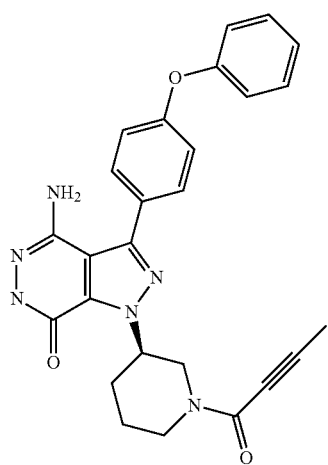 [SMILES: CC#CC(=O)N1CCC[C@@H](n2nc(-c3ccc(Oc4ccccc4)cc3)c3c(N)n[nH]c(=O)c32)C1]

In Example 45, the systhesis process was similar to that in Example 28.

$^1$H NMR (400 MHz, CDCl$_3$): δ ppm 9.29 (br. s., 1H), 7.62 (t, J=8.4 Hz, 2H), 7.42-7.35 (m, 2H), 7.20-7.05 (m, 5H), 5.61-5.41 (m, 1H), 4.79-4.48 (m, 2H), 4.46-4.26 (m, 3H), 3.88 (dd, J=9.5, 13.0 Hz, 1H), 3.58-3.41 (m, 1H), 3.29-2.94 (m, 2H), 2.38-2.16 (m, 2H), 2.02 (s, 2H), 1.90 (s, 1H).

LCMS (ESI) m/z: 469 (M+1).

Scheme 37

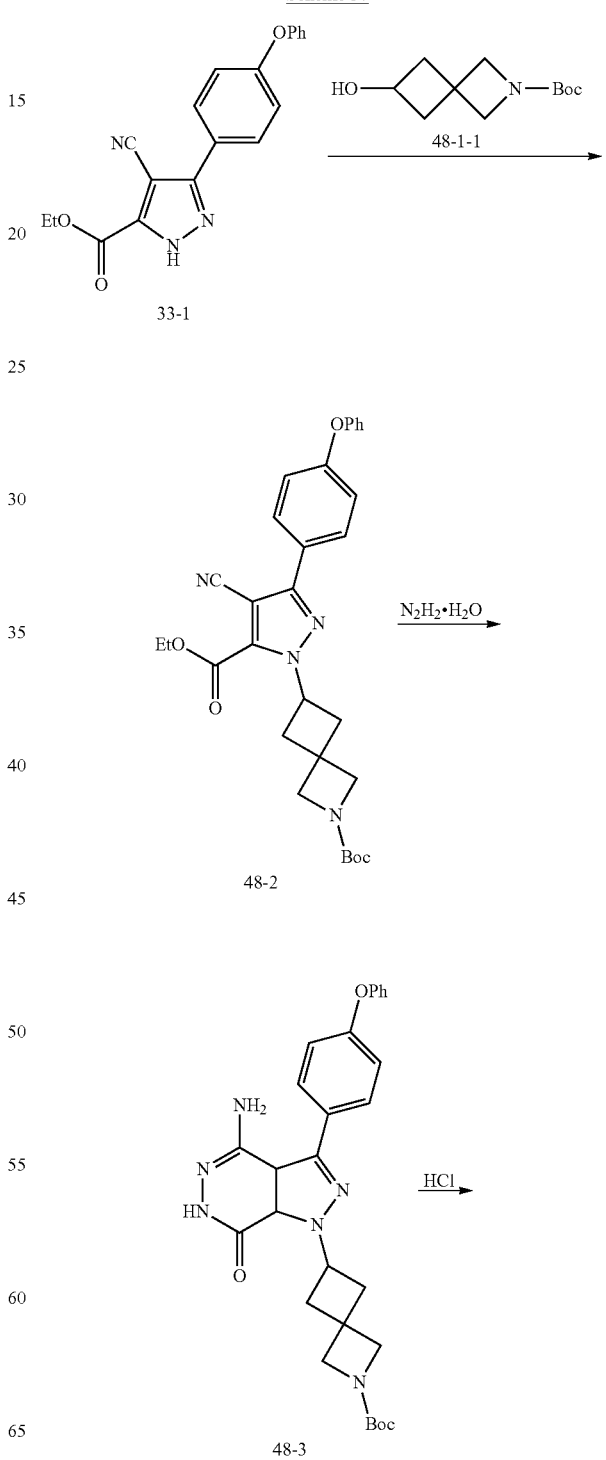

253

-continued

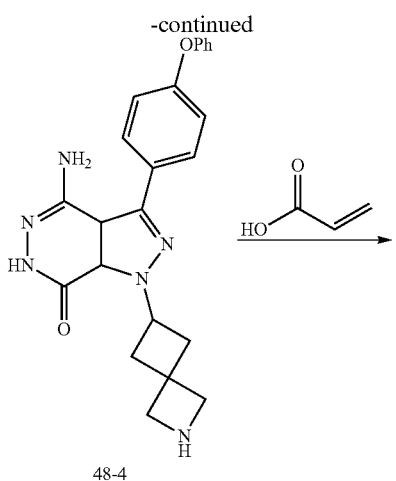

48-4

Example 46

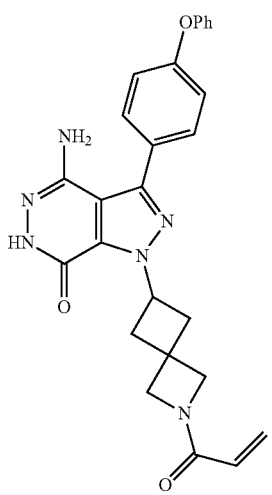 [SMILES: C=CC(=O)N1CC2(CC(n3nc(-c4ccc(Oc5ccccc5)cc4)c4c(N)n[nH]c(=O)c43)C2)C1]

254

Compound 48-2

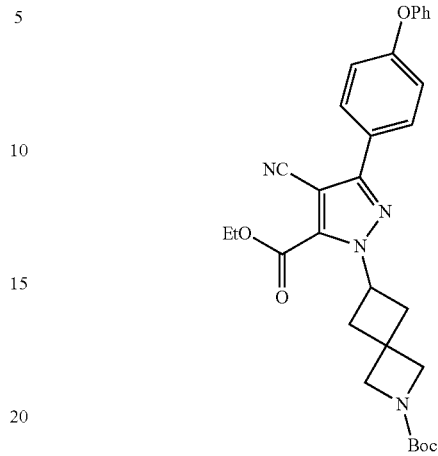

To a solution of compound 33-1 (150 mg, 0.45 mmol) in THF (3 mL) was added PPh$_3$ (142 mg, 0.54 mmol) and diisopropylazodicarboxylate (70 mg, 0.54 mmol) under nitrogen atmosphere at 0° C. and the reaction solution was stirred 5 min, after which compound 48-1-1 (95 mg, 0.45 mmol) was added slowly and the resulting reaction solution was stirred at 15° C. for 14 h, followed by filtration. Water (5 mL) was added into the filtrate, and the aqueous phase was extracted with EtOAc. The organic phases were combined, dried over anhydrous Na$_2$SO$_4$ and evaporated to give a crude product which was purified by TLC (PE/EtOAc=3/1) to afford the title compound 48-2 (yellow oil, 180 mg, Yield 76%).

LCMS (ESI) m/z: 529 (M+1).

Compound 48-3

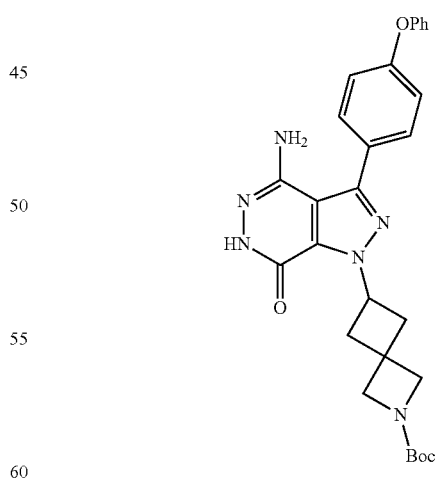

Compound 48-2 (180 mg, 0.34 mmol) was added into N$_2$H$_4$.H$_2$O (85%, 2 mL), and the reaction mixture was heated to 100° C. and stirred for 6 h. The mixture was evaporated and water (5 mL) was added into the residue. The resulting residue was extracted with EtOAc (5 mL×2). The organic phase was dried over anhydrous Na$_2$SO$_4$, filtered and concentrated to give the title compound 48-3 (yellow oil, 120 mg, Yield 69%) which can be used for the next step without further purification.

LCMS (ESI) m/z: 515 (M+1)

Compound 48-4

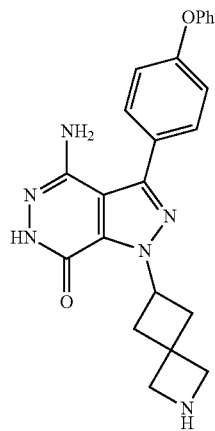 [SMILES: Nc1n[nH]c(=O)c2c1c(-c1ccc(Oc3ccccc3)cc1)nn2C1CC2(CNC2)C1]

To a solution of 10% HCl (8 mL) was added compound 48-3 (80 mg, 0.16 mmol), and the reaction solution was stirred at 25° C. for 8 h. After TLC indicated the reaction was complete, the mixture was evaporated and water (10 mL) was added into the residue. The resulting residue was extracted with EtOAc (10 mL×2). The organic phase was dried over anhydrous $Na_2SO_4$, filtered and evaporated to give the title compound (white solid, 45 mg, 70%) which can be used for the next step without further purification.

LCMS (ESI) m/z: 415 (M+1)

Compound 48-5

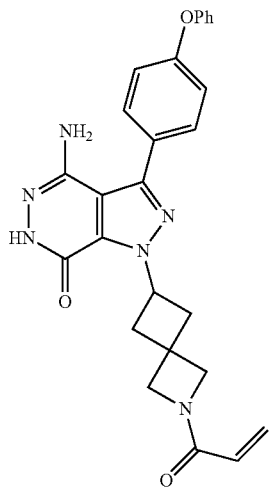 [SMILES: C=CC(=O)N1CC2(CC(n3nc(-c4ccc(Oc5ccccc5)cc4)c4c(N)n[nH]c(=O)c43)C2)C1]

To a mixture of HATU (28.9 mg, 0.12 mmol) and DIPEA (31 mg, 0.24 mmol) in DCM (5 mL) was added acrylic acid (8.6 mg, 0.12 mmol) under nitrogen atmosphere at 0° C., and the reaction mixture was stirred at 0° C. for 10 min, after which compound 48-4 (50 mg, 0.12 mmol) was added, and the resulting reaction mixture was stirred at 25° C. for 12 h. To the mixture, water (20 mL) was added, and the resulting mixture was extracted with DCM (5 mL×3). The organic phases were combined, dried over anhydrous $Na_2SO_4$, filtered and evaporated. The residue was purified by column chromatography to give a crude product which was purified by preparative HPLC to afford the title compound 48-5 (yellow solid, 15 mg, Yield 27%).

$^1$H NMR (400 MHz, $d_6$-DMSO): δ ppm 9.62 (br. s., 1H), 7.56 (d, J=8.6 Hz, 2H), 7.37-7.30 (m, 2H), 7.05 (dd, J=8.2, 17.5 Hz, 5H), 6.30-6.23 (m, 1H), 6.17-6.06 (m, 1H), 6.00-5.92 (m, 1H), 5.61 (t, J=8.8 Hz, 1H), 4.49 (d, J=13.9 Hz, 2H), 4.31-4.06 (m, 4H), 2.95 (t, J=8.9 Hz, 2H), 2.82-2.72 (m, 2H).

LCMS (ESI) m/z: 469 (M+1).

Scheme 38

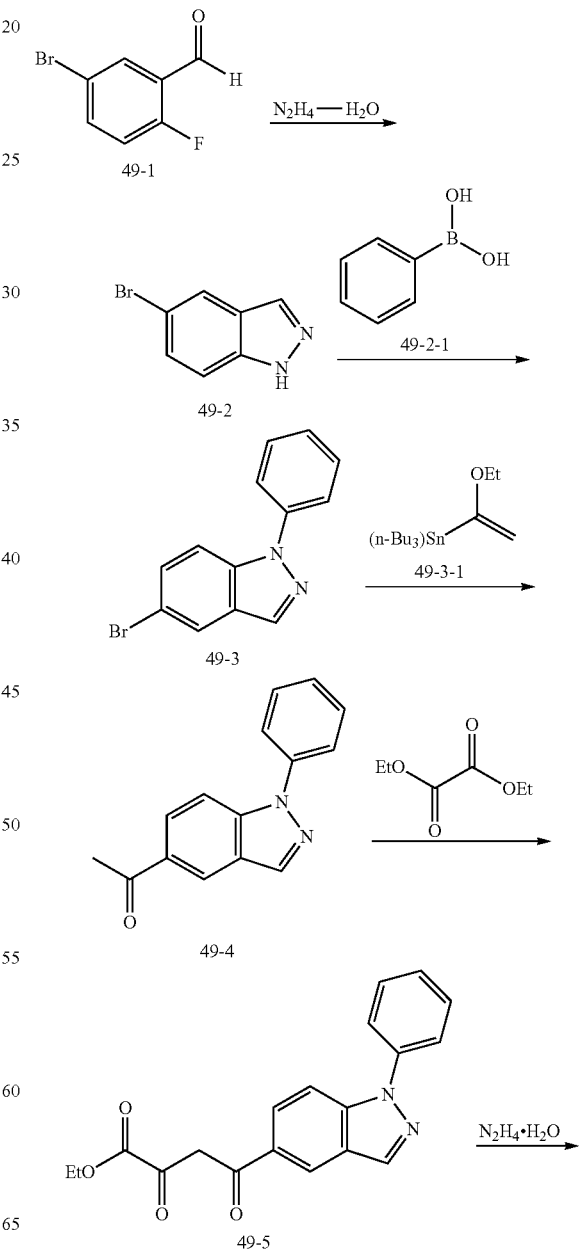

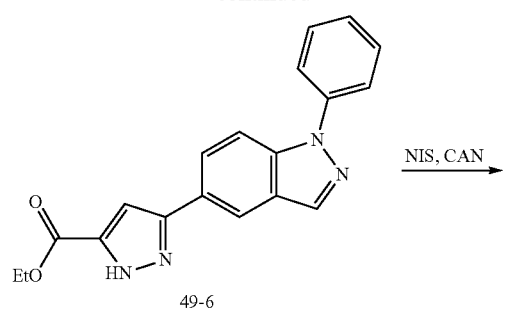
49-6
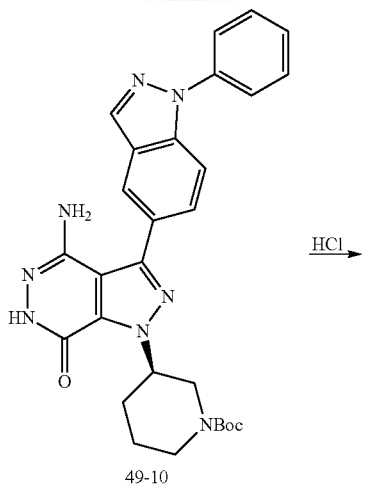
49-10
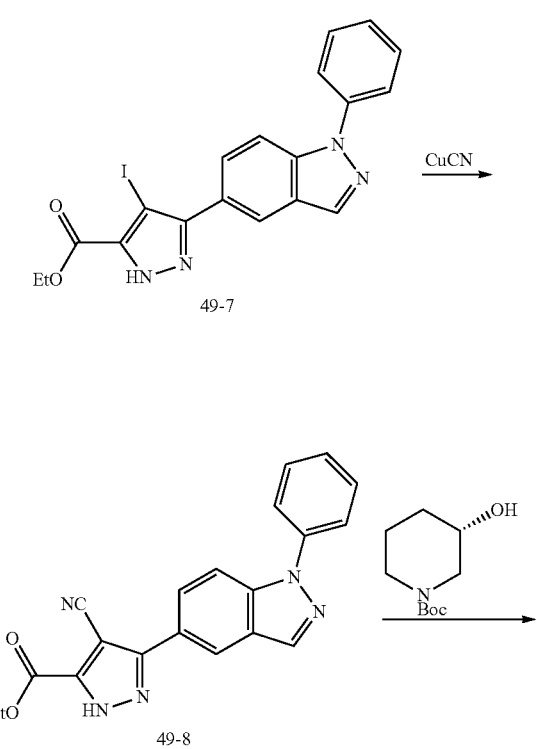
49-7
49-8
49-9
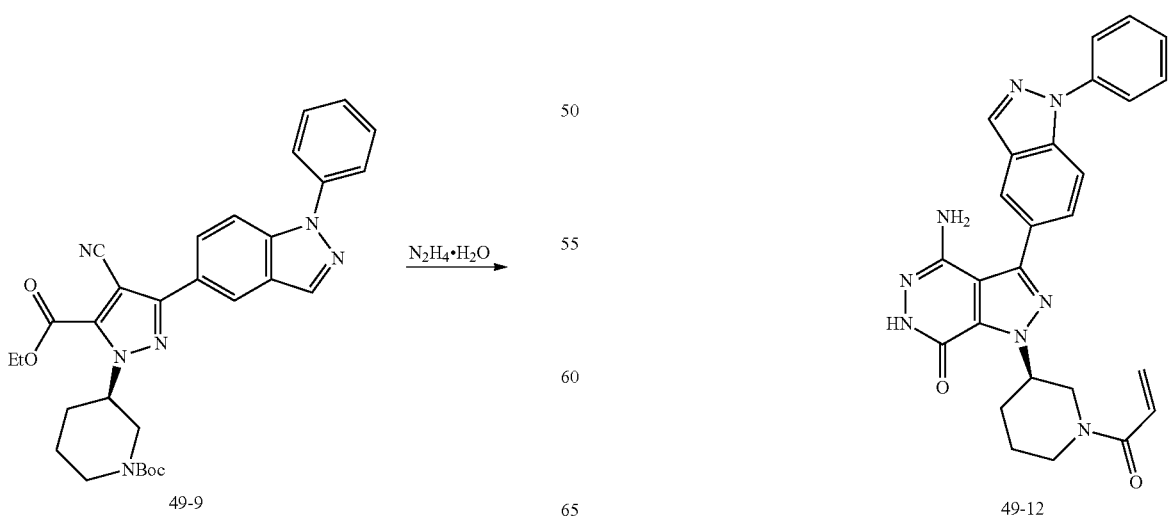
49-11
49-12

Example 47

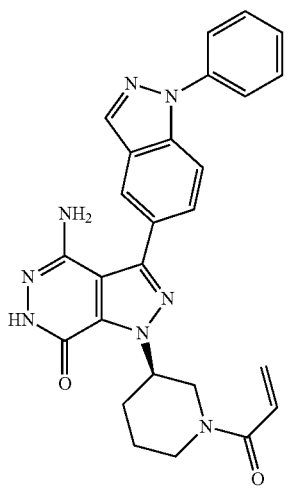 [SMILES: C=CC(=O)N1CCC[C@@H](n2nc(-c3ccc4c(cnn4-c4ccccc4)c3)c3c(N)n[nH]c(=O)c32)C1]

Compound 49-2

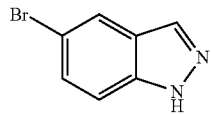

To N$_2$H$_4$·H$_2$O (85%, 30 mL) was added compound 49-1 (600 mg, 3 mmol), and the reaction solution was heated to 100° C. and stirred for 12 h. To the solution, water (50 mL) and DCM (20 mL) were added and the resulting solution was extracted with DCM (20 mL×2). The organic phase was dried over anhydrous Na$_2$SO$_4$, filtered and evaporated to give title compound 49-2 (white solid, 400 mg, Yield 96%).

LCMS (ESI) m/z: 199 (M+2)

Compound 49-3

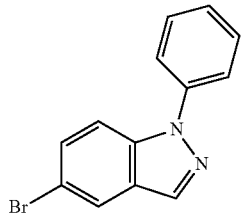 [SMILES: Brc1ccc2c(cnn2-c2ccccc2)c1]

To a solution of compound 49-2 (400 mg, 2 mmol), compound 49-2-1 (448 mg, 4 mmol) and Cu(Ac)$_2$ (724 mg, 4 mmol) in DCM (20 mL) was added pyridine (640 mg, 8 mmol) under oxygen atmosphere, and the reaction solution was stirred at 15° C. for 12 h. After LCMS indicated the reaction was complete, water (50 mL) was added into the solution, and the resulting solution was extracted with DCM (50 mL×3). The organic phase was dried over anhydrous Na$_2$SO$_4$, filtered and evaporated to give a crude product which was purified by preparative HPLC to give the title compound 49-3 (white solid, 100 mg, Yield 96%).

$^1$H NMR (400 MHz, d$_6$-DMSO): δ ppm 8.14 (s, 1H), 7.95 (d, J=1.32 Hz, 1H), 7.69 (d, J=7.94 Hz, 2H), 7.63 (d, J=9.04 Hz, 1H), 7.59-7.47 (m, 3H), 7.43-7.35 (m, 1H).

LCMS (ESI) m/z: 273 (M+1).

Compound 49-4

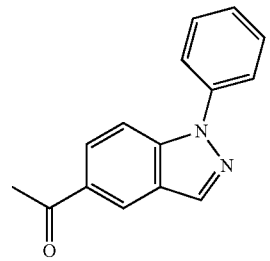 [SMILES: CC(=O)c1ccc2c(cnn2-c2ccccc2)c1]

To a solution of compound 49-3 (3 g, 11 mmol) in dioxane (40 mL) was added compound 49-3-1 (5.6 g, 15.4 mmol) and Ph(PPh$_3$)$_2$Cl$_2$ (400 mg, 0.55 mmol), and the reaction mixture was stirred at 120° C. for 12 h. To this mixture, 10% HCl solution (50 mL) was added. The resulting solution was stirred at 20° C. for 1 h, followed by extraction with EtOAc (50 mL×2). The organic phase was washed with water (50 mL×3), dried over anhydrous Na$_2$SO$_4$, filtered and evaporated to give a crude product which was purified by column chromatography to afford the title compound 49-4 (white solid, 1.8 g, Yield 70%).

LCMS (ESI) m/z: 237 (M+1).

Compound 49-5

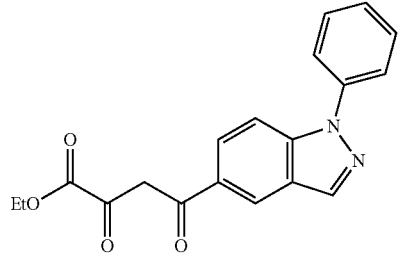 [SMILES: CCOC(=O)C(=O)CC(=O)c1ccc2c(cnn2-c2ccccc2)c1]

To a solution of compound 49-4 (1.8 g, 7.6 mmol) in toluene (30 mL) was added NaH (0.37 g, 9.15 mmol) and the reaction solution was stirred at 20° C. for 10 min, after which diethyl oxalate (2.2 g, 15.2 mmol) was added and the mixture was stirred at 80° C. for 15 min. The reaction solution was extracted with EtOAc (50 mL×2) and then washed with water (50 mL×3). The organic phase was dried over anhydrous Na$_2$SO$_4$, filtered and evaporated to give a crude product which was purified by column chromatography to give the title compound 49-5 (yellow solid, 2.2 g, Yield 86%).

$^1$H NMR (400 MHz, d$_6$-DMSO): δ ppm 8.56 (s, 1H), 8.36 (s, 1H), 8.09 (dd, J=1.00, 9.03 Hz, 1H), 7.81 (d, J=9.03 Hz, 1H), 7.73 (d, J=8.03 Hz, 2H), 7.59 (t, J=7.78 Hz, 2H), 7.49-7.39 (m, 1H), 7.19 (s, 1H), 4.43 (q, J=7.19 Hz, 2H), 1.44 (t, J=7.28 Hz, 3H).

LCMS (ESI) m/z: 337 (M+1).

Compound 49-6

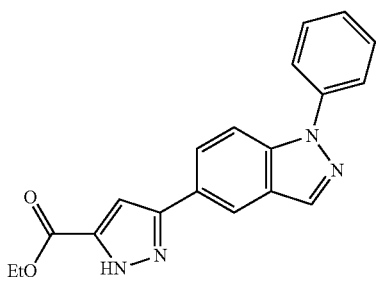 [SMILES: CCOC(=O)c1cc(-c2ccc3c(cnn3-c3ccccc3)c2)n[nH]1]

To a solution of compound 49-5 (2 g, 5.96 mmol) in EtOH was added HOAc (10 mL) and the mixture was stirred at 20° C. for 0.5 h, after which $N_2H_4 \cdot H_2O$ (85%, 3 g, 29.8 mmol) was added and the resulting mixture was stirred at 20° C. for 1 h. After TLC indicated the reaction was complete, saturated $NaHCO_3$ solution (100 mL) was added to this mixture, and the solution was extracted with EtOAc (50 mL×2). The organic phase was dried over anhydrous $Na_2SO_4$, filtered and evaporated to give the title compound 49-6 (yellow solid, 1.9 g, Yield 96%).

$^1$H NMR (400 MHz, $d_6$-DMSO): δ ppm 8.24 (s, 1H), 8.19 (s, 1H), 7.92-7.85 (m, 1H), 7.83-7.77 (m, 1H), 7.74 (d, J=7.50 Hz, 2H), 7.56 (t, J=7.83 Hz, 2H), 7.43-7.35 (m, 1H), 7.17 (s, 1H), 4.43 (q, J=7.06 Hz, 2H), 1.43 (t, J=7.17 Hz, 3H).

LCMS (ESI) m/z: 333 (M+1).

Compound 49-7

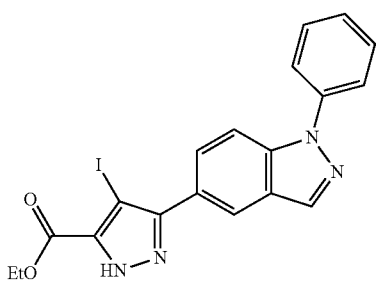 [SMILES: CCOC(=O)c1[nH]nc(-c2ccc3c(cnn3-c3ccccc3)c2)c1I]

To a solution of compound 49-6 (2.1 g, 6.25 mmol) in acetonitrile (50 mL) was added N-Iodosuccinimide (1.4 g, 6.25 mmol) and CAN (0.34 g, 0.63 mmol), and the reaction solution was stirred at 80° C. for 1 h. After LCMS indicated the reaction was complete, water (100 mL) was added to this mixture, and the solution was extracted with EtOAc (50 mL×2). The organic phase was dried over anhydrous $Na_2SO_4$, filtered and evaporated to give a crude product which was purified by column chromatography to afford the title compound 49-7 (yellow solid, 2.8 g, Yield 98%).

LCMS (ESI) m/z: 459 (M+1).

Compound 49-8

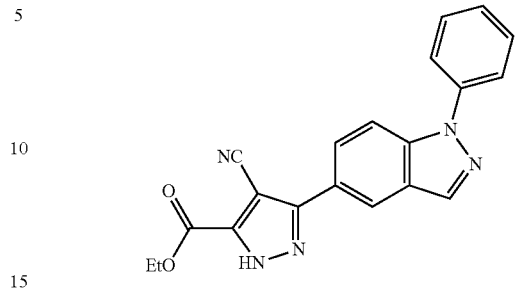

To a solution of compound 49-7 (2.8 g, 6.1 mmol) in DMF (30 mL) was added CuCN (1.1 g, 12.2 mmol) and Pd(dppf)Cl$_2$ (438 mg, 0.6 mmol) under nitrogen atmosphere, and the reaction solution was stirred at 120° C. for 12 h. After LCMS indicated the reaction was complete, the reaction solution was cooled down to r.t, and water (50 mL) was added. The resulting solution was extracted with EtOAc (10 mL×2), and the organic phase was dried over anhydrous $Na_2SO_4$, filtered and evaporated to give the title compound 49-8 (black oil, 600 mg, Yield 27.5%) as crude product.

LCMS (ESI) m/z: 358 (M+1).

Compound 49-9

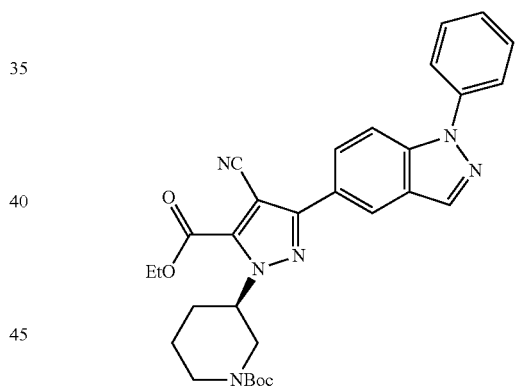

To THF solution (10 mL) was added PPh$_3$ (890 mg, 3.4 mmol) and diisopropylazodicarboxylate (445 mg, 3.4 mmol) under nitrogen atmosphere at 0° C. and the reaction solution was stirred for 30 min, after which a solution of compound 49-8 (600 mg, 1.7 mmol) in THF (5 mL) was added and the resulting reaction solution was stirred for 30 min. Then a solution of compound (S)-1-BOC-3-Hydroxypiperidine (512 mg, 2.55 mmol) in THF (5 mL) was added dropwise and the reaction solution was warmed to 25° C. and stirred for 12 h. After TLC indicated the reaction was complete, Saturated NH$_4$Cl solution (50 mL) was added into the solution, and the resulting solution was extracted with EtOAc (20 mL×3). The organic phase was dried over anhydrous $Na_2SO_4$, filtered and evaporated to give a crude product which was purified by column chromatography to afford the title compound 49-9 (white solid, 500 mg, Yield 56%).

LCMS (ESI) m/z: 485 (M+1-56).

Compound 49-10

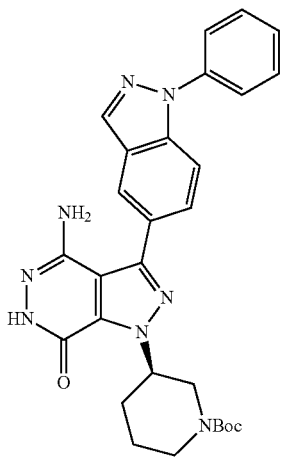 [SMILES: CC(C)(C)OC(=O)N1CCC[C@@H](n2nc(-c3ccc4c(cnn4-c4ccccc4)c3)c3c(N)n[nH]c(=O)c32)C1]

Compound 49-9 (500 mg, 0.9 mmol) was added into N₂H₄·H₂O (85%, 10 mL), and the reaction mixture was heated to 100° C. and stirred for 12 h. After LCMS indicated the reaction was complete, water (50 mL) and DCM (20 mL) were added to this mixture, and the resulting solution was extracted with DCM (20 mL×2). The organic phase was dried over anhydrous Na₂SO₄, filtered and evaporated to give the title compound 49-10 (white solid, 450 mg, Yield 88%).

LCMS (ESI) m/z: 527 (M+1)

Compound 49-11

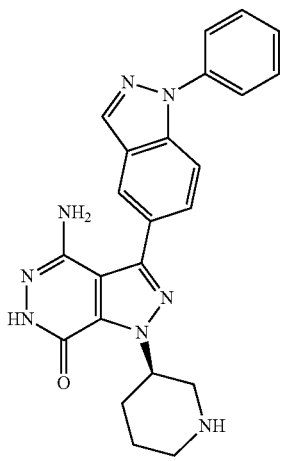 [SMILES: Nc1n[nH]c(=O)c2c1c(-c1ccc3c(cnn3-c3ccccc3)c1)nn2[C@@H]1CCCNC1]

Compound 49-10 (450 mg, 0.85 mmol) was added into 10% HCl solution (2 mL), and the reaction mixture was stirred at 25° C. for 8 h. After TLC indicated the reaction was complete, the mixture was evaporated and water (2 mL) was added into the residue. Then the residue was extracted with EtOAc (3 mL×2), and the organic phase was dried over anhydrous Na₂SO₄, filtered and evaporated to give the title compound 49-11 (white solid, 280 mg, Yield 77%).

LCMS (ESI) m/z: 427 (M+1).

Compound 49-12

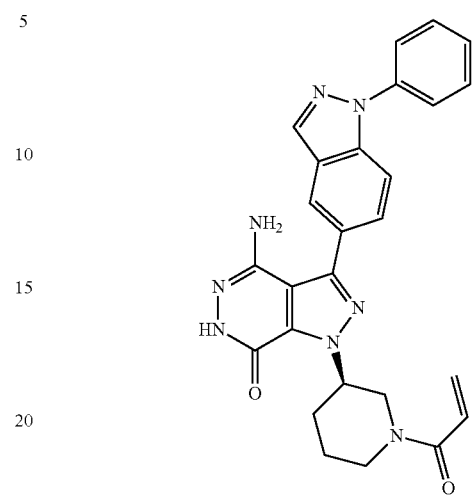

To a mixture of HATU (44.58 mg, 0.12 mmol) and DIPEA (30.3 mg, 0.24 mmol) in DCM (5 mL) was added acrylic acid (8.45 mg, 0.12 mmol) under nitrogen atmosphere and the reaction mixture was stirred at 20° C. for 10 min, after which compound 49-11 (50 mg, 0.12 mmol) was added, and the reaction mixture was stirred at 25° C. for 12 h. After LCMS indicated the reaction was complete, water (5 mL) was added and the mixture was extracted with DCM (10 mL×3). The organic phases were combined, dried over anhydrous Na₂SO₄, filtered and evaporated. The residue was purified by column chromatography to give a crude product which was purified by preparative HPLC to afford the title compound 49-12 (yellow solid, 32 mg, Yield 56.8%).

¹H NMR (400 MHz, MeOD): δ ppm 7.45 (d, J=8.6 Hz, 2H), 7.40-7.23 (m, 2H), 7.15 (t, J=7.5 Hz, 1H), 7.09 (dd, J=8.3, 12.0 Hz, 4H), 6.84-6.69 (m, 1H), 6.14 (t, J=16.3 Hz, 1H), 5.73-5.63 (d, J=10.8 Hz, 1H), 5.50 (dd, J=4.0, 9.2 Hz, 1H), 4.63-4.52 (m, 1H), 4.34-4.23 (m, 1H), 4.09-3.98 (m, 1H), 3.77-3.66 (m, 1H), 2.99 (d, J=17.6 Hz, 1H), 2.80 (s, 1H), 2.40 (d, J=10.0 Hz, 1H), 2.27 (d, J=4.9 Hz, 2H), 2.12-2.03 (m, 1H), 1.69 (br. s., 1H).

LCMS (ESI) m/z: 481 (M+1).

Scheme 39

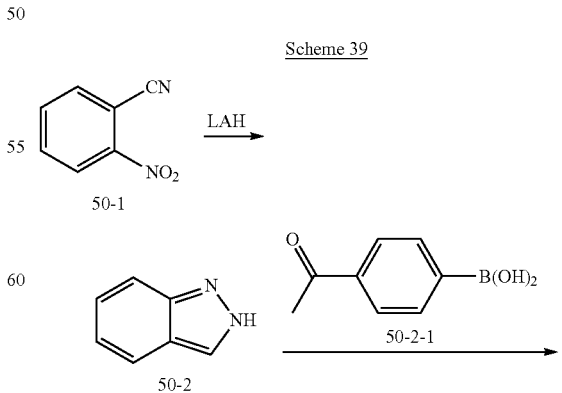

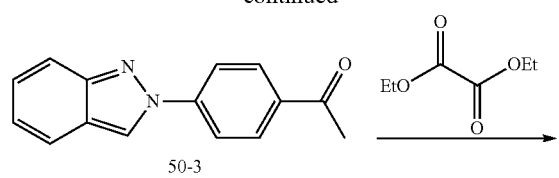
50-3
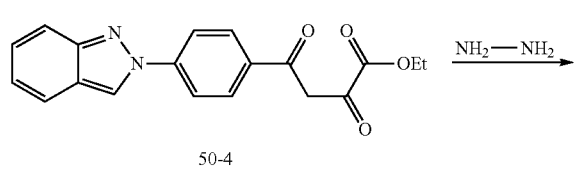
50-4
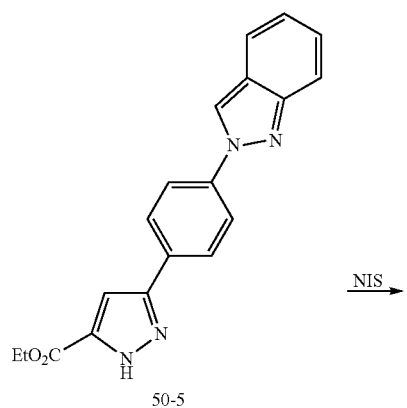
50-5
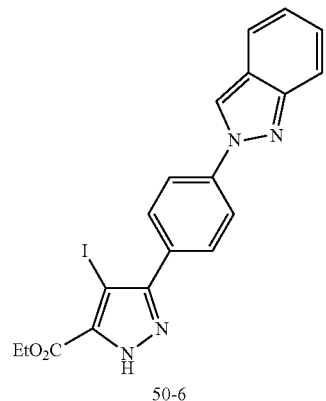
50-6
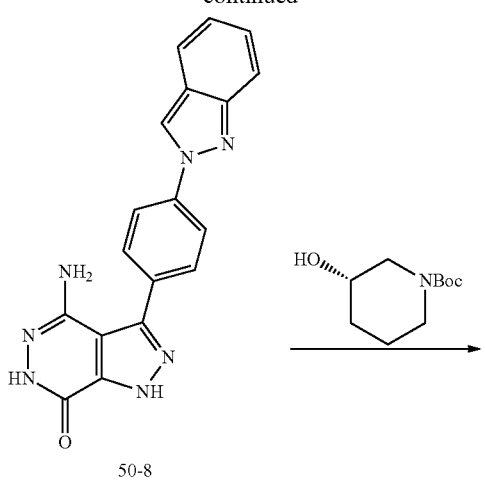
50-8
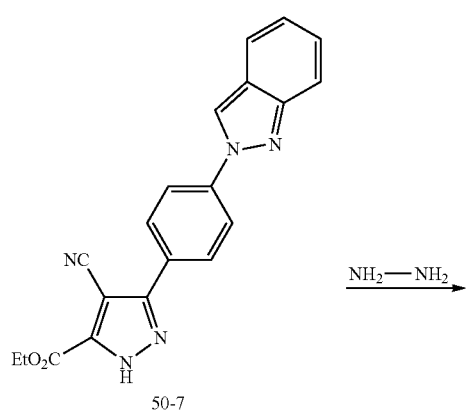
50-9
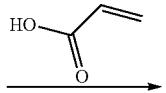
50-10

-continued

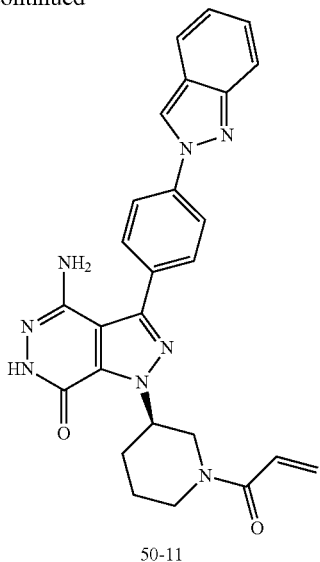

50-11

Example 48

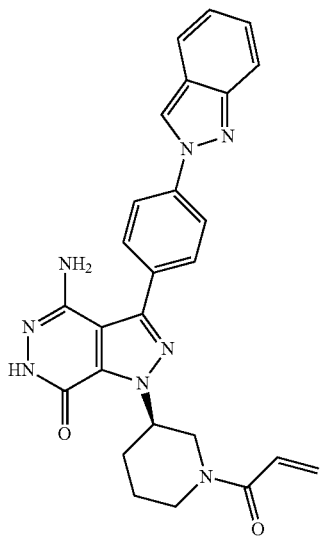 [SMILES: C=CC(=O)N1CCC[C@@H](n2nc(-c3ccc(-n4cc5ccccc5n4)cc3)c3c(N)n[nH]c(=O)c32)C1]

Compound 50-2

To a solution of compound 50-1 (2 g, 13.6 mmol) in THF (25 mL) was added slowly LAH powder (500 mg, 13.6 mmol) in portions at 0° C., and the reaction solution was stirred at 80° C. for 12 h. After LCMS indicated the reaction was complete, NaOH solution (25 mL, 1N) was added to this solution, and the resulting solution was stirred for 2 h followed by filtration. The filtrate was extracted with EtOAc (25 mL×5), and the organic phase was dried over anhydrous $Na_2SO_4$, filtered and evaporated to give a residue which was purified by column chromatography to afford the title compound 50-2 (yellow solid, 0.75 g, Yield 56.8%).

LCMS (ESI) m/z: 119 (M+1).

Compound 50-3

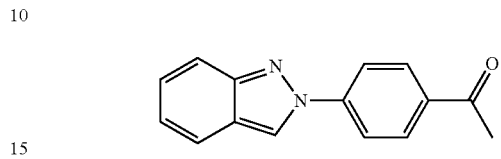

To a solution of compound 50-2 (750 mg, 6.4 mmol) and compound 50-2-1 (1050 mg, 6.4 mmol) in THF (20 mL) was added $Cu(Ac)_2$ (2300 mg, 12.8 mmol) and pyridine (5 mL) under oxygen atmosphere, and the reaction mixture was stirred at 80° C. for 12 h. After TLC indicated the reaction was complete, water (40 mL) was added into the mixture, and the resulting solution was extracted with EtOAc (25 mL×3). The organic phase was dried over anhydrous $Na_2SO_4$, filtered and evaporated to give a crude product which was purified by column chromatography to afford the title compound 50-3 (brown oil, 400 mg, Yield 37.5%).

$^1$H NMR (400 MHz, $d_6$-DMSO$_6$): δ ppm 8.14 (s, 1H), 7.95 (d, J=1.32 Hz, 1H), 7.69 (d, J=7.94 Hz, 2H), 7.63 (d, J=9.04 Hz, 1H), 7.59-7.47 (m, 3H), 7.43-7.35 (m, 1H).

LCMS (ESI) m/z: 237 (M+1).

Compound 50-4

To a solution of compound 50-3 (400 mg, 1.7 mmol) in THF (20 mL) was added NaH (80 mg, 3.4 mmol) and the reaction solution was stirred at 20° C. for 10 min, after which diethyl oxalate (250 mg, 1.7 mmol) was added and the reaction solution was stirred at 70° C. for 2 h. After TLC indicated the reaction was complete, water (50 mL) was added into the solution, and the resulting solution was extracted with EtOAc (50 mL×4). The organic phase was dried over anhydrous $Na_2SO_4$, filtered and evaporated to give a crude product which was purified by column chromatography to afford the title compound 50-4 (yellow solid, 280 mg, Yield 49%).

$^1$H NMR (400 MHz, $d_6$-DMSO): δ ppm 8.36 (s, 1H), 8.24 (s, 1H), 8.09 (dd, J=1.00, 9.03 Hz, 1H), 7.81 (d, J=9.03 Hz, 1H), 7.73 (d, J=8.03 Hz, 2H), 7.59 (t, J=7.78 Hz, 2H), 7.49-7.39 (m, 1H), 7.19 (s, 1H), 4.43 (q, J=7.19 Hz, 2H), 1.44 (t, J=7.28 Hz, 3H).

LCMS (ESI) m/z: 337 (M+1).

Compound 50-5

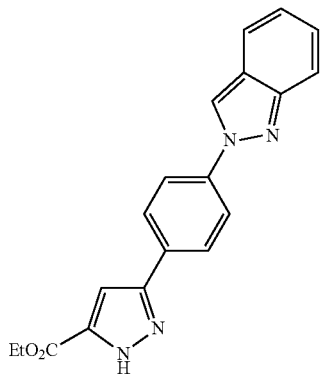 [SMILES: CCOC(=O)c1cc(-c2ccc(-n3cc4ccccc4n3)cc2)n[nH]1]

Compound 50-4 (25 mg, 0.07 mmol) was added into N₂H₄.H₂O (85%, 11 mg, 0.35 mmol), and the reaction mixture was stirred at 90° C. for 5 h. After TLC indicated the reaction was complete, water (5 mL) was added to this mixture, and the resulting mixture was extracted with EtOAc (5 mL×3). The organic phase was dried over anhydrous Na₂SO₄, filtered and evaporated to give the title compound 50-5 (yellow solid, 10 mg, Yield 40%).

¹H NMR (400 MHz, d₆-DMSO): δ ppm 8.11 (s, 1H), 7.95 (s, 1H), 7.91-7.84 (m, 1H), 7.83-7.77 (m, 1H), 7.74 (d, J=7.50 Hz, 2H), 7.56 (t, J=7.83 Hz, 2H), 7.43-7.35 (m, 1H), 7.17 (s, 1H), 4.43 (q, J=7.06 Hz, 2H), 1.43 (t, J=7.17 Hz, 3H).

LCMS (ESI) m/z: 333 (M+1).

Compound 50-6

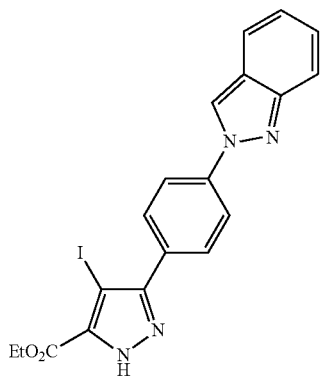 [SMILES: CCOC(=O)c1[nH]nc(-c2ccc(-n3cc4ccccc4n3)cc2)c1I]

To a solution of compound 50-5 (100 mg, 0.3 mmol) in acetonitrile (20 mL) was added N-Iodosuccinimide (68 mg, 1.4 mmol) and CAN (17 mg, 0.3 mmol), and the reaction solution was stirred at 90° C. for 12 h. After TLC indicated the reaction was complete, water (10 mL) was added into the solution, and the resulting solution was extracted with EtOAc (10 mL×2). The organic phase was dried over anhydrous Na₂SO₄, filtered and evaporated to give a crude product which was purified by column chromatography to afford the title compound 50-6 (yellow solid, 60 mg, Yield 43.5%).

LCMS (ESI) m/z: 459 (M+1).

Compound 50-7

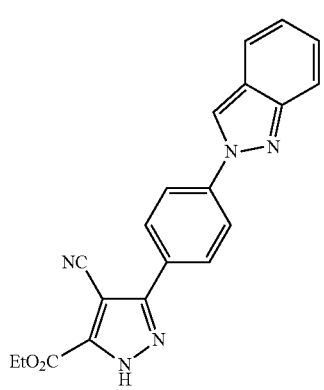 [SMILES: CCOC(=O)c1[nH]nc(-c2ccc(-n3cc4ccccc4n3)cc2)c1C#N]

To a solution of compound 50-6 (300 mg, 0.7 mmol) in DMF (20 mL) was added CuCN (180 mg, 2.1 mmol) and Pd(dppf)Cl₂ (40 mg, 0.07 mmol) under nitrogen atmosphere, and the reaction solution was stirred at 90° C. for 2 h. After TLC indicated the reaction was complete, the reaction solution was cooled down to r.t., and water (50 mL) was added. The resulting solution was extracted with EtOAc (5 mL×3). The organic phase was dried over anhydrous Na₂SO₄, filtered and evaporated to give a crude product which was purified by column chromatography to afford the title compound 50-7 (yellow solid, 60 mg, Yield 37.5%).

LCMS (ESI) m/z: 358 (M+1).

Compound 50-8

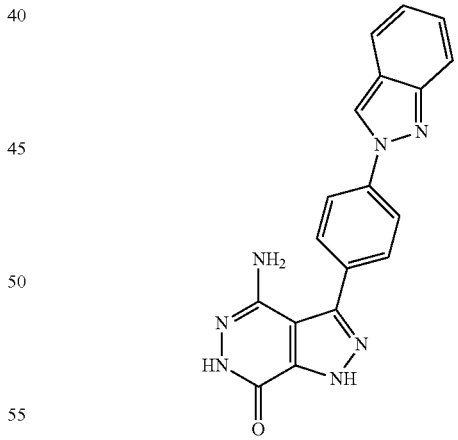

Compound 50-7 (105 mg, 0.29 mmol) was added into N₂H₄.H₂O (85%, 2 mL), and the reaction mixture was heated to 100° C. and stirred for 6 h. After LCMS indicated the reaction was complete, water (5 mL) was added to this mixture, and the resulting solution was extracted with EtOAc (5 mL×2). The organic phase was dried over anhydrous Na₂SO₄, filtered and evaporated to give the title compound 50-8 (yellow oil, 90 mg, Yield 69%).

LCMS (ESI) m/z: 344 (M+1).

Compound 50-9

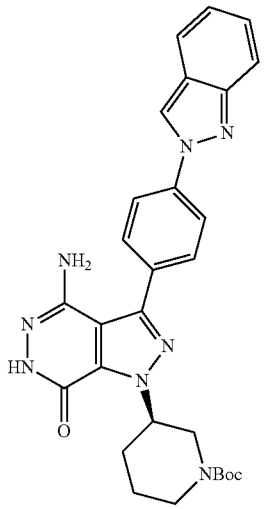 [SMILES: CC(C)(C)OC(=O)N1CCC[C@@H](n2nc(-c3ccc(-n4cc5ccccc5n4)cc3)c3c(N)n[nH]c(=O)c32)C1]

To a solution of compound 50-8 (950 mg, 1.65 mmol) in THF (15 mL) was added PPh$_3$ (519 mg, 1.98 mmol) and diisopropylazodicarboxylate (259 mg, 1.98 mmol) under nitrogen atmosphere at 0° C. and the reaction solution was stirred for 5 min, after which a solution of compound (S)-1-BOC-3-Hydroxypiperidine (398 mg, 1.98 mmol) in THF (5 mL) was added dropwise. Then the resulting solution was warmed to 25° C. and stirred for 14 h. After TLC indicated the reaction was complete, water (15 mL) was added to this mixture, and the resulting solution was extracted with DCM (20 mL×3). The organic phase was dried over anhydrous Na$_2$SO$_4$, filtered and evaporated to give a crude product which was purified by column chromatography to afford the title compound 50-9 (brown oil, 50 mg, Yield 34.5%).

LCMS (ESI) m/z: 527 (M+1).

Compound 50-10

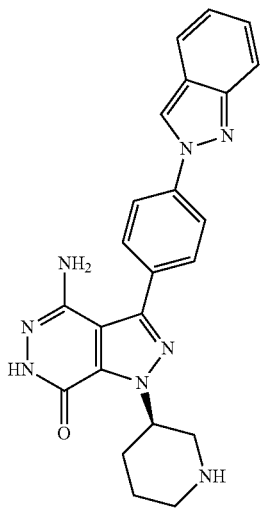 [SMILES: Nc1n[nH]c(=O)c2c1c(-c1ccc(-n3cc4ccccc4n3)cc1)nn2[C@@H]1CCCNC1]

Compound 50-9 (50 mg, 0.095 mmol) was added into 10% HCl solution (2 mL), and the reaction mixture was stirred at 25° C. for 8 h. After TLC indicated the reaction was complete, the mixture was evaporated and water (2 mL) was added into the residue. Then the residue was extracted with EtOAc (5 mL×2), and the organic phase was dried over anhydrous Na$_2$SO$_4$, filtered and evaporated to give the title compound 50-10 (white solid, 40 mg, Yield 98%).

LCMS (ESI) m/z: 427 (M+1).

Compound 50-11

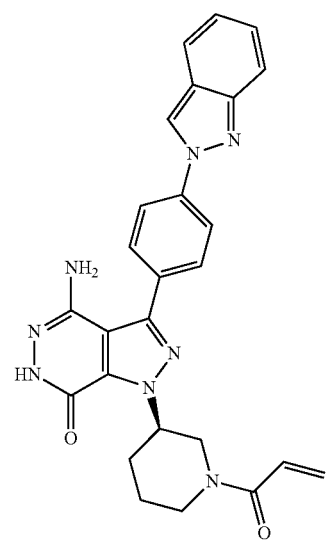 [SMILES: C=CC(=O)N1CCC[C@@H](n2nc(-c3ccc(-n4cc5ccccc5n4)cc3)c3c(N)n[nH]c(=O)c32)C1]

To a mixture of HATU (94.51 mg, 248.55 µmol) and DIPEA (64.25 mg, 497.10 µmol) in DCM (10 mL) was added acrylic acid (17.91 mg, 248.55 µmol) under nitrogen atmosphere, and the reaction mixture was stirred at 20° C. for 10 min, after which compound 50-10 (106.00 mg, 248.55 µmol) was added, and the resulting reaction mixture was stirred at 25° C. for 12 h. After LCMS indicated the reaction was complete, water (5 mL) was added to the mixture, and the resulting mixture was extracted with DCM (10 mL×3). The organic phases were combined, dried over anhydrous Na$_2$SO$_4$, filtered and evaporated. The residue was purified by column chromatography to give a crude product which was purified by preparative HPLC to afford the title compound 50-11 (white solid, 27 mg, Yield 21.9%).

$^1$H NMR (400 MHz, MeOD): δ ppm 7.66 (d, J=8.6 Hz, 2H), 7.43-7.36 (m, 2H), 7.16 (t, J=7.5 Hz, 1H), 7.09 (dd, J=8.3, 12.0 Hz, 4H), 6.84-6.69 (m, 1H), 6.14 (t, J=16.3 Hz, 1H), 5.73 (d, J=10.5 Hz, 1H), 5.63 (d, J=10.8 Hz, 1H), 5.50 (dd, J=4.0, 9.2 Hz, 1H), 4.63-4.52 (m, 1H), 4.34-4.23 (m, 1H), 4.09-3.98 (m, 1H), 3.77-3.66 (m, 1H), 2.99 (d, J=17.6 Hz, 1H), 2.80 (s, 1H), 2.40 (d, J=10.0 Hz, 1H), 2.27 (d, J=4.9 Hz, 1H), 2.12-2.03 (m, 1H), 1.69 (br. s., 1H).

LCMS (ESI) m/z: 481 (M+1).

Scheme 40
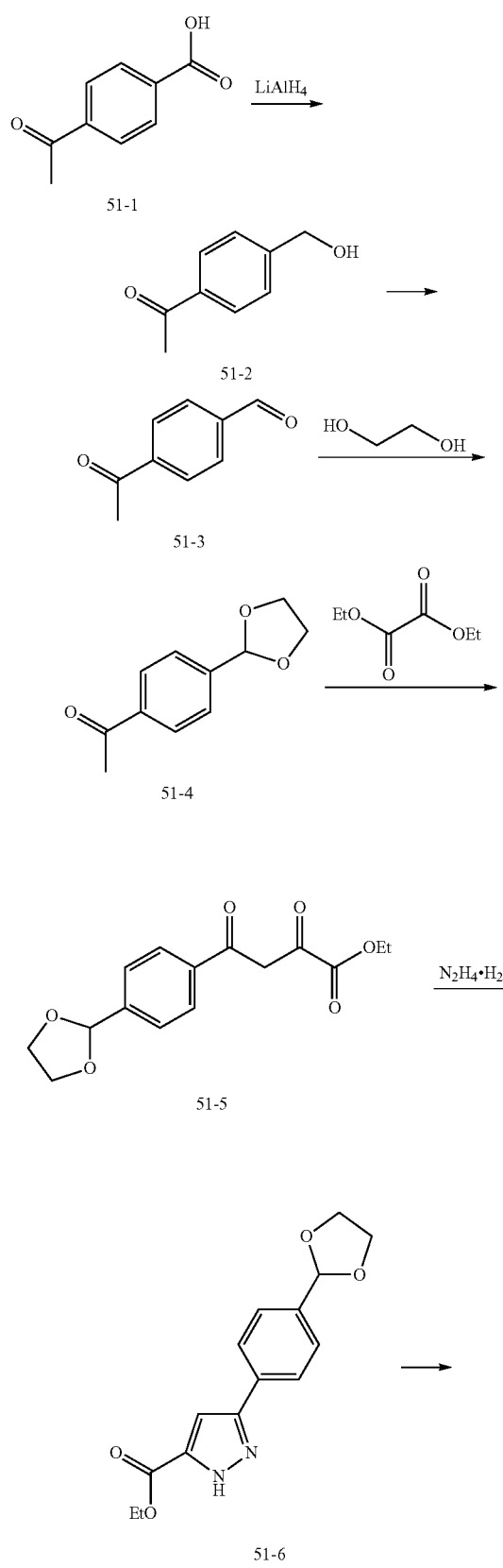
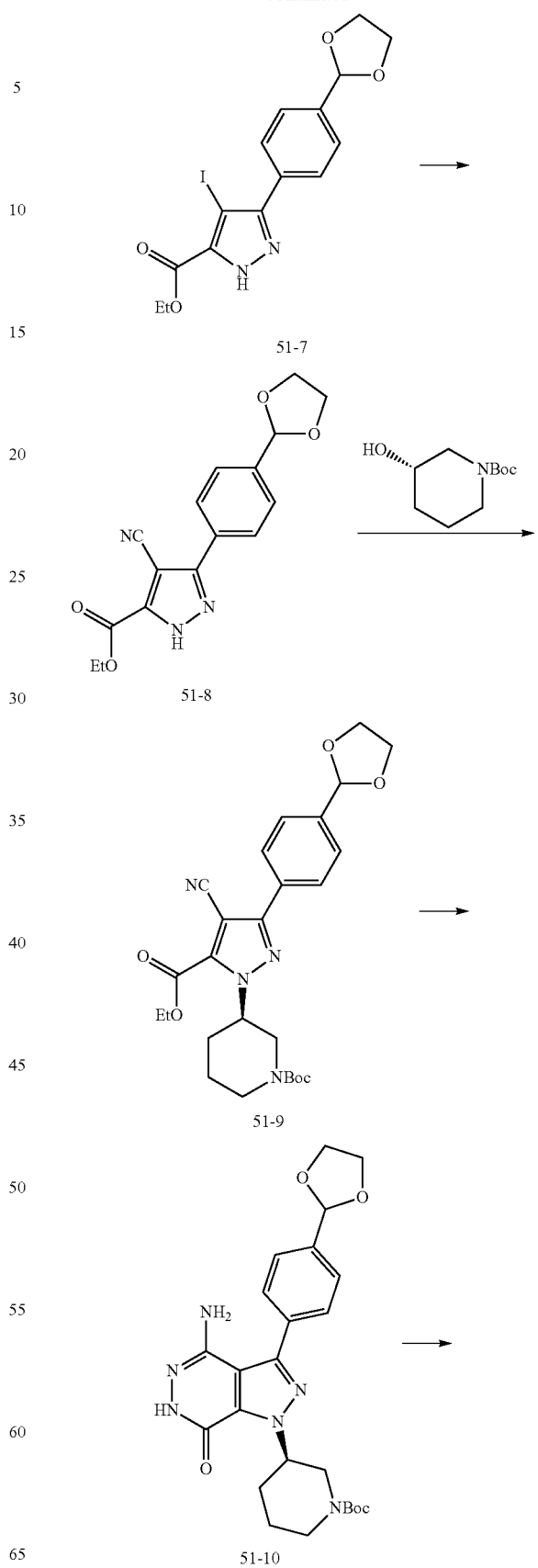

-continued

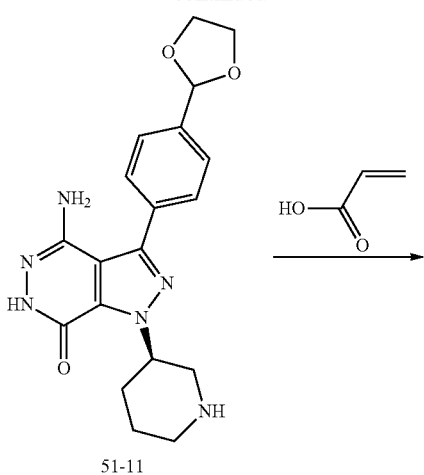

51-11

Example 49

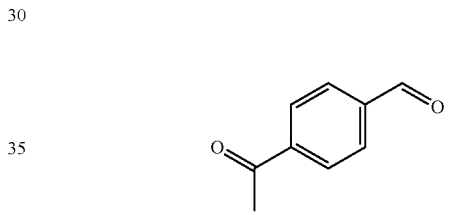

51-12

Compound 51-2

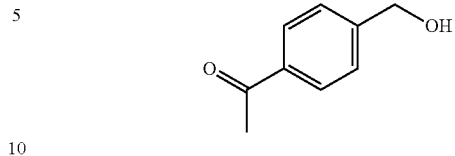

To a solution of compound 51-1 (5 g, 300 mmol) in THF (400 mL) was added slowly LAH powder (1.14 g, 3 00 mmol) in portions at 0° C., and the reaction solution was stirred at 25° C. for 12 h. After LCMS indicated the reaction was complete, NaOH solution (1 mol/L, 400 mL) was added to this solution, and the resulting solution was stirred for 2 h followed by filtration. The filtrate was extracted with EtOAc (50 mL×5), and the organic phase was dried over anhydrous $Na_2SO_4$, filtered and evaporated to give the title compound 51-2 (yellow oil, 3.5 g) which was directly used for the next step without any purification.

$^1$H NMR (400 MHz, $CDCl_3$): δ ppm 9.84-9.75 (m, 1H), 7.70 (d, J=8.1 Hz, 2H), 7.41 (d, J=8.1 Hz, 2H), 4.83 (q, J=6.4 Hz, 1H), 4.25-4.03 (m, 1H), 3.26 (s, 1H), 1.38 (d, J=6.6 Hz, 3H).

LCMS (ESI) m/z: 151 (M+1).

Compound 51-3

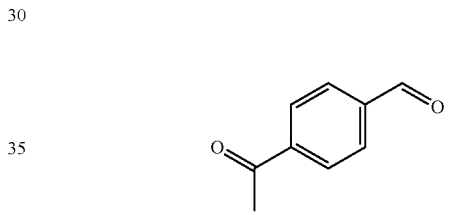

To a solution of compound 51-2 (350 mg, 2.3 mmol) in DCM (15 mL) was added Dess-Martin periodinane (990 mg, 2.3 mmol), and the reaction solution was stirred at 25° C. for 12 h. After TLC indicated the reaction was complete, water (25 mL) was added into the reaction solution, and the resulting solution was extracted with DCM (15 mL×3). The organic phase was dried over anhydrous $Na_2SO_4$, filtered and evaporated to give a crude product which was purified by column chromatography to afford the title compound 51-3 (yellow oil, 250 mg, Yield 71%).

LCMS (ESI) m/z: 149 (M+1).

Compound 51-4

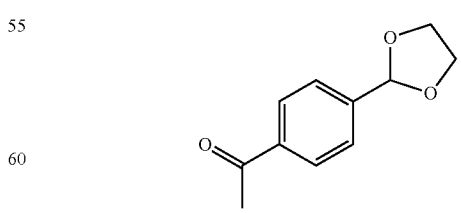

To a solution of compound 51-3 (500 mg, 3.4 mmol) and ethylene glycol (250 mg, 250 mmol) in THF (15 mL) was added neutral alumina (650 mg, 6.8 mmol), and the reaction solution was stirred at 25° C. for 12 h. After TLC indicated the reaction was complete, water (15 mL) was added into the reaction solution, and the resulting solution was extracted with EtOAc (20 mL×4). The organic phase was dried over anhydrous Na$_2$SO$_4$, filtered and evaporated to give a crude product which was purified by column chromatography to give the title compound 51-4 (yellow oil, 400 mg, Yield 62%).

LCMS (ESI) m/z: 193 (M+1).

Compound 51-5

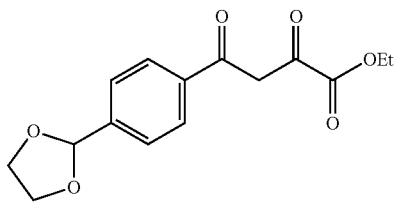 [SMILES: CCOC(=O)C(=O)CC(=O)c1ccc(C2OCCO2)cc1]

To a solution of compound 51-4 (75 mg, 0.39 mmol) in THF (2 mL) was added NaH (19 mg, 0.34 mmol) and the reaction solution was stirred at 20° C. for 10 min, after which diethyl oxalate (57 mg, 0.39 mmol) was added and the reaction solution was stirred at 70° C. for 2 h. After TLC indicated the reaction was complete, water (5 mL) was added into the solution, and the resulting solution was extracted with EtOAc (5 mL×4). The organic phase was dried over anhydrous Na$_2$SO$_4$, filtered and evaporated to give a crude product which was purified by column chromatography to afford the title compound 51-5 (yellow solid, 45 mg, Yield 37.5%).

$^1$H NMR (400 MHz, d$_6$-DMSO): δ ppm 7.52 (s, 1H), 7.34 (s, 1H), 7.31 (dd, J=1.00, 9.03 Hz, 1H), 7.11 (d, J=9.03 Hz, 1H), 6.73 (d, J=8.03 Hz, 2H), 6.59 (t, J=7.78 Hz, 2H), 6.49-6.39 (m, 1H), 6.19 (s, 1H), 4.43 (q, J=7.19 Hz, 2H), 1.44 (t, J=7.28 Hz, 3H).

LCMS (ESI) m/z: 293 (M+1).

Compound 51-6

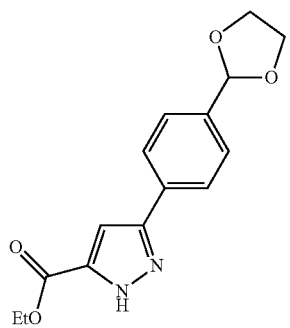 [SMILES: CCOC(=O)c1cc(-c2ccc(C3OCCO3)cc2)n[nH]1]

Compound 51-5 (45 mg, 0.15 mmol) was added into N$_2$H$_4$·H$_2$O (24 mg, 0.75 mmol), and the reaction mixture was stirred at 90° C. for 5 h. After TLC indicated the reaction was complete, water (5 mL) was added to this mixture, and the resulting mixture was extracted with EtOAc (5 mL×3). The organic phase was dried over anhydrous Na$_2$SO$_4$, filtered and evaporated to give the title compound 51-6 (yellow solid, 41 mg, Yield 91%).

Compound 51-7

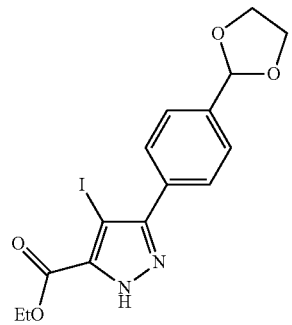 [SMILES: CCOC(=O)c1[nH]nc(-c2ccc(C3OCCO3)cc2)c1I]

To a mixture of compound 51-6 (45 mg, 0.14 mmol) in acetonitrile (5 mL) was added NIS (31 mg, 0.14 mmol) and CAN (7.6 mg, 0.014 mmol), and the reaction mixture was stirred at 90° C. for 12 h. After TLC indicated the reaction was complete, water (5 mL) was added to this mixture, and the resulting mixture was extracted with EtOAc (5 mL×5). The organic phase was dried over anhydrous Na$_2$SO$_4$, filtered and evaporated to give a crude product which was purified by column chromatography to afford the title compound 51-7 (yellow solid, 30 mg, Yield 46.8%).

LCMS (ESI) m/z: 415 (M+1).

Compound 51-8

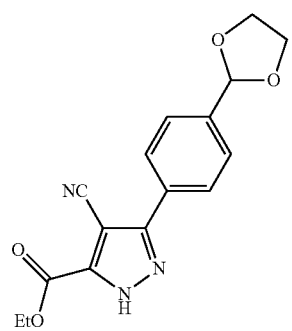 [SMILES: CCOC(=O)c1[nH]nc(-c2ccc(C3OCCO3)cc2)c1C#N]

To a solution of compound 51-7 (30 mg, 0.07 mmol) in DMF (2 mL) was added CuCN (18 mg, 0.21 mmol) and Pd(dppf)Cl$_2$ (4 mg, 0.007 mmol) under nitrogen atmosphere and the reaction solution was stirred at 90° C. for 2 h. After TLC e indicated the reaction was complete, the reaction solution was cooled down to r.t., and water (5 mL) was added. The resulting solution was extracted with EtOAc (5 mL×3). The organic phase was dried over anhydrous Na$_2$SO$_4$, filtered and evaporated to give a crude product which was purified by column chromatography to give the title compound 51-8 (yellow solid, 20 mg, Yield 91%).

LCMS (ESI) m/z: 314 (M+1).

Compound 51-9

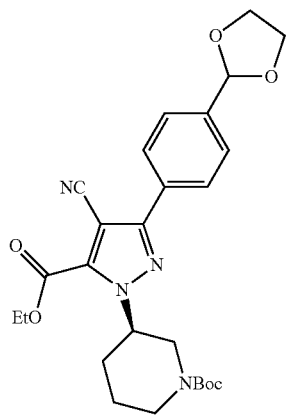 [SMILES: CCOC(=O)c1c(C#N)c(-c2ccc(C3OCCO3)cc2)nn1[C@@H]1CCCN(C(=O)OC(C)(C)C)C1]

To a solution of compound 51-8 (300 mg, 9.58 mmol) in THF (15 mL) was added PPh₃ (300 mg, 9.58 mmol) and DIAD (125 mg, 9.58 mmol) under nitrogen atmosphere at 0° C. and the reaction solution was stirred for 5 min, after which a solution of compound (S)-1-BOC-3-Hydroxypiperidine (207 mg, 9.58 mmol) in THF (5 mL) was added dropwise. Then the resulting solution was warmed to 25° C. and stirred for 14 h. After TLC indicated the reaction was complete, water (15 mL) was added to this mixture, and the resulting solution was extracted with DCM (20 mL×3). The organic phase was dried over anhydrous Na₂SO₄, filtered and evaporated to give a crude product which was purified by column chromatography to afford the title compound 51-9 (brown oil, 180 mg, Yield 38%).

LCMS (ESI) m/z: 497 (M+1).

Compound 51-10

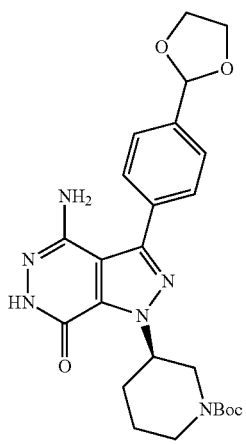 [SMILES: CC(C)(C)OC(=O)N1CCC[C@@H](n2nc(-c3ccc(C4OCCO4)cc3)c3c(N)n[nH]c(=O)c32)C1]

Compound 51-9 (180 mg, 0.29 mmol) was added into N₂H₄·H₂O (85%, 2 mL), and the reaction mixture was heated to 100° C. and stirred for 6 h. After LCMS indicated the reaction was complete, water (5 mL) was added to this mixture, and the resulting solution was extracted with EtOAc (5 mL×2). The organic phase was dried over anhydrous Na₂SO₄, filtered and evaporated to give the title compound 51-10 (yellow oil, 160 mg, Yield 90%).

LCMS (ESI) m/z: 483 (M+1).

Compound 51-11

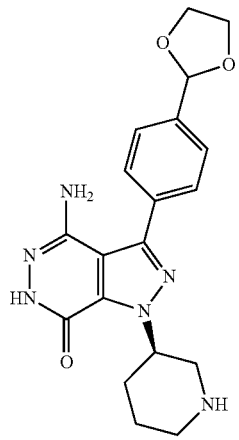 [SMILES: Nc1n[nH]c(=O)c2c1c(-c1ccc(C3OCCO3)cc1)nn2[C@@H]1CCCNC1]

Compound 51-10 (50 mg, 0.095 mmol) was added into 10% HCl solution (2 mL), and the reaction solution was stirred at 25° C. for 8 h. After TLC indicated the reaction was complete, the mixture was evaporated and saturated Na₂CO₃ solution (3 mL) was added. The resulting solution was extracted with EtOAc (3 mL×2). The organic phase was dried over anhydrous Na₂SO₄, filtered and evaporated to give the title compound 51-11 (white solid, 80 mg, Yield 56%).

LCMS (ESI) m/z: 383 (M+1).

¹H NMR (400 MHz, CDCl₃): δ ppm 7.56 (d, J=8.5 Hz, 2H), 7.01 (d, J=8.5 Hz, 2H), 5.48-5.38 (m, 1H), 5.04 (br. s., 2H), 4.88-4.77 (m, 1H), 4.12 (q, J=7.2 Hz, 1H), 3.40-3.28 (m, 1H), 3.18 (dd, J=10.0, 12.0 Hz, 1H), 3.05 (d, J=13.1 Hz, 1H), 2.70 (t, J=10.8 Hz, 1H), 2.37-2.17 (m, 2H), 1.90 (dd, J=13.1, 15.6 Hz, 4H), 1.72 (br. s., 4H).

LCMS (ESI) m/z: 383 (M+1).

Compound 51-12

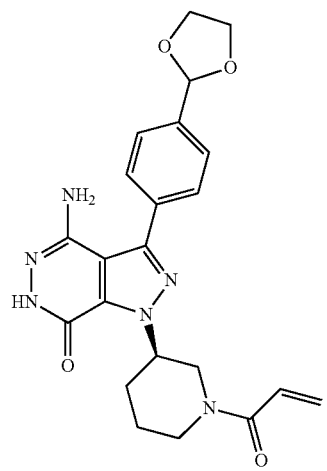 [SMILES: C=CC(=O)N1CCC[C@@H](n2nc(-c3ccc(C4OCCO4)cc3)c3c(N)n[nH]c(=O)c32)C1]

To a mixture of HATU (33.99 mg, 104.60 μmol) and DIPEA (270.4 mg, 209.2 μmol) in DCM (5 mL) was added acrylic acid (7.54 mg, 104.60 μmmol) under nitrogen atmosphere and the reaction mixture was stirred at 20° C. for 10 min, after which compound 51-11 (40 mg, 104.60 μmol) was added, and the resulting reaction mixture was stirred at 25° C. for 12 h. After LCMS indicated the reaction was complete, water (5 mL) was added to the mixture, and the resulting mixture was extracted with DCM (10 mL×3). The organic phases were combined, dried over anhydrous Na$_2$SO$_4$, filtered and evaporated to give a residue which was purified by column chromatography to afford the title compound 51-12 (white solid, 20 mg, Yield 43.81%).

1H NMR (400 MHz, CDCl$_3$): δ ppm 7.66 (d, J=8.5 Hz, 2H), 7.11 (d, J=8.5 Hz, 2H), 6.74-6.69 (m, 1H), 6.44 (t, J=16.3 Hz, 1H), 5.48-5.38 (m, 1H), 5.04 (br. s., 2H), 4.88-4.77 (m, 1H), 4.12 (q, J=7.2 Hz, 1H), 3.40-3.28 (m, 1H), 3.18 (dd, J=10.0, 12.0 Hz, 1H), 3.05 (d, J=13.1 Hz, 1H), 2.40 (t, J=10.8 Hz, 1H), 2.27-2.17 (m, 2H), 1.90 (dd, J=13.1, 15.6 Hz, 4H), 1.62 (br. s., 4H).

Scheme 41

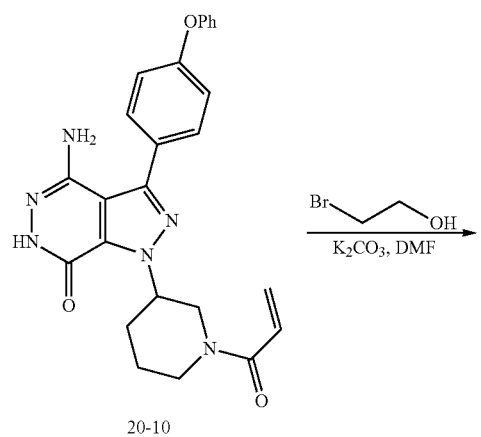

20-10

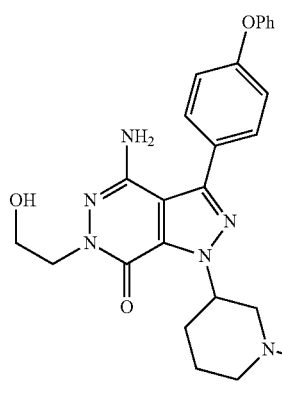

52-2

Example 50

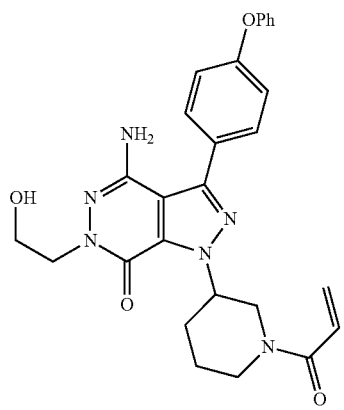 [SMILES: C=CC(=O)N1CCCC(n2nc(-c3ccc(Oc4ccccc4)cc3)c3c(N)nn(CCO)c(=O)c32)C1]

Compound 52-2

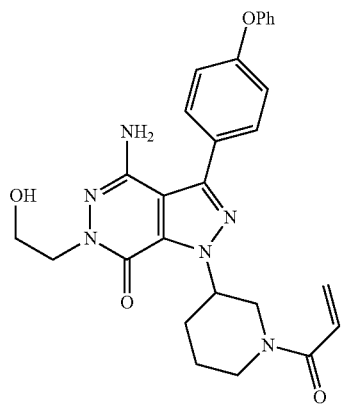 [SMILES: C=CC(=O)N1CCCC(n2nc(-c3ccc(Oc4ccccc4)cc3)c3c(N)nn(CCO)c(=O)c32)C1]

To a solution of compound 20-10 (70 mg, 0.154 mmol) and K$_2$CO$_3$ (84.8 mg, 0.614 mmol) in DMF (3 mL) was added 2-bromoethanol (57.5 mg, 0.461 mmol) and the reaction solution was stirred at 80° C. for 16 h. The solution was filtered and the filtrate was evaporated to give a crude product which was purified by preparative HPLC to give the title compound 52-2 (white solid, 8.68 mg, Yield 11%).

$^1$H NMR (400 MHz, d$_6$-DMSO): δ ppm 7.68 (d, J=8.03 Hz, 2H), 7.44 (t, J=7.78 Hz, 2H), 7.09-7.22 (m, 5H), 6.73-6.92 (m, 1H), 6.10 (t, J=16.56 Hz, 1H), 5.58-5.75 (m, 1H), 5.45 (brs, 1H), 5.32 (brs, 2H), 4.78 (t, J=5.65 Hz, 1H), 4.56 (d, J=11.54 Hz, 1H), 4.20-4.35 (m, 1H), 4.03 (brs, 3H), 3.66-3.75 (m, 2H), 3.52-3.62 (m, 1H), 2.96 (d, J=12.05 Hz, 1H), 2.18 (brs, 2H), 1.94 (d, J=13.05 Hz, 1H), 1.52 (brs, 1H).

Scheme 42

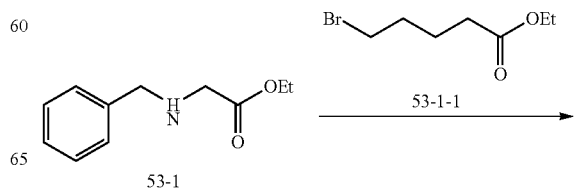

53-1

-continued
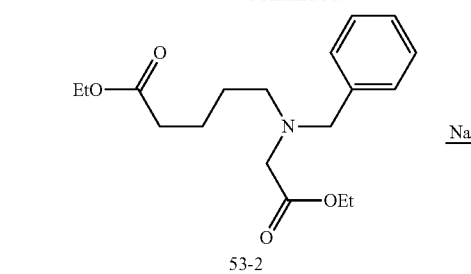
53-2
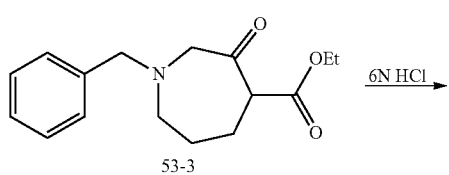
53-3
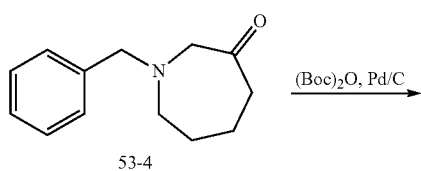
53-4
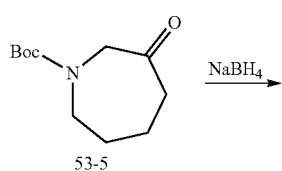
53-5
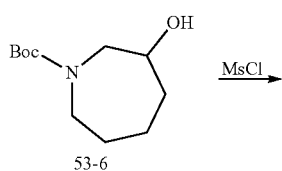
53-6
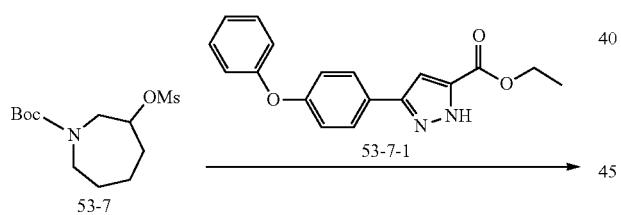
53-7, 53-7-1
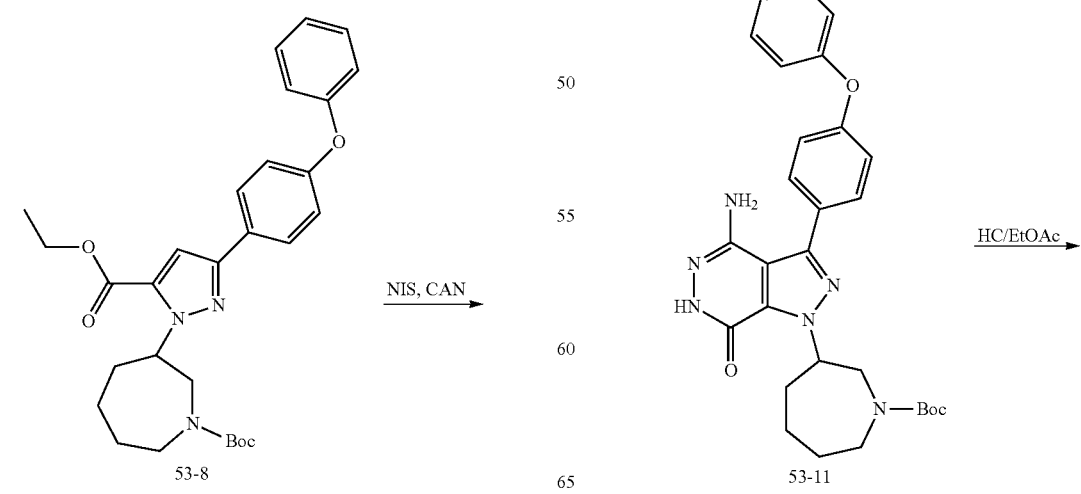
53-8
-continued
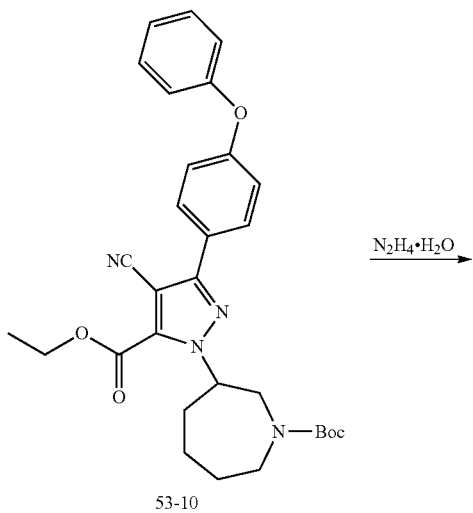
53-9, 53-10, 53-11

-continued

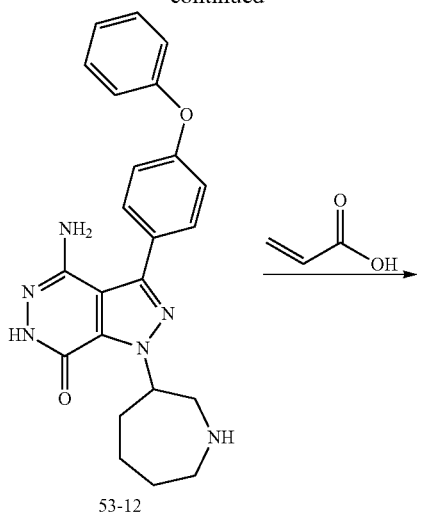

53-12

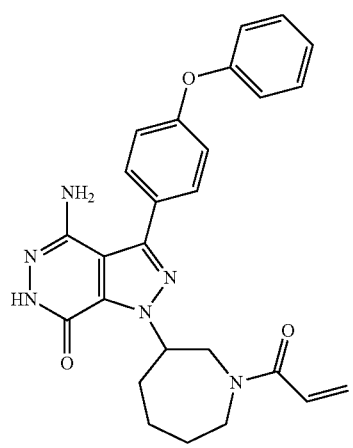 [SMILES: C=CC(=O)N1CCCCC(n2nc(-c3ccc(Oc4ccccc4)cc3)c3c(N)n[nH]c(=O)c32)C1]

53-13

Example 51

Compound 53-2

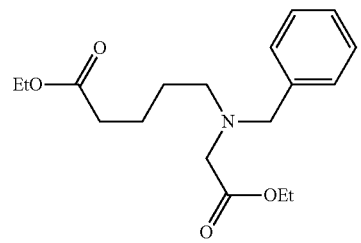 [SMILES: CCOC(=O)CCCCN(CC(=O)OCC)Cc1ccccc1]

Compound 53-1 (12.5 g, 0.22 mol), compound 53-1-1 (50.6 g, 0.242 mol) and TEA (26.7 g, 0.264 mol) were added to acetonitrile (530 mL) under nitrogen atmosphere, and the reaction solution was heated to 60° C. and stirred for 12 h, followed by evaporation. Water was added and the resulting solution was extracted with EtOAc. The organic phase was dried over anhydrous $Na_2SO_4$, filtered and evaporated to give a residue which was purified by column chromatography to afford the title compound 53-2 (yellow oil, 50.5 g, Yield 71%).

$^1$H NMR (400 MHz, $d_6$-DMSO): δ ppm 7.37-7.24 (m, 5H), 4.20-13 (m, 4H), 3.79 (m, 2H), 3.31 (s, 2H), 2.69-2.65 (s, 2H), 2.32-2.28 (m, 2H), 1.69-1.64 (m, 2H), 1.57-1.55 (m, 2H), 1.30-1.25 (m, 6H).

Compound 53-3

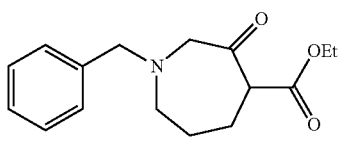 [SMILES: CCOC(=O)C1CCCN(Cc2ccccc2)CC1=O]

To a solution of compound 53-2 (53.3 g, 0.166 mol) in THF (533 mL) was added slowly NaH (13.3 g, 60%, 0.332 mol) in portions under nitrogen atmosphere at 0° C. and the reaction solution was stirred at reflux for 12 h, followed by evaporated and washed with water and saturated brine. The organic phase was dried over anhydrous $Na_2SO_4$, filtered and evaporated to give a crude product which was purified by column chromatography to afford the title compound 53-3 (yellow oil, 18 g, Yield 39%).

$^1$H NMR (400 MHz, $d_6$-DMSO): δ ppm 7.40-7.25 (m, 5H), 4.26-4.15 (m, 2H), 3.88 (t, 1H), 3.75-3.62 (m, 2H), 3.72-3.67 (q, 2H), 2.63-2.59 (m, 2H), 1.81 (m, 1H), 1.68 (m, 1H), 1.67 (m, 1H), 1.66 (m, 1H), 1.28-1.21 (t, 3H).

Compound 53-4

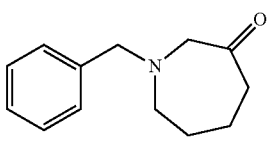 [SMILES: O=C1CCCCN(Cc2ccccc2)C1]

Compound 53-3 (18 g, 65.5 mmol) was added into HCl solution (6 mol/L, 180 mL) under nitrogen atmosphere, and the reaction solution was stirred at reflux for 12 h. After TLC indicated the reaction was complete, the reaction solution was cooled down to r.t. and adjusted to a pH greater than 9 with NaOH solution. The resulting solution was extracted with a mixture of DCM/MeOH (10/1) (200 mL×2). The organic phase was washed with saturated brine, dried over anhydrous Na$_2$SO$_4$, filtered and evaporated to give the title compound 53-4 (yellow oil, 11.9 g, Yield 89%).

$^1$H NMR (400 MHz, d$_6$-DMSO): δ ppm 7.38-7.27 (m, 5H), 3.72 (s, 2H), 3.27 (s, 2H), 2.76-2.71 (m, 4H), 1.75 (m, 4H)

Compound 53-5

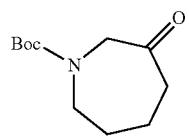

To a solution of compound 53-4 (5.4 g, 26.6 mmol) in MeOH (1000 mL) was added wet Pd/C (3 g, 50% of water content) and (Boc)$_2$O (6.4 g, 29.3 mmol) in a bottle for hydrogenation, and the reaction solution was stirred at hydrogenation conditions (H$_2$, 50 psi) at r.t. for 12 h. After TLC indicated the reaction was complete, the reaction solution was filtered and the filtrate was evaporated to give the title compound 53-5 (oil, 5.6 g, Yield 100%).

$^1$H NMR (400 MHz, d$_6$-DMSO): δ ppm 4.04-3.96 (m, 2H), 3.45-3.36 (m, 2H), 2.55-2.52 (m, 2H), 1.85-1.72 (m, 4H), 1.53-1.48 (m, 9H)

Compound 53-6

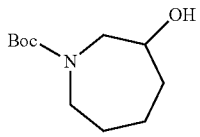

To a solution of compound 53-5 (5.5 g, 25.8 mmol) in MeOH (55 mL) was added slowly sodium borohydride (NaBH$_4$) (0.98 g, 25.8 mmol) in portions at 0° C. After TLC indicated the reaction was complete, the reaction solution was adjusted to pH 5 to 6 with HCl solution, followed by filtration and extraction with DCM (100 mL×3). The organic phase was dried over anhydrous Na$_2$SO$_4$, filtered and evaporated to give the title compound 53-6 (oil, 4.8 g, Yield 87%).

$^1$H NMR (400 MHz, d$_6$-DMSO): δ ppm 3.95-3.93 (m, 1H), 3.71-3.62 (m, 2H), 3.40 (m, 1H), 3.32-3.28 (m, 1H), 3.03 (m, 1H), 1.88-1.65 (m, 4H), 1.55-1.36 (m, 11H)

Compound 53-7

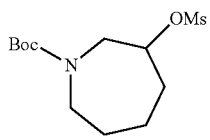 [SMILES: CC(C)(C)OC(=O)N1CCCCC(OS(C)(=O)=O)C1]

To a solution of compound 53-6 (4.8 g, 22.3 mmol) and TEA (4.5 g, 11.6 mmol) in DCM (50 mL) was added dropwise methylsufonyl chloride (3.8 g, 33.5 mmol) under nitrogen atmosphere at 0° C. and the reaction solution was stirred at 20° C. for 12 h. After TLC indicated the reaction was complete, the reaction was quenched with water and the solution was extracted with DCM (100 mL×3). The organic phase was dried over anhydrous Na$_2$SO$_4$, filtered and evaporated to give the title compound 53-7 (oil, 6.5 g, Yield 100%).

$^1$H NMR (400 MHz, d$_6$-DMSO): δ ppm 4.90-4.85 (m, 1H), 3.97-3.94 (m, 1H), 3.60-3.75 (m, 1H), 3.31-3.30 (m, 1H), 3.17-3.04 (m, 4H), 2.00-1.88 (m, 1H), 1.82-1.69 (m, 4H), 1.50-1.27 (m, 10H)

Compound 53-8

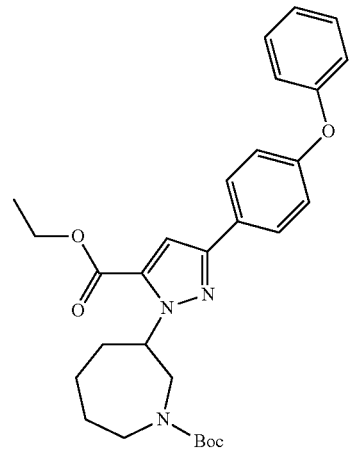 [SMILES: CCOC(=O)c1cc(-c2ccc(Oc3ccccc3)cc2)nn1C1CCCCN(C(=O)OC(C)(C)C)C1]

To a solution of compound 53-7-1 (7.65 g, 24.83 mmol) in DMF (50 mL) was added slowly NaH (2.0 g, 49.65 mmol) in portions at r.t. and the reaction solution was stirred at r.t. for 30 min, after which a solution of compound 53-7 in DMF (50 mL) was added and the reaction solution was stirred at reflux for 12 h. After TLC indicated the reaction was complete, the resulting reaction solution was evaporated and concentrated to give a crude product which was purified by column chromatography to afford the title compound 53-8 (colourless oil, 2.8 g, Yield 22%).

$^1$H NMR (400 MHz, d$_6$-DMSO): δ ppm 7.81-7.79 (m, 2H), 7.39-7.35 (m, 2H), 7.14 (m, 1H), 7.08-7.05 (m, 5H), 5.56-5.53 (m, 1H), 4.42-4.30 (m, 2H), 4.17-4.14 (m, 1H), 3.95-3.94 (m, 1H), 3.69-3.65 (m, 1H), 3.19-3.16 (m, 1H), 2.11-2.02 (m, 4H), 1.63 (m, 2H), 1.50-1.41 (m, 9H), 1.30-1.27 (m, 3H).

Compound 53-9

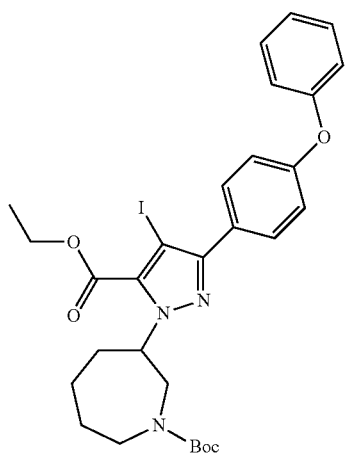 [SMILES: CCOC(=O)c1c(I)c(-c2ccc(Oc3ccccc3)cc2)nn1C1CCCCN(C(=O)OC(C)(C)C)C1]

To a solution of compound 53-8 (2.2 g, 4.36 mmol) in acetonitrile (44 mL) was added NIS (0.98 g, 4.36 mmol) and CAN (358 mg, 0.65 mmol) under nitrogen atmosphere and the reaction mixture was stirred at 80° C. for 1 h. After LCMS indicated the reaction was complete, water (30 mL) was added to this mixture, and the resulting mixture was extracted with DCM (200 mL×2). The organic phase was dried over anhydrous Na$_2$SO$_4$, filtered and evaporated to give a crude product which was purified by column chromatography to give the title compound 53-9 (yellow oil, 2.3 g, Yield 83%).

$^1$H NMR (400 MHz, d$_6$-DMSO): δ ppm 7.77-7.75 (m, 2H), 7.41-7.37 (m, 2H), 7.18-7.14 (m, 1H), 7.10-7.08 (m, 4H), 5.42-5.36 (m, 1H), 4.48-4.45 (m, 2H), 4.17 (m, 1H), 3.95-3.90 (m, 1H), 3.67-3.57 (m, 1H), 3.16-3.13 (m, 1H), 2.13-1.98 (m, 4H), 1.74 (m, 1H), 1.53-1.47 (m, 12H).

Compound 53-10

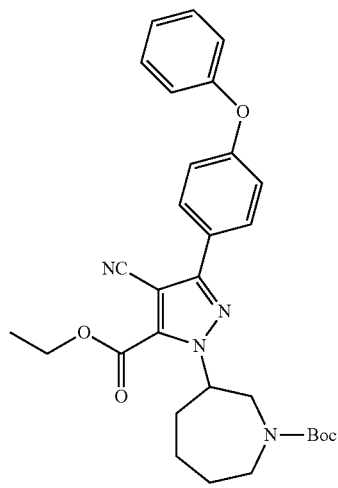 [SMILES: CCOC(=O)c1c(C#N)c(-c2ccc(Oc3ccccc3)cc2)nn1C1CCCCN(C(=O)OC(C)(C)C)C1]

To a solution of compound 53-9 (1.89 g, 3 mmol), zinc powder (390 mg, 6.0 mmol) and Zn(CN)$_2$ (703 mg, 6.0 mmol) in DMF (19 mL) was added Pd(dppf)Cl$_2$ (219.6 mg, 0.3 mmol) and Pd$_2$(dba)$_3$ (274.5 mg, 0.3 mmol) under nitrogen atmosphere and the reaction solution was stirred at reflux for 12 h, after which water (30 mL) was added and the resulting solution was extracted with EtOAc (150 mL×2). The organic phase was dried over anhydrous Na$_2$SO$_4$, filtered and evaporated to give a crude product which was purified by column chromatography to afford the title compound 53-10 (white solid, 0.7 g, Yield 44%).

$^1$H NMR (400 MHz, d$_6$-DMSO): δ ppm 7.97-7.95 (m, 2H), 7.39-7.35 (m, 2H), 7.17-7.14 (m, 1H), 7.09-7.06 (m, 4H), 5.55-5.47 (m, 1H), 4.51-4.46 (m, 2H), 3.94-3.88 (m, 1H), 3.65-3.59 (m, 1H), 3.18-3.13 (m, 1H), 2.07-2.00 (m, 4H), 1.56-1.54 (m, 2H), 1.50-1.44 (m, 12H).

Compound 53-11

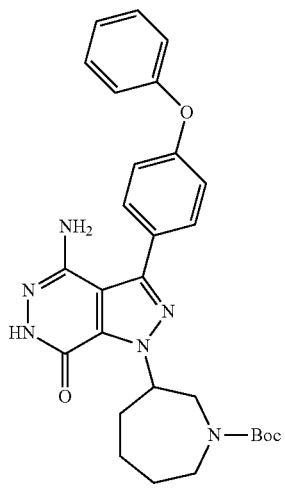 [SMILES: CC(C)(C)OC(=O)N1CCCCC(n2nc(-c3ccc(Oc4ccccc4)cc3)c3c(N)n[nH]c(=O)c32)C1]

Compound 53-10 (300 mg, 0.57 mmol) was added into N$_2$H$_4$.H$_2$O (85%, 5.4 mL) and the reaction mixture was heated and refluxed and stirred for 2 h, after which water (50 mL) and DCM (20 mL) were added and the resulting solution was extracted with DCM (20 mL×2). The organic phase was dried over anhydrous Na$_2$SO$_4$, filtered and evaporated to give the title compound 53-11 (white solid, 292 mg, Yield 100%).

$^1$H NMR (400 MHz, d$_6$-DMSO): δ ppm 7.67-7.65 (m, 2H), 7.42-7.40 (m, 2H), 7.20 (m, 1H), 7.17-7.11 (m, 4H), 5.83-5.70 (m, 1H), 4.13-3.88 (m, 2H), 3.76-3.72 (m, 2H), 3.51-3.23 (m, 1H), 2.18-2.16 (m, 1H), 2.02-1.95 (m, 2H), 1.76-1.62 (m, 2H), 1.48-1.31 (m, 12H).

Compound 53-12

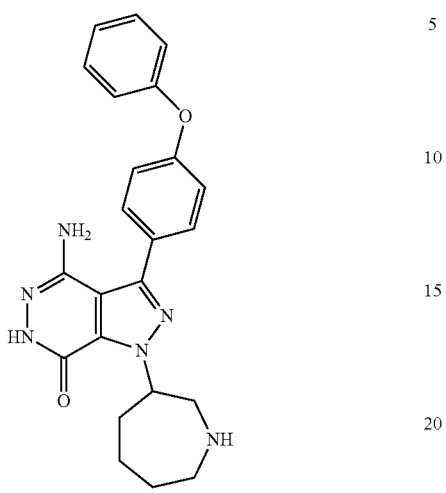

Compound 53-11 (292 mg, 0.57 mmol) was added into 10% HCl solution (6 mL) in an ice bath, and the reaction solution was stirred at 25° C. for 8 h. After TLC indicated the reaction was complete, the mixture was evaporated and water (2 mL) was added. The resulting solution was extracted with EtOAc (3 mL×2). The organic phase was dried over anhydrous $Na_2SO_4$, filtered and evaporated to give the title compound 53-12 (yellow solid, 265 mg, Yield 96%).

Compound 53-13

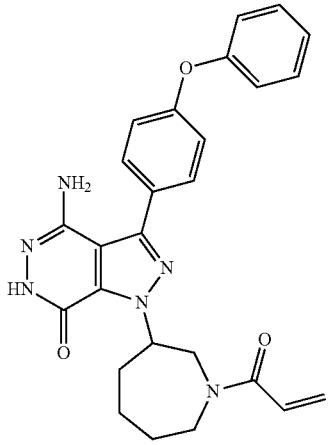 [SMILES: C=CC(=O)N1CCCCC(n2nc(-c3ccc(Oc4ccccc4)cc3)c3c(N)n[nH]c(=O)c32)C1]

To a mixture of HATU (227 mg, 0.59 mmol) and DIPEA (279 mg, 2.16 mmol) in DCM (12 mL) was added acrylic acid (43 mg, 0.59 mmol) under nitrogen atmosphere and the reaction mixture was stirred at 20° C. for 10 min, after which compound 53-12 (265 mg, 0.54 mmol) was added and the resulting mixture was stirred at 25° C. for 2 h. After LCMS indicated the reaction was complete, water (10 mL) was added to this mixture, and the resulting solution was extracted with DCM (20 mL×2). The organic phases were combined, dried over anhydrous $Na_2SO_4$, filtered and evaporated to give a crude product which was purified by preparative HPLC to afford the title compound 53-13 (white solid, 36.3 mg, Yield 14%).

$^1$H NMR (400 MHz, $d_6$-DMSO): δ ppm 9.41-9.34 (m, 1H), 7.66-7.64 (m, 2H), 7.43-7.41 (m, 2H), 7.23-7.21 (m, 1H), 7.17-7.11 (m, 4H), 6.82-6.79 (m, 1H), 6.65-6.60 (m, 1H), 6.43-6.39 (m, 1H), 5.78-5.73 (m, 2H), 4.48-4.44 (m, 2H), 4.27-4.16 (m, 1H), 4.40-3.90 (m, 1H), 3.88-3.85 (m, 1H), 3.65-3.60 (m, 1H), 3.28-3.25 (m, 1H), 2.35 (m, 1H), 2.23-2.21 (m, 1H), 2.05 (m, 1H), 1.84 (m, 1H), 1.67-1.64 (m, 1H).

LCMS (ESI) m/z: 471 (M+1).

Example 52

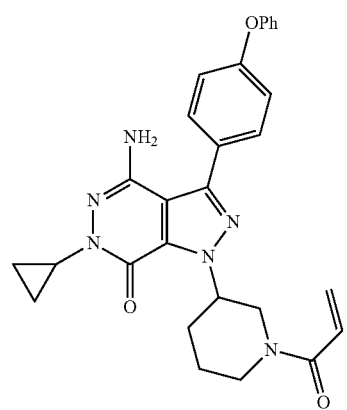 [SMILES: C=CC(=O)N1CCCC(n2nc(-c3ccc(Oc4ccccc4)cc3)c3c(N)nn(C4CC4)c(=O)c32)C1]

In Example 52, the systhesis process was similar to that in Example 50.

$^1$H NMR (400 MHz, $d_6$-DMSO): δ ppm 7.69 (d, J=8.53 Hz, 2H), 7.670 (s, 2H), 7.115-7.466 (m, 5H), 6.822-6.867 (m, 1H), 6.04-6.19 (m, 1H), 5.59-5.77 (m, 1H), 5.42-5.56 (m, 1H), 5.28 (brs, 2H), 4.51-4.62 (m, 1H), 4.22-4.41 (m, 1H), 3.89-4.11 (m, 2H), 3.51-3.65 (m, 1H), 2.84-3.03 (m, 1H), 2.083-2.094 (m, 2H), 1.93 (m, 1H), 1.54 (m, 1H), 1.03 (brs, 2H), 0.871-0.890 (m, 2H).

Scheme 43

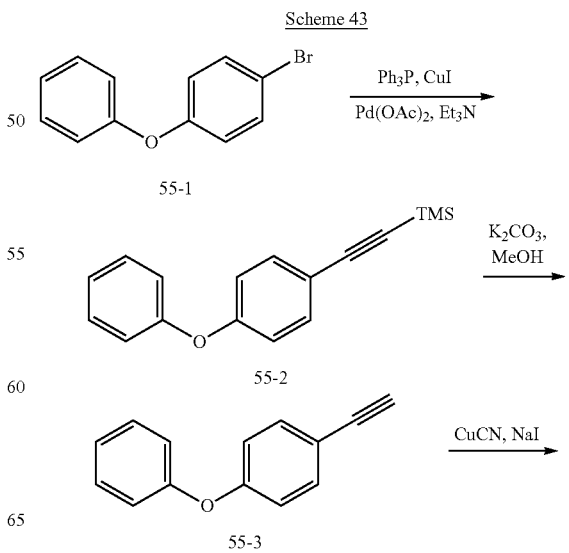

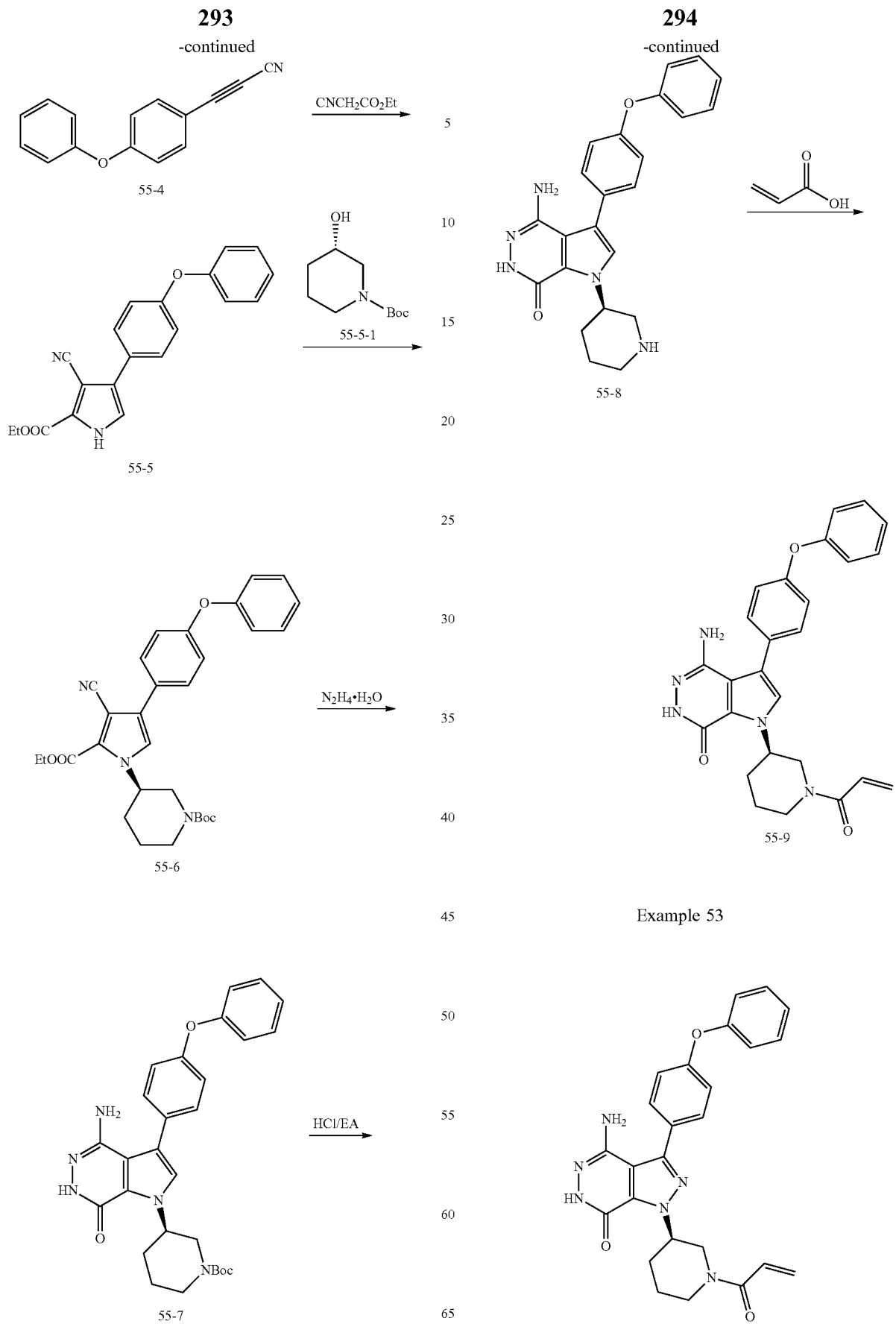

Compound 55-2

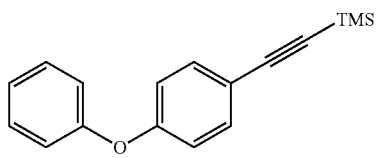 [SMILES: C[Si](C)(C)C#Cc1ccc(Oc2ccccc2)cc1]

To a solution of compound 55-1 (16 g, 64 mmol) in TEA (160 mL) was added PPh$_3$ (1.68 g, 6.4 mmol), cuprous iodide (0.6 g, 3.2 mmol), palladium acetate (0.72 g, 3.2 mmol) and trimethylchlorosilane (10.7 g, 96 mmol) and the reaction solution was stirred at 90° C. for 12 h, after which water (100 mL) was added and the resulting solution was extracted with EtOAc (100 mL×4). The organic phases were combined, dried over anhydrous Na$_2$SO$_4$, filtered and evaporated to give a crude product which was purified by column chromatography to afford the title compound 55-2 (yellow solid, 15 g, Yield 88%).

$^1$H NMR (400 MHz, CDCl$_3$): δ ppm 7.45 (d, J=8.78 Hz, 2H), 7.35-7.41 (m, 2H), 7.13-7.19 (m, 1H), 7.04 (d, J=7.78 Hz, 2H), 6.93 (d, J=8.78 Hz, 2H), 0.27 (s, 9H).

Compound 55-3

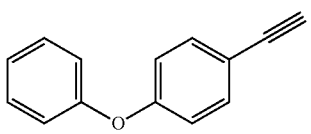

To a solution of compound 55-2 (15.2 g, 57.1 mmol) in MeOH (30 mL) was added K$_2$CO$_3$ (3.9 g, 28.5 mmol) and the reaction solution was stirred at 25° C. for 3 h, after which water (20 mL) was added and the resulting solution was extracted with EtOAc (50 mL×3). The organic phases were combined, dried over anhydrous Na$_2$SO$_4$, filtered and evaporated to give a crude product which was purified by column chromatography to afford the title compound 55-3 (yellow oil, 9 g, Yield 81.8%).

$^1$H NMR (400 MHz, CDCl$_3$): δ ppm 7.46 (d, J=9.03 Hz, 2H), 7.38 (s, 2H), 7.13-7.19 (m, 1H), 7.04 (d, J=8.03 Hz, 2H), 6.92 (d, J=8.78 Hz, 2H), 3.74 (s, 1H).

Compound 55-4

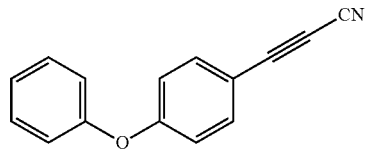 [SMILES: N#CC#Cc1ccc(Oc2ccccc2)cc1]

To a 250 mL 3-necked flask was added slowly acetonitrile (30 mL) and dimethyl sulfoxide (60 mL) followed by CuCN (5.6 g, 61.8 mmol), sodium iodide (NaI) (0.68 g, 4.4 mmol), compound 55-3 (6 g, 30.9 mmol) and trimethylchlorosilane (6.68 g, 61.8 mmol), and the reaction solution was stirred at 60° C. for 24 h. To this solution, water (20 mL) was added and the resulting solution was extracted with EtOAc (20 mL×3). The organic phases were combined, dried over anhydrous Na$_2$SO$_4$, filtered and evaporated to give a crude product which was purified by column chromatography to afford the title compound 55-4 (yellow oil, 3.36 g, Yield 50%).

$^1$H NMR (400 MHz, CDCl$_3$): δ ppm 7.59 (d, J=8.78 Hz, 2H), 7.44 (s, 2H), 7.25 (s, 1H), 7.09 (d, J=7.78 Hz, 2H), 6.96-7.02 (m, 2H).

Compound 55-5

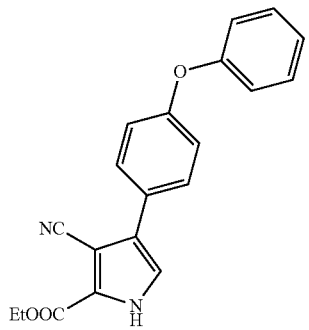 [SMILES: CCOC(=O)c1[nH]cc(-c2ccc(Oc3ccccc3)cc2)c1C#N]

To a solution of 1,3-bis(diphenylphosphine) propane (0.35 g, 0.86 mmol) in dioxane (20 mL) was added ethyl isocyanoacetate (0.98 g, 8.67 mmol) and compound 55-4 (1.9 g, 8.67 mmol) and the reaction solution was stirred at 100° C. for 5 h, after which water (20 mL) was added and the resulting solution was extracted with EtOAc (20 mL×3). The organic phases were combined, dried over anhydrous Na$_2$SO$_4$, filtered and evaporated to give a crude product which was purified by column chromatography to afford the title compound 55-5 (yellow oil, 1.4 g, Yield 50%).

$^1$H NMR (400 MHz, CDCl$_3$): δ ppm 9.95 (brs, 1H), 7.62 (d, J=8.53 Hz, 1H), 7.51 (d, J=8.53 Hz, 1H), 7.39 (t, J=7.78 Hz, 3H), 7.13-7.18 (m, 2H), 7.08 (dd, J=6.53, 2.01 Hz, 4H), 4.48 (q, J=7.19 Hz, 2H), 1.45-1.50 (m, 3H).

Compound 55-6

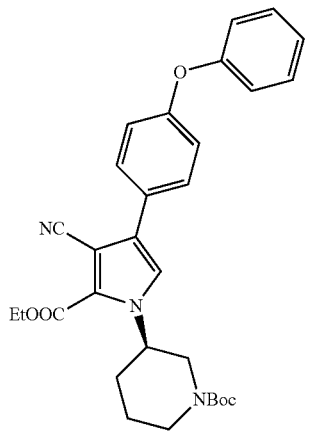 [SMILES: CCOC(=O)c1c(C#N)c(-c2ccc(Oc3ccccc3)cc2)cn1[C@@H]1CCCN(C(=O)OC(C)(C)C)C1]

To a solution of compound 55-5 (3.6 g, 7.32 mmol) in THF (10 mL) was added PPh$_3$ (0.9 g, 3.6 mmol) and DIAD (0.7 g, 3.6 mmol) under nitrogen atmosphere at 0° C. and the reaction solution was stirred for 30 min, after which a solution of compound 55-5-1 (0.58 g, 2.9 mmol) in THF (5 mL) was added dropwise and the resulting solution was warmed to 25° C. and stirred for 16 h. Water (10 mL) was added and the resulting solution was extracted with EtOAc (10 mL×4). The organic phase was dried over anhydrous Na₂SO₄, filtered and evaporated to give a crude product which was purified by column chromatography to afford the title compound 55-6 (brown oil, 4 g, Yield 90%).

LCMS (ESI) m/z: 516 (M+1).

Compound 55-7

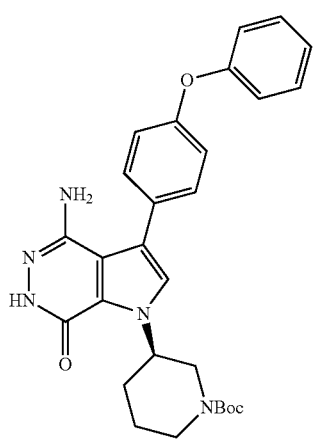 [SMILES: CC(C)(C)OC(=O)N1CCC[C@@H](n2cc(-c3ccc(Oc4ccccc4)cc3)c3c(N)n[nH]c(=O)c32)C1]

Compound 55-6 (0.5 g, 0.97 mmol) was added into N₂H₄.H₂O (85%, 20 mL) and the reaction solution was heated to 120° C. and stirred for 3 h, after which water (50 mL) and DCM (20 mL) were added and the resulting solution was extracted with DCM (30 mL×3). The organic phase was dried over anhydrous Na₂SO₄ and washed with PE to give the title compound 55-7 (white solid, 480 mg) as crude product.

LCMS (ESI) m/z: 502 (M+1)

Compound 55-8

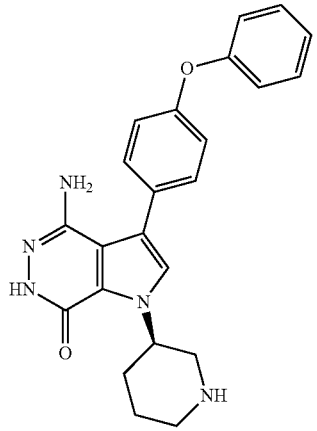 [SMILES: Nc1n[nH]c(=O)c2c1c(-c1ccc(Oc3ccccc3)cc1)cn2[C@@H]1CCCNC1]

To a solution of saturated HCl-EtOAc (10 mL) was added compound 55-7 (0.5 g, 0.99 mmol) and the reaction solution was stirred at 18° C. for 2 h, followed by filtration. The filtrate was extracted with EtOAc, and the organic phase was evaporated to give the title compound 55-8 (white solid, 200 mg, Yield 100%).

LCMS (ESI) m/z: 402 (M+1).

Compound 55-9

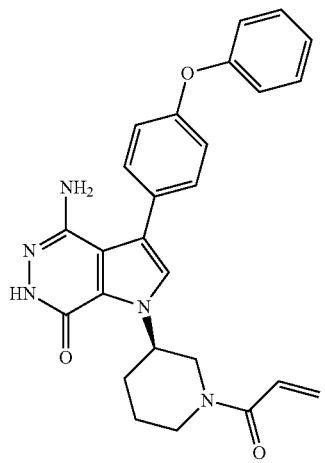

To a mixture of HATU (0.42 g, 1.1 mmol) and DIPEA (0.46 g, 3.6 mmol) in DCM (10 mL) was added acrylic acid (79 mg, 1.1 mmol) and compound 55-8 (0.5 g, 0.9 mmol) under nitrogen atmosphere and the reaction mixture was stirred at 18° C. for 1.5 h, after which water (30 mL) was added and the resulting solution was extracted with DCM (20 mL×4). The organic phases were combined, dried over anhydrous Na₂SO₄, filtered and evaporated to give a crude product which was purified by preparative HPLC to afford the title compound 55-9 (white solid, 6.4 mg, Yield 2%).

¹H NMR (400 MHz, MeOD): δ ppm 7.617 (s, 1H), 7.428-7.505 (m, 2H), 7.389-7.049 (m, 2H), 7.173-7.191 (m, 1H), 7.067-7.106 (m, 3H), 6.80-6.98 (m, 1H), 6.19-6.27 (m, 1H), 5.72-5.82 (m, 1H), 5.44-5.55 (m, 1H), 4.71-4.82 (m, 1H), 4.55-4.63 (m, 1H), 4.44-4.52 (m, 1H), 4.08-4.18 (m, 1H), 3.41-3.51 (m, 1H), 2.81-2.92 (m, 1H), 1.99-2.17 (m, 2H), 1.73-1.95 (s, 1H), 1.24-1.30 (s, 1H).

LCMS (ESI) m/z: 456 (M+1).

Example 54

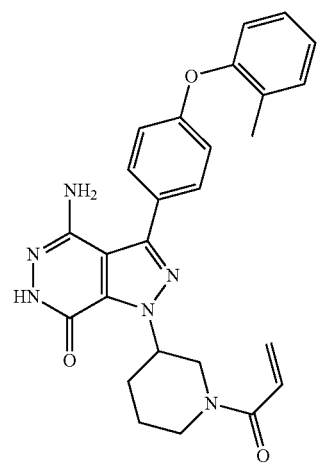 [SMILES: C=CC(=O)N1CCCC(n2nc(-c3ccc(Oc4ccccc4C)cc3)c3c(N)n[nH]c(=O)c32)C1]

In, Example 54, the systhesis process was similar to that in Example 20.

¹H NMR (400 MHz, d₆-DMSO): δ ppm 9.921 (s, 1H), 7.608-7.587 (d, 2H), 7.316-7.298 (d, 1H), 7.239-7.220 (d, 1H), 7.166-7.149 (d, 1H), 7.042-7.000 (d, 3H), 6.644-6.616 (d, 1H), 6.288-6.247 (d, 1H), 5.661 (s, 1H), 5.501 (s, 1H), 4.706 (s, 3H), 4.297-4.006 (s, 1H), 3.615 (s, 1H), 3.507-3.203 (s, 1H), 2.862 (s, 1H), 2.261 (s, 1H) 2.019 (s, 3H), 1.984 (s, 1H), 1.776 (s, 1H).

LCMS (ESI) m/z: 471 (M+1).

Example 55

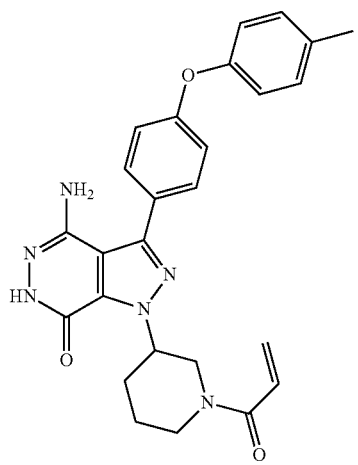 [SMILES: C=CC(=O)N1CCCC(n2nc(-c3ccc(Oc4ccc(C)cc4)cc3)c3c(N)n[nH]c(=O)c32)C1]

In Example 55, the systhesis process was similar to that in Example 20.

¹H NMR (400 MHz, CDCl₃): δ ppm 7.615-7.594 (d, 1H), 7.214-7.193 (d, 2H), 7.117-7.096 (d, 2H), 7.004-6.983 (d, 2H), 6.616 (s, 2H), 6.294-6.252 (d, 1H), 5.676 (s, 1H), 5.492 (s, 1H), 4.843 (s, 1H), 4.602 (s, 1H), 4.442 (s, 1H), 4.321 (s, 2H), 3.987 (s, 1H), 3.615-3.214 (s, 2H), 2.866 (s, 1H), 2.259 (s, 3H), 2.019-1.986 (d, 1H), 1.775 (s, 1H).

LCMS (ESI) m/z: 471 (M+1).

Example 56

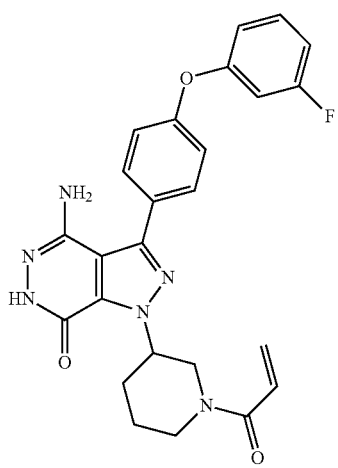 [SMILES: C=CC(=O)N1CCCC(n2nc(-c3ccc(Oc4cccc(F)c4)cc3)c3c(N)n[nH]c(=O)c32)C1]

In Example 56, the systhesis process was similarly to that in Example 20.

¹H NMR (400 MHz, CDCl₃): δ ppm 10.374 (s, 1H), 7.676-7.655 (d, 2H), 7.365-7.327 (q, 1H), 7.182-7.161 (d, 2H), 6.889-6.854 (m, 2H), 6.812-6.806 (d, 1H), 6.785-6.781 (m, 1H), 6.275-6.234 (m, 1H), 5.698-5.613 (m, 1H), 5.495 (s, 1H), 4.931 (s, 2H), 4.592-4.543 (m, 0.5H), 4.321-4.289 (m, 0.5H), 3.971 (m, 0.5H), 3.640-3.506 (m, 1H), 3.213 (m, 0.5H), 2.872 (m, 0.5H), 2.400-2.248 (m, 2H), 2.018-1.985 (m, 1H), 1.769-1.739 (m, 1H).

Scheme 44

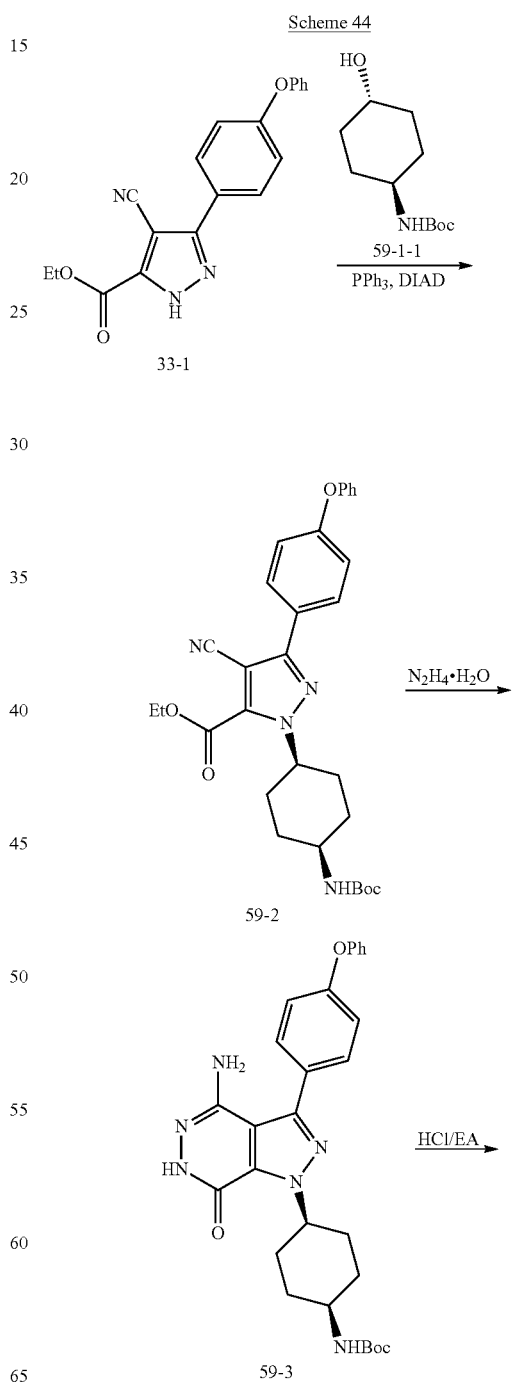

-continued

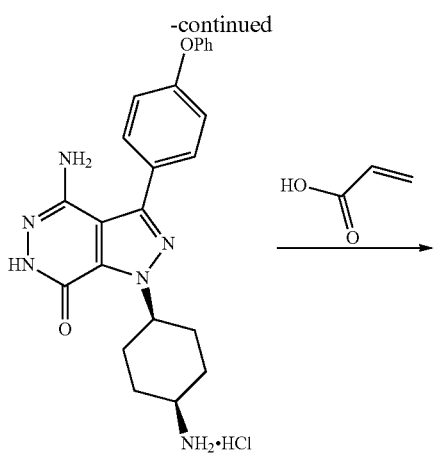

59-4

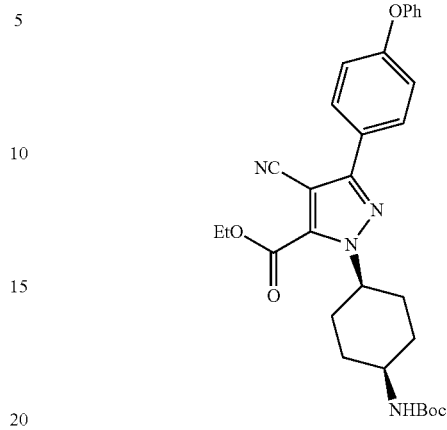

Compound 59-2

To a solution of compound 33-1 (100 mg, 0.3 mmol) and PPh₃ (118 mg, 0145 mmol) in anhydrous DCM (5 ml) was added DIAD (59 mg, 0.45 mmol) under nitrogen atmosphere at 0° C. and the reaction solution was stirred for 10 min, after which compound 59-1-1 (96.8 mg, 0.45 mmol) was added. Then the reaction solution was warmed to r.t. and stirred for 12 h. After TLC indicated the reaction was complete, saturated NH₄Cl solution (aq., 10 ml) was added to this solution and the aqueous phase was extracted with EtOAc (20 ml) three times. The organic phases were combined, washed with saturated brine (10 ml) once, dried over anhydrous Na₂SO₄, filtered and subjected to rotary evaporation to give a residue which was purified by column chromatography to afford the title compound 59-2 (white solid, 50 mg, Yield 31%).

LCMS (ESI) m/z: 531 (M+1).

¹H NMR (400 MHz, CDCl₃): δ ppm 7.96 (d, J=8.38 Hz, 2H), 7.32-7.41 (m, 2H), 7.15 (t, J=7.39 Hz, 1H), 7.08 (dd, J₁=12.13, J₂=8.38 Hz, 4H), 5.19 (br. s., 1H), 4.82 (br. s., 1H), 4.47 (q, J=7.06 Hz, 2H), 3.88 (br. s., 1H), 2.07-2.21 (m, 2H), 1.88-2.02 (m, 4H), 1.70-1.81 (m, 2H), 1.43-1.51 (m, 9H), 1.21-1.29 (m, 3H)

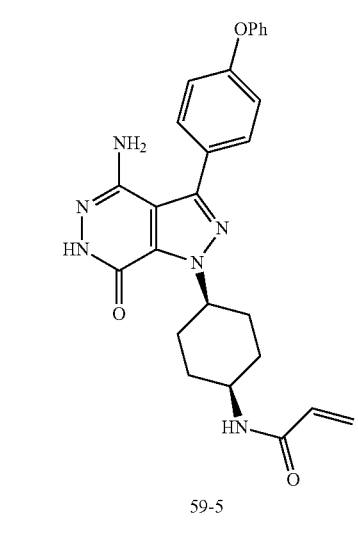 [SMILES: C=CC(=O)N[C@H]1CC[C@@H](n2nc(-c3ccc(Oc4ccccc4)cc3)c3c(N)n[nH]c(=O)c32)CC1]

59-5

Example 57

Compound 59-3

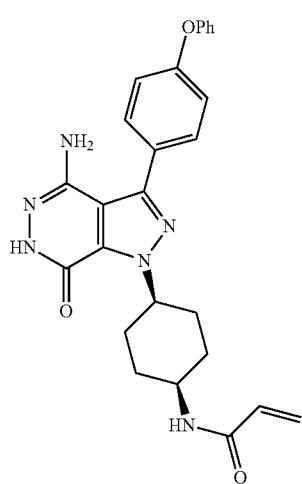 [SMILES: C=CC(=O)N[C@H]1CC[C@@H](n2nc(-c3ccc(Oc4ccccc4)cc3)c3c(N)n[nH]c(=O)c32)CC1]

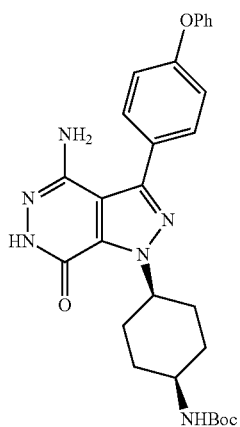

Example 59-2 (80 mg, 0.15 mmol) was added into N₂H₄·H₂O (85%, 2 ml) and the reaction mixture was heated to 100° C. and refluxed for 5 h. After LCMS indicated the reaction was complete, the mixture was cooled down to r.t., and diluted with water (10 ml). The aqueous phase was extracted with EtOAc (20 ml) three times, and the organic phase was washed with saturated brine (10 ml) once, dried over anhydrous $Na_2SO_4$, filtered and subjected to rotary evaporation to give the title compound 59-3 (50 mg, Yield 64%) which was directly used for the next step without purification.

LCMS (ESI) m/z: 517 (M+1).

Compound 59-4

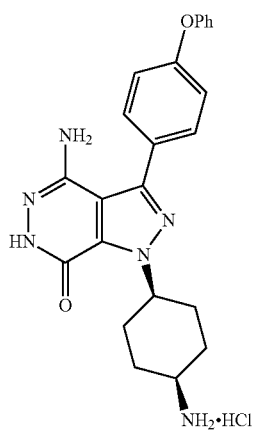

Compound 59-3 (50 mg, 0.01 mmol) was dissolved in a solution of HCl in EtOAc (2 mL, 4 M) and the reaction mixture was stirred at r.t. for 4 h. After LCMS indicated the reaction was complete, the reaction mixture was subjected to rotary evaporation to give the title compound 59-4 (55 mg, Yield 64%) which was directly used for the next step without purification.

LCMS (ESI) m/z: 431 (M+1).

Compound 59-5

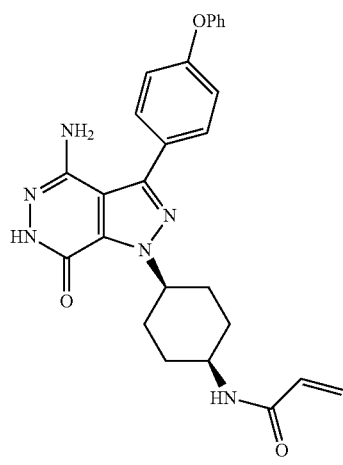 [SMILES: C=CC(=O)N[C@H]1CC[C@@H](n2nc(-c3ccc(Oc4ccccc4)cc3)c3c(N)n[nH]c(=O)c32)CC1]

Acrylic acid (10 mg, 0.1 mmol), HATU (57.3 mg, 0.15 mmol) and DIPEA (0.1 mL) were dissolved in anhydrous DCM (2 mL) under nitrogen atmosphere and the reaction mixture was stirred at r.t. for 10 min, after which compound 59-4 (30 mg, 0.07 mmol) was added. The resulting mixture was stirred at r.t. for 1 h. After LCMS indicated the reaction was complete, the mixture was diluted with water (10 mL) and the aqueous phase was extracted with DCM (10 mL) three times. The organic phase was washed with saturated brine (10 ml) once, dried over anhydrous $Na_2SO_4$, filtered and subjected to rotary evaporation to give a crude product which was purified by preparative liquid chromatography to afford the title compound 59-5 (6 mg, Yield 23.5%).

LCMS (ESI) m/z: 471 (M+1).

$^1$H NMR (400 MHz, $CDCl_3$): δ ppm 9.16 (s, 1H), 7.62 (d, J=8.60 Hz, 2H), 7.36-7.42 (m, 2H), 7.15-7.21 (m, 1H), 7.13 (d, J=8.60 Hz, 2H), 7.08 (d, J=7.94 Hz, 2H), 6.31-6.40 (m, 1H), 6.27 (d, J=10.14 Hz, 1H), 5.65 (dd, $J_1$=9.92 Hz, $J_2$=1.54 Hz, 1H), 4.43 (br. s., 2H), 2.36-2.47 (m, 2H), 1.95-2.08 (m, 4H), 1.79 (t, J=13.23 Hz, 2H)

Example 58

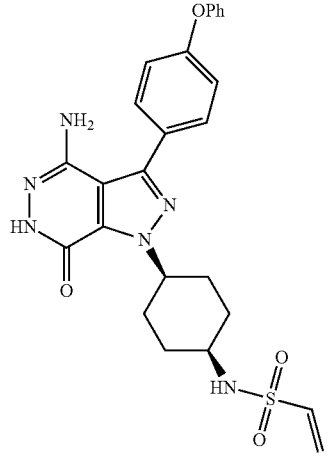 [SMILES: C=CS(=O)(=O)N[C@H]1CC[C@@H](n2nc(-c3ccc(Oc4ccccc4)cc3)c3c(N)n[nH]c(=O)c32)CC1]

In Example 58, the systhesis process was similar to that in Example 57.

LCMS (ESI) m/z: 507 (M+1).

$^1$H NMR (400 MHz, $CDCl_3$): δ ppm 7.69 (d, J=8.60 Hz, 2H), 7.37-7.43 (m, 2H), 7.07-7.19 (m, 4H), 6.68 (dd, J=10.03, 16.43 Hz, 1H), 6.15 (d, J=16.54 Hz, 1H), 5.94 (d, J=9.92 Hz, 1H), 3.46-3.55 (m, 1H), 3.25 (s, 1H), 2.29-2.37 (m, 1H), 1.87-2.09 (m, 2H), 1.80 (t, J=13.56 Hz, 1H).

Example 59
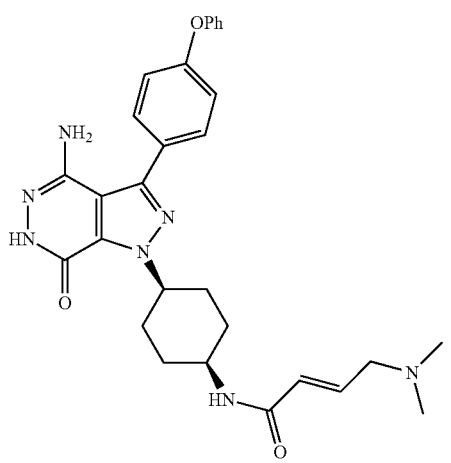 [SMILES: CN(C)C/C=C/C(=O)N[C@H]1CC[C@@H](n2nc(-c3ccc(Oc4ccccc4)cc3)c3c(N)n[nH]c(=O)c32)CC1]
In Example 59, the systhesis process was similar to that in Example 57.
LCMS (ESI) m/z: 528 (M+1).
$^1$H NMR (400 MHz, CDCl$_3$): δ ppm 7.68 (d, J=8.6 Hz, 2H), 7.46-7.32 (m, 2H), 7.23-6.99 (m, 5H), 6.85-6.69 (m, 1H), 6.26 (d, J=15.2 Hz, 1H), 5.49 (br. s., 1H), 4.13 (br. s., 1H), 3.23 (d, J=7.1 Hz, 2H), 2.35 (s, 6H), 2.01 (t, J=13.7 Hz, 4H), 1.89-1.77 (m, 2H), 1.36 (d, J=6.6 Hz, 2H)
Scheme 45
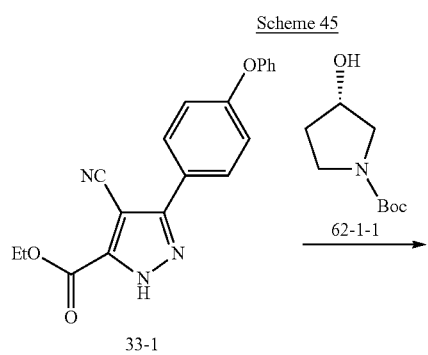
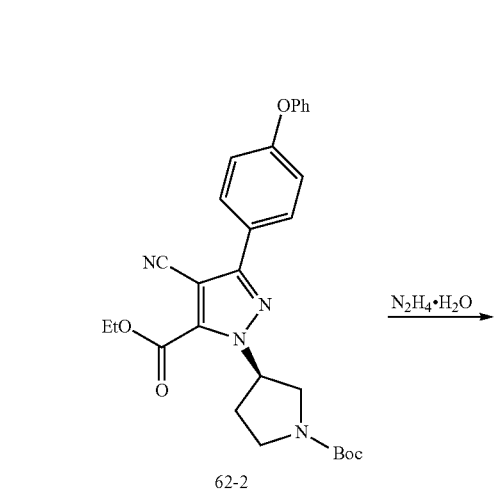
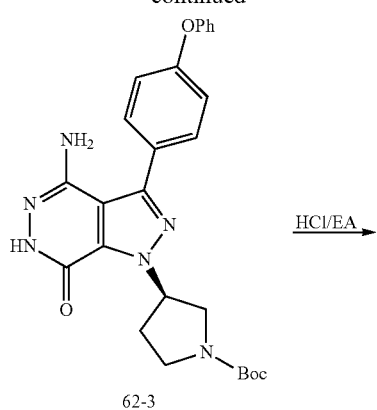
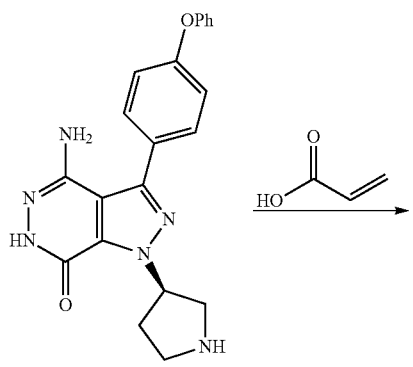
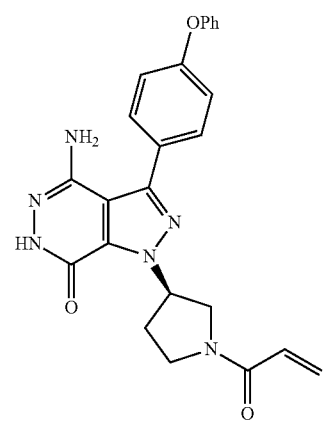

Example 60

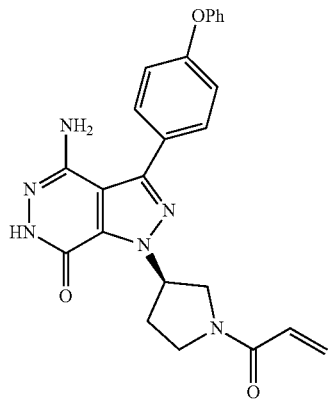 [SMILES: C=CC(=O)N1CC[C@@H](n2nc(-c3ccc(Oc4ccccc4)cc3)c3c(N)n[nH]c(=O)c32)C1]

Compound 62-2

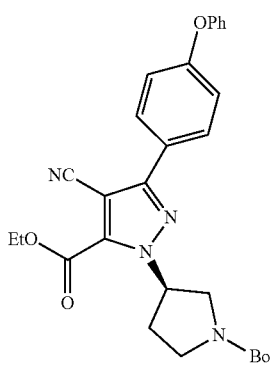

To compound 33-1 (1.0 g, 3.0 mmol) and PPh₃ (1.1 g, 5.4 mmol) in anhydrous DCM (25 ml) was added DIAD (0.91 g, 4.5 mmol) under nitrogen atmosphere at 0° C. and the reaction solution was stirred for 10 min, after which compound 62-1-1 (0.84 g, 4.5 mmol) was added. The reaction solution was warmed to r.t. and stirred for 12 h. After TLC indicated the reaction was complete, saturated NH₄Cl (aq., 200 mL) was added to this solution, and the aqueous phase was extracted with EtOAc (200 mL) three times. The organic phases were combined, washed with saturated brine (100 mL) once, dried over anhydrous Na₂SO₄, filtered and subjected to rotary evaporation to give a crude product which was purified by column chromatography to afford the title compound 62-2 (white solid, 1.3 g, Yield 86.7%).

LCMS (ESI) m/z: 503 (M+1).

Compound 62-3

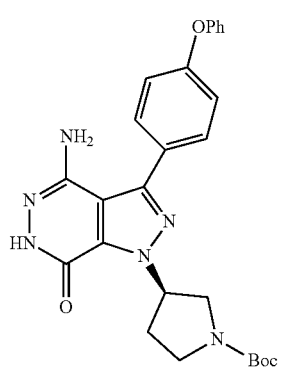 [SMILES: CC(C)(C)OC(=O)N1CC[C@@H](n2nc(-c3ccc(Oc4ccccc4)cc3)c3c(N)n[nH]c(=O)c32)C1]

Compound 62-2 (400 mg, 0.8 mmol) was added into N₂H₄·H₂O (85%, 5 mL), and the reaction mixture was heated to 100° C. and refluxed for 12 h. After LCMS indicated the reaction was complete, the reaction mixture was cooled down to r.t., and washed with water (20 mL). The aqueous phase was extracted with EtOAc (30 mL) three times, and the organic phase was washed with saturated brine (20 mL) once, dried over anhydrous Na₂SO₄, filtered and subjected to rotary evaporation to give the title compound 62-3 (180 mg, Yield 46%) which was directly used for the next step without purification.

LCMS (ESI) m/z: 489 (M+1).

$^1$H NMR (400 MHz, MeOD): δ ppm 7.64 (d, J=8.60 Hz, 2H), 7.32-7.44 (m, 2H), 7.14 (t, J=7.39 Hz, 1H), 7.05 (t, J=8.71 Hz, 4H), 4.08 (q, J=7.06 Hz, 1H), 3.83 (d, J=3.53 Hz, 2H), 3.64-3.74 (m, 1H), 3.45-3.56 (m, 1H), 2.39-2.51 (m, 2H), 1.42 (d, J=8.16 Hz, 9H)

Compound 62-4

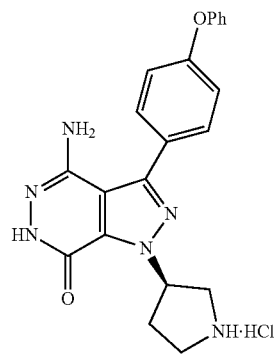

Compound 62-3 (80 mg, 0.16 mmol) was dissolved in a solution of HCl in EtOAc (2 mL, 4 M), and the reaction mixture was stirred at r.t. for 4 h. After LCMS indicated the reaction was complete, the reaction mixture was dried by rotary evaporation to give the title compound 62-4 (55 mg, crude) which was directly used for the next step without any purification.

LCMS (ESI) m/z: 389 (M+1)

Compound 62-5

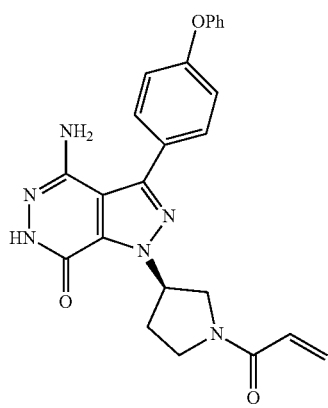 [SMILES: C=CC(=O)N1CC[C@@H](n2nc(-c3ccc(Oc4ccccc4)cc3)c3c(N)n[nH]c(=O)c32)C1]

Compound 62-4 (50 mg, 0.128 mmol, crude), HATU (73 mg, 14 mmol) and DIPEA (41 mg, 0.384 mmol) were dissolved in anhydrous DCM (10 mL) under N₂ atmosphere and the reaction solution was stirred at r.t. for 10 min, after which acrylic acid (14 mg, 0.193 mmol) was added and the resulting solution was stirred at r.t. for 1 h. After LCMS indicated the reaction was complete, the reaction solution was diluted with water (10 mL) and the aqueous phase was extracted with DCM (10 mL) three times. The organic phase was washed with saturated brine (10 mL) once, dried over anhydrous Na₂SO₄, filtered and subjected to rotary evaporation to give a crude product which was purified by preparative liquid chromatography to afford the title compound 62-5 (17 mg, Yield 30%).

LCMS (ESI) m/z: 443 (M+1).

¹H NMR (400 MHz, CDCl₃): δ ppm 7.63-7.67 (m, 2H), 7.36-7.42 (m, 2H), 7.13-7.18 (m, 1H), 7.04-7.11 (m, 4H), 6.53-6.71 (m, 1H), 6.16-6.36 (m, 1H), 5.68-5.78 (m, 1H), 4.12-4.19 (m, 1H), 3.96-4.08 (m, 2H), 3.82-3.93 (m, 1H), 3.69-3.78 (m, 1H), 2.56-2.64 (m, 1H), 2.48-2.55 (m, 1H)

Example 61

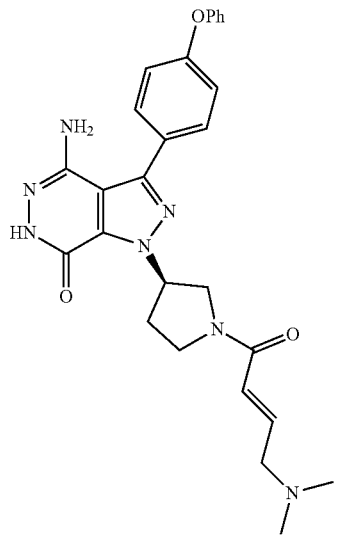 [SMILES: CN(C)C/C=C/C(=O)N1CC[C@@H](n2nc(-c3ccc(Oc4ccccc4)cc3)c3c(N)n[nH]c(=O)c32)C1]

In Example 61, the synthesis process was similar to that in Example 60.

LCMS (ESI) m/z: 500 (M+1).

¹H NMR (400 MHz, CDCl₃): δ ppm 7.64 (d, J=7.3 Hz, 2H), 7.39 (t, J=7.9 Hz, 2H), 7.16 (t, J=7.3 Hz, 1H), 7.07 (t, J=7.8 Hz, 3H), 6.81 (dd, J=5.9, 15.2 Hz, 1H), 6.53-6.39 (m, 1H), 6.24-6.16 (m, 1H), 4.15 (d, J=5.4 Hz, 1H), 4.10-3.94 (m, 2H), 3.88 (d, J=11.5 Hz, 1H), 3.72 (dd, J=6.5, 12.1 Hz, 1H), 3.14 (dd, J=6.6, 13.4 Hz, 2H), 2.63-2.50 (m, 2H), 2.25 (s, 3H), 2.22 (s, 2H)

Scheme 46

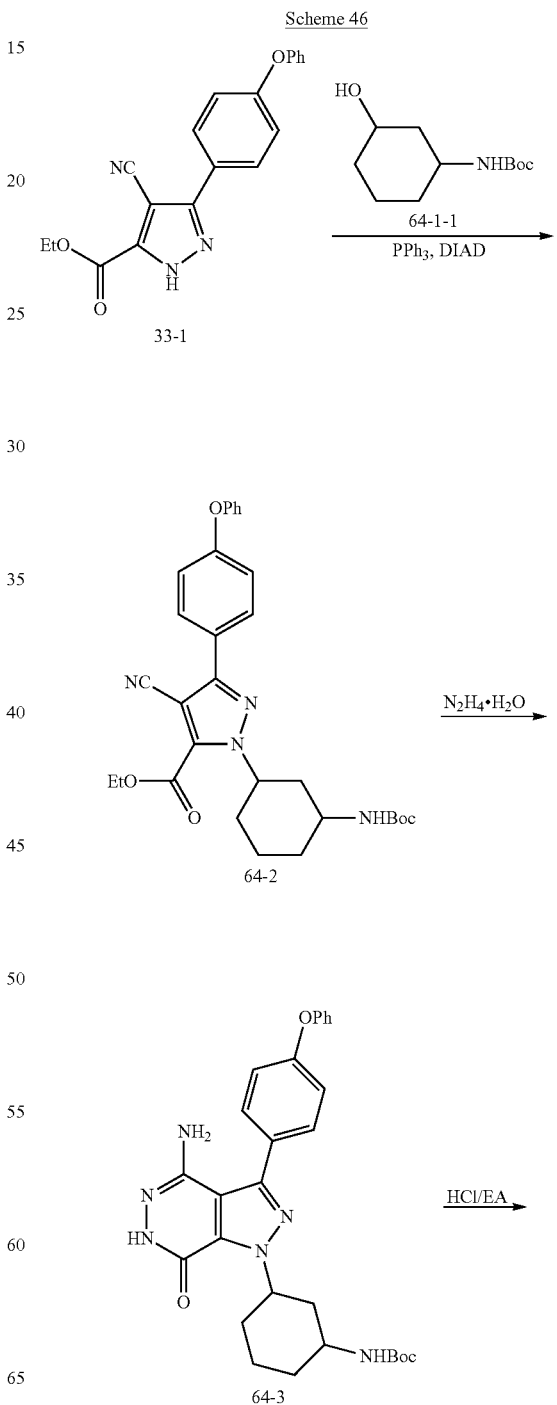

-continued

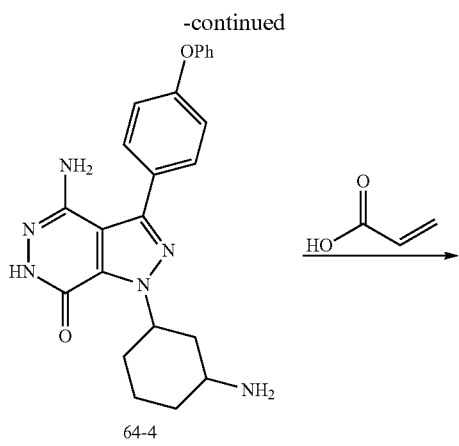
64-4

Compound 64-2

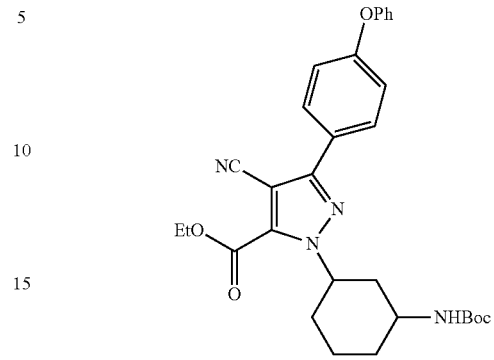

To a solution of compound 33-1 (300 mg, 0.7 mmol) and PPh₃ (354 g, 1.35 mmol) in anhydrous DCM (10 mL) was added DIAD (272 mg, 1.35 mmol) under nitrogen atmosphere at 0° C. and the reaction solution was stirred for 10 min, after which compound 64-1-1 (290 mg, 1.35 mmol) was added. The resulting reaction solution was warmed to r.t. and stirred for 12 h. After TLC indicated the reaction was complete, saturated NH₄Cl solution (aq., 50 mL) was added to this solution, and the aqueous phase was extracted with EtOAc (200 mL) three times. The organic phases were combined, washed with saturated brine (20 mL) once, dried over anhydrous Na₂SO₄, filtered and subjected to rotary evaporation to give a residue which was purified by column chromatography to afford the title compound 64-2 (white solid, 380 mg, Yield 79.6%).

LCMS (ESI) m/z: 431 (M-100).

Compound 64-3

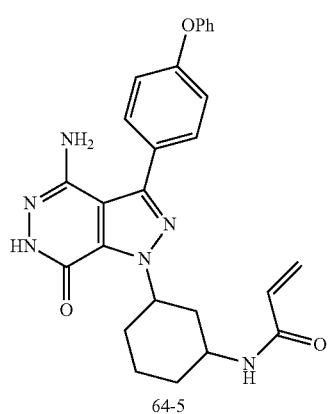 [SMILES: C=CC(=O)NC1CCCC(n2nc(-c3ccc(Oc4ccccc4)cc3)c3c(N)n[nH]c(=O)c32)C1]
64-5

Example 62

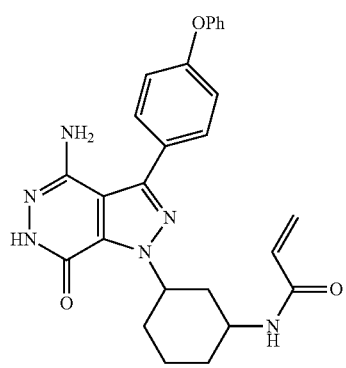 [SMILES: C=CC(=O)NC1CCCC(n2nc(-c3ccc(Oc4ccccc4)cc3)c3c(N)n[nH]c(=O)c32)C1]

Compound 64-2 (380 mg, 0.72 mmol) was added into N₂H₄·H₂O (85%, 4 mL), and the reaction mixture was heated to 100° C. and refluxed for 8 h. After LCMS indicated the reaction was complete, the reaction mixture was cooled down to r.t. and washed with water (20 mL). The aqueous phase was extracted with EtOAc (30 mL) three times. The organic phase was washed with saturated brine (20 mL) once, dried over anhydrous Na₂SO₄, filtered and evaporated to dryness by rotatory evaporation to give the title compound 64-3 (300 mg, Yield 81%) which was directly used for the next step without purification.

LCMS (ESI) m/z: 517 (M+1)

Compound 64-4

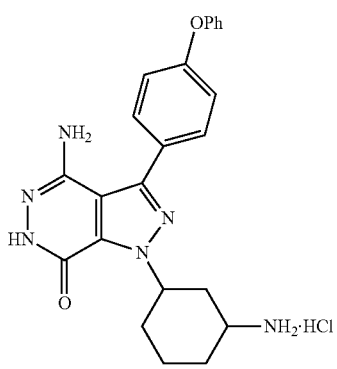

Compound 64-3 (300 mg, 0.58 mmol) was dissolved in a solution of HCl in EtOAc (6 mL, 4 M) and the reaction mixture was stirred at r.t. for 4 h. After LCMS indicated the reaction was complete, the reaction mixture was evaporated to dryness by rotatory evaporation to give the title compound 64-4 (260 mg, crude) which was directly used for the next step without purification.

LCMS (ESI) m/z: 452 (M+1).

$^1$H NMR (400 MHz, CDCl$_3$): δ ppm 7.63-7.76 (m, 2H), 7.35-7.47 (m, 2H), 7.02-7.25 (m, 5H), 5.72 (t, J=4.65 Hz, 1H), 3.98-4.13 (m, 1H), 2.42-2.65 (m, 1H), 1.85-2.31 (m, 4H), 1.55-1.83 (m, 1H)

Compound 64-5

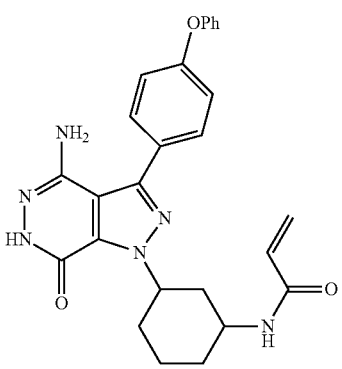 [SMILES: C=CC(=O)NC1CCCC(n2nc(-c3ccc(Oc4ccccc4)cc3)c3c(N)n[nH]c(=O)c32)C1]

Compound 64-4 (100 mg, 0.24 mmol, crude), HATU (137 mg, 0.36 mmol) and DIPEA (78.4 mg, 0.72 mmol) were dissolved in anhydrous DCM (5 mL) under nitrogen atmosphere and the reaction mixture was stirred at r.t. for 10 min, after which acrylic acid (26 mg, 0.36 mmol) was added and the resulting mixture was stirred at r.t. for 1 h. After LCMS indicated the reaction was complete, the reaction mixture was washed with water (230 mL) and the aqueous phase was extracted with DCM (50 mL) three times. The organic phase was washed with saturated brine (20 mL) once, dried over anhydrous Na$_2$SO$_4$, filtered and evaporated to dryness by rotatory evaporation to give a crude product which was purified by preparative liquid chromatography to afford the title compound 64-5 (60 mg, Yield 18%).

LCMS (ESI) m/z: 471 (M+1).

$^1$H NMR (400 MHz, MeOD): δ ppm 7.71 (d, J=9.03 Hz, 2H), 7.38-7.49 (m, 2H), 7.05-7.24 (m, 5H), 6.34-6.49 (m, 1H), 6.18-6.31 (m, 1H), 5.68 (dd, J=1.51, 10.04 Hz, 1H), 4.51 (br. s., 1H), 3.63-3.77 (m, 1H), 3.20 (d, J=7.53 Hz, 1H), 2.30-2.47 (m, 1H), 2.14-2.23 (m, 1H), 2.09 (d, J=6.02 Hz, 2H), 1.71-1.97 (m, 3H)

Example 63

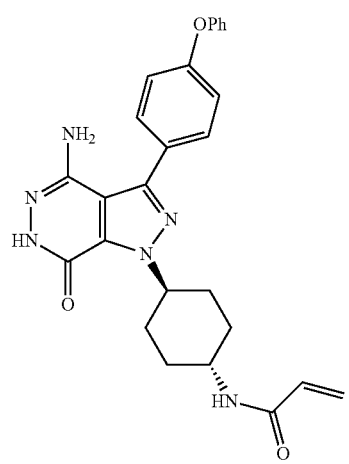 [SMILES: C=CC(=O)N[C@H]1CC[C@H](n2nc(-c3ccc(Oc4ccccc4)cc3)c3c(N)n[nH]c(=O)c32)CC1]

In Example 63, the systhesis process was similar to that in Example 57.

LCMS (ESI) m/z: 471 (M+1).

$^1$H NMR (400 MHz, CDCl$_3$): δ ppm 9.16 (s, 1H), 7.62 (d, J=8.60 Hz, 2H), 7.36-7.42 (m, 2H), 7.15-7.21 (m, 1H), 7.13 (d, J=8.60 Hz, 2H), 7.08 (d, J=7.94 Hz, 2H), 6.31-6.40 (m, 1H), 6.27 (d, J=10.14 Hz, 1H), 5.65 (dd, J$_1$=9.92 Hz, J$_2$=1.54 Hz, 1H), 4.43 (br. s., 2H), 4.01 (s., 1H), 2.36-2.47 (m, 1H), 1.95-2.08 (m, 4H), 1.79 (t, J=13.23 Hz, 2H)

Example 64

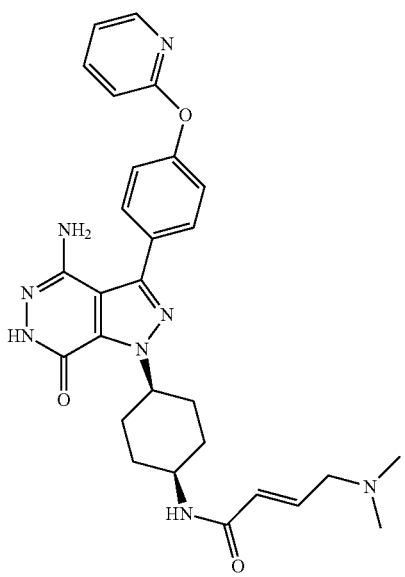 [SMILES: CN(C)C/C=C/C(=O)N[C@H]1CC[C@@H](n2nc(-c3ccc(Oc4ccccn4)cc3)c3c(N)n[nH]c(=O)c32)CC1]

In Example 64, the systhesis process was similar to that in Example 39.
LCMS (ESI) m/z: 529 (M+1). $^1$H NMR (400 MHz, MeOD): δ ppm 8.17 (d, J=3.51 Hz, 1H), 7.88-7.96 (m, 1H), 7.77 (d, J=8.53 Hz, 2H), 7.30 (d, J=8.53 Hz, 2H), 7.15-7.23 (m, 1H), 7.12 (d, J=8.03 Hz, 1H), 6.71-6.88 (m, 1H), 6.34 (d, J=15.56 Hz, 1H), 5.47-5.62 (m, 1H), 4.62 (s, 2H), 4.17 (br. s., 1H), 2.49 (br. s., 6H), 2.27-2.41 (m, 2H), 2.06 (t, J=12.30 Hz, 4H), 1.80-1.95 (m, 2H)
Example 65
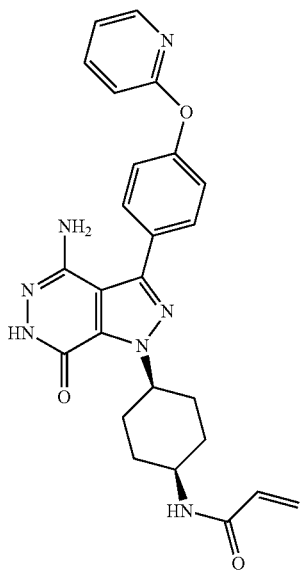 [SMILES: C=CC(=O)N[C@H]1CC[C@@H](n2nc(-c3ccc(Oc4ccccn4)cc3)c3c(N)n[nH]c(=O)c32)CC1]
In Example 65, the systhesis process was similar to that in Example 39.
LCMS (ESI) m/z: 472 (M+1).
$^1$H NMR (400 MHz, CDCl$_3$): δ ppm 9.15 (s, 1H), 8.22 (d, J=3.51 Hz, 1H), 7.65-7.81 (m, 2H), 7.31 (d, J=8.03 Hz, 2H), 6.98-7.11 (m, 2H), 6.71 (br. s., 1H), 6.18-6.44 (m, 2H), 5.67 (d, J=10.04 Hz, 1H), 5.24 (br. s., 1H), 4.42 (br. s., 1H), 4.38 (s., 2H), 2.32-2.49 (m, 2H), 2.03 (t, J=14.05 Hz, 4H), 1.81 (br. s., 2H)
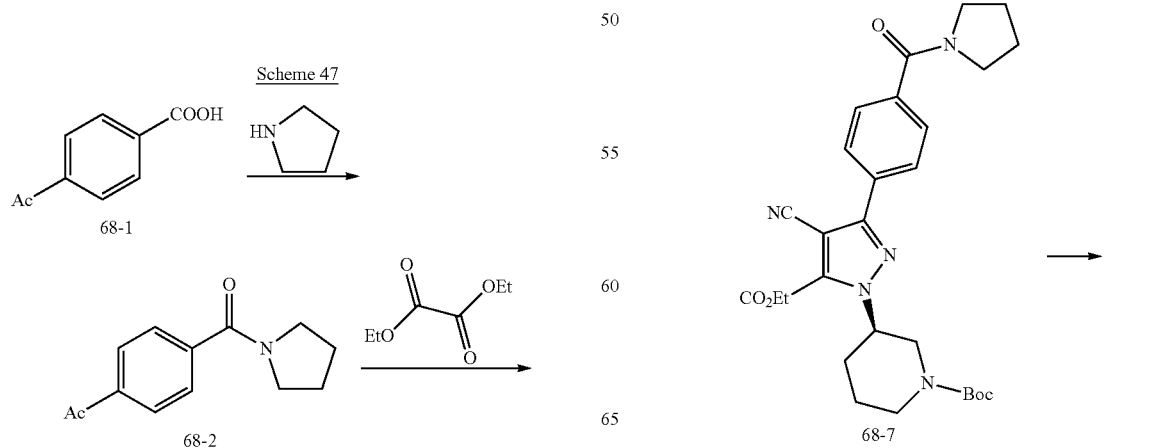
Scheme 47

-continued

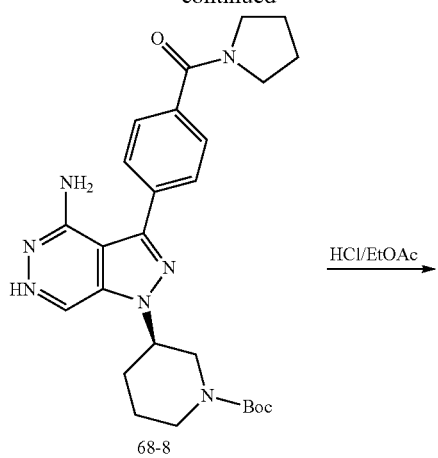

68-8

HCl/EtOAc →

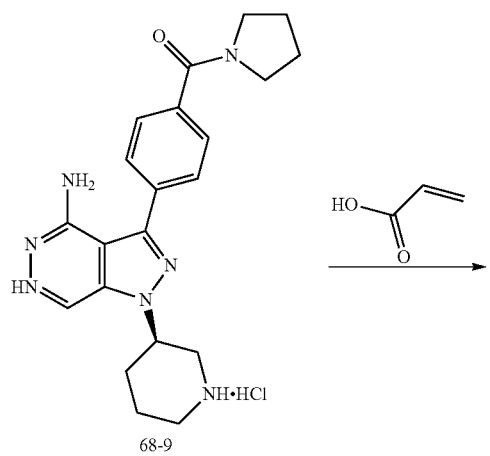

68-9

HO—⫶⫶⫶ (acrylic acid) →

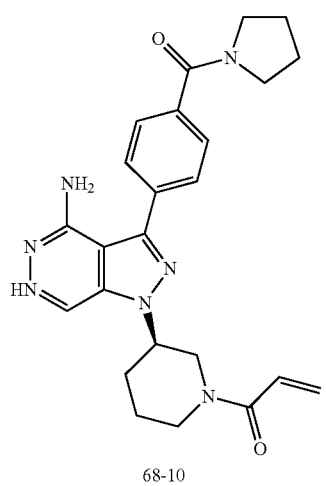

68-10

Example 66

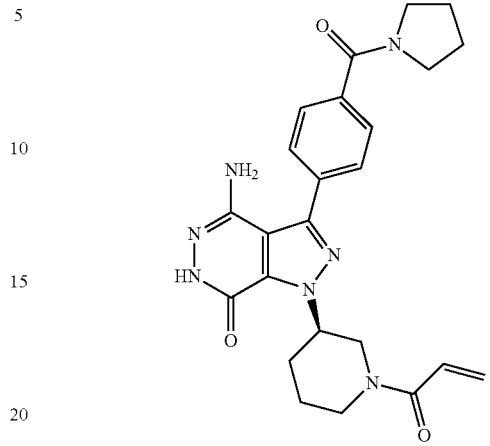

Compound 68-2

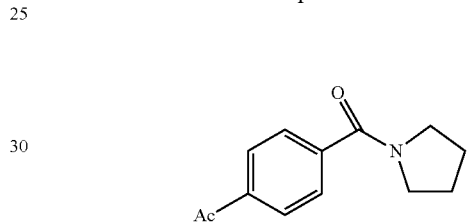

Pyrrolidine (1.3 g, 18.27 mmol), HATU (6.95 g, 18.2 mmol) and DIPEA (4.72 g, 36.5 mmol) were dissolved in anhydrous DCM (20 mL) under nitrogen atmosphere and the reaction solution was stirred at r.t. for 10 min, after which compound 68-1 (2.0 g, 12.18 mmol) was added. The reaction solution was stirred at r.t. for 1 h. After LCMS indicated the reaction was complete, the reaction mixture was diluted with water (100 mL) and the aqueous phase was extracted with DCM (150 mL) three times. The organic phase was washed with saturated brine (50 mL) once, dried over anhydrous Na$_2$SO$_4$, filtered and evaporated to dryness by rotatory evaporation to give a residue which was purified by silica gel column chromatography to afford the title compound 68-2 (light yellow solid, 2.0 g, Yield 88%).

LCMS (ESI) m/z: 218 (M+1)

Compound 68-3

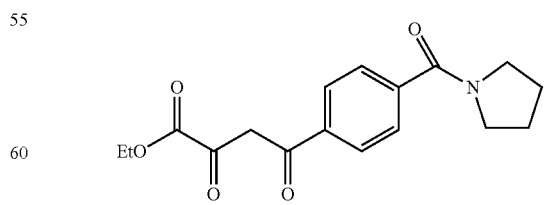

Compound 68-2 (1.7 g, 7.82 mmol) and diethyl oxalate (2.86 g, 19.5 mmol) were dissolved in anhydrous THF (20 mL) and the reaction solution was heated to 85° C. and stirred for 10 min under N$_2$ atmosphere, after which NaH (0.56 g, 14.0 mmol, purity 60%) was added slowly and the resulting solution was stirred for 2 h. After TLC indicated the reaction was complete, saturated NH₄Cl solution (aq., 100 mL) was added to this solution, and the aqueous phase was extracted with EtOAc (100 mL) three times. The organic phases were combined, washed with saturated brine (50 mL) once, dried over anhydrous Na₂SO₄, filtered and evaporated to dryness by rotary evaporation to give a residue which was purified by silica gel column chromatography to afford the title compound 68-3 (white solid, 800 mg, Yield 32.4%).

LCMS (ESI) m/z: 318 (M+1)

Compound 68-4

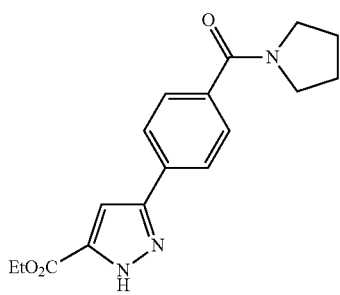 [SMILES: CCOC(=O)c1cc(-c2ccc(C(=O)N3CCCC3)cc2)n[nH]1]

To a solution of compound 68-3 (1.9 g, 5.99 mmol) and HOAc (3.8 mL) in EtOH (3.8 mL) was added slowly 80% N₂H₄.H₂O (0.6 g, 17.9 mmol) under nitrogen atmosphere and the reaction solution was stirred at r.t. for 30 min. After TLC indicated the reaction was complete, the reaction was quenched with water (100 mL) and the aqueous phase was extracted with EtOAc (100 mL) three times. The organic phases were combined, washed with saturated brine (20 mL) once, dried over anhydrous Na₂SO₄, filtered and evaporated to dryness by rotary evaporation to give a residue which was purified by silica gel column chromatography to afford the title compound 68-4 (light yellow solid, 1.6 g, Yield 85.3%).

LCMS (ESI) m/z: 314 (M+1)

Compound 68-5

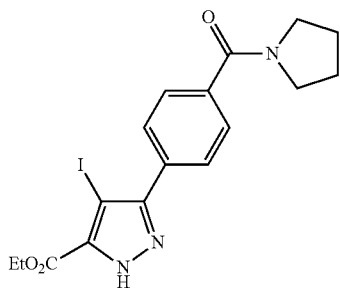 [SMILES: CCOC(=O)c1[nH]nc(-c2ccc(C(=O)N3CCCC3)cc2)c1I]

Compound 68-4 (1.5 g, 4.79 mmol), NIS (1.08 g, 4.79 mmol) and CAN (394 mg, 0.72 mmol) were dissolved in acetonitrile (12 mL) under nitrogen atmosphere and the reaction solution was heated to 80° C. and stirred for 1 h. After LCMS indicated the reaction was complete, the reaction was quenched with water (50 mL) and the aqueous phase was extracted with EtOAc (100 mL) three times. The organic phases were combined, washed with saturated brine (20 mL) once, dried over anhydrous Na₂SO₄, filtered and evaporated to dryness by rotary evaporation to give a residue which was purified by silica gel column chromatography to afford the title compound 68-5 (light yellow solid, 1.5 g, Yield 71.3%).

LCMS (ESI) m/z: 440 (M+1)

Compound 68-6

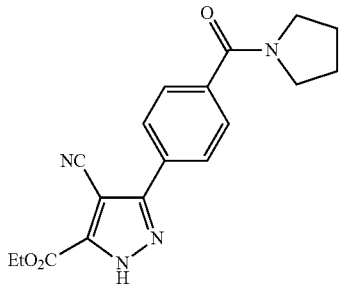 [SMILES: CCOC(=O)c1[nH]nc(-c2ccc(C(=O)N3CCCC3)cc2)c1C#N]

To a solution of compound 68-5 (520 mg, 1.18 mmol), cupric cyanide (Cu(CN)₂) (211 mg, 2.36 mmol) in anhydrous DMF (5 mL) was added Pd(dppf)Cl₂ (43 mg, 0.59 mmol) under nitrogen atmosphere and the reaction solution was heated to 100° C. and reacted for 12 h. After TLC indicated the reaction was complete, the reaction solution was cooled down to r.t. and the reaction was quenched with water (20 mL). The aqueous phase was extracted with EtOAc (50 mL) three times. Then the organic phases were combined, washed with saturated brine (20 mL) once, dried over anhydrous Na₂SO₄, filtered and evaporated to dryness by rotary evaporation to give a residue which was purified by silica gel column chromatography to afford the title compound 68-6 (white solid, 200 mg, Yield 50%).

LCMS (ESI) m/z: 339 (M+1)

Compound 68-7

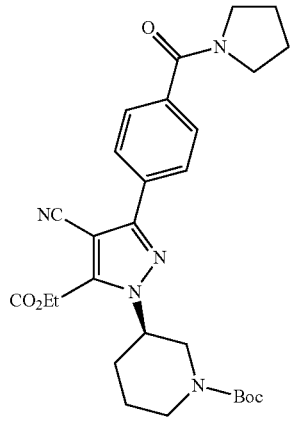 [SMILES: CCOC(=O)c1c(C#N)c(-c2ccc(C(=O)N3CCCC3)cc2)nn1[C@@H]1CCCN(C(=O)OC(C)(C)C)C1]

To a solution of compound 68-6 (200 mg, 0.59 mmol) and PPh₃ (310 mg, 1.18 mmol) in anhydrous THF (10 mL) was added DIAD (239 mg, 1.18 mmol) under nitrogen atmosphere at 0° C. and the reaction solution was stirred for 10 min, after which compound (S)-1-BOC-3-Hydroxypiperidine (238 mg, 1.18 mmol) was added. Then the resulting solution was warmed to r.t. and stirred for 12 h. After TLC indicated the reaction was complete, saturated NH₄Cl solution (aq., 20 mL) was added to this mixture, and the aqueous phase was extracted with EtOAc (20 mL) three times. The organic phases were combined, washed with saturated brine (10 mL) once, dried over anhydrous Na₂SO₄, filtered and evaporated to dryness by rotatory evaporation to give a residue which was purified by column chromatography to afford the title compound 68-7 (white solid, 180 mg, Yield 60%).

LCMS (ESI) m/z: 522 (M-100)

Compound 68-8

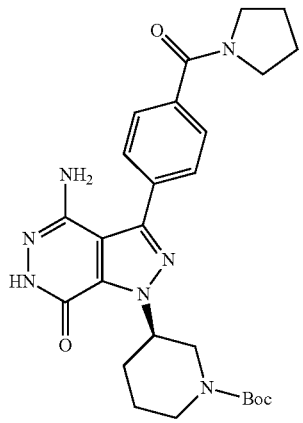 [SMILES: CC(C)(C)OC(=O)N1CCC[C@@H](n2nc(-c3ccc(C(=O)N4CCCC4)cc3)c3c(N)n[nH]c(=O)c32)C1]

Compound 68-7 (100 mg, 0.38 mmol) was added into N₂H₄·H₂O (85%, 4 mL), and the reaction solution was heated to 100° C. and refluxed for 8 h. After LCMS indicated the reaction was complete, the reaction solution was cooled down to r.t. and diluted with water (20 mL). The aqueous phase was extracted with EtOAc (30 mL) three times. The organic phase was washed with saturated brine (20 mL) once, dried over anhydrous Na₂SO₄, filtered and evaporated to dryness by rotatory evaporation to give the title compound 68-8 (60 mg, Yield 61%) which was directly used for the next step without purification.

LCMS (ESI) m/z: 408 (M+1)

Compound 68-9

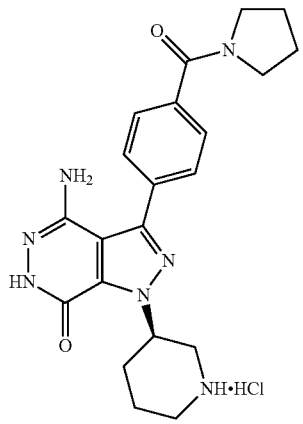

Compound 68-8 (60 mg, 0.12 mmol) was dissolved in a solution of HCl in EtOAc (5 mL, 4 M) and the reaction solution was stirred at r.t. for 3 h. After LCMS indicated the reaction was complete, the reaction solution was evaporated to dryness by rotatory evaporation to give the title compound 68-9 (40 mg, crude) which was directly used for the next step without purification.

LCMS (ESI) m/z: 408 (M+1)

Compound 68-10

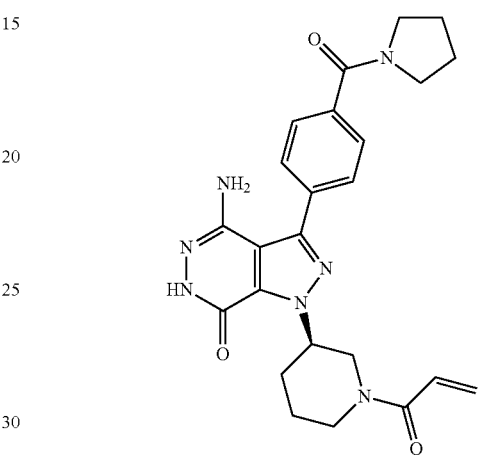

Acrylic acid (4 mg, 0.05 mmol), HATU (21 mg, 0.05 mmol) and DIPEA (28.5 mg, 0.22 mmol) were dissolved in anhydrous DCM (5 mL) under nitrogen atmosphere and the reaction solution was stirred at r.t. for 10 min, after which compound 68-9 (15 mg, 0.036 mmol) was added and the resulting solution was stirred at r.t. for 1 h. After LCMS indicated the reaction was complete, the reaction solution was diluted with water (10 mL) and the aqueous phase was extracted with DCM (20 mL) three times. The organic phase was washed with saturated brine (10 mL) once, dried over anhydrous Na₂SO₄, filtered and evaporated to dryness by rotatory evaporation to give a crude product which was purified by preparative liquid chromatography to afford the title compound 68-10 (6 mg, Yield 35.4%).

LCMS (ESI) m/z: 462 (M+1).

$^1$H NMR (400 MHz, MeOD): δ ppm 7.81 (d, J=8.16 Hz, 2H), 7.67 (d, J=8.16 Hz, 2H), 6.66-6.90 (m, 1H), 6.15 (t, J=17.20 Hz, 1H), 5.59-5.80 (m, 1H), 5.53 (br. s., 1H), 4.18-4.40 (m, 2H), 3.74-3.90 (m, 1H), 3.62 (t, J=6.84 Hz, 3H), 3.52 (t, J=6.51 Hz, 2H), 2.29 (d, J=4.63 Hz, 2H), 1.89-2.13 (m, 6H)

Example 67
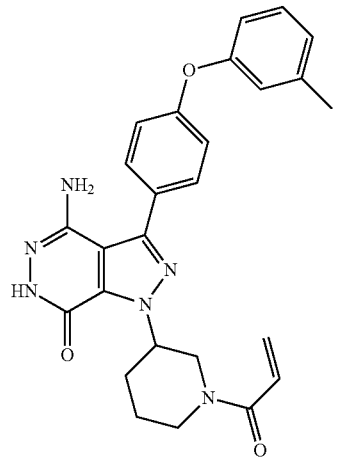 [SMILES: C=CC(=O)N1CCCC(n2nc(-c3ccc(Oc4cccc(C)c4)cc3)c3c(N)n[nH]c(=O)c32)C1]
In Example 67, the systhesis process was similar to that in Example 20.
$^1$H NMR (400 MHz, CDCl$_3$): δ ppm 7.90 (d, 2H), 7.88 (d, 1H), 7.646-7.648 (d, 2H), 7.015-7.150 (m, 2H), 6.90-6.96 (m, 1H), 6.793-6.835 (m, 1H), 6.151-6.240 (m, 1H), 5.66-5.81 (m, 1H) 5.14-5.25 (m, 1H), 4.61-4.69 (m, 1H), 4.27-4.39 (m, 1H), 4.06-4.16 (m, 1H), 3.68-3.80 (m, 1H) 3.42-3.54 (m, 1H), 3.121-3.174 (m, 1H), 2.507 (s, 3H), 2.274 (s., 2H), 1.2.055 (s, 1H), 1.676 (s, 1H).
Example 68
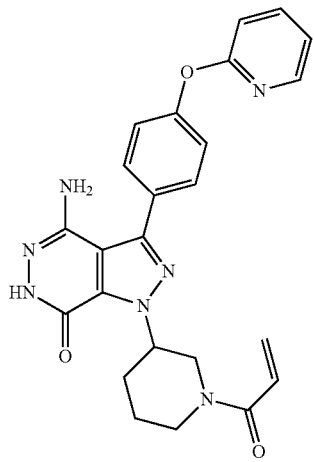 [SMILES: C=CC(=O)N1CCCC(n2nc(-c3ccc(Oc4ccccn4)cc3)c3c(N)n[nH]c(=O)c32)C1]
In Example 68, the systhesis process was similar to that in Example 20.
LCMS (ESI) m/z: 458 (M+1).
$^1$H NMR (400 MHz, CDCl$_3$-d): δ ppm 10.091-9.975 (d, 1H), 8.241-8.230 (t, 1H), 7.779-7.710 (m, 2H), 7.322-7.302 (d, 1H), 7.090-7.007 (m, 1H), 6.655-6.629 (d, 1H), 6.292-6.251 (d, 1H), 5.729-5.502 (m, 1H), 4.844-4.778 (d, 2H), 4.617-4.585 (d, 1H), 4.338-4.306 (d, 1H), 4.010 (s, 1H), 3.644-3.521 (m, 1H), 3.223 (s, 1H), 2.864-2.838 (d, 1H), 2.350 (s, 1H), 2.026-1.993 (d, 1H), 1.780 (s, 1H), 1.601 (s, 1H).
Scheme 48
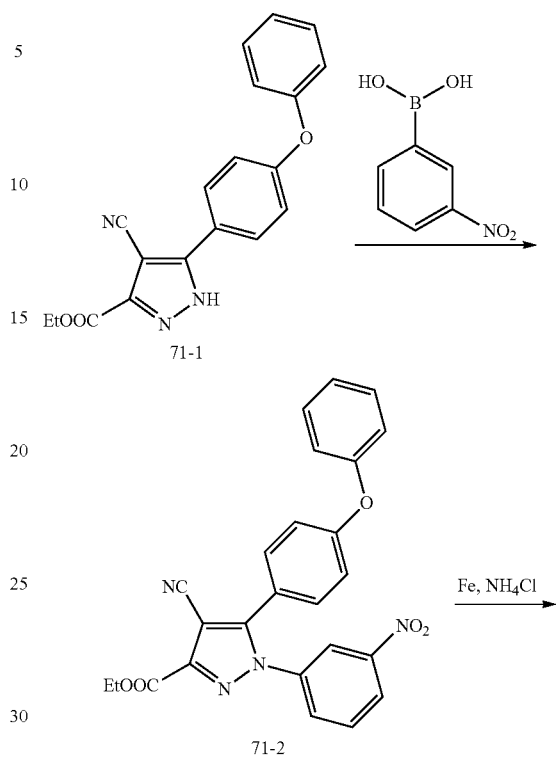
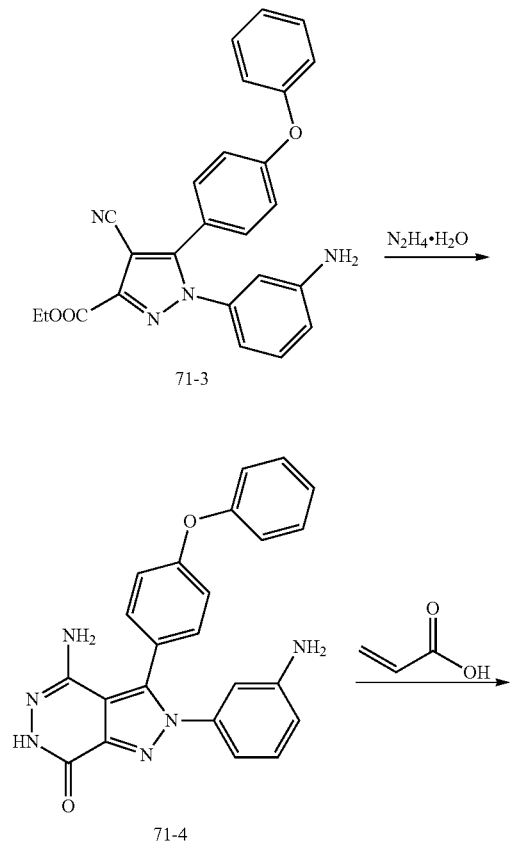

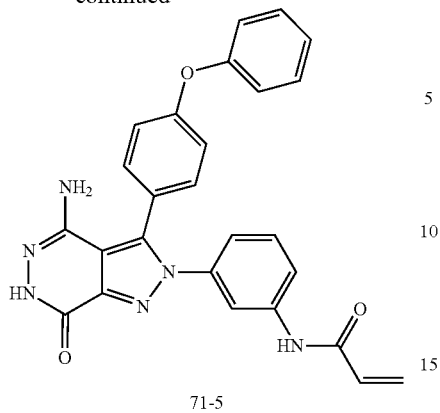

71-5

Example 69

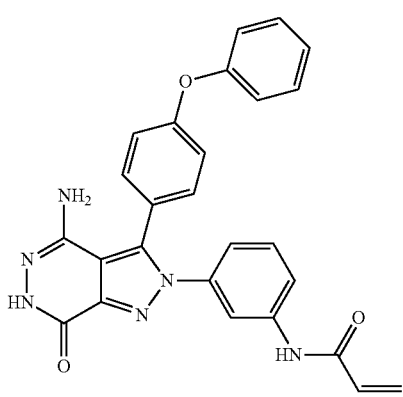 [SMILES: C=CC(=O)Nc1cccc(-n2nc3c(=O)[nH]nc(N)c3c2-c2ccc(Oc3ccccc3)cc2)c1]

Compound 71-2

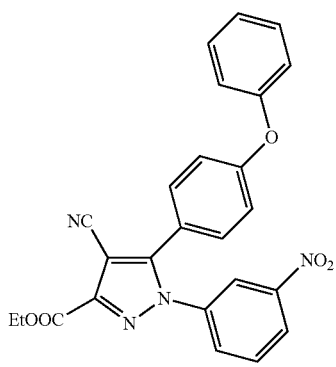 [SMILES: CCOC(=O)c1nn(-c2cccc([N+](=O)[O-])c2)c(-c2ccc(Oc3ccccc3)cc2)c1C#N]

To a solution of compound 71-1 (4 g, 11.9 mmol), 3-nitrophenylboronic acid (4 g, 24 mmol) and pyridine (2 g, 24 mmol) in DCM (80 mL) was added Cu(Ac)$_2$ (3.2 g, 18 mmol) and the reaction solution was stirred at oxygen atmosphere for 48 h, followed by filtration and concentration. The residue was purified by column chromatography to give the title compound 71-2 (yellow solid, 4 g, Yield 74%).

$^1$H NMR (400 MHz, CDCl$_3$): δ ppm 8.417 (s, 2H), 8.036-8.018 (d, 2H), 7.860 (s, 1H), 7.736 (s, 1H), 7.400 (s, 2H), 7.186-7.106 (m, 5H), 4.446-4.429 (d, 2H), 1.415 (s, 3H).

Compound 71-3

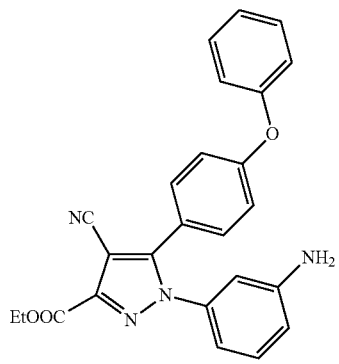

Compound 71-2 (2 g, 4.4 mmol) was dissolved in EtOH (30 mL) and water (6 mL) at r.t., after which iron powder (1.2 g, 22 mmol) and NH$_4$Cl (1.2 g, 22 mmol) were added. The reaction solution was heated to 60° C. and stirred for 2 h, followed by filtration. The filtrate was evaporated to dryness by rotatory evaporation to give the title compound 71-3 (yellow solid, 1.7 g, Yield 94%) which was used for the next step without purification.

$^1$H NMR (400 MHz, CDCl$_3$): δ ppm 7.925-7.951 (d, 2H), 7.287-7.730 (m, 2H), 7.178-7.198 (m, 2H), 6.991-7.010 (m, 6H), 6.698-6.730 (m, 3H), 4.279-4.333 (m, 2H), 1.275 (s, 3H).

Compound 71-4

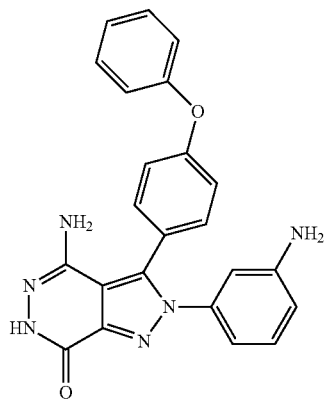 [SMILES: Nc1cccc(-n2nc3c(=O)[nH]nc(N)c3c2-c2ccc(Oc3ccccc3)cc2)c1]

Compound 71-3 (1.2 g, 2.8 mmol) was added into N$_2$H$_4$.H$_2$O (85%, 20 mL), and the reaction solution was heated to 100° C. and refluxed for 3 h, followed by cooled down to r.t. and diluted with water (20 mL). The aqueous phase was extracted with EtOAc (30 mL) three times. Then the organic phase was washed with saturated brine (20 mL) once, dried over anhydrous Na$_2$SO$_4$, filtered and evaporated to dryness by rotatory evaporation to give the title compound 71-4 (yellow powder, 400 mg, Yield 36.3%).

LCMS (ESI) m/z: 411 (M+1)

Compound 71-5

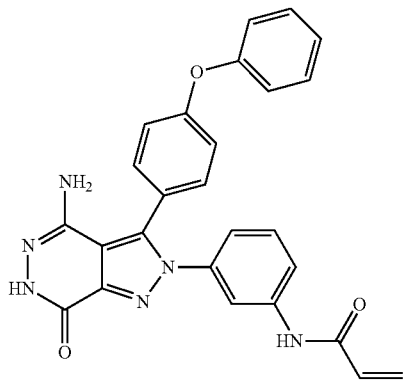 [SMILES: C=CC(=O)Nc1cccc(-n2nc3c(=O)[nH]nc(N)c3c2-c2ccc(Oc3ccccc3)cc2)c1]

Acrylic acid (35 mg, 0.48 mmol), HATU (222 mg, 0.58 mmol) and TEA (98 mg, 0.96 mmol) were dissolved in anhydrous DMF (4 mL) under nitrogen atmosphere and the reaction solution was stirred at r.t. for 10 min, after which compound 71-4 (200 mg, 0.78 mmol) was added and the resulting solution was stirred at r.t. for 48 h, followed by diluted with water (20 mL). The aqueous phase was extracted with DCM (20 mL) three times. Then the organic phase was washed with saturated brine (10 mL) once, dried over anhydrous $Na_2SO_4$, filtered and evaporated to dryness by rotatory evaporation to give a crude product which was purified by preparative liquid chromatography to afford the title compound 71-5 (yellow solid, 3.7 mg, Yield 1.7%).

$^1$H NMR (400 MHz, $CDCl_3$): δ ppm 8.094 (s, 1H), 7.732-7.753 (d, 3H), 7.378-7.471 (m, 4H), 7.077-7.142 (m, 5H), 6.332-6.423 (m, 2H), 5.757-5.787 (d, 1H).

-continued

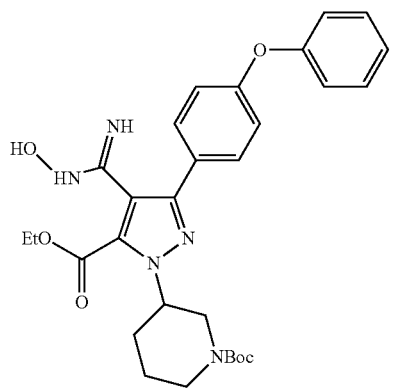

72-2

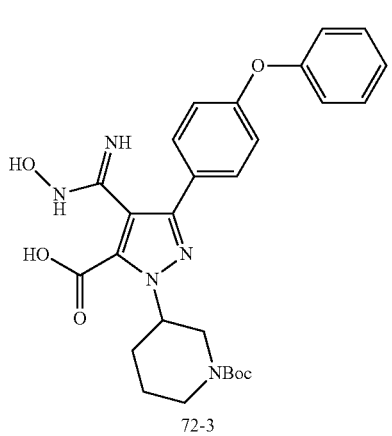

72-3

Scheme 49

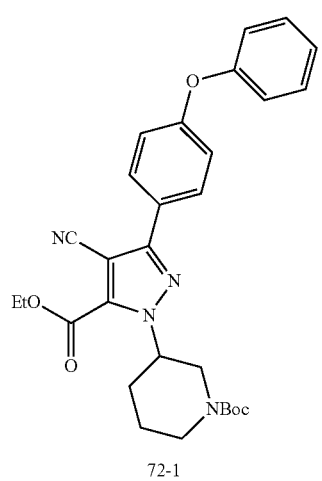

72-1

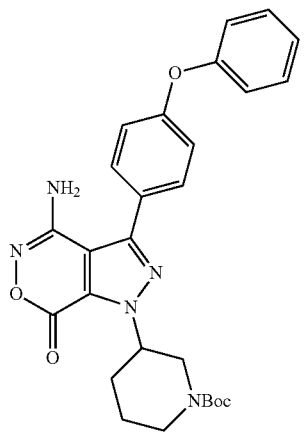

72-4

329
-continued

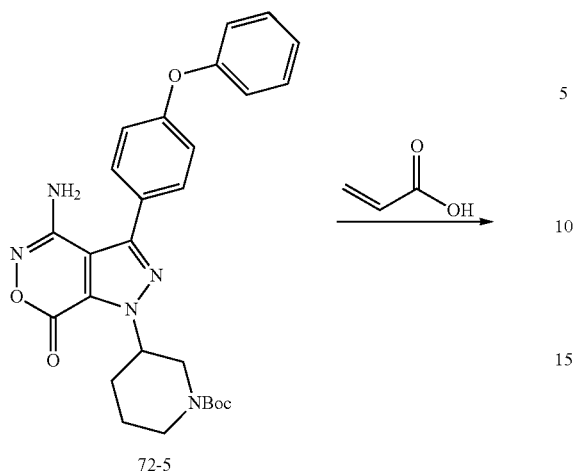

72-5

Example 70

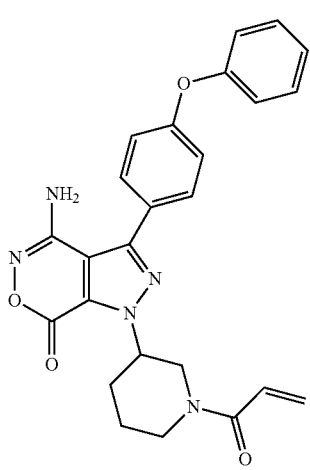 [SMILES: C=CC(=O)N1CCCC(n2nc(-c3ccc(Oc4ccccc4)cc3)c3c(N)noc(=O)c32)C1]

72-6

330

Compound 72-2

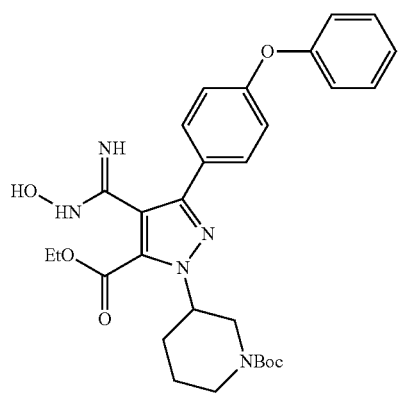 [SMILES: CCOC(=O)c1c(C(=N)NO)c(-c2ccc(Oc3ccccc3)cc2)nn1C1CCCN(C(=O)OC(C)(C)C)C1]

The solution of compound 72-1 (1 g, 1.94 mol), hydroxylamine hydrochloride (NH$_2$OH.HCl) (153.2 g, 1.63 mol) and TEA (294.5 mg, 2.91 mmol) in EtOH (20 mL) was stirred at 80° C. for 16 h, and then water (20 mL) was added to quench the reaction. The aqueous phase was extracted with DCM (30 mL) three times. Then the organic phases were combined, dried over anhydrous Na$_2$SO$_4$, filtered and evaporated to dryness by rotatory evaporation to give the title compound 72-2 (white solid, 490 mg) which was directly used for the next step without any purification.

LCMS (ESI) m/z: 550 (M+1)

Compound 72-3

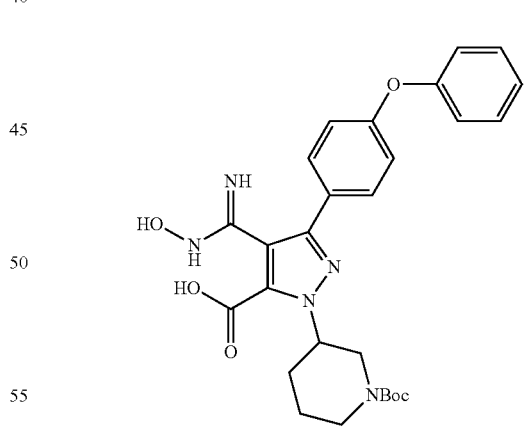

Compound 72-2 (450 mg, 0.82 mmol) and LiOH (103 mg, 2.46 mmol) were dissolved in THF (5 mL), EtOH (5 mL) and water (5 mL), and the reaction solution was stirred at r.t. for 14 h. After TLC indicated the reaction was complete, the reaction solution was evaporated to dryness by rotatory evaporation to give the title compound 72-3 (white solid, 480 mg) which was directly used for the next step without any purification.

LCMS (ESI) m/z: 522 (M+1)

Compound 72-4

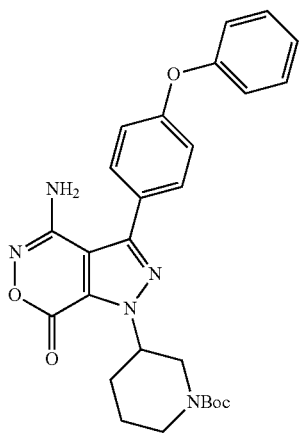 [SMILES: Nc1noc(=O)c2c1c(-c1ccc(Oc3ccccc3)cc1)nn2C1CCCNC1]

The solution of compound 72-3 (400 mg, 0.768 mmol), tri(n-propyl) phosphoric anhydride (T₃P) (490 mg, 1.54 mmol) and TEA (233 mg, 2.3 mmol) in DCM (20 mL) was stirred at r.t. for 14 h, and then water (20 mL) was added to quench the reaction. The aqueous phase was extracted with DCM (30 mL) three times. Then the organic phases were combined, dried over anhydrous Na₂SO₄, filtered and evaporated to dryness by rotatory evaporation to give the title compound 72-4 (white solid, 60 mg, 20%).

¹H NMR (400 MHz, CDCl₃): δ ppm 8.138-8.117 (d, 2H), 7.373-7.335 (t, 2H), 7.141-7.039 (m, 5H), 4.970 (s, 2H), 4.873 (s, 1H), 4.263 (s, 1H), 4.076 (s, 1H), 3.433-3.376 (t, 1H), 2.903 (s, 1H), 2.213 (s, 1H), 1.923 (s, 1H), 1.692 (s, 1H), 1.458 (s, 1H).

Compound 72-5

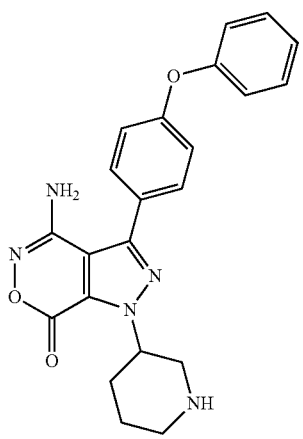

Compound 72-4 (56 mg, 0.111 mmol) was dissolved in a solution of HCl in EtOAc (5 mL, 4 M) and the reaction solution was stirred at r.t. for 2 h, followed by filtration. The filter cake was washed with EtOAc and the organic phase was evaporated to dryness by rotatory evaporation to give the title compound 72-5 (50 mg, 100%) which was directly used for the next step without any purification.

LCMS (ESI) m/z: 404 (M+1)

Compound 72-6

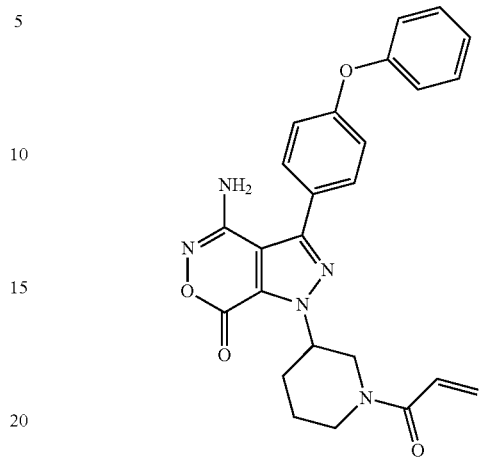

Compound acrylic acid (7.2 mg, 0.099 mmol), HATU (32.8 mg, 0.099 mmol) and DIPEA (63.8 mg, 0.49 mmol) were dissolved in anhydrous DCM (4 mL) under nitrogen atmosphere and the reaction solution was stirred at r.t. for 10 min, after which compound 72-5 (40 mg, 0.099 mmol) was added and the resulting reaction solution was stirred at r.t. for 48 h. To this solution, water (20 mL) was added, and the aqueous phase was extracted with DCM (20 mL) three times. The organic phase was washed with saturated brine (10 mL) once, dried over anhydrous Na₂SO₄, filtered and concentrated to dryness by rotatory evaporation to give a crude product which was purified by preparative liquid chromatography to afford the title compound 72-6 (white solid, 3 mg, Yield 6.7%).

¹H NMR (400 MHz, CDCl₃): δ ppm 8.412-8.122 (d, 2H), 7.378-7.338 (t, 2H), 7.146-7.040 (m, 5H), 6.662-6.593 (m, 1H), 6.343-6.304 (d, 1H), 5.748-5.679 (m, 1H), 5.054-4.993 (d, 2H), 4.910-4.895 (d, 1H), 4.596-4.224 (d, 1H), 4.026-3.970 (t, 1H), 3.638-3.580 (t, 1H), 3.226-2.899 (d, 1H), 2.368-2.272 (t, 2H), 2.025-1.990 (d, 1H), 1.739-1.707 (d, 1H).

Example 71

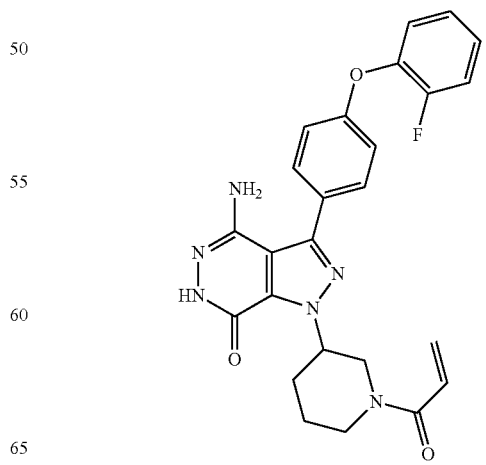

In Example 71, the systhesis process was similar to that in Example 20.
LCMS (ESI) m/z: 475 (M+1).
$^1$H NMR (400 MHz, CDCl$_3$): δ ppm 10.484 (s, 1H), 7.640-7.618 (m, 2H), 7.242-7.182 (d, 4H), 7.121-7.100 (m, 2H), 6.685-6.616 (t, 1H), 6.320-6.239 (t, 1H), 5.734-5.489 (m, 2H), 4.994 (s, 2H), 4.881-4.296 (m, 2H), 3.637-3.497 (t, 1H), 3.205-2.830 (m, 1H), 2.425-2.339 (m, 2H), 2.019-1.985 (d, 1H), 1.772 (s, 1H)
Scheme 50
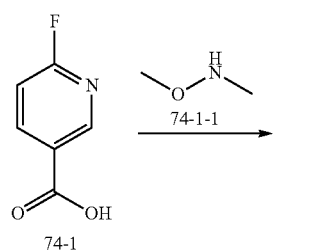
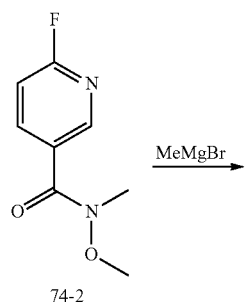
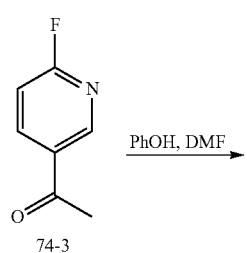
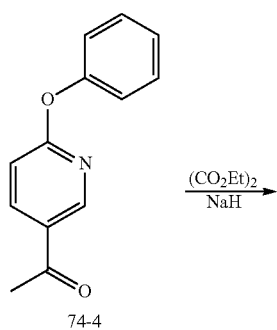
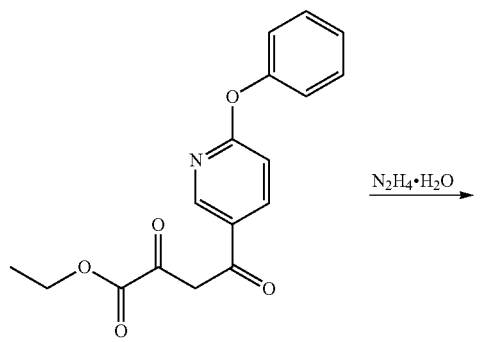
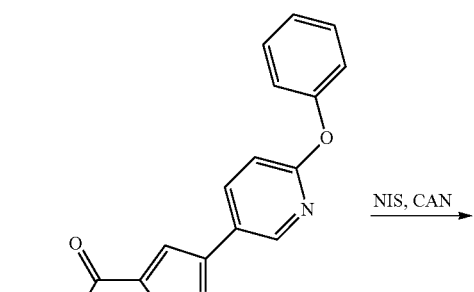
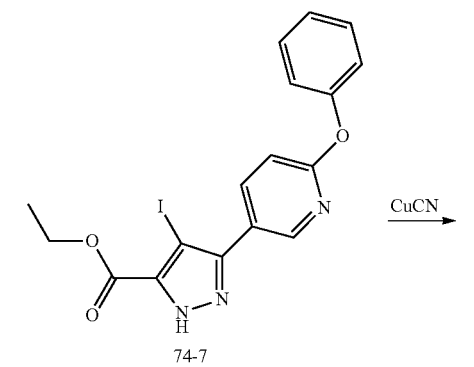
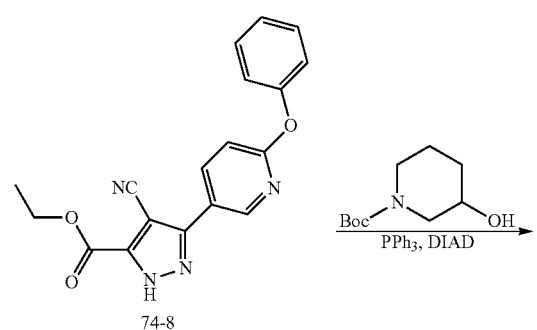

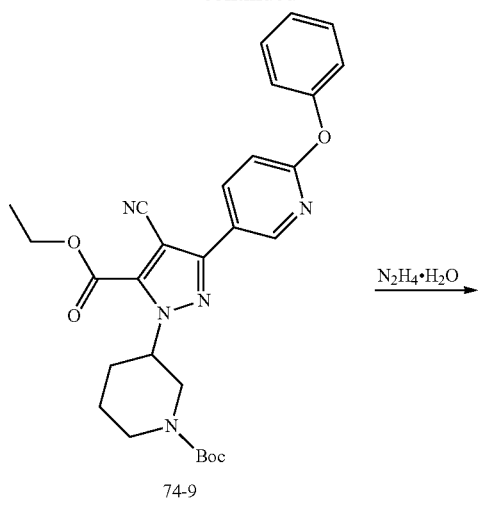
74-9
N₂H₄·H₂O →
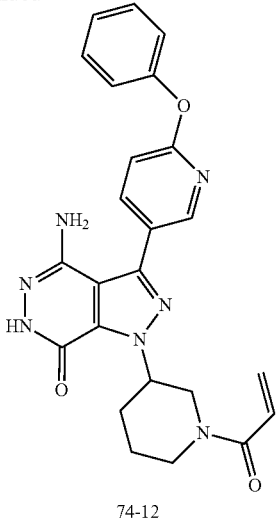
74-12
Example 72
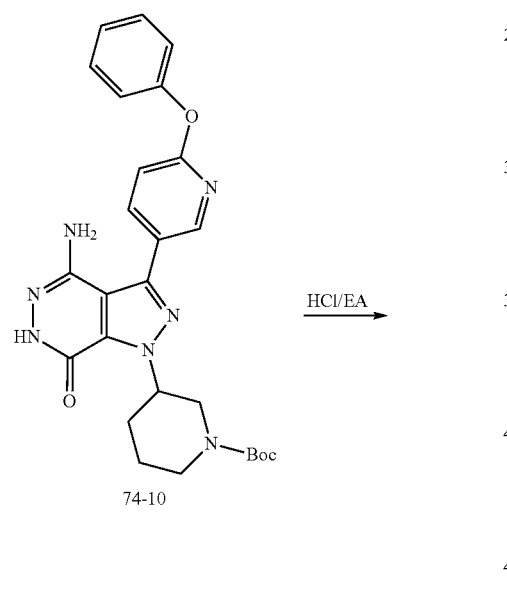
74-10
HCl/EA →
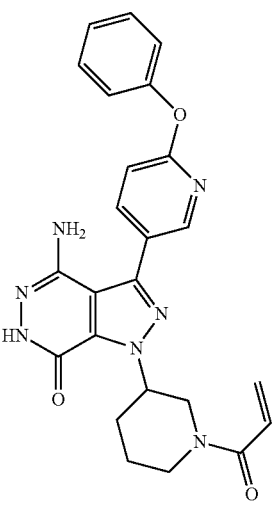 [SMILES: C=CC(=O)N1CCCC(n2nc(-c3ccc(Oc4ccccc4)nc3)c3c(N)n[nH]c(=O)c32)C1]
Compound 74-2
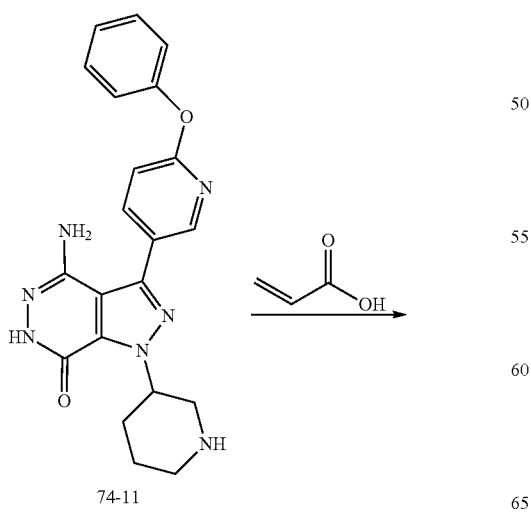
74-11
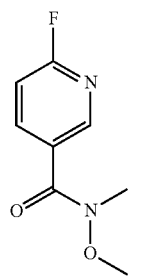
To a solution of compound 74-1 (18.6 g, 0.13 mol) and TEA (40 g, 0.39 mol) in DCM (330 mL) was added EDCI (35.5 g, 0.2 mol) under nitrogen atmosphere at −10° C. and the reaction solution was stirred at −10° C. for 10 min, after which HOBt (26.7 g, 0.20 mol) was added and the resulting solution was stirred at −10° C. for 10 min. Then to this solution, compound 74-1-1 (13.5 g, 0.14 mol) and DMAP (2.0 g) were added and the reaction solution was stirred at r.t. for 12 h. After TLC indicated the reaction was complete, the reaction was quenched with water (100 mL), and the reaction solution was extracted with EtOAc (100 mL) three times. The organic phase was washed with saturated brine (100 mL) once, dried over anhydrous Na$_2$SO$_4$, filtered and evaporated to dryness by rotatory evaporation to give the title compound 74-2 (18.7 g, 77%)

$^1$H NMR (400 MHz, CDCl$_3$): δ ppm 8.64 (s, 1H), 8.21-8.16 (m, 1H), 6.99-6.96 (m, 1H), 3.56 (s, 3H), 3.39 (s, 3H)

Compound 74-3

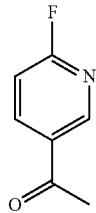

To a solution of compound 74-2 (18.7 g, 10.16 mmol) in anhydrous THF (340 mL) was added slowly methylmagnesium bromide (MeMgBr) (51 mL, 3.0 M ethyl ether (Et$_2$O) solution, 15.24 mmol) under nitrogen atmosphere at −78° C., and then the reaction solution was warmed to 25° C. and stirred for 2 h. After TLC indicated the reaction was complete, the reaction solution was diluted with water (100 mL), and the aqueous phase was extracted with EtOAc (500 mL) three times. The organic phases were combined, washed with saturated brine (100 mL) once, dried over anhydrous Na$_2$SO$_4$ and evaporated to dryness by rotatory evaporation to give a crude product which was purified by column chromatography to afford the title compound 74-3 (white solid, 9.6 g, Yield 68%).

$^1$H NMR (400 MHz, CDCl$_3$): δ ppm 8.83-8.82 (m, 1H), 8.40-8.36 (m, 1H), 7.06-7.03 (m, 1H), 2.64 (s, 3H).

Compound 74-4

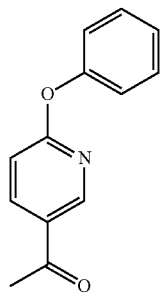 [SMILES: CC(=O)c1ccc(Oc2ccccc2)nc1]

To a solution of compound 74-3 (9.6 g, 69.1 mmol) and phenol (9.7 g, 103 mmol) in anhydrous DMF (90 mL) was added potassium tert-butoxide (15.4 g, 138.2 mmol) and the reaction solution was stirred at 100° C. for 6 h, after which water (90 mL) was added to quench the reaction and the aqueous phase was extracted with EtOAc (90 mL) three times. The organic phases were combined, dried over anhydrous Na$_2$SO$_4$, filtered and evaporated to dryness by rotatory evaporation to give a crude product which was purified by column chromatography to afford the title compound 74-4 (white solid, 3.3 g, 22%).

$^1$H NMR (400 MHz, CDCl$_3$): δ ppm 8.80-8.79 (m, 1H), 8.30-8.27 (m, 1H), 7.49-7.45 (m, 2H), 7.31-7.29 (m, 1H), 7.20-7.18 (m, 2H), 7.01-6.99 (m, 1H), 2.60 (s, 3H)

Compound 74-5

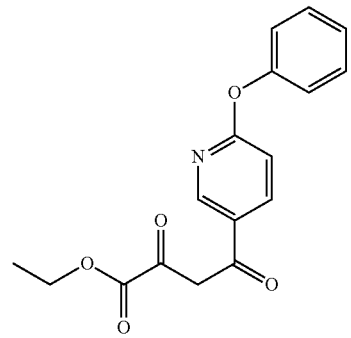 [SMILES: CCOC(=O)C(=O)CC(=O)c1ccc(Oc2ccccc2)nc1]

Compound 74-4 (2.6 g, 12.2 mmol) and diethyl oxalate (4.5 g, 30.5 mmol) were dissolved in anhydrous toluene (24 mL) and the reaction solution was heated to 85° C. and stirred for 10 min under nitrogen atmosphere, after which NaH (0.73 g, 18.3 mmol, purity 60%) was added slowly and the resulting solution was stirred for 10 min. After TLC indicated the reaction was complete, the reaction solution was adjusted to pH 5 to 6 with saturated NH$_4$Cl solution (aq., 50 mL) and the aqueous phase was extracted with EtOAc (100 mL) three times. The organic phases were combined, washed with saturated brine (50 mL) once, dried over anhydrous Na$_2$SO$_4$, filtered and evaporated to dryness by rotatory evaporation to give a residue which was purified by silica gel column chromatography to afford the title compound 74-5 (3 g, Yield 79%).

$^1$H NMR (400 MHz, CDCl$_3$): δ ppm 8.84 (m, 1H), 8.31-8.29 (m, 1H), 7.49-7.46 (m, 2H), 7.30-7.29 (m, 1H), 7.20-7.18 (m, 2H), 7.05-7.01 (m, 2H), 4.45-4.39 (q, 2H), 1.45-1.41 (t, 3H)

Compound 74-6

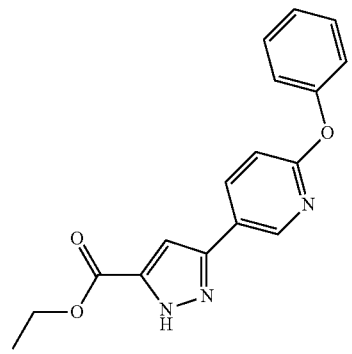 [SMILES: CCOC(=O)c1cc(-c2ccc(Oc3ccccc3)nc2)n[nH]1]

To a solution of compound 74-5 (2.2 g, 7 mmol) and HOAc (4.2 mL) in EtOH (32 mL) was added slowly N₂H₄.H₂O (85%, 1.05 g, 21 mmol) under nitrogen atmosphere at r.t., and the reaction solution was stirred at r.t. for 30 min. After TLC indicated the reaction was complete, water (100 mL) was added to quench the reaction and the aqueous phase was extracted with EtOAc (100 mL) three times. The organic phases were combined, washed with saturated brine (20 mL) once, dried over anhydrous Na₂SO₄, filtered and evaporated to dryness by rotatory evaporation to give a residue which was purified by silica gel column chromatography to afford the title compound 74-6 (light yellow solid, 1.88 g, Yield 87%).

¹H NMR (400 MHz, CDCl₃): δ ppm 8.61 (m, 1H), 8.16-8.14 (m, 1H), 7.46-7.42 (m, 2H), 729-7.24 (m, 1H), 7.20-7.18 (m, 2H), 7.10 (m, 1H), 7.00-6.98 (m, 1H), 4.47-4.42 (q, 2H), 1.45-1.42 (t, 3H)

Compound 74-7

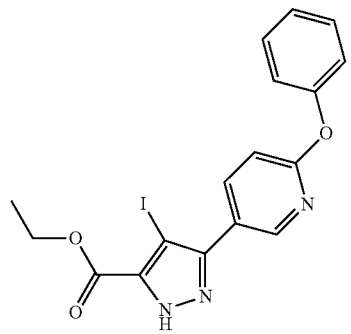 [SMILES: CCOC(=O)c1[nH]nc(-c2ccc(Oc3ccccc3)nc2)c1I]

Compound 74-6 (1.08 g, 3.5 mmol), N-Iodosuccinimide (0.79 g, 3.5 mmol) and CAN (288 mg, 0.52 mmol) were dissolved in acetonitrile (21 mL) under nitrogen atmosphere and the reaction solution was heated to 80° C. and reacted for 1 h. After LCMS indicated the reaction was complete, water (50 mL) was added to quench the reaction and the aqueous phase was extracted with EtOAc (100 mL) three times. The organic phases were combined, washed with saturated brine (20 mL) once, dried over anhydrous Na₂SO₄, filtered and evaporated to dryness by rotatory evaporation to give a residue which was purified by silica gel column chromatography to afford the title compound 74-7 (oily liquid, 1.5 g, Yield 97.7%).

¹H NMR (400 MHz, CDCl₃): δ ppm 11.33 (br, 1H), 8.65 (m, 1H), 8.13-8.11 (m, 1H), 7.46-7.42 (m, 2H), 7.29-7.25 (m, 1H), 7.21-7.20 (m, 2H), 7.03-7.01 (m, 1H), 4.50-4.45 (q, 2H), 1.48-1.44 (t, 3H)

Compound 74-8

To a solution of compound 74-7 (1.70 g, 3.91 mmol) and Cu(CN)₂ (704 mg, 7.82 mmol) in anhydrous DMF (17 mL) was added Pd(dppf)Cl₂ (286 mg, 0.39 mmol) under nitrogen atmosphere and the reaction solution was heated to 100° C. and reacted for 12 h. After TLC indicated the reaction was complete, the reaction solution was cooled down to r.t. Water (120 mL) was added to quench the reaction, and the aqueous phase was extracted with EtOAc (150 mL) three times. The organic phases were combined, washed with saturated brine (20 mL) once, dried over anhydrous Na₂SO₄, filtered and evaporated to dryness by rotatory evaporation to give a residue which was purified by silica gel column chromatography to afford the title compound 74-8 (oily liquid, 620 mg, Yield 48%).

¹H NMR (400 MHz, CDCl₃): δ ppm 13.78 (br, 1H), 8.81 (m, 1H), 8.33-8.31 (m, 1H), 7.47-7.43 (m, 2H), 7.29-7.26 (m, 1H), 7.20-7.18 (m, 2H), 7.05 (m, 1H), 4.53-4.48 (q, 2H), 1.49-1.45 (t, 3H)

Compound 74-9

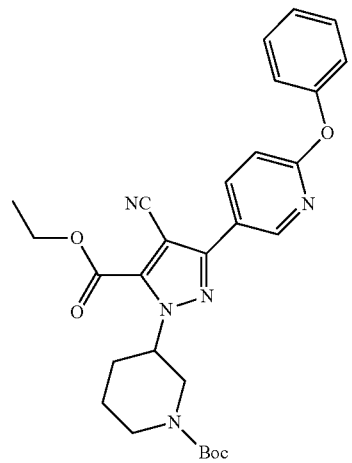 [SMILES: CCOC(=O)c1c(C#N)c(-c2ccc(Oc3ccccc3)nc2)nn1C1CCCN(C(=O)OC(C)(C)C)C1]

To a solution of compound 74-8 (326.5 mg, 0.98 mmol) and PPh₃ (257 mg, 0.98 mmol) in anhydrous THF (5 mL) was added DIAD (198 mg, 0.98 mmol) under nitrogen atmosphere at 0° C. and the reaction solution was stirred for 10 min, after which compound 1-BOC-3-hydroxypiperidine (216 mg, 1.08 mmol) was added and the resulting solution was warmed to r.t. and stirred for 12 h. After TLC indicated the reaction was complete, saturated NH₄Cl solution (aq., 200 mL) was added to this solution, and the aqueous phase was extracted with EtOAc (200 mL) three times. The organic phases were combined, washed with saturated brine (100 mL) once, dried over anhydrous Na₂SO₄, filtered and evaporated to dryness by rotatory evaporation to give a residue which was purified by column chromatography to afford the title compound 74-9 (white solid, 430 mg, Yield 85%).

¹H NMR (400 MHz, CDCl₃): δ ppm 8.79 (d, 1H), 8.27-8.24 (dd, 1H), 7.43-7.39 (t, 2H), 7.24-7.15 (m, 3H), 6.99-6.97 (m, 1H), 5.21-5.14 (m, 1H), 4.49-4.44 (q, 2H), 4.27-4.18 (m, 1H), 4.11-4.09 (m, 1H), 3.36-3.30 (m, 1H), 2.87-2.82 (m, 1H), 2.15 (m, 2H), 1.88 (m, 1H), 1.66-1.62 (m, 1H), 1.47-1.39 (m, 12H)

Compound 74-10

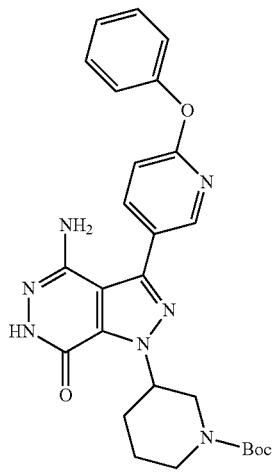 [SMILES: CC(C)(C)OC(=O)N1CCCC(n2nc(-c3ccc(Oc4ccccc4)nc3)c3c(N)n[nH]c(=O)c32)C1]

Compound 74-9 (477 mg, 0.92 mmol) was added into N₂H₄—H₂O (85%, 8.4 mL), and the reaction solution was heated to 100° C. and refluxed for 1.5 h, followed by cooled down to r.t. and diluted with water (20 mL). The aqueous phase was extracted with EtOAc (30 mL) three times. Then the organic phase was washed with saturated brine (20 mL) once, dried over anhydrous Na₂SO₄, filtered and evaporated to dryness by rotatory evaporation to give the title compound 74-10 (358 mg, Yield 77%) which was directly used for the next step without any purification.

¹H NMR (400 MHz, CDCl₃): δ ppm 8.53 (m, 1H), 8.05-8.03 (m, 1H), 7.48-7.44 (m, 2H), 7.29-7.20 (m, 2H), 7.08-7.06 (m, 1H), 6.89-6.86 (m, 1H), 5.50 (m, 1H), 4.61 (m, 2H), 4.28 (m, 1H), 4.06-4.02 (m, 1H), 3.49 (m, 2H), 2.24-2.19 (m, 2H), 1.98-1.92 (m, 1H), 1.74 (m, 1H), 1.44 (s, 9H)

Compound 74-11

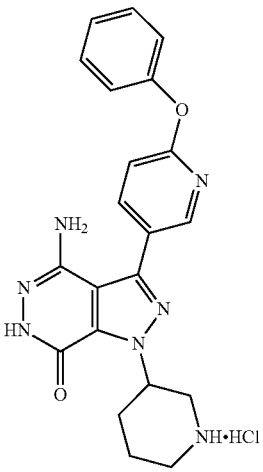

Compound 74-10 (358 mg, 0.6 mmol) was dissolved in a solution of HCl in EtOAc (5 mL, 4 M) and the reaction solution was stirred at r.t. for 3 h. After LCMS indicated the reaction was complete, the reaction solution was evaporated to dryness by rotatory evaporation to give the title compound 74-11 (yellow solid, 470 mg, crude) which was directly used for the next step without any purification.

Compound 74-12

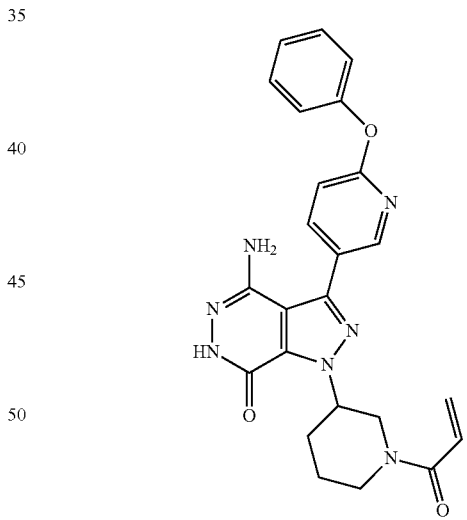

Acrylic acid (99 mg, 1.18 mmol), HATU (454.3 mg, 1.18 mmol) and DIPEA (552 mg, 4.28 mmol) were dissolved in anhydrous DCM (24 mL) under nitrogen atmosphere and the reaction solution was stirred at r.t. for 10 min, after which compound 74-11 (470 mg, 1.07 mmol) was added and the resulting solution was stirred at r.t. for 1 h. After LCMS indicated the reaction was complete, the reaction solution was diluted with water (10 mL), and the aqueous phase was extracted with DCM (20 mL) three times. Then the organic phase was washed with saturated brine (10 mL) once, dried over anhydrous Na₂SO₄, filtered and evaporated to dryness by rotatory evaporation to give a crude product which was purified by preparative liquid chromatography to afford the title compound 74-12 (white solid, 31.4 mg, 6.4%).
LCMS (ESI) m/z: 458 (M+1). $^1$H NMR (400 MHz, CDCl$_3$): δ ppm 8.66 (m, 1H), 8.53 (m, 1H), 8.05-8.03 (m, 1H), 7.49-7.45 (m, 2H), 7.23-7.21 (m, 2H), 7.10-7.08 (m, 1H), 6.65 (m, 1H), 6.31 (m, 1H), 5.69 (m, 1H), 5.53 (m, 1H), 4.82 (m, 1H), 4.56 (m, 1H), 4.46 (br, 2H), 4.33 (m, 1H), 3.98 (m, 1H), 3.59 (m, 2H), 3.27 (m, 1H), 2.92 (m, 1H), 2.36-2.23 (m, 3H), 2.02 (m, 1H), 1.77 (m, 1H).
Example 73
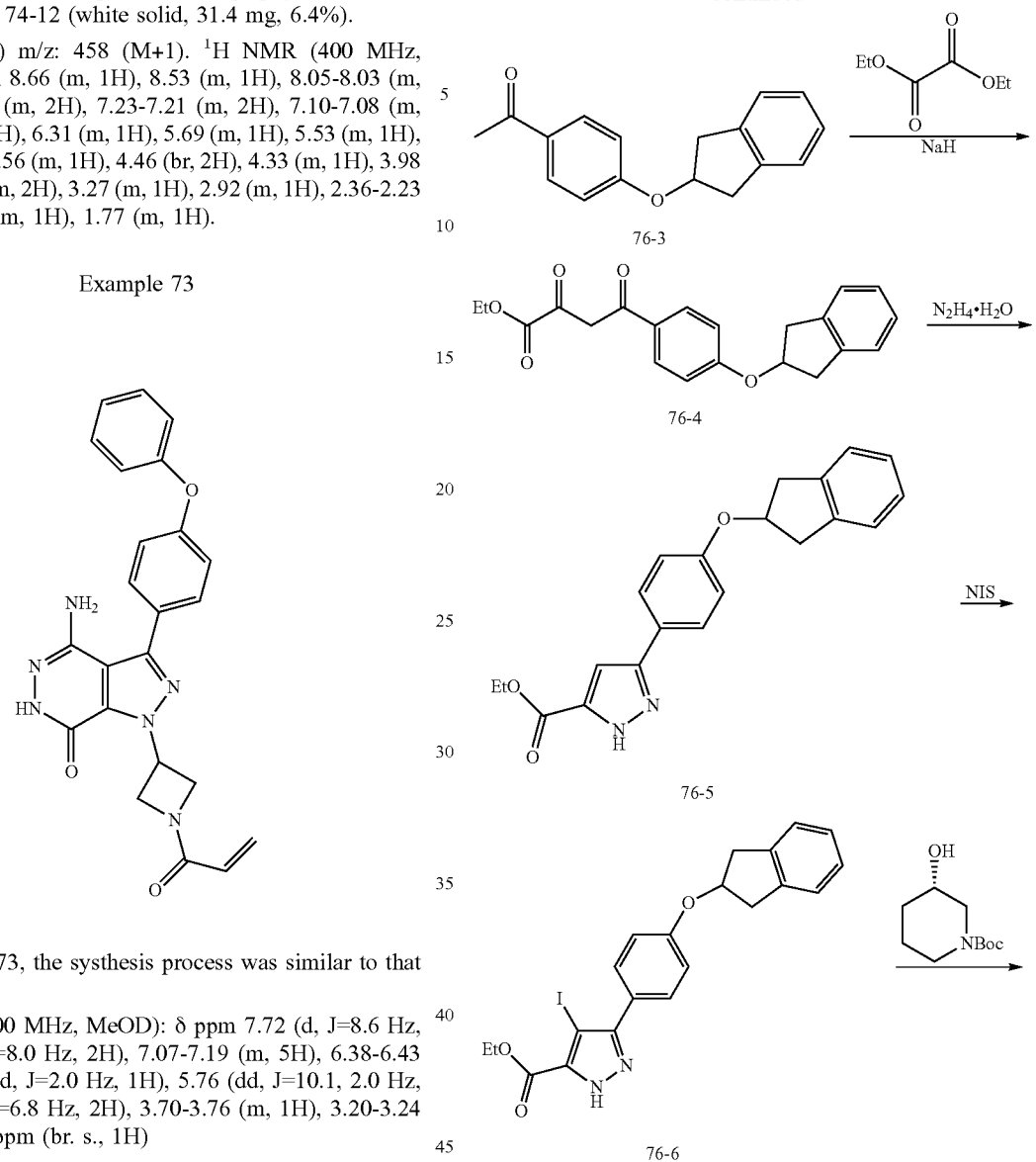
In Example 73, the systhesis process was similar to that in Example 20.
$^1$H NMR (400 MHz, MeOD): δ ppm 7.72 (d, J=8.6 Hz, 2H), 7.40 (t, J=8.0 Hz, 2H), 7.07-7.19 (m, 5H), 6.38-6.43 (m, 2H), 6.29 (d, J=2.0 Hz, 1H), 5.76 (dd, J=10.1, 2.0 Hz, 1H), 4.59 (d, J=6.8 Hz, 2H), 3.70-3.76 (m, 1H), 3.20-3.24 (m, 1H), 2.66 ppm (br. s., 1H)
LCMS (ESI) m/z: 429 (M+1).
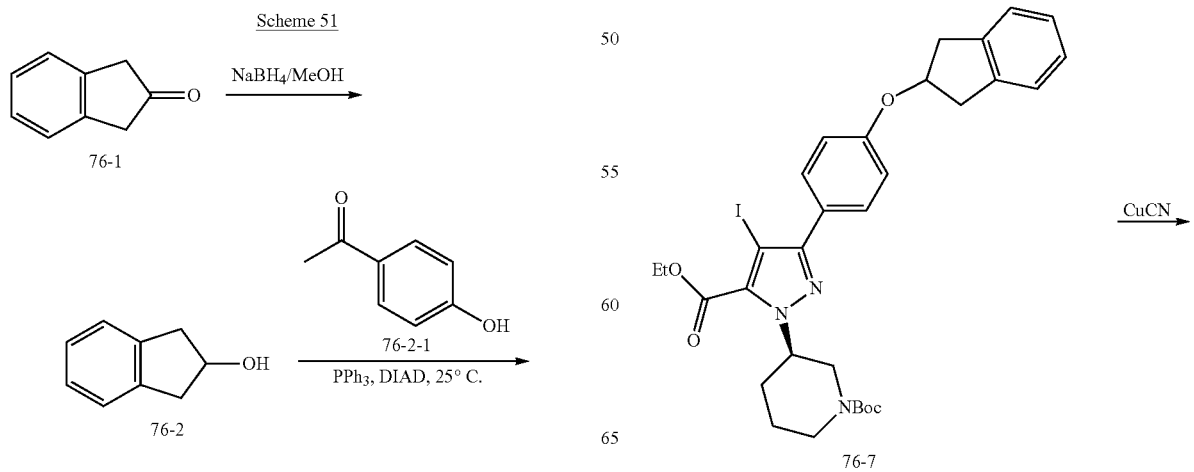

-continued

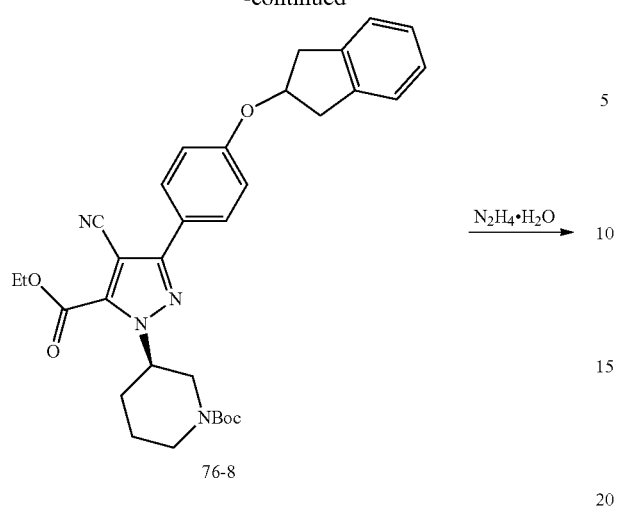

76-8

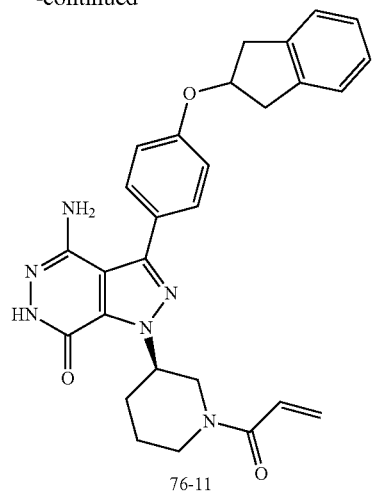

76-11

Example 74

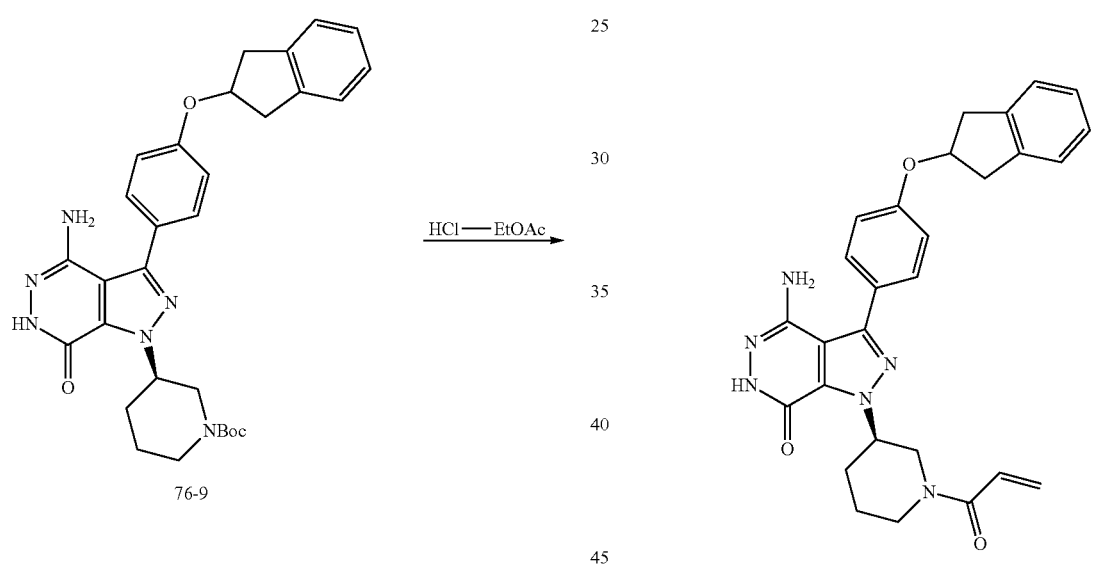

Compound 76-2

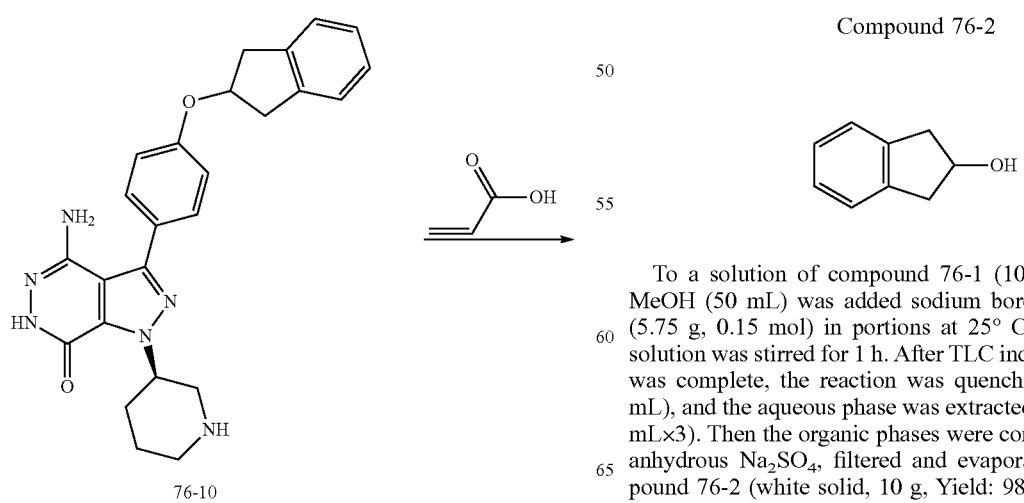

To a solution of compound 76-1 (10 g, 0.076 mol) in MeOH (50 mL) was added sodium borohydride (NaBH$_4$) (5.75 g, 0.15 mol) in portions at 25° C. and the reaction solution was stirred for 1 h. After TLC indicated the reaction was complete, the reaction was quenched with water (30 mL), and the aqueous phase was extracted with EtOAc (100 mL×3). Then the organic phases were combined, dried over anhydrous Na$_2$SO$_4$, filtered and evaporated to give compound 76-2 (white solid, 10 g, Yield: 98%).

LCMS (ESI) m/z: 135 (M+1)

Compound 76-3

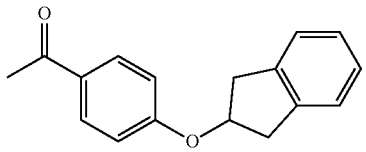 [SMILES: CC(=O)c1ccc(OC2Cc3ccccc3C2)cc1]

To a solution of PPh₃ (11.6 g, 0.044 mmol) and DIAD (9.0 g, 0.044 mmol) in THF (50 mL) was added separately compound 76-2 (5 g, 0.037 mol) and compound 76-2-1 (7.6 g, 0.056 mol) at 0° C., and the reaction solution was stirred at 25° C. for 2 h. After TLC indicated the reaction was complete, the reaction solution was washed with water (200 mL×2), and the aqueous phase was extracted with EtOAc (600 mL×3). Then the organic phases were combined, dried over anhydrous Na₂SO₄, filtered and evaporated to give a residue which was purified by column chromatography (PE:EtOAc=5:1) to afford compound 76-3 (white solid, 3.6 g, Yield: 38%).

LCMS (ESI) m/z: 253 (M+1)

Compound 76-4

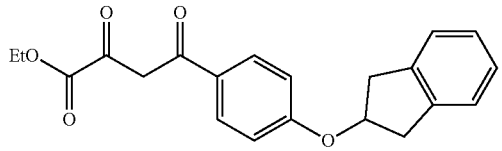 [SMILES: CCOC(=O)C(=O)CC(=O)c1ccc(OC2Cc3ccccc3C2)cc1]

To a solution of compound 76-3 (3 g, 11.9 mol) in toluene (30 mL) was added NaH (857 mg, 35.7 mmol, 60%) at 0° C. and the reaction solution was stirred for 15 min, after which diethyl oxalate (3.48 g, 23.8 mmol) was added and the resulting solution was heated to 80° C. and reacted for 6 h. After TLC indicated the reaction was complete, the reaction solution was washed with water (300 mL), and the aqueous phase was extracted with DCM (500 mL×2). Then the organic phase were combined, dried over anhydrous Na₂SO₄, filtered and evaporated to give a residue which was purified by column chromatography (PE:EtOAc=10:1) to afford compound 76-4 (yellow solid, 1.2 g, Yield: 30%).

LCMS (ESI) m/z: 353 (M+1)

Compound 76-5

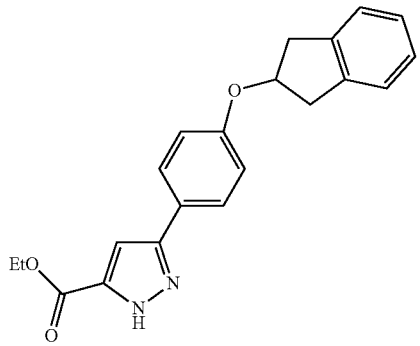 [SMILES: CCOC(=O)c1cc(-c2ccc(OC3Cc4ccccc4C3)cc2)n[nH]1]

To a mixture of compound 76-4 (1.2 g, 3.4 mmol) in EtOH (20 mL) and HOAc (2 mL) was added N₂H₄·H₂O (85%, 220 mg, 6.8 mmol) at 25° C., and the reaction solution was stirred for 30 min. After of TLC indicated the reaction was complete, the reaction solution was washed with NaHCO₃ solution (200 mL), and the aqueous phase was extracted with EtOAc (500 mL×2). Then the organic phases were combined, dried over anhydrous Na₂SO₄, filtered and evaporated to give compound 76-5 (yellow solid, 1.4 g, Yield: 98%) which was directly used for the next step without further purification.

LCMS (ESI) m/z: 349 (M+1)

Compound 76-6

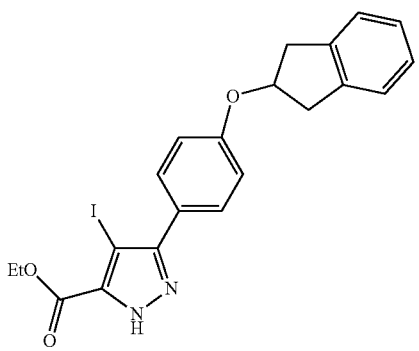 [SMILES: CCOC(=O)c1[nH]nc(-c2ccc(OC3Cc4ccccc4C3)cc2)c1I]

To a solution of compound 76-5 (1.4 g, 4.0 mmol), N-Iodosuccinimide (905 mg, 4.0 mmol) in acetonitrile (15 mL) was added CAN (328 mg, 0.6 mmol), and the reaction solution was heated to 80° C. and stirred for 2 h. After LCMS indicated the reaction was complete, the reaction solution was washed with water (200 mL), and the aqueous phase was extracted with EtOAc (1000 mL×2). The organic phases were combined, dried over anhydrous Na₂SO₄, filtered and evaporated to give a residue which was purified by column chromatography (PE:EtOAc=2:1) to afford compound 76-6 (yellow solid, 930 mg, Yield: 50%).

LCMS (ESI) m/z: 475 (M+1)

Compound 76-7

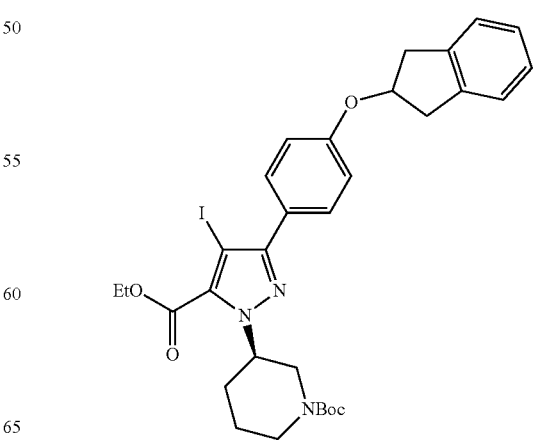

To a solution of PPh₃ (400 mg, 1.52 mmol) and DIAD (308 mg, 1.52 mmol) in THF (5 mL) was added separately compound 76-6 (600 mg, 1.27 mmol) and compound (S)-1-BOC-3-Hydroxypiperidine (600 mg, 1.27 mmol) at 0° C. and the resulting solution was stirred at 25° C. for 8 h. After TLC indicated the reaction was complete, the reaction solution was washed with water (50 mL×1), and the aqueous phase was extracted with EtOAc (100 mL×3). The organic phases were combined, dried over anhydrous Na₂SO₄, filtered and evaporated to give a residue which was purified by column chromatography (PE:EtOAc=10:1) to afford compound 76-7 (yellow oil, 600 mg, Yield: 73%).

LCMS (ESI) m/z: 658 (M+1)

Compound 76-8

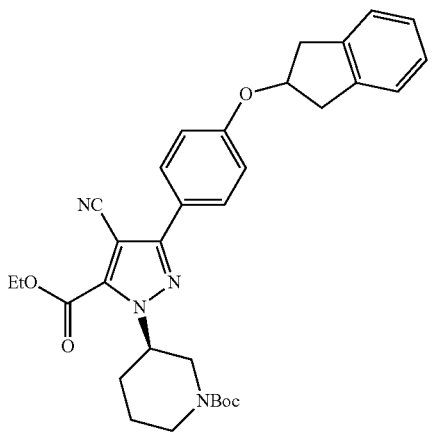 [SMILES: CCOC(=O)c1c(C#N)c(-c2ccc(OC3Cc4ccccc4C3)cc2)nn1[C@@H]1CCCN(C(=O)OC(C)(C)C)C1]

To a solution of compound 76-7 (600 mg, 0.91 mmol) and CuCN (162 mg, 1.82 mmol) in DMF (5 mL) was added Pd(dppf)Cl₂ (66 mg, 0.091 mmol) and Pd₂(dba)₃ (83 mg, 0.091 mmol) under nitrogen atmosphere at r.t., and the reaction solution was stirred under nitrogen atmosphere at 100° C. for 16 h. After TLC indicated the reaction was complete, the reaction solution was cooled down to r.t. and filtered with diatomite. The filtrate was washed with water (100 mL), and the aqueous phase was extracted with EtOAc (300 mL×3). The organic phases were combined, dried over anhydrous Na₂SO₄, filtered and evaporated to give a crude product which was purified by column chromatography (PE:EtOAc=1:1) to afford compound 76-8 (yellow solid, 260 mg, Yield: 52%).

LCMS (ESI) m/z: 557 (M+1)

Compound 76-9

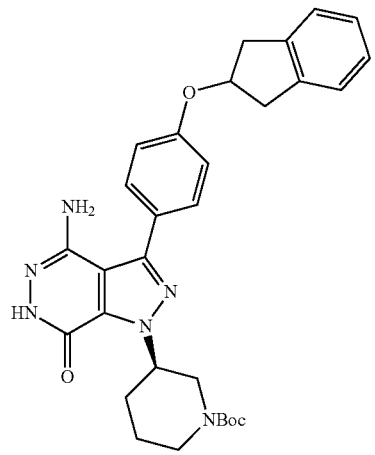 [SMILES: CC(C)(C)OC(=O)N1CCC[C@@H](n2nc(-c3ccc(OC4Cc5ccccc5C4)cc3)c3c(N)n[nH]c(=O)c32)C1]

The mixture of compound 76-8 (400 mg, 0.72 mmol) in N₂H₄—H₂O (85%, 5 mL) was stirred at 80° C. for 2 h. After TLC (PE:EtOAc=2:1) indicated the reaction was complete, the reaction solution was washed with water (100 mL), and the aqueous phase was extracted with EtOAc (300 mL×3). The organic phases were combined, dried over anhydrous Na₂SO₄, filtered and evaporated to give compound 76-9 (yellow solid, 350 mg, Yield 90%).

LCMS (ESI) m/z: 543 (M+1)

Compound 76-10

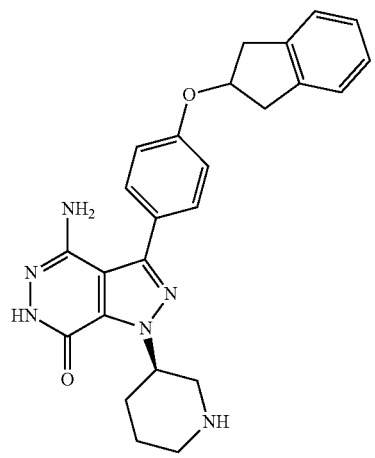 [SMILES: Nc1n[nH]c(=O)c2c1c(-c1ccc(OC3Cc4ccccc4C3)cc1)nn2[C@@H]1CCCNC1]

To a solution of HCl in EtOAc (3 mL, 4 M) was added compound 76-9 (300 mg, 0.55 mmol) at r.t. and the reaction solution was stirred for 1 h. After TLC indicated the reaction was complete, the reaction solution was adjusted to pH 8 with NaHCO₃ solution (100 mL), and the aqueous phase was extracted with EtOAc (200 mL×2). Then the organic phases were combined, dried over anhydrous Na₂SO₄, filtered and evaporated to give compound 76-10 (yellow solid, 280 mg, Yield 90%).

LCMS (ESI) m/z: 443 (M+1)

Compound 76-11

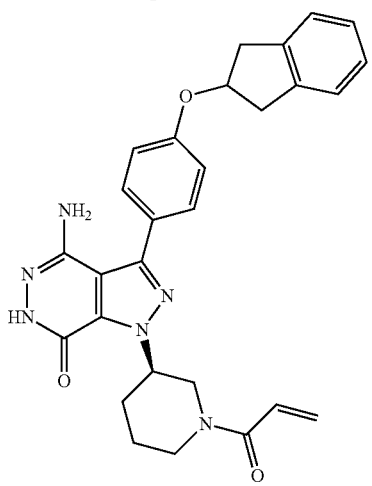 [SMILES: C=CC(=O)N1CCC[C@@H](n2nc(-c3ccc(OC4Cc5ccccc5C4)cc3)c3c(N)n[nH]c(=O)c32)C1]

To a solution of compound 76-10 (240 mg, 0.54 mmol), HATU (307 mg, 0.81 mmol) and DIPEA (139 mg, 1.08 mmol) in anhydrous DCM (5 mL) was added acrylic acid (58 mg, 0.81 mmol) and the reaction solution was stirred at 25° C. for 1 h. After TLC (PE:EtOAc=1:1) indicated the reaction was complete, the reaction solution was washed with NaHCO₃ solution (30 mL×1), and the aqueous phase was extracted with EtOAc (100 mL×2). Then the organic phases were combined, dried over anhydrous Na₂SO₄, filtered and evaporated to give a residue which was purified by preparative HPLC to afford compound 76-11 (yellow solid, 32 mg, Yield: 20%).

$^1$H NMR (400 MHz, CDCl$_3$): δ ppm 10.76 (br. s., 1H), 7.61-7.55 (m, J=8.6 Hz, 2H), 7.30-7.26 (m, 2H), 7.24-7.20 (m, 2H), 7.08-7.03 (m, J=8.6 Hz, 2H), 6.68-6.57 (m, 1H), 6.33-6.21 (m, 1H), 5.71 (d, J=10.0 Hz, 1H), 5.62 (d, J=10.3 Hz, 1H), 5.47 (br. s., 1H), 5.25 (dt, J=3.1, 6.1 Hz, 1H), 5.17 (br. s., 1H), 5.11-4.87 (m, 1H), 4.60-4.31 (m, 1H), 3.99-3.60 (m, 1H), 3.43 (dd, J=6.1, 16.6 Hz, 2H), 3.23 (dd, J=2.7, 16.6 Hz, 2H), 2.84 (t, J=11.9 Hz, 1H), 2.32 (d, J=8.8 Hz, 1H), 1.99 (d, J=13.0 Hz, 1H), 1.75 (d, J=11.2 Hz, 1H), 1.62 (br. s., 1H)

LCMS (ESI) m/z: 497 (M+1)

Example 75

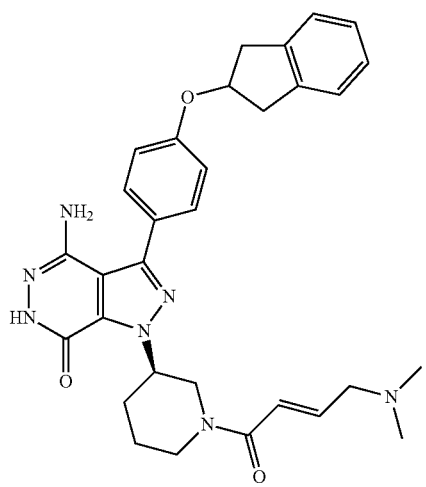 [SMILES: CN(C)C/C=C/C(=O)N1CCC[C@@H](n2nc(-c3ccc(OC4Cc5ccccc5C4)cc3)c3c(N)n[nH]c(=O)c32)C1]

In Example 75 aqueous phase was similar to that of Example 74.

$^1$H NMR (400 MHz, CDCl$_3$): δ ppm 11.27 (br. s., 1H), 7.58 (d, J=8.6 Hz, 2H), 7.28 (d, J=5.1 Hz, 2H), 7.21 (dd, J=3.3, 5.3 Hz, 2H), 7.05 (d, J=8.4 Hz, 2H), 6.88-6.76 (m, 1H), 6.46 (d, J=15.0 Hz, 1H), 5.49 (dd, J=5.2, 9.4 Hz, 1H), 5.37-5.30 (m, 2H), 5.24 (td, J=3.1, 5.9 Hz, 1H), 4.88-4.58 (m, 1H), 4.29-4.01 (m, 1H), 3.72-3.59 (m, 1H), 3.45 (d, J=6.0 Hz, 1H), 3.41 (d, J=6.2 Hz, 1H), 3.24 (d, J=2.2 Hz, 1H), 3.20 (d, J=2.2 Hz, 1H), 3.08 (br. s., 1H), 3.01 (br. s., 1H), 2.26 (br. s., 3H), 2.18 (s, 3H), 1.96 (br. s., 3H), 1.75 (br. s., 1H).

LCMS (ESI) m/z: 554 (M+1)

Scheme 52

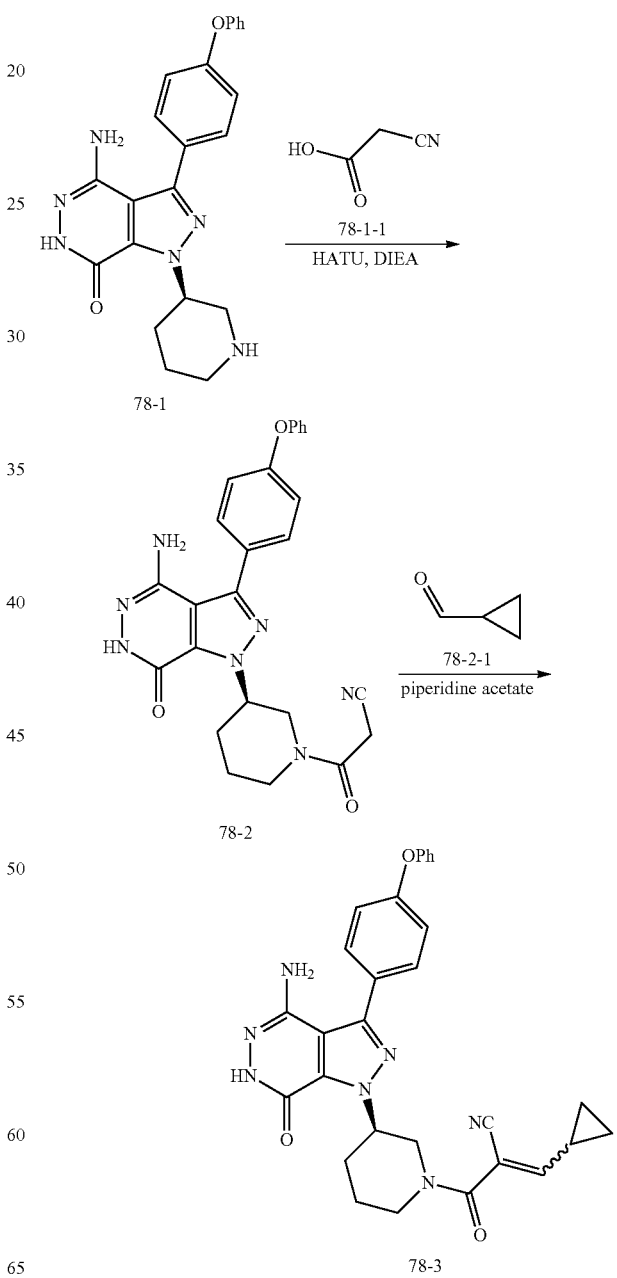

Example 76

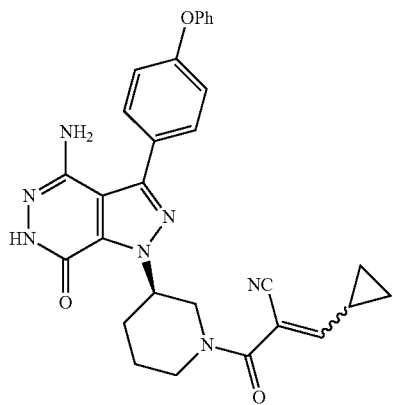 [SMILES: N#CC(=CC1CC1)C(=O)N1CCC[C@@H](n2nc(-c3ccc(Oc4ccccc4)cc3)c3c(N)n[nH]c(=O)c32)C1]

Compound 78-3

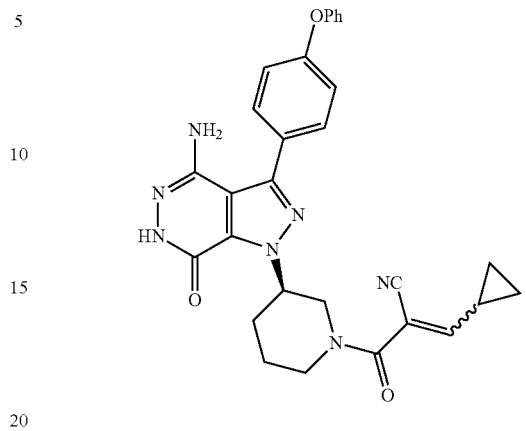

To a solution of compound 78-2 (70 mg, 0.15 mmol) and piperidineacetic acid (88 mg, 0.225 mmol) in anhydrous EtOH (5 mL) was added compound 78-2-1 (31 mg, 0.45 mmol) and the reaction solution was heated to 60° C. and stirred for 16 h. After LCMS indicated the reaction was complete, the reaction solution was washed with water (20 mL), and the aqueous phase was extracted with DCM (20 mL×2). Then the organic phases were combined, dried over anhydrous $Na_2SO_4$, filtered and evaporated to give a residue which was purified by preparative HPLC to afford compound 78-3 (yellow solid, 35 mg, Yield: 62%).

$^1$H NMR (400 MHz, MeOD): δ ppm 7.67 (d, J=8.80 Hz, 2H), 7.33-7.45 (m, 2H), 7.22-7.03 (m, 5H), 6.39 (d, J=11.00 Hz, 1H), 5.62-5.53 (m, 1H), 4.91 (br. s., 1H), 3.97-3.84 (m, 1H), 2.44-1.64 (m, 5H), 2.30 (br. s., 1H), 1.40-0.64 (m, 5H).

LCMS (ESI) m/z: 457 (M+1)

Example 77

Compound 78-2

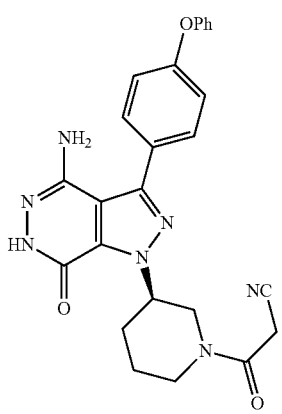 [SMILES: N#CCC(=O)N1CCC[C@@H](n2nc(-c3ccc(Oc4ccccc4)cc3)c3c(N)n[nH]c(=O)c32)C1]

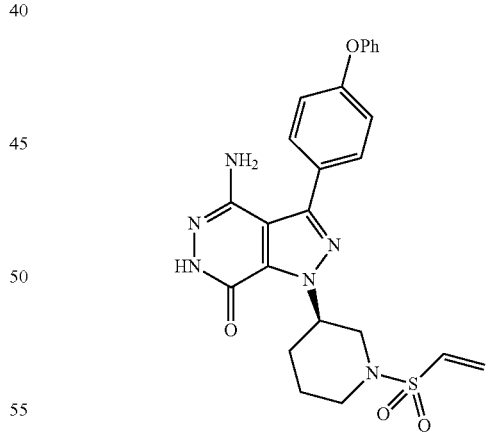

To a solution of compound 78-1 (100 mg, 0.21 mmol), HATU (121.5 mg, 0.31 mmol) and DIPEA (108 mg, 0.84 mmol) in anhydrous DCM (5 mL) was added compound 78-1-1 (21.5 mg, 0.25 mmol) at 25° C. and the reaction solution was stirred at 25° C. for 4 h. After LCMS indicated the reaction was complete, the reaction solution was washed with water (10 mL×1), and the aqueous phase was extracted with EtOAc (10 mL×2). Then the organic phases were combined, dried over anhydrous $Na_2SO_4$, filtered and evaporated to give a residue which was purified by preparative TLC (DCM:MeOH=15:1) to afford compound 78-2 (yellow solid, 90 mg, Yield: 70%).

LCMS (ESI) m/z: 470 (M+1)

In Example 77, the systhesis process was similar to that in Example 28.

$^1$H NMR (400 MHz, MeOD): δ ppm 7.66 (d, J=8.56 Hz, 2H), 7.45-7.33 (m, 2H), 7.22-6.99 (m, 5H), 6.70 (dd, J=10.03, 16.38 Hz, 1H), 6.23-6.04 (m, 2H), 5.68-5.54 (m, 1H), 3.95 (dd, J=4.03, 11.62 Hz, 1H), 3.71 (d, J=12.23 Hz, 1H), 3.27-3.21 (m, 1H), 2.79 (dt, J=2.69, 12.10 Hz, 1H), 2.31-2.11 (m, 2H), 2.00 (d, J=13.94 Hz, 1H), 1.89-1.74 (m, 1H).

LCMS (ESI) m/z: 493 (M+1)

Scheme 53

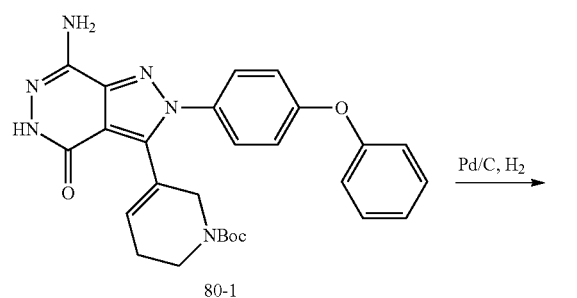

80-1

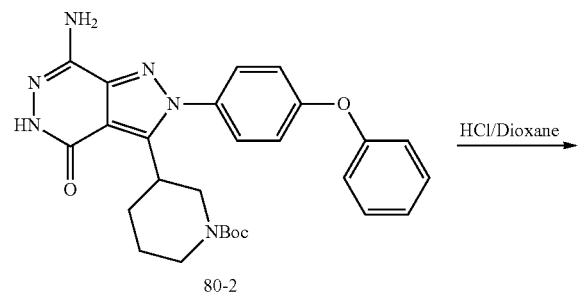

80-2

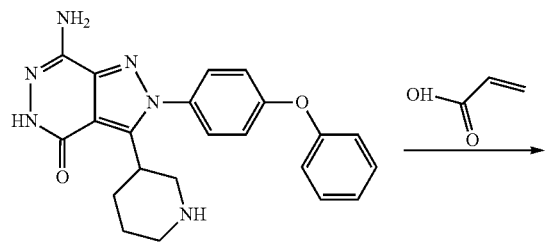

80-3

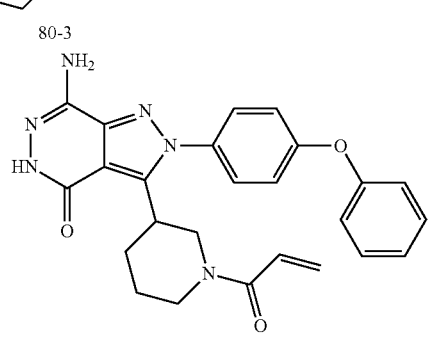

80-4

Example 78

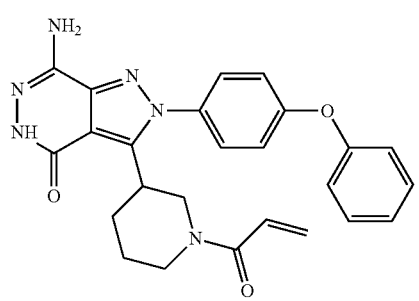 [SMILES: C=CC(=O)N1CCCC(c2c3c(=O)[nH]nc(N)c3nn2-c2ccc(Oc3ccccc3)cc2)C1]

Compound 80-2

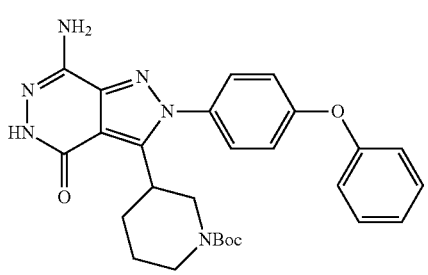 [SMILES: CC(C)(C)OC(=O)N1CCCC(c2c3c(=O)[nH]nc(N)c3nn2-c2ccc(Oc3ccccc3)cc2)C1]

To a solution of compound 80-1 (300 mg, 0.60 mmol) in MeOH (1 mL) was added Pd/C (10 mg), and the reaction mixture was hydrogenated at a pressure of 40 psi for 15 h. After LCMS indicated the reaction was complete, the reaction solution was cooled down to r.t. and filtered with diatomite. The filter cake was washed with MeOH (20 mL) and then the filtrate was concentrated to dryness to give a crude product which was purified by preparative HPLC to afford compound 80-2 (white solid, 241 mg, Yield: 80%).

LCMS (ESI) m/z: 503 (M+1)

Compound 80-3

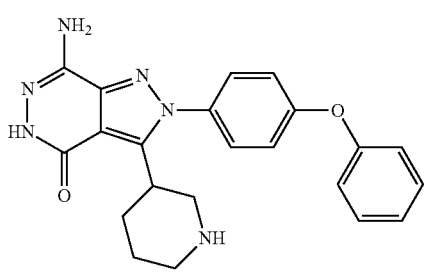 [SMILES: Nc1n[nH]c(=O)c2c(C3CCCNC3)n(-c3ccc(Oc4ccccc4)cc3)nc12]

To a solution of compound 80-2 (200 mg, 0.398 mmol) in DCM (3 mL) was added HCl-dioxane (1 mL, 4 M) at 25° C. and the reaction solution was stirred at 20° C. for 1 h. After LCMS indicated the reaction was complete, then the reaction solution was adjusted to pH 8 with NaHCO₃ solution (15 mL), and the aqueous phase was extracted with DCM (50 mL×2). The organic phases were combined, dried over anhydrous Na₂SO₄, filtered and evaporated to give compound 80-3 (white solid, 150 mg, Yield 93.7%).

LCMS (ESI) m/z: 403 (M+1)

Compound 80-4

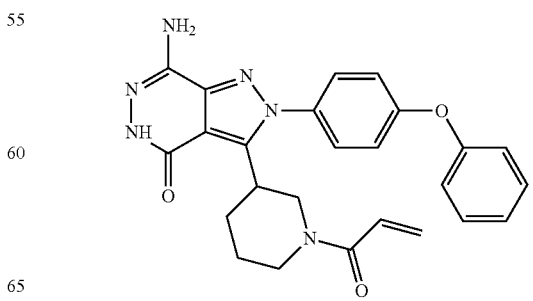

To a solution of compound 80-3 (40 mg, 0.0994 mmol), HATU (76 mg, 0.198 mmol) and TEA (20 mg, 0.198 mmol) in anhydrous DCM (1 mL) was added acrylic acid (7.2 mg, 0.0994 mmol) at 25° C. and the reaction solution was stirred at 25° C. for 1 h. After LCMS indicated the reaction was complete, the reaction solution was washed with NH$_4$Cl (5 mL×1), and the aqueous phase was extracted with DCM (20 mL×2). The organic phases were combined, dried over anhydrous Na$_2$SO$_4$, filtered and evaporated to give a residue which was purified by preparative HPLC (basic) to afford compound 80-4 (white solid, 16 mg, Yield: 36.5%).

$^1$H NMR (400 MHz, CDCl$_3$): δ ppm 8.60 (s, 1H), 8.10-8.12 (m, 2H), 7.73-7.76 (m, 4H), 7.52-7.57 (m, 2H), 7.37 (d, J=8.03 Hz, 2H), 7.15 (d, J=8.53 Hz, 2H), 7.05 (br. s., 1H), 6.57-6.67 (m, 1H), 6.31 (d, J=16.56 Hz, 1H), 5.68-5.73 (m, 1H), 4.67 (br. s., 2H), 4.61 (s, 1H), 4.07 (d, J=12.55 Hz, 1H), 4.01 (s, 1H), 3.11 (t, J=12.05 Hz, 1H), 2.71 (d, J=17.07 Hz, 1H).

LCMS (ESI) m/z: 457 (M+1)

Example 79

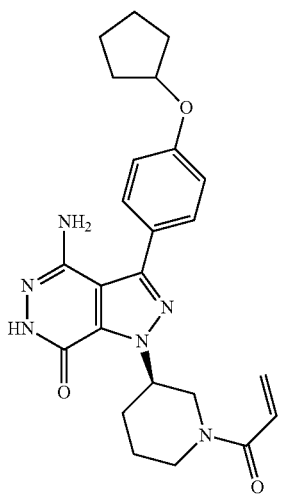 [SMILES: C=CC(=O)N1CCC[C@@H](n2nc(-c3ccc(OC4CCCC4)cc3)c3c(N)n[nH]c(=O)c32)C1]

In Example 79, the systhesis process was similar to that in Example 33.

$^1$H NMR (400 MHz, CDCl$_3$): δ ppm 7.48 (d, J=8.60 Hz, 2H), 6.94 (d, J=8.60 Hz, 2H), 6.71-6.45 (m, 1H), 6.34-6.11 (m, 1H), 5.79-5.38 (m, 1H), 5.08-4.86 (m, 1H), 4.82-4.69 (m, 1H), 4.53 (d, J=13.23 Hz, 1H), 4.24 (d, J=10.58 Hz, 1H), 3.53 (t, J=11.58 Hz, 1H), 2.82-2.69 (m, 1H), 2.37-2.17 (m, 1H), 1.99-1.71 (m, 8H), 1.60-1.48 (m, 6H).

LCMS (ESI) m/z: 449 (M+1)

Example 80

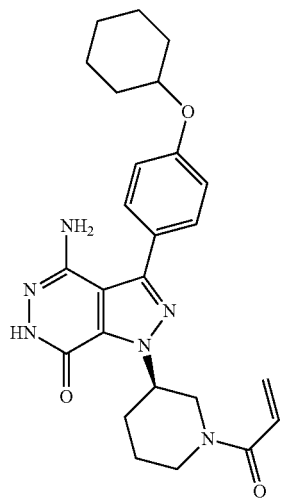 [SMILES: C=CC(=O)N1CCC[C@@H](n2nc(-c3ccc(OC4CCCCC4)cc3)c3c(N)n[nH]c(=O)c32)C1]

In Example 80, the systhesis process was similar to that in Example 33.

$^1$H NMR (400 MHz, CDCl$_3$): δ ppm 7.48 (d, J=8.60 Hz, 2H), 6.96 (d, J=8.38 Hz, 2H), 6.71-6.42 (m, 1H), 6.31-6.08 (m, 1H), 5.72-5.45 (m, 1H), 5.06-4.82 (m, 1H), 4.53 (d, J=11.91 Hz, 1H), 4.34-4.09 (m, 2H), 3.53 (t, J=11.58 Hz, 1H), 2.88-2.61 (m, 1H), 2.46-2.13 (m, 1H), 2.07-1.18 (m, 14H).

LCMS (ESI) m/z: 463 (M+1)

Example 81

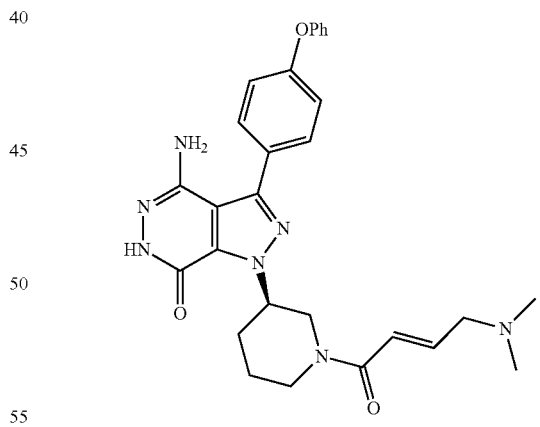

In Example 81, the systhesis process was similar to that in Example 28.

$^1$H NMR (400 MHz, CDCl$_3$): δ ppm 7.61 (d, J=8.60 Hz, 2H), 7.46-7.34 (m, 2H), 7.20-7.02 (m, 5H), 6.81 (d, J=13.89 Hz, 1H), 6.44 (d, J=14.99 Hz, 1H), 5.57-5.30 (m, 3H), 4.85-4.50 (m, 1H), 4.28 (d, J=11.47 Hz, 1H), 4.00 (d, J=12.35 Hz, 1H), 3.66 (t, J=11.25 Hz, 1H), 3.54-3.38 (m, 1H), 3.26-2.93 (m, 2H), 2.84 (t, J=12.02 Hz, 1H), 2.38-2.12 (m, 8H), 1.97 (d, J=13.67 Hz, 1H).

LCMS (ESI) m/z: 514 (M+1)

Scheme 54
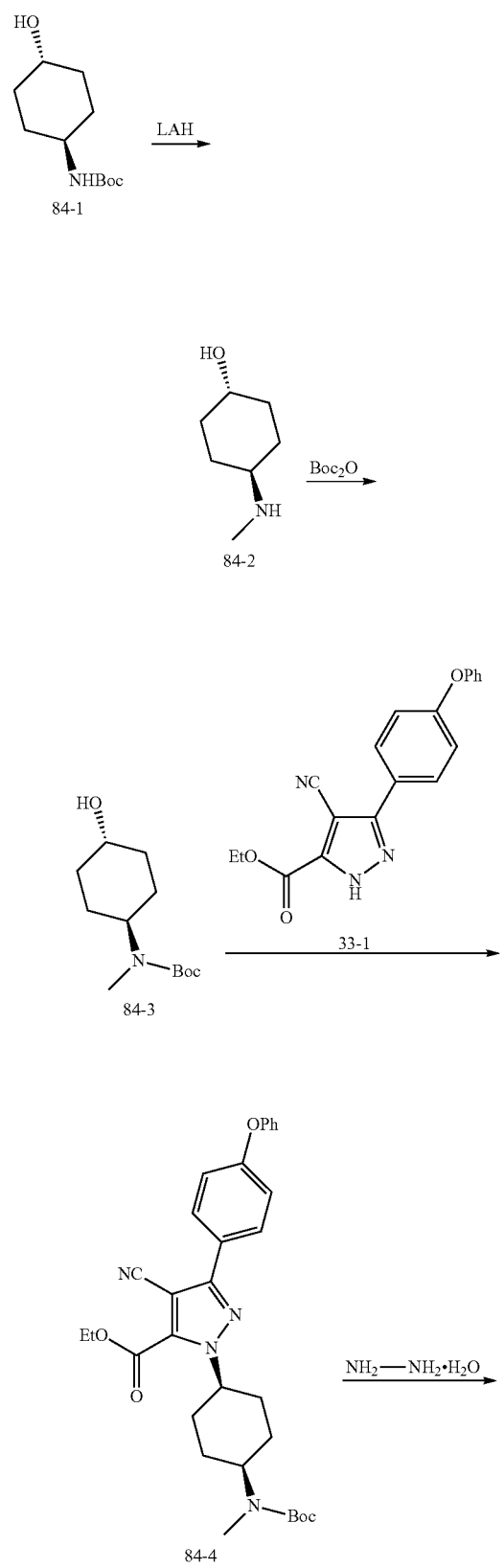
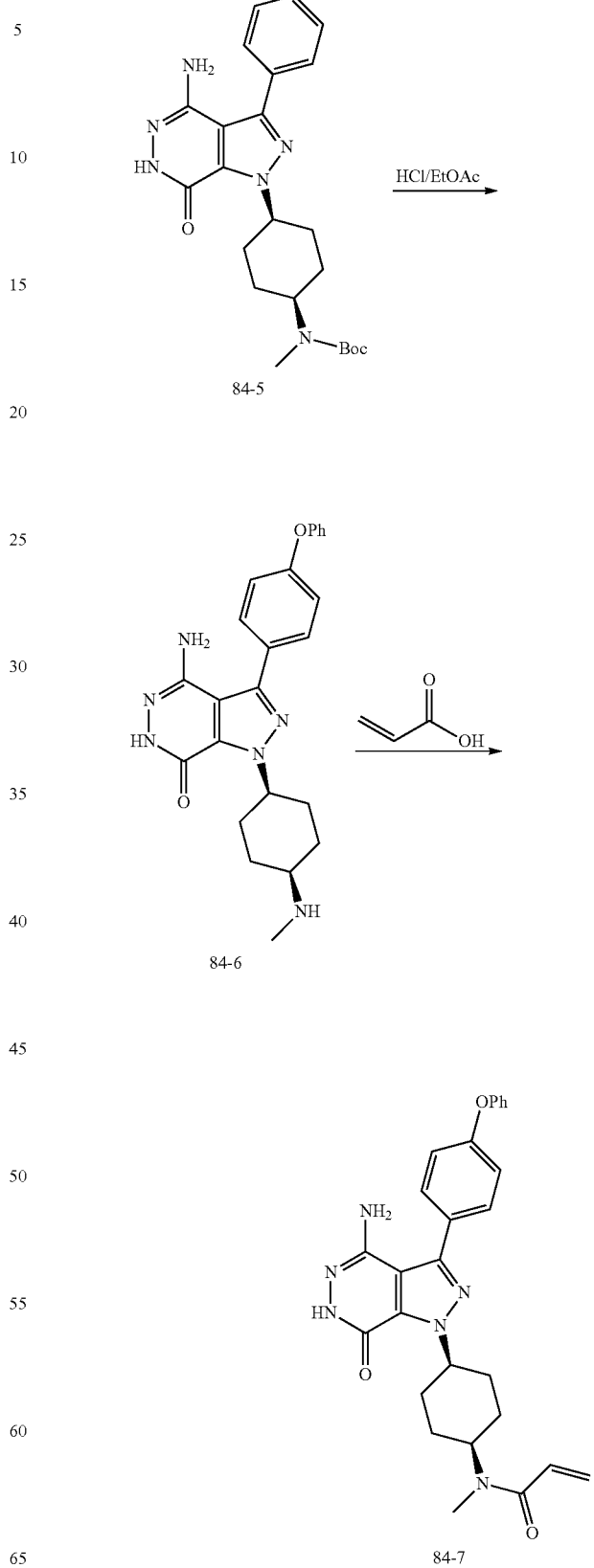

Example 82

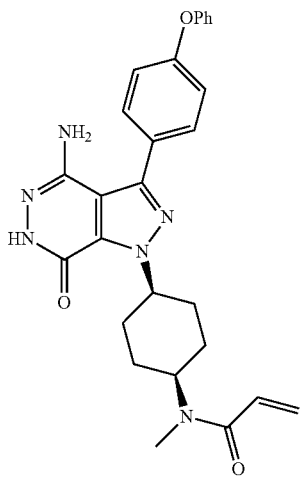 [SMILES: C=CC(=O)N(C)[C@H]1CC[C@@H](n2nc(-c3ccc(Oc4ccccc4)cc3)c3c(N)n[nH]c(=O)c32)CC1]

Compound 84-2

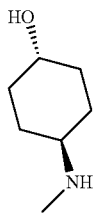

To a solution of compound 84-1 (910 mg, 4.23 mmol) in anhydrous THF (15 mL) was added LAH (177 mg, 4.66 mmol) and the reaction solution was stirred at 25° C. for 45 min. After TLC indicated the reaction was complete, the reaction was quenched with water (30 mL×1), and the aqueous phase was extracted with EtOAc (50 mL×2). Then the organic phases were combined, dried over anhydrous $Na_2SO_4$, filtered and evaporated to give compound 84-2 (white solid, 140 mg, Yield 25.6%).

$^1$H NMR (400 MHz, $CDCl_3$): δ ppm 3.60 (t, J=10.58, 1H), 2.41 (s, 3H), 2.31 (t, J=10.79, 1H), 1.92-1.97 (m, 4H), 1.25-1.34 (m, 2H), 1.05-1.15 (m, 2H).

LCMS (ESI) m/z: 130 (M+1)

Compound 84-3

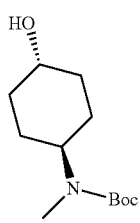 [SMILES: CN(C(=O)OC(C)(C)C)[C@H]1CC[C@H](O)CC1]

To a solution of compound 84-2 (140 mg, 1.085 mmol) in DCM (4 mL) was added Boc anhydride (473 mg, 2.170 mmol) and TEA (329 mg, 3.255 mmol), and the reaction solution was stirred at 20° C. for 30 min. After of TLC indicated the reaction was complete, the reaction was quenched with water (30 mL×1), and the aqueous phase was extracted with EtOAc (50 mL×2). Then the organic phases were combined, dried over anhydrous $Na_2SO_4$, filtered and evaporated to give compound 84-3 (yellow oil, 180 mg, Yield 72.4%).

$^1$H NMR (400 MHz, $CDCl_3$): δ ppm 6.31 (br. s., 1H), 5.14-5.21 (m, 1H), 4.97 (d, J=6.24 Hz, 2H), 4.48 (d, J=7.09 Hz, 2H), 3.36 (t, J=11.49 Hz, 1H), 2.85 (t, J=11.62 Hz, 1H), 2.18 (br. s., 1H), 1.89 (br. s., 1H), 1.60-1.66 (m, 1H), 1.47 (t, 3H), 1.44 (s, 9H).

LCMS (ESI) m/z: 230 (M+1)

Compound 84-4

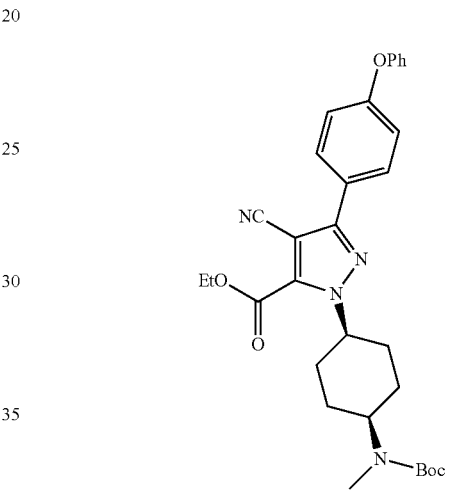

To a solution of $PPh_3$ (1.2 g, 4.63 mmol) and DIAD (935 mg, 4.63 mmol) in THF (15 mL) was added separately compound 33-1 (1.03 g, 3.09 mmol) and compound 84-3 (1.4 g, 6.18 mmol) at 0° C., and then the reaction solution was warmed to 25° C. and reacted for 5 h. After LCMS indicated the reaction was complete, the reaction solution was washed with $NH_4Cl$ solution (aq., 15 mL×1), and the aqueous phase was extracted with DCM (40 mL×3). Then the organic phases were combined, dried over anhydrous $Na_2SO_4$, filtered and evaporated to give a crude product which was purified by column chromatography (PE:EtOAc=10:1) to afford compound 84-4 (white solid, 1.34 g, Yield 79.7%).

$^1$H NMR (400 MHz, $CDCl_3$): δ ppm 7.99 (d, J=8.53 Hz, 2H), 7.37-7.41 (m, 2H), 7.15-7.19 (m, 1H), 7.08-7.10 (m, 4H), 5.44 (br. s., 1H), 4.48 (q, J=7.03 Hz, 2H), 2.79 (s, 3H), 2.18-2.23 (m, 4H), 2.05 (s, 1H), 2.02 (br. s., 1H), 1.61 (br. s., 1H), 1.59 (s, 2H), 1.50 (s, 1H), 1.47 (s, 9H), 1.26 (t, J=7 Hz, 3H).

LCMS (ESI) m/z: 545 (M+1)

Compound 84-5

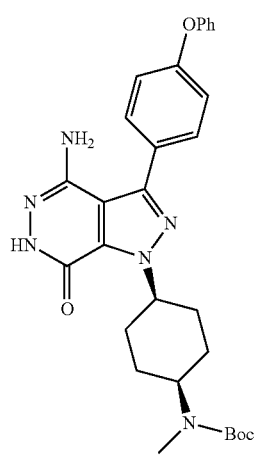 [SMILES: CN(C(=O)OC(C)(C)C)[C@H]1CC[C@@H](n2nc(-c3ccc(Oc4ccccc4)cc3)c3c(N)n[nH]c(=O)c32)CC1]

The mixture of compound 84-4 (1.86 g, 3.42 mmol) in N$_2$H$_4$·H$_2$O (85%, 10 mL) was stirred at 80° C. for 7 h. After LCMS indicated the reaction was complete, the reaction mixture was washed with water (15 mL), and the aqueous phase was extracted with DCM (40 mL×3). The organic phases were combined, dried over anhydrous Na$_2$SO$_4$, filtered and evaporated to give a crude product which was purified by column chromatography (PE:EtOAc=10:1) to afford compound 84-5 (yellow oil, 1.1 g, Yield 39.4%).

$^1$H NMR (400 MHz, CDCl$_3$): δ ppm 7.65 (d, J=9.03 Hz, 2H), 7.40-7.44 (m, 1H), 7.18-7.22 (m, 1H), 7.12 (dd, J=8.03, 3.51 Hz, 4H), 5.74 (br. s., 1H), 4.96 (br. s., 2H), 2.79 (s, 3H), 2.27 (d, J=11.54 Hz, 4H), 2.09 (br. s., 2H), 1.58 (br. s., 2H), 1.47 (s, 9H).

LCMS (ESI) m/z: 531 (M+1)

Compound 84-6

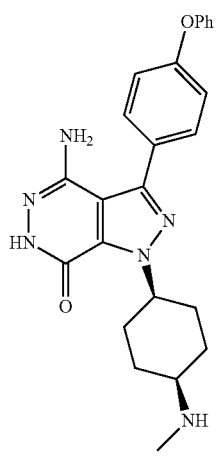 [SMILES: CN[C@H]1CC[C@@H](n2nc(-c3ccc(Oc4ccccc4)cc3)c3c(N)n[nH]c(=O)c32)CC1]

To a solution of compound 84-5 (1.1 g, 2.075 mmol) in EtOAc (5 mL) was added HCl-EtOAc (1 mL, 4 M) at 25° C. and the reaction solution was stirred at 20° C. for 1 h. After LCMS indicated the reaction was complete, the reaction solution was adjusted to pH 8 with NaHCO$_3$ (15 mL), and the aqueous phase was extracted with EtOAc (50 mL×2). The organic phases were combined, dried over anhydrous Na$_2$SO$_4$, filtered and evaporated to give compound 84-6 (yellow solid, 880 mg, Yield 98.6%).

$^1$H NMR (400 MHz, CDCl$_3$): δ ppm 7.65 (d, J=8.56 Hz, 2H), 7.38-7.42 (m, 2H), 7.18 (t, J=7.34 Hz, 1H), 7.11 (dd, J=13.69, 8.31 Hz, 4H), 5.40-5.47 (m, 1H), 4.93 (br. s., 2H), 2.79 (br. s., 1H), 2.43 (s, 3H), 2.30-2.39 (m, 2H), 1.88-2.00 (m, 5H), 1.70-1.77 (m, 2H), 1.25-1.29 (m, 1H).

LCMS (ESI) m/z: 431 (M+1)

Compound 84-7

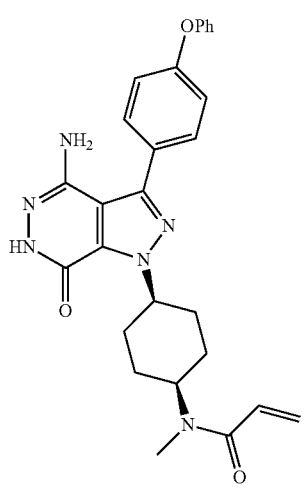

To a solution of compound 84-6 (90 mg, 0.21 mmol), HATU (120 mg, 0.32 mmol) and DIPEA (55 mg, 0.42 mmol) in anhydrous DCM (5 mL) was added acrylic acid (15 mg, 0.21 mmol) at 25° C. and the reaction solution was stirred at 25° C. for 3.5 h. After LCMS indicated the reaction was complete, the reaction solution was washed with water (5 mL×1), and the aqueous phase was extracted with EtOAc (10 mL×3). The organic phases were combined, dried over anhydrous Na$_2$SO$_4$, filtered and evaporated to give a residue which was purified by preparative HPLC (basic) to afford compound 84-7 (white solid, 30 mg, Yield 29.5%).

$^1$H NMR (400 MHz, CDCl$_3$): δ ppm 7.71 (d, J=8.56 Hz, 1H), 7.38-7.42 (m, 2H), 7.17 (t, J=7.46 Hz, 1H), 7.11 (dd, J=14.79, 8.19 Hz, 4H), 6.68-6.89 (m, 1H), 6.18 (dd, J=16.38, 11.49 Hz, 1H), 5.77 (br. s., 1H), 5.69-5.73 (m, 1H), 4.64 (br. s., 1H), 4.05-4.12 (m, 1H), 2.91-3.02 (m, 3H), 2.46-2.53 (m, 1H), 2.35-2.41 (m, 1H), 2.25-2.29 (m, 2H), 2.09-2.20 (m, 2H), 1.54-1.63 (m, 2H).

LCMS (ESI) m/z: 485 (M+1)

Example 83

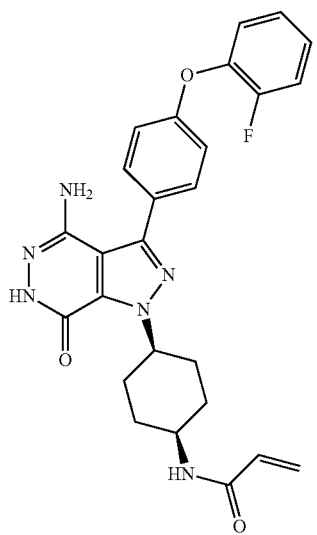 [SMILES: C=CC(=O)N[C@H]1CC[C@@H](n2nc(-c3ccc(Oc4ccccc4F)cc3)c3c(N)n[nH]c(=O)c32)CC1]

In Example 83, the systhesis process was similar to that in Example 57.

¹H NMR (400 MHz, CDCl₃): δ ppm 9.86 (br. s., 1H), 7.63 (d, J=8.53 Hz, 2H), 7.18-7.24 (m, 4H), 7.11 (d, J=8.53 Hz, 2H), 6.59 (br. s., 1H), 6.33-6.37 (m, 1H), 6.20-6.27 (m, 1H), 5.64 (dd, J=10.29, 1.25 Hz, 1H), 5.24 (t, J=11.29 Hz, 1H), 4.61 (s, 2H), 4.40 (d, J=4.02 Hz, 1H), 2.33-2.43 (m, 2H), 1.99-2.06 (m, 4H), 1.77-1.84 (m, 2H).

LCMS (ESI) m/z: 489 (M+1)

Example 84

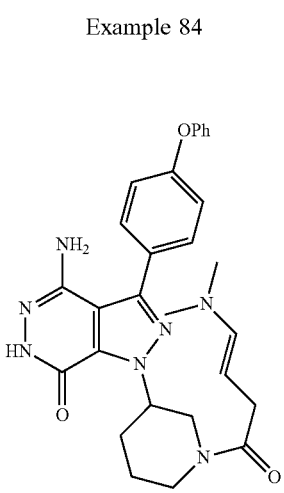

In Example 84, the systhesis process was similar to that in Example 20.

¹H NMR (400 MHz, d₆-DMSO): δ ppm 11.774 (s, 1H), 7.681-7.659 (d, 2H), 7.456-7.416 (t, 2H), 7.210-7.104 (m, 5H), 6.614-6.531 (t, 2H), 5.399 (s, 1H), 5.150 (s, 2H), 4.525-4.499 (d, 1H), 4.266-4.236 (d, 1H), 4.118 (s, 1H), 3.974 (s, 1H), 3.621-3.590 (d, 1H), 3.154 (s, 1H), 3.039 (s, 1H), 2.234-2.173 (d, 7H), 1.977-1.973 (d, 1H), 1.534 (s, 1H).

LCMS (ESI) m/z: 514 (M+1).

Example 85

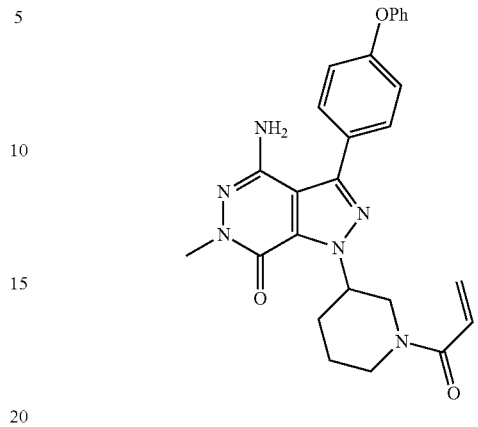

In Example 85, the systhesis process was similar to that in Example 50.

¹H NMR (400 MHz, CDCl₃): δ ppm 7.567-7.548 (d, 2H), 7.321 (s, 2H), 7.106-7.003 (m, 4H), 6.548 (s, 1H), 6.217 (s, 1H), 5.601-5.527 (d, 2H), 4.792 (s, 1H), 4.499 (s, 1H), 4.193 (s, 2H), 3.922 (s, 1H), 3.613 (s, 3H), 3.400 (s, 1H), 3.128 (s, 1H), 2.801 (s, 1H), 2.243 (s, 2H), 1.932-1.902 (d, 1H), 1.688 (s, 1H).

LCMS (ESI) m/z: 471 (M+1).

Example 86

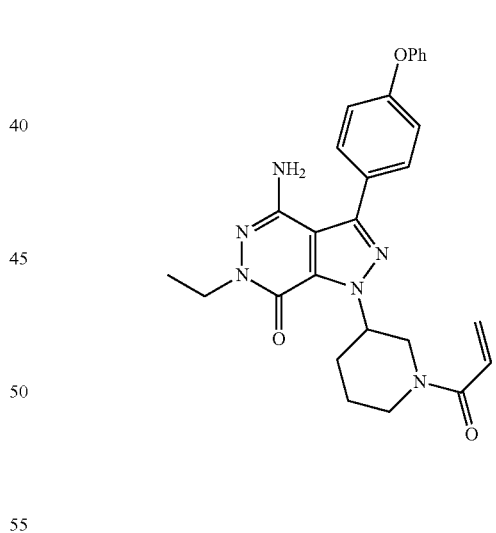

In Example 86, the systhesis process was similar to that in Example 50.

¹H NMR (400 MHz, d₆-DMSO): δ ppm 7.68 (d, J=8.28 Hz, 2H), 7.44 (t, J=7.78 Hz, 2H), 7.09-7.22 (m, 5H), 6.73-6.92 (m, 1H), 6.10 (t, J=16.06 Hz, 1H), 5.57-5.75 (m, 1H), 5.46 (br. s., 1H), 5.32 (br. s., 2H), 4.55 (d, J=9.54 Hz, 1H), 4.20-4.36 (m, 1H), 4.00 (d, J=16.06 Hz, 3H), 3.56 (d, J=10.79 Hz, 1H), 2.94 (br. s., 1H), 2.18 (br. s., 2H), 1.92 (br. s., 1H), 1.52 (br. s., 1H), 1.26 (t, J=7.03 Hz, 3H).

LCMS (ESI) m/z: 485 (M+1)

367
Example 87
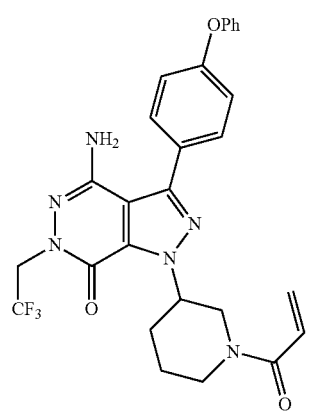 [SMILES: C=CC(=O)N1CCCC(n2nc(-c3ccc(Oc4ccccc4)cc3)c3c(N)nn(CC(F)(F)F)c(=O)c32)C1]
In Example 87, the systhesis process was similar to that in Example 52.
$^1$H NMR (400 MHz, $d_6$-DMSO): δ ppm 7.61-7.75 (m, 2H), 7.44 (brs, 2H), 7.13 (brs, 5H), 6.68-6.95 (m, 1H), 6.09 (brs, 1H), 5.30-5.80 (m, 5H), 4.79 (brs, 2H), 4.57 (brs, 1H), 4.16-4.39 (m, 1H), 4.03 (brs, 1H), 3.59 (brs, 1H), 2.98 (brs, 1H), 2.20 (brs, 2H), 1.94 (brs, 1H), 1.54 (brs, 1H).
LCMS (ESI) m/z: 539 (M+1).
368
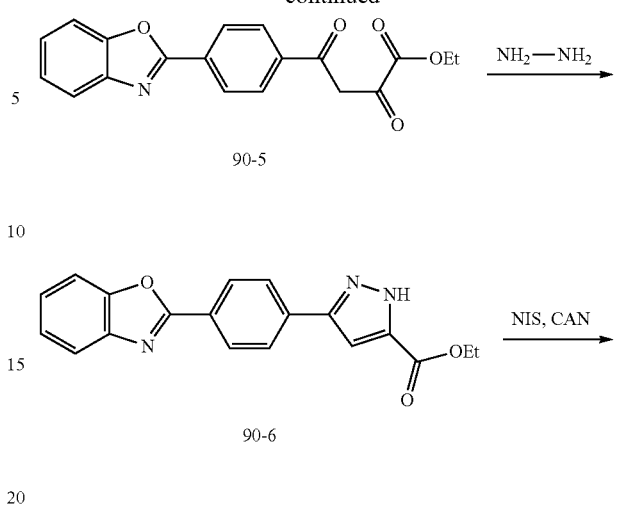
Scheme 55
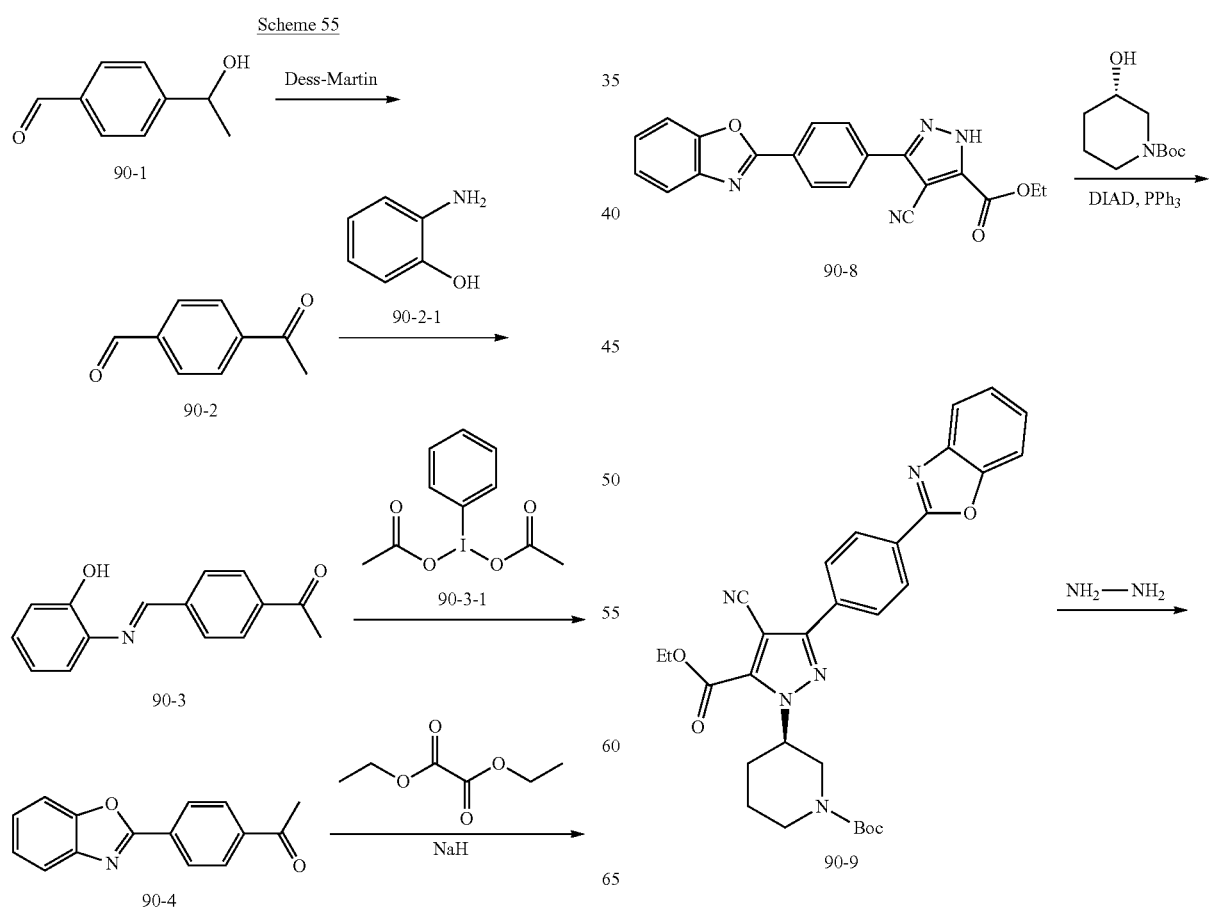

-continued

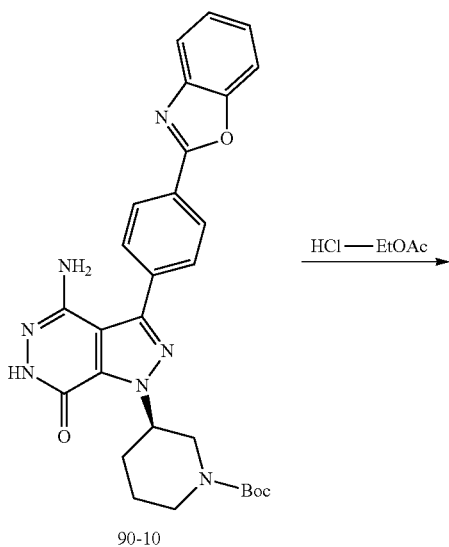

90-10

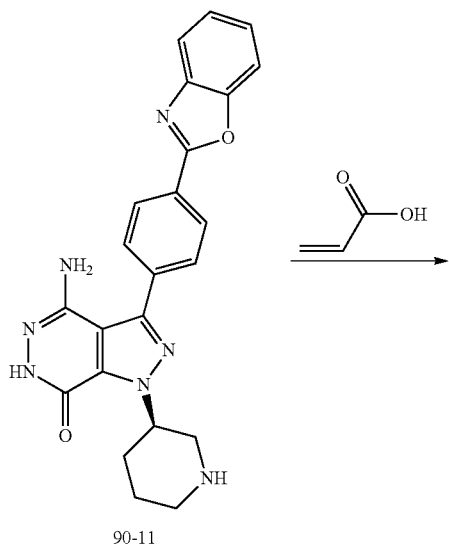

90-11

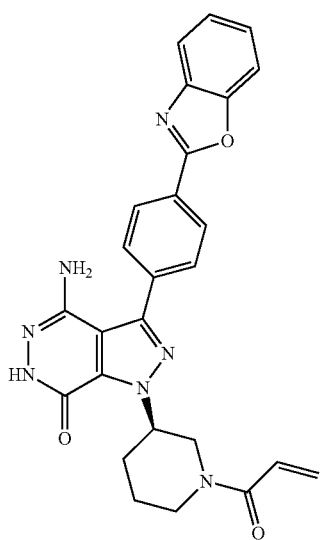 [SMILES: C=CC(=O)N1CCC[C@@H](n2nc(-c3ccc(-c4nc5ccccc5o4)cc3)c3c(N)n[nH]c(=O)c32)C1]

90-12

Example 88

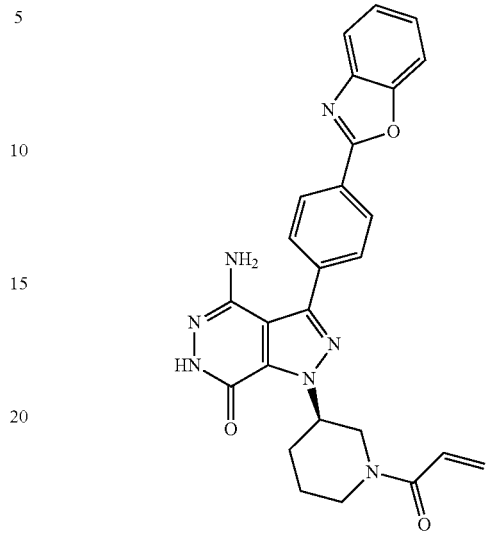

Compound 90-2

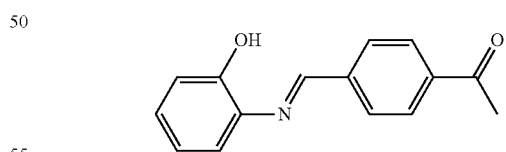

To a solution of compound 90-1 (6.60 g, 43.95 mmol) in DCM (100 mL) was added Dess-Martin periodinane (20.50 g, 48.35 mmol) and the reaction solution was stirred at 23° C. for 1 h. After TLC indicated the reaction was complete, the reaction solution was washed with water (150 mL), and the aqueous phase was extracted with EtOAc (150 mL×2). The organic phases were combined, dried over anhydrous $Na_2SO_4$, filtered and evaporated to give compound 90-2 (yellow oil, 5.95 g, Yield 91.37%).

LCMS (ESI) m/z: 149 (M+1)

Compound 90-3

To a solution of compound 90-2 g, 33.75 mmol) in MeOH (100 mL) was added compound 90-2-1 (3.68 g, 33.75 mmol), and the reaction solution was stirred at 23° C. for 6 h. After TLC indicated the reaction was complete. Then the reaction solution was evaporated and concentrated to give compound 90-3 (yellow solid, 8 g, Yield 99.07%).

$^1$H NMR (400 MHz, $CDCl_3$): δ ppm 8.75 (s, 1H), 8.05-8.07 (m, 2H), 7.99-8.02 (m, 2H), 7.33 (d, J=8.07 Hz, 1H), 7.21-7.23 (m, 1H), 7.03 (d, J=8.07 Hz, 1H), 6.90-6.94 (m, 1H), 6.66-6.80 (m, 1H), 2.65 (s, 3H).

LCMS (ESI) m/z: 240 (M+1)

Compound 90-4

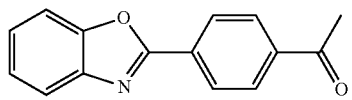

To a solution of compound 90-3 (5.00 g, 20.90 mmol) in DCM (60 mL) was added compound 90-3-1 (8.08 g, 25.08 mmol), and the reaction solution was stirred at 25° C. for 2 h. After TLC indicated the reaction was complete, the reaction solution was washed with water (20 mL), and the aqueous phase was extracted with DCM (20 mL×2). The organic phases were combined, dried over anhydrous $Na_2SO_4$, filtered and evaporated to give a crude product which was purified by column chromatography (PE: EtOAc=10:3) to afford compound 90-4 (yellow solid, 2.10 g, Yield 42.35%).

LCMS (ESI) m/z: 238 (M+1).

Compound 90-5

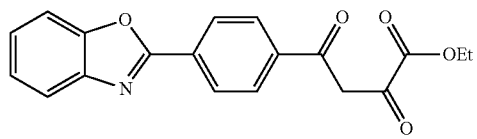 [SMILES: CCOC(=O)C(=O)CC(=O)c1ccc(-c2nc3ccccc3o2)cc1]

To a solution of compound 90-4 (2.00 g, 8.43 mmol) in toluene (25 mL) was added NaH (242.78 mg, 10.12 mmol) and the reaction solution was stirred for 10 min, after which diethyl oxalate (2.46 g, 16.86 mmol) was added and the resulting reaction solution was heated to 80° C. and stirred for 1 h. After TLC indicated the reaction was complete, the reaction solution was washed with $NH_4Cl$ solution (aq., 20 mL), and the aqueous phase was extracted with EtOAc (50 mL×2). The organic phases were combined, dried over anhydrous $Na_2SO_4$, filtered and evaporated to give a residue which was purified by column chromatography to afford compound 90-5 (yellow solid, 2.00 g, Yield 70.33%).

$^1$H NMR (400 MHz, $CDCl_3$): δ ppm 8.40 (d, J=8.53 Hz, 2H), 8.16 (d, J=8.53 Hz, 2H), 7.81-7.84 (m, 1H), 7.62-7.65 (m, 1H), 7.39-7.44 (m, 2H), 7.14 (s, 1H), 4.40-4.46 (m, 2H), 1.44 (t, J=7.03 Hz, 3H).

LCMS (ESI) m/z: 338 (M+1)

Compound 90-6

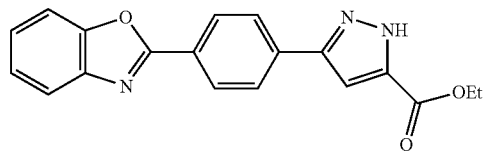 [SMILES: CCOC(=O)c1[nH]nc(-c2ccc(-c3nc4ccccc4o3)cc2)c1I]

The solution of compound 90-5 (2.60 g, 7.71 mmol) in EtOH (25 mL) and HOAc (2 mL) was stirred at 25° C. for 20 min, after which $N_2H_4\cdot H_2O$ (85%, 463.16 mg, 9.25 mmol) was added and the reaction solution was stirred at 25° C. for 1 h. After TLC indicated the reaction was complete, the reaction solution was washed with $Na_2CO_3$ solution (aq., 50 mL×2), and the aqueous phase was extracted with EtOAc (100 mL×2). The organic phases were combined, dried over anhydrous $Na_2SO_4$, filtered and evaporated to give compound 90-6 (yellow solid, 1.5 g, Yield 58.36%).

LCMS (ESI) m/z: 334 (M+1)

Compound 90-7

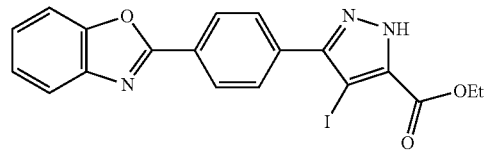

To a solution of compound 90-6 (1.70 g, 5.10 mmol) and NIS (2.87 g, 12.75 mmol) in acetonitrile (20 mL) was added CAN (559.18 mg, 1.02 mmol) at 25° C., and the reaction solution was stirred at 120° C. for 5 h. After LCMS indicated the reaction was complete, the reaction solution was washed with water (20 mL×2) and saturated brine (10 mL×1), and the aqueous phase was extracted with EtOAc (30 mL×2). The organic phases were combined, dried over anhydrous $Na_2SO_4$, filtered and evaporated to give a crude product which was purified by column chromatography (PE:EtOAc equals to 10:1 to 5:1) to afford compound 90-7 (yellow solid, 2.2 g, Yield 93.93%).

$^1$H NMR (400 MHz, $CDCl_3$): δ ppm 8.34 (br. s., 2H), 7.96-8.04 (m, 2H), 7.84 (t, J=8.53 Hz, 2H), 7.43-7.49 (m, 2H), 4.35 (br. s., 2H), 1.35 (br. s., 3H).

LCMS (ESI) m/z: 460 (M+1)

Compound 90-8

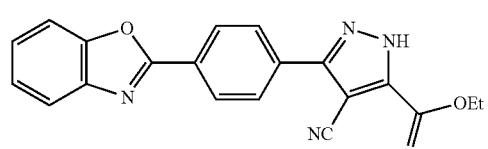

To a solution of compound 90-7 (2.20 g, 4.79 mmol) and CuCN (1.29 g, 14.37 mmol) in DMF (20 mL) was added $Pd(dppf)Cl_2$ (70.10 mg, 95.81 μmol) under nitrogen atmosphere at 25° C., and then the reaction solution was stirred under nitrogen atmosphere at 120° C. for 10 h. After LCMS indicated the reaction was complete, the reaction solution was cooled down to r.t. and filtered with diatomite. The filtrate was washed with water (20×3 mL), and the aqueous phase was extracted with EtOAc (30 mL×2). The organic phases were combined, dried over anhydrous $Na_2SO_4$, filtered and evaporated to give a crude product which was purified by column chromatography (PE:EtOAc=2:1) to afford compound 90-8 (yellow solid, 700 mg, Yield 41%).

$^1$H NMR (400 MHz, $CDCl_3$): δ ppm 8.41 (d, J=8.53 Hz, 2H), 8.12 (d, J=8.03 Hz, 2H), 7.85 (t, J=9.03 Hz, 2H), 7.43-7.50 (m, 2H), 4.41 (q, J=7.03 Hz, 2H), 1.36 (t, J=7.03 Hz, 3H).

LCMS (ESI) m/z: 359 (M+1).

Compound 90-9

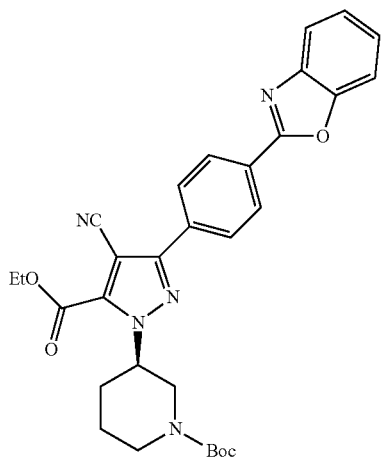 [SMILES: CCOC(=O)c1c(C#N)c(-c2ccc(-c3nc4ccccc4o3)cc2)nn1[C@@H]1CCCN(C(=O)OC(C)(C)C)C1]

To a solution of PPh₃ (491.01 mg, 1.87 mmol) and DIAD (378.54 mg, 1.87 mmol) in THF (5 mL) was added separately compound 90-8 (560.00 mg, 1.56 mmol) and compound (S)-1-BOC-3-Hydroxypiperidine (627.93 mg, 3.12 mmol) at 0° C., and then the reaction solution was warmed to 25° C. and reacted for 10 h. After LCMS indicated the reaction was complete, the reaction solution was washed with saturated NH₄Cl solution (aq., 10 mL×2), and the aqueous phase was extracted with EtOAc (20 mL×2). The organic phases were combined, dried over anhydrous Na₂SO₄, filtered and evaporated to give a crude product which was purified by column chromatography (PE: EtOAc=10:1) to afford compound 90-9 (yellow solid, 600 mg, Yield 71.01%).

¹H NMR (400 MHz, CDCl₃): δ ppm 8.37 (d, J=8.53 Hz, 2H), 8.19 (d, J=8.53 Hz, 2H), 7.79-7.82 (m, 1H), 7.61-7.63 (m, 1H), 7.38-7.40 (m, 2H), 5.23 (br. s., 1H), 4.52 (q, J=7.19 Hz, 2H), 3.51 (br. s., 2H), 3.41 (dd, J=12.55, 10.04 Hz, 1H), 2.22 (br. s., 2H), 1.88 (br. s., 3H), 1.50 (t, J=7.28 Hz, 3H), 1.46 (s, 9H).

LCMS (ESI) m/z: 542 (M+1).

Compound 90-1

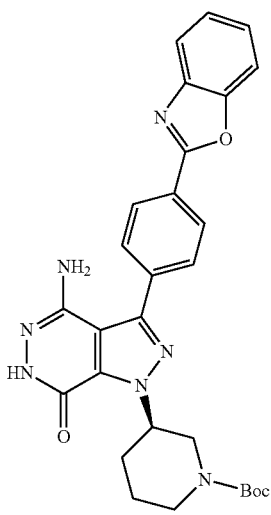 [SMILES: CC(C)(C)OC(=O)N1CCC[C@@H](n2nc(-c3ccc(-c4nc5ccccc5o4)cc3)c3c(N)n[nH]c(=O)c32)C1]

To a solution of compound 90-9 (300.00 mg, 0.55 mmol) in DCM (3 mL) was added N₂H₄.H₂O (85%, 831.79 mg, 16.63 mmol), and then the reaction solution was stirred at 50° C. for 16 h. After LCMS indicated the reaction was complete, the reaction solution was washed with saturated brine (30 mL), and the aqueous phase was extracted with DCM (80 mL×2). The organic phases were combined, dried over anhydrous Na₂SO₄, filtered and evaporated to give compound 90-10 (white solid, 220 mg, Yield 75.3%).

LCMS (ESI) m/z: 528 (M+1).

Compound 9041

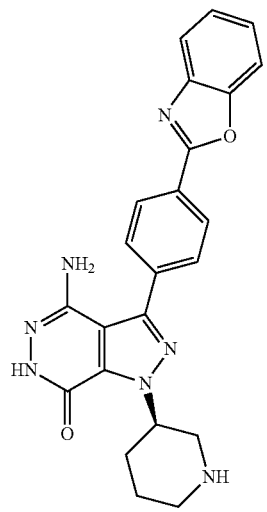 [SMILES: Nc1n[nH]c(=O)c2c1c(-c1ccc(-c3nc4ccccc4o3)cc1)nn2[C@@H]1CCCNC1]

To a solution of compound 90-10 (220.00 mg, 0.42 mmol) in EtOAc (2 mL) was added HCl-EtOAc (8 mL, 4 M) at 25° C., and then the reaction solution was stirred at 25° C. for 20 min. After LCMS indicated the reaction was complete, then the reaction solution was adjusted to pH 8 with NaHCO₃ (20 mL), and the aqueous phase was extracted with EtOAc (80 mL×2). The organic phases were combined, dried over anhydrous Na₂SO₄, filtered and evaporated to give compound 90-11 (yellow solid, 200 mg, Yield 98.0%).

LCMS (ESI) m/z: 428 (M+1).

Compound 90-12

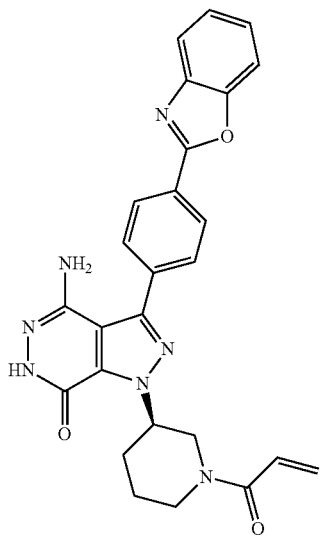 [SMILES: C=CC(=O)N1CCC[C@@H](n2nc(-c3ccc(-c4nc5ccccc5o4)cc3)c3c(N)n[nH]c(=O)c32)C1]

To a solution of compound 90-11 (200.00 mg, 0.47 mmol), HATU (212.80 mg, 0.56 mmol) and DIPEA (72.76 mg, 0.56 mmol) in anhydrous DCM (3 mL) was added acrylic acid (33.84 mg, 0.47 mmol) at 25° C., and then the reaction solution was stirred at 25° C. for 2 h. After LCMS indicated the reaction was complete, the reaction solution was washed with water (20 mL×1), and the aqueous phase was extracted with EtOAc (50 mL×3). The organic phases were combined, dried over anhydrous Na$_2$SO$_4$, filtered and evaporated to give a residue which was purified by preparative HPLC (basic) to afford compound 90-12 (white solid, 20 mg, Yield 8.9%).

$^1$H NMR (400 MHz, CDCl$_3$): δ ppm 10.55 (br. s., 1H), 8.42 (d, J=7.9 Hz, 2H), 7.87 (d, J=8.2 Hz, 2H), 7.83-7.78 (m, 1H), 7.64-7.60 (m, 1H), 7.42-7.36 (m, 2H), 6.71-6.59 (m, 1H), 6.33-6.19 (m, 1H), 5.75-5.62 (m, 1H), 5.52 (br. s., 1H), 4.99 (br. s., 1H), 4.32 (d, J=11.9 Hz, 1H), 3.97 (d, J=13.0 Hz, 1H), 3.66-3.53 (m, 1H), 3.23 (br. s., 1H), 2.86 (t, J=10.7 Hz, 1H), 2.35 (br. s., 1H), 2.00 (d, J=13.7 Hz, 1H), 1.75 (d, J=13.9 Hz, 2H)

LCMS (ESI) m/z: 482 (M+1)

Example 89

In Example 89, the systhesis process was similar to that in Example 32.

LCMS (ESI) m/z: 472 (M+1)

$^1$H NMR (400 MHz, CDCl$_3$): δ ppm 10.26 (br. s., 1H), 8.08 (d, J=4.00 Hz, 1H), 7.70 (d, J=8.00 Hz, 2H), 7.27-7.32 (m, 2H), 6.89 (d, J=8.00 Hz, 1H), 6.82 (s, 1H), 6.55-6.71 (m, 1H), 6.20-6.34 (m, 1H), 5.60-5.76 (m, 1H), 5.42-5.57 (m, 1H), 4.77-4.98 (m, 2H), 4.63-4.26 (m, 1H), 4.04-3.43 (m, 2H), 3.26-2.79 (m, 1H), 2.39 (s, 3H), 2.37-2.18 (m, 2H), 1.94-2.05 (m, 1H), 1.72-1.84 (m, 1H)

Example 90

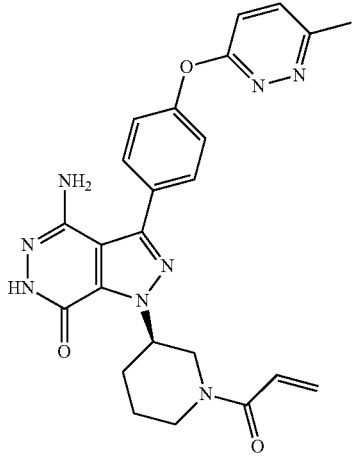

In Example 90, the systhesis process was similar to that in Example 32.

LCMS (ESI) m/z: 473 (M+1)

$^1$H NMR (400 MHz, d$_6$DMSO): ppm 11.77 (s, 1H), 7.64-7.71 (m, 3H), 7.20 (d, J=8.56 Hz, 2H), 6.99 (d, J=8.31 Hz, 1H), 6.80 (dq, J=16.51, 10.56 Hz, 1H), 6.07 (t, J=16.38 Hz, 1H), 5.53-5.72 (m, 1H), 5.36 (br. s., 1H), 5.14 (br. s., 2H), 4.25-4.55 (m, 1H), 3.95-4.24 (m, 1H), 2.61-2.99 (m, 2H), 2.26-2.41 (m, 2H), 2.23 (s, 3H), 2.17 (d, J=15.90 Hz, 2H), 1.91 (d, J=13.45 Hz, 1H).

Example 91

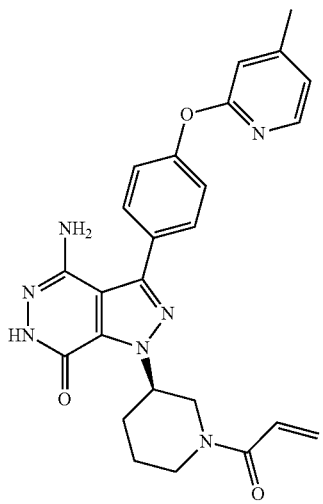 [SMILES: C=CC(=O)N1CCC[C@@H](n2nc(-c3ccc(Oc4cc(C)ccn4)cc3)c3c(N)n[nH]c(=O)c32)C1]

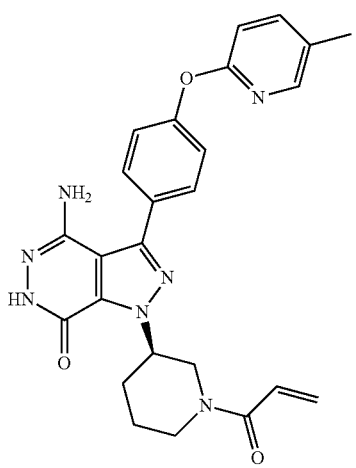

In Example 91, the systhesis process was similar to that in Example 32.

LCMS (ESI) m/z: 472 (M+1)

¹H NMR (400 MHz, CDCl₃): δ ppm 10.45 (br. s., 1H), 7.97 (s, 1H), 7.62 (d, J=8.56 Hz, 2H), 7.50 (d, J=8.31 Hz, 1H), 7.20 (d, J=2.93 Hz, 2H), 6.85 (d, J=8.31 Hz, 1H), 6.58-6.50 (m, 1H), 6.20 (t, J=15.4 Hz, 1H), 5.58-5.56 (m, 1H), 5.43 (s, 1H), 4.95 (d, J=36.2 Hz, 2H), 4.79-4.52 (m, 1H), 4.25-3.92 (m, 1H), 3.36-3.60 (m, 1H), 3.14-2.79 (m, 1H), 2.36-2.33 (m, 2H), 2.25 (s, 3H), 1.93 (d, J=13.45 Hz, 1H), 1.69 (d, J=10.52 Hz, 1H).

Example 92

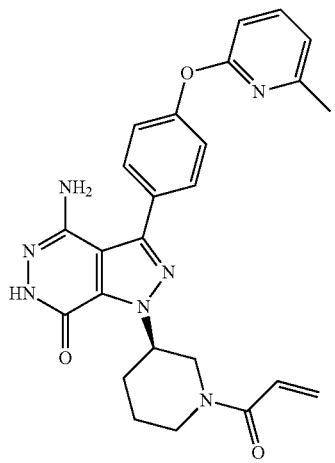 [SMILES: C=CC(=O)N1CCC[C@@H](n2nc(-c3ccc(Oc4cccc(C)n4)cc3)c3c(N)n[nH]c(=O)c32)C1]

In Example 92, the systhesis process was similar to that in Example 32.

LCMS (ESI) m/z: 472 (M+1)

¹H NMR (400 MHz, CDCl₃): δ ppm 10.88 (br. s., 1H), 7.68 (d, J=8.6 Hz, 2H), 7.63 (t, J=7.7 Hz, 1H), 7.29 (d, J=8.4 Hz, 2H), 6.95 (d, J=7.5 Hz, 1H), 6.74 (d, J=8.2 Hz, 1H), 6.69-6.56 (m, 1H), 6.33-6.22 (m, 1H), 5.71 (d, J=10.1 Hz, 1H), 5.63 (d, J=10.6 Hz, 1H), 5.50 (br. s., 1H), 5.19 (d, J=18.3 Hz, 2H), 4.87-4.60 (m, 1H), 4.32-4.00 (m, 1H), 3.67-3.49 (m, 1H), 3.21-2.82 (m, 1H), 2.48 (s, 3H), 2.38-2.29 (m, 1H), 2.00 (d, J=13.5 Hz, 1H), 1.76 (br. s., 1H)

Example 93

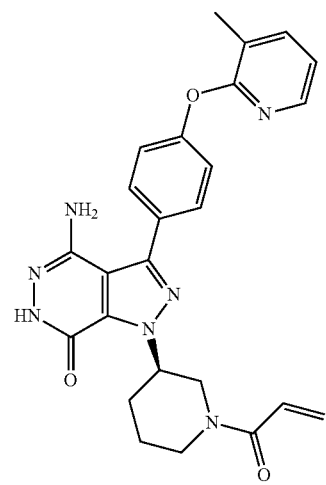 [SMILES: C=CC(=O)N1CCC[C@@H](n2nc(-c3ccc(Oc4ncccc4C)cc3)c3c(N)n[nH]c(=O)c32)C1]

In Example 93, the systhesis process was similar to that in Example 32.

LCMS (ESI) m/z: 472 (M+1)

¹H NMR (400 MHz, CDCl₃): δ ppm 10.88 (br. s., 1H), 7.67 (d, J=8.6 Hz, 2H), 7.62 (t, J=7.7 Hz, 1H), 7.28 (d, J=8.4 Hz, 2H), 6.94 (d, J=7.5 Hz, 1H), 6.73 (d, J=8.2 Hz, 1H), 6.68-6.56 (m, 1H), 6.32-6.21 (m, 1H), 5.70 (d, J=10.1 Hz, 1H), 5.62 (d, J=10.6 Hz, 1H), 5.49 (br. s., 1H), 5.18 (d, J=18.3 Hz, 2H), 4.86-4.59 (m, 1H), 4.31-3.99 (m, 1H), 3.65-3.45 (m, 1H), 3.20-2.82 (m, 1H), 2.47 (s, 3H), 2.40-2.28 (m, 1H), 1.99 (d, J=13.5 Hz, 1H), 1.76 (br. s., 1H)

Scheme 56

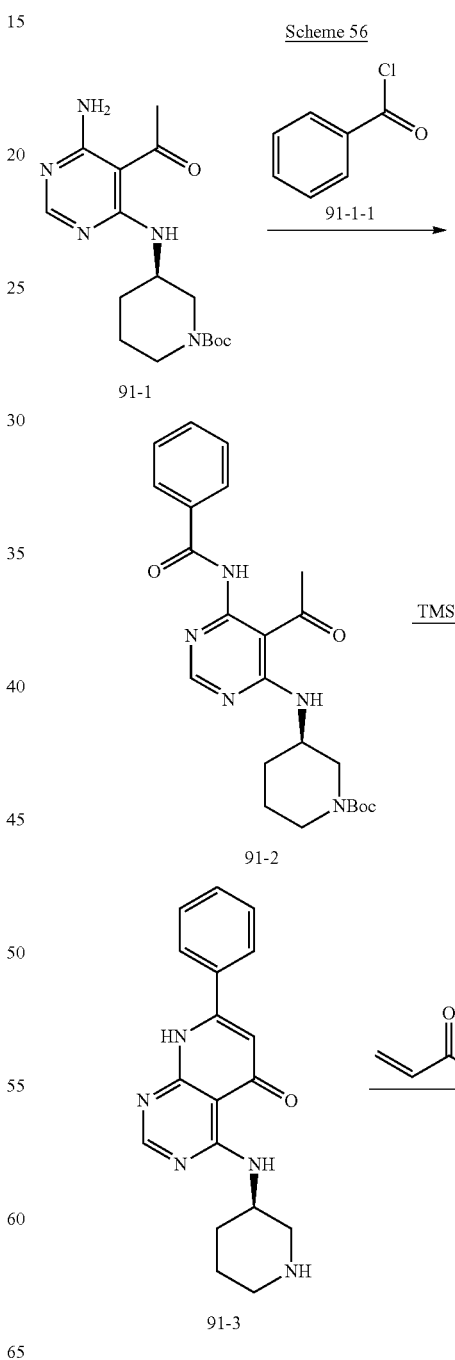

-continued

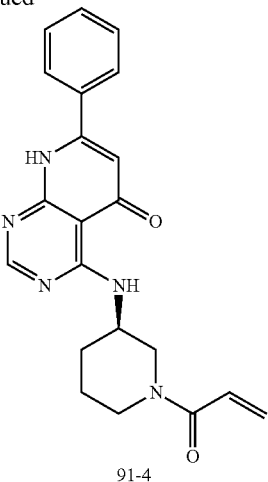

91-4

Example 94

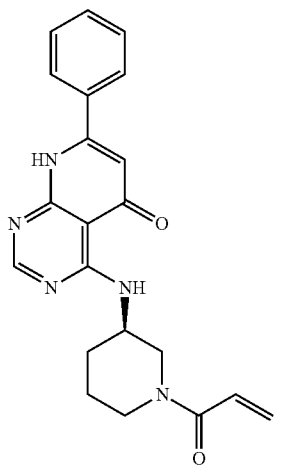 [SMILES: C=CC(=O)N1CCC[C@@H](Nc2ncnc3[nH]c(-c4ccccc4)cc(=O)c23)C1]

The Synthesis of Compound 91-2

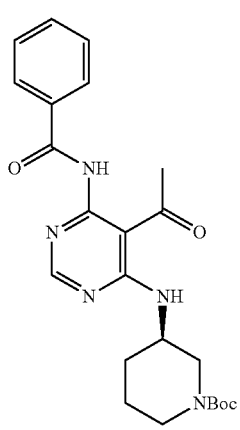 [SMILES: CC(=O)c1c(NC(=O)c2ccccc2)ncnc1N[C@@H]1CCCN(C(=O)OC(C)(C)C)C1]

To a solution of compound 91-1 (400 mg, 1.2 mmol) and compound 91-1-1 (168 mg, 1.2 mmol) in DCM (10 mL) was added TEA (121 mg, 1.2 mmol), and then the reaction solution was stirred at 40° C. for 12 h. After TLC indicated the reaction was complete, the reaction was quenched with water (10 mL), and the aqueous phase was extracted with DCM (10 mL×2). The organic phases were combined, washed with saturated NH$_4$Cl solution (20 mL) and saturated NaCl solution (20 mL) separately, dried over anhydrous Na$_2$SO$_4$, filtered and evaporated to dryness by rotatory evaporation to give compound 91-2 (400 mg, Yield 76%) which was directly used for the next step.

LCMS (ESI) m/z: 440 (M+1)

The Synthesis of Compound 91-3

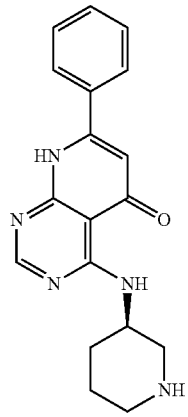 [SMILES: O=c1cc(-c2ccccc2)[nH]c2ncnc(N[C@@H]3CCCNC3)c12]

To a solution of compound 91-2 (50 mg, 0.11 mmol) and TEA (0.2 mL) in dichloroethane (EDC) was added TMSOTf (70 mg, 0.31 mmol), and then the reaction solution was heated to 95° C. and stirred for 12 h under nitrogen atmosphere. After TLC indicated the reaction was complete, the reaction solution was cooled down to r.t., and the reaction was quenched with MeOH (10 mL). Then the reaction solution was washed with NaOH (2 mL, 2M), and the aqueous phase was extracted with EtOAc (10 mL×2). The organic phases were combined, dried over anhydrous Na$_2$SO$_4$ and concentrated to give compound 91-3 (20 mg, Yield 55%) which was directly used for the next step.

LCMS (ESI) m/z: 322 (M+1)

The Synthesis of Compound 91-4

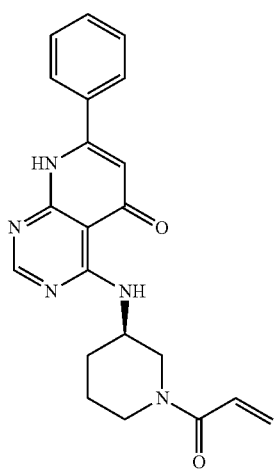

To a solution of compound 91-3 (20 mg, 0.06 mmol) and acryloyl chloride (5.6 mg, 0.062 mmol) in DCM (1.0 mL) was added TEA (12.5 mg, 0.124 mmol), and then the reaction solution was stirred at 25° C. for 0.5 h. After TLC indicated the reaction was complete, the reaction solution was washed with saturated NH₄Cl solution (10 mL), and the aqueous phase was extracted with DCM (20 mL×2). The organic phases were combined, dried over anhydrous Na₂SO₄, filtered and evaporated to dryness by rotatory evaporation to give a crude product which was purified by preparative HPLC to afford compound 91-4 (5 mg, Yield 22%, white solid).

LCMS (ESI) m/z: 376 (M+1)

Scheme 57

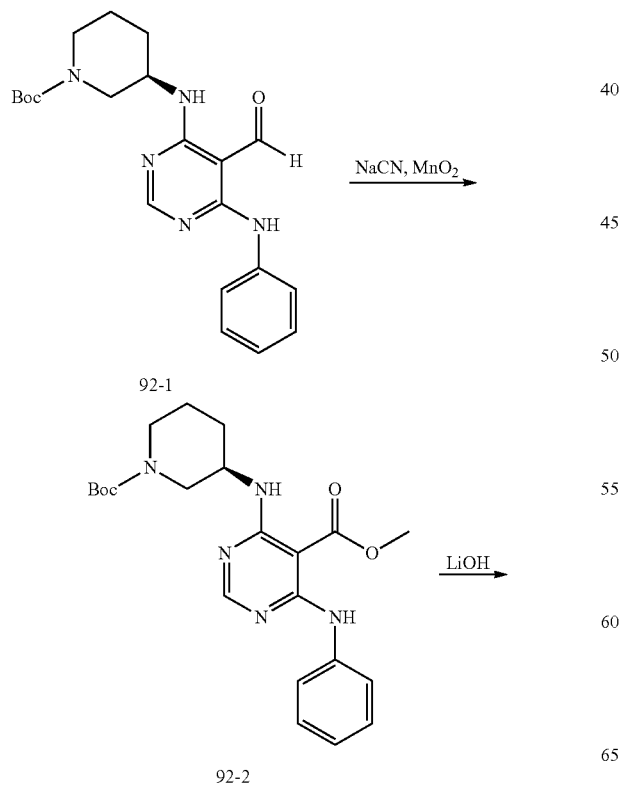

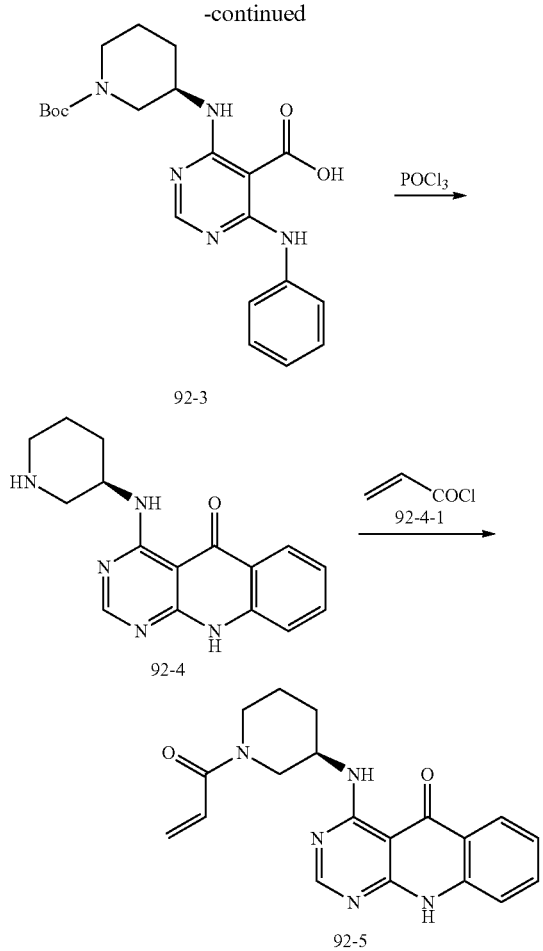

Example 95

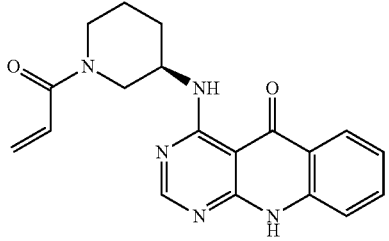 [SMILES: C=CC(=O)N1CCC[C@@H](Nc2ncnc3[nH]c4ccccc4c(=O)c23)C1]

The Synthesis of Compound 92-2

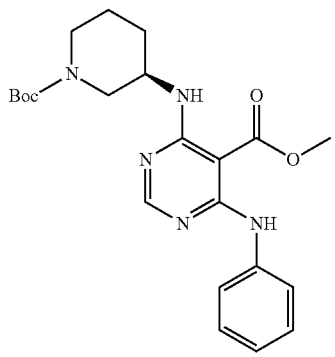 [SMILES: COC(=O)c1c(Nc2ccccc2)ncnc1N[C@@H]1CCCN(C(=O)OC(C)(C)C)C1]

To a solution of compound 92-1 (200 mg, 0.5 mmol) in MeOH (5 mL) was added sodium cyanide (22.5 mg, 2.5 mmol) at 25° C. and the reaction solution was stirred for 5 min, after which MnO$_2$ (652.5 mg, 7.5 mmol) was added and the resulting reaction solution was heated to 80° C. and stirred for 12 h. After TLC indicated the reaction was complete, the reaction solution was diluted with DCM (20 mL), filtered and concentrated to give compound 92-2 (210 mg, Yield 98%).

LCMS (ESI) m/z: 350 (M+1)

The Synthesis of Compound 92-3

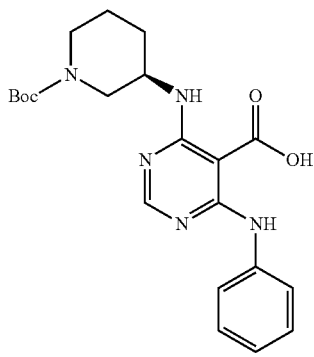 [SMILES: CC(C)(C)OC(=O)N1CCC[C@@H](Nc2ncnc(Nc3ccccc3)c2C(=O)O)C1]

To a solution of compound 92-2 (210 mg, 0.5 mmol) in MeOH (4 mL) and water (2 mL) was added LiOH (52 mg, 1.22 mmol), and the reaction solution was stirred at r.t. for 12 h. After TLC indicated the reaction was complete, the reaction solution was concentrated and extracted with EtOAc (30 mL×3). The organic phases were combined, dried over anhydrous Na$_2$SO$_4$ and concentrated to give compound 92-3 (200 mg, Yield 97%).

LCMS (ESI) m/z: 314 (M+1-Boc)

The Synthesis of Compound 92-4

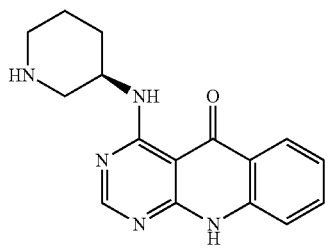 [SMILES: O=c1c2ccccc2[nH]c2ncnc(N[C@@H]3CCCNC3)c12]

Compound 92-3 (200 mg, 0.5 mmol) was dissolved in phosphorus oxychloride (POCl$_3$) (5 mL), and the reaction solution was stirred at 90° C. for 12 h. To this solution, ice water was added, and the aqueous phase was extracted with DCM (20 mL×2). The organic phases were combined, washed with saturated NaHCO$_3$ solution (aq., 20 mL), dried over anhydrous Na$_2$SO$_4$ and concentrated to give compound 92-4 (30 mg, Yield 20%).

LCMS (ESI) m/z: 296 (M+1)

The Synthesis of Compound 92-5

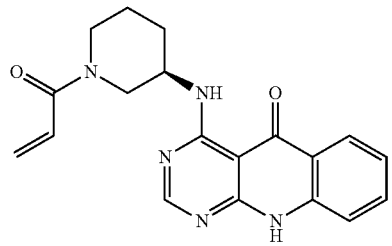 [SMILES: C=CC(=O)N1CCC[C@@H](Nc2ncnc3[nH]c4ccccc4c(=O)c23)C1]

To a solution of compound 92-4 (30 mg, 0.1 mmol) in DCM (2 mL) was added successively DIPEA (13 mg, 0.1 mmol) and compound 92-4-1 (14 mg, 0.15 mmol), and the reaction solution was stirred at r.t. for 2 h. After TLC indicated the reaction was complete, the reaction was quenched with water (20 mL), and the aqueous phase was extracted with DCM (20 mL×2). The organic phases were combined, washed with saturated NH$_4$Cl solution (20 mL) and saturated NaCl solution (aq., 20 mL) separately, dried over anhydrous Na$_2$SO$_4$ and concentrated to give a crude product which was purified by HPLC to afford compound 92-5 (5 mg, Yield 13.9%, white solid).

LCMS (ESI) m/z: 350 (M+1).

Scheme 58

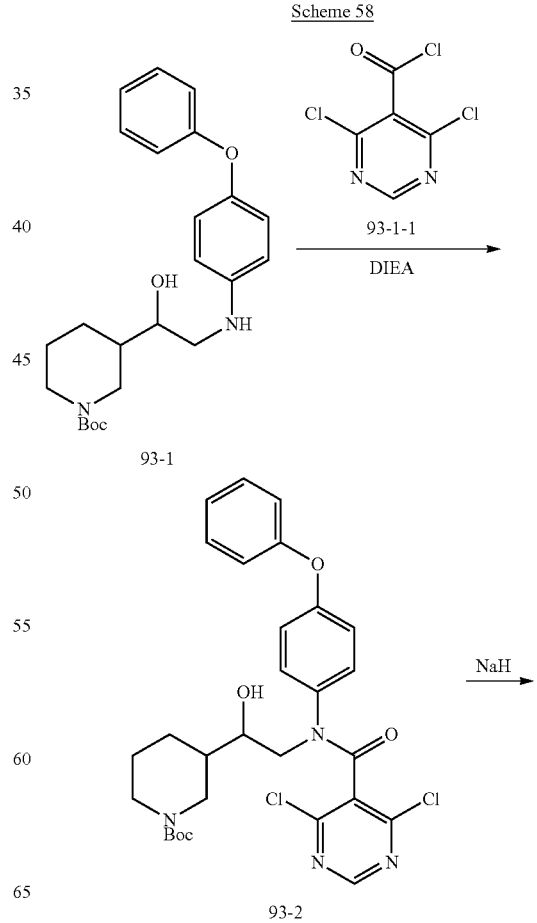

385
-continued

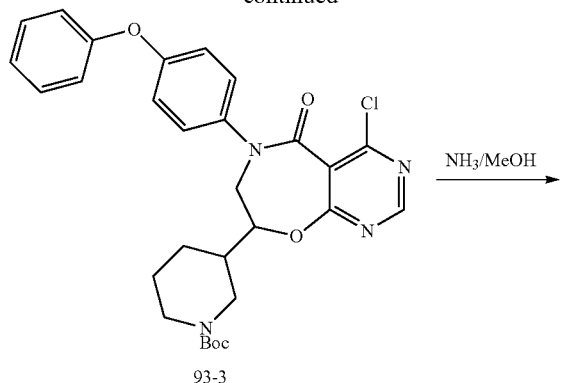
93-3

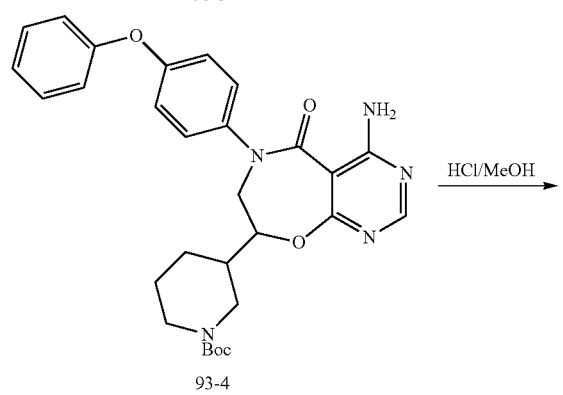
93-4

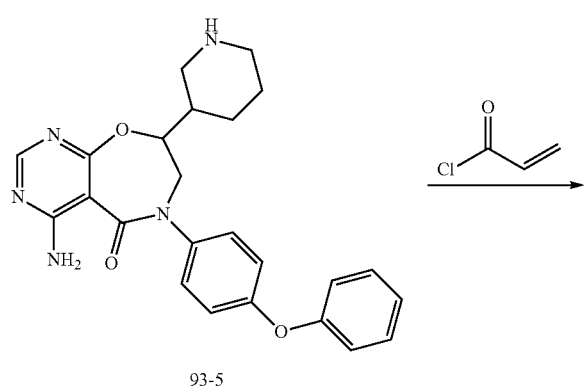
93-5

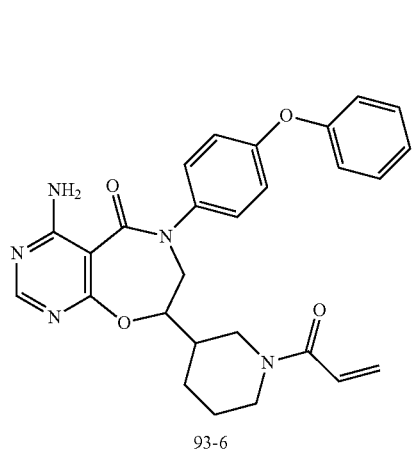
93-6

NH₃/MeOH

HCl/MeOH

Example 96

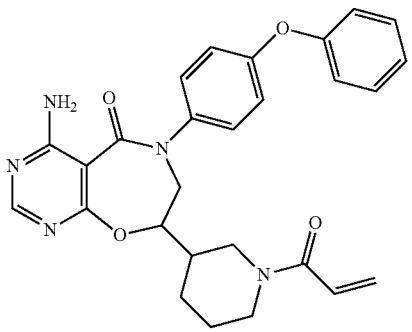 [SMILES: C=CC(=O)N1CCCC(C2CN(c3ccc(Oc4ccccc4)cc3)C(=O)c3c(N)ncnc3O2)C1]

The Synthesis of Compound 93-2

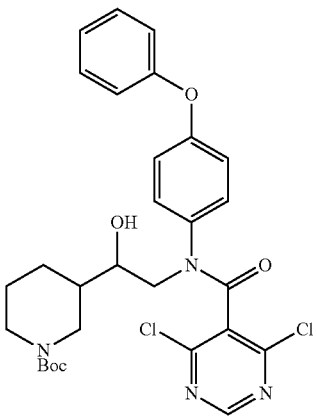 [SMILES: CC(C)(C)OC(=O)N1CCCC(C(O)CN(C(=O)c2c(Cl)ncnc2Cl)c2ccc(Oc3ccccc3)cc2)C1]

To a solution of compound 93-1 (1.5 g, 3.64 mmol) and DIPEA (0.9 g, 7.28 mmol) in DCM (15 mL) was added compound 93-1-1 (0.82 g, 4 mmol) at 0° C., and the reaction solution was stirred at r.t. for 12 h. After TLC indicated the reaction was complete, the reaction was quenched with water (15 mL), and the aqueous phase was extracted with DCM (20 mL×2). The organic phases were combined, washed with saturated NaCl solution (aq., 15 mL), dried over anhydrous Na₂SO₄ and concentrated to give a crude product which was purified by column chromatography to afford compound 93-2 (500 mg, Yield 23%).

LCMS (ESI) m/z: 487 (M+1-Boc)

The Synthesis of Compound 93-3

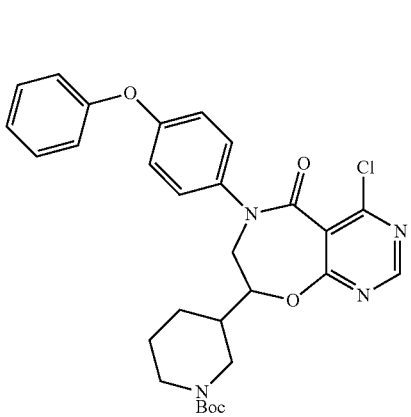 [SMILES: CC(C)(C)OC(=O)N1CCCC(C2CN(c3ccc(Oc4ccccc4)cc3)C(=O)c3c(Cl)ncnc3O2)C1]

To a solution of compound 93-2 (50 mg, 0.085 mmol) in DMF (2 ml) was added NaH (2 mg, 0.085 mmol) at 0° C., and the reaction solution was stirred at r.t. for 12 h. After TLC indicated the reaction was complete, EtOAc (50 mL) was added, and the organic phase was washed with water (30 mL×3), dried over anhydrous Na₂SO₄ and concentrated to give a residue which was purified by column chromatography to afford compound 93-3 (30 mg, Yield 65%).

LCMS (ESI) m/z: 451 (M+1-Boc)

The Synthesis of Compound 93-4

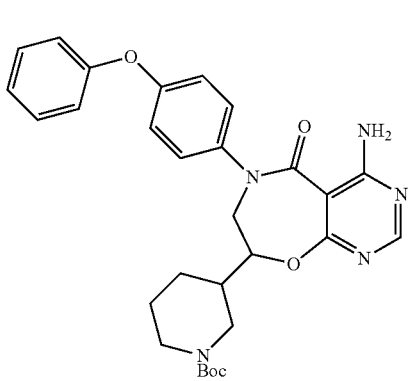 [SMILES: CC(C)(C)OC(=O)N1CCCC(C2CN(c3ccc(Oc4ccccc4)cc3)C(=O)c3c(N)ncnc3O2)C1]

Compound 93-3 (30 mg, 0.0543 mmol) was added into the canister, followed by a solution of ammonia in MeOH (5 mL), and the reaction solution was heated to 70° C. and reacted for 12 h. After TLC indicated the reaction was complete. The reaction solution was concentrated, and then the saturated NaHCO₃ solution (20 mL) was added. The aqueous phase was extracted with EtOAc (20 mL×3). The organic phases were combined, washed with saturated NaCl solution (aq., 20 mL), dried over anhydrous Na₂SO₄ and concentrated to give compound 93-4 (25 mg, Yield 86%) which was directly used for the next step.

LCMS (ESI) m/z: 431 (M+1-Boc)

The Synthesis of Compound 93-5

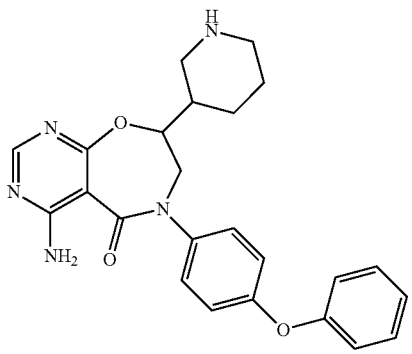 [SMILES: Nc1ncnc2c1C(=O)N(c1ccc(Oc3ccccc3)cc1)CC(C1CCCNC1)O2]

The solution of compound 93-4 (20 mg, 0.037 mmol) in a solution of hydrogen chloride in MeOH (5 mL) was stirred at r.t. for 4 h. After TLC indicated the reaction was complete, the reaction solution was concentrated, and then water (20 mL) was added. The aqueous phase was extracted with EtOAc (20 mL×3). The organic phases were combined, washed with saturated NaCl solution (aq., 20 mL), dried over anhydrous Na₂SO₄ and concentrated to give compound 93-5 (15 mg, Yield 94%) which was directly used for the next step.

LCMS (ESI) m/z: 431 (M+1)

The Synthesis of Compound 91-6

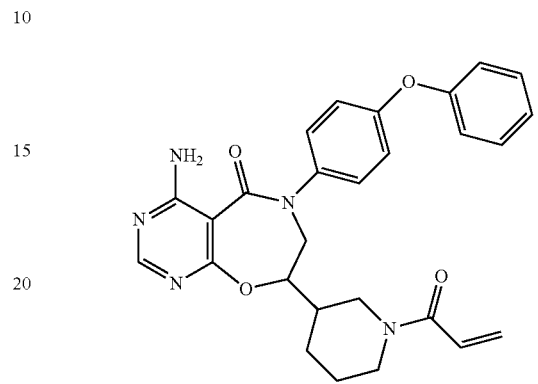

To a solution of compound 93-5 (200 mg, 0.46 mmol) and DIPEA (60 mg, 0.46 mmol) in DCM (8 mL) was added acryloyl chloride (41.4 mg, 0.46 mmol) at 0° C., and then the reaction solution was stirred at r.t. for 4 h and washed with water (10 mL). The organic phase was dried over anhydrous Na₂SO₄ and concentrated to give a residue which was purified by column chromatography to afford compound 93-6 (180 mg, Yield 81.35%, white solid).

LCMS (ESI) m/z: 486 (M+1)

Example 97

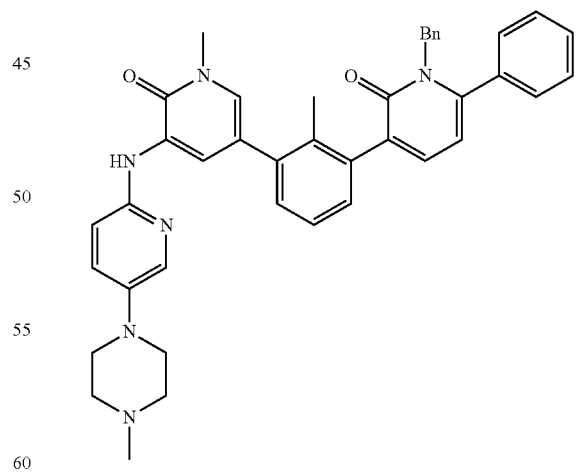

In Example 97, the systhesis process was similar to that in Example 12.

LCMS (ESI) m/z: 559 (M+1)

Example 98

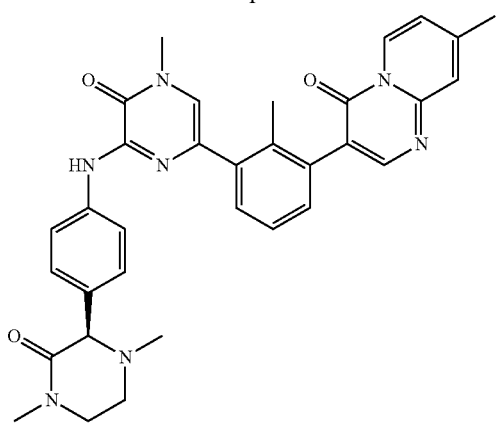

In Example 98, the systhesis process was similar to that in Example 6.

LCMS (ESI) m/z: 575 (M+1)

$^1$H NMR (CDCl$_3$, 400 MHz): δ ppm 9.11-9.09 (m, 1H), 8.37-8.34 (m, 2H), 7.84-7.82 (m, 2H), 7.53 (s, 1H), 7.44-7.33 (m, 1H), 7.31-7.28 (m, 4H), 7.07-7.05 (m, 1H), 6.77 (s, 1H), 3.76-3.70 (m, 1H), 3.62 (s, 1H), 3.26-3.23 (m, 3H), 3.06-3.05 (m, 1H), 3.03-2.98 (m, 1H), 2.70-2.70 (m, 3H), 2.55 (m, 1H), 2.34 (s, 3H), 2.20 (s, 3H), 2.01-2.00 (m, 3H)

Scheme 59

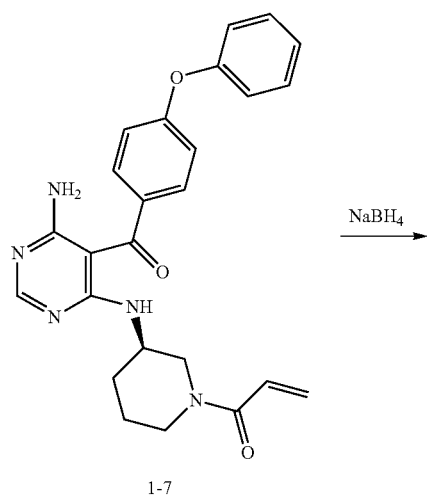

1-7

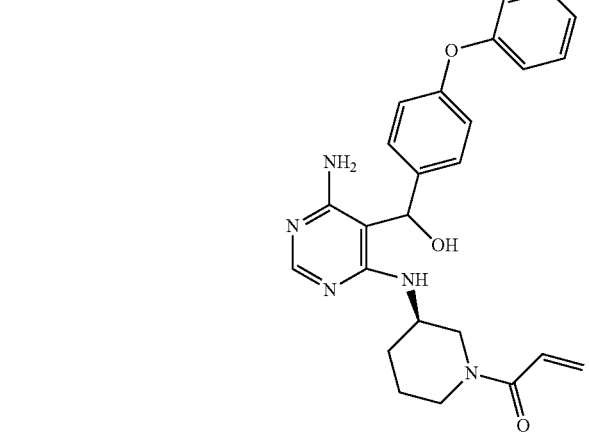

94-1

Example 99

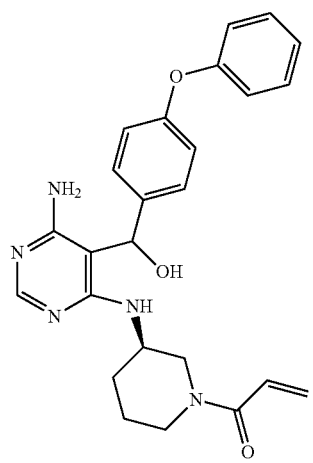 [SMILES: C=CC(=O)N1CCC[C@@H](Nc2ncnc(N)c2C(O)c2ccc(Oc3ccccc3)cc2)C1]

The Synthesis of Compound 94-1

To a solution of compound 1-7 (45 mg, 0.101 mmol) in MeOH (10 mL) was added sodium borohydride (7.65 mg, 0.202 mmol) at 0° C., and the reaction solution was stirred at 0° C. for 0.5 h. After TLC indicated the reaction was complete, the solvent was removed by rotatory evaporation, and the saturated NH$_4$Cl solution (aq., 10 mL) was added into the residue. The aqueous phase was extracted with EtOAc (20 mL×2). The organic phases were combined, dried over anhydrous Na$_2$SO$_4$ and concentrated to give a residue which was purified by preparative HPLC to afford compound 94-1 (22 mg, Yield 48%, white solid).

LCMS (ESI) m/z: 446 (M+1)

$^1$H NMR (MeOD, 400 MHz): δ ppm 7.89-7.91 (d, J=8 Hz, 1H), 7.20-7.27 (m, 4H), 6.90-7.17 (m, 1H), 6.83-6.88 (m, 4H), 6.35-6.39 (m, 1H), 6.03-6.08 (m, 1H), 5.63-5.71 (m, 2H), 3.96-4.08 (m, 1H), 3.43-3.62 (m, 3H), 3.26 (m, 1H), 1.68-1.71 (m, 1H), 1.44-1.53 (m, 3H)

Scheme 60

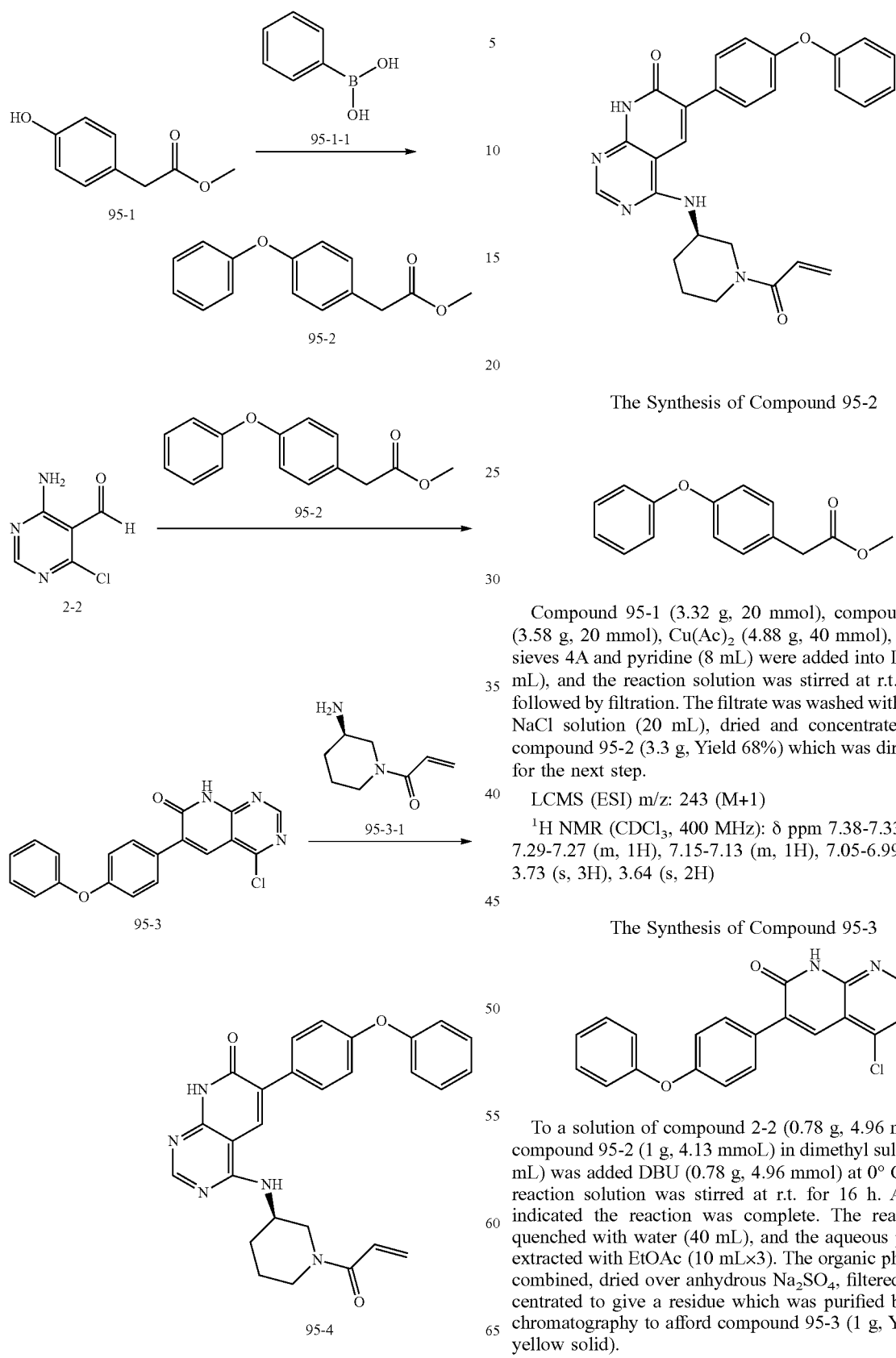

Example 100

The Synthesis of Compound 95-2

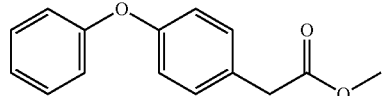

Compound 95-1 (3.32 g, 20 mmol), compound 95-1-1 (3.58 g, 20 mmol), Cu(Ac)$_2$ (4.88 g, 40 mmol), molecular sieves 4A and pyridine (8 mL) were added into DCM (100 mL), and the reaction solution was stirred at r.t. for 12 h, followed by filtration. The filtrate was washed with saturated NaCl solution (20 mL), dried and concentrated to give compound 95-2 (3.3 g, Yield 68%) which was directly used for the next step.

LCMS (ESI) m/z: 243 (M+1)

$^1$H NMR (CDCl$_3$, 400 MHz): δ ppm 7.38-7.33 (m, 2H), 7.29-7.27 (m, 1H), 7.15-7.13 (m, 1H), 7.05-6.99 (m, 5H), 3.73 (s, 3H), 3.64 (s, 2H)

The Synthesis of Compound 95-3

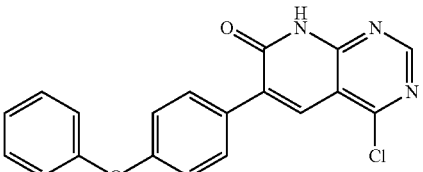

To a solution of compound 2-2 (0.78 g, 4.96 mmol) and compound 95-2 (1 g, 4.13 mmoL) in dimethyl sulfoxide (10 mL) was added DBU (0.78 g, 4.96 mmol) at 0° C., and the reaction solution was stirred at r.t. for 16 h. After TLC indicated the reaction was complete. The reaction was quenched with water (40 mL), and the aqueous phase was extracted with EtOAc (10 mL×3). The organic phases were combined, dried over anhydrous Na$_2$SO$_4$, filtered and concentrated to give a residue which was purified by column chromatography to afford compound 95-3 (1 g, Yield 71%, yellow solid).

LCMS (ESI) m/z: 350 (M+1)

393

The Synthesis of Compound 95-4

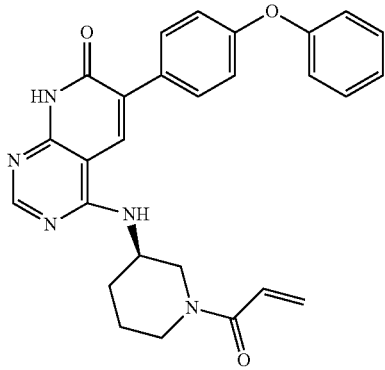 [SMILES: C=CC(=O)N1CCC[C@@H](Nc2ncnc3[nH]c(=O)c(-c4ccc(Oc5ccccc5)cc4)cc23)C1]

To a solution of compound 95-3 (250 mg, 0.72 mmol) in EtOH (5 mL) was added compound 95-3-1 (100 mg, 0.65 mmol) and DIPEA (168 mg, 1.29 mmoL), and the reaction solution was heated to 60° C. and stirred for 1 h. After TLC indicated the reaction was complete, the reaction solution was concentrated directly to give a crude product which was purified by preparative HPLC to afford compound 95-4 (30 mg, Yield 20%, white solid).

LCMS (ESI) m/z: 468 (M+1)

$^1$H NMR (DMSO, 400 MHz): δ ppm 8.43-8.41 (m, 1H), 8.34-8.30 (m, 1H), 7.86-7.78 (m, 1H), 7.44-7.40 m, 2H), 7.16-7.10 (m, 2H), 7.08-7.06 (m, 1H), 7.04-6.77 (m, 4H), 6.74-6.73 (m, 1H), 6.11-6.07 (m, 1H), 5.69-5.64 (m, 1H), 4.58-4.55 (m, 1H), 4.22-4.00 (m, 3H), 3.09-2.84 (m, 1H), 2.06-2.03 (m, 1H), 1.84-1.81 (m, 1H), 1.76-1.69 (m, 1H), 1.64-1.1.61 (m, 1H), 1.47-1.17 (m, 1H)

Example 101

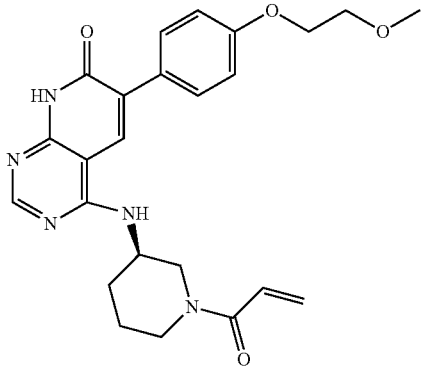 [SMILES: C=CC(=O)N1CCC[C@@H](Nc2ncnc3[nH]c(=O)c(-c4ccc(OCCOC)cc4)cc23)C1]

In Example 101, the synthesis process was similar to that in Example 100.

LCMS (ESI) m/z: 450 (M+1)

$^1$H NMR (CDCl$_3$, 400 MHz): δ ppm 8.38-8.37 (m, 2H), 8.32-8.29 (m, 1H), 7.88-7.70 (m, 2H), 7.03-7.00 (m, 2H), 6.82-6.75 (m, 1H), 6.11-6.07 (m, 1H), 5.69-5.64 (m, 1H), 4.15-4.14 (m, 1H), 4.13 (s, 2H), 3.78-3.67 (m, 2H), 3.61-3.51 (m, 3H), 2.69-2.37 (m, 4H), 2.05-2.03 (m, 1H), 1.84-1.76 (m, 1H), 1.28-1.24 (m, 3H)

394

Scheme 61

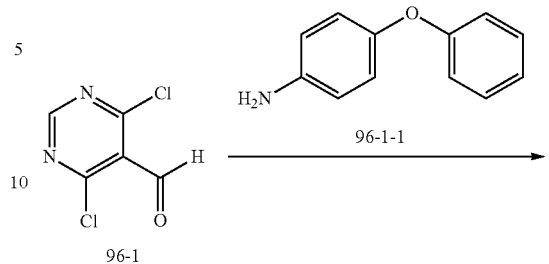

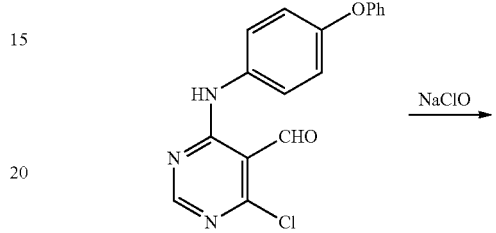

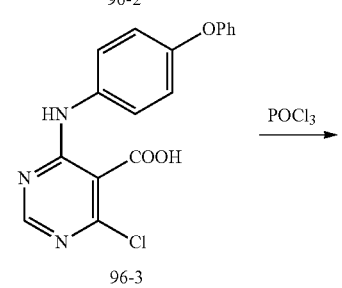

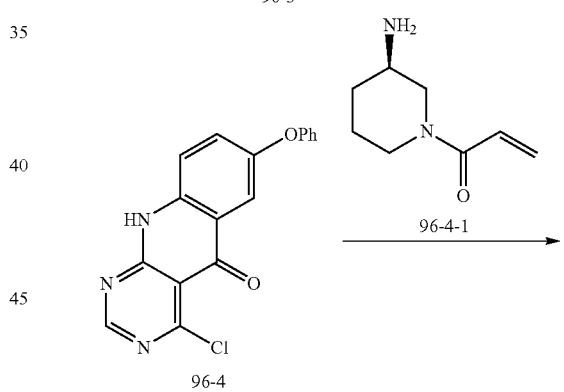

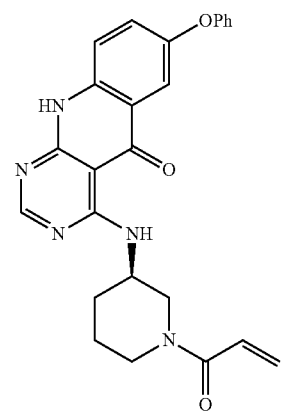 [SMILES: C=CC(=O)N1CCC[C@@H](Nc2ncnc3[nH]c4ccc(Oc5ccccc5)cc4c(=O)c23)C1]

Example 102

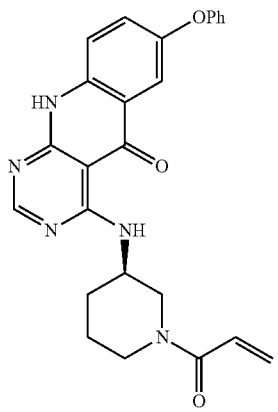

The Synthesis of Compound 96-2

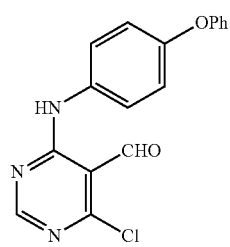 [SMILES: O=Cc1c(Cl)ncnc1Nc1ccc(Oc2ccccc2)cc1]

To a solution of compound 96-1 (2 g, 11.4 mmol) in DCM (20 mL) was added separately compound 96-1-1 (2.1 g, 11.4 mmol) and DIPEA (2.94 g, 22.8 mmol) under nitrogen atmosphere at 0° C., and the reaction solution was stirred at r.t. for 2 h. After TLC indicated the reaction was complete, the reaction was quenched with water (20 mL), and the aqueous phase was extracted with DCM (10 mL×2). The organic phases were combined, dried over anhydrous $Na_2SO_4$ and evaporated to dryness by rotatory evaporation to give a residue which was purified by column chromatography to afford compound 96-2 (2.5 g, Yield 67.6%).

LCMS (ESI) m/z: 326 (M+1)

The Synthesis of Compound 96-3

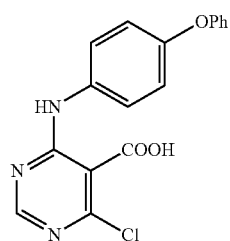 [SMILES: O=C(O)c1c(Cl)ncnc1Nc1ccc(Oc2ccccc2)cc1]

To a solution of compound 96-2 (1.0 g, 3 mmol), 2-methyl-2-butane (1.05 g, 15 mmol) and sodium dihydrogen phosphate ($NaH_2PO_4$) (1.44 g, 12 mmol) in tert-butanol (30 mL) and water (10 mL) was added sodium hypochlorite (NaClO) (1.08 g, 12 mmol), and the reaction solution was stirred at r.t. for 16 h. After TLC indicated the reaction was complete, the reaction solution was diluted with water (20 mL), and was adjusted to weakly acidic with diluted HCl (10 mL, 4 M). Then the aqueous phase was extracted with DCM (10 mL×2), and the organic phases were combined, dried over anhydrous $Na_2SO_4$, concentrated and evaporated to dryness by rotatory evaporation to give compound 96-3 (500 mg, Yield 49%) which was directly used for the next step.

LCMS (ESI) m/z: 342 (M+1)

The Synthesis of Compound 97-4

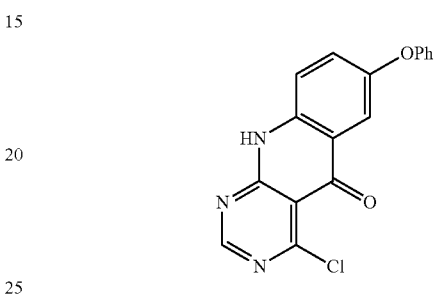

The solution of compound 96-3 (500 mg, 1.47 mmol) in $POCl_3$ (5 mL) was heated to 80° C. and reacted for 3 h. After TLC indicated the reaction was complete, the reaction solution was cooled down to r.t. and then added slowly into ice water (20 mL). The aqueous phase was extracted with DCM (20 mL×3), and the organic phases were combined, dried over anhydrous $Na_2SO_4$ and concentrated to give a crude product which was purified by column chromatography to afford compound 96-4 (300 mg, Yield 63.3%, yellow oily liquid).

LCMS (ESI) m/z: 324 (M+1)

The Synthesis of Compound 96-5

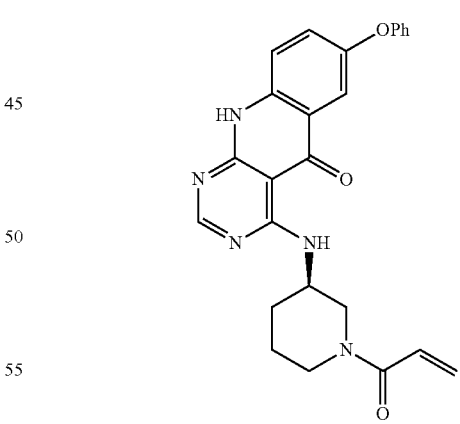

To a solution of compound 96-4 (50 mg, 0.15 mmol) and DIPEA (38.7 mg, 0.3 mmol) in tert-butanol (2 mL) was added compound 96-4-1 (23.1 mg, 0.15 mmol) under nitrogen atmosphere at 0° C., and the reaction solution was heated to 80° C. and stirred for 3 h. After TLC indicated the reaction was complete, water (20 mL) was added into this solution to quench the reaction, and the aqueous phase was extracted with EtOAc (20 mL×3). The organic phases were combined, dried over anhydrous $Na_2SO_4$ and evaporated to dryness by rotatory evaporation to give a crude product which was purified by preparative HPLC to afford compound 96-5 (11 mg, Yield 16.7%, white solid).

LCMS (ESI) m/z: 442 (M+1)

¹H NMR (MeOD, 400 MHz): δ ppm 8.47 (s, 1H), 7.68-7.68 (m, 2H), 7.58-7.56 (m, 1H), 7.43-7.39 (m, 2H), 7.22-7.20 (m, 1H), 7.07-7.05 (m, 2H), 6.70-6.80 (d, J=40 Hz, 1H), 6.13-6.09 (d, J=16.8 Hz, 1H), 5.70 (s, 1H), 4.26 (s, 1H), 3.81-3.57 (m, 4H), 2.13-1.62 (m, 4H)

Example 103

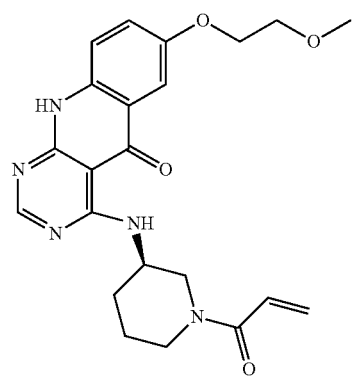 [SMILES: C=CC(=O)N1CCC[C@@H](Nc2ncnc3[nH]c4ccc(OCCOC)cc4c(=O)c23)C1]

In Example 103, the systhesis process was similar to that in Example 102.

LCMS (ESI) m/z: 424 (M+1)

¹H NMR (MeOD, 400 MHz): δ ppm 8.45 (s, 1H), 7.67 (s, 1H), 7.58-7.60 (d, J=8 MHz, 1H), 7.46-7.48 (d, J=8 MHz, 1H), 6.80 (s, 1H), 6.12-6.22 (m, 1H), 5.64-5.80 (m, 1H), 4.27 (s, 1H), 4.24-4.25 (m, 2H), 3.81-3.82 (m, 4H), 3.71-3.72 (m, 1H), 2.70-2.71 (m, 1H), 3.47 (s, 3H), 2.18 (s, 1H), 1.96 (s, 2H), 1.8 (s, 1H)

Example 104

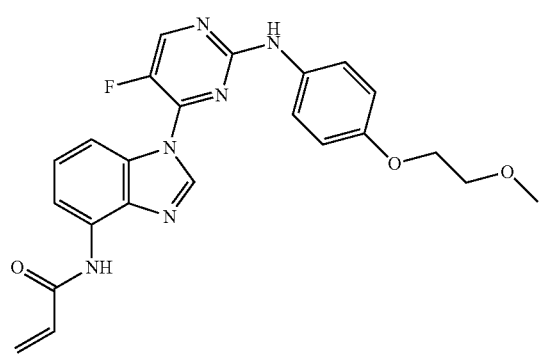 [SMILES: C=CC(=O)Nc1cccc2c1ncn2-c1nc(Nc2ccc(OCCOC)cc2)ncc1F]

In Example 104, the systhesis process was similar to that in Example 14.

LCMS (ESI) m/z: 449 (M+1)

¹H NMR (CDCl₃, 400 MHz): δ ppm 8.63 (s, 1H), 8.42-8.41 (d, J=3.6 Hz, 1H), 8.13 (s, 1H), 8.07-8.05 (d, J=8.4 Hz, 1H), 7.51 (m, 2H), 7.44-7.42 (d, J=8.4 Hz, 2H), 7.06 (s, 1H), 6.98-6.96 (d, J=8.8 Hz, 2H), 6.50-6.46 (d, J=16.8 Hz, 1H), 6.33-6.26 (m, 1H), 5.81-5.79 (d, J=10.4 Hz, 1H), 4.17-4.15 (t, 2H), 3.80-3.78 (t, 2H), 3.48 (s, 3H).

Example 105

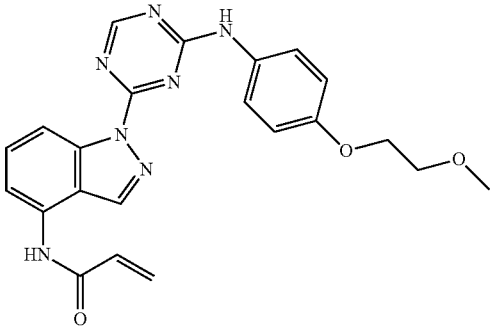 [SMILES: C=CC(=O)Nc1cccc2c1cnn2-c1ncnc(Nc2ccc(OCCOC)cc2)n1]

In Example 105, the systhesis process was similar to that in Example 15.

LCMS (ESI) m/z: 432 (M+1)

¹H NMR (CDCl₃, 400 MHz): δ ppm 8.64 (s, 2H), 8.31 (s, 1H), 7.83-7.75 (m, 2H), 7.39-7.45 (m, 3H), 6.90 (s, 2H), 6.48-6.44 (m, 1H), 6.36-6.34 (m, 1H), 5.79-5.77 (m, 1H), 4.08 (s, 2H), 4.51 (s, 1H), 3.71 (s, 2H), 3.40 (s, 3H).

Example 106

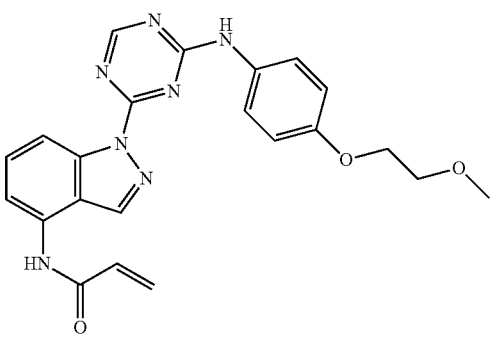 [SMILES: C=CC(=O)Nc1cccc2c1cnn2-c1ncnc(Nc2ccc(OCCOC)cc2)n1]

In Example 106, the systhesis process was similar to that in Example 15.

LCMS (ESI) m/z: 432 (M+1)

¹H NMR (DMSO, 400 MHz): δ ppm 10.19 (s, 1H), 9.89 (s, 1H), 8.98 (s, 1H), 8.72 (s, 1H), 8.16-8.14 (d, J=8 Hz, 1H), 7.60-7.57 (d, J=8.8 Hz, 2H), 7.32 (m, 1H), 7.02-7.00 (d, J=8.4 Hz, 2H), 6.85-6.79 (m, 1H), 6.33-6.28 (m, 1H), 5.77-5.74 (m, 1H), 5.68 (s, 1H), 4.16-4.14 (t, 2H), 3.71-3.68 (t, 2H), 3.35 (s, 3H).

Scheme 62

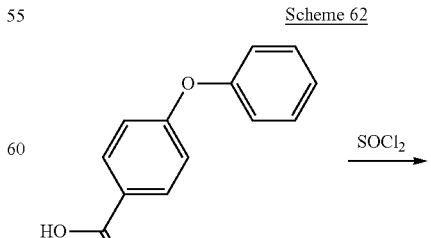

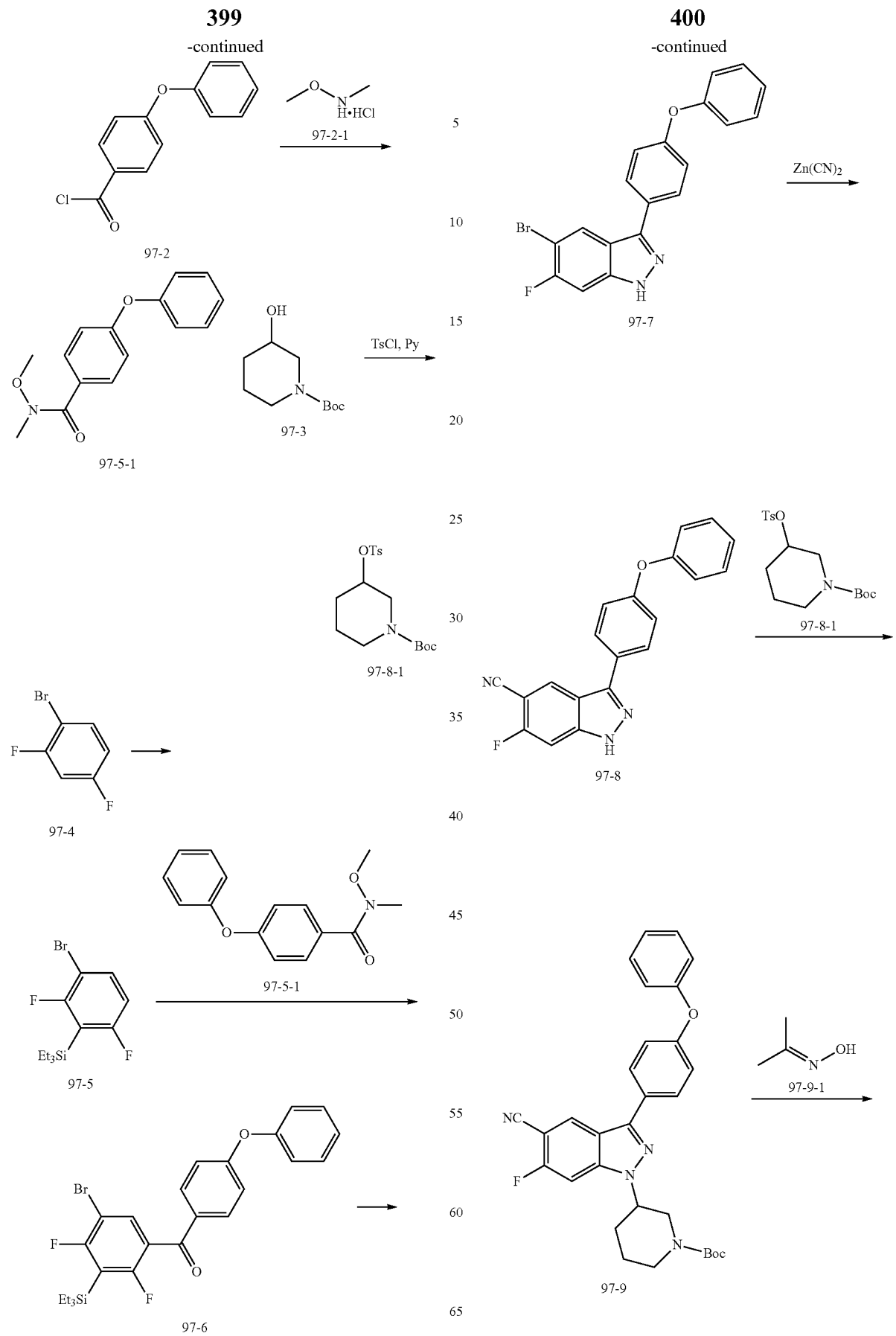

401
-continued

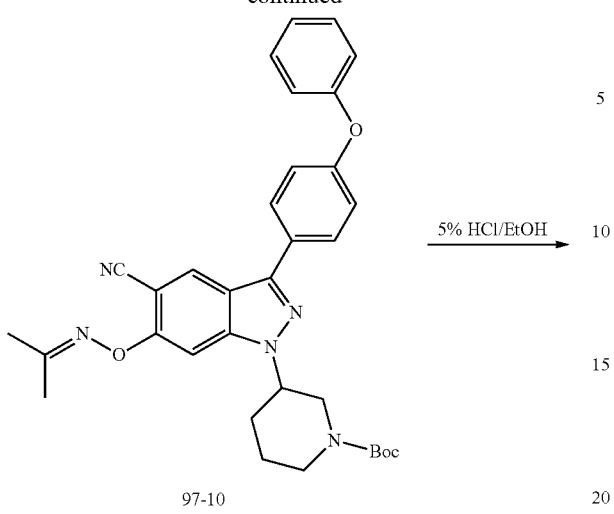

97-10

→ 5% HCl/EtOH

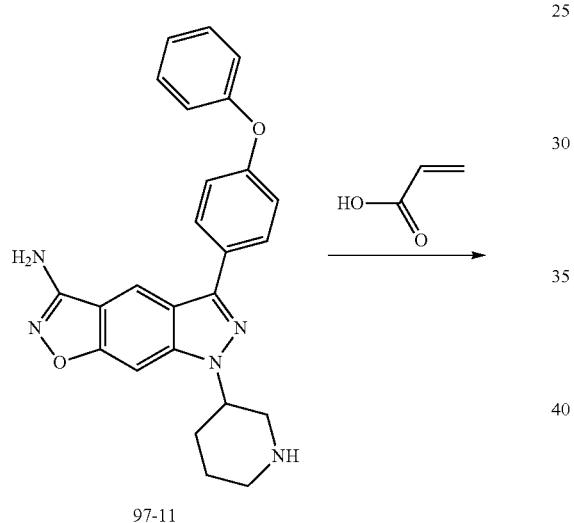

97-11

↓ 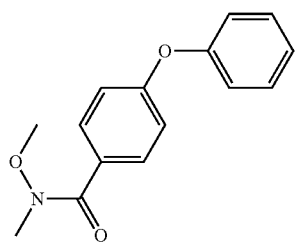

97-12

402

Example 107

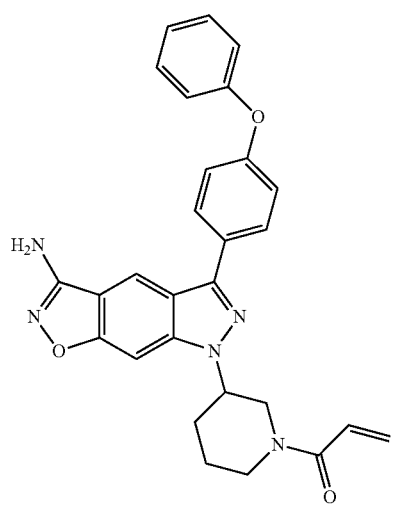 [SMILES: C=CC(=O)N1CCCC(n2nc(-c3ccc(Oc4ccccc4)cc3)c3cc4c(N)noc4cc32)C1]

The Synthesis of Compound 97-2

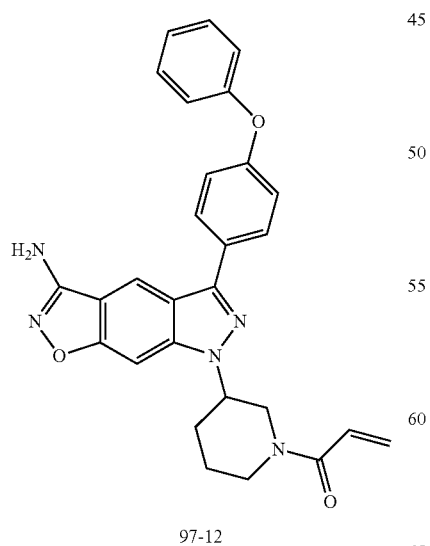

Compound 97-1 (10 g, 46 mmol) and DMF (two drops) were dissolved in thionyl chloride (SOCl$_2$) (30 mL), and the reaction solution was stirred at 70° C. for 3 h. After TLC indicated the reaction was complete, the reaction solution was concentrated to give compound 97-2 (10.6 g, Yield 100%, yellow oily liquid) which was directly used for the next step.

LCMS (ESI) m/z: 234 (M+1)

The Synthesis of Compound 97-5-1

To a solution of compound 97-2-1 (5.03 g, 51 mmol) and TEA (19 mL, 140 mmol) in DCM (150 mL) was added a solution of compound 97-2 (10.6 g, 46 mmol) in DCM (50 mL) at 0° C., and the reaction solution was warmed to r.t.

and stirred for 18 h. After TLC indicated the reaction was complete, water (100 mL) was added to this solution, and the resulting solution was extracted with EtOAc (50 mL×3). The organic phase was dried over anhydrous Na$_2$SO$_4$, filtered and evaporated to dryness by rotatory evaporation to give a crude product which was purified by column chromatography to afford compound 97-5-1 (12 g, Yield 99%, yellow oily liquid).

LCMS (ESI) m/z: 258 (M+1)

$^1$H NMR (CDCl$_3$, 400 MHz): δ ppm 7.72 (d, J=8.8 Hz, 2H), 7.40-7.36 (m, 2H), 7.17 (d, J=8.0 Hz, 1H), 7.06 (d, J=8.0 Hz, 2H), 6.99 (d, J=8.8 Hz, 2H), 3.57 (s, 3H), 3.36 (s, 3H)

The Synthesis of Compound 97-8-1

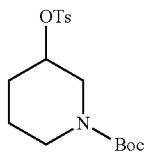 [SMILES: Cc1ccc(S(=O)(=O)OC2CCCN(C(=O)OC(C)(C)C)C2)cc1]

To a solution of compound 97-3 (1 g, 4.97 mmol) and pyridine (Py) (1.18 mL, 14.9 mmol) in DCM (30 mL) was added p-toluenesulfonyl chloride (TsCl) (1.89 g, 9.94 mmol) at 0° C., and the reaction solution was warmed to r.t. and stirred for 18 h. After TLC indicated the reaction was complete, the reaction was quenched with water (20 mL), and the reaction solution was extracted with EtOAc (50 mL×3). The organic phase was dried over anhydrous Na$_2$SO$_4$, filtered and evaporated to dryness by rotatory evaporation to give a crude product which was purified by column chromatography to afford compound 97-8-1 (700 mg, Yield 39%, white solid).

LCMS (ESI) m/z: 356 (M+1)

$^1$H NMR (CDCl$_3$, 400 MHz): δ ppm 7.79 (d, J=8.0 Hz, 2H), 7.33 (d, J=8.0 Hz, 2H), 4.44 (br. s., 1H), 3.55 (d, J=12.4 Hz, 1H), 3.38-3.32 (m, 1H), 3.25 (br. s., 1H), 2.43 (s, 3H), 1.83 (br. s., 1H), 1.77-1.70 (m, 2H), 1.45-1.41 (m, 11H)

The Synthesis of Compound 97-5

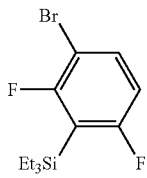

To a solution of compound 97-4 (10 g, 51 mmol) in anhydrous THF (100 mL) was added slowly LDA (25 mL, 62 mmol) at −78° C., and the reaction solution was stirred for 1 h, after which ethylchlorosilane (10.5 mL, 57 mmol) was added and the resulting solution was stirred −78° C. for 2 h. After TLC indicated the reaction was complete, the reaction was quenched with saturated NH$_4$Cl solution (aq., 100 mL), and the aqueous phase was extracted with EtOAc (200 mL×3). The organic phases were combined, dried over anhydrous Na$_2$SO$_4$, filtered and evaporated to dryness by rotatory evaporation to give compound 97-5 (15.7 g, Yield 100%, colourless oily liquid) which was directly used for the next step.

LCMS (ESI) m/z: 309 (M+1)

$^1$H NMR (CDCl$_3$, 400 MHz): δ ppm 7.53-7.47 (m, 1H), 6.74 (t, J=8.4 Hz, 1H), 0.98-0.82 (m, 15H)

The Synthesis of Compound 97-6

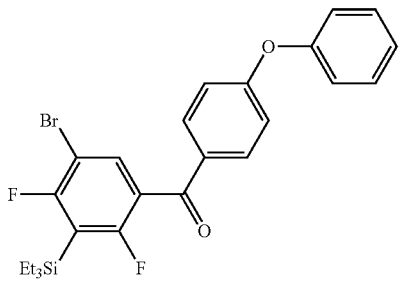

To a solution of compound 97-5 (14 g, 46 mmol) in anhydrous THF (140 mL) was added slowly LDA (18.4 mL, 46 mmol) at −78° C. and the reaction solution was stirred for 1 h, after which compound 97-5-1 (12 g, 46 mmol) was added and the reaction solution was stirred at −78° C. for 2 h. After TLC indicated the reaction was complete, the reaction was quenched with saturated NH$_4$Cl solution (100 mL), and the aqueous phase was extracted with EtOAc (200 mL×3). The organic phases were combined, dried over anhydrous Na$_2$SO$_4$, filtered and evaporated to dryness by rotatory evaporation to give a crude product which was purified by column chromatography to afford compound 97-6 (11 g, Yield 47%, yellow oily liquid).

LCMS (ESI) m/z: 505 (M+1)

$^1$H NMR (CDCl$_3$, 400 MHz): δ ppm 7.80-7.77 (m, 2H), 7.44-7.40 (m, 2H), 7.23 (t, J=7.6 Hz, 2H), 7.10 (d, J=8.0 Hz, 2H), 7.01 (d, J=8.6 Hz, 2H), 1.03-0.87 (m, 15H)

The Synthesis of Compound 97-7

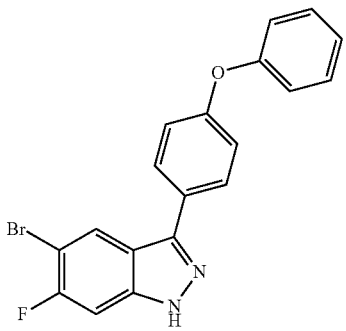 [SMILES: Fc1cc2[nH]nc(-c3ccc(Oc4ccccc4)cc3)c2cc1Br]

To a solution of compound 97-6 (5.3 g, 10.53 mmol) in ethylene glycol (20 mL) was added N$_2$H$_4$.H$_2$O (0.62 mL, 10.53 mmol), and the reaction solution was heated to 130° C. and stirred for 18 h. After TLC indicated the reaction was complete, the reaction was quenched with water (100 mL), and the aqueous phase was extracted with EtOAc (50 mL×3). The organic phases were combined, washed with saturated NaCl solution (50 mL), dried over anhydrous Na$_2$SO$_4$, filtered and evaporated to dryness by rotatory evaporation to give a crude product which was purified by column chromatography to afford compound 97-7 (900 mg, Yield 22%, yellow solid).

LCMS (ESI) m/z: 383 (M+1)

$^1$H NMR (CDCl$_3$, 400 MHz): δ ppm 11.2 (s, 1H), 8.16 (d, J=6.4 Hz, 1H), 7.84 (d, J=8.4 Hz, 2H), 7.39-7.35 (m, 2H), 7.16-7.13 (m, 4H), 7.08 (d, J=8.4 Hz, 2H)

The Synthesis of Compound 97-8

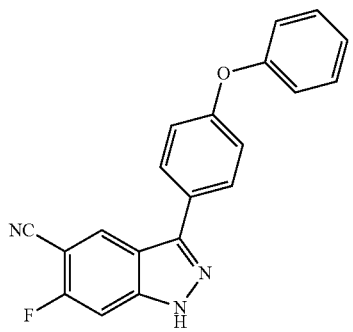 [SMILES: N#Cc1cc2c(-c3ccc(Oc4ccccc4)cc3)n[nH]c2cc1F]

To a solution of compound 97-7 (900 mg, 10.53 mmol) and Zn(CN)$_2$ (550 mg, 4.7 mmol) in DMF (20 mL) was added DPPF (1.56 g, 2.82 mmol) and Pd$_2$(dba)$_3$ (1.07 g, 1.17 mmol) under nitrogen atmosphere, and the reaction solution was heated to 100° C. and reacted for 4 h. After TLC indicated the reaction was complete, the reaction was quenched with water (60 mL), and the aqueous phase was extracted with EtOAc (30 mL×3). The organic phases were combined, washed with saturated NaCl solution (10 mL), dried over anhydrous Na$_2$SO$_4$, filtered and evaporated to dryness by rotatory evaporation to give a residue which was purified by column chromatography to afford compound 97-8 (570 mg, Yield 74%, yellow solid).

LCMS (ESI) m/z: 330 (M+1)

$^1$H NMR (CDCl$_3$, 400 MHz): δ ppm 11.5 (s, 1H), 8.31 (d, J=6.0 Hz, 1H), 7.83 (d, J=8.8 Hz, 2H), 7.42-7.35 (m, 2H), 7.27-7.24 (m, 1H), 7.19-7.15 (m, 3H), 7.09 (d, J=7.6 Hz, 2H)

The Synthesis of Compound 97-9

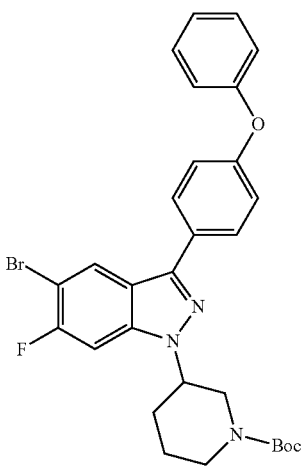 [SMILES: CC(C)(C)OC(=O)N1CCCC(n2nc(-c3ccc(Oc4ccccc4)cc3)c3cc(Br)c(F)cc32)C1]

The solution of compound 97-8 (570 mg, 1.73 mmol), compound 97-8-1 (615 mg, 1.73 mmol) and Cs$_2$CO$_3$ (1.7 g, 5.19 mmol) in DMF (15 mL) was heated to 90° C. under nitrogen atmosphere and reacted for 18 h, after which water (60 mL) was added and the resulting solution was extracted with EtOAc (30 mL×3). The organic phases were combined, washed with NaCl solution (10 mL), dried over anhydrous Na$_2$SO$_4$, filtered and evaporated to give a residue which was purified by column chromatography to afford compound 97-9 (150 mg, Yield 17%, yellow solid).

LCMS (ESI) m/z: 413 (M+1-Boc)

$^1$H NMR (CDCl$_3$, 400 MHz): δ ppm 8.28 (d, J=4.8 Hz, 1H), 7.82 (d, J=8.8 Hz, 2H), 7.39 (t, J=8.0 Hz, 2H), 7.29 (br. s., 1H), 7.18-7.14 (m, 3H), 7.08 (d, J=8.0 Hz, 2H), 4.40-4.34 (m, 1H), 4.13-4.12 (m, 1H), 2.91-2.85 (m, 1H), 2.42-2.32 (m, 1H), 2.24-2.21 (m, 1H), 1.96 (d, J=11.0 Hz, 1H), 1.70 (d, J=12.5 Hz, 1H), 1.53-1.41 (m, 11H)

The Synthesis of Compound 97-10

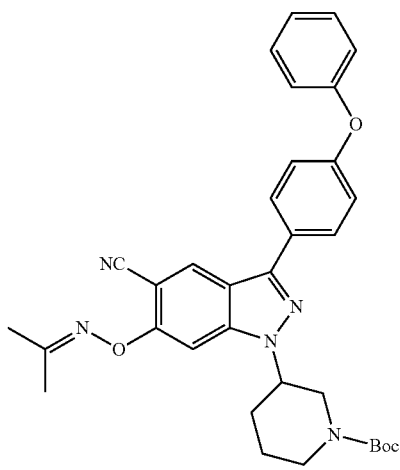 [SMILES: CC(C)=NOc1cc2c(cc1C#N)c(-c1ccc(Oc3ccccc3)cc1)nn2C1CCCN(C(=O)OC(C)(C)C)C1]

The solution of compound 97-9 (150 mg, 292 μmol) and potassium t-butoxide (49 mg, 439 mmol) in DMF (5 mL) was stirred at 0° C. for 0.5 h, after which compound 97-9-1 (32 mg, 439 μmol) was added. The resulting solution was warmed to r.t. and stirred for 0.5 h. After TLC indicated the reaction was complete, the reaction was quenched with water (30 mL), and the aqueous phase was extracted with EtOAc (10 mL×3). Then the organic phases were combined, washed with saturated NaCl solution (aq., 20 mL), dried over anhydrous Na$_2$SO$_4$, filtered and evaporated to dryness by rotatory evaporation to give compound 97-10 (100 mg, Yield 61%, yellow solid) which was directly used for the next step.

LCMS (ESI) m/z: 466 (M+1-Boc)

The Synthesis of Compound 97-11

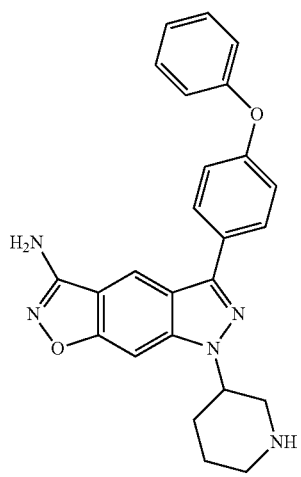 [SMILES: Nc1noc2cc3c(cc12)c(-c1ccc(Oc2ccccc2)cc1)nn3C1CCCNC1]

To a mixture of 5% HCl (7 mL) and EtOH (7 mL) was added compound 98-10 (100 mg, 0.17 mmol), and the reaction solution was stirred at 90° C. for 18 h. After TLC indicated the reaction was complete, the reaction solution was evaporated and the saturated NaHCO₃ solution (aq., 30 mL) was added. Then the resulting solution was extracted with EtOAc (10 mL×3), and the organic phase was dried over anhydrous Na₂SO₄, filtered and evaporated to dryness by rotatory evaporation to give the title compound 97-11 (75 mg, Yield 100%, yellow solid).

LCMS (ESI) m/z: 426 (M+1).

The Synthesis of Compound 97-12

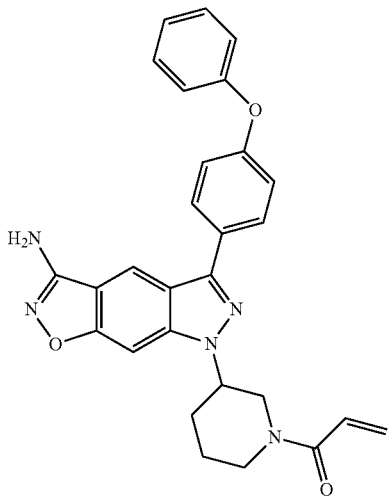 [SMILES: C=CC(=O)N1CCCC(n2nc(-c3ccc(Oc4ccccc4)cc3)c3cc4c(N)noc4cc32)C1]

To a mixture of compound 97-11 (56 mg, 0.13 mmol) and TEA (0.03 mL, 221 µmol) in DCM (5 mL) was added acrylic acid (6.7 mg, 73 µmol) under nitrogen atmosphere, and the reaction solution was stirred at 25° C. for 1 h. After LCMS indicated the reaction was complete, water (5 mL) was added, and the resulting solution was extracted with DCM (10 mL×3). The organic phases were combined, dried over anhydrous Na₂SO₄, filtered and evaporated to dryness by rotatory evaporation to give a residue which was purified by column chromatography to afford a crude product. The crude product was purified by preparative HPLC to obtain compound 97-12 (11 mg, Yield 31%, white solid).

LCMS (ESI) m/z: 480 (M+1)

¹H NMR (CDCl₃, 400 MHz): δ ppm 8.07 (br. s., 1H), 7.90 (d, J=8.8 Hz, 2H), 7.40-7.36 (m, 3H), 7.18-7.14 (m, 3H), 7.09 (d, J=8.0 Hz, 2H), 6.70-6.51 (m, 1H), 6.39-6.30 (m, 1H), 5.78-5.70 (m, 1H), 4.97 (d, J=12.0 Hz, 1H), 4.64 (br. s., 2H), 4.22-4.08 (m, 1H), 3.79 (br. s., 1H), 3.32-3.23 (m, 1H), 2.92 (br. s., 1H), 2.44 (br. s., 1H), 2.32 (d, J=10 Hz, 1H), 2.06 (d, J=13.6 Hz, 1H), 1.74 (d, J=12.0 Hz, 1H)

Scheme 63

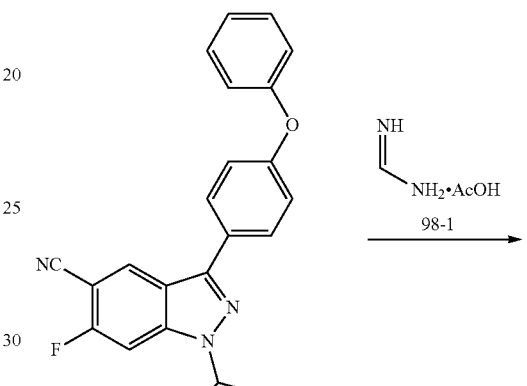

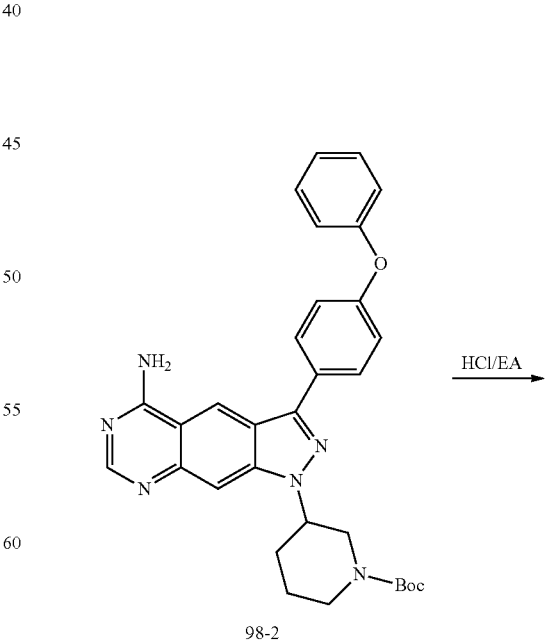

409

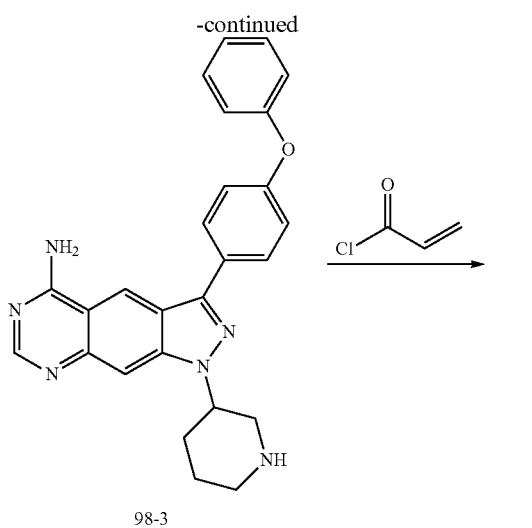

410

The Synthesis of Compound 98-2

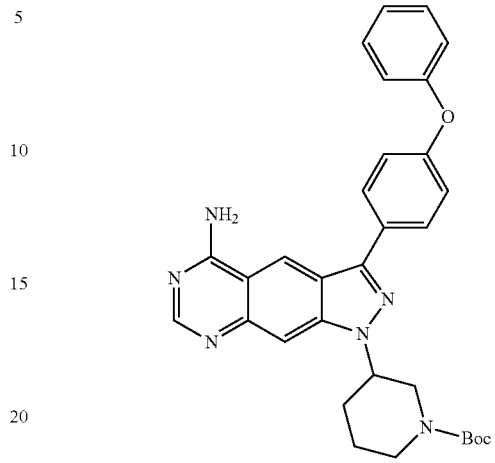

To a solution of compound 98-1 (210 mg, 0.41 mmol) in anhydrous DMF (5 mL) was added NaH (162 mg, 4.06 mmol), and the reaction solution was stirred at r.t. for 1 h, after which compound 97-9 (260 mg, 507 μmol) was added and the resulting solution was heated to 100° C. and stirred for 18 h. After TLC indicated the reaction was complete, the reaction was quenched with water (30 mL), and the aqueous phase was extracted with EtOAc (10 mL×3). Then the organic phases were combined, washed with the saturated NaCl solution (aq., 20 mL), dried over anhydrous $Na_2SO_4$, filtered and concentrated to give compound 98-2 (30 mg, Yield 14%, yellow solid) which was directly used for the next step.

LCMS (ESI) m/z: 437 (M+1)

The Synthesis of Compound 98-3

Example 108

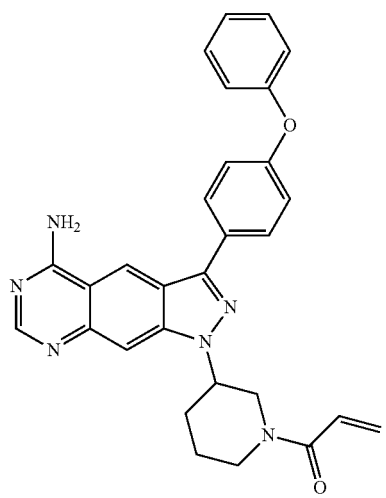 [SMILES: C=CC(=O)N1CCCC(n2nc(-c3ccc(Oc4ccccc4)cc3)c3cc4c(N)ncnc4cc32)C1]

To a solution of HCl in EtOAc (1 mL, 4 M) was added compound 98-2 (30 mg, 55 μmol), and the reaction solution was stirred at 25° C. for 1 h. After TLC indicated the reaction was complete, the reaction solution was evaporated and saturated $NaHCO_3$ solution (aq., 10 mL) was added. The resulting solution was extracted with EtOAc (10 mL×3), and the organic phase was dried over anhydrous Na$_2$SO$_4$, filtered and evaporated to dryness by rotatory evaporation to give the title compound 98-3 (24 mg, Yield 100%, yellow solid) which was directly used for the next step.

LCMS (ESI) m/z: 437 (M+1).

The Synthesis of Compound 98-4

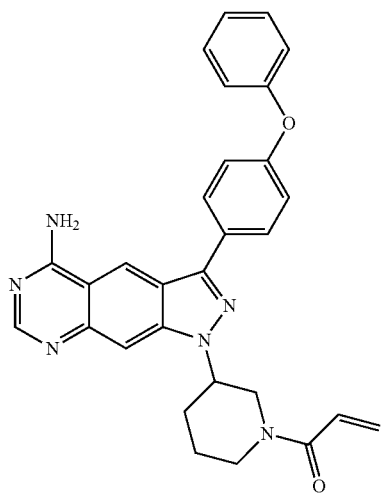 [SMILES: C=CC(=O)N1CCCC(n2nc(-c3ccc(Oc4ccccc4)cc3)c3cc4c(N)ncnc4cc32)C1]

To a mixture of compound 98-3 (24 mg, 54 μmol) and TEA (0.03 mL, 221 μmol) in DCM (5 mL) was added acryloyl chloride (5 mg, 54 μmol) under nitrogen atmosphere, and the reaction solution was stirred at 25° C. for 1 h. After LCMS indicated the reaction was complete, water (5 mL) was added, and the resulting solution was extracted with DCM (10 mL×3). Then the organic phases were combined, dried over anhydrous Na$_2$SO$_4$, filtered and evaporated to give a residue which was purified by column chromatography to afford a crude product. The crude product was purified by preparative HPLC to obtain compound 98-4 (2 mg, Yield 7.4%, white solid).

LCMS (ESI) m/z: 491 (M+1)

$^1$H NMR (CDCl$_3$, 400 MHz): δ ppm 9.04 (br. s., 1H), 8.20-8.07 (m, 3H), 77.40-7.37 (m, 2H), 7.22 (d, J=8.0 Hz, 2H), 7.16 (t, J=7.6 Hz, 2H), 7.10 (d, J=7.6 Hz, 2H), 6.74-6.62 (m, 1H), 6.40 (d, J=16.6 Hz, 1H), 5.80 (d, J=10.6 Hz, 1H), 5.01 (br. s., 1H), 4.72 (br. s., 1H), 4.06-4.15 (m, 2H), 3.56 (br. s., 1H), 3.38 (br. s., 1H), 2.32-2.36 (d, J=13.2 Hz, 2H), 2.05 (br. s., 1H), 1.40 (br. s., 2H).

Example 109

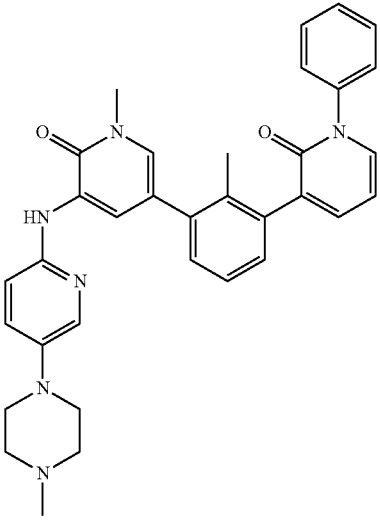 [SMILES: Cc1c(-c2cc(Nc3ccc(N4CCN(C)CC4)cn3)c(=O)n(C)c2)cccc1-c1cccn(-c2ccccc2)c1=O]

In Example 109, the synthesis process was similar to that in Example 12.

LCMS (ESI) m/z: 559 (M+1)

Example 110

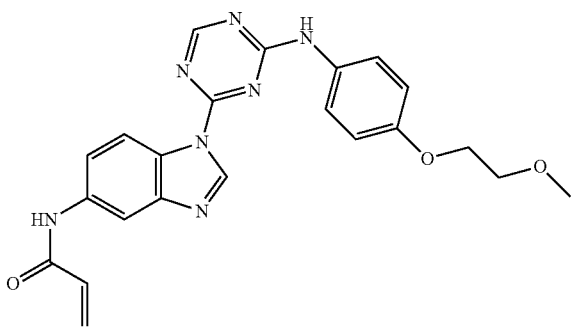 [SMILES: C=CC(=O)Nc1ccc2c(c1)ncn2-c1ncnc(Nc2ccc(OCCOC)cc2)n1]

In Example 110, the synthesis process was similar to that in Example 15.

LCMS (ESI) m/z: 432 (M+1)

Example 111

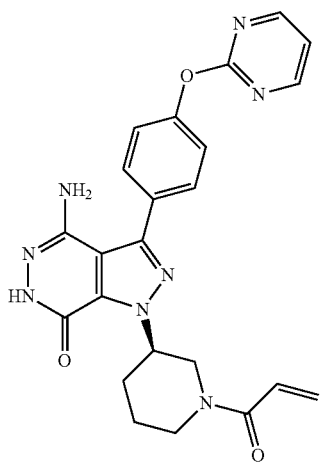 [SMILES: C=CC(=O)N1CCC[C@@H](n2nc(-c3ccc(Oc4ncccn4)cc3)c3c(N)n[nH]c(=O)c32)C1]

In Example 111, the synthesis process was similar to that in Example 32.

LCMS (ESI) m/z: 459 (M+1)

$^1$H NMR (CDCl$_3$, 400 MHz): δ ppm 10.29-9.99 (m, 1H), 8.61 (d, J=4.77 Hz, 2H), 7.76 (d, J=8.53 Hz, 2H), 7.38 (d, J=8.28 Hz, 2H), 7.11 (t, J=4.77 Hz, 1H), 6.64 (d, J=10.79 Hz, 1H), 6.26 (d, J=15.31 Hz, 1H), 5.64 (d, J=10.54 Hz, 1H), 5.50 (br. s., 1H), 4.74-5.01 (m, 2H), 4.64-4.72 (m, 1H), 3.90-4.43 (m, 1H), 3.46-3.68 (m, 1H), 2.81-3.13 (m, 1H), 2.35 (br. s., 2H), 2.01 (d, J=12.80 Hz, 1H), 1.77 (br. s., 1H)

Assay of Inhibition Activity of BTK In Vitro

Object:

The inhibition of compounds on BTK kinase was evaluated by chemiluminescence method detected by Envision, using the IC$_{50}$ value of the compounds as index.

Materials:
BTK kinase: Invitrogen-PR5442A
HTRF Assay Kit: Cisbio-62TKOPEJ
Plate for compound preparation: Greiner-781280
Assay Plate: 384-well plate: PerkinElmer-6007299
ATP: Sigma-A7699
Cisbio HTRF Kit: Cisbio-62TKOPEJ
Centrifuge: Eppendorf-5810R
Reader: PerkinElmer-Envision-2104-0010
Bravo: Agilent Technologies-Bravo Procedures and Methods:

Gradient Dilution of Compounds:

The test compound was dissolved with DMSO to be of 1 mM as a stock solution. Such a stock solution was diluted with DMSO by 10-fold, thereby obtaining an initial solution in a concentration of 1 μM which was added into wells at the second column in a plate. 20 μL DMSO was added to other wells using Bravo. Then, 10 μL of the initial solution was transferred from wells at the second column to wells at the third column, followed by mixing obtained solution in the wells at the third column, thereby obtain a first diluted solution in a concentration of 1/3 μM. Subsequently, 10 μL of the first diluted solution was further transferred from wells at the third column to wells at the fourth column, followed by mixing obtained solution in the wells at the fourth column, thereby obtain a second diluted solution in a concentration of 1/9 μM. Such a three-fold serial dilution was performed 10 times, with 11 solutions in series diluted concentrations and a final diluted solution in a concentration of 0.017 nM obtained.

All diluted solutions were further diluted by 25-fold with ultrapure water, thus obtain test solutions, which were equilibrated at r.t. for 30 min before use.

Enzymatic Reaction:

To 2.5 μL of test solution, which was pipetted into each well of Assay plate using Bravo, 5 μL kinase mixture was added using the multi-channel pipettor. The mixture was centrifuged at 1000 rpm for 20 s, followed by incubation at 23° C. for 30 min. The reaction was initiated by 2.5 μL ATP mixture which was pipetted into the wells by Multidrop.

The reaction mixture of BTK kinase (10 μL) included 1.0 nM BTK, 1 μM biotin-TK1 peptide and 20 μM ATP. The reaction buffer included 50 mM Hepes (pH7.5), 10 mM MgCl$_2$ and 0.01 mM NaV$_3$VO$_4$. The kinase mixture was reacted in incubator at 23° C. for 90 mim.

Completion of Reaction:

The reaction was stopped by adding 10 μL Detection Reagent to each well of Assay plate, and the plate was left in incubator at 23° C. for 1 h before read on Envision.

Data analysis: The IC$_{50}$ values of compounds were calculated using Excel fit.

The experimental results were listed in Table 1:

TABLE 1

| IC$_{50}$ values of Examples tested by Envision | |
|---|---|
| Test samples (title compounds) | BTK IC$_{50}$ (μM) |
| Example 1 | B |
| Example 2 | C |
| Example 3 | C |
| Example 4 | C |
| Example 5 | C |
| Example 6 | C |
| Example 7 | C |
| Example 8 | C |
| Example 9 | C |
| Example 10 | C |
| Example 11 | C |
| Example 12 | C |
| Example 13 | C |
| Example 14 | C |
| Example 15 | C |
| Example 16 | B |
| Example 17 | C |
| Example 18 | C |
| Example 19 | C |
| Example 20 | A |
| Example 21 | C |
| Example 22 | A |
| Example 23 | C |
| Example 24 | C |
| Example 25 | B |
| Example 26 | C |
| Example 27 | C |
| Example 28 | A |
| Example 29 | C |
| Example 30 | B |
| Example 31 | A |
| Example 32 | A |
| Example 33 | A |
| Example 34 | A |
| Example 35 | A |
| Example 36 | A |
| Example 37 | A |
| Example 38 | A |
| Example 39 | A |
| Example 40 | C |
| Example 41 | A |
| Example 42 | B |
| Example 43 | A |
| Example 44 | A |
| Example 45 | A |
| Example 46 | A |
| Example 47 | C |

TABLE 1-continued

IC$_{50}$ values of Examples tested by Envision

| Test samples (title compounds) | BTK IC$_{50}$ (μM) |
|---|---|
| Example 48 | A |
| Example 49 | A |
| Example 50 | B |
| Example 51 | A |
| Example 52 | A |
| Example 53 | A |
| Example 54 | A |
| Example 55 | A |
| Example 56 | A |
| Example 57 | A |
| Example 58 | A |
| Example 59 | A |
| Example 60 | A |
| Example 61 | A |
| Example 62 | A |
| Example 63 | A |
| Example 64 | B |
| Example 65 | A |
| Example 66 | A |
| Example 67 | C |
| Example 68 | A |
| Example 69 | A |
| Example 70 | C |
| Example 71 | A |
| Example 72 | A |
| Example 73 | A |
| Example 74 | A |
| Example 75 | A |
| Example 76 | A |
| Example 77 | A |
| Example 78 | B |
| Example 79 | A |
| Example 80 | A |
| Example 81 | A |
| Example 82 | A |
| Example 83 | A |
| Example 84 | A |
| Example 85 | B |
| Example 86 | C |
| Example 87 | C |
| Example 88 | A |
| Example 89 | A |
| Example 90 | B |
| Example 91 | A |
| Example 92 | A |
| Example 93 | A |
| Example 107 | C |
| Example 108 | C | noted:
A ≤ 0.1 μM;
0.1 μM < B ≤ 1.0 μM;
1.0 μM < C ≤ 10 μM

The results showed that the compounds of the present disclosure can be used to inhibit the activity of BTK, therefore being capable of being used in the manufacture of medicament for inhibiting BTK.

In the description of this specification, the terms "one embodiment", "some embodiments", "examples", "specific examples" or "some examples" and the like are intended to be a combination of the specific features, structures, materials or characteristics described in connection with the embodiments or examples is included in at least one embodiment or example of the present disclosure. In the present specification, the schematic expression of the terminology described above does not necessarily refer to the same embodiment or example. Moreover, the particular features, structures, materials, or characteristics described herein may be combined in any suitable embodiment or example in any suitable manner.

While the examples of the disclosure have been shown and described above, it should be understood that the examples described above are exemplary and not be construed as limited to the examples of the disclosure. The changes, modifications, replacements and variations may be made in present examples by the skilled person in the art within the scope of the present invention, without departing from the principles and purposes of the present invention.

What is claimed is:

1. A compound of formula (I), or a pharmaceutically acceptable salt, a tautomer, a stereoisomer, an N-oxide, a hydrate, or a solvate,

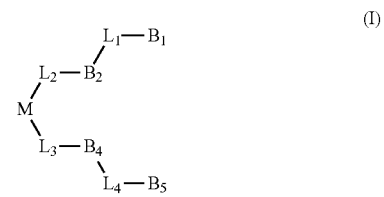

wherein M is

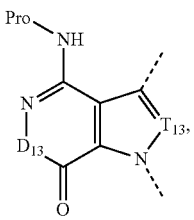

where $T_{13}$ is N; $D_{13}$ is N(Pro); Pro is H; $B_1$ is

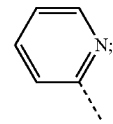

$B_2$ is selected from

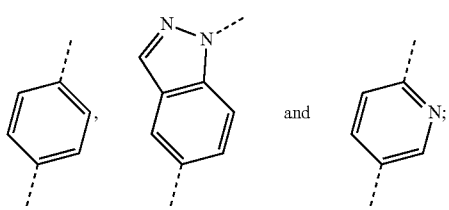

$B_4$ is selected from

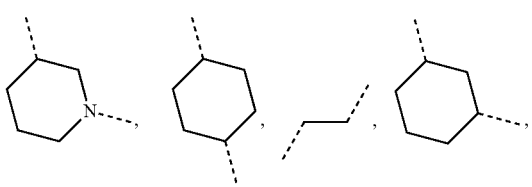

-continued
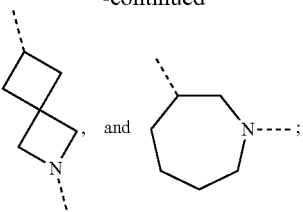
$B_5$ is selected from
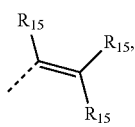
where each $R_{15}$ is independently H or
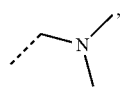
$L_1$ is —O—;
$L_2$ and $L_3$ each are a single bond; and
$L_4$ is selected from
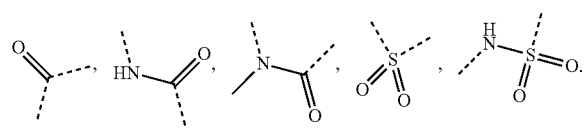
2. The compound according to claim 1, wherein the compound is any one selected from:
(6)
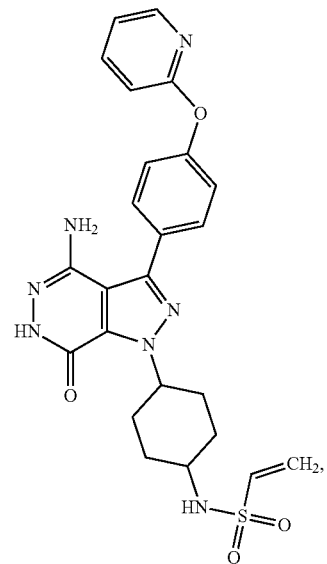
(7)
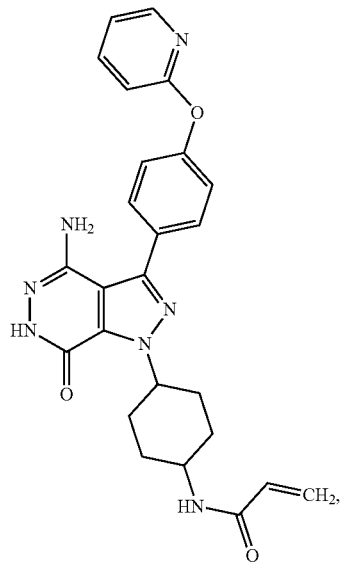
(8)
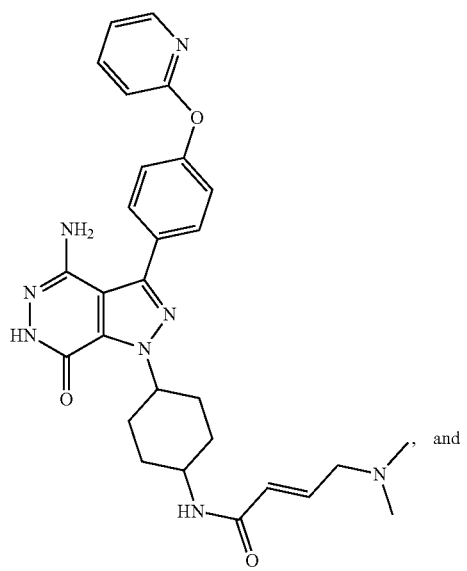
and
(28)
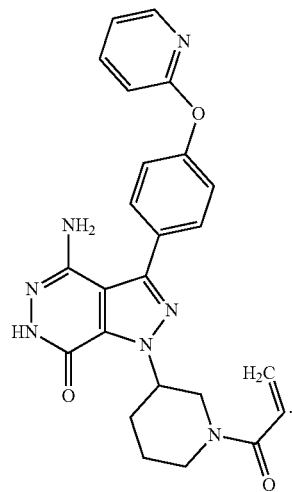

3. The compound according to claim 1, wherein the compound is any one selected from:
(6)
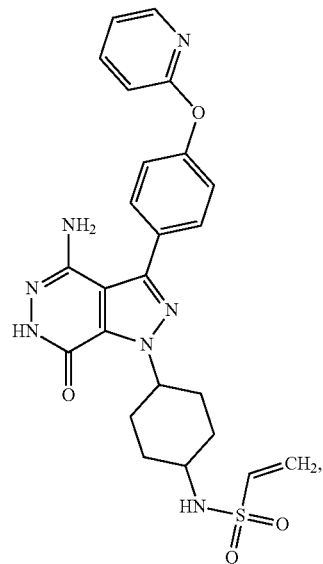
(7)
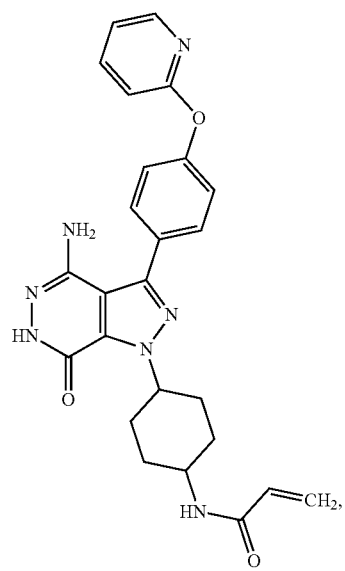
(8)
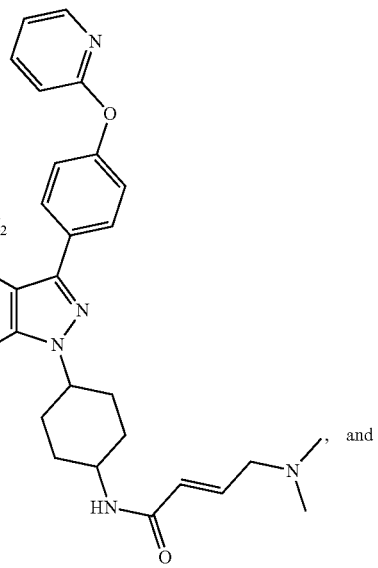
, and
(28)
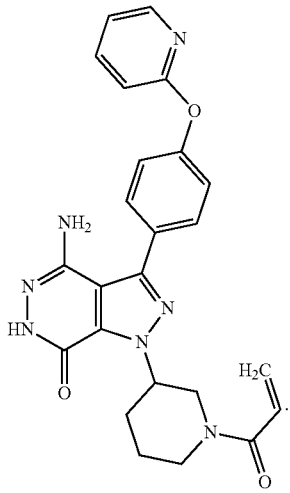
4. The compound according to claim 1, wherein the compound is
(28)
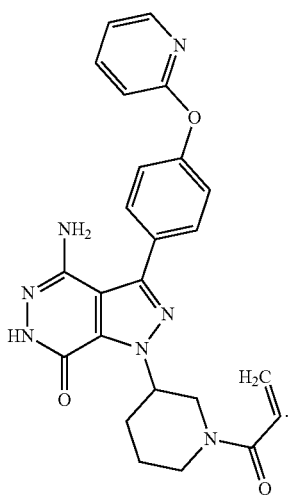

5. The compound according to claim 1, wherein the compound is

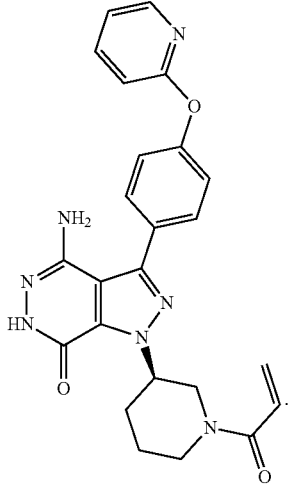

(28a)

6. A compound of formula (I), or a pharmaceutically acceptable salt, a tautomer, a stereoisomer, an N-oxide, a hydrate, or a solvate,

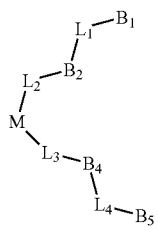

(I)

wherein M is

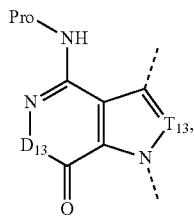

where $T_{13}$ is N; $D_{13}$ is N(Pro); Pro is H;

$B_1$ is selected from

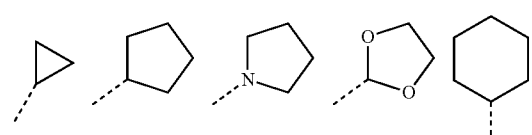

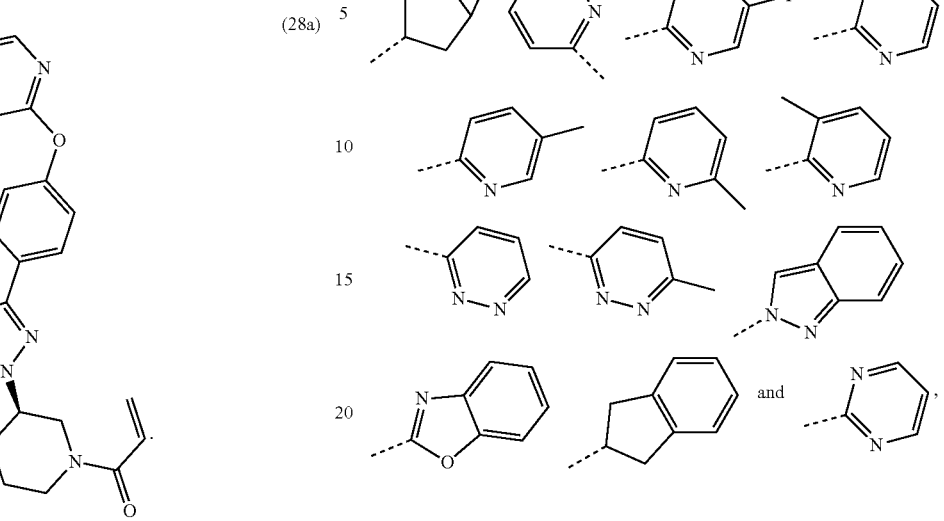

each are unsubstituted or independently substituted with $C_{1-6}$ alkyl or halogen;

$B_2$ is selected from

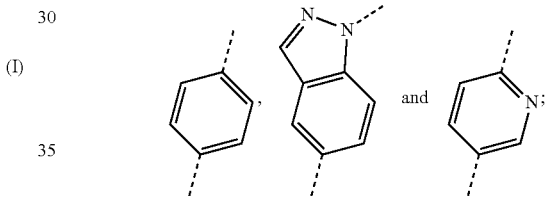

$B_4$ is selected from

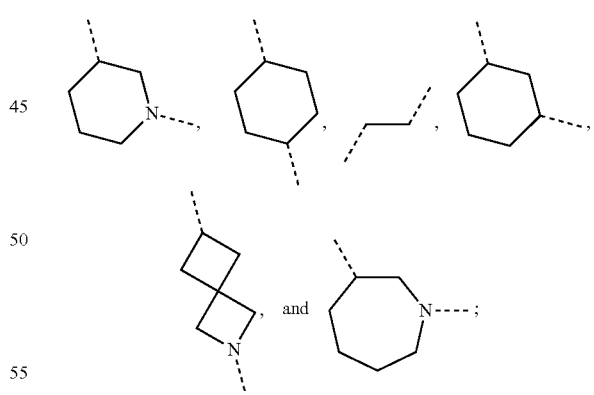

$B_5$ is selected from

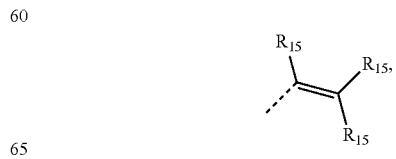

where each $R_{15}$ is independently H or
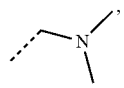
$L_1$ is a single bond or
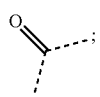
$L_2$ and $L_3$ each are a single bond; and
$L_4$ is selected from
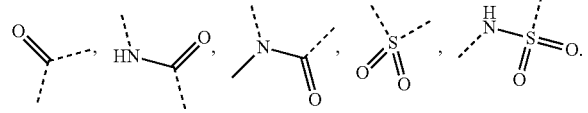
7. The compound according to claim 6, wherein the compound is any one selected from:
(1)
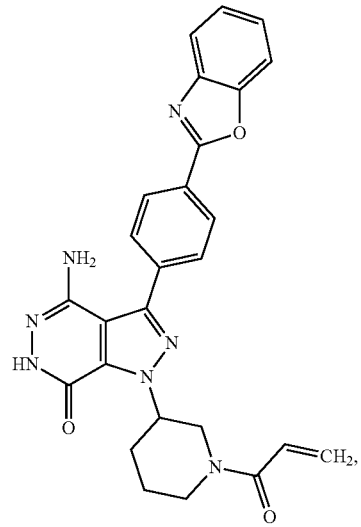
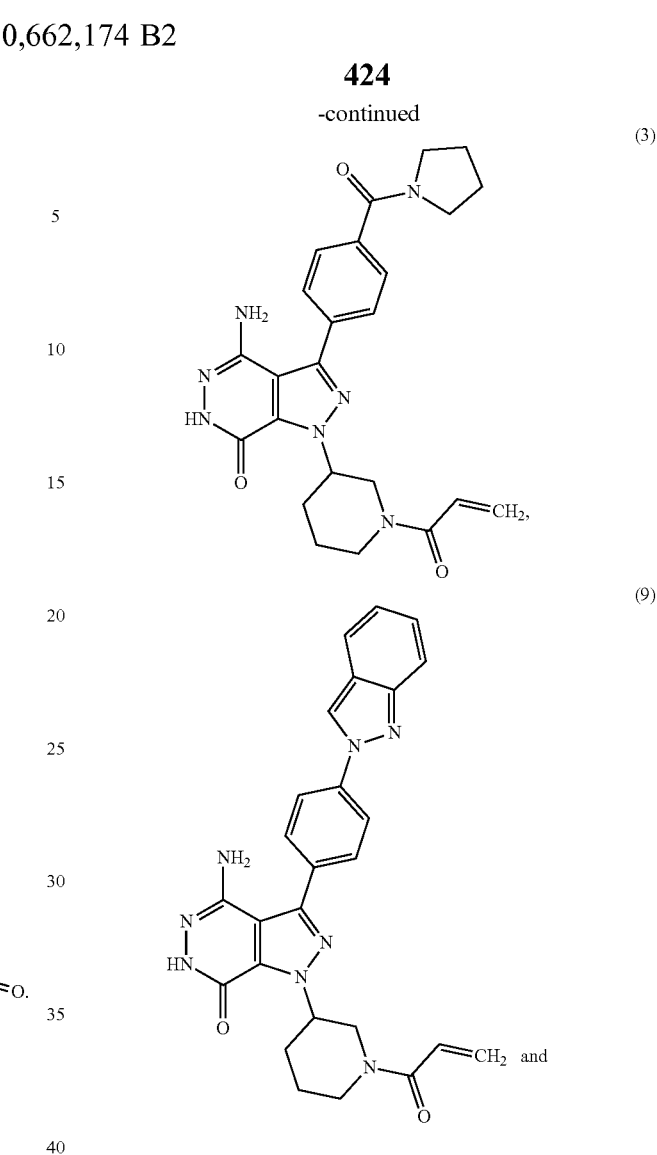
8. The compound according to claim 6, wherein the compound is any one selected from:
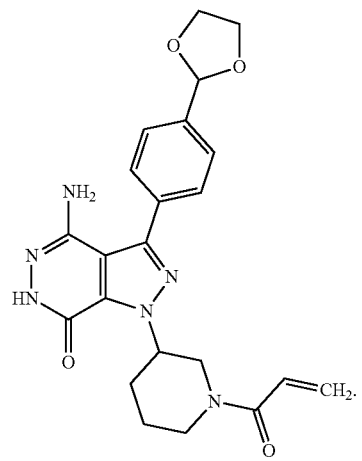

(1a)
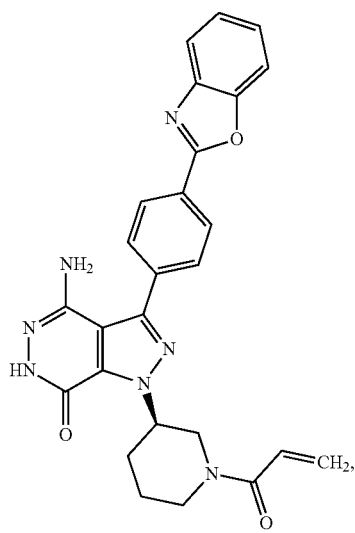
(9a)
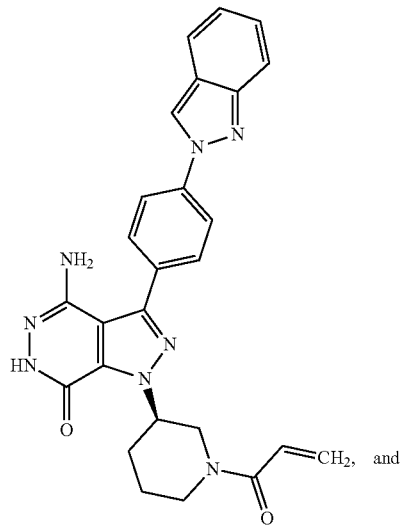
and
(3a)
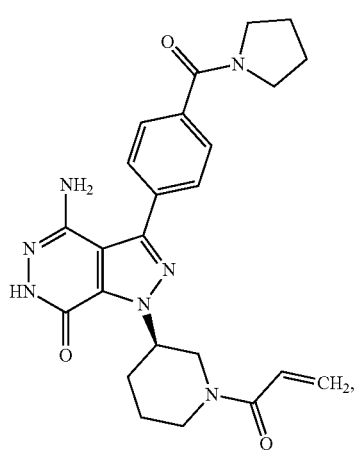
(16a)
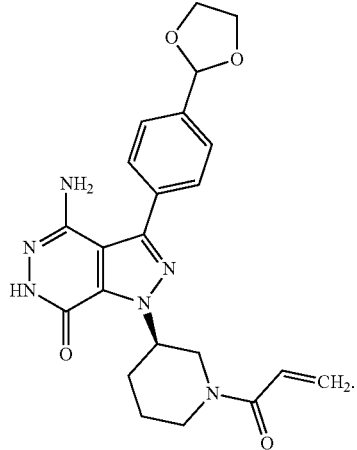
* * * * *